(12) United States Patent
Stokes et al.

(10) Patent No.: US 8,492,560 B2
(45) Date of Patent: Jul. 23, 2013

(54) QUINAZOLINE DERIVATIVES AS ANGIOGENESIS INHIBITORS

(75) Inventors: Elaine S E Stokes, Macclesfield (GB); Darren Mckerrecher, Macclesfield (GB); Laurent F A Hennequin, Reims (FR); Patrick Ple, Reims (FR)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 13/090,405

(22) Filed: Apr. 20, 2011

(65) Prior Publication Data

US 2012/0197027 A1     Aug. 2, 2012

Related U.S. Application Data

(60) Continuation of application No. 11/169,122, filed on Jun. 29, 2005, now abandoned, which is a division of application No. 09/913,020, filed as application No. PCT/GB00/00373 on Feb. 8, 2000, now Pat. No. 7,074,800.

(30) Foreign Application Priority Data

Feb. 10, 1999   (EP) .................................... 99400305

(51) Int. Cl.
    *C07D 209/08*      (2006.01)

(52) U.S. Cl.
    USPC ........................................................ 548/469

(58) Field of Classification Search
    USPC ........................................................ 548/469
    See application file for complete search history.

(56) References Cited

U.S. PATENT DOCUMENTS

| | | | |
|---|---|---|---|
| 3,843,683 A | 10/1974 | Bell | |
| 5,409,930 A | 4/1995 | Spada et al. | |
| 5,411,963 A | 5/1995 | Dreikorn et al. | |
| 5,480,883 A | 1/1996 | Spada et al. | |
| 5,646,153 A | 7/1997 | Spada et al. | |
| 5,710,158 A | 1/1998 | Myers et al. | |
| 5,714,493 A | 2/1998 | Myers et al. | |
| 5,721,237 A | 2/1998 | Myers et al. | |
| 5,736,534 A | 4/1998 | Arnold | |
| 5,859,009 A | 1/1999 | Schaper et al. | |
| RE36,256 E | 7/1999 | Spada et al. | |
| 6,017,945 A | 1/2000 | Rawson et al. | |
| 6,046,206 A | 4/2000 | Pamukcu et al. | |
| 6,057,320 A | 5/2000 | Spada et al. | |
| 6,153,617 A | 11/2000 | Bridges | |
| 6,162,804 A | 12/2000 | Bilodeau et al. | |
| 6,225,318 B1 | 5/2001 | Sabolov-Jaynes et al. | |
| 6,265,411 B1 | 7/2001 | Thomas et al. | |
| 6,294,532 B1 | 9/2001 | Thomas et al. | |
| 6,531,491 B1 | 3/2003 | Kania et al. | |
| 6,645,969 B1 | 11/2003 | Myers et al. | |
| 6,887,874 B2 | 5/2005 | Hennequin | |
| 7,268,230 B2 | 9/2007 | Hennequin | |
| 7,371,765 B2 | 5/2008 | Hennequin | |

| | | |
|---|---|---|
| 2002/0177601 A1 | 11/2002 | Himmelsbach et al. |
| 2003/0207878 A1 | 11/2003 | Hennequin |
| 2006/0148819 A1 | 7/2006 | Hennequin |
| 2007/0129387 A1 | 6/2007 | McCabe |
| 2008/0027069 A1 | 1/2008 | Hennequin |
| 2008/0058342 A1 | 3/2008 | Hennequin |
| 2008/0221322 A1 | 9/2008 | Arnott et al. |
| 2008/0312273 A1 | 12/2008 | Hennequin |
| 2009/0028943 A1 | 1/2009 | Cahill et al. |
| 2009/0156821 A1 | 6/2009 | Hennequin |

FOREIGN PATENT DOCUMENTS

| | | |
|---|---|---|
| DE | 19614718 A1 | 10/1997 |
| EP | 0326330 A2 | 8/1989 |
| EP | 0602851 A1 | 6/1994 |
| EP | 0602851 B1 | 10/1996 |
| EP | 0837063 A1 | 4/1998 |
| EP | 1029853 A1 | 8/2000 |

(Continued)

OTHER PUBLICATIONS

Bridges et al., "Enantioselective Inhibition of the Epidermal Growth Factor Receptor Tyrosine Kinase by 4-(a-Phenethylamino)quinazolines," Bioogranic & Medicinal Chemistry, 3: 1651-1656 (1995).

(Continued)

*Primary Examiner* — Shawquia Young
(74) *Attorney, Agent, or Firm* — Morgan, Lewis & Bockius LLP

(57) ABSTRACT

The invention relates to the use of compounds of formula (I) and salts thereof, in the manufacture of a medicament for use in the production of an antiangiogenic and/or vascular permeability reducing effect in warm-blooded animals, processes for the preparation of such compounds, pharmaceutical compositions containing a compound of formula I or a pharmaceutically acceptable salt thereof as active ingredient and compounds of formula I. The compounds of formula I and the pharmaceutically acceptable salts thereof inhibit the effects of VEGF, a property of value in the treatment of a number of disease states including cancer and rheumatoid arthritis.

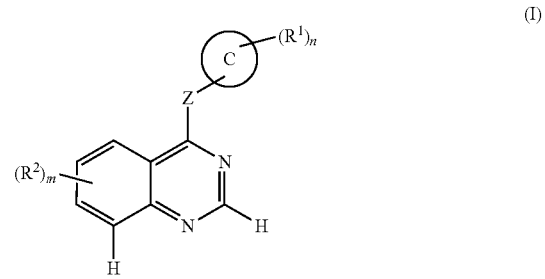

4 Claims, No Drawings

FOREIGN PATENT DOCUMENTS

| | | |
|---|---|---|
| GB | 2345486 A | 7/2000 |
| WO | 87/04321 A2 | 7/1987 |
| WO | 92/20642 A1 | 11/1992 |
| WO | 95/15758 A2 | 6/1995 |
| WO | 95/19169 A2 | 7/1995 |
| WO | 95/23141 A1 | 8/1995 |
| WO | 95/24190 A2 | 9/1995 |
| WO | 96/29301 A1 | 9/1996 |
| WO | 96/39145 A1 | 12/1996 |
| WO | 97/03069 A1 | 1/1997 |
| WO | 97/17329 A1 | 5/1997 |
| WO | 97/22596 A1 | 6/1997 |
| WO | 97/30034 A1 | 8/1997 |
| WO | 97/42187 A1 | 11/1997 |
| WO | 98/02434 A1 | 1/1998 |
| WO | 98/54093 A1 | 12/1998 |
| WO | 99/06396 A1 | 2/1999 |
| WO | 99/10349 A1 | 3/1999 |
| WO | 99/21859 A1 | 5/1999 |
| WO | 99/35132 A1 | 7/1999 |
| WO | 99/35146 A1 | 7/1999 |
| WO | 00/06554 A1 | 2/2000 |
| WO | 00/12497 A2 | 3/2000 |
| WO | 00/44728 A1 | 8/2000 |
| WO | 00/55141 A1 | 9/2000 |
| WO | 01/02369 A2 | 1/2001 |
| WO | 01/29025 A2 | 4/2001 |
| WO | 02/12226 A1 | 2/2002 |
| WO | 02/12227 A2 | 2/2002 |
| WO | 02/12228 A1 | 2/2002 |
| WO | 03/064413 A1 | 8/2003 |
| WO | 2005/014582 A1 | 2/2005 |
| WO | 2005/061488 A1 | 7/2005 |
| WO | 2007/060402 A1 | 5/2007 |

OTHER PUBLICATIONS

Gazit et al., "Tyrophostins IV-Highly Potent Inhibitors . . . Relationship Study of 4-Anilidoquinazolines," Bioorganic & Medicinal Chemistry, 4: 1203-1207 (1996).

Gibson et al., "Epidermal Growth Factor Receptor Tyrosine Kinase: Structure-Activity Relationships and Antitumour Activity of Novel Quinazolines," Bioorganic & Medicinal Chemistry Letters, 7: 2723-2728 (1997).

Hara et al., "On the Amination of Azaheterocycles: A New Procedure for the Introduction of an Amino Group (1)," Journal of Heterocyclic Chemistry, 19: 1285-1287 (1982).

Hennequin et al., "Design and Structure-Activity Relationship of a New Class of Potent VEGF Receptor Tyrosine Kinase Inhibitors," Journal of Medicinal Chemistry, 42: 5369-5389 (1999).

Karminski et al., Chemical Abstracts, 100: 34492 (1984).

Karminski et al., "The Synthesis of Some Quinazoline Derivatives and their Biological Properties," Journal of Environmental Science Health, B18: 599-610 (1983).

Sinyak et al., Chemical Abstracts, 140: 199594 (1986).

Sinyak et al., "Synthesis and Biological Properties of Derivatives of 4-Heterylmercaptoquinazoline," Zaporozh's Medical Institute pp. 103-106, translated from Khimiko-farmatsevticheskii Zhurnal, 20: 168-171 (1984).

Flaugh et al., "Synthesis and Evaluation of the Antiovulatory Activity of a Variety of Melatonin Analogues," American Chemical Society, 22: 63-69 (1979).

QUINAZOLINE DERIVATIVES AS ANGIOGENESIS INHIBITORS

RELATED APPLICATIONS

The present application is a Continuation Application of U.S. patent application Ser. No. 11/169,122, filed Jun. 29, 2005 now abandoned, which is a Divisional Application of U.S. patent application Ser. No. 09/913,020, filed May 6, 2002 now U.S. Pat. No. 7,074,800, which is a U.S. National Phase Application of International Application No. PCT/GB2000/00373, filed Feb. 8, 2000, which claims the benefit of European Patent Application No. 99400305.1, filed Feb. 10, 1999, all of which are hereby incorporated by reference in their entirety.

The present invention relates to quinazoline derivatives, processes for their preparation, pharmaceutical compositions containing them as active ingredient, methods for the treatment of disease states associated with angiogenesis and/or increased vascular permeability, to their use as medicaments and to their use in the manufacture of medicaments for use in the production of antiangiogenic and/or vascular permeability reducing effects in warm-blooded animals such as humans.

Normal angiogenesis plays an important role in a variety of processes including embryonic development, wound healing and several components of female reproductive function. Undesirable or pathological angiogenesis has been associated with disease states including diabetic retinopathy, psoriasis, cancer, rheumatoid arthritis, atheroma, Kaposi's sarcoma and haemangioma (Fan et al, 1995, Trends Pharmacol. Sci. 16: 57-66; Folkman, 1995, Nature Medicine 1: 27-31). Alteration of vascular permeability is thought to play a role in both normal and pathological physiological processes (Cullinan-Bove et al, 1993, Endocrinology 133: 829-837; Senger et al, 1993, Cancer and Metastasis Reviews, 12: 303-324). Several polypeptides with in vitro endothelial cell growth promoting activity have been identified including, acidic and basic fibroblast growth factors (aFGF & bFGF) and vascular endothelial growth factor (VEGF). By virtue of the restricted expression of its receptors, the growth factor activity of VEGF, in contrast to that of the FGFs, is relatively specific towards endothelial cells. Recent evidence indicates that VEGF is an important stimulator of both normal and pathological angiogenesis (Jakeman et al, 1993, Endocrinology, 133: 848-859; Kolch et al, 1995, Breast Cancer Research and Treatment, 36:139-155) and vascular permeability (Connolly et al, 1989, J. Biol. Chem. 264: 20017-20024). Antagonism of VEGF action by sequestration of VEGF with antibody can result in inhibition of tumour growth (Kim et al, 1993, Nature 362: 841-844). Basic FGF (bFGF) is a potent stimulator of angiogenesis (e.g. Hayek et al, 1987, Biochem. Biophys. Res. Commun. 147: 876-880) and raised levels of FGFs have been found in the serum (Fujimoto et al, 1991, Biochem. Biophys. Res. Commun. 180: 386-392) and urine (Nguyen et al, 1993, J. Natl. Cancer. Inst. 85: 241-242) of patients with cancer.

Receptor tyrosine kinases (RTKs) are important in the transmission of biochemical signals across the plasma membrane of cells. These transmembrane molecules characteristically consist of an extracellular ligand-binding domain connected through a segment in the plasma membrane to an intracellular tyrosine kinase domain. Binding of ligand to the receptor results in stimulation of the receptor-associated tyrosine kinase activity which leads to phosphorylation of tyrosine residues on both the receptor and other intracellular molecules. These changes in tyrosine phosphorylation initiate a signalling cascade leading to a variety of cellular responses. To date, at least nineteen distinct RTK subfamilies, defined by amino acid sequence homology, have been identified. One of these subfamilies is presently comprised by the fms-like tyrosine kinase receptor, Flt or Flt1, the kinase insert domain-containing receptor, KDR (also referred to as Flk-1), and another fms-like tyrosine kinase receptor, Flt4. Two of these related RTKs, Flt and KDR, have been shown to bind VEGF with high affinity (De Vries et al, 1992, Science 255: 989-991; Terman et al, 1992, Biochem. Biophys. Res. Comm. 1992, 187: 1579-1586). Binding of VEGF to these receptors expressed in heterologous cells has been associated with changes in the tyrosine phosphorylation status of cellular proteins and calcium fluxes.

The present invention is based on the discovery of compounds that surprisingly inhibit the effects of VEGF, a property of value in the treatment of disease states associated with angiogenesis and/or increased vascular permeability such as cancer, diabetes, psoriasis, rheumatoid arthritis, Kaposi's sarcoma, haemangioma, acute and chronic nephropathies, atheroma, arterial restenosis, autoimmune diseases, acute inflammation, excessive scar formation and adhesions, endometriosis, dysfunctional uterine bleeding and ocular diseases with retinal vessel proliferation. Compounds of the present invention generally possess higher potency against VEGF receptor tyrosine kinase than against epidermal growth factor (EGF) receptor tyrosine kinase. Compounds of the invention which have been tested possess activity against VEGF receptor tyrosine kinase such that they may be used in an amount sufficient to inhibit VEGF receptor tyrosine kinase whilst demonstrating no significant activity against EGF receptor tyrosine kinase. Compounds of the present invention generally possess higher potency against VEGF receptor tyrosine kinase than against FGF R1 receptor tyrosine kinase. Compounds of the invention which have been tested possess activity against VEGF receptor tyrosine kinase such that they may be used in an amount sufficient to inhibit VEGF receptor tyrosine kinase whilst demonstrating no significant activity against FGF R1 receptor tyrosine kinase.

According to one aspect of the present invention there is provided the use of a compound of the formula I:

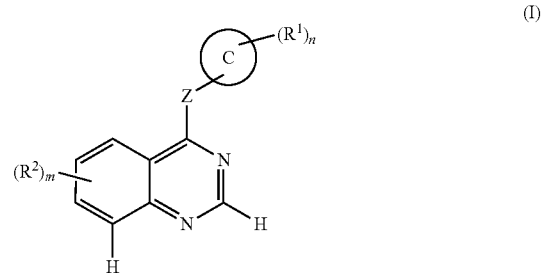

wherein:
ring C is an 8, 9, 10, 12 or 13-membered bicyclic or tricyclic moiety which moiety may be saturated or unsaturated, which may be aromatic or non-aromatic, and which optionally may contain 1-3 heteroatoms selected independently from O, N and S;
Z is —O—, —NH—, —S—, —CH$_2$— or a direct bond;
n is an integer from 0 to 5;
m is an integer from 0 to 3;
$R^2$ represents hydrogen, hydroxy, halogeno, cyano, nitro, trifluoromethyl, C$_{1-3}$alkoxy, C$_{1-3}$alkylsulphanyl, —NR$^3$R$^4$ (wherein R$^3$ and R$^4$, which may be the same or different, each represents hydrogen or C$_{1-3}$alkyl), or R$^5$X$^1$—

(wherein $X^1$ represents a direct bond, —O—, —CH$_2$—, —OC(O)—, —C(O)—, —S—, —SO—, —SO$_2$—, —NR$^6$C(O)—, —C(O)NR$^7$—, —SO$_2$NR$^8$—, —NR$^9$SO$_2$— or —NR$^{10}$— (wherein R$^6$, R$^7$, R$^8$, R$^9$ and R$^{10}$ each independently represents hydrogen, C$_{1-3}$alkyl or C$_{1-3}$alkoxyC$_{2-3}$alkyl), and R$^5$ is selected from one of the following twenty-two groups:

1) hydrogen, oxiranylC$_{1-4}$alkyl or C$_{1-5}$alkyl which may be unsubstituted or which may be substituted with one or more groups selected from hydroxy, fluoro, chloro, bromo and amino;
2) C$_{1-5}$alkylX$^2$C(O)R$^{11}$ (wherein X$^2$ represents —O— or —NR$^{12}$— (in which R$^{12}$ represents hydrogen, C$_{1-3}$alkyl or C$_{1-3}$alkoxyC$_{2-3}$alkyl) and R$^{11}$ represents C$_{1-3}$alkyl, —NR$^{13}$R$^{14}$ or —OR$^{15}$ (wherein R$^{13}$, R$^{14}$ and R$^{15}$ which may be the same or different each represents hydrogen, C$_{1-5}$alkyl or C$_{1-3}$alkoxyC$_{2-3}$alkyl));
3) C$_{1-5}$alkylX$^3$R$^{16}$ (wherein X$^3$ represents —O—, —S—, —SO—, —SO$_2$—, —OC(O)—, —NR$^{17}$C(O)—, —C(O)NR$^{18}$—, —SO$_2$NR$^{19}$—, —NR$^{20}$SO$_2$— or —NR$^{21}$— (wherein R$^{17}$, R$^{18}$, R$^{19}$, R$^{20}$ and R$^{21}$ each independently represents hydrogen, C$_{1-3}$alkyl or C$_{1-3}$alkoxyC$_{2-3}$alkyl) and R$^{16}$ represents hydrogen, C$_{1-3}$alkyl, cyclopentyl, cyclohexyl or a 5-6-membered saturated heterocyclic group with 1-2 heteroatoms, selected independently from O, S and N, which C$_{1-3}$alkyl group may bear 1 or 2 substituents selected from oxo, hydroxy, halogeno and C$_{1-4}$alkoxy and which cyclic group may bear 1 or 2 substituents selected from oxo, hydroxy, halogeno, cyano, C$_{1-4}$cyanoalkyl, C$_{1-4}$alkyl, C$_{1-4}$hydroxyalkyl, C$_{1-4}$alkoxy, C$_{1-4}$alkoxyC$_{1-4}$alkyl, C$_{1-4}$alkylsulphonylC$_{1-4}$alkyl, C$_{1-4}$alkoxycarbonyl, C$_{1-4}$aminoalkyl, C$_{1-4}$alkylamino, di(C$_{1-4}$alkyl)amino, C$_{1-4}$alkylaminoC$_{1-4}$alkyl, di(C$_{1-4}$alkyl)aminoC$_{1-4}$alkyl, C$_{1-4}$alkylaminoC$_{1-4}$alkoxy, di(C$_{1-4}$alkyl)aminoC$_{1-4}$alkoxy and a group —(—O—)$_f$(C$_{1-4}$alkyl)$_g$ringD (wherein f is 0 or 1, g is 0 or 1 and ring D is a 5-6-membered saturated heterocyclic group with 1-2 heteroatoms, selected independently from O, S and N, which cyclic group may bear one or more substituents selected from C$_{1-4}$alkyl));
4) C$_{1-5}$alkylX$^4$C$_{1-5}$alkylX$^5$R$^{22}$ (wherein X$^4$ and X$^5$ which may be the same or different are each —O—, —S—, —SO—, —SO$_2$—, —NR$^{23}$C(O)—, —C(O)NR$^{24}$—, —SO$_2$NR$^{25}$—, —NR$^{26}$SO$_2$— or —NR$^{27}$— (wherein R$^{23}$, R$^{24}$, R$^{25}$, R$^{26}$ and R$^{27}$ each independently represents hydrogen, C$_{1-3}$alkyl or C$_{1-3}$alkoxyC$_{2-3}$alkyl) and R$^{22}$ represents hydrogen, C$_{1-3}$alkyl or C$_{1-3}$alkoxyC$_{2-3}$alkyl);
5) R$^{28}$ (wherein R$^{28}$ is a 5-6-membered saturated heterocyclic group (linked via carbon or nitrogen) with 1-2 heteroatoms, selected independently from O, S and N, which heterocyclic group may bear 1 or 2 substituents selected from oxo, hydroxy, halogeno, cyano, C$_{1-4}$cyanoalkyl, C$_{1-4}$alkyl, C$_{1-4}$hydroxyalkyl, C$_{1-4}$alkoxy, C$_{1-4}$alkoxyC$_{1-4}$alkyl, C$_{1-4}$alkylsulphonylC$_{1-4}$alkyl, C$_{1-4}$alkoxycarbonyl, C$_{1-4}$aminoalkyl, C$_{1-4}$alkylamino, di(C$_{1-4}$alkyl)amino, C$_{1-4}$alkylaminoC$_{1-4}$alkyl, di(C$_{1-4}$alkyl)aminoC$_{1-4}$alkyl, C$_{1-4}$alkylaminoC$_{1-4}$alkoxy, di(C$_{1-4}$alkyl)aminoC$_{1-4}$alkoxy and a group —(—O—)$_f$(C$_{1-4}$alkyl)$_g$ringD (wherein f is 0 or 1, g is 0 or 1 and ring D is a 5-6-membered saturated heterocyclic group with 1-2 heteroatoms, selected independently from O, S and N, which cyclic group may bear one or more substituents selected from C$_{1-4}$alkyl));
6) C$_{1-5}$alkylR$^{28}$ (wherein R$^{28}$ is as defined hereinbefore);
7) C$_{2-5}$alkenylR$^{28}$ (wherein R$^{28}$ is as defined hereinbefore);
8) C$_{2-5}$alkynylR$^{28}$ (wherein R$^{28}$ is as defined hereinbefore);
9) R$^{29}$ (wherein R$^{29}$ represents a pyridone group, a phenyl group or a 5-6-membered aromatic heterocyclic group (linked via carbon or nitrogen) with 1-3 heteroatoms selected from O, N and S, which pyridone, phenyl or aromatic heterocyclic group may carry up to 5 substituents selected from hydroxy, halogeno, amino, C$_{1-4}$alkyl, C$_{1-4}$alkoxy, C$_{1-4}$hydroxyalkyl, C$_{1-4}$aminoalkyl, C$_{1-4}$alkylamino, C$_{1-4}$hydroxyalkoxy, carboxy, trifluoromethyl, cyano, —C(O)NR$^{30}$R$^{31}$, —NR$^{32}$C(O)R$^{33}$ (wherein R$^{30}$, R$^{31}$, R$^{32}$ and R$^{33}$, which may be the same or different, each represents hydrogen, C$_{1-4}$alkyl or C$_{1-3}$alkoxyC$_{2-3}$alkyl) and a group —(—O—)$_f$(C$_{1-4}$alkyl)$_g$ringD (wherein f is 0 or 1, g is 0 or 1 and ring D is a 5-6-membered saturated heterocyclic group with 1-2 heteroatoms, selected independently from O, S and N, which cyclic group may bear one or more substituents selected from C$_{1-4}$alkyl));
10) C$_{1-5}$alkylR$^{29}$ (wherein R$^{29}$ is as defined hereinbefore);
11) C$_{2-5}$alkenylR$^{29}$ (wherein R$^{29}$ is as defined hereinbefore);
12) C$_{2-5}$alkynylR$^{29}$ wherein R$^{29}$ is as defined hereinbefore);
13) C$_{1-5}$alkylX$^6$R$^{29}$ (wherein X$^6$ represents —O—, —S—, —SO—, —SO$_2$—, —NR$^{34}$C(O)—, —C(O)NR$^{35}$—, —SO$_2$NR$^{36}$—, —NR$^{37}$SO$_2$— or —NR$^{38}$— (wherein R$^{34}$, R$^{35}$, R$^{36}$, R$^{37}$ and R$^{38}$ each independently represents hydrogen, C$_{1-3}$alkyl or C$_{1-3}$alkoxyC$_{2-3}$alkyl) and R$^{29}$ is as defined hereinbefore);
14) C$_{2-5}$alkenylX$^7$R$^{29}$ (wherein X$^7$ represents —O—, —S—, —SO—, —SO$_2$—, —NR$^{39}$C(O)—, —C(O)NR$^{40}$—, —SO$_2$NR$^{41}$—, —NR$^{42}$SO$_2$— or —NR$^{43}$— (wherein R$^{39}$, R$^{40}$, R$^{41}$, R$^{42}$ and R$^{43}$ each independently represents hydrogen, C$_{1-3}$alkyl or C$_{1-3}$alkoxyC$_{2-3}$alkyl) and R$^{29}$ is as defined hereinbefore);
15) C$_{2-5}$alkynylX$^8$R$^{29}$ (wherein X$^8$ represents —O—, —S—, —SO—, —SO$_2$—, —NR$^{44}$C(O)—, —C(O)NR$^{45}$—, —SO$_2$NR$^{46}$—, —NR$^{47}$SO$_2$— or —NR$^{48}$— (wherein R$^{44}$, R$^{45}$, R$^{46}$, R$^{47}$ and R$^{48}$ each independently represents hydrogen, C$_{1-3}$alkyl or C$_{1-3}$alkoxyC$_{2-3}$alkyl) and R$^{29}$ is as defined hereinbefore);
16) C$_{1-4}$alkylX$^9$C$_{1-4}$alkylR$^{29}$ (wherein X$^9$ represents —O—, —S—, —SO—, —SO$_2$—, —NR$^{49}$C(O)—, —C(O)NR$^{50}$—, —SO$_2$NR$^{51}$—, —NR$^{52}$SO$_2$— or —NR$^{53}$— (wherein R$^{49}$, R$^{50}$, R$^{51}$, R$^{52}$ and R$^{53}$ each independently represents hydrogen, C$_{1-3}$alkyl or C$_{1-3}$alkoxyC$_{2-3}$alkyl) and R$^{29}$ is as defined hereinbefore);
17) C$_{1-4}$alkylX$^9$C$_{1-4}$alkylR$^{28}$ (wherein X$^9$ and R$^{28}$ are as defined hereinbefore);
18) C$_{2-5}$alkenyl which may be unsubstituted or which may be substituted with one or more groups selected from hydroxy, fluoro, amino, C$_{1-4}$alkylamino, N,N-di(C$_{1-4}$alkyl)amino, aminosulphonyl, N—C$_{1-4}$alkylaminosulphonyl and N,N-di(C$_{1-4}$alkyl)aminosulphonyl;
19) C$_{2-5}$alkynyl which may be unsubstituted or which may be substituted with one or more groups selected from hydroxy, fluoro, amino, C$_{1-4}$alkylamino, N,N-di(C$_{1-4}$alkyl)amino, aminosulphonyl, N—C$_{1-4}$alkylaminosulphonyl and N,N-di(C$_{1-4}$alkyl)aminosulphonyl;
20) C$_{2-5}$alkenylX$^9$C$_{1-4}$alkylR$^{28}$ (wherein X$^9$ and R$^{28}$ are as defined hereinbefore);
21) C$_{2-5}$alkynylX$^9$C$_{1-4}$alkylR$^{28}$ (wherein X$^9$ and R$^{28}$ are as defined hereinbefore); and
22) C$_{1-4}$alkylR$^{54}$(C$_{1-4}$alkyl)$_q$(X$^9$)$_r$R$^{55}$ (wherein X$^9$ is as defined hereinbefore, q is 0 or 1, r is 0 or 1, and R$^{54}$ and R$^{55}$ are each independently selected from hydrogen, C$_{1-3}$alkyl, cyclopentyl, cyclohexyl and a 5-6-membered saturated heterocyclic group with 1-2 heteroatoms, selected independently from O, S and N, which C$_{1-3}$alkyl group may bear 1 or 2 substituents selected from oxo, hydroxy, halogeno and C$_{1-4}$alkoxy and which cyclic group may bear 1 or 2 substituents selected from oxo, hydroxy, halogeno, cyano, C$_{1-4}$cyanoalkyl, C$_{1-4}$alkyl, C$_{1-4}$hydroxyalkyl, $C_{1-4}$alkoxy, $C_{1-4}$alkoxy$C_{1-4}$alkyl, $C_{1-4}$alkylsulphonyl $C_{1-4}$alkyl, $C_{1-4}$alkoxycarbonyl, $C_{1-4}$aminoalkyl, $C_{1-4}$alkylamino, di($C_{1-4}$alkyl)amino, $C_{1-4}$alkylamino$C_{1-4}$alkyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy and a group —(—O—)$_f$ ($C_{1-4}$alkyl)$_g$ringD (wherein f is 0 or 1, g is 0 or 1 and ring D is a 5-6-membered saturated heterocyclic group with 1-2 heteroatoms, selected independently from O, S and N, which cyclic group may bear one or more substituents selected from $C_{1-4}$alkyl), with the proviso that $R^{54}$ cannot be hydrogen);

and additionally wherein any $C_{1-5}$alkyl, $C_{2-5}$alkenyl or $C_{2-5}$alkynyl group in $R^5X^1$— may bear one or more substituents selected from hydroxy, halogeno and amino);

$R^1$ represents hydrogen, oxo, halogeno, hydroxy, $C_{1-4}$alkoxy, $C_{1-4}$alkyl, $C_{1-4}$alkoxymethyl, $C_{1-4}$alkanoyl, $C_{1-4}$haloalkyl, cyano, amino, $C_{2-5}$alkenyl, $C_{2-5}$alkynyl, $C_{1-4}$alkanoyloxy, nitro, $C_{1-4}$alkanoylamino, $C_{1-4}$alkoxycarbonyl, $C_{1-4}$alkylsulphanyl, $C_{1-4}$alkylsulphinyl, $C_{1-4}$alkylsulphonyl, carbamoyl, N—$C_{1-4}$alkylcarbamoyl, N,N-di($C_{1-4}$alkyl)carbamoyl, aminosulphonyl, N—$C_{1-4}$alkylaminosulphonyl, N,N-di($C_{1-4}$alkyl)aminosulphonyl, N—($C_{1-4}$alkylsulphonyl)amino, N—($C_{1-4}$alkylsulphonyl)-N—($C_{1-4}$alkyl) amino, N,N-di($C_{1-4}$alkylsulphonyl)amino, a $C_{3-7}$alkylene chain joined to two ring C carbon atoms, $C_{1-4}$alkanoylamino$C_{1-4}$alkyl, carboxy or a group $R^{56}X^{10}$ (wherein $X^{10}$ represents a direct bond, —O—, —$CH_2$—, —OC(O)—, —C(O)—, —S—, —SO—, —$SO_2$—, —$NR^{57}$C(O)—, —C(O)$NR^{58}$—, —$SO_2NR^{59}$—, —$NR^{60}SO_2$— or —$NR^{61}$— (wherein $R^{57}$, $R^{58}$, $R^{59}$, $R^{60}$ and $R^{61}$ each independently represents hydrogen, $C_{1-3}$alkyl or $C_{1-3}$alkoxy$C_{2-3}$alkyl), and $R^{56}$ is selected from one of the following twenty-two groups:

1) hydrogen, oxiranyl$C_{1-4}$alkyl or $C_{1-5}$alkyl which may be unsubstituted or which may be substituted with one or more groups selected from hydroxy, fluoro, chloro, bromo and amino;
2) $C_{1-5}$alkyl$X^{11}$C(O)$R^{62}$ (wherein $X^{11}$ represents —O— or —$NR^{63}$— (in which $R^{63}$ represents hydrogen, $C_{1-3}$alkyl or $C_{1-3}$alkoxy$C_{2-3}$alkyl) and $R^{62}$ represents $C_{1-3}$alkyl, —$NR^{64}R^{65}$ or —$OR^{66}$ (wherein $R^{64}$, $R^{65}$ and $R^{66}$ which may be the same or different each represents hydrogen, $C_{1-5}$alkyl or $C_{1-3}$alkoxy$C_{2-3}$alkyl));
3) $C_{1-5}$alkyl$X^{12}R^{67}$ (wherein $X^{12}$ represents —O—, —S—, —SO—, —$SO_2$—, —OC(O)—, —$NR^{68}$C(O)—, —C(O)$NR^{69}$—, —$SO_2NR^{70}$—, —$NR^{71}SO_2$— or —$NR^{72}$— (wherein $R^{68}$, $R^{69}$, $R^{70}$, $R^{71}$ and $R^{72}$ each independently represents hydrogen, $C_{1-3}$alkyl or $C_{1-3}$alkoxy$C_{2-3}$alkyl) and $R^{67}$ represents hydrogen, $C_{1-3}$alkyl, cyclopentyl, cyclohexyl or a 5-6-membered saturated heterocyclic group with 1-2 heteroatoms, selected independently from O, S and N, which $C_{1-3}$alkyl group may bear 1 or 2 substituents selected from oxo, hydroxy, halogeno and $C_{1-4}$alkoxy and which cyclic group may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl$C_{1-4}$alkyl, $C_{1-4}$alkoxycarbonyl, $C_{1-4}$aminoalkyl, $C_{1-4}$alkylamino, di($C_{1-4}$alkyl)amino, $C_{1-4}$alkylamino$C_{1-4}$alkyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy and a group —(—O—)$_f$($C_{1-4}$alkyl)$_g$ringD (wherein f is 0 or 1, g is 0 or 1 and ring D is a 5-6-membered saturated heterocyclic group with 1-2 heteroatoms, selected independently from O, S and N, which cyclic group may bear one or more substituents selected from $C_{1-4}$alkyl));
4) $C_{1-5}$alkyl$X^{13}C_{1-5}$alkyl$X^{14}R^{73}$ (wherein $X^{13}$ and $X^{14}$ which may be the same or different are each —O—, —S—, —SO—, —$SO_2$—, —$NR^{74}$C(O)—, —C(O)$NR^{75}$—, —$SO_2NR^{76}$—, —$NR^{77}SO_2$— or —$NR^{78}$— (wherein $R^{74}$, $R^{75}$, $R^{76}$, $R^{77}$ and $R^{78}$ each independently represents hydrogen, $C_{1-3}$alkyl or $C_{1-3}$alkoxy$C_{2-3}$alkyl) and $R^{73}$ represents hydrogen, $C_{1-3}$alkyl or $C_{1-3}$alkoxy$C_{2-3}$alkyl);
5) $R^{79}$ (wherein $R^{79}$ is a 5-6-membered saturated heterocyclic group (linked via carbon or nitrogen) with 1-2 heteroatoms, selected independently from O, S and N, which heterocyclic group may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl$C_{1-4}$alkyl, $C_{1-4}$alkoxycarbonyl, $C_{1-4}$aminoalkyl, $C_{1-4}$alkylamino, di($C_{1-4}$alkyl)amino, $C_{1-4}$alkylamino$C_{1-4}$alkyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy and a group —(—O—)$_f$($C_{1-4}$alkyl)$_g$ringD (wherein f is 0 or 1, g is 0 or 1 and ring D is a 5-6-membered saturated heterocyclic group with 1-2 heteroatoms, selected independently from O, S and N, which cyclic group may bear one or more substituents selected from $C_{1-4}$alkyl));
6) $C_{1-5}$alkyl$R^{79}$ (wherein $R^{79}$ is as defined hereinbefore);
7) $C_{2-5}$alkenyl$R^{79}$ (wherein $R^{79}$ is as defined hereinbefore);
8) $C_{2-5}$alkynylV (wherein $R^{79}$ is as defined hereinbefore);
9) $R^{80}$ (wherein $R^{80}$ represents a pyridone group, a phenyl group or a 5-6-membered aromatic heterocyclic group (linked via carbon or nitrogen) with 1-3 heteroatoms selected from O, N and S, which pyridone, phenyl or aromatic heterocyclic group may carry up to 5 substituents selected from hydroxy, halogeno, amino, $C_{1-4}$alkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, trifluoromethyl, cyano, —C(O)$NR^{81}R^{82}$, —$NR^{83}$C(O)$R^{84}$ (wherein $R^{81}$, $R^{82}$, $R^{83}$ and $R^{84}$, which may be the same or different, each represents hydrogen, $C_{1-4}$alkyl or $C_{1-3}$alkoxy$C_{2-3}$alkyl) and a group —(—O—)$_f$($C_{1-4}$alkyl)$_g$ringD (wherein f is 0 or 1, g is 0 or 1 and ring D is a 5-6-membered saturated heterocyclic group with 1-2 heteroatoms, selected independently from O, S and N, which cyclic group may bear one or more substituents selected from $C_{1-4}$alkyl));
10) $C_{1-5}$alkyl$R^{80}$ (wherein $R^{80}$ is as defined hereinbefore);
11) $C_{2-5}$alkenyl$R^{80}$ (wherein $R^{80}$ is as defined hereinbefore);
12) $C_{2-5}$alkynyl$R^{80}$ wherein $R^{80}$ is as defined hereinbefore);
13) $C_{1-5}$alkyl$X^{15}R^{80}$ (wherein $X^{15}$ represents —O—, —S—, —SO—, —$SO_2$—, —$NR^{85}$C(O)—, —C(O)$NR^{86}$—, —$SO_2NR^{87}$—, —$NR^{88}SO_2$— or —$NR^{89}$— (wherein $R^{85}$, $R^{86}$, $R^{87}$, $R^{88}$ and $R^{89}$ each independently represents hydrogen, $C_{1-3}$alkyl or $C_{1-3}$alkoxy$C_{2-3}$alkyl) and $R^{80}$ is as defined hereinbefore);
14) $C_{2-5}$alkenyl$X^{16}R^{80}$ (wherein $X^{16}$ represents —O—, —S—, —SO—, —$SO_2$—, —$NR^{90}$C(O)—, —C(O)$NR^{91}$—, —$SO_2NR^{92}$—, —$NR^{93}SO_2$— or —$NR^{94}$— (wherein $R^{90}$, $R^{91}$, $R^{92}$, $R^{93}$ and $R^{94}$ each independently represents hydrogen, $C_{1-3}$alkyl or $C_{1-3}$alkoxy$C_{2-3}$alkyl) and $R^{80}$ is as defined hereinbefore);
15) $C_{2-5}$alkynyl$X^{17}R^{80}$ (wherein $X^{17}$ represents —O—, —S—, —SO—, —$SO_2$—, —$NR^{95}$C(O)—, —C(O)$NR^{96}$—, —$SO_2NR^{97}$—, —$NR^{98}SO_2$— or —$NR^{99}$— (wherein $R^{95}$, $R^{96}$, $R^{97}$, $R^{98}$ and $R^{99}$ each independently represents hydrogen, $C_{1-3}$alkyl or $C_{1-3}$alkoxy$C_{2-3}$alkyl) and $R^{80}$ is as defined hereinbefore);
16) $C_{1-4}$alkyl$X^{18}C_{1-4}$alkyl$R^{80}$ (wherein $X^{18}$ represents —O—, —S—, —SO—, —$SO_2$—, —$NR^{100}$C(O)—, —C(O)$NR^{101}$—, —$SO_2NR^{102}$—, —$NR^{103}SO_2$— or —$NR^{104}$— (wherein $R^{100}$, $R^{101}$, $R^{102}$, $R^{103}$ and $R^{104}$ each independently represents hydrogen, $C_{1-3}$alkyl or $C_{1-3}$alkoxy$C_{2-3}$alkyl) and $R^{80}$ is as defined hereinbefore);
17) $C_{1-4}$alkyl$X^{18}C_{1-4}$alkyl$R^{79}$ (wherein $X^{18}$ and $R^{79}$ are as defined hereinbefore);
18) $C_{2-5}$alkenyl which may be unsubstituted or which may be substituted with one or more groups selected from hydroxy, fluoro, amino, $C_{1-4}$alkylamino, N,N-di($C_{1-4}$alkyl)amino, aminosulphonyl, N—$C_{1-4}$alkylaminosulphonyl and N,N-di($C_{1-4}$alkyl)aminosulphonyl;
19) $C_{2-5}$alkynyl which may be unsubstituted or which may be substituted with one or more groups selected from hydroxy, fluoro, amino, $C_{1-4}$alkylamino, N,N-di($C_{1-4}$alkyl)amino, aminosulphonyl, N—$C_{1-4}$alkylaminosulphonyl and N,N-di($C_{1-4}$alkyl)aminosulphonyl;
20) $C_{2-5}$alkenyl$X^{18}C_{1-4}$alkyl$R^{79}$ (wherein $X^{18}$ and $R^{79}$ are as defined hereinbefore);
21) $C_{2-5}$alkynyl$X^{18}C_{1-4}$alkyl$R^{79}$ (wherein $X^{18}$ and $R^{79}$ are as defined hereinbefore); and
22) $C_{1-4}$alkyl$R^{105}(C_{1-4}$alkyl$)_x(X^{18})_yR^{106}$ (wherein $X^{18}$ is as defined hereinbefore, x is 0 or 1, y is 0 or 1, and $R^{105}$ and $R^{106}$ are each independently selected from hydrogen, $C_{1-3}$alkyl, cyclopentyl, cyclohexyl and a 5-6-membered saturated heterocyclic group with 1-2 heteroatoms, selected independently from O, S and N, which $C_{1-3}$alkyl group may bear 1 or 2 substituents selected from oxo, hydroxy, halogeno and $C_{1-4}$alkoxy and which cyclic group may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl$C_{1-4}$alkyl, $C_{1-4}$alkoxycarbonyl, $C_{1-4}$aminoalkyl, $C_{1-4}$alkylamino, di($C_{1-4}$alkyl)amino, $C_{1-4}$alkylamino$C_{1-4}$alkyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy and a group —(—O—)$_f(C_{1-4}$alkyl$)_g$ringD (wherein f is 0 or 1, g is 0 or 1 and ring D is a 5-6-membered saturated heterocyclic group with 1-2 heteroatoms, selected independently from O, S and N, which cyclic group may bear one or more substituents selected from $C_{1-4}$alkyl) with the proviso that $R^{105}$ cannot be hydrogen);
and additionally wherein any $C_{1-5}$alkyl, $C_{2-5}$alkenyl or $C_{2-5}$alkynyl group in $R^{56}X^{10}$— may bear one or more substituents selected from hydroxy, halogeno and amino);
or a salt thereof, or a prodrug thereof for example an ester or an amide, in the manufacture of a medicament for use in the production of an antiangiogenic and/or vascular permeability reducing effect in warm-blooded animals such as humans.

According to another aspect of the present invention there is provided the use of compounds of the formula I:

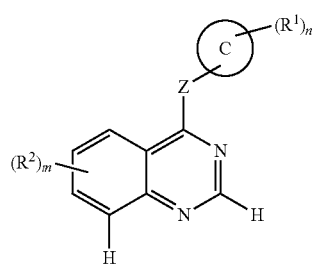

wherein:
ring C is a 9-10-membered bicyclic moiety which may be saturated or unsaturated, which may be aromatic or non-aromatic, and which optionally may contain 1-3 heteroatoms selected independently from O, N and S;
Z is —O—, —NH—, —S—, —CH$_2$— or a direct bond;
$R^1$ represents hydrogen, oxo, halogeno, hydroxy, $C_{1-4}$alkoxy, $C_{1-4}$alkyl, $C_{1-4}$alkoxymethyl, $C_{1-4}$alkanoyl, $C_{1-4}$haloalkyl, cyano, amino, $C_{2-5}$alkenyl, $C_{2-5}$alkynyl, $C_{1-3}$alkanoyloxy, nitro, $C_{1-4}$alkanoylamino, $C_{1-4}$alkoxycarbonyl, $C_{1-4}$alkylsulphanyl, $C_{1-4}$alkylsulphinyl, $C_{1-4}$alkylsulphonyl, carbamoyl, N—$C_{1-4}$alkylcarbamoyl, N,N-di($C_{1-4}$alkyl)carbamoyl, aminosulphonyl, N—$C_{1-4}$alkylaminosulphonyl, N,N-di($C_{1-4}$alkyl)aminosulphonyl, N—($C_{1-4}$alkylsulphonyl)amino, N—($C_{1-4}$alkylsulphonyl)-N—($C_{1-4}$alkyl)amino, N,N-di($C_{1-4}$alkylsulphonyl)amino or a $C_{3-7}$alkylene chain joined to two ring C carbon atoms;
n is an integer from 0 to 5;
m is an integer from 0 to 3;
$R^2$ represents hydrogen, hydroxy, halogeno, cyano, nitro, trifluoromethyl, $C_{1-3}$alkyl, $C_{1-3}$alkoxy, $C_{1-3}$alkylsulphanyl, —NR$^3$R$^4$ (wherein R$^3$ and R$^4$, which may be the same or different, each represents hydrogen or $C_{1-3}$alkyl), or $R^5X^1$— (wherein $X^1$ represents a direct bond, —O—, —CH$_2$—, —OC(O)—, —C(O)—, —S—, —SO—, —SO$_2$—, —NR$^6$C(O)—, —C(O)NR$^7$—, —SO$_2$NR$^8$—, —NR$^9$SO$_2$— or —NR$^{10}$— (wherein R$^6$, R$^7$, R$^8$, R$^9$ and R$^{10}$ each independently represents hydrogen, $C_{1-3}$alkyl or $C_{1-3}$alkoxy$C_{2-3}$alkyl), and R$^5$ is selected from one of the following twenty-one groups:
1) hydrogen or $C_{1-5}$alkyl which may be unsubstituted or which may be substituted with one or more groups selected from hydroxy, fluoro and amino;
2) $C_{1-5}$alkyl$X^2C(O)R^{11}$ (wherein $X^2$ represents —O— or —NR$^{12}$— (in which R$^{12}$ represents hydrogen, $C_{1-3}$alkyl or $C_{1-3}$alkoxy$C_{2-3}$alkyl) and R$^{11}$ represents $C_{1-3}$alkyl, —NR$^{13}$R$^{14}$ or —OR$^{15}$ (wherein R$^{13}$, R$^{14}$ and R$^{15}$ which may be the same or different each represents hydrogen, $C_{1-3}$alkyl or $C_{1-3}$alkoxy$C_{2-3}$alkyl));
3) $C_{1-5}$alkyl$X^3R^{16}$ (wherein $X^3$ represents —O—, —S—, —SO—, —SO$_2$—, —OC(O)—, —NR$^{17}$C(O)—, —C(O)NR$^{18}$—, —SO$_2$NR$^{19}$—, —NR$^{20}$SO$_2$— or —NR$^{21}$— (wherein R$^{17}$, R$^{18}$, R$^{19}$, R$^{20}$ and R$^{21}$ each independently represents hydrogen, $C_{1-3}$alkyl or $C_{1-3}$alkoxy$C_{2-3}$alkyl) and R$^{16}$ represents hydrogen, $C_{1-3}$alkyl, cyclopentyl, cyclohexyl or a 5-6-membered saturated heterocyclic group with 1-2 heteroatoms, selected independently from O, S and N, which $C_{1-3}$alkyl group may bear 1 or 2 substituents selected from oxo, hydroxy, halogeno and $C_{1-4}$alkoxy and which cyclic group may bear 1 or 2 substituents selected from oxo, hydroxy, halogeno, $C_{1-4}$alkyl, $C_{1-4}$hydroxyalkyl and $C_{1-4}$alkoxy);
4) $C_{1-5}$alkyl$X^4C_{1-5}$alkyl$X^5R^{22}$ (wherein $X^4$ and $X^5$ which may be the same or different are each —O—, —S—, —SO—, —SO$_2$—, —NR$^{23}$C(O)—, —C(O)NR$^{24}$—, —SO$_2$NR$^{25}$—, —NR$^{26}$SO$_2$— or —NR$^{27}$— (wherein R$^{23}$, R$^{24}$, R$^{25}$, R$^{26}$ and R$^{27}$ each independently represents hydrogen, $C_{1-3}$alkyl or $C_{1-3}$alkoxy$C_{2-3}$alkyl) and R$^{22}$ represents hydrogen or $C_{1-3}$alkyl);
5) R$^{28}$ (wherein R$^{28}$ is a 5-6-membered saturated heterocyclic group (linked via carbon or nitrogen) with 1-2 heteroatoms, selected independently from O, S and N, which heterocyclic group may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl and $C_{1-4}$alkylsulphonyl$C_{1-4}$alkyl);
6) $C_{1-5}$alkylR$^{28}$ (wherein R$^{28}$ is as defined hereinbefore);
7) $C_{2-5}$alkenylR$^{28}$ (wherein R$^{28}$ is as defined hereinbefore);
8) $C_{2-5}$alkynylR$^{28}$ wherein R$^{28}$ is as defined hereinbefore);

9) $R^{29}$ (wherein $R^{29}$ represents a pyridone group, a phenyl group or a 5-6-membered aromatic heterocyclic group (linked via carbon or nitrogen) with 1-3 heteroatoms selected from O, N and S, which pyridone, phenyl or aromatic heterocyclic group may carry up to 5 substituents on an available carbon atom selected from hydroxy, halogeno, amino, $C_{1-4}$alkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, trifluoromethyl, cyano, —C(O)$NR^{30}R^{31}$ and —$NR^{32}$C(O)$R^{33}$ (wherein $R^{30}$, $R^{31}$, $R^{32}$ and $R^{33}$, which may be the same or different, each represents hydrogen, $C_{1-4}$alkyl or $C_{1-3}$alkoxy$C_{2-3}$alkyl));

10) $C_{1-5}$alkyl$R^{29}$ (wherein $R^{29}$ is as defined hereinbefore);

11) $C_{2-5}$alkenyl$R^{29}$ (wherein $R^{29}$ is as defined hereinbefore);

12) $C_{2-5}$alkynyl$R^{29}$ (wherein $R^{29}$ is as defined hereinbefore);

13) $C_{1-5}$alkyl$X^6R^{29}$ (wherein $X^6$ represents —O—, —S—, —SO—, —$SO_2$—, —$NR^{34}$C(O)—, —C(O)$NR^{35}$—, —$SO_2NR^{36}$—, —$NR^{37}SO_2$— or —$NR^{38}$— (wherein $R^{34}$, $R^{35}$, $R^{36}$, $R^{37}$ and $R^{38}$ each independently represents hydrogen, $C_{1-3}$alkyl or $C_{1-3}$alkoxy$C_{2-3}$alkyl) and $R^{29}$ is as defined hereinbefore);

14) $C_{2-5}$alkenyl$X^7R^{29}$ (wherein $X^7$ represents —O—, —S—, —SO—, —$SO_2$—, —$NR^{39}$C(O)—, —C(O)$NR^{40}$—, —$SO_2NR^{41}$—, —$NR^{42}SO_2$— or —$NR^{43}$— (wherein $R^{39}$, $R^{40}$, $R^{41}$, $R^{42}$ and $R^{43}$ each independently represents hydrogen, $C_{1-3}$alkyl or $C_{1-3}$alkoxy$C_{2-3}$alkyl) and $R^{29}$ is as defined hereinbefore);

15) $C_{2-5}$alkynyl$X^8R^{29}$ (wherein $X^8$ represents —O—, —S—, —SO—, —$SO_2$—, —$NR^{44}$C(O)—, —C(O)$NR^{45}$—, —$SO_2NR^{46}$—, —$NR^{47}SO_2$— or —$NR^{48}$— (wherein $R^{44}$, $R^{45}$, $R^{46}$, $R^{47}$ and $R^{48}$ each independently represents hydrogen, $C_{1-3}$alkyl or $C_{1-3}$alkoxy$C_{2-3}$alkyl) and $R^{29}$ is as defined hereinbefore);

16) $C_{1-3}$alkyl$X^9C_{1-3}$alkyl$R^{29}$ (wherein $X^9$ represents —O—, —S—, —SO—, —$SO_2$—, —$NR^{49}$C(O)—, —C(O)$NR^{50}$—, —$SO_2NR^{51}$—, —$NR^{52}SO_2$— or —$NR^{53}$— (wherein $R^{49}$, $R^{50}$, $R^{51}$, $R^{52}$ and $R^{53}$ each independently represents hydrogen, $C_{1-3}$alkyl or $C_{1-3}$alkoxy$C_{2-3}$alkyl) and $R^{29}$ is as defined hereinbefore);

17) $C_{1-3}$alkyl$X^9C_{1-3}$alkyl$R^{28}$ (wherein $X^9$ and $R^{28}$ are as defined hereinbefore);

18) $C_{2-5}$alkenyl which may be unsubstituted or which may be substituted with one or more groups selected from hydroxy, fluoro, amino, $C_{1-4}$alkylamino, N,N-di($C_{1-4}$alkyl)amino, aminosulphonyl, N—$C_{1-4}$alkylaminosulphonyl and N,N-di($C_{1-4}$alkyl)aminosulphonyl;

19) $C_{2-5}$alkynyl which may be unsubstituted or which may be substituted with one or more groups selected from hydroxy, fluoro, amino, $C_{1-4}$alkylamino, N,N-di($C_{1-4}$alkyl)amino, aminosulphonyl, N—$C_{1-4}$alkylaminosulphonyl and N,N-di($C_{1-4}$alkyl)aminosulphonyl;

20) $C_{2-5}$alkenyl$X^9C_{1-4}$alkyl$R^{28}$ (wherein $X^9$ and $R^{28}$ are as defined hereinbefore); and 21) $C_{2-5}$alkynyl$X^9C_{1-4}$alkyl$R^{28}$ (wherein $X^9$ and $R^{28}$ are as defined hereinbefore);

and salts thereof, and prodrugs thereof for example esters, amides and sulphides, in the manufacture of a medicament for use in the production of an antiangiogenic and/or vascular permeability reducing effect in warm-blooded animals such as humans.

Preferably ring C is a 9-10-membered aromatic bicyclic moiety which may optionally contain 1-3 heteroatoms selected independently from O, N and S.

More preferably ring C is a 9-10-membered heteroaromatic bicyclic moiety which contains 1-3 heteroatoms selected independently from O, N and S.

Particularly ring C is a 9-10-membered heteroaromatic bicyclic moiety which contains 1 or 2 nitrogen atoms.

According to one aspect of the present invention ring C is a 9-membered heteroaromatic bicyclic moiety which contains 1 or 2 nitrogen atoms, for example indolyl.

According to another aspect of the present invention ring C is a 10-membered heteroaromatic bicyclic moiety which contains 1 or 2 nitrogen atoms, for example quinolinyl.

Especially ring C is indolyl or quinolinyl.

Preferably Z is —O—, —NH—, —S— or a direct bond.

More preferably Z is —O—, —NH— or —S—.

Particularly Z is —O— or —S—, especially —O—.

Advantageously $X^{10}$ represents a direct bond, —O—, —S—, —$NR^{57}$C(O)—, —$NR^{60}SO_2$— or —$NR^{61}$— (wherein $R^{57}$, $R^{60}$ and $R^{61}$ each independently represents hydrogen, $C_{1-2}$alkyl or $C_{1-2}$alkoxyethyl).

Preferably $X^{10}$ represents a direct bond, —O—, —S—, —$NR^{57}$C(O)—, —$NR^{60}SO_2$— (wherein $R^{57}$ and $R^{60}$ each independently represents hydrogen or $C_{1-2}$alkyl) or NH.

More preferably $X^{10}$ represents —O—, —S—, —$NR^{57}$C(O)— (wherein $R^{57}$ represents hydrogen or $C_{1-2}$alkyl) or NH.

Particularly $X^{10}$ represents —O— or —$NR^{57}$C(O)— (wherein $R^{57}$ represents hydrogen or $C_{1-2}$alkyl), more particularly —O— or —NHC(O)—, especially —O—.

According to another aspect of the present invention $X^{10}$ represents —O— or a direct bond.

Advantageously $X^{12}$ represents —O—, —S—, —SO—, —$SO_2$—, —$NR^{68}$C(O)—, —$NR^{71}SO_2$— or —$NR^{72}$— (wherein $R^{68}$, $R^{71}$ and $R^{72}$ each independently represents hydrogen, $C_{1-2}$alkyl or $C_{1-2}$alkoxyethyl).

Preferably $X^{12}$ represents —O—, —S—, —SO—, —$SO_2$— or —$NR^{72}$— (wherein $R^{72}$ represents hydrogen, $C_{1-2}$alkyl or $C_{1-2}$alkoxyethyl).

More preferably $X^{12}$ represents —O— or —$NR^{72}$— (wherein $R^{72}$ represents hydrogen or $C_{1-2}$alkyl).

According to another aspect of the present invention $X^{12}$ represents —O—, —$SO_2$—, —$NR^{71}SO_2$— or —$NR^{72}$— (wherein $R^{71}$ and $R^{72}$ each independently represents hydrogen, $C_{1-2}$alkyl or $C_{1-2}$alkoxyethyl).

Advantageously $X^{18}$ represents —O—, —S— or —$NR^{104}$— (wherein $R^{104}$ represents hydrogen, $C_{1-2}$alkyl or $C_{1-2}$alkoxyethyl).

Preferably $X^{18}$ represents —O— or —$NR^{104}$— (wherein $R^{104}$ represents hydrogen or $C_{1-2}$alkyl).

According to another aspect of the present invention $X^{18}$ represents —O—, —$CONR^{101}$— or —$NR^{104}$— (wherein $R^{101}$ and $R^{104}$ each independently represents hydrogen or $C_{1-2}$alkyl).

Advantageously $R^{67}$ represents a 5-6-membered saturated heterocyclic group with 1-2 heteroatoms, selected independently from O, S and N, which cyclic group may bear 1 or 2 substituents selected from oxo, hydroxy, halogeno, cyano, $C_{1-3}$cyanoalkyl, $C_{1-3}$alkyl, $C_{1-3}$hydroxyalkyl, $C_{1-3}$alkoxy, $C_{1-2}$alkoxy$C_{1-3}$alkyl, $C_{1-2}$alkylsulphonyl$C_{1-3}$alkyl, $C_{1-3}$alkoxycarbonyl, $C_{1-3}$alkylamino, di($C_{1-3}$alkyl)amino, $C_{1-3}$alkylamino$C_{1-3}$alkyl, di($C_{1-3}$alkyl)amino$C_{1-3}$alkyl, $C_{1-3}$alkylamino$C_{1-3}$alkoxy, di($C_{1-3}$alkyl)amino$C_{1-3}$alkoxy and a group —(—O—)$_f$($C_{1-3}$alkyl)$_g$ringD (wherein f is 0 or 1, g is 0 or 1 and ring D is a 5-6-membered saturated heterocyclic group with 1-2 heteroatoms, selected independently from O, S and N, which cyclic group may bear one or more substituents selected from $C_{1-3}$alkyl).

Preferably $R^{67}$ is pyrrolidinyl, piperazinyl, piperidinyl, imidazolidinyl, azetidinyl, morpholino or thiomorpholino which group may bear 1 or 2 substituents selected from oxo, hydroxy, halogeno, cyano, $C_{1-3}$cyanoalkyl, $C_{1-3}$alkyl, $C_{1-3}$hydroxyalkyl, $C_{1-3}$alkoxy, $C_{1-2}$alkoxy$C_{1-3}$alkyl, $C_{1-2}$alkylsulphonyl$C_{1-3}$alkyl, $C_{1-3}$alkoxycarbonyl, $C_{1-3}$alkylamino, di($C_{1-3}$alkyl)amino, $C_{1-3}$alkylamino$C_{1-3}$alkyl, di($C_{1-3}$alkyl)amino$C_{1-3}$alkyl, $C_{1-3}$alkylamino$C_{1-3}$alkoxy, di($C_{1-3}$alkyl)amino$C_{1-3}$alkoxy and a group —(—O—)$_f$—($C_{1-3}$alkyl)$_g$ringD (wherein f is 0 or 1, g is 0 or 1 and ring D is a heterocyclic group selected from pyrrolidinyl, piperazinyl, piperidinyl, imidazolidinyl, azetidinyl, morpholino and thiomorpholino, which cyclic group may bear one or more substituents selected from $C_{1-3}$alkyl).

More preferably $R^{67}$ is pyrrolidinyl, piperazinyl, piperidinyl, azetidinyl, morpholino or thiomorpholino which group may bear 1 or 2 substituents selected from oxo, hydroxy, halogeno, cyano, $C_{1-3}$cyanoalkyl, $C_{1-3}$alkyl, $C_{1-3}$hydroxyalkyl, $C_{1-3}$alkoxy, $C_{1-2}$alkoxy$C_{1-3}$alkyl, $C_{1-2}$alkylsulphonyl$C_{1-3}$alkyl, $C_{1-3}$alkoxycarbonyl, $C_{1-3}$alkylamino, di($C_{1-3}$alkyl)amino, $C_{1-3}$alkylamino$C_{1-3}$alkyl, di($C_{1-3}$alkyl)amino$C_{1-3}$alkyl, $C_{1-3}$alkylamino$C_{1-3}$alkoxy, di($C_{1-3}$alkyl)amino$C_{1-3}$alkoxy and a group —(—O—)$_f$($C_{1-3}$alkyl)$_g$ringD (wherein f is 0 or 1, g is 0 or 1 and ring D is a heterocyclic group selected from pyrrolidinyl, methylpiperazinyl, piperidinyl, azetidinyl, morpholino and thiomorpholino).

Particularly $R^{67}$ is pyrrolidinyl, piperazinyl, piperidinyl, azetidinyl, morpholino or thiomorpholino which group may bear 1 or 2 substituents selected from a group —(—O—)$_f$—($C_{1-3}$alkyl)$_g$ringD (wherein f is 0 or 1, g is 0 or 1 and ring D is a heterocyclic group selected from pyrrolidinyl, methylpiperazinyl, piperidinyl, azetidinyl, morpholino and thiomorpholino).

Preferably $R^{79}$ is pyrrolidinyl, piperazinyl, piperidinyl, imidazolidinyl, azetidinyl, morpholino or thiomorpholino which group may bear 1 or 2 substituents selected from oxo, hydroxy, halogeno, cyano, $C_{1-3}$cyanoalkyl, $C_{1-3}$alkyl, $C_{1-3}$hydroxyalkyl, $C_{1-3}$alkoxy, $C_{1-2}$alkoxy$C_{1-3}$alkyl, $C_{1-2}$alkylsulphonyl$C_{1-3}$alkyl, $C_{1-3}$alkoxycarbonyl, $C_{1-3}$alkylamino, di($C_{1-3}$alkyl)amino, $C_{1-3}$alkylamino$C_{1-3}$alkyl, di($C_{1-3}$alkyl)amino$C_{1-3}$alkyl, $C_{1-3}$alkylamino$C_{1-3}$alkoxy, di($C_{1-3}$alkyl)amino$C_{1-3}$alkoxy and a group —(—O—)$_f$—($C_{1-3}$alkyl)$_g$ringD (wherein f is 0 or 1, g is 0 or 1 and ring D is a heterocyclic group selected from pyrrolidinyl, piperazinyl, piperidinyl, imidazolidinyl, azetidinyl, morpholino and thiomorpholino, which cyclic group may bear one or more substituents selected from $C_{1-3}$alkyl).

More preferably $R^{79}$ is pyrrolidinyl, piperazinyl, piperidinyl, azetidinyl, morpholino or thiomorpholino which group may bear 1 or 2 substituents selected from oxo, hydroxy, halogeno, cyano, $C_{1-3}$cyanoalkyl, $C_{1-3}$alkyl, $C_{1-3}$hydroxyalkyl, $C_{1-3}$alkoxy, $C_{1-2}$alkoxy$C_{1-3}$alkyl, $C_{1-2}$alkylsulphonyl$C_{1-3}$alkyl, $C_{1-3}$alkoxycarbonyl, $C_{1-3}$alkylamino, di($C_{1-3}$alkyl)amino, $C_{1-3}$alkylamino$C_{1-3}$alkyl, di($C_{1-3}$alkyl)amino$C_{1-3}$alkyl, $C_{1-3}$alkylamino$C_{1-3}$alkoxy, di($C_{1-3}$alkyl)amino$C_{1-3}$alkoxy and a group —(—O—)$_f$($C_{1-3}$alkyl)$_g$ringD (wherein f is 0 or 1, g is 0 or 1 and ring D is a heterocyclic group selected from pyrrolidinyl, methylpiperazinyl, piperidinyl, azetidinyl, morpholino and thiomorpholino).

Particularly $R^{79}$ is pyrrolidinyl, piperazinyl, piperidinyl, azetidinyl, morpholino or thiomorpholino which group may bear 1 or 2 substituents selected from a group —(—O—)$_f$—($C_{1-3}$alkyl)$_g$ringD (wherein f is 0 or 1, g is 0 or 1 and ring D is a heterocyclic group selected from pyrrolidinyl, methylpiperazinyl, piperidinyl, azetidinyl, morpholino and thiomorpholino).

Advantageously $R^{105}$ and $R^{106}$ are each independently a 5-6-membered saturated heterocyclic group with 1-2 heteroatoms, selected independently from O, S and N, which cyclic group may bear 1 or 2 substituents selected from oxo, hydroxy, halogeno, cyano, $C_{1-3}$cyanoalkyl, $C_{1-3}$alkyl, $C_{1-3}$hydroxyalkyl, $C_{1-3}$alkoxy, $C_{1-2}$alkoxy$C_{1-3}$alkyl, $C_{1-2}$alkylsulphonyl$C_{1-3}$alkyl, $C_{1-3}$alkoxycarbonyl, $C_{1-3}$alkylamino, di($C_{1-3}$alkyl)amino, $C_{1-3}$alkylamino$C_{1-3}$alkyl, di($C_{1-3}$alkyl)amino$C_{1-3}$alkyl, $C_{1-3}$alkylamino$C_{1-3}$alkoxy, di($C_{1-3}$alkyl)amino$C_{1-3}$alkoxy and a group —(—O—)$_f$—($C_{1-3}$alkyl)$_g$ringD (wherein f is 0 or 1, g is 0 or 1 and ring D is a 5-6-membered saturated heterocyclic group with 1-2 heteroatoms, selected independently from O, S and N, which cyclic group may bear one or more substituents selected from $C_{1-3}$alkyl).

Preferably $R^{105}$ and $R^{106}$ are each independently selected from pyrrolidinyl, piperazinyl, piperidinyl, imidazolidinyl, azetidinyl, morpholino and thiomorpholino which group may bear 1 or 2 substituents selected from oxo, hydroxy, halogeno, cyano, $C_{1-3}$cyanoalkyl, $C_{1-3}$alkyl, $C_{1-3}$hydroxyalkyl, $C_{1-3}$alkoxy, $C_{1-2}$alkoxy$C_{1-3}$alkyl, $C_{1-2}$alkylsulphonyl $C_{1-3}$alkyl, $C_{1-3}$alkoxycarbonyl, $C_{1-3}$alkylamino, di($C_{1-3}$alkyl)amino, $C_{1-3}$alkylamino$C_{1-3}$alkyl, di($C_{1-3}$alkyl)amino$C_{1-3}$alkyl, $C_{1-3}$alkylamino$C_{1-3}$alkoxy, di($C_{1-3}$alkyl)amino$C_{1-3}$alkoxy and a group —(—O—)$_f$($C_{1-3}$alkyl)$_g$ringD (wherein f is 0 or 1, g is 0 or 1 and ring D is a heterocyclic group selected from pyrrolidinyl, piperazinyl, piperidinyl, imidazolidinyl, azetidinyl, morpholino and thiomorpholino, which cyclic group may bear one or more substituents selected from $C_{1-3}$alkyl).

More preferably $R^{105}$ and $R^{106}$ are each independently selected from pyrrolidinyl, piperazinyl, piperidinyl, azetidinyl, morpholino and thiomorpholino which group may bear 1 or 2 substituents selected from oxo, hydroxy, halogeno, cyano, $C_{1-3}$cyanoalkyl, $C_{1-3}$alkyl, $C_{1-3}$hydroxyalkyl, $C_{1-3}$alkoxy, $C_{1-2}$alkoxy$C_{1-3}$alkyl, $C_{1-2}$alkylsulphonyl $C_{1-3}$alkyl, $C_{1-3}$alkoxycarbonyl, $C_{1-3}$alkylamino, di($C_{1-3}$alkyl)amino, $C_{1-3}$alkylamino$C_{1-3}$alkyl, di($C_{1-3}$alkyl)amino$C_{1-3}$alkyl, $C_{1-3}$alkylamino$C_{1-3}$alkoxy, di($C_{1-3}$alkyl)amino$C_{1-3}$alkoxy and a group —(—O—)$_f$($C_{1-3}$alkyl)$_g$ringD (wherein f is 0 or 1, g is 0 or 1 and ring D is a heterocyclic group selected from pyrrolidinyl, methylpiperazinyl, piperidinyl, azetidinyl, morpholino and thiomorpholino).

Particularly $R^{105}$ and $R^{106}$ are each independently selected from pyrrolidinyl, piperazinyl, piperidinyl, azetidinyl, morpholino and thiomorpholino which group may bear 1 or 2 substituents selected from a group —(—O—)$_f$—($C_{1-3}$alkyl)$_g$ringD (wherein f is 0 or 1, g is 0 or 1 and ring D is a heterocyclic group selected from pyrrolidinyl, methylpiperazinyl, piperidinyl, azetidinyl, morpholino and thiomorpholino).

Advantageously $R^1$ represents oxo, halogeno, hydroxy, $C_{1-4}$alkoxy, $C_{1-4}$alkyl, $C_{1-4}$alkoxymethyl, $C_{1-4}$alkanoyl, $C_{1-4}$haloalkyl, cyano, amino, $C_{2-5}$alkenyl, $C_{2-5}$alkynyl, $C_{1-3}$alkanoyloxy, nitro, $C_{1-4}$alkanoylamino, $C_{1-4}$alkoxycarbonyl, $C_{1-4}$alkylsulphanyl, $C_{1-4}$alkylsulphinyl, $C_{1-4}$alkylsulphonyl, carbamoyl, N—$C_{1-4}$alkylcarbamoyl, N,N-di($C_{1-4}$alkyl)carbamoyl, aminosulphonyl, N—$C_{1-4}$alkylaminosulphonyl, N,N-di($C_{1-4}$alkyl)aminosulphonyl, N—($C_{1-4}$alkylsulphonyl)amino, N—($C_{1-4}$alkylsulphonyl)-N—($C_{1-4}$alkyl)amino, N,N-di($C_{1-4}$alkylsulphonyl)amino, a $C_{3-7}$alkylene chain joined to two ring C carbon atoms, $C_{1-4}$alkanoylamino$C_{1-4}$alkyl, carboxy or a group $R^{56}X^{10}$ (wherein $X^{10}$ is as defined hereinbefore and $R^{56}$ is selected from one of the following nine groups:

1) $C_{1-5}$alkyl$X^{12}R^{67}$ (wherein $X^{12}$ and $R^{67}$ are as defined hereinbefore);
2) $R^{79}$ (wherein $R^{79}$ is as defined hereinbefore);
3) $C_{1-5}$alkyl$R^{79}$ (wherein $R^{79}$ is as defined hereinbefore);
4) $C_{2-5}$alkenyl$R^{79}$ (wherein $R^{79}$ is as defined hereinbefore);
5) $C_{2-5}$alkynyl$R^{79}$ (wherein $R^{79}$ is as defined hereinbefore);
6) $C_{1-3}$alkyl$X^{18}C_{1-3}$alkyl$R^{79}$ (wherein $X^{18}$ and $R^{79}$ are as defined hereinbefore);

7) $C_{2-5}$alkenyl$X^{18}C_{1-4}$alkyl$R^{79}$ (wherein $X^{18}$ and $R^{79}$ are as defined hereinbefore);
8) $C_{2-5}$alkynyl$X^{18}C_{1-4}$alkyl$R^{79}$ (wherein $X^{18}$ and $R^{79}$ are as defined hereinbefore); and
9) $C_{1-3}$alkyl$R^{105}(C_{1-3}$alkyl$)_x(X^{18})_yR^{106}$ (wherein $X^{18}$, x, y, $R^{105}$ and $R^{106}$ are as defined hereinbefore;
and additionally wherein any $C_{1-5}$alkyl, $C_{2-5}$alkenyl or $C_{2-5}$alkynyl group in $R^{56}X^{10}$— may bear one or more substituents selected from hydroxy, halogeno and amino, with the proviso that when $X^{10}$ is a direct bond $R^{56}$ is not $R^{79}$).

Preferably $R^1$ represents oxo, halogeno, hydroxy, $C_{1-2}$alkoxy, $C_{1-2}$alkyl, $C_{1-2}$alkoxymethyl, $C_{2-3}$alkanoyl, $C_{1-2}$haloalkyl, cyano, amino, $C_{2-4}$alkenyl, $C_{2-4}$alkynyl, $C_{2-3}$alkanoyloxy, nitro, $C_{1-3}$alkanoylamino, $C_{1-2}$alkoxycarbonyl, $C_{1-2}$alkylsulphanyl, $C_{1-2}$alkylsulphinyl, $C_{1-2}$alkylsulphonyl, carbamoyl, N—$C_{1-2}$alkylcarbamoyl, N,N-di($C_{1-2}$alkyl)carbamoyl, aminosulphonyl, N—$C_{1-2}$alkylaminosulphonyl, N,N-di($C_{1-2}$alkyl)aminosulphonyl, N—($C_{1-2}$alkylsulphonyl)amino, N—($C_{1-2}$alkylsulphonyl)-N—($C_{1-2}$alkyl)amino or a $C_{3-7}$alkylene chain joined to two ring C carbon atoms.

More preferably $R^1$ represents oxo, hydroxy, $C_{1-2}$alkoxymethyl, amino, halogeno, $C_{1-2}$alkyl, $C_{1-2}$alkoxy, trifluoromethyl, cyano, nitro, $C_{2-3}$alkanoyl.

Particularly $R^1$ represents methyl, ethyl, trifluoromethyl or halogeno.

Especially $R^1$ represents methyl, fluoro, chloro or bromo, more especially methyl or fluoro.

Preferably n is an integer from 0 to 3.

More preferably n is 0, 1 or 2.

Preferably m is an integer from 0 to 2, more preferably 1 or 2, most preferably 2.

Advantageously $X^1$ represents a direct bond, —O—, —S—, —NR$^6$C(O)—, —NR$^9$SO$_2$— or —NR$^{10}$— (wherein $R^6$, $R^9$ and $R^{10}$ each independently represents hydrogen, $C_{1-2}$alkyl or $C_{1-2}$alkoxyethyl).

Preferably $X^1$ represents a direct bond, —O—, —S—, —NR$^6$C(O)—, —NR$^9$SO$_2$— (wherein $R^6$ and $R^9$ each independently represents hydrogen or $C_{1-2}$alkyl) or NH.

More preferably $X^1$ represents —O—, —S—, —NR$^6$C(O)— (wherein $R^6$ represents hydrogen or $C_{1-2}$alkyl) or NH.

Particularly $X^1$ represents —O— or —NR$^6$C(O)— (wherein $R^6$ represents hydrogen or $C_{1-2}$alkyl), more particularly —O— or —NHC(O)—, especially —O—.

According to another aspect of the present invention $X^1$ represents —O— or a direct bond.

Advantageously $X^2$ represents —O— or NR$^{12}$ (wherein $R^{12}$ represents hydrogen, $C_{1-3}$alkyl or $C_{1-2}$alkoxyethyl).

Advantageously $X^3$ represents —O—, —S—, —SO—, —SO$_2$—, —NR$^{17}$C(O)—, —NR$^{20}$SO$_2$— or —NR$^{21}$— (wherein $R^{17}$, $R^{20}$ and $R^{21}$ each independently represents hydrogen, $C_{1-2}$alkyl or $C_{1-2}$alkoxyethyl).

Preferably $X^3$ represents —O—, —S—, —SO—, —SO$_2$— or —NR$^{21}$— (wherein $R^{21}$ represents hydrogen, $C_{1-2}$alkyl or $C_{1-2}$alkoxyethyl).

More preferably $X^3$ represents —O— or —NR$^{21}$— (wherein $R^{21}$ represents hydrogen or $C_{1-2}$alkyl).

According to another aspect of the present invention $X^3$ represents —O—, —SO$_2$—, —NR$^{20}$SO$_2$— or —NR$^{21}$— (wherein $R^{20}$ and $R^{21}$ each independently represents hydrogen, $C_{1-2}$alkyl or $C_{1-2}$alkoxyethyl).

Advantageously $X^4$ and $X^5$ which may be the same or different each represents —O—, —S—, —SO—, —SO$_2$— or —NR$^{27}$— (wherein $R^{27}$ represents hydrogen, $C_{1-3}$alkyl or $C_{1-2}$alkoxyethyl).

Preferably $X^4$ and $X^5$ which may be the same or different each represents —O—, —S— or —NR$^{27}$— (wherein $R^{27}$ represents hydrogen, $C_{1-2}$alkyl or $C_{1-2}$alkoxyethyl).

More preferably $X^4$ and $X^5$ which may be the same or different each represents —O— or —NH—.

Advantageously $X^6$ represents —O—, —S— or —NR$^{38}$— (wherein $R^{38}$ represents hydrogen, $C_{1-2}$ alkyl or $C_{1-2}$alkoxyethyl).

Preferably $X^6$ represents —O— or —NR$^{38}$— (wherein $R^{38}$ represents hydrogen or $C_{1-2}$alkyl).

Advantageously $X^7$ represents —O—, —S— or —NR$^{43}$— (wherein $R^{43}$ represents hydrogen, $C_{1-2}$alkyl or $C_{1-2}$alkoxyethyl).

Preferably $X^7$ represents —O— or —NR$^{43}$— (wherein $R^{43}$ represents hydrogen or $C_{1-2}$alkyl).

Advantageously $X^8$ represents —O—, —S— or —NR$^{48}$— (wherein $R^{48}$ represents hydrogen, $C_{1-2}$alkyl or $C_{1-2}$alkoxyethyl).

Preferably $X^8$ represents —O— or —NR$^{48}$— (wherein $R^{48}$ represents hydrogen or $C_{1-2}$alkyl).

Advantageously $X^9$ represents —O—, —S— or —NR$^{53}$— (wherein $R^{53}$ represents hydrogen, $C_{1-2}$alkyl or $C_{1-2}$alkoxyethyl).

Preferably $X^9$ represents —O— or —NR$^{53}$— (wherein $R^{53}$ represents hydrogen or $C_{1-2}$alkyl).

According to another aspect of the present invention $X^9$ represents —O—, —CONR$^{50}$— or —NR$^{53}$— (wherein $R^{50}$ and $R^{53}$ each independently represents hydrogen or $C_{1-2}$alkyl).

Conveniently $R^{28}$ is pyrrolidinyl, piperazinyl, piperidinyl, imidazolidinyl, azetidinyl, morpholino or thiomorpholino which group may bear 1 or 2 substituents selected from oxo, hydroxy, halogeno, cyano, $C_{1-3}$cyanoalkyl, $C_{1-3}$alkyl, $C_{1-3}$hydroxyalkyl, $C_{1-3}$alkoxy, $C_{1-2}$alkoxy$C_{1-3}$alkyl, $C_{1-2}$alkylsulphonyl$C_{1-3}$alkyl, $C_{1-3}$alkoxycarbonyl, $C_{1-3}$alkylamino, di($C_{1-3}$alkyl)amino, $C_{1-3}$alkylamino$C_{1-3}$alkyl, di($C_{1-3}$alkyl)amino$C_{1-3}$alkyl, $C_{1-3}$alkylamino$C_{1-3}$alkoxy, di($C_{1-3}$alkyl)amino$C_{1-3}$alkoxy and a group —(—O—)$_f$(C$_{1-3}$alkyl)$_g$ringD (wherein f is 0 or 1, g is 0 or 1 and ring D is a heterocyclic group selected from pyrrolidinyl, piperazinyl, piperidinyl, imidazolidinyl, azetidinyl, morpholino and thiomorpholino, which cyclic group may bear one or more substituents selected from $C_{1-3}$alkyl).

Advantageously $R^{28}$ is pyrrolidinyl, piperazinyl, piperidinyl, azetidinyl, morpholino or thiomorpholino which group may bear 1 or 2 substituents selected from oxo, hydroxy, halogeno, cyano, $C_{1-3}$cyanoalkyl, $C_{1-3}$alkyl, $C_{1-3}$hydroxyalkyl, $C_{1-3}$alkoxy, $C_{1-2}$alkoxy$C_{1-3}$alkyl, $C_{1-2}$alkylsulphonyl$C_{1-3}$alkyl, $C_{1-3}$alkoxycarbonyl, $C_{1-3}$alkylamino, di($C_{1-3}$alkyl)amino, $C_{1-3}$alkylamino$C_{1-3}$alkyl, di($C_{1-3}$alkyl)amino$C_{1-3}$alkyl, $C_{1-3}$alkylamino$C_{1-3}$alkoxy, di($C_{1-3}$alkyl)amino$C_{1-3}$alkoxy and a group —(—O—)$_f$(C$_{1-3}$alkyl)$_g$ringD (wherein f is 0 or 1, g is 0 or 1 and ring D is a heterocyclic group selected from pyrrolidinyl, methylpiperazinyl, piperidinyl, azetidinyl, morpholino and thiomorpholino).

In one embodiment of the present invention $R^{28}$ is pyrrolidinyl, piperazinyl, piperidinyl, azetidinyl, morpholino or thiomorpholino which group may bear 1 or 2 substituents selected from a group —(—O—)$_f$(C$_{1-3}$alkyl)$_g$ringD (wherein f is 0 or 1, g is 0 or 1 and ring D is a heterocyclic group selected from pyrrolidinyl, methylpiperazinyl, piperidinyl, azetidinyl, morpholino and thiomorpholino).

Particularly $R^{28}$ is pyrrolidinyl, piperazinyl, piperidinyl, azetidinyl, morpholino or thiomorpholino which group may bear 1 or 2 substituents selected from oxo, hydroxy, halogeno, cyano, $C_{1-3}$cyanoalkyl, $C_{1-3}$alkyl, $C_{1-3}$hydroxyalkyl, $C_{1-3}$alkoxy, $C_{1-2}$alkoxy$C_{1-3}$alkyl and $C_{1-2}$alkylsulphonyl $C_{1-3}$alkyl.

According to another aspect of the present invention, preferably $R^{28}$ is pyrrolidinyl, piperazinyl, piperidinyl, morpholino or thiomorpholino which group may bear 1 or 2 substituents selected from oxo, hydroxy, halogeno, cyano, $C_{1-3}$cyanoalkyl, $C_{1-3}$alkyl, $C_{1-3}$hydroxyalkyl, $C_{1-3}$alkoxy, $C_{1-2}$alkoxy$C_{1-3}$alkyl and $C_{1-2}$alkylsulphonyl$C_{1-3}$alkyl.

Where $R^{29}$ is a 5-6-membered aromatic heterocyclic group, it preferably has 1 or 2 heteroatoms, selected from O, N and S, of which more preferably one is N, and may be substituted as hereinbefore defined.

$R^{29}$ is particularly a pyridone, phenyl, pyridyl, imidazolyl, thiazolyl, thienyl, triazolyl or pyridazinyl group which group may be substituted as hereinbefore defined, more particularly a pyridone, pyridyl, imidazolyl, thiazolyl or triazolyl group, especially a pyridone, pyridyl, imidazolyl or triazolyl group which group may be substituted as hereinbefore defined.

In one embodiment of the invention $R^{29}$ represents a pyridone, phenyl or 5-6-membered aromatic heterocyclic group with 1 to 3 heteroatoms selected from O, N and S, which group may preferably carry up to 2 substituents, more preferably up to one substituent, selected from the group of substituents as hereinbefore defined.

In the definition of $R^{29}$, conveniently substituents are selected from halogeno, $C_{1-4}$alkyl, $C_{1-4}$alkoxy, cyano and a group —(—O—)$_f$($C_{1-3}$alkyl)$_g$ringD (wherein f is 0 or 1, g is 0 or 1 and ring D is a heterocyclic group selected from pyrrolidinyl, piperazinyl, piperidinyl, imidazolidinyl, azetidinyl, morpholino and thiomorpholino, which cyclic group may bear one or more substituents selected from $C_{1-3}$alkyl).

In the definition of $R^{29}$, more conveniently substituents are selected from chloro, fluoro, methyl, ethyl and a group —(—O—)$_f$($C_{1-3}$alkyl)$_g$ringD (wherein f is 0 or 1, g is 0 or 1 and ring D is a heterocyclic group selected from pyrrolidinyl, methylpiperazinyl, piperidinyl, azetidinyl, morpholino and thiomorpholino).

According to another emodiment of the present invention in the definition of $R^{29}$, conveniently substituents are selected from halogeno, $C_{1-4}$alkyl, $C_{1-4}$alkoxy and cyano, more conveniently substituents are selected from chloro, fluoro, methyl and ethyl. Advantageously $R^{54}$ and $R^{55}$ are each independently a 5-6-membered saturated heterocyclic group with 1-2 heteroatoms, selected independently from O, S and N, which cyclic group may bear 1 or 2 substituents selected from oxo, hydroxy, halogeno, cyano, $C_{1-3}$cyanoalkyl, $C_{1-3}$alkyl, $C_{1-3}$hydroxyalkyl, $C_{1-3}$alkoxy, $C_{1-2}$alkoxy$C_{1-3}$alkyl, $C_{1-2}$alkylsulphonyl$C_{1-3}$alkyl, $C_{1-3}$alkoxycarbonyl and a group —(—O—)$_f$($C_{1-3}$alkyl)$_g$ringD (wherein f is 0 or 1, g is 0 or 1 and ring D is a 5-6-membered saturated heterocyclic group with 1-2 heteroatoms, selected independently from O, S and N, which cyclic group may bear one or more substituents selected from $C_{1-3}$alkyl).

Preferably $R^{54}$ and $R^{55}$ are each selected from pyrrolidinyl, piperazinyl, piperidinyl, imidazolidinyl, azetidinyl, morpholino and thiomorpholino which group may bear 1 or 2 substituents selected from oxo, hydroxy, halogeno, cyano, $C_{1-3}$cyanoalkyl, $C_{1-3}$alkyl, $C_{1-3}$hydroxyalkyl, $C_{1-3}$alkoxy, $C_{1-2}$alkoxy$C_{1-3}$alkyl, $C_{1-2}$alkylsulphonyl$C_{1-3}$alkyl, $C_{1-3}$alkoxycarbonyl and a group —(—O—)$_f$($C_{1-3}$alkyl)$_g$ringD (wherein f is 0 or 1, g is 0 or 1 and ring D is a heterocyclic group selected from pyrrolidinyl, piperazinyl, piperidinyl, imidazolidinyl, azetidinyl, morpholino and thiomorpholino, which cyclic group may bear one or more substituents selected from $C_{1-3}$alkyl).

More preferably $R^{54}$ and $R^{55}$ are each selected from pyrrolidinyl, piperazinyl, piperidinyl, azetidinyl, morpholino and thiomorpholino which group may bear 1 or 2 substituents selected from oxo, hydroxy, halogeno, cyano, $C_{1-3}$cyanoalkyl, $C_{1-3}$alkyl, $C_{1-3}$hydroxyalkyl, $C_{1-3}$alkoxy, $C_{1-2}$alkoxy$C_{1-3}$alkyl, $C_{1-2}$alkylsulphonyl$C_{1-3}$alkyl, $C_{1-3}$alkoxycarbonyl and a group —(—O—)$_f$($C_{1-3}$alkyl)$_g$ringD (wherein f is 0 or 1, g is 0 or 1 and ring D is a heterocyclic group selected from pyrrolidinyl, methylpiperazinyl, piperidinyl, azetidinyl, morpholino and thiomorpholino).

Particularly $R^{54}$ and $R^{55}$ are each selected from pyrrolidinyl, piperazinyl, piperidinyl, azetidinyl, morpholino and thiomorpholino which group may bear 1 or 2 substituents selected from a group —(—O—)$_f$($C_{1-3}$alkyl)$_g$ringD (wherein f is 0 or 1, g is 0 or 1 and ring D is a heterocyclic group selected from pyrrolidinyl, methylpiperazinyl, piperidinyl, azetidinyl, morpholino and thiomorpholino).

More particularly $R^{54}$ and $R^{55}$ are each selected from pyrrolidinyl, piperazinyl, piperidinyl, azetidinyl, morpholino and thiomorpholino which group is unsubstituted.

Conveniently $R^2$ represents hydroxy, halogeno, cyano, nitro, trifluoromethyl, $C_{1-3}$alkyl, amino or $R^5X^1$— [wherein $X^1$ is as hereinbefore defined and $R^5$ is selected from one of the following twenty-two groups:
1) oxiranyl$C_{1-4}$alkyl or $C_{1-5}$alkyl which may be unsubstituted or which may be substituted with one or more groups selected from fluoro, chloro and bromo, or $C_{2-5}$alkyl which may be unsubstituted or substituted with one or more groups selected from hydroxy and amino;
2) $C_{2-3}$alkyl$X^2$C(O)$R^{11}$ (wherein $X^2$ is as hereinbefore defined and $R^{11}$ represents $C_{1-3}$alkyl, —N$R^{13}R^{14}$ or —O$R^{15}$ (wherein $R^{13}$, and $R^{14}$ and $R^{15}$ which may be the same or different are each $C_{1-3}$alkyl or $C_{1-2}$alkoxyethyl));
3) $C_{2-4}$alkyl$X^3R^{16}$ (wherein $X^3$ is as hereinbefore defined and $R^{16}$ represents hydrogen, $C_{1-3}$alkyl, cyclopentyl, cyclohexyl or a 5-6-membered saturated heterocyclic group with 1-2 heteroatoms, selected independently from O, S and N, which $C_{1-3}$alkyl group may bear 1 or 2 substituents selected from oxo, hydroxy, halogeno and $C_{1-3}$alkoxy and which cyclic group may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy $C_{1-4}$alkyl, $C_{1-4}$alkylsulphonyl$C_{1-4}$alkyl, $C_{1-4}$alkoxycarbonyl, $C_{1-4}$alkylamino, di($C_{1-4}$alkyl)amino, $C_{1-4}$alkylamino$C_{1-4}$alkyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy and a group —(—O—)$_f$($C_{1-4}$alkyl)$_g$ringD (wherein f is 0 or 1, g is 0 or 1 and ring D is a 5-6-membered saturated heterocyclic group with 1-2 heteroatoms, selected independently from O, S and N, which cyclic group may bear one or more substituents selected from $C_{1-4}$alkyl));
4) $C_{2-3}$alkyl$X^4C_{2-3}$alkyl$X^5R^{22}$ (wherein $X^4$ and $X^5$ are as hereinbefore defined and $R^{22}$ represents hydrogen or $C_{1-3}$alkyl);
5) $R^{28}$ (wherein $R^{28}$ is as defined hereinbefore);
6) $C_{1-5}$alkyl$R^{107}$ (wherein $R^{107}$ is a 5-6-membered saturated heterocyclic group with 1-2 heteroatoms, selected independently from O, S and N, which heterocyclic group is linked to $C_{1-5}$alkyl through a carbon atom and which heterocyclic group may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl$C_{1-4}$alkyl, $C_{1-4}$alkoxycarbonyl, $C_{1-4}$alkylamino, di($C_{1-4}$alkyl)amino, $C_{1-4}$alkylamino $C_{1-4}$alkyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy and a group —(—O—)$_f$(C$_{1-4}$alkyl)$_g$ringD (wherein f is 0 or 1, g is 0 or 1 and ring D is a 5-6-membered saturated heterocyclic group with 1-2 heteroatoms, selected independently from O, S and N, which cyclic group may bear one or more substituents selected from C$_{1-4}$alkyl)) or C$_{2-5}$alkylR$^{108}$ (wherein R$^{108}$ is a 5-6-membered saturated heterocyclic group with 1-2 heteroatoms, of which one is N and the other may be selected independently from O, S and N, which heterocyclic group is linked to C$_{2-5}$alkyl through a nitrogen atom and which heterocyclic group may bear 1 or 2 substituents selected from oxo, hydroxy, halogeno, cyano, C$_{1-4}$cyanoalkyl, C$_{1-4}$alkyl, C$_{1-4}$hydroxyalkyl, C$_{1-4}$alkoxy, C$_{1-4}$alkoxyC$_{1-4}$alkyl, C$_{1-4}$alkylsulphonyl C$_{1-4}$alkyl, C$_{1-4}$alkoxycarbonyl, C$_{1-4}$alkylamino, di(C$_{1-4}$alkyl)amino, C$_{1-4}$alkylaminoC$_{1-4}$alkyl, di(C$_{1-4}$alkyl)aminoC$_{1-4}$alkyl, C$_{1-4}$alkylaminoC$_{1-4}$alkoxy, di(C$_{1-4}$alkyl)aminoC$_{1-4}$alkoxy and a group —(—O—)$_f$ (C$_{1-4}$alkyl)$_g$ringD (wherein f is 0 or 1, g is 0 or 1 and ring D is a 5-6-membered saturated heterocyclic group with 1-2 heteroatoms, selected independently from O, S and N, which cyclic group may bear one or more substituents selected from C$_{1-4}$alkyl));
7) C$_{3-4}$alkenylR$^{109}$ (wherein R$^{109}$ represents R$^{107}$ or R$^{108}$ as defined hereinbefore);
8) C$_{3-4}$alkynylR$^{109}$ (wherein R$^{109}$ represents R$^{107}$ or R$^{108}$ as defined hereinbefore);
9) R$^{29}$ (wherein R$^{29}$ is as defined hereinbefore);
10) C$_{1-5}$alkylR$^{29}$ (wherein R$^{29}$ is as defined hereinbefore);
11) C$_{3-5}$alkenylR$^{29}$ (wherein R$^{29}$ is as defined hereinbefore);
12) C$_{3-5}$alkynylR$^{29}$ (wherein R$^{29}$ is as defined hereinbefore);
13) C$_{1-5}$alkylX$^6$R$^{29}$ (wherein X$^6$ and R$^{29}$ are as defined hereinbefore);
14) C$_{4-5}$alkenylX$^7$R$^{29}$ (wherein X$^7$ and R$^{29}$ are as defined hereinbefore);
15) C$_{4-5}$alkynylX$^8$R$^{29}$ (wherein X$^8$ and R$^{29}$ are as defined hereinbefore);
16) C$_{2-3}$alkylX$^9$C$_{1-3}$alkylR$^{29}$ (wherein X$^9$ and R$^{29}$ are as defined hereinbefore);
17) C$_{2-3}$alkylX$^9$C$_{1-3}$alkylR$^{28}$ (wherein X$^9$ and R$^{28}$ are as defined hereinbefore);
18) C$_{2-5}$alkenyl which may be unsubstituted or which may be substituted with one or more groups selected from hydroxy, fluoro, amino, C$_{1-4}$alkylamino, N,N-di(C$_{1-4}$alkyl)amino, aminosulphonyl, N—C$_{1-4}$alkylaminosulphonyl and N,N-di(C$_{1-4}$alkyl)aminosulphonyl;
19) C$_{2-5}$alkynyl which may be unsubstituted or which may be substituted with one or more groups selected from hydroxy, fluoro, amino, C$_{1-4}$alkylamino, N,N-di(C$_{1-4}$alkyl)amino, aminosulphonyl, N—C$_{1-4}$alkylaminosulphonyl and N,N-di(C$_{1-4}$alkyl)aminosulphonyl;
20) C$_{2-5}$alkenylX$^9$C$_{1-3}$alkylR$^{28}$ (wherein X$^9$ and R$^{28}$ are as defined hereinbefore);
21) C$_{2-5}$alkynylX$^9$C$_{1-3}$alkylR$^{28}$ (wherein X$^9$ and R$^{28}$ are as defined hereinbefore); and
22) C$_{1-3}$alkylR$^{54}$ (C$_{1-3}$alkyl)$_q$(X$^9$)$_r$R$^{55}$ (wherein X$^9$, q, r, R$^{54}$ and R$^{55}$ are as defined hereinbefore); and additionally wherein any C$_{1-5}$alkyl, C$_{2-5}$alkenyl or C$_{2-5}$alkynyl group in R$^5$X$^1$— may bear one or more substituents selected from hydroxy, halogeno and amino].

Advantageously R$^2$ represents hydroxy, halogeno, cyano, nitro, trifluoromethyl, C$_{1-3}$alkyl, amino or R$^5$X$^1$—[wherein X$^1$ is as hereinbefore defined and R$^5$ is selected from one of the following twenty-two groups:
1) C$_{1-4}$alkyl which may be unsubstituted or which may be substituted with one or more groups selected from fluoro, chloro and bromo, or C$_{2-5}$alkyl which may be unsubstituted or substituted with one or more groups selected from hydroxy and amino;
2) C$_{2-3}$alkylX$^2$C(O)R$^{11}$ (wherein X$^2$ is as hereinbefore defined and R$^{11}$ represents —NR$^{13}$R$^{14}$ or —OR$^{15}$ (wherein R$^{13}$, R$^{14}$ and R$^{15}$ which may be the same or different are each C$_{1-4}$alkyl or C$_{1-2}$alkoxyethyl));
3) C$_{2-4}$alkylX$^3$R$^{16}$ (wherein X$^3$ is as hereinbefore defined and R$^{16}$ is a group selected from C$_{1-3}$alkyl, cyclopentyl, cyclohexyl, pyrrolidinyl, piperazinyl, piperidinyl, imidazolidinyl, azetidinyl and tetrahydropyranyl, which C$_{1-3}$alkyl group may bear 1 or 2 substituents selected from oxo, hydroxy, halogeno and C$_{1-2}$alkoxy and which cyclopentyl, cyclohexyl, pyrrolidinyl, piperazinyl, piperidinyl, imidazolidinyl, azetidinyl or tetrahydropyranyl group may bear 1 or 2 substituents selected from oxo, hydroxy, halogeno, cyano, C$_{1-3}$cyanoalkyl, C$_{1-3}$alkyl, C$_{1-3}$hydroxyalkyl, C$_{1-3}$alkoxy, C$_{1-2}$alkoxyC$_{1-3}$alkyl, C$_{1-2}$alkylsulphonyl C$_{1-3}$alkyl, C$_{1-3}$alkoxycarbonyl, C$_{1-3}$alkylamino, di(C$_{1-3}$alkyl)amino, C$_{1-3}$alkylaminoC$_{1-3}$alkyl, di(C$_{1-3}$alkyl)aminoC$_{1-3}$alkyl, C$_{1-3}$alkylaminoC$_{1-3}$alkoxy, di(C$_{1-3}$alkyl)aminoC$_{1-3}$alkoxy and a group —(—O—)$_f$ (C$_{1-3}$alkyl)$_g$ringD (wherein f is 0 or 1, g is 0 or 1 and ring D is a heterocyclic group selected from pyrrolidinyl, piperazinyl, piperidinyl, imidazolidinyl, azetidinyl, morpholino and thiomorpholino, which cyclic group may bear one or more substituents selected from C$_{1-3}$alkyl));
4) C$_{2-3}$alkylX$^4$C$_{2-3}$alkylX$^5$R$^{22}$ (wherein X$^4$ and X$^5$ are as hereinbefore defined and R$^{22}$ represents hydrogen or C$_{1-3}$alkyl);
5) R$^{28}$ (wherein R$^{28}$ is as defined hereinbefore);
6) C$_{1-4}$alkylR$^{110}$ (wherein R$^{110}$ is a group selected from pyrrolidinyl, piperazinyl, piperidinyl, imidazolidin-1-yl, azetidinyl, 1,3-dioxolan-2-yl, 1,3-dioxan-2-yl, 1,3-dithiolan-2-yl and 1,3-dithian-2-yl, which group is linked to C$_{1-4}$alkyl through a carbon atom and which group may bear 1 or 2 substituents selected from oxo, hydroxy, halogeno, cyano, C$_{1-3}$cyanoalkyl, C$_{1-3}$alkyl, C$_{1-3}$hydroxyalkyl, C$_{1-3}$alkoxy, C$_{1-2}$alkoxyC$_{1-3}$alkyl, C$_{1-2}$alkylsulphonyl C$_{1-3}$alkyl, C$_{1-3}$alkoxycarbonyl, C$_{1-3}$alkylamino, di(C$_{1-3}$alkyl)amino, C$_{1-3}$alkylaminoC$_{1-3}$alkyl, di(C$_{1-3}$alkyl)aminoC$_{1-3}$alkyl, C$_{1-3}$alkylaminoC$_{1-3}$alkoxy, di(C$_{1-3}$alkyl)aminoC$_{1-3}$alkoxy and a group —(—O—)$_f$ (C$_{1-3}$alkyl)$_g$ringD (wherein f is 0 or 1, g is 0 or 1 and ring D is a heterocyclic group selected from pyrrolidinyl, piperazinyl, piperidinyl, imidazolidinyl, azetidinyl, morpholino and thiomorpholino, which cyclic group may bear one or more substituents selected from C$_{1-3}$alkyl)) or C$_{2-4}$alkylR$^{111}$ (wherein R$^{111}$ is a group selected from morpholino, thiomorpholino, azetidin-1-yl, pyrrolidin-1-yl, piperazin-1-yl and piperidino which group may bear 1 or 2 substituents selected from oxo, hydroxy, halogeno, cyano, C$_{1-3}$cyanoalkyl, C$_{1-3}$alkyl, C$_{1-3}$hydroxyalkyl, C$_{1-3}$alkoxy, C$_{1-2}$alkoxyC$_{1-3}$alkyl, C$_{1-2}$alkylsulphonylC$_{1-3}$alkyl, C$_{1-3}$alkoxycarbonyl, C$_{1-3}$alkylamino, di(C$_{1-3}$alkyl)amino, C$_{1-3}$alkylaminoC$_{1-3}$ alkyl, di(C$_{1-3}$alkyl)aminoC$_{1-3}$alkyl, C$_{1-3}$alkylaminoC$_{1-3}$alkoxy, di(C$_{1-3}$ alkyl)aminoC$_{1-3}$alkoxy and a group —(—O—)$_f$(C$_{1-3}$alkyl)$_g$ringD (wherein f is 0 or 1, g is 0 or 1 and ring D is a heterocyclic group selected from pyrrolidinyl, piperazinyl, piperidinyl, imidazolidinyl, azetidinyl, morpholino and thiomorpholino, which cyclic group may bear one or more substituents selected from C$_{1-3}$alkyl));
7) C$_{3-4}$alkenylR$^{112}$ (wherein R$^{112}$ represents R$^{110}$ or R$^{111}$ as defined hereinbefore);
8) C$_{3-4}$alkynylR$^{112}$ (wherein R$^{112}$ represents R$^{110}$ or R$^{111}$ as defined hereinbefore);

9) $R^{29}$ (wherein $R^{29}$ is as defined hereinbefore);
10) $C_{1-4}$alkyl$R^{29}$ (wherein $R^{29}$ is as defined hereinbefore);
11) 1-$R^{29}$prop-1-en-3-yl or 1-$R^{29}$but-2-en-4-yl (wherein $R^{29}$ is as defined hereinbefore with the proviso that when $R^5$ is 1-$R^{29}$prop-1-en-3-yl, $R^{29}$ is linked to the alkenyl group via a carbon atom);
12) 1-$R^{29}$prop-1-yn-3-yl or 1-$R^{29}$but-2-yn-4-yl (wherein $R^{29}$ is as defined hereinbefore with the proviso that when $R^5$ is 1-$R^{29}$prop-1-yn-3-yl, $R^{29}$ is linked to the alkynyl group via a carbon atom);
13) $C_{1-5}$alkyl$X^6R^{29}$ (wherein $X^6$ and $R^{29}$ are as defined hereinbefore);
14) 1-($R^{29}X^7$)but-2-en-4-yl (wherein $X^1$ and $R^{29}$ are as defined hereinbefore);
15) 1-($R^{29}X^8$)but-2-yn-4-yl (wherein $X^8$ and $R^{29}$ are as defined hereinbefore);
16) $C_{2-3}$alkyl$X^9C_{1-3}$alkyl$R^{29}$ (wherein $X^9$ and $R^{29}$ are as defined hereinbefore);
17) $C_{2-3}$alkyl$X^9C_{1-3}$alkyl$R^{28}$ (wherein $X^9$ and $R^{28}$ are as defined hereinbefore);
18) $C_{2-5}$alkenyl which may be unsubstituted or which may be substituted with one or more fluorine atoms or with one or two groups selected from hydroxy, fluoro, amino, $C_{1-4}$alkylamino, N,N-di($C_{1-4}$alkyl)amino, aminosulphonyl, N—$C_{1-4}$alkylaminosulphonyl and N,N-di($C_{1-4}$alkyl)aminosulphonyl;
19) $C_{2-5}$alkynyl which may be unsubstituted or which may be substituted with one or more fluorine atoms or with one or two groups selected from hydroxy, fluoro, amino, $C_{1-4}$alkylamino, N,N-di($C_{1-4}$alkyl)amino, aminosulphonyl, N—$C_{1-4}$alkylaminosulphonyl and N,N-di($C_{1-4}$alkyl) aminosulphonyl;
20) $C_{2-4}$alkenyl$X^9C_{1-3}$alkyl$R^{28}$ (wherein $X^9$ and $R^{28}$ are as defined hereinbefore);
21) $C_{2-4}$alkynyl$X^9C_{1-3}$alkyl$R^{28}$ (wherein $X^9$ and $R^{28}$ are as defined hereinbefore); and
22) $C_{1-3}$alkyl$R^{54}(C_{1-3}$alkyl$)_q(X^9)_rR^{55}$ (wherein $X^9$, q, r, $R^{54}$ and $R^{55}$ are as defined hereinbefore); and additionally wherein any $C_{1-5}$alkyl, $C_{2-5}$alkenyl or $C_{2-5}$alkynyl group in $R^5X^1$— may bear one or more substituents selected from hydroxy, halogeno and amino].

Preferably $R^2$ represents hydroxy, halogeno, nitro, trifluoromethyl, $C_{1-3}$alkyl, cyano, amino or $R^5X^1$— [wherein $X^1$ is as hereinbefore defined and $R^5$ is selected from one of the following twenty groups:
1) $C_{1-3}$alkyl which may be unsubstituted or which may be substituted with one or more groups selected from fluoro, chloro and bromo, or $C_{2-3}$alkyl which may be unsubstituted or substituted with one or more groups selected from hydroxy and amino;
2) 2-(3,3-dimethylureido)ethyl, 3-(3,3-dimethylureido)propyl, 2-(3-methylureido)ethyl, 3-(3-methylureido)propyl, 2-ureidoethyl, 3-ureidopropyl, 2-(N,N-dimethylcarbamoyloxy)ethyl, 3-(N,N-dimethylcarbamoyloxy)propyl, 2-(N-methylcarbamoyloxy)ethyl, 3-(N-methylcarbamoyloxy)propyl, 2-(carbamoyloxy)ethyl, 3-(carbamoyloxy)propyl, or 2-(N-methyl-N-(butoxycarbonyl)amino)ethyl;
3) $C_{2-3}$alkyl$X^3R^{16}$ (wherein $X^3$ is as hereinbefore defined and $R^{16}$ is a group selected from $C_{1-3}$alkyl, cyclopentyl, cyclohexyl, pyrrolidinyl, piperidinyl, piperazinyl, azetidinyl, imidazolidinyl and tetrahydropyranyl which group is linked to $X^3$ through a carbon atom and which $C_{1-3}$alkyl group may bear 1 or 2 substituents selected from hydroxy, halogeno and $C_{1-2}$alkoxy and which cyclopentyl, cyclohexyl, pyrrolidinyl, piperidinyl, piperazinyl, azetidinyl, imidazolidinyl or tetrahydropyranyl group may bear one substituent selected from oxo, hydroxy, halogeno, cyano, $C_{1-2}$cyanoalkyl, $C_{1-2}$alkyl, $C_{1-2}$hydroxyalkyl, $C_{1-2}$alkoxy, $C_{1-2}$alkoxy$C_{1-3}$alkyl, $C_{1-2}$alkylsulphonyl$C_{1-3}$alkyl, $C_{1-2}$alkoxycarbonyl, $C_{1-3}$alkylamino, di($C_{1-3}$alkyl)amino, $C_{1-3}$alkylamino$C_{1-3}$alkyl, di($C_{1-3}$alkyl)amino$C_{1-3}$alkyl, $C_{1-3}$alkylamino$C_{1-3}$alkoxy, di($C_{1-3}$alkyl)amino$C_{1-3}$alkoxy and a group —(—O—)$_f$($C_{1-3}$alkyl)$_g$ringD (wherein f is 0 or 1, g is 0 or 1 and ring D is a heterocyclic group selected from pyrrolidinyl, methylpiperazinyl, piperidinyl, azetidinyl, morpholino and thiomorpholino));
4) $C_{2-3}$alkyl$X^4C_{2-3}$alkyl$X^5R^{22}$ (wherein $X^4$ and $X^5$ are as hereinbefore defined and $R^{22}$ represents hydrogen or $C_{1-2}$alkyl);
5) $R^{28}$ (wherein $R^{28}$ is as defined hereinbefore);
6) $C_{1-3}$alkyl$R^{110}$ (wherein $R^{110}$ is a group selected from pyrrolidinyl, piperazinyl, piperidinyl, azetidinyl, imidazolidinyl, 1,3-dioxolan-2-yl, 1,3-dioxan-2-yl, 1,3-dithiolan-2-yl and 1,3-dithian-2-yl, which group is linked to $C_{1-3}$alkyl through a carbon atom and which group may bear 1 or 2 substituents selected from oxo, hydroxy, halogeno, cyano, $C_{1-2}$cyanoalkyl, $C_{1-2}$alkyl, $C_{1-2}$hydroxyalkyl, $C_{1-2}$alkoxy, $C_{1-2}$alkoxy$C_{1-3}$alkyl, $C_{1-2}$alkylsulphonyl$C_{1-3}$alkyl, $C_{1-2}$alkoxycarbonyl, $C_{1-3}$alkylamino, di($C_{1-3}$alkyl)amino, $C_{1-3}$alkylamino$C_{1-3}$alkyl, di($C_{1-3}$alkyl)amino$C_{1-3}$alkyl, $C_{1-3}$alkylamino$C_{1-3}$alkoxy, di($C_{1-3}$alkyl)amino$C_{1-3}$alkoxy and a group —(—O—)$_f$($C_{1-3}$alkyl)$_g$ringD (wherein f is 0 or 1, g is 0 or 1 and ring D is a heterocyclic group selected from pyrrolidinyl, methylpiperazinyl, piperidinyl, azetidinyl, morpholino and thiomorpholino)) or $C_{2-3}$alkyl$R^{111}$ (wherein $R^{111}$ is a group selected from morpholino, thiomorpholino, azetidin-1-yl, pyrrolidin-1-yl, piperazin-1-yl and piperidino which group may bear 1 or 2 substituents selected from oxo, hydroxy, halogeno, cyano, $C_{1-2}$cyanoalkyl, $C_{1-2}$alkyl, $C_{1-2}$hydroxyalkyl, $C_{1-2}$alkoxy, $C_{1-2}$alkoxy$C_{1-3}$alkyl, $C_{1-2}$alkylsulphonyl$C_{1-3}$alkyl, $C_{1-2}$alkoxycarbonyl, $C_{1-3}$alkylamino, di($C_{1-3}$alkyl)amino, $C_{1-3}$alkylamino$C_{1-3}$alkyl, di($C_{1-3}$alkyl)amino$C_{1-3}$alkyl, $C_{1-3}$alkylamino$C_{1-3}$alkoxy, di($C_{1-3}$alkyl)amino$C_{1-3}$alkoxy and a group —(—O—)$_f$($C_{1-3}$alkyl)$_g$ringD (wherein f is 0 or 1, g is 0 or 1 and ring D is a heterocyclic group selected from pyrrolidinyl, methylpiperazinyl, piperidinyl, azetidinyl, morpholino and thiomorpholino));
7) $R^{29}$ (wherein $R^{29}$ is as defined hereinbefore);
8) $C_{1-4}$alkyl$R^{29}$ (wherein $R^{29}$ is as defined hereinbefore);
9) 1-$R^{29}$but-2-en-4-yl (wherein $R^{29}$ is as defined hereinbefore);
10) 1-$R^{29}$but-2-yn-4-yl (wherein $R^{29}$ is as defined hereinbefore);
11) $C_{1-3}$alkyl$X^6R^{29}$ (wherein $X^6$ and $R^{29}$ are as defined hereinbefore);
12) 1-($R^{29}X^7$)but-2-en-4-yl (wherein $X^7$ and $R^{29}$ are as defined hereinbefore);
13) 1-($R^{29}X^8$)but-2-yn-4-yl (wherein $X^8$ and $R^{29}$ are as defined hereinbefore);
14) $C_{2-3}$alkyl$X^9C_{1-3}$alkyl$R^{29}$ (wherein $X^9$ and $R^{29}$ are as defined hereinbefore);
15) $C_{2-3}$alkyl$X^9C_{1-3}$alkyl$R^{28}$ (wherein $X^9$ and $R^{28}$ are as defined hereinbefore);
16) $C_{2-5}$alkenyl which may be unsubstituted or which may be substituted with one or more fluorine atoms or with one or two groups selected from hydroxy, fluoro, amino, $C_{1-4}$alkylamino, N,N-di($C_{1-4}$alkyl)amino, aminosulphonyl, N—$C_{1-4}$alkylaminosulphonyl and N,N-di($C_{1-4}$alkyl) aminosulphonyl;
17) $C_{2-5}$alkynyl which may be unsubstituted or which may be substituted with one or more fluorine atoms or with one or two groups selected from hydroxy, fluoro, amino, $C_{1-4}$alkylamino, N,N-di($C_{1-4}$alkyl)amino, aminosulphonyl, N—$C_{1-4}$alkylaminosulphonyl and N,N-di($C_{1-4}$alkyl)aminosulphonyl;
18) $C_{2-3}$alkenyl$X^9C_{1-3}$alkyl$R^{28}$ (wherein $X^9$ and $R^{28}$ are as defined hereinbefore);
19) $C_{2-3}$alkynyl$X^9C_{1-3}$alkyl$R^{28}$ (wherein $X^9$ and $R^{28}$ are as defined hereinbefore); and
20) $C_{1-3}$alkyl$R^{54}(C_{1-3}$alkyl$)_q(X^9)_rR^{55}$ (wherein $X^9$, q, r, $R^{54}$ and $R^{55}$ are as defined hereinbefore);
and additionally wherein any $C_{1-5}$alkyl, $C_{2-5}$alkenyl or $C_{2-5}$alkynyl group in $R^5X^1$— may bear one or more substituents selected from hydroxy, halogeno and amino].

More preferably $R^2$ represents hydroxy, $C_{1-3}$alkyl, amino or $R^5X^1$— [wherein $X^1$ is as hereinbefore defined and $R^5$ represents methyl, ethyl, benzyl, trifluoromethyl, 2,2,2-trifluoroethyl, 2-hydroxyethyl, 3-hydroxypropyl, 2-methoxyethyl, 3-methoxypropyl, 2-(methylsulphinyl)ethyl, 2-(methylsulphonyl)ethyl, 2-(ethylsulphinyl)ethyl, 2-(ethylsulphonyl)ethyl, 2-(N,N-dimethylsulphamoyl)ethyl, 2-(N-methylsulphamoyl)ethyl, 2-sulphamoylethyl, 2-(methylamino)ethyl, 3-(methylamino)propyl, 2-(ethylamino)ethyl, 3-(ethylamino)propyl, 2-(N,N-dimethylamino)ethyl, 3-(N,N-dimethylamino)propyl, 2-(N,N-diethylamino)ethyl, 3-(N,N-diethylamino)propyl, 2-(N-methyl-N-methylsulphonylamino)ethyl, 3-(N-methyl-N-methylsulphonylamino)propyl, 2-morpholinoethyl, 3-morpholinopropyl, 2-piperidinoethyl, 3-piperidinopropyl, 2-(methylpiperidino)ethyl, 3-(methylpiperidino)propyl, 2-(ethylpiperidino)ethyl, 3-(ethylpiperidino)propyl, 2-((2-methoxyethyl)piperidino)ethyl, 3-((2-methoxyethyl)piperidino)propyl, 2-((2-methylsulphonyl)ethylpiperidino)ethyl, 3-((2-methylsulphonyl)ethylpiperidino)propyl, piperidin-3-ylmethyl, piperidin-4-ylmethyl, 2-(piperidin-3-yl)ethyl, 2-(piperidin-4-yl)ethyl, 3-(piperidin-3-yl)propyl, 3-(piperidin-4-yl)propyl, 2-(piperidin-2-yl)ethyl, 3-(piperidin-2-yl)propyl, (1-methylpiperidin-3-yl)methyl, (1-methylpiperidin-4-yl)methyl, (1-cyanomethylpiperidin-3-yl)methyl, (1-cyanomethylpiperidin-4-yl)methyl, 2-(methylpiperidin-3-yl)ethyl, 2-(methylpiperidin-4-yl)ethyl, 2-(1-cyanomethylpiperidin-3-yl)ethyl, 2-(1-cyanomethylpiperidin-4-yl)ethyl, 3-(methylpiperidin-3-yl)propyl, 3-(methylpiperidin-4-yl)propyl, 3-(1-cyanomethylpiperidin-3-yl)propyl, 3-(1-cyanomethylpiperidin-4-yl)propyl, 2-(ethylpiperidin-3-yl)ethyl, 2-(ethylpiperidin-4-yl)ethyl, 3-(ethylpiperidin-3-yl)propyl, 3-(ethylpiperidin-4-yl)propyl, ((2-methoxyethyl)piperidin-3-yl)methyl, ((2-methoxyethyl)piperidin-4-yl)methyl, 2-((2-methoxyethyl)piperidin-3-yl)ethyl, 2-((2-methoxyethyl)piperidin-4-yl)ethyl, 3-((2-methoxyethyl)piperidin-3-yl)propyl, 3-((2-methoxyethyl)piperidin-4-yl)propyl, (1-(2-methylsulphonylethyl)piperidin-3-yl)methyl, (1-(2-methylsulphonylethyl)piperidin-4-yl)methyl, 2-((2-methylsulphonylethyl)piperidin-3-yl)ethyl, 2-((2-methylsulphonylethyl)piperidin-4-yl)ethyl, 3((2-methylsulphonylethyl)piperidin-3-yl)propyl, 3-((2-methylsulphonylethyl)piperidin-4-yl)propyl, 1-isopropylpiperidin-2-ylmethyl, 1-isopropylpiperidin-3-ylmethyl, 1-isopropylpiperidin-4-ylmethyl, 2-(1-isopropylpiperidin-2-yl)ethyl, 2-(1-isopropylpiperidin-3-yl)ethyl, 2-(1-isopropylpiperidin-4-yl)ethyl, 3-(1-isopropylpiperidin-2-yl)propyl, 3-(1-isopropylpiperidin-3-yl)propyl, 3-(1-isopropylpiperidin-4-yl)propyl, 2-(piperidin-4-yloxy)ethyl, 3-(piperidin-4-yloxy)propyl, 2-(1-(cyanomethyl)piperidin-4-yloxy)ethyl, 3-(1-(cyanomethyl)piperidin-4-yloxy)propyl, 2-(1-(2-cyanoethyl)piperidin-4-yloxy)ethyl, 3-(1-(2-cyanoethyl)piperidin-4-yloxy)propyl, 2-(piperazin-1-yl)ethyl, 3-(piperazin-1-yl)propyl, (pyrrolidin-2-yl)methyl, 2-(pyrrolidin-1-yl)ethyl, 3-(pyrrolidin-1-yl)propyl, (2-oxo-tetrahydro-2H-pyrrolidin-5-yl)methyl, 5(R)-(2-oxo-tetrahydro-2H-pyrrolidin-5-yl)methyl, (5S)-(2-oxo-tetrahydro-2H-pyrrolidin-5-yl)methyl, (1,3-dioxolan-2-yl)methyl, 2-(1,3-dioxolan-2-yl)ethyl, 2-(2-methoxyethylamino)ethyl, 2-(N-(2-methoxyethyl)-N-methylamino)ethyl, 2-(2-hydroxyethylamino)ethyl, 3-(2-methoxyethylamino)propyl, 3-(N-(2-methoxyethyl)-N-methylamino)propyl, 3-(2-hydroxyethylamino)propyl, 2-methylthiazol-4-ylmethyl, 2-acetamidothiazol-4-ylmethyl, 1-methylimidazol-2-ylmethyl, 2-(imidazol-1-yl)ethyl, 2-(2-methylimidazol-1-yl)ethyl, 2-(2-ethylimidazol-1-yl)ethyl, 3-(2-methylimidazol-1-yl)propyl, 3-(2-ethylimidazol-1-yl)propyl, 2-(1,2,3-triazol-1-yl)ethyl, 2-(1,2,3-triazol-2-yl)ethyl, 2-(1,2,4-triazol-1-yl)ethyl, 2-(1,2,4-triazol-4-yl)ethyl, 4-pyridylmethyl, 2-(4-pyridyl)ethyl, 3-(4-pyridyl)propyl, 2-(4-pyridyloxy)ethyl, 2-(4-pyridylamino)ethyl, 2-(4-oxo-1,4-dihydro-1-pyridyl)ethyl, 2-(2-oxo-imidazolidin-1-yl)ethyl, 3-(2-oxo-imidazolidin-1-yl)propyl, 2-thiomorpholinoethyl, 3-thiomorpholinopropyl, 2-(1,1-dioxothiomorpholino)ethyl, 3-(1,1-dioxothiomorpholino)propyl, 2-(2-methoxyethoxy)ethyl, 2-(4-methylpiperazin-1-yl)ethyl, 3-(4-methylpiperazin-1-yl)propyl, 3-(methylsulphinyl)propyl, 3-(methylsulphonyl)propyl, 3-(ethylsulphinyl)propyl, 3-(ethylsulphonyl)propyl, 2-(5-methyl-1,2,4-triazol-1-yl)ethyl, morpholino, 2-((N-(1-methylimidazol-4-ylsulphonyl)-N-methyl)amino)ethyl, 2-((N-(3-morpholinopropylsulphonyl)-N-methyl)amino)ethyl, 2-((N-methyl-N-4-pyridyl)amino)ethyl, 3-(4-oxidomorpholino)propyl, 2-(2-(4-methylpiperazin-1-yl)ethoxy)ethyl, 3-(2-(4-methylpiperazin-1-yl)ethoxy)propyl, 2-(2-morpholinoethoxy)ethyl, 3-(2-morpholinoethoxy)propyl, 2-(tetrahydropyran-4-yloxy)ethyl, 3-(tetrahydropyran-4-yloxy)propyl, 2-((2-(pyrrolidin-1-yl)ethyl)carbamoyl)vinyl, 3-((2-(pyrrolidin-1-yl)ethyl)carbamoyl)prop-2-en-1-yl, 1-(2-pyrrolidinylethyl)piperidin-4-ylmethyl, 1-(3-pyrrolidinylpropyl)piperidin-4-ylmethyl, 1-(2-piperidinylethyl)piperidin-4-ylmethyl, 1-(3-piperidinylpropyl)piperidin-4-ylmethyl, 1-(2-morpholinoethyl)piperidin-4-ylmethyl, 1-(3-morpholinopropyl)piperidin-4-ylmethyl, 1-(2-thiomorpholinoethyl)piperidin-4-ylmethyl, 1-(3-thiomorpholinopropyl)piperidin-4-ylmethyl, 1-(2-azetidinylethyl)piperidin-4-ylmethyl or 1-(3-azetidinylpropyl)piperidin-4-ylmethyl, 3-morpholino-2-hydroxypropyl, (2R)-3-morpholino-2-hydroxypropyl, (2S)-3-morpholino-2-hydroxypropyl, 3-piperidino-2-hydroxypropyl, (2R)-3-piperidino-2-hydroxypropyl, (2S)-3-piperidino-2-hydroxypropyl, 3-pyrrolidin-1-yl-2-hydroxypropyl, (2R)-3-pyrrolidin-1-yl-2-hydroxypropyl, (2S)-3-pyrrolidin-1-yl-2-hydroxypropyl, 3-(1-methylpiperazin-4-yl)-2-hydroxypropyl, (2R)-3-(1-methylpiperazin-4-yl)-2-hydroxypropyl (2S)-3(1-methylpiperazin-4-yl)-2-hydroxypropyl, 3-(N,N-diethylamino)-2-hydroxypropyl, (2R)-3-(N,N-diethylamino)-2-hydroxypropyl, (2S)-3-(N,N-diethylamino)-2-hydroxypropyl, 3-(isopropylamino)-2-hydroxypropyl, (2R)-3-(isopropylamino)-2-hydroxypropyl, (2S)-3-(isopropylamino)-2-hydroxypropyl, 3-(N,N-diisopropylamino)-2-hydroxypropyl, (2R)-3-N,N-diisopropylamino-2-hydroxypropyl or (2S)-3-N,N-diisopropylamino)-2-hydroxypropyl].

Particularly $R^2$ represents $C_{1-3}$alkyl, amino or $R^5X^1$— [wherein $X^1$ is as hereinbefore defined and $R^5$ represents ethyl, benzyl, trifluoromethyl, 2,2,2-trifluoroethyl, 2-hydroxyethyl, 3-hydroxypropyl, 2-methoxyethyl, 3-methoxypropyl, 2-(methylsulphinyl)ethyl, 2-(methylsulphonyl)ethyl, 2-(ethylsulphinyl)ethyl, 2-(ethylsulphonyl)ethyl, 2-(N,N-dimethylsulphamoyl)ethyl, 2-(N-methylsulphamoyl)ethyl, 2-sulphamoylethyl, 2-(methylamino)ethyl, 3-(methylamino)propyl, 2-(ethylamino)ethyl, 3-(ethylamino)propyl, 2-(N,N-dimethylamino)ethyl, 3-(N,N-dimethylamino)propyl, 2-(N,N-diethylamino)ethyl, 3-(N,N-diethylamino)propyl, 2-(N-methyl-N-methylsulphonylamino) ethyl, 3-(N-methyl-N-methylsulphonylamino)propyl, 2-morpholinoethyl, 3-morpholinopropyl, 2-piperidinoethyl, 3-piperidinopropyl, 2-(methylpiperidino)ethyl, 3-(methylpiperidino)propyl, 2-(ethylpiperidino)ethyl, 3-(ethylpiperidino)propyl, 2-((2-methoxyethyl)piperidino)ethyl, 3-((2-methoxyethyl)piperidino)propyl, 2-((2-methylsulphonyl)ethylpiperidino)ethyl, 3-((2-methylsulphonyl)ethylpiperidino)propyl, piperidin-3-ylmethyl, piperidin-4-ylmethyl, 2-(piperidin-3-yl)ethyl, 2-(piperidin-4-yl)ethyl, 3-(piperidin-3-yl)propyl, 3-(piperidin-4-yl)propyl, 2-(piperidin-2-yl)ethyl, 3-(piperidin-2-yl)propyl, (1-methylpiperidin-3-yl)methyl, (1-methylpiperidin-4-yl)methyl, (1-cyanomethylpiperidin-3-yl)methyl, (1-cyanomethylpiperidin-4-yl)methyl, 2-(methylpiperidin-3-yl)ethyl, 2-(methylpiperidin-4-yl)ethyl, 2-(1-cyanomethylpiperidin-3-yl)ethyl, 2-(1-cyanomethylpiperidin-4-yl)ethyl, 3-(methylpiperidin-3-yl)propyl, 3-(methylpiperidin-4-yl)propyl, 3-(1-cyanomethylpiperidin-3-yl)propyl, 3-(1-cyanomethylpiperidin-4-yl)propyl, 2-(ethylpiperidin-3-yl)ethyl, 2-(ethylpiperidin-4-yl)ethyl, 3-(ethylpiperidin-3-yl)propyl, 3-(ethylpiperidin-4-yl)propyl, ((2-methoxyethyl)piperidin-3-yl)methyl, ((2-methoxyethyl)piperidin-4-yl)methyl, 2-((2-methoxyethyl)piperidin-3-yl)ethyl, 2-((2-methoxyethyl)piperidin-4-yl)ethyl, 3-((2-methoxyethyl)piperidin-3-yl)propyl, 3-((2-methoxyethyl)piperidin-4-yl)propyl, (1-(2-methylsulphonylethyl)piperidin-3-yl)methyl, (1-(2-methylsulphonylethyl)piperidin-4-yl)methyl, 2-((2-methylsulphonylethyl)piperidin-3-yl)ethyl, 2-((2-methylsulphonylethyl)piperidin-4-yl)ethyl, 3-((2-methylsulphonylethyl)piperidin-3-yl)propyl, 3-((2-methylsulphonylethyl)piperidin-4-yl)propyl, 1-isopropylpiperidin-2-ylmethyl, 1-isopropylpiperidin-3-ylmethyl, 1-isopropylpiperidin-4-ylmethyl, 2-(1-isopropylpiperidin-2-yl)ethyl, 2-(1-isopropylpiperidin-3-yl)ethyl, 2-(1-isopropylpiperidin-4-yl)ethyl, 3-(1-isopropylpiperidin-2-yl)propyl, 3-(1-isopropylpiperidin-3-yl)propyl, 3-(1-isopropylpiperidin-4-yl)propyl, 2-(piperidin-4-yloxy)ethyl, 3-(piperidin-4-yloxy)propyl, 2-(1-(cyanomethyl)piperidin-4-yloxy)ethyl, 3-(1-(cyanomethyl)piperidin-4-yloxy)propyl, 2-(1-(2-cyanoethyl)piperidin-4-yloxy)ethyl, 3-(1-(2-cyanoethyl)piperidin-4-yloxy)propyl, 2-(piperazin-1-yl)ethyl, 3-(piperazin-1-yl)propyl, (pyrrolidin-2-yl)methyl, (pyrrolidin-1-yl)ethyl, 3-(pyrrolidin-1-yl)propyl, (2-oxo-tetrahydro-2H-pyrrolidin-5-yl)methyl, 5(R)-(2-oxo-tetrahydro-2H-pyrrolidin-5-yl)methyl, (5S)-(2-oxo-tetrahydro-2H-pyrrolidin-5-yl)methyl, (1,3-dioxolan-2-yl)methyl, 2-(1,3-dioxolan-2-yl)ethyl, 2-(2-methoxyethylamino)ethyl, 2-(N-(2-methoxyethyl)-N-methylamino)ethyl, 2-(2-hydroxyethylamino)ethyl, 3-(2-methoxyethylamino)propyl, 3-(N-(2-methoxyethyl)-N-methylamino)propyl, 3-(2-hydroxyethylamino)propyl, 2-methylthiazol-4-ylmethyl, 2-acetamidothiazol-4-ylmethyl, 1-methylimidazol-2-ylmethyl, 2-(imidazol-1-yl)ethyl, 2-(2-methylimidazol-1-yl)ethyl, 2-(2-ethylimidazol-1-yl)ethyl, 3-(2-methylimidazol-1-yl)propyl, 3-(2-ethylimidazol-1-yl)propyl, 2-(1,2,3-triazol-1-yl)ethyl, 2-(1,2,3-triazol-2-yl)ethyl, 2-(1,2,4-triazol-1-yl)ethyl, 2-(1,2,4-triazol-4-yl)ethyl, 4-pyridylmethyl, 2-(4-pyridyl)ethyl, 3-(4-pyridyl)propyl, 2-(4-pyridyloxy)ethyl, 2-(4-pyridylamino)ethyl, 2-(4-oxo-1,4-dihydro-1-pyridyl)ethyl, 2-(2-oxo-imidazolidin-1-yl)ethyl, 3-(2-oxo-imidazolidin-1-yl)propyl, 2-thiomorpholinoethyl, 3-thiomorpholinopropyl, 2-(1,1-dioxothiomorpholino)ethyl, 3-(1,1-dioxothiomorpholino)propyl, 2-(2-methoxyethoxy)ethyl, 2-(4-methylpiperazin-1-yl)ethyl, 3-(4-methylpiperazin-1-yl)propyl, 3-(methylsulphinyl)propyl, 3-(methylsulphonyl)propyl, 3-(ethylsulphinyl)propyl, 3-(ethylsulphonyl)propyl, 2-(5-methyl-1,2,4-triazol-1-yl)ethyl, morpholino, 2-((N-(1-methylimidazol-4-ylsulphonyl)-N-methyl)amino)ethyl, 2-((N-(3-morpholinopropylsulphonyl)-N-methyl)amino)ethyl, 2-((N-methyl-N-4-pyridyl)amino)ethyl, 3-(4-oxidomorpholino) propyl, 2-(2-(4-methylpiperazin-1-yl)ethoxy)ethyl, 3-(2-(4-methylpiperazin-1-yl)ethoxy)propyl, 2-(2-morpholinoethoxy)ethyl, 3-(2-morpholinoethoxy)propyl, 2-(tetrahydropyran-4-yloxy)ethyl, 3-(tetrahydropyran-4-yloxy)propyl, 2-((2-(pyrrolidin-1-yl)ethyl)carbamoyl)vinyl, 3-((2-(pyrrolidin-1-yl)ethyl)carbamoyl)prop-2-en-1-yl, 1-(2-pyrrolidinylethyl)piperidin-4-ylmethyl, 1-(3-pyrrolidinylpropyl)piperidin-4-ylmethyl, 1-(2-piperidinylethyl)piperidin-4-ylmethyl, 1-(3-piperidinylpropyl)piperidin-4-ylmethyl, 1-(2-morpholinoethyl)piperidin-4-ylmethyl, 1-(3-morpholinopropyl)piperidin-4-ylmethyl, 1-(2-thiomorpholinoethyl)piperidin-4-ylmethyl, 1-(3-thiomorpholinopropyl)piperidin-4-ylmethyl, 1-(2-azetidinylethyl)piperidin-4-ylmethyl or 1-(3-azetidinylpropyl)piperidin-4-ylmethyl, 3-morpholino-2-hydroxypropyl, (2R)-3-morpholino-2-hydroxypropyl, (2S)-3-morpholino-2-hydroxypropyl, 3-piperidino-2-hydroxypropyl, (2R)-3-piperidino-2-hydroxypropyl, (2S)-3-piperidino-2-hydroxypropyl, 3-pyrrolidin-1-yl-2-hydroxypropyl, (2R)-3-pyrrolidin-1-yl-2-hydroxypropyl, (2S)-3-pyrrolidin-1-yl-2-hydroxypropyl, 3-(1-methylpiperazin-4-yl)-2-hydroxypropyl, (2R)-3-(1-methylpiperazin-4-yl)-2-hydroxypropyl, (2S)-3-(1-methylpiperazin-4-yl)-2-hydroxypropyl, 3-(N,N-diethylamino)-2-hydroxypropyl, (2R)-3-(N,N-diethylamino)-2-hydroxypropyl, (2S)-3-(N,N-diethylamino)-2-hydroxypropyl, 3-(isopropylamino)-2-hydroxypropyl, (2R)-3-(isopropylamino)-2-hydroxypropyl, (2S)-3-(isopropylamino)-2-hydroxypropyl, 3-(N,N-diisopropylamino)-2-hydroxypropyl, (2R)-3-(N,N-diisopropylamino)-2-hydroxypropyl or (2S)-3-(N,N-diisopropylamino)-2-hydroxypropyl].

More particularly $R^2$ represents $C_{1-3}$alkyl, amino or $R^5X^1$— [wherein $X^1$ is as hereinbefore defined and $R^5$ represents ethyl, trifluoromethyl, 2,2,2-trifluoroethyl, 2-hydroxyethyl, 3-hydroxypropyl, 2-methoxyethyl, 3-methoxypropyl, 2-(methylsulphinyl)ethyl, 2-(methylsulphonyl)ethyl, 2-(ethylsulphinyl)ethyl, 2-(ethylsulphonyl)ethyl, 2-(N,N-dimethylsulphamoyl)ethyl, 2-(N-methylsulphamoyl)ethyl, 2-sulphamoylethyl, 2-(methylamino)ethyl, 3-(methylamino) propyl, 2-(ethylamino)ethyl, 3-(ethylamino)propyl, 2-(N,N-dimethylamino)ethyl, 3-(N,N-dimethylamino)propyl, 2-(N,N-diethylamino)ethyl, 3-(N,N-diethylamino)propyl, 2-(N-methyl-N-methylsulphonylamino)ethyl, 3-(N-methyl-N-methylsulphonylamino)propyl, 2-morpholinoethyl, 3-morpholinopropyl, 2-piperidinoethyl, 3-piperidinopropyl, 2-(methylpiperidino)ethyl, 3-(methylpiperidino)propyl, 2-(ethylpiperidino)ethyl, 3-(ethylpiperidino)propyl, 2-((2-methoxyethyl)piperidino)ethyl, 3-((2-methoxyethyl)piperidino)propyl, 2-((2-methylsulphonyl)ethylpiperidino)ethyl, 3-((2-methylsulphonyl)ethylpiperidino)propyl, piperidin-3-ylmethyl, piperidin-4-ylmethyl, 2-(piperidin-3-yl)ethyl, 2-(piperidin-4-yl)ethyl, 3-(piperidin-3-yl)propyl, 3-(piperidin-4-yl)propyl, 2-(piperidin-2-yl)propyl, 3-(piperidin-2-yl)propyl, (1-methylpiperidin-3-yl)methyl, (1-methylpiperidin-4-yl)methyl, (1-cyanomethylpiperidin-3-yl)methyl, (1-cyanomethylpiperidin-4-yl)methyl, 2-(methylpiperidin-3-yl)ethyl, 2-(methylpiperidin-4-yl)ethyl, 2-(1-cyanomethylpiperidin-3-yl)ethyl, 2-(1-cyanomethylpiperidin-4-yl) ethyl, 3-(methylpiperidin-3-yl)propyl, 3-(methylpiperidin-4-yl)propyl, 3-(1-cyanomethylpiperidin-3-yl)propyl, 3-(1-cyanomethylpiperidin-4-yl)propyl, 2-(ethylpiperidin-3-yl)

ethyl, 2-(ethylpiperidin-4-yl)ethyl, 3-(ethylpiperidin-3-yl)propyl, 3-(ethylpiperidin-4-yl)propyl, ((2-methoxyethyl)piperidin-3-yl)methyl, ((2-methoxyethyl)piperidin-4-yl)methyl, 2-((2-methoxyethyl)piperidin-3-yl)ethyl, 2-((2-methoxyethyl)piperidin-4-yl)ethyl, 3-((2-methoxyethyl)piperidin-3-yl)propyl, 3-((2-methoxyethyl)piperidin-4-yl)propyl, (1-(2-methylsulphonylethyl)piperidin-3-yl)methyl, (1-(2-methylsulphonylethyl)piperidin-4-yl)methyl, 2-((2-methylsulphonylethyl)piperidin-3-yl)ethyl, 2-((2-methylsulphonylethyl)piperidin-4-yl)ethyl, 3-((2-methylsulphonylethyl)piperidin-3-yl)propyl, 3-((2-methylsulphonylethyl)piperidin-4-yl)propyl, 1-isopropylpiperidin-2-ylmethyl, 1-isopropylpiperidin-3-ylmethyl, 1-isopropylpiperidin-4-ylmethyl, 2-(1-isopropylpiperidin-2-yl)ethyl, 2-(1-isopropylpiperidin-3-yl)ethyl, 2-(1-isopropylpiperidin-4-yl)ethyl, 3-(1-isopropylpiperidin-2-yl)propyl, 3-(1-isopropylpiperidin-3-yl)propyl, 3-(1-isopropylpiperidin-4-yl)propyl, 2-(piperidin-4-yloxy)ethyl, 3-(piperidin-4-yloxy)propyl, 2-(1-(cyanomethyl)piperidin-4-yloxy)ethyl, 3-(1-(cyanomethyl)piperidin-4-yloxy)propyl, 2-(1-(2-cyanoethyl)piperidin-4-yloxy)ethyl, 3-(1-(2-cyanoethyl)piperidin-4-yloxy)propyl, 2-(piperazin-1-yl)ethyl, 3-(piperazin-1-yl)propyl, (pyrrolidin-2-yl)methyl, 2-(pyrrolidin-1-yl)ethyl, 3-(pyrrolidin-1-yl)propyl, (2-oxo-tetrahydro-2H-pyrrolidin-5-yl)methyl, 5(R)-(2-oxo-tetrahydro-2H-pyrrolidin-5-yl)methyl, (5S)-(2-oxo-tetrahydro-2H-pyrrolidin-5-yl)methyl, (1,3-dioxolan-2-yl)methyl, 2-(1,3-dioxolan-2-yl)ethyl, 2-(2-methoxyethylamino)ethyl, 2-(N-(2-methoxyethyl)-N-methylamino)ethyl, 2-(2-hydroxyethylamino)ethyl, 3-(2-methoxyethylamino)propyl, 3-(N-(2-methoxyethyl)-N-methylamino)propyl, 3-(2-hydroxyethylamino)propyl, 2-(1,2,3-triazol-1-yl)ethyl, 2-(1,2,3-triazol-2-yl)ethyl, 2-(1,2,4-triazol-1-yl)ethyl, 2-(1,2,4-triazol-4-yl)ethyl, 4-pyridylmethyl, 2-(4-pyridyl)ethyl, 3-(4-pyridyl)propyl, 2-(4-pyridyloxy)ethyl, 2-(4-pyridylamino)ethyl, 2-(4-oxo-1,4-dihydro-1-pyridyl)ethyl, 2-(2-oxo-imidazolidin-1-yl)ethyl, 3-(2-oxo-imidazolidin-1-yl)propyl, 2-thiomorpholinoethyl, 3-thiomorpholinopropyl, 2-(1,1-dioxothiomorpholino)ethyl, 3-(1,1-dioxothiomorpholino)propyl, 2-(2-methoxyethoxy)ethyl, 2-(4-methylpiperazin-1-yl)ethyl, 3-(4-methylpiperazin-1-yl)propyl, 3-(methylsulphinyl)propyl, 3-(methylsulphonyl)propyl, 3-(ethylsulphinyl)propyl, 3-(ethylsulphonyl)propyl, 2-(5-methyl-1,2,4-triazol-1-yl)ethyl, morpholino, 2-((N-(3-morpholinopropylsulphonyl)-N-methyl)amino)ethyl, 2-((N-methyl-N⁴-pyridyl)amino)ethyl, 3-(4-oxidomorpholino)propyl, 2-(2-(4-methylpiperazin-1-yl)ethoxy)ethyl, 3-(2-(4-methylpiperazin-1-yl)ethoxy)propyl, 2-(2-morpholinoethoxy)ethyl, 3-(2-morpholinoethoxy)propyl, 2-(tetrahydropyran-4-yloxy)ethyl, 3-(tetrahydropyran-4-yloxy)propyl, 2-((2-(pyrrolidin-1-yl)ethyl)carbamoyl)vinyl, 3-((2-(pyrrolidin-1-yl)ethyl)carbamoyl)prop-2-en-1-yl, 1-(2-pyrrolidinylethyl)piperidin-4-ylmethyl, 1-(3-pyrrolidinylpropyl)piperidin-4-ylmethyl, 1-(2-piperidinylethyl)piperidin-4-ylmethyl, 1-(3-piperidinylpropyl)piperidin-4-ylmethyl, 1-(2-morpholinoethyl)piperidin-4-ylmethyl, 1-(3-morpholinopropyl)piperidin-4-ylmethyl, 1-(2-thiomorpholinoethyl)piperidin-4-ylmethyl, 1-(3-thiomorpholinopropyl)piperidin-4-ylmethyl, 1-(2-azetidinylethyl)piperidin-4-ylmethyl or 1-(3-azetidinylpropyl)piperidin-4-ylmethyl, 3-morpholino-2-hydroxypropyl, (2R)-3-morpholino-2-hydroxypropyl, (2S)-3-morpholino-2-hydroxypropyl, 3-piperidino-2-hydroxypropyl, (2R)-3-piperidino-2-hydroxypropyl, (2S)-3-piperidino-2-hydroxypropyl, 3-pyrrolidin-1-yl-2-hydroxypropyl, (2R)-3-pyrrolidin-1-yl-2-hydroxypropyl, (2S)-3-pyrrolidin-1-yl-2-hydroxypropyl, 3-(1-methylpiperazin-4-yl)-2-hydroxypropyl, (2R)-3-(1-methylpiperazin-4-yl)-2-hydroxypropyl, (2S)-3-(1-methylpiperazin-4-yl)-2-hydroxypropyl, 3-(N,N-diethylamino)-2-hydroxypropyl, (2R)-3-(N,N-diethylamino)-2-hydroxypropyl, (2S)-3-(N,N-diethylamino)-2-hydroxypropyl, 3-(isopropylamino)-2-hydroxypropyl, (2R)-3-(isopropylamino)-2-hydroxypropyl, (2S)-3-(isopropylamino)-2-hydroxypropyl, 3-(N,N-diisopropylamino)-2-hydroxypropyl, (2R)-3-(N,N-diisopropylamino)-2-hydroxypropyl or (2S)-3-(N,N-diisopropylamino)-2-hydroxypropyl].

In another aspect $R^2$ represents ethoxy, trifluoromethoxy, 2,2,2-trifluoroethoxy, 2-hydroxyethoxy, 3-hydroxypropoxy, 2-methoxyethoxy, 3-methoxypropoxy, 2-(methylsulphinyl)ethoxy, 2-(methylsulphonyl)ethoxy, 2-(ethylsulphinyl)ethoxy, 2-(ethylsulphonyl)ethoxy, 2-(N,N-dimethylsulphamoyl)ethoxy, 2-(N-methylsulphamoyl)ethoxy, 2-sulphamoylethoxy, 2-(methylamino)ethoxy, 3-(methylamino)propoxy, 2-(ethylamino)ethoxy, 3-(ethylamino)propoxy, 2-(N,N-dimethylamino)ethoxy, 3-(N,N-dimethylamino)propoxy, 2-(N,N-diethylamino)ethoxy, 3-(N,N-diethylamino)propoxy, 2-(N-methyl-N-methylsulphonylamino)ethoxy, 3-(N-methyl-N-methylsulphonylamino)propoxy, 2-morpholinoethoxy, 3-morpholinopropoxy, 2-piperidinoethoxy, 3-piperidinopropoxy, 2-(methylpiperidino)ethoxy, 3-(methylpiperidino)propoxy, 2-(ethylpiperidino)ethoxy, 3-(ethylpiperidino)propoxy, 2-((2-methoxyethyl)piperidino)ethoxy, 3-((2-methoxyethyl)piperidino)propoxy, 2-((2-methylsulphonyl)ethylpiperidino)ethoxy, 3-((2-methylsulphonyl)ethylpiperidino)propoxy, piperidin-3-ylmethoxy, piperidin-4-ylmethoxy, 2-(piperidin-3-yl)ethoxy, 2-(piperidin-4-yl)ethoxy, 3-(piperidin-3-yl)propoxy, 3-(piperidin-4-yl)propoxy, 2-(piperidin-2-yl)ethoxy, 3-(piperidin-2-yl)propoxy, (1-methylpiperidin-3-yl)methoxy, (1-methylpiperidin-4-yl)methoxy, (1-cyanomethylpiperidin-3-yl)methoxy, (1-cyanomethylpiperidin-4-yl)methoxy, 2-(methylpiperidin-3-yl)ethoxy, 2-(methylpiperidin-4-yl)ethoxy, 2-(1-cyanomethylpiperidin-3-yl)ethoxy, 2-(1-cyanomethylpiperidin-4-yl)ethoxy, 3-(methylpiperidin-3-yl)propoxy, 3-(methylpiperidin-4-yl)propoxy, 3-(1-cyanomethylpiperidin-3-yl)propoxy, 3-(1-cyanomethylpiperidin-4-yl)propoxy, 2-(ethylpiperidin-3-yl)ethoxy, 2-(ethylpiperidin-4-yl)ethoxy, 3-(ethylpiperidin-3-yl)propoxy, 3-(ethylpiperidin-4-yl)propoxy, ((2-methoxyethyl)piperidin-3-yl)methoxy, ((2-methoxyethyl)piperidin-4-yl)methoxy, 2-((2-methoxyethyl)piperidin-3-yl)ethoxy, 2-((2-methoxyethyl)piperidin-4-yl)ethoxy, 3-((2-methoxyethyl)piperidin-3-yl)propoxy, 3-((2-methoxyethyl)piperidin-4-yl)propoxy, (1-(2-methylsulphonylethyl)piperidin-3-yl)methoxy, (1-(2-methylsulphonylethyl)piperidin-4-yl)methoxy, 2-((2-methylsulphonylethyl)piperidin-3-yl)ethoxy, 2-((2-methylsulphonylethyl)piperidin-4-yl)ethoxy, 3-((2-methylsulphonylethyl)piperidin-3-yl)propoxy, 3-((2-methylsulphonylethyl)piperidin-4-yl)propoxy, 1-isopropylpiperidin-2-ylmethoxy, 1-isopropylpiperidin-3-ylmethoxy, 1-isopropylpiperidin-4-ylmethoxy, 2-(1-isopropylpiperidin-2-yl)ethoxy, 2-(1-isopropylpiperidin-3-yl)ethoxy, 2-(1-isopropylpiperidin-4-yl)ethoxy, 3-(1-isopropylpiperidin-2-yl)propoxy, 3-(1-isopropylpiperidin-3-yl)propoxy, 3-(1-isopropylpiperidin-4-yl)propoxy, 2-(piperidin-4-yloxy)ethoxy, 3-(piperidin-4-yloxy)propoxy, 2-(1-(cyanomethyl)piperidin-4-yloxy)ethoxy, 3-(1-(cyanomethyl)piperidin-4-yloxy)propoxy, 2-(1-(2-cyanoethyl)piperidin-4-yloxy)ethoxy, 3-(1-(2-cyanoethyl)piperidin-4-yloxy)propoxy, 2-(piperazin-1-yl)ethoxy, 3-(piperazin-1-yl)propoxy, (pyrrolidin-2-yl)methoxy, 2-(pyrrolidin-1-yl)ethoxy, 3-(pyrrolidin-1-yl)

propoxy, (2-oxo-tetrahydro-2H-pyrrolidin-5-yl)methoxy, 5(R)-(2-oxo-tetrahydro-2H-pyrrolidin-5-yl)methoxy, (5S)-(2-oxo-tetrahydro-2H-pyrrolidin-5-yl)methoxy, (1,3-dioxolan-2-yl)methoxy, 2-(1,3-dioxolan-2-yl)ethoxy, 2-(2-methoxyethylamino)ethoxy, 2-(N-(2-methoxyethyl)-N-methylamino)ethoxy, 2-(2-hydroxyethylamino)ethoxy, 3-(2-methoxyethylamino)propoxy, 3-(N-(2-methoxyethyl)-N-methylamino)propoxy, 3-(2-hydroxyethylamino)propoxy, 2-(1,2,3-triazol-1-yl)ethoxy, 2-(1,2,3-triazol-2-yl)ethoxy, 2-(1,2,4-triazol-1-yl)ethoxy, 2-(1,2,4-triazol-4-yl)ethoxy, 4-pyridylmethoxy, 2-(4-pyridyl)ethoxy, 3-(4-pyridyl)propoxy, 2-(4-pyridyloxy)ethoxy, 2-(4-pyridylamino)ethoxy, 2-(4-oxo-1,4-dihydro-1-pyridyl)ethoxy, 2-(2-oxo-imidazolidin-1-yl)ethoxy, 3-(2-oxo-imidazolidin-1-yl)propoxy, 2-thiomorpholinoethoxy, 3-thiomorpholinopropoxy, 2-(1,1-dioxothiomorpholino)ethoxy, 3-(1,1-dioxothiomorpholino)propoxy, 2-(2-methoxyethoxy)ethoxy, 2-(4-methylpiperazin-1-yl)ethoxy, 3-(4-methylpiperazin-1-yl)propoxy, 3-(methylsulphinyl)propoxy, 3-(methylsulphonyl)propoxy, 3-(ethylsulphinyl)propoxy, 3-(ethylsulphonyl)propoxy, 2-(5-methyl-1,2,4-triazol-1-yl)ethoxy, 2-((N-(3-morpholinopropyl)sulphonyl)-N-methyl)amino)ethoxy, 2-((N-methyl-N-4-pyridyl)amino)ethoxy, 3-(4-oxidomorpholino)propoxy, 2-(2-(4-methylpiperazin-1-yl)ethoxy)ethoxy, 3-(2-(4-methylpiperazin-1-yl)ethoxy)propoxy, 2-(2-morpholinoethoxy)ethoxy, 3-(2-morpholinoethoxy)propoxy, 2-(tetrahydropyran-4-yloxy)ethoxy, 3-(tetrahydropyran-4-yloxy)propoxy, 2-((2-(pyrrolidin-1-yl)ethyl)carbamoyl)vinyl, 3-((2-(pyrrolidin-1-yl)ethyl)carbamoyl)prop-2-en-1-yloxy, 1-(2-pyrrolidinylethyl)piperidin-4-ylmethoxy, 1-(3-pyrrolidinylpropyl)piperidin-4-ylmethoxy, 1-(2-piperidinylethyl)piperidin-4-ylmethoxy, 1-(3-piperidinylpropyl)piperidin-4-ylmethoxy, 1-(2-morpholinoethyl)piperidin-4-ylmethoxy, 1-(3-morpholinopropyl)piperidin-4-ylmethoxy, 1-(2-thiomorpholinoethyl)piperidin-4-ylmethoxy, 1-(3-thiomorpholinopropyl)piperidin-4-ylmethoxy, 1-(2-azetidinylethyl)piperidin-4-ylmethoxy or 1-(3-azetidinylpropyl)piperidin-4-ylmethoxy, 3-morpholino-2-hydroxypropoxy, (2R)-3-morpholino-2-hydroxypropoxy, (2S)-3-morpholino-2-hydroxypropoxy, 3-piperidino-2-hydroxypropoxy, (2R)-3-piperidino-2-hydroxypropoxy, (2S)-3-piperidino-2-hydroxypropoxy, 3-pyrrolidin-1-yl-2-hydroxypropoxy, (2R)-3-pyrrolidin-1-yl-2-hydroxypropoxy, (2S)-3-pyrrolidin-1-yl-2-hydroxypropoxy, 3-(1-methylpiperazin-4-yl)-2-hydroxypropoxy, (2R)-3-(1-methylpiperazin-4-yl)-2-hydroxypropoxy, (2S)-3-(1-methylpiperazin-4-yl)-2-hydroxypropoxy, 3-(N,N-diethylamino)-2-hydroxypropoxy, (2R)-3-(N,N-diethylamino)-2-hydroxypropoxy, (2S)-3-(N,N-diethylamino)-2-hydroxypropoxy, 3-(isopropylamino)-2-hydroxypropoxy, (2R)-3-(isopropylamino)-2-hydroxypropoxy, (2S)-3-(isopropylamino)-2-hydroxypropoxy, 3-(N,N-diisopropylamino)-2-hydroxypropoxy, (2R)-3-(N,N-diisopropylamino)-2-hydroxypropoxy or (2S)-3-(N,N-diisopropylamino)-2-hydroxypropoxy.

According to another aspect of the present invention conveniently $R^2$ represents hydroxy, halogeno, nitro, trifluoromethyl, $C_{1-3}$alkyl, cyano, amino or $R^5X^1$— [wherein $X^1$ is as hereinbefore defined and $R^5$ is selected from one of the following twenty-one groups:

1) $C_{1-5}$alkyl which may be unsubstituted or substituted with one or more fluorine atoms, or $C_{2-5}$alkyl which may be unsubstituted or substituted with one or more groups selected from hydroxy and amino;
2) $C_{2-3}$alkyl$X^2$C(O)$R^{11}$ (wherein $X^2$ is as hereinbefore defined and $R^{11}$ represents $C_{1-3}$alkyl, —$NR^{13}R^{14}$ or —$OR^{15}$ (wherein $R^{13}$, $R^{14}$ and $R^{15}$ which may be the same or different are each $C_{1-2}$alkyl or $C_{1-2}$alkoxyethyl));
3) $C_{2-4}$alkyl$X^3R^{16}$ (wherein $X^3$ is as hereinbefore defined and $R^{11}$ represents hydrogen, $C_{1-3}$alkyl, cyclopentyl, cyclohexyl or a 5-6-membered saturated heterocyclic group with 1-2 heteroatoms, selected independently from O, S and N, which $C_{1-3}$alkyl group may bear 1 or 2 substituents selected from oxo, hydroxy, halogeno and $C_{1-3}$alkoxy and which cyclic group may bear 1 or 2 substituents selected from oxo, hydroxy, halogeno, $C_{1-4}$alkyl, $C_{1-4}$hydroxyalkyl and $C_{1-4}$alkoxy);
4) $C_{2-3}$alkyl$X^4C_{2-3}$alkyl$X^5R^{22}$ (wherein $X^4$ and $X^5$ are as hereinbefore defined and $R^{22}$ represents hydrogen or $C_{1-3}$alkyl);
5) $C_{1-5}$alkyl$R^{129}$ (wherein $R^{129}$ is a 5-6-membered saturated heterocyclic group with 1-2 heteroatoms, selected independently from O, S and N, which heterocyclic group is linked to $C_{1-5}$alkyl through a carbon atom and which heterocyclic group may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl and $C_{1-4}$alkylsulphonyl$C_{1-4}$alkyl) or $C_{2-5}$alkyl$R^{130}$ (wherein $R^{130}$ is a 5-6-membered saturated heterocyclic group with 1-2 heteroatoms of which one is N and the other is selected independently from O, S and N, which heterocyclic group is linked to $C_{2-5}$alkyl through a nitrogen atom and which heterocyclic group may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl and $C_{1-4}$alkylsulphonyl$C_{1-4}$alkyl);
6) $C_{3-4}$alkenyl$R^{131}$ (wherein $R^{131}$ represents $R^{129}$ or $R^{130}$ as defined hereinbefore);
7) $C_{3-4}$alkynyl$R^{131}$ (wherein $R^{131}$ represents $R^{129}$ or $R^{139}$ as defined hereinbefore);
8) $R^{29}$ (wherein $R^{29}$ is as defined hereinbefore);
9) $C_{1-5}$alkyl$R^{29}$ (wherein $R^{29}$ is as defined hereinbefore);
10) $C_{3-5}$alkenyl$R^{29}$ (wherein $R^{29}$ is as defined hereinbefore);
11) $C_{3-5}$alkynyl$R^{29}$ (wherein $R^{29}$ is as defined hereinbefore);
12) $C_{1-5}$alkyl$X^6R^{29}$ (wherein $X^6$ and $R^{29}$ are as defined hereinbefore);
13) $C_{4-5}$alkenyl$X^7R^{29}$ (wherein $X^7$ and $R^{29}$ are as defined hereinbefore);
14) $C_{4-5}$alkynyl$X^8R^{29}$ (wherein $X^8$ and $R^{29}$ are as defined hereinbefore);
15) $C_{2-3}$alkyl$X^9C_{1-2}$alkyl$R^{29}$ (wherein $X^9$ and $R^{29}$ are as defined hereinbefore);
16) $R^{28}$ (wherein $R^{28}$ is as defined hereinbefore);
17) $C_{2-3}$alkyl$X^9C_{1-2}$alkyl$R^{28}$ (wherein $X^9$ and $R^{28}$ are as defined hereinbefore);
18) $C_{2-5}$alkenyl which may be unsubstituted or which may be substituted with one or more groups selected from hydroxy, fluoro, amino, $C_{1-4}$alkylamino, N,N-di($C_{1-4}$alkyl)amino, aminosulphonyl, N—$C_{1-4}$alkylaminosulphonyl and N,N-di($C_{1-4}$alkyl)aminosulphonyl;
19) $C_{2-5}$alkynyl which may be unsubstituted or which may be substituted with one or more groups selected from hydroxy, fluoro, amino, $C_{1-4}$alkylamino, N,N-di($C_{1-4}$alkyl)amino, aminosulphonyl, N—$C_{1-4}$alkylaminosulphonyl and N,N-di($C_{1-4}$alkyl)aminosulphonyl;
20) $C_{2-5}$alkenyl$X^9C_{1-3}$alkyl$R^{28}$ (wherein $X^9$ and $R^{28}$ are as defined hereinbefore); and
21) $C_{2-5}$alkynyl$X^9C_{1-3}$alkyl$R^{28}$ (wherein $X^9$ and $R^{28}$ are as defined hereinbefore)].

According to another aspect of the present invention advantageously $R^2$ represents hydroxy, halogeno, nitro, trifluoromethyl, $C_{1-3}$alkyl, cyano, amino or $R^5X^1$— [wherein $X^1$ is as hereinbefore defined and $R^5$ is selected from one of the following twenty-one groups:

1) $C_{1-4}$alkyl which may be unsubstituted or substituted with one or more fluorine atoms, or $C_{2-4}$alkyl which may be unsubstituted or substituted with 1 or 2 groups selected from hydroxy and amino;
2) $C_{2-3}$alkyl$X^2C(O)R^{11}$ (wherein $X^2$ is as hereinbefore defined and $R^{11}$ represents —$NR^{13}R^{14}$ or —$OR^{15}$ (wherein $R^{13}$, $R^{14}$ and $R^{15}$ which may be the same or different are each $C_{1-2}$alkyl or $C_{1-2}$alkoxyethyl));
3) $C_{2-4}$alkyl$X^3R^{16}$ (wherein $X^3$ is as hereinbefore defined and $R^{16}$ is a group selected from $C_{1-3}$alkyl, cyclopentyl, cyclohexyl, pyrrolidinyl, piperidinyl and tetrahydropyranyl which group is linked to $X^3$ through a carbon atom and which $C_{1-3}$alkyl group may bear 1 or 2 substituents selected from oxo, hydroxy, halogeno and $C_{1-2}$alkoxy and which cyclopentyl, cyclohexyl, pyrrolidinyl or piperidinyl group may carry one substituent selected from oxo, hydroxy, halogeno, $C_{1-2}$alkyl, $C_{1-2}$hydroxyalkyl and $C_{1-2}$alkoxy);
4) $C_{2-3}$alkyl$X^4C_{2-3}$alkyl$X^5R^{22}$ (wherein $X^4$ and $X^5$ are as hereinbefore defined and $R^{22}$ represents hydrogen or $C_{1-3}$alkyl);
5) $C_{1-4}$alkyl$R^{132}$ (wherein $R^{132}$ is a group selected from pyrrolidinyl, piperazinyl, piperidinyl, 1,3-dioxolan-2-yl, 1,3-dioxan-2-yl, 1,3-dithiolan-2-yl and 1,3-dithian-2-yl, which group is linked to $C_{1-4}$alkyl through a carbon atom and which group may carry 1 or 2 substituents selected from oxo, hydroxy, halogeno, cyano, $C_{1-3}$cyanoalkyl, $C_{1-3}$alkyl, $C_{1-3}$hydroxyalkyl, $C_{1-3}$alkoxy, $C_{1-2}$alkoxy$C_{1-3}$alkyl and $C_{1-2}$alkylsulphonyl$C_{1-3}$alkyl) or $C_{2-4}$alkyl$R^{133}$ (wherein $R^{133}$ is a group selected from morpholino, thiomorpholino, pyrrolidin-1-yl, piperazin-1-yl and piperidino which group may carry 1 or 2 substituents selected from oxo, hydroxy, halogeno, cyano, $C_{1-3}$cyanoalkyl, $C_{1-3}$alkyl, $C_{1-3}$hydroxyalkyl, $C_{1-3}$alkoxy, $C_{1-2}$alkoxy$C_{1-3}$alkyl and $C_{1-2}$alkylsulphonyl$C_{1-3}$alkyl);
6) $C_{3-4}$alkenyl$R^{134}$ (wherein $R^{134}$ represents $R^{132}$ or $R^{133}$ as defined hereinbefore);
7) $C_{3-4}$alkynyl$R^{134}$ (wherein $R^{134}$ represents $R^{132}$ or $R^{133}$ as defined hereinbefore);
8) $R^{29}$ (wherein $R^{29}$ is as defined hereinbefore);
9) $C_{1-4}$alkyl$R^{29}$ (wherein $R^{29}$ is as defined hereinbefore);
10) 1-$R^{29}$prop-1-en-3-yl or 1-$R^{29}$but-2-en-4-yl (wherein $R^{29}$ is as defined hereinbefore with the proviso that when $R^5$ is 1-$R^{29}$prop-1-en-3-yl, $R^{29}$ is linked to the alkenyl group via a carbon atom);
11) 1-$R^{29}$prop-1-yn-3-yl or 1-$R^{29}$but-2-yn-4-yl (wherein $R^{29}$ is as defined hereinbefore with the proviso that when $R^5$ is 1-$R^{29}$prop-1-yn-3-yl, $R^{29}$ is linked to the alkynyl group via a carbon atom);
12) $C_{1-5}$alkyl$X^6R^{29}$ (wherein $X^6$ and $R^{29}$ are as defined hereinbefore);
13) 1-($R^{29}X^7$)but-2-en-4-yl (wherein $X^7$ and $R^{29}$ are as defined hereinbefore);
14) 1-($R^{29}X^8$)but-2-yn-4-yl (wherein $X^8$ and $R^{29}$ are as defined hereinbefore);
15) $C_{2-3}$alkyl$X^9C_{1-2}$alkyl$R^{29}$ (wherein $X^9$ and $R^{29}$ are as defined hereinbefore);
16) $R^{28}$ (wherein $R^{28}$ is as defined hereinbefore);
17) $C_{2-3}$alkyl$X^9C_{1-2}$alkyl$R^{28}$ (wherein $X^9$ and $R^{28}$ are as defined hereinbefore);
18) $C_{2-5}$alkenyl which may be unsubstituted or which may be substituted with one or more fluorine atoms or with one or two groups selected from hydroxy, amino, $C_{1-4}$alkylamino, N,N-di($C_{1-4}$alkyl)amino, aminosulphonyl, N—$C_{1-4}$alkylaminosulphonyl and N,N-di($C_{1-4}$alkyl)aminosulphonyl;
19) $C_{2-5}$alkynyl which may be unsubstituted or which may be substituted with one or more fluorine atoms or with one or two groups selected from hydroxy, amino, $C_{1-4}$alkylamino, N,N-di($C_{1-4}$alkyl)amino, aminosulphonyl, N—$C_{1-4}$alkylaminosulphonyl and N,N-di($C_{1-4}$alkyl)aminosulphonyl;
20) $C_{2-4}$alkenyl$X^9C_{1-3}$alkyl$R^{28}$ (wherein $X^9$ and $R^{28}$ are as defined hereinbefore); and
21) $C_{2-4}$alkynyl$X^9C_{1-3}$alkyl$R^{28}$ (wherein $X^9$ and $R^{28}$ are as defined hereinbefore)].

According to another aspect of the present invention preferably $R^2$ represents hydroxy, halogeno, nitro, trifluoromethyl, $C_{1-3}$alkyl, cyano, amino or $R^5X^1$— [wherein $X^1$ is as hereinbefore defined and $R^5$ is selected from one of the following nineteen groups:

1) $C_{1-3}$alkyl which may be unsubstituted or substituted with one or more fluorine atoms, or $C_{2-3}$alkyl which may be unsubstituted or substituted with 1 or 2 groups selected from hydroxy and amino;
2) 2-(3,3-dimethylureido)ethyl, 3-(3,3-dimethylureido)propyl, 2-(3-methylureido)ethyl, 3-(3-methylureido)propyl, 2-ureidoethyl, 3-ureidopropyl, 2-(N,N-dimethylcarbamoyloxy)ethyl, 3-(N,N-dimethylcarbamoyloxy)propyl, 2-(N-methylcarbamoyloxy)ethyl, 3-(N-methylcarbamoyloxy)propyl, 2-(carbamoyloxy)ethyl, 3-(carbamoyloxy)propyl;
3) $C_{2-3}$alkyl$X^3R^{16}$ (wherein $X^3$ is as defined hereinbefore and $R^{16}$ is a group selected from $C_{1-2}$alkyl, cyclopentyl, cyclohexyl, pyrrolidinyl, piperidinyl and tetrahydropyranyl which group is linked to $X^3$ through a carbon atom and which $C_{1-2}$alkyl group may bear 1 or 2 substituents selected from hydroxy, halogeno and $C_{1-2}$alkoxy and which cyclopentyl, cyclohexyl, pyrrolidinyl or piperidinyl group may carry one substituent selected from oxo, hydroxy, halogeno, $C_{1-2}$alkyl, $C_{1-2}$hydroxyalkyl and $C_{1-2}$alkoxy);
4) $C_{2-3}$alkyl$X^4C_{2-3}$alkyl$X^5R^{22}$ (wherein $X^4$ and $X^5$ are as hereinbefore defined and $R^{22}$ represents hydrogen or $C_{1-2}$alkyl);
5) $C_{1-2}$alkyl$R^{132}$ (wherein $R^{132}$ is a group selected from pyrrolidinyl, piperazinyl, piperidinyl, 1,3-dioxolan-2-yl, 1,3-dioxan-2-yl, 1,3-dithiolan-2-yl and 1,3-dithian-2-yl, which group is linked to $C_{1-2}$alkyl through a carbon atom and which group may carry one substituent selected from oxo, hydroxy, halogeno, cyano, $C_{1-3}$cyanoalkyl, $C_{1-3}$alkyl, $C_{1-3}$hydroxyalkyl, $C_{1-3}$alkoxy, $C_{1-2}$alkoxy$C_{1-3}$alkyl and $C_{1-2}$alkylsulphonyl$C_{1-3}$alkyl) or $C_{2-3}$alkyl$R^{133}$ (wherein $R^{133}$ is a group selected from morpholino, thiomorpholino, piperidino, piperazin-1-yl and pyrrolidin-1-yl which group may carry one or two substituents selected from oxo, hydroxy, halogeno, cyano, $C_{1-3}$cyanoalkyl, $C_{1-3}$alkyl, $C_{1-3}$hydroxyalkyl, $C_{1-3}$alkoxy, $C_{1-2}$alkoxy$C_{1-3}$alkyl and $C_{1-2}$alkylsulphonyl$C_{1-3}$alkyl);
6) $R^{29}$ (wherein $R^{29}$ is as defined hereinbefore);
7) $C_{1-4}$alkyl$R^{29}$ (wherein $R^{29}$ is as defined hereinbefore);
8) 1-$R^{29}$but-2-en-4-yl (wherein $R^{29}$ is as defined hereinbefore);
9) 1-$R^{29}$but-2-yn-4-yl (wherein $R^{29}$ is as defined hereinbefore);
10) $C_{1-5}$alkyl$X^6R^{29}$ (wherein $X^6$ and $R^{29}$ are as defined hereinbefore);
11) 1-($R^{29}X^7$)but-2-en-4-yl (wherein $X^7$ and $R^{29}$ are as defined hereinbefore);
12) 1-($R^{29}X^8$)but-2-yn-4-yl (wherein $X^8$ and $R^{29}$ are as defined hereinbefore);

13) ethylX$^9$-methylR$^{29}$ (wherein X$^9$ and R$^{29}$ are as defined hereinbefore);
14) R$^{28}$ (wherein R$^{28}$ is as defined hereinbefore);
15) ethylX$^9$C$_{1-2}$alkylR$^{28}$ (wherein X$^9$ and R$^{28}$ are as defined hereinbefore);
16) C$_{2-5}$alkenyl which may be unsubstituted or which may be substituted with one or more fluorine atoms or with one or two groups selected from hydroxy, amino, C$_{1-4}$alkylamino, N,N-di(C$_{1-4}$alkyl)amino, aminosulphonyl, N—C$_{1-4}$alkylaminosulphonyl and N,N-di(C$_{1-4}$alkyl)aminosulphonyl;
17) C$_{2-5}$alkynyl which may be unsubstituted or which may be substituted with one or more fluorine atoms or with one or two groups selected from hydroxy, amino, C$_{1-4}$alkylamino, N,N-di(C$_{1-4}$alkyl)amino, aminosulphonyl, N—C$_{1-4}$alkylaminosulphonyl and N,N-di(C$_{1-4}$alkyl)aminosulphonyl;
18) C$_{2-3}$alkenylX$^9$C$_{1-3}$alkylR$^{28}$ (wherein X$^9$ and R$^{28}$ are as defined hereinbefore); and
19) C$_{2-3}$alkynylX$^9$C$_{1-3}$alkylR$^{28}$ (wherein X$^9$ and R$^{28}$ are as defined hereinbefore)].

According to another aspect of the present invention more preferably R$^2$ represents hydroxy, C$_{1-3}$alkyl, amino or R$^5$X$^1$— [wherein X$^1$ is as hereinbefore defined and R$^5$ represents methyl, ethyl, benzyl, trifluoromethyl, 2,2,2-trifluoroethyl, 2-hydroxyethyl, 3-hydroxypropyl, 2-methoxyethyl, 3-methoxypropyl, 2-(methylsulphinyl)ethyl, 2-(methylsulphonyl)ethyl, 2-(N,N-dimethylsulphamoyl)ethyl, 2-(N-methylsulphamoyl)ethyl, 2-sulphamoylethyl, 2-(N,N-dimethylamino)ethyl, 3-(N,N-dimethylamino)propyl, 2-morpholinoethyl, 3-morpholinopropyl, 2-piperidinoethyl, 3-piperidinopropyl, 2-(methylpiperidino)ethyl, 3-(methylpiperidino)propyl, 2-(ethylpiperidino)ethyl, 3-(ethylpiperidino)propyl, 2-((2-methoxyethyl)piperidino)ethyl, 3-((2-methoxyethyl)piperidino)propyl, 2-((2-methylsulphonyl)ethylpiperidino)ethyl, 3-((2-methylsulphonyl)ethylpiperidino)propyl, piperidin-3-ylmethyl, piperidin-4-ylmethyl, 2-(piperidin-3-yl)ethyl, 2-(piperidin-4-yl)ethyl, 3-(piperidin-3-yl)propyl, 3-(piperidin-4-yl)propyl, (1-methylpiperidin-3-yl)methyl, (1-methylpiperidin-4-yl)methyl, (1-cyanomethylpiperidin-3-yl)methyl, (1-cyanomethylpiperidin-4-yl)methyl, 2-(methylpiperidin-3-yl)ethyl, 2-(methylpiperidin-4-yl)ethyl, 2-(1-cyanomethylpiperidin-3-yl)ethyl, 2-(1-cyanomethylpiperidin-4-yl)ethyl, 3-(methylpiperidin-3-yl)propyl, 3-(methylpiperidin-4-yl)propyl, 3-(1-cyanomethylpiperidin-3-yl)propyl, 3-(1-cyanomethylpiperidin-4-yl)propyl, 2-(ethylpiperidin-3-yl)ethyl, 2-(ethylpiperidin-4-yl)ethyl, 3-(ethylpiperidin-3-yl)propyl, 3-(ethylpiperidin-4-yl)propyl, ((2-methoxyethyl)piperidin-3-yl)methyl, ((2-methoxyethyl)piperidin-4-yl)methyl, 2-((2-methoxyethyl)piperidin-3-yl)ethyl, 2-((2-methoxyethyl)piperidin-4-yl)ethyl, 3-((2-methoxyethyl)piperidin-3-yl)propyl, 3-((2-methoxyethyl)piperidin-4-yl)propyl, (1-(2-methylsulphonylethyl)piperidin-3-yl)methyl, (1-(2-methylsulphonylethyl)piperidin-4-yl)methyl, 2-((2-methylsulphonylethyl)piperidin-3-yl)ethyl, 2-((2-methylsulphonylethyl)piperidin-4-yl)ethyl, 3-((2-methylsulphonylethyl)piperidin-3-yl)propyl, 3-((2-methylsulphonylethyl)piperidin-4-yl)propyl, 1-isopropylpiperidin-2-ylmethyl, 1-isopropylpiperidin-3-ylmethyl, 1-isopropylpiperidin-4-ylmethyl, 2-(1-isopropylpiperidin-2-yl)ethyl, 2-(1-isopropylpiperidin-3-yl)ethyl, 2-(1-isopropylpiperidin-4-yl)ethyl, 3-(1-isopropylpiperidin-2-yl)propyl, 3-(1-isopropylpiperidin-3-yl)propyl, 3-(1-isopropylpiperidin-4-yl)propyl, 2-(piperazin-1-yl)ethyl, 3-(piperazin-1-yl)propyl, (pyrrolidin-2-yl)methyl, 2-(pyrrolidin-1-yl)ethyl, 3-(pyrrolidin-1-yl)propyl, (2-oxo-tetrahydro-2H-pyrrolidin-5-yl)methyl, (1,3-dioxolan-2-yl)methyl, 2-(1,3-dioxolan-2-yl)ethyl, 2-(2-methoxyethylamino)ethyl, 2-(N-(2-methoxyethyl)-N-methylamino)ethyl, 2-(2-hydroxyethylamino) ethyl, 3-(2-methoxyethylamino)propyl, 3-(N-(2-methoxyethyl)-N-methylamino)propyl, 3-(2-hydroxyethylamino)propyl, 2-methylthiazol-4-ylmethyl, 2-acetamidothiazol-4-ylmethyl, 1-methylimidazol-2-ylmethyl, 2-(imidazol-1-yl)ethyl, 2-(2-methylimidazol-1-yl)ethyl, 2-(2-ethylimidazol-1-yl)ethyl, 3-(2-methylimidazol-1-yl)propyl, 3-(2-ethylimidazol-1-yl)propyl, 2-(1,2,3-triazol-1-yl)ethyl, 2-(1,2,3-triazol-2-yl)ethyl, 2-(1,2,4-triazol-1-yl)ethyl, 2-(1,2,4-triazol-4-yl)ethyl, 4-pyridylmethyl, 2-(4-pyridyl)ethyl, 3-(4-pyridyl)propyl, 2-(4-pyridyloxy)ethyl, 2-(4-pyridylamino)ethyl, 2-(4-oxo-1,4-dihydro-1-pyridyl)ethyl, 2-thiomorpholinoethyl, 3-thiomorpholinopropyl, 2-(1,1-dioxothiomorpholino)ethyl, 3-(1,1-dioxothiomorpholino)propyl, 2-(2-methoxyethoxy)ethyl, 2-(4-methylpiperazin-1-yl)ethyl, 3-(4-methylpiperazin-1-yl)propyl, 3-(methylsulphinyl)propyl, 3-(methylsulphonyl)propyl, 2-(5-methyl-1,2,4-triazol-1-yl)ethyl, morpholino, 2-((N-(1-methylimidazol-4-ylsulphonyl)-N-methyl)amino)ethyl, 24(N-(3-morpholinopropylsulphonyl)-N-methyl)amino)ethyl, 2-((N-methyl-N-4-pyridyl)amino)ethyl, 3-(4-oxidomorpholino)propyl, 2-(2-(4-methylpiperazin-1-yl)ethoxy)ethyl, 3-(2-(4-methylpiperazin-1-yl)ethoxy)propyl, 2-(2-morpholinoethoxy)ethyl, 3-(2-morpholinoethoxy)propyl, 2-(tetrahydropyran-4-yloxy)ethyl, 3-(tetrahydropyran-4-yloxy)propyl, 2-((2-(pyrrolidin-1-yl)ethyl)carbamoyl)vinyl or 3-((2-(pyrrolidin-1-yl)ethyl)carbamoyl)prop-2-en-1-yl].

According to another aspect of the present invention particularly R$^2$ represents C$_{1-3}$alkyl, amino or R$^5$X$^1$— [wherein X$^1$ is as hereinbefore defined and R$^5$ represents ethyl, benzyl, trifluoromethyl, 2,2,2-trifluoroethyl, 2-hydroxyethyl, 3-hydroxypropyl, 2-methoxyethyl, 3-methoxypropyl, 2-(methylsulphinyl)ethyl, 2-(methylsulphonyl)ethyl, 2-(N,N-dimethylsulphamoyl)ethyl, 2-(N-methylsulphamoyl)ethyl, 2-sulphamoylethyl, 2-(N,N-dimethylamino)ethyl, 3-(N,N-dimethylamino)propyl, 2-morpholinoethyl, 3-morpholinopropyl, 2-piperidinoethyl, 3-piperidinopropyl, 2-(methylpiperidino)ethyl, 3-(methylpiperidino)propyl, 2-(ethylpiperidino)ethyl, 3-(ethylpiperidino)propyl, 2-((2-methoxyethyl)piperidino)ethyl, 3-((2-methoxyethyl)piperidino)propyl, 24(2-methylsulphonyethylpiperidino)ethyl, 3-((2-methylsulphonyl)ethylpiperidino)propyl, piperidin-3-ylmethyl, piperidin-4-ylmethyl, 2-(piperidin-3-yl)ethyl, 2-(piperidin-4-yl)ethyl, 3-(piperidin-3-yl)propyl, 3-(piperidin-4-yl)propyl, (1-methylpiperidin-3-yl)methyl, (1-methylpiperidin-4-yl)methyl, (1-cyanomethylpiperidin-3-yl)methyl, (1-cyanomethylpiperidin-4-yl)methyl, 2-(methylpiperidin-3-yl)ethyl, 2-(methylpiperidin-4-yl)ethyl, 2-(1-cyanomethylpiperidin-3-yl)ethyl, 2-(1-cyanomethylpiperidin-4-yl)ethyl, 3-(methylpiperidin-3-yl)propyl, 3-(methylpiperidin-4-yl)propyl, 3-(1-cyanomethylpiperidin-3-yl)propyl, 3-(1-cyanomethylpiperidin-4-yl)propyl, 2-(ethylpiperidin-3-yl)ethyl, 2-(ethylpiperidin-4-yl)ethyl, 3-(ethylpiperidin-3-yl)propyl, 3-(ethylpiperidin-4-yl)propyl, ((2-methoxyethyl)piperidin-3-yl)methyl, ((2-methoxyethyl)piperidin-4-yl)methyl, 2-((2-methoxyethyl)piperidin-3-yl)ethyl, 2-((2-methoxyethyl)piperidin-4-yl)ethyl, 3-((2-methoxyethyl)piperidin-3-yl)propyl, 3-((2-methoxyethyl)piperidin-4-yl)propyl, (1-(2-methylsulphonylethyl)piperidin-3-yl)methyl, (1-(2-methylsulphonylethyl)piperidin-4-yl)methyl, 2-((2-methylsulphonylethyl)piperidin-3-yl)ethyl, 2-((2-methylsulphonylethyl)piperidin-4-yl)ethyl, 3-((2-methylsulphonylethyl)piperidin-3-yl)propyl, 3-((2-methylsulphonylethyl)piperidin-4-yl)propyl, 1-isopropylpiperidin-2-ylmethyl, 1-isopropylpiperidin-3-ylmethyl, 1-isopropylpiperidin-4-ylmethyl, 2-(1-isopropylpiperidin-2-yl)ethyl, 2-(1-isopropylpiperidin-3-yl)ethyl, 2-(1-isopropylpiperidin-4-yl)ethyl, 3-(1-isopropylpiperidin-2-yl)

propyl, 3-(1-isopropylpiperidin-3-yl)propyl, 3-(1-isopropylpiperidin-4-yl)propyl, 2-(piperazin-1-yl)ethyl, 3-(piperazin-1-yl)propyl, (pyrrolidin-2-yl)methyl, 2-(pyrrolidin-1-yl)ethyl, 3-(pyrrolidin-1-yl)propyl, (2-oxo-tetrahydro-2H-pyrrolidin-5-yl)methyl, (1,3-dioxolan-2-yl)methyl, 2-(1,3-dioxolan-2-yl)ethyl, 2-(2-methoxyethylamino)ethyl, 2-(N-(2-methoxyethyl)-N-methylamino)ethyl, 2-(2-hydroxyethylamino)ethyl, 3-(2-methoxyethylamino)propyl, 3-(N-(2-methoxyethyl)-N-methylamino)propyl, 3-(2-hydroxyethylamino)propyl, 2-methylthiazol-4-ylmethyl, 2-acetamidothiazol-4-ylmethyl, 1-methylimidazol-2-ylmethyl, 2-(imidazol-1-yl)ethyl, 2-(2-methylimidazol-1-yl)ethyl, 2-(2-ethylimidazol-1-yl)ethyl, 3-(2-methylimidazol-1-yl)propyl, 3-(2-ethylimidazol-1-yl)propyl, 2-(1,2,3-triazol-1-yl)ethyl, 2-(1,2,3-triazol-2-yl)ethyl, 2-(1,2,4-triazol-1-yl)ethyl, 2-(1,2,4-triazol-4-yl)ethyl, 4-pyridylmethyl, 2-(4-pyridyl)ethyl, 3-(4-pyridyl)propyl, 2-(4-pyridyloxy)ethyl, 2-(4-pyridylamino)ethyl, 2-(4-oxo-1,4-dihydro-1-pyridyl)ethyl, 2-thiomorpholinoethyl, 3-thiomorpholinopropyl, 2-(1,1-dioxothiomorpholino)ethyl, 3-(1,1-dioxothiomorpholino)propyl, 2-(2-methoxyethoxy)ethyl, 2-(4-methylpiperazin-1-yl)ethyl, 3-(4-methylpiperazin-1-yl)propyl, 3-(methylsulphinyl)propyl, 3-(methylsulphonyl)propyl, 2-(5-methyl-1,2,4-triazol-1-yl)ethyl, morpholino, 2-((N-(1-methylimidazol-4-ylsulphonyl)-N-methyl)amino)ethyl, 2-((N-(3-morpholinopropylsulphonyl)-N-methyl)amino)ethyl, 2-((N-methyl-N-4-pyridyl)amino)ethyl, 3-(4-oxidomorpholino)propyl, 2-(2-(4-methylpiperazin-1-yl)ethoxy)ethyl, 3-(2-(4-methylpiperazin-1-yl)ethoxy)propyl, 2-(2-morpholinoethoxy)ethyl, 3-(2-morpholinoethoxy)propyl, 2-(tetrahydropyran-4-yloxy)ethyl, 3-(tetrahydropyran-4-yloxy)propyl, 2((2-(pyrrolidin-1-yl)ethyl)carbamoyl)vinyl or 3-((2-(pyrrolidin-1-yl)ethyl)carbamoyl)prop-2-en-1-yl].

According to another aspect of the present invention more particularly $R^2$ represents $C_{1-3}$alkyl, amino or $R^5X^1$— [wherein $X^1$ is as hereinbefore defined and $R^5$ represents ethyl, trifluoromethyl, 2,2,2-trifluoroethyl, 2-hydroxyethyl, 3-hydroxypropyl, 2-methoxyethyl, 3-methoxypropyl, 2-(methylsulphinyl)ethyl, 2-(methylsulphonyl)ethyl, 2-(N,N-dimethylsulphamoyl)ethyl, 2-(N-methylsulphamoyl)ethyl, 2-sulphamoylethyl, 2-(N,N-dimethylamino)ethyl, 3-(N,N-dimethylamino)propyl, 2-morpholinoethyl, 3-morpholinopropyl, 2-piperidinoethyl, 3-piperidinopropyl, 2-(methylpiperidino)ethyl, 3-(methylpiperidino)propyl, 2-(ethylpiperidino)ethyl, 3-(ethylpiperidino)propyl, 2-((2-methoxyethyl)piperidino)ethyl, 3-((2-methoxyethyl)piperidino)propyl, 2-((2-methylsulphonyl)ethylpiperidino)ethyl, 3-((2-methylsulphonyl)ethylpiperidino)propyl, piperidin-3-ylmethyl, piperidin-4-ylmethyl, 2-(piperidin-3-yl)ethyl, 2-(piperidin-4-yl)ethyl, 3-(piperidin-3-yl)propyl, 3-(piperidin-4-yl)propyl, (1-methylpiperidin-3-yl)methyl, (1-methylpiperidin-4-yl)methyl, (1-cyanomethylpiperidin-3-yl)methyl, (1-cyanomethylpiperidin-4-yl)methyl, 2-(methylpiperidin-3-yl)ethyl, 2-(methylpiperidin-4-yl)ethyl, 2-(1-cyanomethylpiperidin-3-yl)ethyl, 2-(1-cyanomethylpiperidin-4-yl)ethyl, 3-(methylpiperidin-3-yl)propyl, 3-(methylpiperidin-4-yl)propyl, 3-(1-cyanomethylpiperidin-3-yl)propyl, 3-(1-cyanomethylpiperidin-4-yl)propyl, 2-(ethylpiperidin-3-yl)ethyl, 2-(ethylpiperidin-4-yl)ethyl, 3-(ethylpiperidin-3-yl)propyl, 3-(ethylpiperidin-4-yl)propyl, ((2-methoxyethyl)piperidin-3-yl)methyl, ((2-methoxyethyl)piperidin-4-yl)methyl, 2((2-methoxyethyl)piperidin-3-yl)ethyl, 2-((2-methoxyethyl)piperidin-4-yl)ethyl, 3((2-methoxyethyl)piperidin-3-yl)propyl, 3-((2-methoxyethyl)piperidin-4-yl)propyl, (1-(2-methylsulphonylethyl)piperidin-3-yl)methyl, (1-(2-methylsulphonylethyl)piperidin-4-yl)methyl, 2-((2-methylsulphonylethyl)piperidin-3-yl)ethyl, 2-((2-methylsulphonylethyl)piperidin-4-yl)ethyl, 3-((2-methylsulphonylethyl)piperidin-3-yl)propyl, 3-((2-methylsulphonylethyl)piperidin-4-yl)propyl, 1-isopropylpiperidin-2-ylmethyl, 1-isopropylpiperidin-3-ylmethyl, 1-isopropylpiperidin-4-ylmethyl, 2-(1-isopropylpiperidin-2-yl)ethyl, 2-(1-isopropylpiperidin-3-yl)ethyl, 2-(1-isopropylpiperidin-4-yl)ethyl, 3-(1-isopropylpiperidin-2-yl)propyl, 3-(1-isopropylpiperidin-3-yl)propyl, 3-(1-isopropylpiperidin-4-yl)propyl, 2-(piperazin-1-yl)ethyl, 3-(piperazin-1-yl)propyl, (pyrrolidin-2-yl)methyl, 2-(pyrrolidin-1-yl)ethyl, 3-(pyrrolidin-1-yl)propyl, (2-oxo-tetrahydro-2H-pyrrolidin-5-yl)methyl, (1,3-dioxolan-2-yl)methyl, 2-(1,3-dioxolan-2-yl)ethyl, 2-(2-methoxyethylamino)ethyl, 2-(N-(2-methoxyethyl)-N-methylamino)ethyl, 2-(2-hydroxyethylamino)ethyl, 3-(2-methoxyethylamino)propyl, 3-(N-(2-methoxyethyl)-N-methylamino)propyl, 3-(2-hydroxyethylamino)propyl, 2-thiomorpholinoethyl, 3-thiomorpholinopropyl, 2-(1,1-dioxothiomorpholino)ethyl, 3-(1,1-dioxothiomorpholino)propyl, 2-(2-methoxyethoxy)ethyl, 2-(4-methylpiperazin-1-yl)ethyl, 3-(4-methylpiperazin-1-yl)propyl, 3-(methylsulphinyl)propyl, 3-(methylsulphonyl)propyl, morpholino, 2-((N-(3-morpholinopropylsulphonyl)-N-methyl)amino)ethyl, 2-((N-methyl-N-4-pyridyl)amino)ethyl, 3-(4-oxidomorpholino)propyl, 2-(2-(4-methylpiperazin-1-yl)ethoxy)ethyl, 3-(2-(4-methylpiperazin-1-yl)ethoxy)propyl, 2-(2-morpholinoethoxy)ethyl, 3-(2-morpholinoethoxy)propyl, 2-(tetrahydropyran-4-yloxy)ethyl, 3-(tetrahydropyran-4-yloxy)propyl, 2-((2-(pyrrolidin-1-yl)ethyl)carbamoyl)vinyl or 3-((2-(pyrrolidin-1-yl)ethyl)carbamoyl)prop-2-en-1-yl].

According to another embodiment of the present invention in another aspect $R^2$ represents methoxy, 2-methoxyethoxy, 2-(2-methoxyethoxy)ethoxy, 3-methoxypropoxy, 2-methylsulphonylethoxy, 3-methylsulphonylpropoxy, benzyloxy, 2-(tetrahydropyran-4-yloxy)ethoxy, 3-(tetrahydropyran-4-yloxy)propoxy, 2-(4-methylpiperazin-1-yl)ethoxy, 3-(4-methylpiperazin-1-yl)propoxy, 2-morpholinoethoxy, 3-morpholinopropoxy, 2-(imidazol-1-yl)ethoxy, 3-(imidazol-1-yl)propoxy 2-(1,1-dioxothiomorpholino)ethoxy, 3-(1,1-dioxothiomorpholino)propoxy, 2-(1,2,3-triazol-1-yl)ethoxy, 3-(1,2,3-triazol-1-yl)propoxy, 2-(1,2,4-triazol-1-yl)ethoxy, 2-((N-methyl-N-4-pyridyl)amino)ethoxy, 2-(N,N-dimethylamino)ethoxy, 3-(N,N-dimethylamino)propoxy, 2-(N-methoxyacetyl-N-methylamino)ethoxy, 3-(N-methoxyacetyl-N-methylamino)propoxy, 1-methylpiperidin-3-ylmethoxy, 1-methylpiperidin-4-ylmethoxy, (1-cyanomethylpiperidin-3-yl)methoxy, (1-cyanomethylpiperidin-4-yl)methoxy, 2-(1-cyanomethylpiperidin-3-yl)ethoxy, 2-(1-cyanomethylpiperidin-4-yl)ethoxy, 3-(1-cyanomethylpiperidin-3-yl)propoxy, 3-(1-cyanomethylpiperidin-4-yl)propoxy, ((2-methoxyethyl)piperidin-3-yl)methoxy, ((2-methoxyethyl)piperidin-4-yl)methoxy, 2-(N-(2-methoxyethyl)-N-methylamino)ethoxy, 4-(pyrrolidin-1-yl)but-2-en-yloxy, 2-(2-oxopyrrolidin-1-yl)ethoxy, 3-(2-oxopyrrolidin-1-yl)propoxy, (pyrrolidin-2-yl)methoxy, 2-(pyrrolidin-1-yl)ethoxy, 3-(pyrrolidin-1-yl)propoxy, 2-(2-(pyrrolidin-1-yl)ethoxy)ethoxy, (2-oxo-tetrahydro-2H-pyrrolidin-5-yl)methoxy, 2-(2-(4-methylpiperazin-1-yl)ethoxy)ethoxy, 2-piperidinoethoxy, 3-piperidinopropoxy, 2-(methylpiperidino)ethoxy, 3-(methylpiperidino)propoxy, 2-(ethylpiperidino)ethoxy, 3-(ethylpiperidino)propoxy, 2-((2-methoxyethyl)piperidino)ethoxy, 3-((2-methoxyethyl)piperidino)propoxy, 1-(2-methylsulphonylethyl)piperidin-3-ylmethoxy, 1-(2-methylsulphonylethyl)piperidin-4-ylmethoxy, 2-((2-methylsulphonyl)ethylpiperidino)ethoxy, 3-((2-methylsulphonyl)ethylpiperidino)propoxy, piperidin-3-ylmethoxy, piperidin-4-ylmethoxy, 2-(piperidin-3-yl)ethoxy, 2-(piperidin-4-yl)ethoxy, 3-(piperidin-3-yl)propoxy, 3-(piperidin-4-yl)propoxy, 2-(methylpiperidin-3-yl)ethoxy, 2-(methylpiperidin-4-yl)ethoxy, 3-(methylpiperidin-3-yl)propoxy, 3-(methylpiperidin-4-yl)propoxy, 2-(ethylpiperidin-3-yl)ethoxy, 2-(ethylpiperidin-4-yl)ethoxy, 3-(ethylpiperidin-3-yl)propoxy, 3-(ethylpiperidin-4-yl)propoxy, 2-((2-methoxyethyl)piperidin-3-yl)ethoxy, 2-((2-methoxyethyl)piperidin-4-yl)ethoxy, 3-((2-methoxyethyl)piperidin-3-yl)propoxy, 3-((2-methoxyethyl)piperidin-4-yl)propoxy, 2-((2-methylsulphonylethyl)piperidin-3-yl)ethoxy, 2-((2-methylsulphonylethyl)piperidin-4-yl)ethoxy, 3-((2-methylsulphonylethyl)piperidin-3-yl)propoxy, 3-((2-methylsulphonylethyl)piperidin-4-yl)propoxy, 1-isopropylpiperidin-2-ylmethoxy, 1-isopropylpiperidin-3-ylmethoxy, 1-isopropylpiperidin-4-ylmethoxy, 2-(1-isopropylpiperidin-2-yl)ethoxy, 2-(1-isopropylpiperidin-3-yl)ethoxy, 2-(1-isopropylpiperidin-4-yl)ethoxy, 3-(1-isopropylpiperidin-2-yl)propoxy, 3-(1-isopropylpiperidin-3-yl)propoxy, 3-(1-isopropylpiperidin-4-yl)propoxy, 2-(2-(4-methylpiperazin-1-yl)ethoxy)ethoxy, 3-(2-(4-methylpiperazin-1-yl)ethoxy)propoxy, 2-(2-morpholinoethoxy)ethoxy, 3-(2-morpholinoethoxy)propoxy, 2-((2-(pyrrolidin-1-yl)ethyl)carbamoyl)vinyl or 342-(pyrrolidin-1-yl)ethyl)carbamoyl)prop-2-en-1-yl.

Where one of the $R^2$ substituents is $R^5X^1$— the substituent $R^5X^1$— is preferably at the 6- or 7-position of the quinazoline ring, more preferably at the 7-position of the quinazoline ring.

When one of the $R^2$ substituents is at the 6-position of the quinazoline ring it is preferably hydrogen, halogeno, $C_{1-3}$alkyl, trifluoromethyl, $C_{1-3}$alkoxy, $C_{1-3}$alkylsulphanyl or —$NR^3R^4$ (wherein $R^3$ and $R^4$ are as defined hereinbefore).

When one of the $R^2$ substituents is at the 6-position of the quinazoline ring it is more preferably $C_{1-3}$alkoxy, especially methoxy.

In another aspect of the present invention there is provided the use of compounds of the formula Ia:

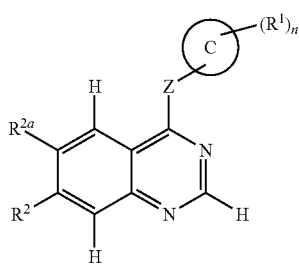

(Ia)

[wherein:
ring C, $R^1$, $R^2$, n and Z are as defined hereinbefore with the provisos that $R^2$ is not hydrogen and that Z is not $CH_2$ or a direct bond; and
$R^{2a}$ represents hydrogen, halogeno, $C_{1-3}$alkyl, trifluoromethyl, $C_{1-3}$alkoxy, $C_{1-3}$alkylsulphanyl, —$NR^{3a}R^{4a}$ (wherein $R^{3a}$ and $R^{4a}$, which may be the same or different, each represents hydrogen or $C_{1-3}$alkyl), or $R^{5a}(CH_2)_{za}X^{1a}$ (wherein $R^{5a}$ is a 5- or 6-membered saturated heterocyclic group with 1-2 heteroatoms, selected independently from O, S and N, which heterocyclic group may bear 1 or 2 substituents selected from oxo, hydroxy, halogeno, cyano, $C_{1-4}$cyanoalkyl, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl$C_{1-4}$alkyl, $C_{1-4}$alkoxycarbonyl, $C_{1-4}$aminoalkyl, $C_{1-4}$alkylamino, di($C_{1-4}$alkyl)amino, $C_{1-4}$alkylamino$C_{1-4}$alkyl, di($C_{1-4}$alkyl)amino$C_{1-4}$alkyl, $C_{1-4}$alkylamino$C_{1-4}$alkoxy, di($C_{1-4}$alkyl)amino$C_{1-4}$alkoxy and a group —(—O—)$_f$ ($C_{1-4}$alkyl)$_g$ringD (wherein f is 0 or 1, g is 0 or 1 and ring D is a 5-6-membered saturated heterocyclic group with 1-2 heteroatoms, selected independently from O, S and N, which cyclic group may bear one or more substituents selected from $C_{1-4}$alkyl), za is an integer from 0 to 4 and $X^{1a}$ represents a direct bond, —O—, —$CH_2$—, —S—, —SO—, —$SO_2$—, —$NR^{6a}C(O)$—, —$C(O)NR^{7a}$—, —$SO_2NR^{8a}$—, —$NR^{9a}SO_2$— or —$NR^{10a}$— (wherein $R^{6a}$, $R^{7a}$, $R^{8a}$, $R^{9a}$ and $R^{10a}$ each independently represents hydrogen, $C_{1-3}$alkyl or $C_{1-3}$alkoxy$C_{2-3}$alkyl));

and salts thereof, and prodrugs thereof for example esters and amides, in the manufacture of a medicament for use in the production of an antiangiogenic and/or vascular permeability reducing effect in warm-blooded animals such as humans.

In another aspect of the present invention there is provided the use of compounds of the formula Ia:

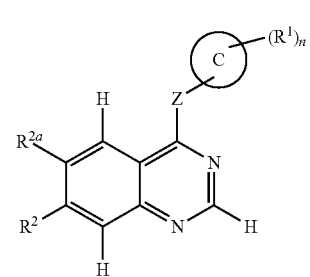

(Ia)

[wherein:
ring C, $R^1$, $R^2$, n and Z are as defined hereinbefore with the provisos that $R^2$ is not hydrogen and that Z is not $CH_2$ or a direct bond; and
$R^{2a}$ represents hydrogen, halogeno, $C_{1-3}$alkyl, trifluoromethyl, $C_{1-3}$alkoxy, $C_{1-3}$alkylsulphanyl, —$NR^{3a}R^{4a}$ (wherein $R^{3a}$ and $R^{4a}$, which may be the same or different, each represents hydrogen or $C_{1-3}$alkyl), or $R^{5a}(CH_2)_{za}X^{1a}$ (wherein $R^{5a}$ is a 5- or 6-membered saturated heterocyclic group with 1-2 heteroatoms, selected independently from O, S and N, which heterocyclic group may bear 1 or 2 substituents selected from oxo, hydroxy, halogeno, $C_{1-4}$alkyl, $C_{1-4}$hydroxyalkyl and $C_{1-4}$alkoxy, za is an integer from 0 to 4 and $X^{1a}$ represents a direct bond, —O—, —$CH_2$—, —S—, —SO—, —$SO_2$—, —$NR^{6a}C(O)$—, —$C(O)NR^{7a}$—, —$SO_2NR^{8a}$—, —$NR^{9a}SO_2$— or —$NR^{10a}$— (wherein $R^{6a}$, $R^{7a}$, $R^{8a}$, $R^{9a}$ and $R^{10a}$ each independently represents hydrogen, $C_{1-3}$alkyl or $C_{1-3}$alkoxy$C_{2-3}$alkyl));

and salts thereof, and prodrugs thereof for example esters, amides and sulphides, in the manufacture of a medicament for use in the production of an antiangiogenic and/or vascular permeability reducing effect in warm-blooded animals such as humans.

Advantageously $X^{1a}$ represents —O—, —S—, —$NR^{6a}C(O)$—, —$NR^{9a}SO_2$— or —$NR^{10a}$— (wherein $R^{6a}$, $R^{9a}$ and $R^{10a}$ each independently represents hydrogen, $C_{1-2}$alkyl or $C_{1-2}$alkoxyethyl).

Preferably $X^{1a}$ represents —O—, —S—, —$NR^{6a}CO$—, —$NR^{9a}SO_2$— (wherein $R^{6a}$ and $R^{9a}$ each independently represents hydrogen or $C_{1-2}$alkyl) or NH.

More preferably $X^{1a}$ represents —O—, —S—, —$NR^{6a}CO$— (wherein $R^{6a}$ represents hydrogen or $C_{1-2}$alkyl) or NH.

Particularly $X^{1a}$ represents —O— or —NR$^{6a}$CO— (wherein R$^{6a}$ represents hydrogen or C$_{1-2}$alkyl), more particularly —O— or —NHCO—, especially —O—.

Preferably za is an integer from 1 to 3.

Preferably R$^{5a}$ is a group selected from pyrrolidinyl, piperazinyl, piperidinyl, imidazolidinyl, azetidinyl, morpholino and thiomorpholino which group may bear 1 or 2 substituents selected from oxo, hydroxy, halogeno, cyano, C$_{1-3}$cyanoalkyl, C$_{1-3}$alkyl, C$_{1-3}$hydroxyalkyl, C$_{1-3}$alkoxy, C$_{1-2}$alkoxyC$_{1-3}$alkyl, C$_{1-2}$alkylsulphonylC$_{1-3}$alkyl, C$_{1-3}$alkoxycarbonyl, C$_{1-3}$alkylamino, di(C$_{1-3}$alkyl)amino, C$_{1-3}$alkylaminoC$_{1-3}$alkyl, di(C$_{1-3}$alkyl)aminoC$_{1-3}$alkyl, C$_{1-3}$alkylaminoC$_{1-3}$alkoxy, di(C$_{1-3}$alkyl)aminoC$_{1-3}$alkoxy and a group —(—O—)$_f$(C$_{1-3}$alkyl)$_g$ringD (wherein f is 0 or 1, g is 0 or 1 and ring D is a heterocyclic group selected from pyrrolidinyl, piperazinyl, piperidinyl, imidazolidinyl, azetidinyl, morpholino and thiomorpholino, which cyclic group may bear one or more substituents selected from C$_{1-3}$alkyl).

More preferably R$^{5a}$ is a group selected from pyrrolidinyl, piperazinyl, piperidinyl, azetidinyl, morpholino and thiomorpholino which group may bear 1 or 2 substituents selected from oxo, hydroxy, halogeno, cyano, C$_{1-3}$cyanoalkyl, C$_{1-3}$alkyl, C$_{1-3}$hydroxyalkyl, C$_{1-3}$alkoxy, C$_{1-2}$alkoxy C$_{1-3}$alkyl, C$_{1-2}$alkylsulphonylC$_{1-3}$alkyl, C$_{1-3}$alkoxycarbonyl, C$_{1-3}$alkylamino, di(C$_{1-3}$alkyl)amino, C$_{1-3}$alkylamino C$_{1-3}$alkyl, di(C$_{1-3}$alkyl)aminoC$_{1-3}$alkyl, C$_{1-3}$alkylamino C$_{1-3}$alkoxy, di(C$_{1-3}$alkyl)aminoC$_{1-3}$alkoxy and a group —(—O—)$_f$(C$_{1-3}$alkyl)$_g$ringD (wherein f is 0 or 1, g is 0 or 1 and ring D is a heterocyclic group selected from pyrrolidinyl, methylpiperazinyl, piperidinyl, azetidinyl, morpholino and thiomorpholino).

Particularly R$^{5a}$ is pyrrolidinyl, piperazinyl, piperidinyl, azetidinyl, morpholino or thiomorpholino which group may bear 1 or 2 substituents selected from a group —(—O—)$_1$(C$_{1-3}$alkyl)$_g$ringD (wherein f is 0 or 1, g is 0 or 1 and ring D is a heterocyclic group selected from pyrrolidinyl, methylpiperazinyl, piperidinyl, azetidinyl, morpholino and thiomorpholino).

According to another aspect of the present invention preferably R$^{5a}$ is a group selected from pyrrolidinyl, piperazinyl, piperidinyl, morpholino and thiomorpholino which group may carry 1 or 2 substituents selected from oxo, hydroxy, halogeno, C$_{1-2}$alkyl, C$_{1-2}$hydroxyalkyl and C$_{1-2}$alkoxy.

Advantageously R$^{2a}$ represents C$_{1-3}$alkyl, C$_{1-3}$alkoxy, amino or R$^{5a}$(CH$_2$)$_{za}$X$^{1a}$ (wherein R$^{5a}$, X$^{1a}$ and za are as defined hereinbefore). Another advantageous value of R$^{2a}$ is hydrogen.

Preferably R$^{2a}$ is methyl, ethyl, methoxy, ethoxy or R$^{5a}$(CH$_2$)$_{za}$X$^{1a}$ (wherein R$^{5a}$, X$^{1a}$ and za are as defined hereinbefore). Another preferred value of R$^{2a}$ is hydrogen.

More preferably R$^{2a}$ is methyl, ethyl, methoxy, ethoxy or R$^{5a}$(CH$_2$)$_{za}$X$^{1a}$ (wherein R$^{5a}$ is a group selected from pyrrolidinyl, piperazinyl, piperidinyl, morpholino and thiomorpholino which group may carry 1 or 2 substituents selected from oxo, hydroxy, halogeno, C$_{1-2}$alkyl, C$_{1-2}$hydroxyalkyl and C$_{1-2}$alkoxy, X$^{1a}$ is —O—, —S—, —NR$^{6a}$C(O)—, —NR$^{9a}$SO$_2$— (wherein R$^{6a}$ and R$^{9a}$ each independently represents hydrogen or C$_{1-2}$alkyl) or NH, and za is an integer from 1 to 3).

Particularly R$^{2a}$ represents methyl, methoxy or R$^{5a}$(CH$_2$)$_{za}$X$^{1a}$ (wherein R$^{5a}$, X$^{1a}$ and za are as defined hereinbefore).

More particularly R$^{2a}$ represents methoxy.

In a further aspect of the present invention there is provided the use of compounds of the formula Ib:

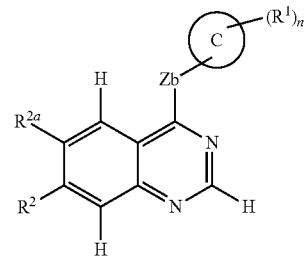

(Ib)

[wherein:
ring C, R$^1$, R$^2$, R$^{2a}$ and n are as defined hereinbefore with the proviso that R$^2$ is not hydrogen; and
Zb is —O— or —S—;

and salts thereof, and prodrugs thereof for example esters, amides and sulphides, preferably esters and amides, in the manufacture of a medicament for use in the production of an antiangiogenic and/or vascular permeability reducing effect in warm-blooded animals such as humans.

Preferably Zb is —O—.

According to another aspect of the present invention there are provided compounds of the formula II:

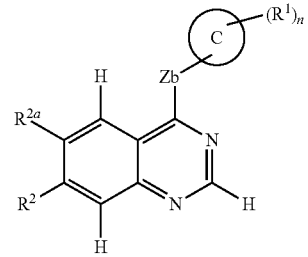

(II)

[wherein:
ring C, R$^1$, R$^2$, R$^{2a}$, Zb and n are as defined hereinbefore with the proviso that R$^2$ is not hydrogen and excluding the compounds:
6,7-dimethoxy-4-(1-naphthylsulphanyl)quinazoline, 6,7-dimethoxy-4-(2-naphthylsulphanyl)quinazoline, 6,7-dimethoxy-4-(1-naphthyloxy)quinazoline and 6,7-dimethoxy-4-(2-naphthyloxy)quinazoline;

and salts thereof, and prodrugs thereof for example esters, amides and sulphides, preferably esters and amides.

According to another aspect of the present invention there are provided compounds of the formula IIa:

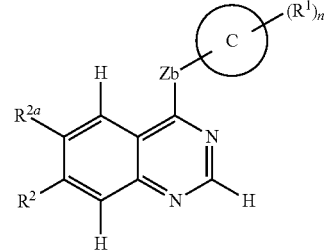

(IIa)

[wherein:
ring C, $R^1$, $R^2$, $R^{2a}$, Zb and n are as defined hereinbefore with the proviso that $R^2$ does not have any of the following values:
hydrogen, substituted or unsubstituted $C^{1-5}$alkyl, halogeno or phenoxy and excluding the compounds:
6,7-dimethoxy-4-(1-naphthylsulphanyl)quinazoline, 6,7-dimethoxy-4-(2-naphthylsulphanyl)quinazoline, 6,7-dimethoxy-4-(1-naphthyloxy)quinazoline and 6,7-dimethoxy-4-(2-naphthyloxy)quinazoline;
and salts thereof, and prodrugs thereof for example esters, amides and sulphides, preferably esters and amides.

According to another aspect of the present invention there are provided compounds of the formula IIb:

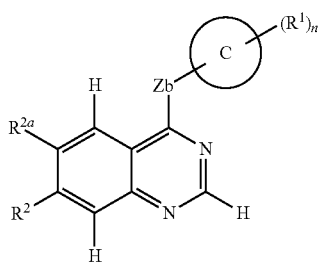

(IIb)

[wherein:
ring C, $R^1$, $R^2$, $R^{2a}$, Zb and n are as defined hereinbefore with the proviso that $R^2$ does not have any of the following values:
hydrogen, substituted or unsubstituted $C_{1-5}$alkyl, halogeno, $C_{1-5}$alkoxy, $C_{2-5}$alkenyl, phenoxy or phenyl$C_{1-5}$alkoxy;
and salts thereof, and prodrugs thereof for example esters, amides and sulphides, preferably esters and amides.

Preferred compounds of the present invention include
6-methoxy-7-((1-methylpiperidin-4-yl)methoxy)-4-(2-naphthyloxy)quinazoline,
6-methoxy-7-((1-methylpiperidin-4-yl)methoxy)-4-(quinolin-7-yloxy)quinazoline,
7-(3-(1,1-dioxothiomorpholino)propoxy)-6-methoxy-4-(quinolin-7-yloxy)quinazoline,
6-methoxy-7-(3-(4-methylpiperazin-1-yl)propoxy)-4-(quinolin-7-yloxy)quinazoline,
6-methoxy-7-((1-methylpiperidin-3-yl)methoxy)-4-(quinolin-7-yloxy)quinazoline,
4-(4-chloroquinolin-7-yloxy)-6-methoxy-7-(3-morpholinopropoxy)quinazoline,
6-methoxy-7-((1-methylpiperidin-4-yl)methoxy)-4-(4-methylquinolin-7-yloxy)quinazoline,
6-methoxy-4-(4-methylquinolin-7-yloxy)-7-(3-(pyrrolidin-1-yl)propoxy)quinazoline,
6-methoxy-7-(2-(2-methoxyethoxy)ethoxy)-4-(quinolin-7-yloxy)quinazoline,
6-methoxy-7-((1-(2-methylsulphonylethyl)piperidin-4-yl)methoxy)-4-(quinolin-7-yloxy)quinazoline,
4-(2,3-dimethylindol-5-yloxy)-6-methoxy-7-(1-methylpiperidin-4-ylmethoxy)quinazoline,
4-(2,3-dimethylindol-5-yloxy)-6-methoxy-7-(3-pyrrolidin-1-ylpropoxy)quinazoline,
6-methoxy-7-(1-methylpiperidin-4-ylmethoxy)-4-(2-trifluoromethylindol-5-yloxy)quinazoline,
6-methoxy-7-(3-pyrrolidin-1-ylpropoxy)-4-(2-trifluoromethylindol-5-yloxy)quinazoline,
(R,S)-4-(3-fluoroquinolin-7-yloxy)-6-methoxy-7-((1-methylpiperidin-3-yl)methoxy)quinazoline,
4-(indol-5-yloxy)-6-methoxy-7-(3-methylsulphonylpropoxy)quinazoline,
7-(3-N,N-dimethylaminopropoxy)-6-methoxy-4-(2-methylindol-5-yloxy)quinazoline,
6-methoxy-4-(2-methylindol-5-yloxy)-7-(2-(2-morpholinoethoxy)ethoxy)quinazoline,
7-(2-(N,N-diethylamino)ethoxy)-6-methoxy-4-(2-methylindol-5-yloxy)quinazoline,
6-methoxy-7-(3-piperidinopropoxy)-4-(quinolin-7-yloxy)quinazoline,
4-(2-methylindol-5-yloxy)-7-(3-morpholinopropoxy)quinazoline,
4-(2-methylindol-5-yloxy)-7-(2-(piperidin-1-yl)ethoxy)quinazoline,
4-(2-methylindol-5-yloxy)-7-(2-(1H-1,2,4-triazol-1-yl)ethoxy)quinazoline,
6-methoxy-7-(3-piperidinopropoxy)-4-(6-trifluoromethylindol-5-yloxy)quinazoline,
7-(3-(methylsulphonyl)propoxy)-4-(2-methylindol-5-yloxy)quinazoline,
7-(3-(N,N-dimethylamino)propoxy)-4-(2,3-dimethylindol-5-yloxy)-6-methoxyquinazoline,
4-(2,3-dimethylindol-5-yloxy)-6-methoxy-7-(1-methylpiperidin-3-ylmethoxy)quinazoline,
7-(2-(N,N-diethylamino)ethoxy)-4-(indol-5-yloxy)-6-methoxyquinazoline,
4-(indol-5-yloxy)-6-methoxy-7-(2-(piperidin-2-yl)ethoxy)quinazoline,
4-(indol-5-yloxy)-6-methoxy-7-(2-(piperidin-1-yl)ethoxy)quinazoline,
4-(indol-6-yloxy)-6-methoxy-7-(3-morpholinopropoxy)quinazoline,
7-(3-(ethylsulphonyl)propoxy)-6-methoxy-4-(2-methylindol-5-yloxy)quinazoline,
6-methoxy-4-(3-methylindol-5-yloxy)-7-(3-piperidinopropoxy)quinazoline,
7-(2-hydroxy-3-piperidinopropoxy)-6-methoxy-4-(2-methylindol-5-yloxy)quinazoline,
7-(2-hydroxy-3-(4-methylpiperazin-1-yl)propoxy)-6-methoxy-4-(2-methylindol-5-yloxy)quinazoline,
6-methoxy-4-(2-methylindol-5-yloxy)-7-(2-(N-methylamino)ethoxy)quinazoline, and
7-(2-hydroxy-3-(isopropylamino)propoxy)-6-methoxy-4-(2-methylindol-5-yloxy)quinazoline, and salts thereof especially hydrochloride salts thereof and prodrugs thereof for example esters and amides.

Especially preferred compounds of the present invention include
6-methoxy-7-(3-morpholinopropoxy)-4-(quinolin-7-yloxy)quinazoline,
6-methoxy-4-(2-methylindol-5-yloxy)-7-((1-methylpiperidin-4-yl)methoxy)quinazoline,
4-(indol-5-yl oxy)-6-methoxy-7-(1-methylpiperidin-4-ylmethoxy)quinazoline,
4-(indol-5-yloxy)-6-methoxy-7-(3-pyrrolidin-1-ylpropoxy)quinazoline,
6-methoxy-4-(2-methylindol-5-yloxy)-7-(3-methylsulphonylpropoxy)quinazoline,
7-((1-cyanomethyl)piperidin-4-ylmethoxy)-6-methoxy-4-(2-methylindol-5-yloxy)quinazoline,
6-methoxy-4-(2-methylindol-5-yloxy)-7-(2-morpholinoethoxy)quinazoline,
6-methoxy-4-(2-methylindol-5-yloxy)-7-(2-pyrrolidin-1-ylethoxy)quinazoline,
6-methoxy-4-(2-methylindol-5-yloxy)-7-(1-methylpiperidin-3-ylmethoxy)quinazoline, 6-methoxy-4-(2-methylindol-5-yloxy)-7-(2-piperidinoethoxy)quinazoline,
6-methoxy-4-(2-methylindol-5-yloxy)-7-(2-(N-methyl-N-(4-pyridyl)amino)ethoxy)quinazoline,
6-methoxy-4-(2-methylindol-5-yloxy)-7-(3-morpholinopropoxy)quinazoline,
6-methoxy-7-(2-(2-methoxyethoxy)ethoxy)-4-(2-methylindol-5-yloxy)quinazoline,
6-methoxy-4-(2-methylindol-5-yloxy)-7-(2-(1H-1,2,4-triazol-1-yl)ethoxy)quinazoline,
6-methoxy-4-(2-methylindol-5-yloxy)-7-(2-(2-(4-methylpiperazin-1-yl)ethoxy)ethoxy)quinazoline,
6-methoxy-4-(2-methylindol-5-yloxy)-7-(3-piperidinopropoxy)quinazoline,
4-(indol-5-yloxy)-6-methoxy-7-(3-piperidinopropoxy)quinazoline
6-methoxy-7-(1-(2-methoxyethyl)piperidin-4-ylmethoxy)-4-(2-methylindol-5-yloxy)quinazoline,
6-methoxy-4-(2-methylindol-5-yloxy)-7-((2-(2-pyrrolidin-1-ylethyl)carbamoyl)vinyl)quinazoline,
6-methoxy-4-(2-methylindol-5-yloxy)-7-(3-(4-methypiperazin-1-yl)propoxy)quinazoline,
6-methoxy-4-(2-methylindol-5-yloxy)-7-(piperidin-4-ylmethoxy)quinazoline,
6-methoxy-4-(2-methylindol-5-yloxy)-7-(2-(piperidin-4-yloxy)ethoxy)quinazoline,
6-methoxy-4-(2-methylindol-5-yloxy)-7-(2-(N-methyl-N-methylsulphonylamino)ethoxy)quinazoline,
7-(2-(1-(2-cyanoethyl)piperidin-4-yloxy)ethoxy)-6-methoxy-4-(2-methylindol-5-yloxy)quinazoline,
4-(2-methylindol-5-yloxy)-7-(3-(pyrrolidin-yl)propoxy)quinazoline,
4-(2-methylindol-5-yloxy)-7-(3-(1,1-dioxothiomorpholino)propoxy)quinazoline, 4-(2-methylindol-5-yloxy)-7-(piperidin-4-ylmethoxy)quinazoline,
4-(indol-5-yloxy)-6-methoxy-7-(2-(2-methoxyethoxy)ethoxy)quinazoline,
7-(3-(N,N-dimethylamino)propoxy)-4-(indol-5-yloxy)-6-methoxyquinazoline,
7-(3-(N,N-diethylamino)propoxy)-4-(indol-5-yloxy)-6-methoxyquinazoline,
7-(3-(1,1-dioxothiomorpholino)propoxy)-4-(indol-5-yloxy)-6-methoxyquinazoline,
4-(indol-5-yloxy)-6-methoxy-7-(2-(4-pyridyloxy)ethoxy)quinazoline,
4-(indol-6-yloxy)-6-methoxy-7-(3-piperidinopropoxy)quinazoline,
7-(1-(2-methoxyethyl)piperidin-4-ylmethoxy)-4-(2-methylindol-5-yloxy)quinazoline,
7-(2-hydroxy-3-morpholinopropoxy)-6-methoxy-4-(2-methylindol-5-yloxy)quinazoline,
7-(2-(1-(2-methoxyethyl)piperidin-4-yl)ethoxy)-6-methoxy-4-(2-methylindol-5-yloxy)quinazoline,
7-(2-hydroxy-3-pyrrolidin-1-ylpropoxy)-6-methoxy-4-(2-methylindol-5-yloxy)quinazoline,
7-(3-(N,N-diethylamino)-2-hydroxypropoxy)-6-methoxy-4-(2-methylindol-5-yloxy)quinazoline,
7-(3-(1,1-dioxothiomorpholino)propoxy)-6-methoxy-4-(2-methylindol-5-yloxy)quinazoline,
6-methoxy-4-(2-methylindol-5-yloxy)-7-(2-(4-pyridyloxy)ethoxy)quinazoline,
4-(indol-5-yloxy)-6-methoxy-7-(3-morpholinopropoxy)quinazoline,
(2R)-6-methoxy-(2-methyl-1H-indol-5-yloxy)-7-(2-hydroxy-3-piperidinopropoxy)quinazoline,
(5R)-6-methoxy-4-(2-methyl-1H-indol-5-yloxy)-7-(2-oxopyrrolidin-5-ylmethoxy)quinazoline,
4-(4-bromoindol-5-yloxy)-6-methoxy-7-(3-piperidinopropoxy)quinazoline,
6-methoxy-4-(2-methylindol-5-yloxy)-7-(1-(2-(pyrrolidin-1-yl)ethyl)-piperidin-4-ylmethoxy)quinazoline,
(2R)-7-(2-hydroxy-3-(pyrrolidin-1-yl)propoxy)-4-(indol-5-yloxy)-6-methoxyquinazoline,
(2R)-7-(2-hydroxy-3-morpholinopropoxy)-4-(indol-5-yloxy)-6-methoxyquinazoline,
(2R)-7-(2-hydroxy-3-piperidinopropoxy)-4-(indol-5-yloxy)-6-methoxyquinazoline,
(2S)-7-(2-hydroxy-3-((N,N-diisopropyl)amino)propoxy)-4-(indol-5-yloxy)-6-methoxyquinazoline,
(2S)-7-(2-hydroxy-3-piperidinopropoxy)-4-(indol-5-yloxy)-6-methoxyquinazoline,
(2R)-7-(2-hydroxy-3-piperidinopropoxy)-6-methoxy-4-(3-methylindol-5-yloxy)quinazoline,
(2R)-7-(2-hydroxy-3-(pyrrolidin-1-yl)propoxy)-6-methoxy-4-(3-methylindol-5-yloxy)quinazoline,
(2R)-7-(2-hydroxy-3-(pyrrolidin-1-yl)propoxy)-6-methoxy-4-(2-methylindol-5-yloxy)quinazoline,
(2R)-7-(2-hydroxy-3-(4-methylpiperazin-1-yl)propoxy)-6-methoxy-4-(2-methylindol-5-yloxy)quinazoline,
6-methoxy-4-(2-methylindol-5-yloxy)-7-(1-(2-morpholinoethyl)piperidin-4-ylmethoxy)quinazoline,
4-(3-fluoro-quinolin-7-yloxy)-6-methoxy-7-(3-piperidinopropoxy)quinazoline,
4-(3-fluoro-quinolin-7-yloxy)-6-methoxy-7-(3-(pyrrolidin-1-yl)propoxy)quinazoline,
6-methoxy-7-(3-(pyrrolidin-1-yl)propoxy)-4-(1H-pyrrolo[2,3-b]pyridin-5-yloxy)quinazoline,
(2S)-6-methoxy-(2-methyl-1H-indol-5-yloxy)-7-(2-hydroxy-3-piperidinopropoxy)quinazoline, and
4-(6-fluoro-2-methylindol-5-yloxy)-6-methoxy-7-(3-(pyrrolidin-1-yl)propoxy)quinazoline,
and salts thereof especially hydrochloride salts thereof and prodrugs thereof for example esters and amides.

More especially preferred compounds of the present invention include
6-methoxy-4-(2-methylindol-5-yloxy)-7-(3-(pyrrolidin-1-yl)propoxy)quinazoline,
4-(4-fluoroindol-5-yloxy)-6-methoxy-7-(1-methylpiperidin-4-ylmethoxy)quinazoline,
4-(4-fluoroindol-5-yloxy)-6-methoxy-7-(3-(4-methylpiperazin-1-yl)propoxy)quinazoline,
4-(6-fluoroindol-5-yloxy)-6-methoxy-7-(3-(pyrrolidin-1-yl)propoxy)quinazoline,
4-(4-fluoroindol-5-yloxy)-6-methoxy-7-(3-(pyrrolidin-1-yl)propoxy)quinazoline,
4-(4-fluoroindol-5-yloxy)-6-methoxy-7-(3-piperidinopropoxy)quinazoline,
4-(4-fluoro-2-methylindol-5-yloxy)-6-methoxy-7-(3-(pyrrolidin-1-yl)propoxy)quinazoline,
4-(4-fluoro-2-methylindol-5-yloxy)-6-methoxy-7-(3-piperidinopropoxy)quinazoline,
4-(4-fluoro-2-methylindol-5-yloxy)-6-methoxy-7-((1-methylpiperidin-4-yl)methoxy)quinazoline,
4-(4-fluoro-2-methylindol-5-yloxy)-6-methoxy-7-(3-(4-methylpiperazin-1-yl)propoxy)quinazoline,
4-(4-fluoroindol-5-yloxy)-6-methoxy-7-(2-(1-methylpiperidin-4-yl)ethoxy)quinazoline,
(2R)-7-(2-hydroxy-3-(pyrrolidin-1-yl)propoxy)-4-(4-fluoro-2-methylindol-5-yloxy)-6-methoxyquinazoline, and
4-(4-fluoro-2-methylindol-5-yloxy)-6-methoxy-7-(2-(1-methylpiperidin-4-yl)ethoxy)quinazoline,
and salts thereof especially hydrochloride salts thereof and prodrugs thereof for example esters and amides.

Thus preferred compounds of the present invention include those, the preparation of which is described in Examples 23, 10, 5, 176, 7, 22, 13, 15, 177, 12, 35, 47, 44, 45, 157, 52, 62, 66, 75, 159, 87, 88, 89, 167, 83, 97, 101, 108, 113, 114, 121, 124, 178, 162, 165, 150 and 166,
and salts thereof especially hydrochloride salts thereof and prodrugs thereof for example esters and amides.

Thus especially preferred compounds of the present invention include those, the preparation of which is described in Examples 2, 11, 34, 36, 186, 151, 57, 54, 55, 58, 56, 60, 61, 64, 65, 67, 68, 71, 72, 74, 70, 77, 79, 80, 82, 86, 122, 107, 110, 112, 117, 118, 119, 123, 161, 147, 163, 164, 63, 78, 115, 320, 318, 290, 252, 292, 293, 294, 301, 299, 279, 280, 305, 269, 246, 266, 267, 182, 321 and 250,
and salts thereof especially hydrochloride salts thereof and prodrugs thereof for example esters and amides.

Thus more especially preferred compounds of the present invention include those, the preparation of which is described in Examples 9, 243, 251, 245, 247, 249, 240, 238, 237, 239, 241, 258 and 322,
and salts thereof especially hydrochloride salts thereof and prodrugs thereof for example esters and amides.

In another embodiment, preferred compounds of the present invention include
6-methoxy-7-(3-morpholinopropoxy)-4-(quinolin-6-yloxy)quinazoline,
(S)-6-methoxy-7-((1-methylpiperidin-3-yl)methoxy)-4-(quinolin-7-yloxy)quinazoline.
6-methoxy-7-(3-morpholinopropoxy)-4-(1-naphthyloxy)quinazoline,
4-(1H-indazol-5-ylamino)-6-methoxy-7-(3-morpholinopropoxy)quinazoline,
6,7-dimethoxy-4-(quinolin-7-yloxy)quinazoline,
6-methoxy-7-((1-methylpiperidin-4-yl)methoxy)-4-(2,2,4-trimethyl-1,2-dihydroquinolin-6-yloxy)quinazoline,
6-methoxy-7-((2-piperidin-1-yl)ethoxy)-4-(quinolin-7-yloxy)quinazoline,
6-methoxy-4-(2-methylquinolin-7-yloxy)-7-(3-pyrrolidin-1-ylpropoxy)quinazoline,
6-methoxy-4-(2-methylquinolin-7-yloxy)-7-((1-(2-methylsulphonylethyl)piperidin-4-yl)methoxy)quinazoline,
6-methoxy-4-(2-methylquinolin-7-yloxy)-7-((1-methylpiperidin-4-yl)methoxy)quinazoline,
4-(2-chloro-1H-benzimidazol-5-yloxy)-6-methoxy-7-((1-methylpiperidin-4-yl)methoxy)quinazoline,
4-(2,4-dimethylquinolin-7-yloxy)-6-methoxy-7-((1-methylpiperidin-4-yl)methoxy)quinazoline,
4-(1H-indazol-6-ylamino)-6-methoxy-7-(3-morpholinopropoxy)quinazoline,
4-(1,3-benzothiazol-6-ylamino)-6-methoxy-7-(3-morpholinopropoxy)quinazoline,
6-methoxy-7-((1-methylpiperidin-4-yl)methoxy)-4-(3-oxo-2H-4H-1,4-benzoxazin-6-yloxy)quinazoline,
7-hydroxy-6-methoxy-4-(quinolin-7-yloxy)quinazoline,
6-methoxy-4-(2-methyl-1,3-benzothiazol-5-yloxy)-7-(3-methylsulphonylpropoxy)quinazoline,
6-methoxy-4-(2-methylindol-5-yloxy)-7-(2-(tetrahydropyran-4-yloxy)ethoxy)quinazoline,
6-methoxy-7-((1-methylpiperidin-4-yl)methoxy)-4-(1,2-cycloheptanebenzimidazol-5-yloxy)quinazoline,
6-methoxy-7-(3-morpholinopropoxy)-4-(quinolin-2-yloxy)quinazoline,
6-methoxy-7-(3-morpholinopropoxy)-4-(3-oxo-1,2-dihydro-3H-indazol-1-yl)quinazoline,
4-(2,3-dihydro-1H-indan-5-ylamino)-6-methoxy-7-(3-morpholinopropoxy)quinazoline,
6-methoxy-4-(2-methyl-4-oxo-4H-chromen-7-yloxy)-7(1-methylpiperidin-4-yl)methoxy)quinazoline,
6-methoxy-4-(4-methyl-4H-1,4-benzoxazin-6-yloxy)-7-((1-methylpiperidin-4-yl)methoxy)quinazoline,
6-methoxy-4-(2-methyl-4-oxo-4H-chromen-7-yloxy)-74(3-pyrrolidin-1-yl)propoxy)quinazoline,
6-methoxy-4-(4-methyl-3,4-dihydro-2H-1,4-benzoxazin-6-yloxy)-7-(3-pyrrolidin-1-ylpropoxy)quinazoline,
7-benzyloxy-6-methoxy-4-(quinolin-7-yloxy)quinazoline,
4-(2,4-dimethylquinolin-7-yloxy)-6-methoxy-7-(3-pyrrolidin-1-ylpropoxy)quinazoline,
6-methoxy-7-(3-methylsulphonylpropoxy)-4-(2-trifluoromethylindol-5-yloxy)quinazoline,
6-methoxy-4-(2-methylquinolin-7-yloxy)-7-(3-methylsulphonylpropoxy)quinazoline,
6-methoxy-7-(3-morpholinopropoxy)-4-(quinazolin-7-yloxy)quinazoline,
6-methoxy-7-(3-pyrrolidin-1-ylpropoxy)-4-(3-oxo-2H-4H-1,4-benzoxazin-6-yloxy)quinazoline,
7-hydroxy-6-methoxy-4-(2-methylindol-5-yloxy)quinazoline,
6,7-dimethoxy-4-(2-methyl-1H-benzimidazol-5-yloxy)quinazoline,
and salts thereof especially hydrochloride salts thereof and prodrugs thereof for example esters, amides and sulphides, preferably esters and amides.

In another embodiment more preferred compounds of the present invention include 6-methoxy-4-(4-methylquinolin-7-yloxy)-7-(3-morpholinopropoxy)quinazoline,
6-methoxy-7-((1-methylpiperidin-4-yl)methoxy)-4-(quinolin-6-yloxy)quinazoline,
6-methoxy-4-(2-methyl-1,3-benzothiazol-5-yloxy)-7-(3-morpholinopropoxy)quinazoline,
(R)-6-methoxy-7-((1-methylpiperidin-3-yl)methoxy)-4-(quinolin-7-yloxy)quinazoline,
6-methoxy-7-(3-pyrrolidin-1-ylpropoxy)-4-(2,2,4-trimethyl-1,2-dihydroquinolin-6-yloxy)quinazoline,
6-methoxy-7-(2-morpholinoethoxy)-4-(quinolin-7-yloxy)quinazoline,
6-methoxy-4-(2-methylindol-5-yloxy)-7-((1-(2-methylsulphonylethyl)piperidin-4-yl)methoxy)quinazoline,
6-methoxy-4-(2-methylindol-5-ylamino)-7-((1-methylpiperidin-4-yl)methoxy)quinazoline,
6-methoxy-4-(2-methylindol-5-ylamino)-7-(3-pyrrolidin-1-ylpropoxy)quinazoline,
4-(4-chloroquinolin-7-yloxy)-6-methoxy-7-(3-methylsulphonylpropoxy)quinazoline,
4-(7-hydroxy-2-naphthyloxy)-6-methoxy-7-(3-methylsulphonylpropoxy)quinazoline,
6-methoxy-7-(3-pyrrolidin-1-ylpropoxy)-4-(2-trifluoromethylindol-5-yloxy)quinazoline,
7-(2-(N,N-dimethylamino)ethoxy)-6-methoxy-4-(2-methylindol-5-yloxy)quinazoline,
6-methoxy-7-(2-(N-(2-methoxyethyl)-N-methylamino)ethoxy)-4-(2-methylindol-5-yloxy)quinazoline,
4-(2,3-dimethylindol-5-ylamino)-6-methoxy-7-((1-methylpiperidin-4-yl)methoxy)quinazoline,
4-(2,3-dimethylindol-5-ylamino)-6-methoxy-7-(3-pyrrolidin-1-ylpropoxy)quinazoline,
(S)-6-methoxy-7-((2-oxo-tetrahydro-2H-pyrrolidin-5-yl)methoxy)-4-(quinolin-7-yloxy)quinazoline,
and salts thereof especially hydrochloride salts thereof and prodrugs thereof for example esters, amides and sulphides, preferably esters and amides.

In another embodiment especially preferred compounds of the present invention include 6-methoxy-4-(2-methylindol-5-yloxy)-7-(3-pyrrolidin-1-yl-propoxy)quinazoline,
4-(2,3-dimethylindol-5-yloxy)-6-methoxy-7-(3-pyrrolidin-1-ylpropoxy)quinazoline,
6-methoxy-4-(2-methylindol-5-yloxy)-7-(3-methylsulphonylpropoxy)quinazoline,
6-methoxy-4-(2-methylindol-5-yloxy)-7-((1-methylpiperidin-3-yl)methoxy)quinazoline,
6-methoxy-4-(2-methylindol-5-yloxy)-7-(2-(piperidin-1-yl)ethoxy)quinazoline,
6-methoxy-7-((1-methylpiperidin-4-yl)methoxy)-4-(quinolin-7-yloxy)quinazoline,
6-methoxy-7-((1-methylpiperidin-3-yl)methoxy)-4-(quinolin-7-yloxy)quinazoline, 6-methoxy-4-(2-methylindol-5-yloxy)-7-((1-methylpiperidin-4-yl)methoxy)quinazoline,
4-(indol-5-yloxy)-6-methoxy-7-((1-methylpiperidin-4-yl)methoxy)quinazoline,
4-(indol-5-yloxy)-6-methoxy-7-(3-pyrrolidin-1-ylpropoxy)quinazoline,
6-methoxy-7-(3-methylsulphonylpropoxy)-4-(quinolin-7-yloxy)quinazoline,
6-methoxy-4-(2-methylindol-5-yloxy)-7-(2-(pyrrolidin-1-yl)ethoxy)quinazoline,
6-methoxy-4-(2-methylindol-5-yloxy)-7-(2-(N-methyl-N-(4-pyridyl)amino)ethoxy)quinazoline,
6-methoxy-4-(2-methylindol-5-yloxy)-7-(3-morpholinopropoxy)quinazoline,
6-methoxy-7-(3-morpholinopropoxy)-4-(quinolin-7-yloxy)quinazoline,
6-methoxy-7-((1-methylpiperidin-4-yl)methoxy)-4-(2-naphthyloxy)quinazoline,
7-(3-(1,1-dioxothiomorpholino)propoxy)-6-methoxy-4-(quinolin-7-yloxy)quinazoline,
6-methoxy-7-(3-(1-methylpiperazin-4-yl)propoxy)-4-(quinolin-7-yloxy)quinazoline,
4-(4-chloroquinolin-7-yloxy)-6-methoxy-7-(3-morpholinopropoxy)quinazoline,
6-methoxy-7-((1-methylpiperidin-4-yl)methoxy)-4-(4-methylquinolin-7-yloxy)quinazoline,
6-methoxy-7-(2-(2-methoxyethoxy)ethoxy)-4-(quinolin-7-yloxy)quinazoline,
6-methoxy-7-((1-(2-methylsulphonylethyl)piperidin-4-yl)methoxy)-4-(quinolin-7-yloxy)-quinazoline,
7-((1-cyanomethylpiperidin-4-yl)methoxy)-6-methoxy-4-(2-methylindol-5-yloxy)quinazoline,
6-methoxy-7-((1-methylpiperidin-4-yl)methoxy)-4-(2-trifluoromethylindol-5-yloxy)quinazoline,
4-(3-fluoroquinolin-7-yloxy)-6-methoxy-7-((1-methylpiperidin-3-yl)methoxy)quinazoline,
6-methoxy-4-(2-methylindol-5-yloxy)-7-(2-morpholinoethoxy)quinazoline,
6-methoxy-7-(2-(2-methoxyethoxy)ethoxy)-4-(2-methylindol-5-yloxy)quinazoline,
7-(3-(N,N-dimethylamino)propoxy)-6-methoxy-4-(2-methylindol-5-yloxy)quinazoline,
7-(3-(1,1-dioxothiomorpholino)propoxy)-6-methoxy-4-(2-methylindol-5-yloxy)quinazoline,
6-methoxy-4-(2-methylindol-5-yloxy)-7-(2-(2-(1-methylpiperazin-4-yl)ethoxy)ethoxy)quinazoline,
6-methoxy-4-(2-methylindol-5-yloxy)-7-(2-(2-morpholinoethoxy)ethoxy)quinazoline,
6-methoxy-4-(4-methylquinolin-7-yloxy)-7-(3-pyrrolidin-1-ylpropoxy)quinazoline,
6-methoxy-4-(2-methylindol-5-yloxy)-7-(2-(1,2,4-triazol-1-yl)ethoxy)quinazoline,
4-(2,3-dimethylindol-5-yloxy)-6-methoxy-7-((1-methylpiperidin-4-yl)methoxy)quinazoline,
4-(indol-5-yloxy)-6-methoxy-7-(3-methylsulphonylpropoxy)quinazoline,
and salts thereof especially hydrochloride salts thereof and prodrugs thereof for example esters, amides and sulphides, preferably esters and amides.

In another aspect of the present invention preferred compounds include
6-methoxy-7-((1-(2-methoxyethyl)piperidin-4-yl)methoxy)-4-(2-methylindol-5-yloxy)quinazoline,
6-methoxy-4-(2-methylindol-5-yloxy)-7-(2-(2-(pyrrolidin-1-yl)ethylcarbamoyl)vinyl)quinazoline,
4-(3-cyanoquinolin-7-yloxy)-6-methoxy-7-((1-methylpiperidin-4-yl)methoxy)quinazoline,
6-methoxy-7-((1-methylpiperidin-3-yl)methoxy)-4-(4-trifluoromethylquinolin-7-yloxy)quinazoline,
6-methoxy-4-(2-methyl-1H-benzimidazol-5-yloxy)-7-((1-methylpiperidin-4-yl)methoxy)quinazoline,
4-(3-carbamoylquinolin-7-yloxy)-6-methoxy-7-((1-methylpiperidin-4-yl)methoxy)quinazoline,
6-methoxy-4-(2-methylindol-5-yloxy)-7-(3-(1-methylpiperazin-4-yl)propoxy)quinazoline,
6-methoxy-4-(2-methylindol-5-yloxy)-7-(piperidin-4-ylmethoxy)quinazoline,
and salts thereof especially hydrochloride salts thereof and prodrugs thereof for example esters, amides and sulphides, preferably esters and amides.

An especially preferred compound of the present invention is
6-methoxy-4-(2-methylindol-5-yloxy)-7-(3-pyrrolidin-1-ylpropoxy)quinazoline
and salts thereof especially hydrochloride salts thereof and prodrugs thereof for example esters, amides and sulphides, preferably esters and amides.

For the avoidance of doubt it is to be understood that where in this specification a group is qualified by 'hereinbefore defined' or 'defined hereinbefore' the said group encompasses the first occurring and broadest definition as well as each and all of the preferred definitions for that group.

In this specification unless stated otherwise the term "alkyl" includes both straight and branched chain alkyl groups but references to individual alkyl groups such as "propyl" are specific for the straight chain version only. An analogous convention applies to other generic terms. Unless otherwise stated the term "alkyl" advantageously refers to chains with 1-6 carbon atoms, preferably 1-4 carbon atoms. The term "alkoxy" as used herein, unless stated otherwise includes "alkyl"—O— groups in which "alkyl" is as hereinbefore defined. The term "aryl" as used herein unless stated otherwise includes reference to a $C_{6-10}$ aryl group which may, if desired, carry one or more substituents selected from halogeno, alkyl, alkoxy, nitro, trifluoromethyl and cyano, (wherein alkyl and alkoxy are as hereinbefore defined). The term "aryloxy" as used herein unless otherwise stated includes "aryl"—O-groups in which "aryl" is as hereinbefore defined. The term "sulphonyloxy" as used herein refers to alkylsulphonyloxy and arylsulphonyloxy groups in which "alkyl" and "aryl" are as hereinbefore defined. The term "alkanoyl" as used herein unless otherwise stated includes formyl and alkylC=O groups in which "alkyl" is as defined hereinbefore, for example $C_2$alkanoyl is ethanoyl and refers to $CH_3C$=O, $C_1$alkanoyl is formyl and refers to CHO. In this specification unless stated otherwise the term "alkenyl" includes both straight and branched chain alkenyl groups but references to individual alkenyl groups such as 2-butenyl are specific for the straight chain version only. Unless otherwise stated the term "alkenyl" advantageously refers to chains with 2-5 carbon atoms, preferably 3-4 carbon atoms. In this specification unless stated otherwise the term "alkynyl" includes both straight and branched chain alkynyl groups but references to individual alkynyl groups such as 2-butynyl are specific for the straight chain version only. Unless otherwise stated the term "alkynyl" advantageously refers to chains with 2-5 carbon atoms, preferably 3-4 carbon atoms. Unless stated otherwise the term "haloalkyl" refers to an alkyl group as defined hereinbefore which bears one or more halogeno groups, such as for example trifluoromethyl.

For the avoidance of any doubt, where $R^2$ has a value of substituted or unsubstituted $C_{1-5}$alkyl, $R^2$ has been selected from $C_{1-3}$alkyl or from a group $R^5X^1$ wherein $X^1$ is a direct bond or —$CH_2$— and $R^5$ is $C_{1-5}$alkyl which may be unsubstituted or which may be substituted with one or more groups selected from hydroxy, fluoro, chloro, bromo and amino.

Within the present invention it is to be understood that a compound of the formula I or a salt thereof may exhibit the phenomenon of tautomerism and that the formulae drawings within this specification can represent only one of the possible tautomeric forms. It is to be understood that the invention encompasses any tautomeric form which inhibits VEGF receptor tyrosine kinase activity and is not to be limited merely to any one tautomeric form utilised within the formulae drawings. The formulae drawings within this specification can represent only one of the possible tautomeric forms and it is to be understood that the specification encompasses all possible tautomeric forms of the compounds drawn not just those forms which it has been possible to show graphically herein.

It will be appreciated that compounds of the formula I or a salt thereof may possess an asymmetric carbon atom. Such an asymmetric carbon atom is also involved in the tautomerism described above, and it is to be understood that the present invention encompasses any chiral form (including both pure enantiomers, scalemic and racemic mixtures) as well as any tautomeric form which inhibits VEGF receptor tyrosine kinase activity, and is not to be limited merely to any one tautomeric form or chiral form utilised within the formulae drawings. It is to be understood that the invention encompasses all optical and diastereomers which inhibit VEGF receptor tyrosine kinase activity. It is further to be understood that in the names of chiral compounds (R,S) denotes any scalemic or racemic mixture while (R) and (S) denote the enantiomers. In the absence of (R,S), (R) or (S) in the name it is to be understood that the name refers to any scalemic or racemic mixture, wherein a scalemic mixture contains R and S enantiomers in any relative proportions and a racemic mixture contains R and S enantiomers in the ration 50:50.

It is also to be understood that certain compounds of the formula I and salts thereof can exist in solvated as well as unsolvated forms such as, for example, hydrated forms. It is to be understood that the invention encompasses all such solvated forms which inhibit VEGF receptor tyrosine kinase activity.

For the avoidance of any doubt, it is to be understood that when $X^1$ is, for example, a group of formula —$NR^6C(O)$—, it is the nitrogen atom bearing the $R^6$ group which is attached to the quinazoline ring and the carbonyl (C(O)) group is attached to $R^5$, whereas when $X^1$ is, for example, a group of formula —$C(O)NR^7$—, it is the carbonyl group which is attached to the quinazoline ring and the nitrogen atom bearing the $R^7$ group is attached to $R^5$. A similar convention applies to the other two atom $X^1$ linking groups such as —$NR^9SO_2$— and —$SO_2NR^8$—. When $X^1$ is —$NR^{10}$— it is the nitrogen atom bearing the $R^{10}$ group which is linked to the quinazoline ring and to $R^5$. An analogous convention applies to other groups. It is further to be understood that when $X^1$ represents —$NR^{10}$— and $R^{10}$ is $C_{1-3}$alkoxy$C_{2-3}$alkyl it is the $C_{2-3}$alkyl moiety which is linked to the nitrogen atom of $X^1$ and an analogous convention applies to other groups.

For the avoidance of any doubt, it is to be understood that in a compound of the formula I when $R^5$ is, for example, a group of formula $C_{1-3}$alkyl$X^9C_{1-3}$alkyl$R^{29}$, it is the terminal $C_{1-3}$alkyl moiety which is linked to $X^1$, similarly when $R^5$ is, for example, a group of formula $C_{2-5}$alkenyl$R^{28}$ it is the $C_{2-5}$alkenyl moiety which is linked to $X^1$ and an analogous convention applies to other groups. When $R^5$ is a group 1-$R^{29}$prop-1-en-3-yl it is the first carbon to which the group $R^{29}$ is attached and it is the third carbon which is linked to $X^1$ and an analogous convention applies to other groups.

For the avoidance of any doubt, it is to be understood that in a compound of the formula I when $R^5$ is, for example, $R^{28}$ and $R^{28}$ is a pyrrolidinyl ring which bears a group —(—O—)$_f$($C_{1-4}$alkyl)$_g$ringD, it is the —O— or $C_{1-4}$alkyl which is linked to the pyrrolidinyl ring, unless f and g are both 0 when it is ring D which is linked to the pyrrolidinyl ring and an analogous convention applies to other groups.

For the avoidance of any doubt, it is to be understood that when $R^{29}$ carries a $C_{1-4}$aminoalkyl substituent it is the $C_{1-4}$alkyl moiety which is attached to $R^{29}$ whereas when $R^{29}$ carries a $C_{1-4}$alkylamino substituent it is the amino moiety which is attached to $R^{29}$ and an analogous convention applies to other groups.

For the avoidance of any doubt, it is to be understood that when $R^{28}$ carries a $C_{1-4}$alkoxy$C_{1-4}$alkyl substituent it is the $C_{1-4}$alkyl moiety which is attached to $R^{28}$ and an analogous convention applies to other groups.

The present invention relates to the compounds of formula I as hereinbefore defined as well as to the salts thereof. Salts for use in pharmaceutical compositions will be pharmaceutically acceptable salts, but other salts may be useful in the production of the compounds of formula I and their pharmaceutically acceptable salts. Pharmaceutically acceptable salts of the invention may, for example, include acid addition salts of the compounds of formula I as hereinbefore defined which are sufficiently basic to form such salts. Such acid addition salts include for example salts with inorganic or organic acids affording pharmaceutically acceptable anions such as with hydrogen halides (especially hydrochloric or hydrobromic acid of which hydrochloric acid is particularly preferred) or with sulphuric or phosphoric acid, or with trifluoroacetic, citric or maleic acid. In addition where the compounds of formula I are sufficiently acidic, pharmaceutically acceptable salts may be formed with an inorganic or organic base which affords a pharmaceutically acceptable cation. Such salts with inorganic or organic bases include for example an alkali metal salt, such as a sodium or potassium salt, an alkaline earth metal salt such as a calcium or magnesium salt, an ammonium salt or for example a salt with methylamine, dimethylamine, trimethylamine, piperidine, morpholine or tris-(2-hydroxyethyl)amine.

A compound of the formula I, or salt thereof, and other compounds of the invention (as hereinafter defined) may be prepared by any process known to be applicable to the preparation of chemically-related compounds. Such processes include, for example, those illustrated in European Patent Applications Publication Nos. 0520722, 0566226, 0602851 and 0635498. Such processes also include, for example, solid phase synthesis. Such processes, are provided as a further feature of the invention and are as described hereinafter. Necessary starting materials may be obtained by standard procedures of organic chemistry. The preparation of such starting materials is described within the accompanying non-limiting Examples. Alternatively necessary starting materials are obtainable by analogous procedures to those illustrated which are within the ordinary skill of an organic chemist.

Thus, the following processes (a) to (f) and (i) to (vi) constitute further features of the present invention.

Synthesis of Compounds of Formula I (a) Compounds of the formula I and salts thereof may be prepared by the reaction of a compound of the formula III:

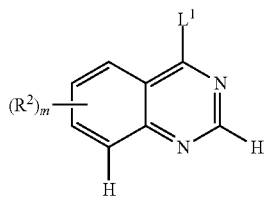

(III)

(wherein $R^2$ and m are as defined hereinbefore and $L^1$ is a displaceable moiety), with a compound of the formula IV:

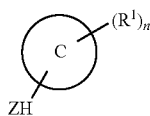

(IV)

(wherein ring C, $R^1$, Z and n are as defined hereinbefore) to obtain compounds of the formula I and salts thereof. A convenient displaceable moiety $L^1$ is, for example, a halogeno, alkoxy (preferably $C_{1-4}$alkoxy), aryloxy, alkylsulphanyl, arylsulphanyl, alkoxyalkylsulphanyl or sulphonyloxy group, for example a chloro, bromo, methoxy, phenoxy, methylsulphanyl, 2-methoxyethylsulphanyl, methanesulphonyloxy or toluene-4-sulphonyloxy group.

The reaction is advantageously effected in the presence of a base. Such a base is, for example, an organic amine base such as, for example, pyridine, 2,6-lutidine, collidine, 4-dimethylaminopyridine, triethylamine, morpholine, N-methylmorpholine or diazabicyclo[5.4.0]undec-7-ene, tetramethylguanidine or for example, an alkali metal or alkaline earth metal carbonate or hydroxide, for example sodium carbonate, potassium carbonate, calcium carbonate, sodium hydroxide or potassium hydroxide. Alternatively such a base is, for example, an alkali metal hydride, for example sodium hydride, or an alkali metal or alkaline earth metal amide, for example sodium amide, sodium bis(trimethylsilyl)amide, potassium amide or potassium bis(trimethylsilyl)amide. The reaction is preferably effected in the presence of an inert solvent or diluent, for example an ether such as tetrahydrofuran or 1,4-dioxan, an aromatic hydrocarbon solvent such as toluene, or a dipolar aprotic solvent such as N,N-dimethylformamide, N,N-dimethylacetamide, N-methylpyrrolidin-2-one or dimethyl sulphoxide. The reaction is conveniently effected at a temperature in the range, for example, 10 to 150° C., preferably in the range 20 to 90° C.

When it is desired to obtain the acid salt, the free base may be treated with an acid such as a hydrogen halide, for example hydrogen chloride, sulphuric acid, a sulphonic acid, for example methane sulphonic acid, or a carboxylic acid, for example acetic or citric acid, using a conventional procedure.

(b) Production of those compounds of formula I and salts thereof wherein at least one $R^2$ is $R^5X^1$ wherein $R^5$ is as defined hereinbefore and $X^1$ is —O—, —S—, —OC(O)— or —$NR^{10}$— (wherein $R^{10}$ independently represents hydrogen, $C_{1-3}$alkyl or $C_{1-3}$alkoxy$C_{2-3}$alkyl) can be achieved by the reaction, conveniently in the presence of a base (as defined hereinbefore in process (a)) of a compound of the formula V:

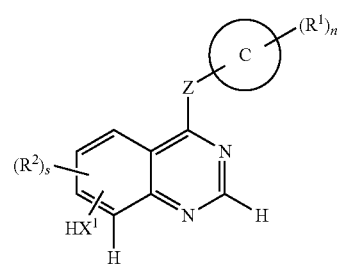

(V)

(wherein ring C, Z, $R^1$, $R^2$ and n are as hereinbefore defined and $X^1$ is as hereinbefore defined in this section and s is an integer from 0 to 2) with a compound of formula VI:

$R^5$-$L^1$    (VI)

(wherein $R^5$ and $L^1$ are as hereinbefore defined), $L^1$ is a displaceable moiety for example a halogeno or sulphonyloxy group such as a bromo, methanesulphonyloxy or toluene-4-sulphonyloxy group, or $L^1$ may be generated in situ from an alcohol under standard Mitsunobu conditions ("Organic Reactions", John Wiley & Sons Inc, 1992, vol 42, chapter 2, David L Hughes). The reaction is preferably effected in the presence of a base (as defined hereinbefore in process (a)) and advantageously in the presence of an inert solvent or diluent (as defined hereinbefore in process (a)), advantageously at a temperature in the range, for example 10 to 150° C., conveniently at about 50° C.

(c) Compounds of the formula I and salts thereof wherein at least one $R^2$ is $R^5X^1$ wherein $R^5$ is as defined hereinbefore and $X^1$ is —O—, —S—, —OC(O)— or —$NR^{10}$— (wherein $R^{10}$ represents hydrogen, $C_{1-3}$alkyl or $C_{1-3}$alkoxy$C_{2-3}$alkyl) may be prepared by the reaction of a compound of the formula VII:

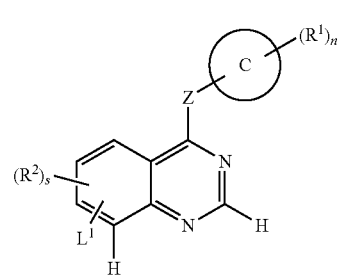

(VII)

with a compound of the formula VIII:

$R^5$—$X^1$—H    (VIII)

(wherein $L^1$, $R^1$, $R^2$, $R^5$, ring C, Z, n and s are all as hereinbefore defined and $X^1$ is as hereinbefore defined in this section). The reaction may conveniently be effected in the presence of a base (as defined hereinbefore in process (a)) and advantageously in the presence of an inert solvent or diluent (as defined hereinbefore in process (a)), advantageously at a temperature in the range, for example 10 to 150° C., conveniently at about 100° C.

(d) Compounds of the formula I and salts thereof wherein at least one $R^2$ is $R^5X^1$ wherein $X^1$ is as defined hereinbefore and $R^5$ is $C_{1-5}$alkyl$R^{113}$, wherein $R^{113}$ is selected from one of the following six groups:

1) $X^{19}C_{1-3}$alkyl (wherein $X^{19}$ represents —O—, —S—, —SO$_2$—, —NR$^{114}$C(O)— or —NR$^{115}$SO$_2$— (wherein $R^{114}$ and $R^{115}$ which may be the same or different are each hydrogen, $C_{1-3}$alkyl or $C_{1-3}$alkoxy$C_{2-3}$alkyl);
2) NR$^{116}$R$^{117}$ (wherein R$^{116}$ and R$^{117}$ which may be the same or different are each hydrogen, $C_{1-3}$alkyl or $C_{1-3}$alkoxy$C_{2-3}$alkyl);
3) $X^{20}C_{1-5}$alkyl$X^5R^{22}$ (wherein $X^{20}$ represents —O—, —S—, —SO$_2$—, —NR$^{118}$C(O)—, —NR$^{119}$SO$_2$— or —NR$^{120}$— (wherein R$^{118}$, R$^{119}$, and R$^{120}$ which may be the same or different are each hydrogen, $C_{1-3}$alkyl or $C_{1-3}$alkoxy$C_{2-3}$alkyl) and $X^5$ and $R^{22}$ are as defined hereinbefore);
4) R$^{28}$ (wherein R$^{28}$ is as defined hereinbefore);
5) $X^{21}R^{29}$ (wherein $X^{21}$ represents —O—, —S—, —SO$_2$—, —NR$^{121}$C(O)—, NR$^{122}$SO$_2$—, or —NR$^{123}$— (wherein R$^{121}$, R$^{122}$, and R$^{123}$ which may be the same or different are each hydrogen, $C_{1-3}$alkyl or $C_{1-3}$alkoxy$C_{2-3}$alkyl) and $R^{29}$ is as defined hereinbefore; and
6) $X^{22}C_{1-3}$alkyl$R^{29}$ (wherein $X^{22}$ represents —O—, —S—, —SO$_2$—, —NR$^{124}$C(O)—, —NR$^{125}$SO$_2$— or —NR$^{126}$— (wherein R$^{124}$, R$^{125}$ and R$^{126}$ each independently represents hydrogen, $C_{1-3}$alkyl or $C_{1-3}$alkoxy$C_{2-3}$alkyl) and $R^{29}$ is as defined hereinbefore);

and additionally R$^{113}$ may be selected from the following three groups:

7) R$^{29}$ (wherein R$^{29}$ is as defined hereinbefore);
8) $X^{22}C_{1-4}$alkyl$R^{28}$ (wherein $X^{22}$ and $R^{28}$ are as defined hereinbefore); and
9) R$^{54}$(C$_{1-4}$alkyl)$_q$(X$^9$)$_r$R$^{55}$ (wherein q, r, X$^9$, R$^{54}$ and R$^{55}$ are as defined hereinbefore);

may be prepared by reacting a compound of the formula IX:

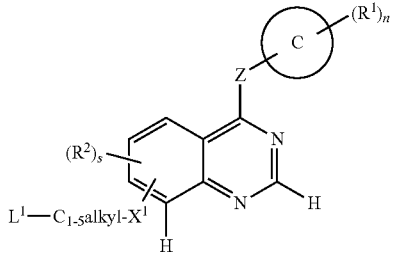

(IX)

(wherein $L^1$, $X^1$, $R^1$, $R^2$, ring C, Z, n and s are as hereinbefore defined) with a compound of the formula X:

(X)

(wherein R$^{113}$ is as defined hereinbefore) to give a compound of the formula I or salt thereof. The reaction may conveniently be effected in the presence of a base (as defined hereinbefore in process (a)) and advantageously in the presence of an inert solvent or diluent (as defined hereinbefore in process (a)), and at a temperature in the range, for example 0 to 150° C., conveniently at about 50° C.

Processes (a) and (b) are preferred over processes (c) and (d).

Process (a) is preferred over processes (b), (c) and (d).

(e) The production of those compounds of the formula I and salts thereof wherein one or more of the substituents (R$^2$)$_m$ is represented by —NR$^{127}$R$^{128}$, where one (and the other is hydrogen) or both of R$^{127}$ and R$^{128}$ are $C_{1-3}$alkyl, may be effected by the reaction of compounds of formula I wherein the substituent (R$^2$)$_m$ is an amino group and an alkylating agent, preferably in the presence of a base as defined hereinbefore. Such alkylating agents are $C_{1-3}$alkyl moieties bearing a displaceable moiety as defined hereinbefore such as $C_{1-3}$alkyl halides for example $C_{1-3}$alkyl chloride, bromide or iodide. The reaction is preferably effected in the presence of an inert solvent or diluent (as defined hereinbefore in process (a)) and at a temperature in the range, for example, 10 to 100° C., conveniently at about ambient temperature. The production of compounds of formula I and salts thereof wherein one or more of the substituents R$^2$ is an amino group may be effected by the reduction of a corresponding compound of formula I wherein the substituent(s) at the corresponding position(s) of the quinazoline group is/are a nitro group(s). The reduction may conveniently be effected as described in process (i) hereinafter. The production of a compound of formula I and salts thereof wherein the substituent(s) at the corresponding position(s) of the quinazoline group is/are a nitro group(s) may be effected by the processes described hereinbefore and hereinafter in processes (a-d) and (i-v) using a compound selected from the compounds of the formulae (I-XXII) in which the substituent(s) at the corresponding position(s) of the quinazoline group is/are a nitro group(s).

f) Compounds of the formula I and salts thereof wherein $X^1$ is —SO— or —SO$_2$— may be prepared by oxidation from the corresponding compound in which $X^1$ is —S— or —SO— (when $X^1$ is —SO$_2$— is required in the final product). Conventional oxidation conditions and reagents for such reactions are well known to the skilled chemist.

Synthesis of Intermediates (i) The compounds of formula III and salts thereof in which $L^1$ is halogeno may for example be prepared by halogenating a compound of the formula XI:

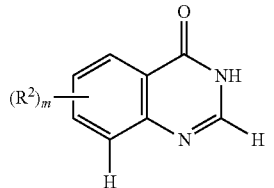

(XI)

wherein $R^2$ and m are as hereinbefore defined).

Convenient halogenating agents include inorganic acid halides, for example thionyl chloride, phosphorus(III)chloride, phosphorus(V)oxychloride and phosphorus(V)chloride. The halogenation reaction may be effected in the presence of an inert solvent or diluent such as for example a halogenated solvent such as methylene chloride, trichloromethane or carbon tetrachloride, or an aromatic hydrocarbon solvent such as benzene or toluene, or the reaction may be effected without the presence of a solvent. The reaction is conveniently effected at a temperature in the range, for example 10 to 150° C., preferably in the range 40 to 100° C.

The compounds of formula XI and salts thereof may, for example, be prepared by reacting a compound of the formula XII:

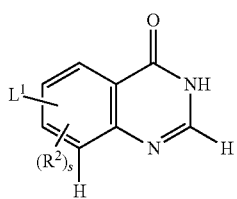

(XII)

(wherein $R^2$, s and $L^1$ are as hereinbefore defined) with a compound of the formula VIII as hereinbefore defined. The reaction may conveniently be effected in the presence of a base (as defined hereinbefore in process (a)) and advantageously in the presence of an inert solvent or diluent (as defined hereinbefore in process (a)), advantageously at a temperature in the range, for example 10 to 150° C., conveniently at about 100° C.

Compounds of formula XI and salts thereof wherein at least one $R^2$ is $R^5X^1$ and wherein $X^1$ is —O—, —S—, —SO—, —SO$_2$—, —C(O)—, —C(O)NR$^7$—, —SO$_2$NR$^8$— or —NR$^{10}$— (wherein $R^7$, $R^8$ and $R^{10}$ each independently represents hydrogen, $C_{1-3}$alkyl or $C_{1-3}$alkoxy$C_{2-3}$alkyl), may for example also be prepared by the reaction of a compound of the formula XIII:

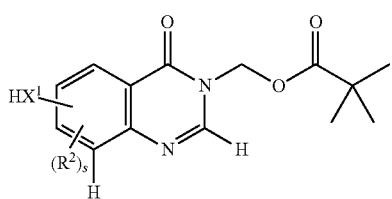

(XIII)

(wherein $R^2$ and s are as hereinbefore defined and $X^1$ is as hereinbefore defined in this section) with a compound of the formula VI as hereinbefore defined. The reaction may for example be effected as described for process (b) hereinbefore. The pivaloyloxymethyl group can then be cleaved by reacting the product with a base such as, for example, aqueous ammonia, triethylamine in water, an alkali metal or alkaline earth metal hydroxide or alkoxide, preferably aqueous ammonia, aqueous sodium hydroxide or aqueous potassium hydroxide, in a polar protic solvent such as an alcohol, for example methanol or ethanol. The reaction is conveniently effected at a temperature in the range 20 to 100° C., preferably in the range 20 to 50° C.

The compounds of formula XI and salts thereof may also be prepared by cyclising a compound of the formula XIV:

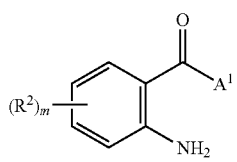

(XIV)

(wherein $R^2$ and m, are as hereinbefore defined, and $A^1$ is an hydroxy, alkoxy (preferably $C_{1-4}$alkoxy) or amino group) whereby to form a compound of formula XI or salt thereof.

The cyclisation may be effected by reacting a compound of the formula XIV, where $A^1$ is an hydroxy or alkoxy group, with formamide or an equivalent thereof effective to cause cyclisation whereby a compound of formula XI or salt thereof is obtained, such as [3-(dimethylamino)-2-azaprop-2-enylidene]dimethylammonium chloride. The cyclisation is conveniently effected in the presence of formamide as solvent or in the presence of an inert solvent or diluent such as an ether for example 1,4-dioxan. The cyclisation is conveniently effected at an elevated temperature, preferably in the range 80 to 200° C. The compounds of formula XI may also be prepared by cyclising a compound of the formula XIV, where $A^1$ is an amino group, with formic acid or an equivalent thereof effective to cause cyclisation whereby a compound of formula XI or salt thereof is obtained. Equivalents of formic acid effective to cause cyclisation include for example a tri-$C_{1-4}$alkoxymethane, for example triethoxymethane and trimethoxymethane. The cyclisation is conveniently effected in the presence of a catalytic amount of an anhydrous acid, such as a sulphonic acid for example p-toluenesulphonic acid, and in the presence of an inert solvent or diluent such as for example a halogenated solvent such as methylene chloride, trichloromethane or carbon tetrachloride, an ether such as diethyl ether or tetrahydrofuran, or an aromatic hydrocarbon solvent such as toluene. The cyclisation is conveniently effected at a temperature in the range, for example 10 to 100° C., preferably in the range 20 to 50° C.

Compounds of formula XIV and salts thereof may for example be prepared by the reduction of the nitro group in a compound of the formula XV:

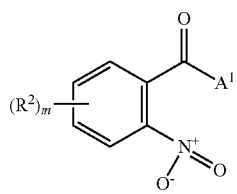

(XV)

(wherein $R^2$, m and $A^1$ are as hereinbefore defined) to yield a compound of formula XIV as hereinbefore defined. The reduction of the nitro group may conveniently be effected by any of the procedures known for such a transformation. The reduction may be carried out, for example, by stirring a solution of the nitro compound under hydrogen at 1 to 4 atmospheres pressure in the presence of an inert solvent or diluent as defined hereinbefore in the presence of a metal effective to catalyse hydrogenation reactions such as palladium or platinum. A further reducing agent is, for example, an activated metal such as activated iron (produced for example by washing iron powder with a dilute solution of an acid such as hydrochloric acid). Thus, for example, the reduction may be effected by heating the nitro compound under hydrogen at 2 atmospheres pressure in the presence of the activated metal and a solvent or diluent such as a mixture of water and alcohol, for example methanol or ethanol, at a temperature in the range, for example 50 to 150° C., conveniently at about 70° C.

Compounds of the formula XV and salts thereof may for example be prepared by the reaction of a compound of the formula XVI:

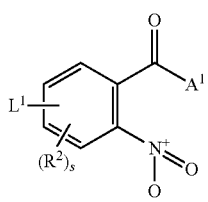

(wherein $R^2$, s, $L^1$ and $A^1$ are as hereinbefore defined) with a compound of the formula VIII as hereinbefore defined to give a compound of the formula XV. The reaction of the compounds of formulae XVI and VIII is conveniently effected under conditions as described for process (c) hereinbefore.

Compounds of formula XV and salts thereof wherein at least one $R^2$ is $R^5X^1$ and wherein $X^1$ is —O—, —S—, —SO$_2$—, —C(O)—, —C(O)NR$^7$—, —SO$_2$NR$^8$— or —NR$^{10}$— (wherein $R^7$, $R^8$ and $R^{10}$ each independently represents hydrogen, $C_{1-3}$alkyl or $C_{1-3}$alkoxy$C_{2-3}$alkyl), may for example also be prepared by the reaction of a compound of the formula XVII:

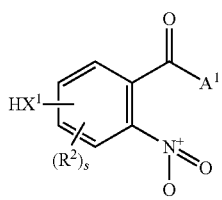

(wherein $R^2$, s and $A^1$ are as hereinbefore defined and $X^1$ is as hereinbefore defined in this section) with a compound of the formula VI as hereinbefore defined to yield a compound of formula XV as hereinbefore defined. The reaction of the compounds of formulae XVII and VI is conveniently effected under conditions as described for process (b) hereinbefore.

The compounds of formula III and salts thereof wherein at least one $R^2$ is $R^5X^1$ and wherein $X^1$ is —CH$_2$— may be prepared for example as described above from a compound of the formula XV (in which $R^2$ is —CH$_3$) or XIII (in which HX$^1$— is —CH$_3$), by radical bromination or chlorination to give a —CH$_2$Br or —CH$_2$Cl group which may then be reacted with a compound of the formula $R^5$—H under standard conditions for such substitution reactions.

The compounds of formula III and salts thereof wherein at least one $R^2$ is $R^5X^1$ and wherein $X^1$ is a direct bond may be prepared for example as described above from a compound of the formula XI, wherein the $R^5$ group is already present in the intermediate compounds (for example in a compound of the formula XV) used to prepare the compound of formula XI.

The compounds of formula III and salts thereof wherein at least one $R^2$ is $R^5X^1$ and wherein $X^1$ is —NR$^6$C(O)— or —NR$^9$SO$_2$— may be prepared for example from a compound of the formula XIII in which HX$^1$— is an —NHR$^6$— or —NHR$^9$— group (prepared for example from an amino group (later functionalised if necessary) by reduction of a nitro group) which is reacted with an acid chloride or sulfonyl chloride compound of the formula $R^5$COCl or $R^5$SO$_2$Cl.

The compounds of formula III and salts thereof wherein at least one $R^2$ is $R^5X^1$ and wherein $X^1$ is —O—, —S—, —SO$_2$—, —OC(O)—, —C(O)NR$^7$—, —SO$_2$NR$^8$— or —NR$^{10}$— (wherein $R^7$, $R^8$ and $R^{10}$ each independently represents hydrogen, $C_{1-3}$alkyl or $C_{1-3}$alkoxy$C_{2-3}$alkyl), may also be prepared for example by reacting a compound of the formula XVIII:

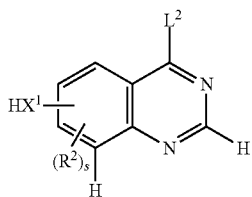

(wherein $R^2$ and s are as hereinbefore defined, $X^1$ is as hereinbefore defined in this section and $L^2$ represents a displaceable protecting moiety) with a compound of the formula VI as hereinbefore defined, whereby to obtain a compound of formula III in which $L^1$ is represented by $L^2$.

A compound of formula XVIII is conveniently used in which $L^2$ represents a phenoxy group which may if desired carry up to 5 substituents, preferably up to 2 substituents, selected from halogeno, nitro and cyano. The reaction may be conveniently effected under conditions as described for process (b) hereinbefore.

The compounds of formula XVIII and salts thereof may for example be prepared by deprotecting a compound of the formula XIX:

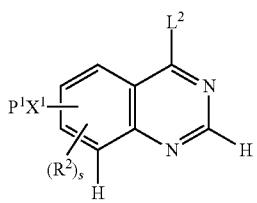

(wherein $R^2$, s and $L^2$ are as hereinbefore defined, $P^1$ is a protecting group and $X^1$ is as hereinbefore defined in the section describing compounds of the formula XVIII). The choice of protecting group $P^1$ is within the standard knowledge of an organic chemist, for example those included in standard texts such as "Protective Groups in Organic Synthesis" T. W. Greene and R. G. M. Wuts, 2nd Ed. Wiley 1991, including N-sulphonyl derivatives (for example, p-toluenesulphonyl), carbamates (for example, t-butyl carbonyl), N-alkyl derivatives (for example, 2-chloroethyl, benzyl) and amino acetal derivatives (for example benzyloxymethyl). The removal of such a protecting group may be effected by any of the procedures known for such a transformation, including those reaction conditions indicated in standard texts such as that indicated hereinbefore, or by a related procedure. Deprotection may be effected by techniques well known in the literature, for example where $P^1$ represents a benzyl group deprotection may be effected by hydrogenolysis or by treatment with trifluoroacetic acid.

One compound of formula III may if desired be converted into another compound of formula III in which the moiety $L^1$ is different. Thus for example a compound of formula III in which $L^1$ is other than halogeno, for example optionally substituted phenoxy, may be converted to a compound of formula III in which $L^1$ is halogeno by hydrolysis of a compound of formula III (in which $L^1$ is other than halogeno) to yield a compound of formula XI as hereinbefore defined, followed by introduction of halide to the compound of formula XI, thus obtained as hereinbefore defined, to yield a compound of formula III in which $L^1$ represents halogen.

(ii) Compounds of formula IV and salts thereof in which ring C is an indolyl may be prepared by any of the methods known in the art, such as for example those described in "Indoles Part I", "Indoles Part II", 1972 John Wiley & Sons Ltd and "Indoles Part III" 1979, John Wiley & Sons Ltd, edited by W. J. Houlihan.

Examples of the preparation of indoles are given in the Examples hereinafter, such as Examples 48, 237, 242, 250 and 291.

Compounds of formula IV and salts thereof in which ring C is a quinolinyl may be prepared by any of the methods known in the art, such as for example those described in "The Chemistry of Heterocyclic Compounds: Quinolines Parts I, II and III", 1982 (Interscience publications) John Wiley & Sons Ltd, edited by G. Jones, and in "Comprehensive Heterocyclic Chemistry Vol II by A. R. Katritzky", 1984 Pergamon Press, edited by A. J. Boulton and A McKillop.

(iii) Compounds of formula V as hereinbefore defined and salts thereof may be made by deprotecting the compound of formula XX:

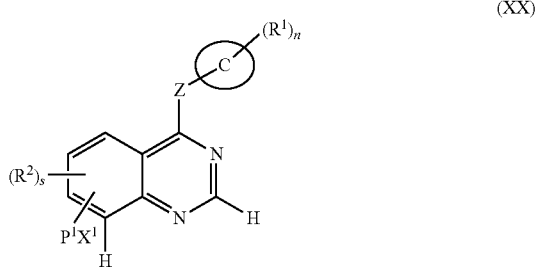

(wherein ring C, Z, $R^1$, $R^2$, $P^1$, n and s are as hereinbefore defined and $X^1$ is as hereinbefore defined in the section describing compounds of the formula V) by a process for example as described in (i) above.

Compounds of the formula XX and salts thereof may be made by reacting compounds of the formulae XIX and IV as hereinbefore defined, under the conditions described in (a) hereinbefore, to give a compound of the formula XX or salt thereof.

(iv) Compounds of the formula VII and salts thereof may be made by reacting a compound of the formula XXI:

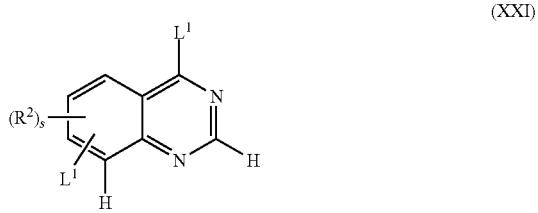

(wherein $R^2$, s and each $L^1$ are as hereinbefore defined and the $L^1$ in the 4-position and the other $L^1$ in a further position on the quinazoline ring may be the same or different) with a compound of the formula IV as hereinbefore defined, the reaction for example being effected by a process as described in (a) above.

(v) Compounds of formula IX as defined hereinbefore and salts thereof may for example be made by the reaction of compounds of formula V as defined hereinbefore with compounds of the formula XXII:

$L^1$-$C_{1-5}$alkyl-$L^1$ (XXII)

(wherein $L^1$ is as hereinbefore defined) to give compounds of formula IX or salts thereof. The reaction may be effected for example by a process as described in (b) above.

(vi) Intermediate compounds wherein $X^1$ is —SO— or —$SO_2$— may be prepared by oxidation from the corresponding compound in which $X^1$ is —S— or —SO— (when $X^1$ is —$SO_2$— is required in the final product). Conventional oxidation conditions and reagents for such reactions are well known to the skilled chemist.

When a pharmaceutically acceptable salt of a compound of the formula I is required, it may be obtained, for example, by reaction of said compound with, for example, an acid using a conventional procedure, the acid having a pharmaceutically acceptable anion.

Many of the intermediates defined herein, for example, those of the formulae V, VII, IX and XX are novel and these are provided as a further feature of the invention. The preparation of these compounds is as described herein and/or is by methods well known to persons skilled in the art of organic chemistry.

The identification of compounds which potently inhibit the tyrosine kinase activity associated with VEGF receptors such as Flt and/or KDR and which inhibit angiogenesis and/or increased vascular permeability is desirable and is the subject of the present invention. These properties may be assessed, for example, using one or more of the procedures set out below:

(a) In Vitro Receptor Tyrosine Kinase Inhibition Test

This assay determines the ability of a test compound to inhibit tyrosine kinase activity. DNA encoding VEGF, FGF or EGF receptor cytoplasmic domains may be obtained by total gene synthesis (Edwards M, International Biotechnology Lab 5(3), 19-25, 1987) or by cloning. These may then be expressed in a suitable expression system to obtain polypeptide with tyrosine kinase activity. For example VEGF, FGF and EGF receptor cytoplasmic domains, which were obtained by expression of recombinant protein in insect cells, were found to display intrinsic tyrosine kinase activity. In the case of the VEGF receptor Flt (Genbank accession number X51602), a 1.7 kb DNA fragment encoding most of the cytoplasmic domain, commencing with methionine 783 and including the termination codon, described by Shibuya et al (Oncogene, 1990, 5: 519-524), was isolated from cDNA and cloned into a baculovirus transplacement vector (for example pAcYM1 (see The Baculovirus Expression System: A Laboratory Guide, L. A. King and R. D. Possee, Chapman and Hall, 1992) or pAc360 or pBlueBacHis (available from Invitrogen Corporation)). This recombinant construct was co-transfected into insect cells (for example *Spodoptera frugiperda* 21(Sf21)) with viral DNA (eg Pharmingen BaculoGold) to prepare recombinant baculovirus. (Details of the methods for the assembly of recombinant DNA molecules and the preparation and use of recombinant baculovirus can be found in standard texts for example Sambrook et al, 1989, Molecular cloning—A Laboratory Manual, 2nd edition, Cold Spring Harbour Laboratory Press and O'Reilly et al, 1992, Baculovirus Expression Vectors—A Laboratory Manual, W. H. Freeman and Co, New York). For other tyrosine kinases for use in assays, cytoplasmic fragments starting from methionine 806 (KDR, Genbank accession number L04947), methionine 668 (EGF receptor, Genbank accession number X00588) and methionine 399 (FGF R1 receptor, Genbank accession number X51803) may be cloned and expressed in a similar manner.

For expression of cFlt tyrosine kinase activity, Sf21 cells were infected with plaque-pure cFlt recombinant virus at a multiplicity of infection of 3 and harvested 48 hours later. Harvested cells were washed with ice cold phosphate buffered saline solution (PBS) (10 mM sodium phosphate pH7.4, 138 mM sodium chloride, 2.7 mM potassium chloride) then resuspended in ice cold HNTG/PMSF (20 mM Hepes pH7.5, 150 mM sodium chloride, 10% v/v glycerol, 1% v/v Triton X100, 1.5 mM magnesium chloride, 1 mM ethylene glycol-bis(βaminoethyl ether) N,N,N',N'-tetraacetic acid (EGTA), 1 mM PMSF (phenylmethylsulphonyl fluoride); the PMSF is added just before use from a freshly-prepared 100 mM solution in methanol) using 1 ml HNTG/PMSF per 10 million cells. The suspension was centrifuged for 10 minutes at 13,000 rpm at 4° C., the supernatant (enzyme stock) was removed and stored in aliquots at −70° C. Each new batch of stock enzyme was titrated in the assay by dilution with enzyme diluent (100 mM Hepes pH 7.4, 0.2 mM sodium orthovanadate, 0.1% v/v Triton X100, 0.2 mM dithiothreitol). For a typical batch, stock enzyme is diluted 1 in 2000 with enzyme diluent and 50 µl of dilute enzyme is used for each assay well.

A stock of substrate solution was prepared from a random copolymer containing tyrosine, for example Poly (Glu, Ala, Tyr) 6:3:1 (Sigma P3899), stored as 1 mg/ml stock in PBS at −20° C. and diluted 1 in 500 with PBS for plate coating.

On the day before the assay 100 µl of diluted substrate solution was dispensed into all wells of assay plates (Nunc maxisorp 96-well immunoplates) which were sealed and left overnight at 4° C.

On the day of the assay the substrate solution was discarded and the assay plate wells were washed once with PBST (PBS containing 0.05% v/v Tween 20) and once with 50 mM Hepes pH7.4.

Test compounds were diluted with 10% dimethylsulphoxide (DMSO) and 25 µl of diluted compound was transferred to wells in the washed assay plates. "Total" control wells contained 10% DMSO instead of compound. Twenty five microliters of 40 mM manganese(II)chloride containing 8 µM adenosine-5'-triphosphate (ATP) was added to all test wells except "blank" control wells which contained manganese(II) chloride without ATP. To start the reactions 50 µl of freshly diluted enzyme was added to each well and the plates were incubated at room temperature for 20 minutes. The liquid was then discarded and the wells were washed twice with PBST. One hundred microliters of mouse IgG anti-phosphotyrosine antibody (Upstate Biotechnology Inc. product 05-321), diluted 1 in 6000 with PBST containing 0.5% w/v bovine serum albumin (BSA), was added to each well and the plates were incubated for 1 hour at room temperature before discarding the liquid and washing the wells twice with PBST. One hundred microliters of horse radish peroxidase (HRP)-linked sheep anti-mouse Ig antibody (Amersham product NXA 931), diluted 1 in 500 with PBST containing 0.5% w/v BSA, was added and the plates were incubated for 1 hour at room temperature before discarding the liquid and washing the wells twice with PBST. One hundred microliters of 2,2'-azino-bis(3-ethylbenzthiazoline-6-sulphonic acid) (ABTS) solution, freshly prepared using one 50 mg ABTS tablet (Boehringer 1204 521) in 50 ml freshly prepared 50 mM phosphate-citrate buffer pH5.0+0.03% sodium perborate (made with 1 phosphate citrate buffer with sodium perborate (PCSB) capsule (Sigma P4922) per 100 ml distilled water), was added to each well. Plates were then incubated for 20-60 minutes at room temperature until the optical density value of the "total" control wells, measured at 405 nm using a plate reading spectrophotometer, was approximately 1.0. "Blank" (no ATP) and "total" (no compound) control values were used to determine the dilution range of test compound which gave 50% inhibtion of enzyme activity.

(b) In Vitro HUVEC Proliferation Assay

This assay determines the ability of a test compound to inhibit the growth factor-stimulated proliferation of human umbilical vein endothelial cells (HUVEC).

HUVEC cells were isolated in MCDB 131 (Gibco BRL)+ 7.5% v/v foetal calf serum (FCS) and were plated out (at passage 2 to 8), in MCDB 131+2% v/v FCS+3 µg/ml heparin+1 µg/ml hydrocortisone, at a concentration of 1000 cells/well in 96 well plates. After a minimum of 4 hours they were dosed with the appropriate growth factor (i.e. VEGF 3 ng/ml, EGF 3 ng/ml or b-FGF 0.3 ng/ml) and compound. The cultures were then incubated for 4 days at 37° C. with 7.5% $CO_2$. On day 4 the cultures were pulsed with 1 µCi/well of tritiated-thymidine (Amersham product TRA 61) and incubated for 4 hours. The cells were harvested using a 96-well plate harvester (Tomtek) and then assayed for incorporation of tritium with a Beta plate counter. Incorporation of radioactivity into cells, expressed as cpm, was used to measure inhibition of growth factor-stimulated cell proliferation by compounds.

(c) In Vivo Solid Tumour Disease Model

This test measures the capacity of compounds to inhibit solid tumour growth.

CaLu-6 tumour xenografts were established in the flank of female athymic Swiss nu/nu mice, by subcutaneous injection of $1 \times 10^6$ CaLu-6 cells/mouse in 100 µl of a 50% (v/v) solution of Matrigel in serum free culture medium. Ten days after cellular implant, mice were allocated to groups of 8-10, so as to achieve comparable group mean volumes. Tumours were measured using vernier calipers and volumes were calculated as: $(l \times w) \times \sqrt{(l \times w)} \times (\pi/6)$, where l is the longest diameter and w the diameter perpendicular to the longest. Test compounds were administered orally once daily for a minimum of 21 days, and control animals received compound diluent. Tumours were measured twice weekly. The level of growth inhibition was calculated by comparison of the mean tumour volume of the control group versus the treatment group using a Student T test and/or a Mann-Whitney Rank Sum Test. The inhibitory effect of compound treatment was considered significant when $p<0.05$.

According to a further aspect of the invention there is provided a pharmaceutical composition which comprises a compound of the formula I as defined hereinbefore or a pharmaceutically acceptable salt thereof, in association with a pharmaceutically acceptable excipient or carrier.

The composition may be in a form suitable for oral administration, for example as a tablet or capsule, for parenteral injection (including intravenous, subcutaneous, intramuscular, intravascular or infusion) for example as a sterile solution, suspension or emulsion, for topical administration for example as an ointment or cream or for rectal administration for example as a suppository. In general the above compositions may be prepared in a conventional manner using conventional excipients.

The compositions of the present invention are advantageously presented in unit dosage form. The compound will normally be administered to a warm-blooded animal at a unit dose within the range 5-5000 mg per square meter body area of the animal, i.e. approximately 0.1-100 mg/kg. A unit dose in the range, for example, 1-100 mg/kg, preferably 1-50 mg/kg is envisaged and this normally provides a therapeutically-effective dose. A unit dose form such as a tablet or capsule will usually contain, for example 1-250 mg of active ingredient.

According to a further aspect of the present invention there is provided a compound of the formula I or a pharmaceutically acceptable salt thereof as defined hereinbefore for use in a method of treatment of the human or animal body by therapy.

We have found that compounds of the present invention inhibit VEGF receptor tyrosine kinase activity and are therefore of interest for their antiangiogenic effects and/or their ability to cause a reduction in vascular permeability.

A further feature of the present invention is a compound of formula I, or a pharmaceutically acceptable salt thereof, for use as a medicament, conveniently a compound of formula I, or a pharmaceutically acceptable salt thereof, for use as a medicament for producing an antiangiogenic and/or vascular permeability reducing effect in a warm-blooded animal such as a human being.

Thus according to a further aspect of the invention there is provided the use of a compound of the formula I, or a pharmaceutically acceptable salt thereof in the manufacture of a medicament for use in the production of an antiangiogenic and/or vascular permeability reducing effect in a warm-blooded animal such as a human being.

According to a further feature of the invention there is provided a method for producing an antiangiogenic and/or vascular permeability reducing effect in a warm-blooded animal, such as a human being, in need of such treatment which comprises administering to said animal an effective amount of a compound of formula I or a pharmaceutically acceptable salt thereof as defined hereinbefore.

As stated above the size of the dose required for the therapeutic or prophylactic treatment of a particular disease state will necessarily be varied depending on the host treated, the route of administration and the severity of the illness being treated. Preferably a daily dose in the range of 1-50 mg/kg is employed. However the daily dose will necessarily be varied depending upon the host treated, the particular route of administration, and the severity of the illness being treated. Accordingly the optimum dosage may be determined by the practitioner who is treating any particular patient.

The antiangiogenic and/or vascular permeability reducing treatment defined hereinbefore may be applied as a sole therapy or may involve, in addition to a compound of the invention, one or more other substances and/or treatments. Such conjoint treatment may be achieved by way of the simultaneous, sequential or separate administration of the individual components of the treatment. In the field of medical oncology it is normal practice to use a combination of different forms of treatment to treat each patient with cancer. In medical oncology the other component(s) of such conjoint treatment in addition to the antiangiogenic and/or vascular permeability reducing treatment defined hereinbefore may be: surgery, radiotherapy or chemotherapy. Such chemotherapy may cover three main categories of therapeutic agent:
(i) other antiangiogenic agents that work by different mechanisms from those defined hereinbefore (for example linomide, inhibitors of integrin $\alpha v \beta 3$ function, angiostatin, razoxin, thalidomide), and including vascular targeting agents (for example combretastatin phosphate and the vascular damaging agents described in International Patent Application Publication No. WO 99/02166 the entire disclosure of which document is incorporated herein by reference, (for example N-acetylcolchinol-O-phosphate));
(ii) cytostatic agents such as antioestrogens (for example tamoxifen, toremifene, raloxifene, droloxifene, iodoxyfene), progestogens (for example megestrol acetate), aromatase inhibitors (for example anastrozole, letrazole, vorazole, exemestane), antiprogestogens, antiandrogens (for example flutamide, nilutamide, bicalutamide, cyproterone acetate), LHRH agonists and antagonists (for example goserelin acetate, luprolide), inhibitors of testosterone 5α-dihydroreductase (for example finasteride), anti-invasion agents (for example metalloproteinase inhibitors like marimastat and inhibitors of urokinase plasminogen activator receptor function) and inhibitors of growth factor function, (such growth factors include for example platelet derived growth factor and hepatocyte growth factor such inhibitors include growth factor antibodies, growth factor receptor antibodies, tyrosine kinase inhibitors and serine/threonine kinase inhibitors); and
(iii) antiproliferative/antineoplastic drugs and combinations thereof, as used in medical oncology, such as antimetabolites (for example antifolates like methotrexate, fluoropyrimidines like 5-fluorouracil, purine and adenosine analogues, cytosine arabinoside); antitumour antibiotics (for example anthracyclines like doxorubicin, daunomycin, epirubicin and idarubicin, mitomycin-C, dactinomycin, mithramycin); platinum derivatives (for example cisplatin, carboplatin); alkylating agents (for example nitrogen mustard, melphalan, chlorambucil, busulphan, cyclophosphamide, ifosfamide, nitrosoureas, thiotepa); antimitotic agents (for example vinca alkaloids like vincristine and taxoids like taxol, taxotere); topoisomerase inhibitors (for example epipodophyllotoxins like etoposide and teniposide, amsacrine, topotecan, and also irinotecan); also enzymes (for example asparaginase); and thymidylate synthase inhibitors (for example raltitrexed);
and additional types of chemotherapeutic agent include:
(iv) biological response modifiers (for example interferon); and
(v) antibodies (for example edrecolomab).

For example such conjoint treatment may be achieved by way of the simultaneous, sequential or separate administration of a compound of formula I as defined hereinbefore, and a vascular targeting agent described in WO 99/02166 such as N-acetylcolchinol-O-phosphate (Exampe 1 of WO 99/02166).

As stated above the compounds defined in the present invention are of interest for their antiangiogenic and/or vascular permeability reducing effects. Such compounds of the invention are expected to be useful in a wide range of disease states including cancer, diabetes, psoriasis, rheumatoid arthritis, Kaposi's sarcoma, haemangioma, acute and chronic nephropathies, atheroma, arterial restenosis, autoimmune diseases, acute inflammation, excessive scar formation and adhesions, endometriosis, dysfunctional uterine bleeding and ocular diseases with retinal vessel proliferation. In particular such compounds of the invention are expected to slow advantageously the growth of primary and recurrent solid tumours of, for example, the colon, breast, prostate, lungs and skin. More particularly such compounds of the invention are expected to inhibit the growth of those primary and recurrent solid tumours which are associated with VEGF, especially those tumours which are significantly dependent on VEGF for their growth and spread, including for example, certain tumours of the colon, breast, prostate, lung, vulva and skin.

In addition to their use in therapeutic medicine, the compounds of formula I and their pharmaceutically acceptable salts are also useful as pharmacological tools in the development and standardisation of in vitro and in vivo test systems for the evaluation of the effects of inhibitors of VEGF receptor tyrosine kinase activity in laboratory animals such as cats, dogs, rabbits, monkeys, rats and mice, as part of the search for new therapeutic agents.

It is to be understood that where the term "ether" is used anywhere in this specification it refers to diethyl ether.

The invention will now be illustrated in the following non-limiting Examples in which, unless otherwise stated:—

(i) evaporations were carried out by rotary evaporation in vacuo and work-up procedures were carried out after removal of residual solids such as drying agents by filtration;

(ii) operations were carried out at ambient temperature, that is in the range 18-25° C. and under an atmosphere of an inert gas such as argon;

(iii) column chromatography (by the flash procedure) and medium pressure liquid chromatography (MPLC) were performed on Merck Kieselgel silica (Art. 9385) or Merck Lichroprep RP-18 (Art. 9303) reversed-phase silica obtained from E. Merck, Darmstadt, Germany;

(iv) yields are given for illustration only and are not necessarily the maximum attainable;

(v) melting points are uncorrected and were determined using a Mettler SP62 automatic melting point apparatus, an oil-bath apparatus or a Koffler hot plate apparatus.

(vi) the structures of the end-products of the formula I were confirmed by nuclear (generally proton) magnetic resonance (NMR) and mass spectral techniques; proton magnetic resonance chemical shift values were measured on the delta scale and peak multiplicities are shown as follows: s, singlet; d, doublet; t, triplet; m, multiplet; br, broad; q, quartet, quin, quintet;

(vii) intermediates were not generally fully characterised and purity was assessed by thin layer chromatography (TLC), high-performance liquid chromatography (HPLC), infra-red (IR) or NMR analysis;

(viii) HPLC were run under 2 different conditions:

1) on a TSK Gel super ODS 2 μM 4.6 mm×5 cm column, eluting with a gradient of methanol in water (containing 1% acetic acid) 20 to 100% in 5 minutes. Flow rate 1.4 ml/minute. Detection: U.V. at 254 nm and light scattering detections;

2) on a TSK Gel super ODS 2 μM 4.6 mm×5 cm column, eluting with a gradient of methanol in water (containing 1% acetic acid) 0 to 100% in 7 minutes. Flow rate 1.4 ml/minute. Detection: U.V. at 254 nm and light scattering detections.

(ix) petroleum ether refers to that fraction boiling between 40-60° C.

(x) the following abbreviations have been used:—
DMF N,N-dimethylformamide
DMSO dimethylsulphoxide
TFA trifluoroacetic acid
NMP 1-methyl-2-pyrrolidinone
THF tetrahydrofuran
HMDS 1,1,1,3,3,3-hexamethyldisilazane.
HPLC RT HPLC retention time
DEAD diethyl azodicarboxylate
DMA dimethylacetamide
DMAP 4-dimethylaminopyridine

EXAMPLE 1

A mixture of 4-chloro-6-methoxy-7-(3-morpholinopropoxy)quinazoline (225 mg, 0.67 mmol), potassium carbonate (106 mg, 0.77 mmol) and 6-hydroxyquinoline (112 mg, 0.77 mmol) in DMF (7.5 ml) was stirred at 100° C. for 5 hours and allowed to cool to ambient temperature. The reaction mixture was treated with 1M aqueous sodium hydroxide solution (40 ml) and stirred at ambient temperature for a few minutes. The crude solid was collected by filtration and washed with water. The resultant solid was dissolved in dichloromethane (2 ml) and filtered through phase separating paper. The filtrate was evaporated under vacuum and the residue was triturated with ether, collected by filtration and dried to give 6-methoxy-7-(3-morpholinopropoxy)-4-(quinolin-6-yloxy)quinazoline (163 mg, 55%).

$^1$H HMR Spectrum: (DMSOd$_6$) 1.98(m, 2H); 2.40(m, 4H); 2.48(t, 2H); 3.59(m, 4H); 4.00(s, 3H); 4.25(t, 2H); 7.40(s, 1H); 7.58(m, 1H); 7.62(s, 1H); 7.74(dd, 1H); 7.92(d, 1H); 8.10(d, 1H); 8.38(d, 1H); 8.55(s, 1H); 8.92(m, 1H)

MS(ESI): 447 (MH)$^+$

| Elemental analysis: | Found | C 65.9 | H 5.7 | N 12.4 |
|---|---|---|---|---|
| C$_{25}$H$_{26}$N$_4$O$_4$ 0.5H$_2$O | Requires | C 65.9 | H 6.0 | N 12.3% |

The starting material was prepared as follows:

A mixture of 2-amino-4-benzyloxy-5-methoxybenzamide (10 g, 0.04 mol), (J. Med. Chem. 1977, vol 20, 146-149), and Gold's reagent (7.4 g, 0.05 mol) in dioxane (100 ml) was stirred and heated at reflux for 24 hours. Sodium acetate (3.02 g, 0.037 mol) and acetic acid (1.65 ml, 0.029 mol) were added to the reaction mixture and it was heated for a further 3 hours. The volatiles were removed by evaporation, water was added to the residue, the solid was collected by filtration, washed with water and dried. Recrystallisation from acetic acid gave 7-benzyloxy-6-methoxy-3,4-dihydroquinazolin-4-one (8.7 g, 84%).

7-Benzyloxy-6-methoxy-3,4-dihydroquinazolin-4-one (35 g, 124 mmol) was suspended in thionyl chloride (440 ml) and DMF (1.75 ml) and heated at reflux for 4 hours. The thionyl chloride was evaporated under vacuum and the residue azeotroped with toluene three times. The residue was dissolved in NMP (250 ml) to give a solution of 7-benzyloxy-4-chloro-6-methoxyquinazoline.

Phenol (29.05 g, 309 mmol) was dissolved in NMP (210 ml), sodium hydride (11.025 g, 60% dispersion in mineral oil) was added in portions with cooling and the mixture was stirred for 3 hours. The viscous suspension was diluted with NMP (180 ml) and stirred overnight. The solution of 7-benzyloxy-4-chloro-6-methoxyquinazoline was added and the suspension stirred at 100° C. for 2.5 hours. The suspension was allowed to cool to ambient temperature and poured into water (1.5 l) with vigorous stirring. The precipitate was collected by filtration, washed with water and dried under vacuum. The residue was dissolved in dichloromethane, washed with brine and filtered through phase separating paper. The filtrate was evaporated under vacuum then triturated with ether to give 7-benzyloxy-6-methoxy-4-phenoxyquinazoline (87.8 g, 83%) as a pale cream solid.

$^1$H HMR Spectrum: (CDCl$_3$) 4.09(s, 3H); 5.34(s, 2H); 7.42(m, 12H); 7.63(s, 1H)

MS(ESI): 359 (MH)$^+$

7-Benzyloxy-6-methoxy-4-phenoxyquinazoline (36.95 g, 105.5 mmol) was suspended in TFA (420 ml) and heated at reflux for 3 hours. The reaction mixture was allowed to cool and evaporated under vacuum. The residue was stirred mechanically in water then basified with saturated aqueous sodium hydrogen carbonate solution and stirred overnight. The water was decanted and the solid suspended in acetone. After stirring the white solid was collected by filtration, washed with acetone and dried to give 7-hydroxy-6-methoxy-4-phenoxyquinazoline (26.61 g, 96%).

¹H HMR Spectrum: (DMSOd₆) 3.97(s, 3H); 7.22(s, 1H); 7.30(m, 3H); 7.47(t, 2H); 7.56(s, 1H); 8.47(s, 1H); 10.70(s, 1H)

MS(ESI): 269 (MH)⁺

Morpholine (52.2 ml, 600 mmol) and 1-bromo-3-chloropropane (30 ml, 300 mmol) were dissolved in dry toluene (180 ml) and heated to 70° C. for 3 hours. The solid was removed by filtration and the filtrate evaporated under vacuum. The resulting oil was decanted from the additional solid residue and the oil was vacuum distilled to yield 1-chloro-3-morpholinopropane (37.91 g, 77%) as an oil.

¹H HMR Spectrum: (DMSOd₆) 1.85(m, 2H); 2.30(t, 4H); 2.38(t, 2H); 3.53(1, 411); 3.65(t, 2H)

MS(ESI): 164 (MH)⁺

7-Hydroxy-6-methoxy-4-phenoxyquinazoline (25.27 g, 0.1 mol) and 1-chloro-3-morpholinopropane (18.48 g, 0.11 mol) were taken up in DMF (750 ml) and potassium carbonate (39.1 g, 0.33 mol) was added. The suspension was heated at 90° C. for 3 hours then allowed to cool. The suspension was filtered and the volatiles were removed by evaporation. The residue was triturated with ethyl acetate and 6-methoxy-7-(3-morpholinopropoxy)-4-phenoxyquinazoline (31.4 g, 84%) was collected by filtration as a yellow crystalline solid.

¹H HMR Spectrum: (DMSOd₆) 1.97(m, 2H); 2.39(t, 4H); 2.47(t, 2H); 3.58(t, 4H); 3.95(s, 3H); 4.23(t, 2H); 7.31(m, 3H); 7.36(s, 1H); 7.49(t, 2H); 7.55(s, 1H); 8.52(s, 1H)

MS(ESI): 396 (MH)⁺

6-Methoxy-7-(3-morpholinopropoxy)-4-phenoxyquinazoline (33.08 g, 84 mmol) was dissolved in 6M aqueous hydrochloric acid (800 ml) and heated at reflux for 1.5 hours. The reaction mixture was decanted and concentrated to 250 ml then basified (pH9) with saturated aqueous sodium hydrogen carbonate solution. The aqueous layer was extracted with dichloromethane (4×400 ml), the organic layer was separated and filtered through phase separating paper. The solid was triturated with ethyl acetate to give 6-methoxy-7-(3-morpholinopropoxy)-3,4-dihydroquinazolin-4-one (23.9 g, 89%) as a white solid.

¹H HMR Spectrum: (DMSOd₆) 1.91(m, 2H); 2.34(t, 4H); 2.42(t, 2H); 3.56(t, 4H); 3.85(s, 3H); 4.12(t, 2H); 7.11(s, 1H); 7.42(s, 1H); 7.96(s, 1H); 12.01(s, 1H)

MS(ESI): 320 (MH)⁺

6-Methoxy-7-(3-morpholinopropoxy)-3,4-dihydroquinazolin-4-one (23.9 g, 75 mmol) was suspended in thionyl chloride (210 ml) and DMF (1.8 ml) then heated at reflux for 1.5 hours. The thionyl chloride was removed by evaporation under vacuum and the residue azeotroped with toluene three times. The residue was taken up in water and basified (pH8) with saturated aqueous sodium hydrogen carbonate solution. The aqueous layer was extracted with dichloromethane (4×400 ml), the organic layer was washed with water and brine then dried (MgSO₄). After filtration the organic layer was concentrated under vacuum to give a yellow solid which was triturated with ethyl acetate to give 4-chloro-6-methoxy-7-(3-morpholinopropoxy)quinazoline (17.39 g, 52%) as a pale cream solid.

¹H HMR Spectrum: (CDCl₃) 2.10-2.16(m, 2H); 2.48(br s, 4H); 2.57(t, 2H); 3.73(t, 4H); 4.05(s, 3H); 4.29(t, 2H); 7.36(s, 1H); 7.39(s, 1H); 8.86(s, 1H)

MS-ESI: 337 [MH]⁺

EXAMPLE 2

A mixture of 4-chloro-6-methoxy-7-(3-morpholinopropoxy)quinazoline (225 mg, 0.67 mmol), (prepared as described for the starting material in Example 1), potassium carbonate (106 mg, 0.77 mmol) and 7-hydroxyquinoline (112 mg, 0.77 mmol) in DMF (7.5 ml) was stirred at 100° C. for 5 hours and allowed to cool to ambient temperature. The reaction mixture was treated with 1M aqueous sodium hydroxide solution (40 ml) and stirred at ambient temperature for a few minutes. The crude solid was collected by filtration washing with water. The resultant solid was dissolved in dichloromethane (2 ml) and filtered through phase separating paper. The filtrate was evaporated under vacuum to give a solid residue which was triturated with ether, filtered and dried to give 6-methoxy-7-(3-morpholinopropoxy)-4-(quinolin-7-yloxy)quinazoline (116 mg, 39%).

¹H HMR Spectrum: (DMSOd₆) 1.98(m, 2H); 2.39(m, 4H); 2.48(t, 2H); 3.59(m, 4H); 4.00(s, 3H); 4.25(t, 2H); 7.40(s, 1H); 7.58(m, 2H); 7.62(s, 1H); 7.92(d, 1H); 8.10(d, 1H); 8.44(d, 1H); 8.55(s, 1H); 8.92(m, 1H)

MS(ESI): 447 (MH)⁺

| Elemental analysis: | Found | C 66.6 | H 5.7 | N 12.4 |
|---|---|---|---|---|
| C₂₅H₂₆N₄O₄ 0.25H₂O | Requires | C 66.6 | H 5.9 | N 12.4% |

EXAMPLE 3

A mixture of 4-chloro-6-methoxy-7-(3-morpholinopropoxy)quinazoline (225 mg, 0.67 mmol), (prepared as described for the starting material in Example 1), potassium carbonate (106 mg, 0.77 mmol) and 1-naphthol (111 mg, 0.77 mmol) in DMF (7.5 ml) was stirred at 100° C. for 5 hours then allowed to cool to ambient temperature. The reaction mixture was treated with 1M aqueous sodium hydroxide solution (40 ml) and stirred at ambient temperature for a few minutes. The reaction mixture was extracted with ethyl acetate and the organic extracts were washed with water. The organic extracts were dried (MgSO₄) and the solvent removed by evaporation. The residue was purified by column chromatography eluting with methylene chloride/methanol (95/5) to give a solid which was triturated with ether, filtered and dried to give 6-methoxy-7-(3-morpholinopropoxy)-4-(1-naphthyloxy)quinazoline (194 mg, 65%).

¹H HMR Spectrum: (DMSOd₆) 1.98(m, 2H); 2.39(m, 4H); 2.48(t, 2H); 3.59(m, 4H); 4.00(s, 3H); 4.26(t, 2H); 7.40(s, 1H); 7.48(m, 2H); 7.58(m, 2H); 7.74(s, 1H); 7.75(d, 1H); 7.92(d, 1H); 8.03(d, 1H); 8.42(s, 1H)

MS(ESI): 446 (MH)⁺

| Elemental analysis: | Found | C 69.9 | H 6.2 | N 9.4 |
|---|---|---|---|---|
| C₂₆H₂₇N₃O₄ | Requires | C 70.1 | H 6.1 | N 9.4% |

EXAMPLE 4

A mixture of 4-chloro-6-methoxy-7-(3-morpholinopropoxy)quinazoline (225 mg, 0.67 mmol), (prepared as described for the starting material in Example 1), potassium carbonate (106 mg, 0.77 mmol) and 7-hydroxy-4-methylquinoline (122 mg, 0.77 mmol), (Chem. Berich. 1967, 100, 2077), in DMF (7.5 ml) was stirred at 100° C. for 5 hours then allowed to cool to ambient temperature. The reaction mixture was treated with 1M aqueous sodium hydroxide solution (40 ml) and stirred at ambient temperature for a few minutes. The crude solid was collected by filtration washing with water. The resultant solid was dissolved in dichloromethane (2 ml) and was filtered through phase separating paper. The filtrate was evaporated under vacuum to give a solid residue which was triturated with ether, filtered and dried to give 6-methoxy-4-(4-methylquinolin-7-yloxy)-7-(3-morpholinopropoxy)quinazoline (175 mg, 57%).

$^1$H HMR Spectrum: (DMSOd$_6$) 1.98(m, 2H); 2.39(m, 4H); 2.48(t, 2H); 2.71(s, 3H); 3.59(m, 4H); 4.00(s, 3H); 4.26(t, 2H); 7.40(s, 1H); 7.41(m, 1H); 7.61(dd, 1H); 7.62(s, 1H); 7.90(d, 1H); 8.20(d, 1H); 8.52(s, 1H); 8.78(d, 1H)

MS(ESI): 461 (MH)$^+$

| Elemental analysis: | Found | C 67.1 | H 5.9 | N 12.1 |
|---|---|---|---|---|
| C$_{26}$H$_{28}$N$_4$O$_4$ 0.2H$_2$O | Requires | C 67.3 | H 6.2 | N 12.1% |

EXAMPLE 5

A mixture of 4-chloro-7-(3-(1,1-dioxothiomorpholino)propoxy)-6-methoxyquinazoline (220 mg, 0.57 mmol), potassium carbonate (106 mg, 0.77 mmol) and 7-hydroxyquinoline (111 mg, 0.76 mmol) in DMF (7.5 ml) was stirred at 100° C. for 5 hours then allowed to cool to ambient temperature. The reaction mixture was treated with 1M aqueous sodium hydroxide solution (40 ml) and stirred at ambient temperature for a few minutes. The crude solid was collected by filtration washing with water. The resultant solid was dissolved in dichloromethane (2 ml) and was filtered through phase separating paper. The filtrate was evaporated under vacuum to give a solid residue which was triturated with ether, filtered and dried to give 7-(3-(1,1-dioxothiomorpholino)propoxy)-6-methoxy-4-(quinolin-7-yloxy)quinazoline (205 mg, 73%).

$^1$H HMR Spectrum: (DMSOd$_6$) 1.98(m, 2H); 2.65(t, 2H); 2.92(m, 4H); 3.10(m, 4H); 4.00(s, 3H); 4.28(t, 2H); 7.42(s, 1H); 7.58(m, 2H); 7.64(s, 1H); 7.92(d, 1H); 8.10(d, 1H); 8.44(d, 1H); 8.55(s, 1H); 8.92(m, 1H)

MS(ESI): 495 (MH)$^+$

| Elemental analysis: | Found | C 60.0 | H 5.0 | N 11.1 |
|---|---|---|---|---|
| C$_{25}$H$_{26}$N$_4$O$_5$S 0.25H$_2$O | Requires | C 60.2 | H 5.4 | N 11.2% |

The starting material was prepared as follows:

7-Benzyloxy-6-methoxy-3,4-dihydroquinazolin-4-one (20.3 g, 124 mmol), (prepared as described for the starting material in Example 1), was taken up in thionyl chloride (440 ml) and DMF (1.75 ml) then heated at reflux for 4 hours. The thionyl chloride was evaporated under vacuum and the residue azeotroped with toluene three times to give 7-benzyloxy-4-chloro-6-methoxyquinazoline.

A mixture of the crude 7-benzyloxy-4-chloro-6-methoxyquinazoline, potassium carbonate (50 g, 362 mmol) and 4-chloro-2-fluorophenol (8.8 ml, 83 mmol) in DMF (500 ml) was stirred at 100° C. for 5 hours then allowed to cool to ambient temperature overnight. The reaction mixture was poured into water (2 l) and was stirred at ambient temperature for a few minutes. The crude solid was collected by filtration washing with water. The resultant solid was dissolved in dichloromethane and filtered through diatomaceous earth. The filtrate was treated with decolourising charcoal, boiled for a few minutes then filtered through diatomaceous earth. The filtrate was filtered through phase separating paper and then evaporated under vacuum to give a solid residue which was triturated with ether, filtered and dried to give 7-benzyloxy-4-(4-chloro-2-fluorophenoxy)-6-methoxyquinazoline (23.2 g, 76%).

$^1$H HMR Spectrum: (DMSOd$_6$) 3.98(s, 3H); 5.34(s, 2H); 7.42(m, 9H); 7.69(dd, 1H); 8.55(s, 1H)

MS(ESI): 411 (MH)$^+$

7-Benzyloxy-4-(4-chloro-2-fluorophenoxy)-6-methoxyquinazoline (1.4 g, 3.4 mmol) was suspended in TFA (15 ml) and heated at reflux for 3 hours. The reaction mixture was allowed to cool, toluene was added and the volatiles were removed by evaporation under vacuum. The residue was triturated with ether and then acetone. The precipitate was collected by filtration and dried to give 4-(4-chloro-2-fluorophenoxy)-7-hydroxy-6-methoxyquinazoline (21.8 g). This was used without further purification in the next step.

$^1$H HMR Spectrum: (DMSOd$_6$) 3.97(s, 3H); 7.22(s, 1H); 7.39(d, 1H); 7.53(m, 2H); 7.67(dd, 1H); 8.46(s, 1H)

MS(ESI): 321 (MH)$^+$

A mixture of 3-amino-1-propanol (650 µl, 8.4 mmol) and vinyl sulphone (1 g, 8.4 mmol) was heated at 110° C. for 45 minutes. The mixture was allowed to cool and was purified by column chromatography eluting with methylene chloride/methanol (95/5) to give 3-(1,1-dioxothiomorpholino)-1-propanol (800 mg, 90%).

$^1$H HMR Spectrum: (CDCl$_3$) 1.7-1.8(m, 2H); 2.73(t, 2H); 3.06(br s, 8H); 3.25(s, 1H); 3.78(t, 2H)

MS-ESI: 194[MH]$^+$ 4-(4-Chloro-2-fluorophenoxy)-7-hydroxy-6-methoxyquinazoline (5.0 g, 15.6 mmol) was suspended in dichloromethane (150 ml) and tributylphosphine (11.1 ml, 44.6 mmol) was added followed by stirring at ambient temperature for 30 minutes. To this mixture was added 3-(1,1-dioxothiomorpholino)-1-propanol (4.2 g, 21.8 mmol) followed by the addition of 1,1'-(azodicarbonyl)dipiperidine (11.7 g, 46.4 mmol) in portions. The mixture was stirred at ambient temperature overnight then diluted with ether (300 ml) and the precipitate was removed by filtration. The residue was chromatographed on silica eluting with dichloromethane and methanol (95/5). The relevant fractions were combined and evaporated to give a solid which was triturated with ethyl acetate filtered and dried to give 4-(4-chloro-2-fluorophenoxy)-7-(3-(1,1-dioxothiomorpholino)propoxy)-6-methoxyquinazoline (5.4 g, 70%).

This was used without further purification in the next step.

$^1$H HMR Spectrum: (DMSOd$_6$) 1.86(m, 2H); 2.65(t, 2H); 2.92(m, 4H); 3.08(m, 4H); 3.97(s, 3H); 4.26(t, 2H); 7.40(m, 1H); 7.42(s, 1H); 7.56(m, 2H); 7.68(dd, 1H); 8.54(s, 1H)

MS(ESI): 496 (MH)$^+$

| Elemental analysis: | Found | C 52.7 | H 4.4 | N 8.3 |
|---|---|---|---|---|
| C$_{22}$H$_{23}$N$_3$ClFO$_5$S 0.25H$_2$O | Requires | C 52.8 | H 4.7 | N 8.4% |

4-(4-Chloro-2-fluorophenoxy)-7-(3-(1,1-dioxothiomorpholino)propoxy)-6-methoxyquinazoline (3.5 g, 7 mmol) was dissolved in 2M aqueous hydrochloric acid (56 ml) and heated at 95° C. for 2 hours. The cooled reaction mixture was treated with solid sodium hydrogen carbonate solution to give a thick paste which was diluted with water and filtered. The solid was transferred to a flask and azeotroped with toluene twice to give a dry solid. The solid was flash chromatographed on silica eluting with dichloromethane and methanol (95/5). The relevant fractions were combined and evaporated to give 7-(3-(1,1-dioxothiomorpholino)propoxy)-6-methoxy-3,4-dihydroquinazolin-4-one (2.26 g, 87%) as a white solid.

MS(ESI): 368 (MH)+

7-(3-(1,1-Dioxothiomorpholino)propoxy)-6-methoxy-3,4-dihydroquinazolin-4-one (4.2 g, 11.4 mmol) was suspended in thionyl chloride (45 ml) and DMF (0.1 ml) then heated at reflux for 2.5 hours. The residue was diluted with toluene, the thionyl chloride was evaporated under vacuum, the residue was then azeotroped with toluene three times. The residue was taken up in water and basified (pH8) with saturated aqueous sodium hydrogen carbonate solution. The aqueous layer was extracted with dichloromethane (×4), the organic layer was washed with water and brine then filtered through phase separating paper. The organic layer was concentrated under vacuum to give an orange solid. The solid was flash chromatographed on silica eluting with dichloromethane and methanol (95/5). The relevant fractions were combined and evaporated to give a solid which was triturated with ether then filtered and dried to give 4-chloro-7-(3-(1,1-dioxothiomorpholino)propoxy)-6-methoxyquinazoline (2.27 g, 52%).

MS(ESI): 386 (MH)+

EXAMPLE 6

6,7-Dimethoxy-3,4-dihydroquinazolin-4-one (290 mg, 1.4 mmol) was suspended in thionyl chloride (5 ml) and DMF (2 drops) and heated at reflux for 2 hours. The thionyl chloride was evaporated under vacuum and the residue azeotroped with toluene three times to give 4-chloro-6,7-dimethoxyquinazoline. A mixture of the crude 4-chloro-6,7-dimethoxyquinazoline, potassium carbonate (970 mg, 7 mmol) and 7-hydroxyquinoline (235 mg, 1.62 mmol) in DMF (10 ml) was stirred at 100° C. for 5 hours and allowed to cool to ambient temperature overnight. The reaction mixture was treated with 1M aqueous sodium hydroxide solution and stirred at ambient temperature for a few minutes. The reaction mixture was extracted with ethyl acetate (×4) and the organic extracts washed with water and brine. The organic extracts were dried (MgSO$_4$), filtered and the solvent removed under vacuum. The residue was triturated with ethyl acetate and then recrystallised from hot ethyl acetate to give 6,7-dimethoxy-4-(quinolin-7-yloxy)quinazoline (110 mg, 24%) as a white solid.

$^1$H HMR Spectrum: (DMSOd$_6$) 4.00(s, 3H); 4.00(s, 3H); 7.40(s, 1H); 7.59(m, 3H); 7.92(d, 1H); 8.08(d, 1H); 8.42(d, 1H); 8.55(s, 1H); 8.92(dd, 1H)

MS(ESI): 334 (MH)+

| Elemental analysis: | Found | C 68.2 | H 4.3 | N 12.5 |
| $C_{19}H_{15}N_3O_3$ | Requires | C 68.5 | H 4.5 | N 12.6% |

The starting material was prepared as follows:

A mixture of 4,5-dimethoxyanthranilic acid (19.7 g) and formamide (10 ml) was stirred and heated at 190° C. for 5 hours. The mixture was allowed to cool to approximately 80° C. and water (50 ml) was added. The mixture was then allowed to stand at ambient temperature for 3 hours. The precipitate was collected by filtration, washed with water and dried to give 6,7-dimethoxy-3,4-dihydroquinazolin-4-one (3.65 g).

EXAMPLE 7

A mixture of (R,S)-4-chloro-6-methoxy-74(1-methylpiperidin-3-yl)methoxy)quinazoline (183 mg, 0.57 mmol), potassium carbonate (106 mg, 0.77 mmol) and 7-hydroxyquinoline (111 mg, 0.77 mmol) in DMF (7 ml) was stirred at 100° C. for 5 hours and allowed to cool to ambient temperature. The reaction mixture was treated with 1M aqueous sodium hydroxide solution (30 ml) and stirred for 10 minutes. The crude solid was collected by filtration washing with water. The resultant solid was dissolved in dichloromethane (2 ml) and filtered through phase separating paper. The filtrate was evaporated under vacuum to give a solid residue which was triturated with ether, filtered and dried to give a scalemic mixture of 6-methoxy-74(1-methylpiperidin-3-yl)methoxy)-4-(quinolin-7-yloxy)quinazoline (149 mg, 61%).

$^1$H HMR Spectrum: (DMSOd$_6$) 1.10(m, 1H); 1.51(m, 1H); 1.64(m, 1H); 1.85(m, 3H); 2.09(m, 1H); 2.15(s, 3H); 2.62(m, 1H); 2.82(m, 1H); 3.99(s, 3H); 4.09(d, 2H); 7.38(s, 1H); 7.55(m, 2H); 7.63(s, 1H); 7.91(d, 1H); 8.10(d, 1H); 8.44(d, 1H); 8.54(s, 1H); 8.93(d, 1H)

MS(ESI): 431 (MH)+

| Elemental analysis: | Found | C 68.7 | H 5.7 | N 12.8 |
| $C_{25}H_{26}N_4O_3$ 0.3H$_2$O | Requires | C 68.9 | H 6.2 | N 12.8% |

The starting material was prepared as follows:

(R)-Ethyl nipecotate (5.7 g 365 mmol), (prepared by resolution of ethyl nipecotate by treatment with L(+)-tartaric acid as described in J. Org. Chem. 1991, (56), 1168), was dissolved in 38.5% aqueous formaldehyde solution (45 ml) and formic acid (90 ml) and the mixture heated at reflux for 18 hours. The mixture was allowed to cool and added dropwise to cooled saturated aqueous sodium hydrogen carbonate solution. The mixture was adjusted to pH12 by addition of sodium hydroxide and the mixture was extracted with methylene chloride. The organic extract was washed with brine, dried (MgSO$_4$) and the solvent removed by evaporation to give (R)-ethyl 1-methylpiperidine-3-carboxylate (4.51 g, 73%) as a colourless oil.

MS-ESI: 172 [MH]+

A solution of (R)-ethyl 1-methylpiperidine-3-carboxylate (5.69 g, 33 mmol) in ether (20 ml) was added dropwise to a stirred solution of lithium aluminium hydride (36.6 ml of a 1M solution in THF, 36.6 mmol) in ether (85 ml) cooled to maintain a reaction temperature of 20° C. The mixture was stirred for 1.5 hours at ambient temperature and then water (1.4 ml), 15% aqueous sodium hydroxide solution (1.4 ml) and then water (4.3 ml) were added. The insolubles were removed by filtration and the volatiles removed from the filtrate by evaporation to give (R)-(1-methylpiperidin-3-yl) methanol (4.02 g, 94%) as a colourless oil.

$^1$H NMR Spectrum: (DMSOd$_6$) 1.06(q, 1H); 1.51-1.94(m, 5H); 2.04(s, 3H); 2.34(br s, 1H); 2.62(m, 1H); 2.78(d, 1H); 3.49(m, 1H); 3.59(m, 1H)

MS-ESI: 130 [MH]+

4-(4-Chloro-2-fluorophenoxy)-7-hydroxy-6-methoxyquinazoline (12.1 g, 38 mmol), (prepared as described for the starting material in Example 5), was suspended in dichloromethane (375 ml) and treated with triphenylphosphine (29.6 g, 113 mmol) then stirred at ambient temperature for 30 minutes. (1-Methylpiperidin-3-yl)methanol (8.25 g, 63.8 mmol) and (R)-(1-methylpiperidin-3-yl)methanol (1.46 g, 11.3 mmol), (CAS 205194-11-2), giving R:S (57.5:42.5 by chiral HPLC) (9.7 g, 75 mmol) were dissolved in dichloromethane (75 ml) and added to the suspension. Diethyl azodicarboxylate (17.7 ml, 75 mmol) was added in portions using a syringe pump and the mixture was then allowed to warm to ambient temperature and stirred overnight. The residue was concentrated under vacuum then chromatographed on silica eluting with dichloromethane followed by dichloromethane/methanol/ammonia (93/6/1). The relevant fractions were combined and evaporated to give an oil. The residue was triturated with ether, filtered and dried to give (R,S)-4-(4-chloro-2-fluorophenoxy)-6-methoxy-74(1-methylpiperidin-3-yl)methoxy)quinazoline (8.7 g, 53%).

$^1$H HMR Spectrum: (DMSOd$_6$) 1.11(m, 1H); 1.50(m, 1H); 1.58-1.98(m, 4H); 2.09(m, 1H); 2.15(s, 3H); 2.62(d, 1H); 2.81(d, 1H); 3.95(s, 3H); 4.09(d, 2H); 7.39(m, 2H); 7.55(m, 2H); 7.67(d, 1H); 8.53(s, 1H)

MS(ESI): 432 (MH)$^+$ (R,S)-4-(4-Chloro-2-fluorophenoxy)-6-methoxy-7-((1-methylpiperidin-3-yl)methoxy)quinazoline (8.7 g, 20 mmol) was dissolved in 2M aqueous hydrochloric acid (150 ml) and heated at reflux for 1.5 hours. The reaction mixture was concentrated then basified (pH9) with saturated aqueous ammonia solution (0.88). The aqueous layer was extracted with dichloromethane (4×400 ml) and the organic extracts filtered through phase separating paper then evaporated under vacuum. The solid was triturated with ether to give (R,S)-6-methoxy-74(1-methylpiperidin-3-yl)methoxy)-3,4-dihydroquinazolin-4-one (4.05 g, 66%) as a white solid.

$^1$H HMR Spectrum: (DMSOd$_6$) 1.05(m, 1H); 1.40-1.95(m, 5H); 2.02(m, 1H); 2.14(s, 3H); 2.59(d, 1H); 2.78(d, 1H); 3.85(s, 3H); 3.95(d, 2H); 7.09(s, 1H); 7.42(s, 1H); 7.95(s, 1H); 12.00(s, 1H)

MS(ESI): 304 (MH)$^+$ (R,S)-6-methoxy-7-((1-methylpiperidin-3-yl)methoxy)-3,4-dihydroquinazolin-4-one (2.72 g, 8.9 mmol) was suspended in thionyl chloride (90 ml) and DMF (0.5 ml) and heated at reflux for 45 minutes. The thionyl chloride was evaporated under vacuum and the residue azeotroped with toluene three times. The residue was taken up in water and basified (pH8) with saturated aqueous sodium hydrogen carbonate solution. The aqueous layer was extracted with ethyl acetate (4×400 ml). The organic extracts were washed with saturated aqueous sodium hydrogen carbonate solution, water and brine then dried (MgSO$_4$). After filtration the organic extracts were concentrated under vacuum then dried overnight at 40° C. under vacuum to give (R,S)-4-chloro-6-methoxy-7-((1-methylpiperidin-3-yl)methoxy)quinazoline (2.62 g, 91%) as a solid.

$^1$H HMR Spectrum: (DMSOd$_6$) 1.10(m, 1H); 1.42-1.96(m, 5H); 2.09(m, 1H); 2.15(s, 3H); 2.60(d, 1H); 2.80(d, 1H); 3.98(s,3H); 4.10(d, 2H); 7.35(s, 1H); 7.42(s, 1H); 8.84(s, 1H)

MS(ESI): 322 (MH)$^+$

EXAMPLE 8

(R,S)-6-Methoxy-74(1-methylpiperidin-3-yl)methoxy)-4-(quinolin-7-yloxy)quinazoline, (prepared as described in Example 7), was chromatographed on Chiral CEL OD (250 mm×4.6 mm), (trade mark of Daicel Chemical Industries Ltd), in isohexane/ethanol/triethylamine/TFA (80/20/0.5/0.25). The relevant fractions for S(RT 12.55) and R(RT 15.88) enantiomers were each combined separately and worked up as follows.

The solution was evaporated under vacuum to give a liquid. This was treated with 5M aqueous sodium hydroxide solution (15 ml) and extracted with ethyl acetate. The organic extracts were washed with water then brine and filtered through phase separating paper. The filtrate was evaporated to give (S)-6-methoxy-7-((1-methylpiperidin-3-yl)methoxy)-4-(quinolin-7-yloxy)quinazoline (50 mg). The same method was used to give (R)-6-methoxy-7-((1-methylpiperidin-3-yl)methoxy)-4-(quinolin-7-yloxy)quinazoline (71 mg).

EXAMPLE 9

A suspension of 4-chloro-6-methoxy-7-(3-(pyrrolidin-1-yl)propoxy)quinazoline (0.13 g, 0.4 mmol), 5-hydroxy-2-methylindole (74 mg, 0.5 mmol) and potassium carbonate (83 mg, 0.6 mmol) in DMF (1.5 ml) was stirred at 100° C. for 2 hours. After cooling to ambient temperature, water (20 ml) was added. The precipitate was collected by filtration, washed with water and dried under vacuum at 60° C. to give 6-methoxy-4-(2-methylindol-5-yloxy)-7-(3-(pyrrolidin-1-yl)propoxy)quinazoline (80 mg, 46%).

$^1$H HMR Spectrum: (DMSOd$_6$, CF$_3$CO$_2$D) 1.9-2.0(m, 2H); 2.05-2.2(m, 2H); 2.25-2.4(m, 2H); 2.43(s, 3H); 3.05-3.2 (m, 2H); 3.35-3.5(m, 2H); 3.65-3.75(m, 2H); 4.12(s, 3H); 4.35-4.5(t, 2H); 7.0(dd, 1H); 7.35(d, 1H); 7.42(d, 1H); 7.6(s, 1H); 7.85(s, 1H); 9.15(s, 1H)

MS(ESI): 433 (MH)$^+$

The starting material was prepared as follows:

A mixture of 4-hydroxy-3-methoxybenzoic acid (8.4 g, 50 mmol), 3-(pyrrolidin-1-yl)propyl chloride (14.75 g, 0.1 mol), (J. Am. Chem. Soc. 1955, 77, 2272), potassium carbonate (13.8 g, 0.1 mol) and potassium iodide (1.66 g, 10 mmol) in DMF (150 ml) was stirred and heated at 100° C. for 3 hours. The mixture was allowed to cool and the insolubles were removed by filtration and the volatiles were removed from the filtrate by evaporation. The residue was dissolved in ethanol (75 ml), 2M aqueous sodium hydroxide (75 ml) was added and the mixture was heated at 90° C. for 2 hours. The mixture was concentrated by evaporation, acidified with concentrated hydrochloric acid, washed with ether and then subjected to purification on a Diaion (trade mark of Mitsubishi) HP20SS resin column, eluting with water and then with a gradient of methanol (0 to 25%) in dilute hydrochloric acid (pH2.2). The methanol was removed by evaporation and the aqueous residue was freeze dried to give 3-methoxy-4-(3-(pyrrolidin-1-yl)propoxy)benzoic acid hydrochloride (12.2 g, 77%).

$^1$H NMR Spectrum: (DMSOd$_6$, CF$_3$CO$_2$D) 2.2(m, 2H); 3.15(t, 2H); 3.3(t, 2H); 3.5(d, 2H); 3.7(t, 2H); 3.82(s, 3H); 4.05(d, 2H); 4.15(t, 2H); 7.07(d, 1H); 7.48(s, 1H); 7.59(d, 1H)

MS-EI: 279 [M.]$^+$

Fuming nitric acid (2.4 ml, 57.9 mmol) was added slowly at 0° C. to a solution of 3-methoxy-4-(3-(pyrrolidin-1-yl) propoxy)benzoic acid hydrochloride (12.15 g, 38.17 mmol) in TFA (40 ml). The cooling bath was removed and the reaction mixture stirred at ambient temperature for 1 hour. The TFA was removed by evaporation and ice/water was added to the residue and the solvent removed by evaporation. The solid residue was dissolved in dilute hydrochloric acid (pH2.2), poured onto a Diaion (trade mark of Mitsubishi) HP20SS resin column and eluted with methanol (gradient 0 to 50%) in water. Concentration of the fractions by evaporation gave a precipitate which was collected by filtration and dried under vacuum over phosphorus pentoxide to give 5-methoxy-2-nitro-4-(3-(pyrrolidin-1-yl)propoxy)benzoic acid hydrochloride (12.1 g, 90%).

$^1$H NMR Spectrum: (DMSOd$_6$, TFA) 1.8-1.9 (m, 2H); 2.0-2.1(m, 2H); 2.1-2.2(m, 2H); 3.0-3.1(m, 2H); 3.3(t, 2H); 3.6-3.7(m, 2H); 3.95(s, 3H); 4.25(t, 2H); 7.35(s, 1H); 7.62(s, 1H)

A solution of 5-methoxy-2-nitro-4-(3-(pyrrolidin-1-yl) propoxy)benzoic acid hydrochloride (9.63 g, 24 mmol) in thionyl chloride (20 ml) and DMF (50 μl) was heated at 45° C. for 1.5 hours. The excess thionyl chloride was removed by evaporation and by azeotroping with toluene (×2). The resulting solid was suspended in THF (250 ml) and methylene chloride (100 ml) and ammonia was bubbled though the mixture for 30 minutes and the mixture stirred for a further 1.5 hours at ambient temperature. The volatiles were removed by evaporation, the residue was dissolved in water and applied to a Diaion (trade mark of Mitsubishi) HP20SS resin column and eluted with water/methanol (100/0 to 95/5). The solvent was removed by evaporation from the fractions containing product and the residue was dissolved in a minimum of methanol and the solution was diluted with ether. The resulting precipitate was collected by filtration, washed with ether and dried under vacuum to give 5-methoxy-2-nitro-4-(3-(pyrrolidin-1-yl)propoxy)benzamide (7.23 g, 73%).

$^1$H NMR Spectrum: (DMSOd$_6$, CF$_3$CO$_2$D) 1.85-1.95(m, 2H); 2-2.1(m, 2H); 2.15-2.25(m, 2H); 3.0-3.1(m, 2H); 3.31(t, 2H); 3.62(t, 2H); 3.93(s, 3H); 4.2(t, 2H); 7.16(s, 1H); 7.60(s, 1H)

MS-EI: 323 [M.]$^+$

Concentrated hydrochloric acid (5 ml) was added to a suspension of 5-methoxy-2-nitro-4-(3-(pyrrolidin-1-yl)propoxy)benzamide (1.5 g, 4.64 mmol) in methanol (20 ml) and the mixture was heated at 50° C. to give a solution. Iron powder (1.3 g, 23.2 mmol) was added in portions and the reaction mixture was then heated at reflux for 1 hour. The mixture was allowed to cool, the insolubles were removed by filtration through diatomaceous earth and the volatiles were removed from the filtrate by evaporation. The residue was purified on a Diaion (trade mark of Mitsubishi) HP20SS resin column, eluting with water and then with dilute hydrochloric acid (pH2). The fractions containing product were concentrated by evaporation and the resulting precipitate was collected by filtration and dried under vacuum over phosphorus pentoxide to give 2-amino-5-methoxy-4-(3-(pyrrolidin-1-yl)propoxy)benzamide hydrochloride (1.44 g, 85%).

$^1$H NMR Spectrum: (DMSOd$_6$, CF$_3$CO$_2$D) 1.9(br s, 2H); 2.05(br s, 2H); 2.2(br s, 2H); 3.05(br s, 2H); 3.3(t, 2H); 3.61(br s, 2H); 3.8(s, 3H); 4.11(t, 2H); 7.05(s, 1H); 7.53(s, 1H)

MS-EI: 293 [M.]$^+$

A mixture of 2-amino-5-methoxy-4-(3-(pyrrolidin-1-yl)propoxy)benzamide hydrochloride (5.92 g, 16.2 mmol) and Gold's reagent (3.5 g, 21.4 mmol) in dioxane (50 ml) was heated at reflux for 5 hours. Acetic acid (0.7 ml) and sodium acetate (1.33 g) were added to the reaction mixture which was heated at reflux for a further 5 hours. The mixture was allowed to cool and the volatiles were removed by evaporation. The residue was dissolved in water, adjusted to pH8 with 2M aqueous sodium hydroxide solution and purified on a Diaion (trademark of Mitsubishi) HP20SS resin column eluting with methanol (gradient 0-50%) in water. The fractions containing product were concentrated by evaporation and then freeze dried to give 4-hydroxy-6-methoxy-7-(3-(pyrrolidin-1-yl)propoxy)quinazoline (4.55 g, 83%).

$^1$H NMR Spectrum: (DMSOd$_6$, CF$_3$CO$_2$D) 1.9(m, 2H); 2.0-2.1(m, 2H); 2.2-2.3(m, 2H); 3.05(m, 2H); 3.34(t, 2H); 3.6-3.7(br s, 2H); 3.94(s, 3H); 4.27(t, 2H); 7.31(s, 1H); 7.55 (s, 1H); 9.02(s, 1H)

A mixture of 4-hydroxy-6-methoxy-7-(3-(pyrrolidin-1-yl)propoxy)quinazoline (1.7 g, 5 mmol) and thionyl chloride (25 ml) containing DMF (0.2 ml) was heated at reflux for 3 hours. Excess thionyl chloride was removed by evaporation and by azeotroping with toluene (×2). The residue was suspended in ether and 10% aqueous solution of sodium hydrogen carbonate was added to the mixture. The organic layer was separated, dried (MgSO$_4$) and the solvent removed by evaporation to give 4-chloro-6-methoxy-7-(3-(pyrrolidin-1-yl)propoxy)quinazoline (1.94 g, quantitative).

$^1$H NMR Spectrum: (CDCl$_3$) 1.8(br s, 4H); 2.17(m, 2H); 2.6(br s, 4H); 2.7(t, 2H); 4.05(s, 3H); 4.3(t, 2H); 7.35(s, 1H); 7.38(s, 1H); 8.86(s, 1H)

MS-ESI: 322[MH]$^+$

EXAMPLE 10

A suspension of 4-chloro-6-methoxy-7-((1-methylpiperidin-4-yl)methoxy)quinazoline (74 mg, 0.23 mmol), potassium carbonate (48 mg, 0.35 mmol) and 7-hydroxyquinoline (40.6 mg, 0.28 mmol) in DMF (1.5 ml) was heated at 100° C. for 3 hours. After cooling, the mixture was stirred for 10 hours at ambient temperature and then overnight at 5° C. After dilution with methylene chloride (5 ml), the mixture was poured onto a column of silica and was eluted with an increasing gradient of methanol/methylene chloride (10/90, 20/80) followed by ammonia/methanol (5%) in methylene chloride (25/75) to give, after removal of the volatiles by evaporation and drying under vacuum, 6-methoxy-7-((1-methylpiperidin-4-yl)methoxy)-4-(quinolin-7-yloxy)quinazoline (82 mg, 88%).

$^1$H NMR Spectrum: (DMSOd$_6$) 1.3-1.5(m, 2H); 1.75-1.9 (m, 3H); 1.9-2.05(m, 2H); 2.12(s, 3H); 2.8-2.9(d, 2H); 4.5(s, 3H); 4.1(d, 2H); 7.4(s, 1H); 7.6(dd, 1H); 7.62(dd, 1H)

MS(ESI): 431 [MH]$^+$

The starting material was prepared as follows:

To a solution of ethyl 4-piperidinecarboxylate (30 g, 0.19 mol) in ethyl acetate (150 ml) cooled at 5° C. was added dropwise a solution of di-tert-butyl dicarbonate (41.7 g, 0.19 mol) in ethyl acetate (75 ml) while maintaining the temperature in the range 0-5° C. After stirring for 48 hours at ambient temperature, the mixture was poured onto water (300 ml). The organic layer was separated, washed successively with water (200 ml), 0.1M aqueous hydrochloric acid (200 ml), saturated sodium hydrogen carbonate (200 ml) and brine (200 ml), dried (MgSO$_4$) and evaporated to give ethyl 4-(1-tert-butyloxycarbonylpiperidine)carboxylate (48 g, 98%).

$^1$H NMR Spectrum: (CDCl$_3$) 1.25(t, 3H); 1.45(s, 9H); 1.55-1.70(m, 2H); 1.8-2.0(d, 2H); 2.35-2.5(m, 1H); 2.7-2.95 (t, 2H); 3.9-4.1(br s, 2H); 4.15(q, 2H)

To a solution of ethyl 4-(1-tert-butyloxycarbonylpiperidine)carboxylate (48 g, 0.19 mol) in dry THF (180 ml) cooled at 0° C. was added dropwise a solution of 1M lithium aluminium hydride in THF (133 ml, 0.133 mol). After stirring at 0° C. for 2 hours, water (30 ml) was added followed by 2M sodium hydroxide (10 ml). The precipitate was filtered through diatomaceous earth and washed with ethyl acetate. The filtrate was washed with water, brine, dried (MgSO$_4$) and evaporated to give 4-hydroxymethyl-1-tert-butyloxycarbonylpiperidine (36.3 g, 89%).

$^1$H NMR Spectrum: (CDCl$_3$) 1.05-1.2(m, 2H); 1.35-1.55 (m, 10H); 1.6-1.8(m, 2H); 2.6-2.8(t, 2H); 3.4-3.6(t, 2H); 4.0-4.2(br s, 2H)

MS (EI): 215 [M.]+

To a solution of 4-hydroxymethyl-1-tert-butyloxycarbonylpiperidine (52.5 g, 0.244 mol) in tert-butyl methyl ether (525 ml) was added 1,4-diazabicyclo[2.2.2]octane (42.4 g, 0.378 mol). After stirring for 15 minutes at ambient temperature, the mixture was cooled to 5° C. and a solution of toluene sulphonyl chloride (62.8 g, 0.33 mmol) in tert-butyl methyl ether (525 ml) was added dropwise over 2 hours while maintaining the temperature at 0° C. After stirring for 1 hour at ambient temperature, petroleum ether (11) was added. The precipitate was removed by filtration. The filtrate was evaporated to give a solid. The solid was dissolved in ether and washed successively with 0.5M aqueous hydrochloric acid (2×500 ml), water, saturated sodium hydrogen carbonate and brine, dried (MgSO$_4$) and evaporated to give 4-(4-methylphenylsulphonyloxymethyl)-1-tert-butyloxycarbonylpiperidine (76.7 g, 85%).

$^1$H NMR Spectrum: (CDCl$_3$) 1.0-1.2(m, 2H); 1.45(s, 9H); 1.65(d, 2H); 1.75-1.9(m, 2H); 2.45(s, 3H); 2.55-2.75(m, 2H); 3.85(d, 1H); 4.0-4.2(br s, 2H); 7.35(d, 2H); 7.8(d, 2H)

MS(ESI): 392 [MNa]$^+$

To a suspension of ethyl 3-methoxy-4-hydroxybenzoate (19.6 g, 0.1 mol) and potassium carbonate (28 g, 0.2 mol) in dry DMF (200 ml) was added 4-(4-methylphenylsulphonyloxymethyl)-1-tert-butyloxycarbonylpiperidine (40 g, 0.11 mol). After stirring at 95° C. for 2.5 hours, the mixture was cooled to ambient temperature and partitioned between water and ethyl acetate/ether. The organic layer was washed with water, brine, dried (MgSO$_4$) and evaporated. The resulting oil was crystallised from petroleum ether and the suspension was stored overnight (at 5° C.). The solid was collected by filtration, washed with petroleum ether and dried under vacuum to give ethyl 3-methoxy-4-(1-tert-butyloxycarbonylpiperidin-4-ylmethoxy)benzoate (35g, 89%).

m.p. 81-83° C.

$^1$H NMR Spectrum: (CDCl$_3$) 1.2-1.35(m, 2H); 1.4(t, 3H); 1.48(s, 9H); 1.8-1.9(d, 2H); 2.0-2.15(m, 2H); 2.75(t, 2H); 3.9(d, 2H); 3.95(s, 3H); 4.05-4.25(br s, 2H); 4.35(q, 2H); 6.85(d, 1H); 7.55(s, 1H); 7.65(d, 1H)

MS(ESI): 416 [MNa]$^+$

| Elemental analysis: | Found | C 63.4 | H 8.0 | N 3.5 |
| --- | --- | --- | --- | --- |
| $C_{21}H_{31}NO_6$ 0.3H$_2$O | Requires | C 63.2 | H 8.0 | N 3.5% |

To a solution of ethyl 3-methoxy-4-(1-tert-butyloxycarbonylpiperidin-4-ylmethoxy)benzoate (35 g, 89 mmol) in formic acid (35 ml) was added formaldehyde (12M, 37% in water, 35 ml, 420 mmol). After stirring at 95° C. for 3 hours, the volatiles were removed by evaporation. The residue was dissolved in methylene chloride and 3M hydrogen chloride in ether (40 ml, 120 mmol) was added. After dilution with ether, the mixture was triturated until a solid was formed. The solid was collected by filtration, washed with ether and dried under vacuum overnight at 50° C. to give ethyl 3-methoxy-4-(1-methylpiperidin-4-ylmethoxy)benzoate (30.6 g, quant.).

$^1$H NMR Spectrum: (DMSOd$_6$) 1.29(t, 3H); 1.5-1.7(m, 2H); 1.95(d, 2H); 2.0-2.15(br s, 1H); 2.72(s, 3H); 2.9-3.1(m, 2H); 3.35-3.5(br s, 2H); 3.85(s, 3H); 3.9-4.05(br s, 2H); 4.3 (q, 2H); 7.1(d, 1H); 7.48(s, 1H); 7.6(d, 1H)

MS(ESI): 308 [MH]$^+$

A solution of ethyl 3-methoxy-4-(1-methylpiperidin-4-ylmethoxy)benzoate (30.6 g, 89 mmol) in methylene chloride (75 ml) was cooled to 0-5° C. TFA (37.5 ml) was added followed by the dropwise addition over 15 minutes of a solution of fuming 24M nitric acid (7.42 ml, 178 mmol) in methylene chloride (15 ml). After completion of the addition, the solution was allowed to warm up and stirred at ambient temperature for 2 hours. The volatiles were removed under vacuum and the residue was dissolved in methylene chloride (50 ml). The solution was cooled to 0-5° C. and ether was added. The precipitate was collected by filtration, and dried under vacuum at 50° C. The solid was dissolved in methylene chloride (500 ml) and 3M hydrogen chloride in ether (30 ml) was added followed by ether (500 ml). The solid was collected by filtration and dried under vacuum at 50° C. to give ethyl 3-methoxy-4-(1-methylpiperidin-4-ylmethoxy)-6-nitrobenzoate (28.4 g, 82%).

$^1$H NMR Spectrum: (DMSOd$_6$) 1.3(t, 3H); 1.45-1.65(m, 2H); 1.75-2.1(m, 3H); 2.75(s, 3H); 2.9-3.05(m, 2H); 3.4-3.5 (d, 2H); 3.95(s, 3H); 4.05(d, 2H); 4.3(q, 2H); 7.32(s, 1H); 7.66(s, 1H)

MS(ESI): 353 [MH]$^+$

A suspension of ethyl 3-methoxy-4-(1-methylpiperidin-4-ylmethoxy)-6-nitrobenzoate (3.89 g, 10 mmol) in methanol (80 ml) containing 10% platinum on activated carbon (50% wet) (389 mg) was hydrogenated at 1.8 atmospheres pressure until uptake of hydrogen ceased. The mixture was filtered and the filtrate was evaporated. The residue was dissolved in water (30 ml) and adjusted to pH10 with a saturated solution of sodium hydrogen carbonate. The mixture was diluted with ethyl acetate/ether (1/1) and the organic layer was separated. The aqueous layer was further extracted with ethyl acetate/ether and the organic layers were combined. The organic layers were washed with water, brine, dried (MgSO$_4$), filtered and evaporated. The resulting solid was triturated in a mixture of ether/petroleum ether, filtered, washed with petroleum ether and dried under vacuum at 60° C. to give ethyl 6-amino-3-methoxy-4-(1-methylpiperidin-4-ylmethoxy)benzoate (2.58 g, 80%).

m.p. 111-112° C.

$^1$H NMR Spectrum: (CDCl$_3$) 1.35(t, 3H); 1.4-1.5(m, 2H); 1.85(m, 3H); 1.95(t, 2H); 2.29(s, 3H); 2.9(d, 2H); 3.8(s, 3H); 3.85(d, 2H); 4.3(q, 2H); 5.55(br s, 2H); 6.13(s, 1H); 7.33(s, 1H)

MS(ESI): 323 [MH]$^+$

| Elemental analysis: | Found | C 62.8 | H 8.5 | N 8.3 |
| --- | --- | --- | --- | --- |
| $C_{17}H_{26}N_2O_4$ 0.2H$_2$O | Requires | C 62.6 | H 8.2 | N 8.6% |

A solution of ethyl 6-amino-3-methoxy-4-(1-methylpiperidin-4-ylmethoxy)benzoate (16.1 g, 50 mmol) in 2-methoxyethanol (160 ml) containing formamidine acetate (5.2 g, 50 mmol) was heated at 115° C. for 2 hours. Formamidine acetate (10.4 g, 100 mmol) was added in portions every 30 minutes during 4 hours. Heating was prolonged for 30 minutes after the last addition. After cooling, the volatiles were removed under vacuum. The solid was dissolved in ethanol (100 ml) and methylene chloride (50 ml). The precipitate was removed by filtration and the filtrate was concentrated to a final volume of 100 ml. The suspension was cooled to 5° C. and the solid was collected by filtration, washed with cold ethanol followed by ether and dried under vacuum overnight at 60° C. to give 6-methoxy-7-(1-methylpiperidin-4-yl)methoxy)-3,4-dihydroquinazolin-4-one (12.7 g, 70%).

$^1$H NMR Spectrum: (DMSOd$_6$) 1.25-1.4(m, 2H); 1.75(d, 2H); 1.9(t, 1H); 1.9(s, 3H); 2.16(s, 2H); 2.8(d, 2H); 3.9(s, 3H); 4.0(d, 2H); 7.11(s, 1H); 7.44(s, 1H); 7.97(s, 1H)

MS(ESI): 304 [MH]$^+$

A solution of 6-methoxy-7-((1-methylpiperidin-4-yl)methoxy)-3,4-dihydroquinazolin-4-one (2.8 g, 9.24 mmol) in thionyl chloride (28 ml) containing DMF (280 µl) was refluxed at 85° C. for 1 hour. After cooling, the volatiles were removed by evaporation. The precipitate was triturated with ether, filtered, washed with ether and dried under vacuum. The solid was dissolved in methylene chloride and saturated aqueous sodium hydrogen carbonate was added. The organic layer was separated, washed with water, brine, dried (MgSO$_4$) and evaporated to give 4-chloro-6-methoxy-7-((1-methylpiperidin-4-yl)methoxy)quinazoline (2.9 g, 98%).

$^1$H NMR Spectrum: (DMSOd$_6$) 1.3-1.5(m, 2H); 1.75-1.9 (m, 3H); 2.0(t, 1H); 2.25(s, 3H); 2.85(d, 2H); 4.02(s, 3H); 4.12(d, 2H); 7.41(s, 1H); 7.46(s, 1H); 8.9(s, 1H)

MS(ESI): 322 [MH]$^+$

EXAMPLE 11

Using a procedure analogous to that described for Example 9, 4-chloro-6-methoxy-7-((1-methylpiperidin-4-yl)methoxy)quinazoline (0.13 g, 04 mmol), (prepared as described for the starting material in Example 10), was reacted with 5-hydroxy-2-methylindole (74 mg, 0.5 mol) to give 6-methoxy-4-(2-methylindol-5-yloxy)-7-((1-methylpiperidin-4-yl)methoxy)quinazoline (137 mg, 79%).

$^1$H NMR Spectrum: (DMSOd$_6$) 1.3-1.45(m, 2H); 1.7-1.95 (m, 5H); 2.15(s, 3H); 2.4(s, 3H); 2.8(d, 2H); 3.98(s, 3H); 4.05(d, 2H); 6.14(s, 1H); 6.88(d, 1H); 7.29(s, 1H); 7.32(d, 1H); 7.35(s, 1H); 7.6(s, 1H); 8.45(s, 1H)

MS(ESI): 433 [MH]+

EXAMPLE 12

To a solution of 4-chloro-6-methoxy-74(1-(2-methylsulphonylethyppiperidin-4-yl)methoxy)quinazoline (115 mg, 0.28 mmol) and 7-hydroxyquinoline (50 mg, 0.33 mmol) in DMF (1.5 ml) was added potassium carbonate (60 mg, 0.42 mmol). The mixture was stirred for 2 hours at 100° C. After cooling, and removal of the volatiles by evaporation, the residue was partitioned between ethyl acetate and water. The organic layer was washed with water, brine, dried (MgSO$_4$) and evaporated. The residue was purified by column chromatography eluting with ethylacetate/methylene chloride/methanol (1/1/0 followed by 40/50/10 and 0/9/1). After removal of the volatiles by evaporation, the residue was triturated with pentane, filtered and dried under vacuum to give 6-methoxy-7-41-(2-methylsulphonylethyl)piperidin-4-yl)methoxy)-4-(quinolin-7-yloxy)quinazoline (110 mg, 76%).

$^1$H NMR Spectrum: (DMSOd$_6$) 1.3-1.45(m, 2H); 1.75-1.9 (m, 3H); 2.05(t, 2H); 2.72(t, 2H); 2.95(d, 2H); 3.05(s, 3H); 3.35-3.45(m, 2H); 4.00(s, 3H); 4.1(d, 2H); 7.41(s, 1H); 7.57 (dd, 1H); 7.62(dd, 1H); 7.65(s, 1H); 7.93(s, 1H); 8.12(d, 1H); 8.45(d, 1H); 8.55(s, 1H); 8.95(d, 1H)

MS(ESI): 523 [MH]$^+$

| Elemental analysis: | Found | C 61.3 | H 6.0 | N 10.6 |
|---|---|---|---|---|
| C$_{27}$H$_{30}$N$_4$O$_5$S 0.4H$_2$O | Requires | C 61.2 | H 5.9 | N 10.6% |

The starting material was prepared as follows:

Sodium hydride (1.44 g of a 60% suspension in mineral oil, 36 mmol) was added in portions over 20 minutes to a solution of 7-benzyloxy-6-methoxy-3,4-dihydroquinazolin-4-one (8.46 g, 30 mmol), (prepared as described for the starting material in Example 1), in DMF (70 ml) and the mixture was stirred for 1.5 hours. Chloromethyl pivalate (5.65 g, 37.5 mmol) was added dropwise and the mixture stirred for 2 hours at ambient temperature. The mixture was diluted with ethyl acetate (100 ml) and poured onto ice/water (400 ml) and 2M hydrochloric acid (4 ml). The organic layer was separated and the aqueous layer extracted with ethyl acetate, the combined extracts were washed with brine, dried (MgSO$_4$) and the solvent removed by evaporation. The residue was triturated with a mixture of ether and petroleum ether, the solid was collected by filtration and dried under vacuum to give 7-benzyloxy-6-methoxy-3-((pivaloyloxy)methyl)-3,4-dihydroquinazolin-4-one (10 g, 84%).

$^1$H NMR Spectrum: (DMSOd$_6$) 1.11(s, 9H); 3.89(s, 3H); 5.3(s, 2H); 5.9(s, 2H); 7.27(s, 1H); 7.35(m, 1H); 7.47(t, 2H); 7.49(d, 2H); 7.51(s, 1H); 8.34(s, 1H)

A mixture of 7-benzyloxy-6-methoxy-3-((pivaloyloxy)methyl)-3,4-dihydroquinazolin-4-one (7 g, 17.7 mmol) and 10% palladium-on-charcoal catalyst (700 mg) in ethyl acetate (250 ml), DMF (50 ml), methanol (50 ml) and acetic acid (0.7 ml) was stirred under hydrogen at atmospheric pressure for 40 minutes. The catalyst was removed by filtration and the solvent removed from the filtrate by evaporation. The residue was triturated with ether, collected by filtration and dried under vacuum to give 7-hydroxy-6-methoxy-3-((pivaloyloxy)methyl)-3,4-dihydroquinazolin-4-one (4.36 g, 80%).

$^1$H NMR Spectrum: (DMSOd$_6$) 1.1(s, 9H); 3.89(s, 3H); 5.89(s, 2H); 7.0(s, 1H); 7.48(s, 1H); 8.5(s, 1H)

A suspension of 7-hydroxy-6-methoxy-3-((pivaloyloxy)methyl)-3,4-dihydroquinazolin-4-one (6.12 g, 20 mmol) potassium carbonate (5.52 g, 40 mmol) in DMF (60 ml) was stirred at ambient temperature for 30 minutes. 4-(4-Methylphenylsulphonyloxymethyl)-1-tert-butyloxycarbonylpiperidine (8.86 g, 24 mmol), (prepared as described for the starting material in Example 10), was added and the mixture was stirred at 100° C. for 2 hours. After cooling, the mixture was poured onto water/ice (400 ml, 1/1) containing 2M hydrochloric acid (10 ml). The precipitate was collected by filtration, washed with water and dried under vacuum over phosphorus pentoxide. The solid was triturated in a mixture of ether/pentane (1/1), collected by filtration and dried to give 6-methoxy-3-((pivaloyloxy)methyl)-7-((1-tert-butyloxycarbonylpiperidin-4-yl)methoxy)-3,4-dihydroquinazolin-4-one (7.9 g, 78.5%).

$^1$H NMR Spectrum: (DMSOd$_6$) 1.1(s, 9H); 1.1-1.3(m, 2H); 1.42(s, 9H); 1.73(d, 2H); 1.93-2.1(br s, 1H); 2.65-2.9(br s, 2H); 3.9(s, 3H); 3.9-4.1(m, 4H); 5.9(s, 2H); 7.2(s, 1H); 7.5(s, 1H); 8.35(s, 1H)

MS(ESI): 526 [MNa]+

A solution of 6-methoxy-3-((pivaloyloxy)methyl)-7-((1-tert-butyloxycarbonylpiperidin-4-yl)methoxy)-3,4-dihydroquinazolin-4-one (7.9 g, 16 mmol) in methylene chloride (80 ml) containing 5.5M hydrogen chloride in isopropanol (80 ml) was stirred for 1 hour at ambient temperature. Ether was added and the solid was collected by filtration, washed with ether and dried under vacuum at 60° C. to give 6-methoxy-7-((piperidin-4-yl)methoxy)-3-((pivaloyloxy)methyl)-3,4-dihydroquinazolin-4-one hydrochloride (6.9 g, 100%).

$^1$H NMR Spectrum: (DMSOd$_6$, CF$_3$CO$_2$D) 1.15(s, 9H); 1.5-1.7(m, 2H); 2.0(d, 2H); 2.2-2.3(br s, 1H); 3.0(t, 2H); 3.4(d, 2H); 3.94(s, 3H); 4.15(d, 2H); 5.97(s, 2H); 7.3(s, 1H); 7.6(s, 1H); 8.65(s, 1H)

MS(ESI): 404 [MH]$^+$

To a solution of 6-methoxy-7-((piperidin-4-yl)methoxy)-3-((pivaloyloxy)methyl)-3,4-dihydroquinazolin-4-one hydrochloride (0.88 g, 2 mmol) and triethylamine (0.3 ml, 2.1 mmol) in methanol (10 ml) and methylene chloride (10 ml) was added potassium carbonate (280 mg, 2 mmol) and methyl vinyl sulfone (0.4 ml, 2.1 mmol). After stirring for 2 hours at ambient temperature, the volatiles were removed under vacuum. The residue was partitioned between ethyl acetate and water. The organic layer was washed with brine, dried (MgSO$_4$) and evaporated to give 6-methoxy-7-41-(2-methylsulphonylethyl)piperidin-4-yl)methoxy)-3-((pivaloyloxy)methyl)-3,4-dihydroquinazolin-4-one (0.55 g, 54%).

$^1$H NMR Spectrum: (DMSOd$_6$) 1.09(s, 9H); 1.25-1.4(m, 2H); 1.7-1.9(m, 3H); 2.0(t, 2H); 2.7(t, 2H); 2.95(d, 2H); 3.02(s, 3H); 3.25-3.45(m, 2H); 3.9(s, 3H); 4.0(d, 2H); 5.9(s, 2H); 7.15(s, 1H); 7.49(s, 1H); 8.35(s, 1H)

MS(ESI): 510 [MH]$^+$.

To a suspension of 6-methoxy-7-((1-(2-methylsulphonylethyppiperidin-4-yl)methoxy)-3-((pivaloyloxy)methyl)-3,4-dihydroquinazolin-4-one (90 mg, 0.18 mmol) in methanol (3 ml) was added 2M aqueous sodium hydroxide (180 μl, 0.35 mmol). After stirring for 2 hours at ambient temperature, the mixture was adjusted to pH10 with 2M hydrochloric acid. The volatiles were removed under vacuum and the residue was suspended in water, filtered, washed with water followed by ether and dried under vacuum at 60° C. to give 6-methoxy-7-((1-(2-methylsulphonylethyl)piperidin-4-yl)methoxy)-3,4-dihydroquinazolin-4-one (55 mg, 79%).

$^1$H NMR Spectrum: (DMSOd$_6$) 1.2-1.4(m, 2H); 1.7-1.85 (m, 3H); 2.0(t, 2H); 2.7(t, 2H); 2.9(d, 2H); 3.02(s, 3H); 3.3-3.5(m, 2H); 3.9(s, 3H); 4.0(d, 2H); 7.11(s, 1H); 7.45(s, 1H); 7.97(s, 1H)

MS(ESI): 396 [MH]$^+$

A solution of 6-methoxy-7-((1-(2-methylsulphonylethyl) piperidin-4-yl)methoxy)-3,4-dihydroquinazolin-4-one (335 mg, 0.85 mmol) in thionyl chloride (5 ml) containing DMF (50 μl) was refluxed for 1 hour. After cooling, the volatiles were removed under vacuum and the residue was triturated with ether and filtered. The solid was suspended in methylene chloride and sodium hydrogen carbonate was added. The organic layer was washed with water, brine, dried (MgSO$_4$) and evaporated. The residue was triturated with ether, filtered and dried under vacuum to give 4-chloro-6-methoxy-74(1-(2-methylsulphonylethyppiperidin-4-ylmethoxy)quinazoline (335 mg, 95%).

$^1$H NMR Spectrum: (DMSOd$_6$) 1.25-1.45(m, 2H); 1.75-1.90(m, 3H); 2.0(t, 2H); 2.7(t, 2H); 2.92(d, 2H); 3.03(s, 3H); 3.2-3.35(m, 2H); 4.0(s, 3H); 4.1(d, 2H); 7.40(s, 1H); 7.45(s, 1H); 8.9(s, 1H)

MS(ESI): 414 [MH]$^+$

EXAMPLE 13

Using a procedure analogous to that described for Example 10, 4-chloro-6-methoxy-7-((1-methylpiperidin-4-yl)methoxy)quinazoline (130 mg, 0.4 mmol), (prepared as described for the starting material in Example 10), was reacted with 4-methyl-7-hydroxyquinoline (80 mg, 0.5 mol), (Chem. Ber. 1967, 100, 2077), to give 6-methoxy-7-((1-methylpiperidin-4-yl)methoxy)-4-(4-methylquinolin-7-yloxy)quinazoline (160 mg, 90%).

$^1$H NMR Spectrum: (DMSOd$_6$) 1.3-1.5(m, 2H); 1.7-1.95 (m, 3H); 1.9(t, 2H); 2.17(s, 3H); 2.74(s, 3H); 2.8(d, 2H); 4.07(s, 3H); 4.1(d, 2H); 7.4(m, 2H); 7.65(dd, 1H); 7.65(s, 1H); 7.9(s, 1H); 8.21(d, 1H); 8.54(s, 1H); 8.78(d, 1H)

MS(ESI): 445 [MH]$^+$

EXAMPLE 14

A solution of 4-chloro-6-methoxy-7-((1-(2-methylsulphonylethyl)piperidin-4-yl)methoxy)quinazoline (115 mg, 0.28 mmol), (prepared as described for the starting material in Example 12), 5-hydroxy-2-methylindole (50 mg, 0.33 mmol) and potassium carbonate (60 mg, 0.42 mmol) in DMF (1.5 ml) was stirred at 100° C. for 2 hours. After cooling, the mixture was partitioned between ethyl acetate and water. The organic layer was washed with water, brine, dried (MgSO$_4$) and evaporated. The residue was purified by chromatography eluting with ethyl acetate/methylene chloride (1/1) followed by methanol/ethyl acetate/methylene chloride (1/4/5 and 1/0/9) to give 6-methoxy-4-(2-methylindol-5-yloxy)-7-41-(2-methylsulphonylethyl)piperidin-4-yl)methoxy)quinazoline (60 mg, 41%).

$^1$H NMR Spectrum: (DMSOd$_6$) 1.3-1.45(m, 2H); 1.75-1.92(m, 3H); 2.02(t, 2H); 2.4(s, 3H); 2.7(t, 2H); 2.95(d, 2H); 3.05(s, 3H); 4.0(s, 3H); 4.05(d, 2H); 6.15(s, 1H); 6.85(dd, 1H); 7.25(s, 1H); 7.3(d, 1H); 7.38(s, 1H); 7.6(s, 1H); 8.45(s, 1H)

MS(ESI): 525 [MH]$^+$

| Elemental analysis: | Found | C 60.7 | H 6.2 | N 10.5 |
|---|---|---|---|---|
| $C_{27}H_{32}O_5S$ 0.5$H_2O$ | Requires | C 60.8 | H 6.2 | N 10.5% |

EXAMPLE 15

Using a procedure analogous to that described for Example 9, 4-chloro-6-methoxy-7-(3-(pyrrolidin-1-yl)propoxy)quinazoline (0.13 g, 0.4 mol), (prepared as described for the starting material in Example 9), was reacted with 7-hydroxy-4-methylquinoline (80 mg, 0.5 mol), (Chem. Berich. 1967, 100, 2077), to give 6-methoxy-4-(4-methylquinolin-7-yloxy)-7-(3-(pyrrolidin-1-yl)propoxy)quinazoline (155 mg, 87%).

$^1$H NMR Spectrum: (DMSOd$_6$) 1.7(br s, 4H); 2.05(m, 2H); 2.5(br s, 4H); 2.6(t, 2H); 2.75(s, 3H); 4.02(s, 3H); 4.3(t, 2H); 7.41(s, 1H); 7.45(d, 1H); 7.65(s, 1H); 7.65(d, 1H); 7.95(s, 1H); 8.25(d, 1H); 8.55(s, 1H); 8.8(d, 1H)

MS(ESI): 445 [MH]$^+$

EXAMPLE 16

Using a procedure analogous to that described for Example 9, 4-chloro-6-methoxy-7-(3-(pyrrolidin-1-yl)propoxy)quinazoline (0.13 g, 0.4 mol), (prepared as described for the starting material in Example 9), was reacted with 2,2,4-trimethyl-1,2-dihydroquinolin-6-ol (95 mg, 0.5 mmol), (IZV. ACAD. NAVK. SSSR. Ser. Khim. 1981, 9, 2008), to give 6-methoxy-7-(3-(pyrrolidin-1-yl)propoxy)-4-(2,2,4-trimethyl-1,2-dihydroquinolin-6-yloxy)quinazoline (90 mg, 47%).

$^1$H NMR Spectrum: (DMSOd$_6$) 1.23(s, 6H); 1.7(br s, 4H); 1.85(s, 3H); 2.0(m, 2H); 2.45(br s, 4H); 2.57(t, 2H); 3.95(s, 3H); 4.25(t, 2H); 5.35(s, 1H); 5.9(s, 1H); 6.5(d, 1H); 6.8(dd, 1H); 6.85(s, 1H); 7.32(s, 1H); 7.52(s, 1H); 8.5(s, 1H)

MS(ESI): 475 [MH]$^+$

EXAMPLE 17

Using a procedure analogous to that described for Example 9, 4-chloro-6-methoxy-7-((1-methylpiperidin-4-yl)methoxy)quinazoline (0.13 g, 0.4 mmol), (prepared as described for the starting material in Example 10), was reacted with 2,2,4-trimethyl-1,2-dihydroquinolin-6-ol (95 mg, 0.5 mmol), (IZV. ACAD. NAVK. SSSR. Ser. Khim. 1981, 9, 2008), to give 6-methoxy-74(1-methylpiperidin-4-yl)methoxy)-4-(2,2,4-trimethyl-1,2-dihydroquinolin-6-yloxy)quinazoline (140 mg, 74%).

$^1$H NMR Spectrum: (DMSOd$_6$) 1.15(s, 6H); 1.3-1.45(m, 2H); 1.7-2.0(m, 8H); 2.16(s, 3H); 2.65-2.85(d, 2H); 4.0(s, 3H); 4.05(d, 2H); 5.35(s, 1H); 5.9(s, 1H); 6.5(d, 1H); 6.80(d, 1H); 6.82(s, 1H); 7.33(s, 1H); 7.5(s, 1H); 8.52(s, 1H)

MS(ESI): 475 [MH]$^+$

EXAMPLE 18

Using a procedure analogous to that described for Example 9, 4-chloro-6-methoxy-7-((1-methylpiperidin-4-yl)methoxy)quinazoline (0.13 g, 0.4 mol), (prepared as described for the starting material in Example 10), was reacted with 2,4- dimethyl-7-hydroxyquinoline (87 mg, 0.5 mmol), (Chem. Berichte, 1903, 36, 4016), to give 4-(2,4-dimethylquinolin-7-yloxy)-6-methoxy-7-((1-methylpiperidin-4-yl)methoxy) quinazoline (61 mg, 33%).

$^1$H NMR Spectrum: (DMSOd$_6$) 1.3-1.5(m, 2H); 1.7-1.95 (m, 5H); 2.2(s, 3H); 2.65(s, 3H); 2.7(s, 3H); 2.75-2.9(br d, 2H); 4.05(s, 3H); 4.1(d, 2H); 7.3(s, 1H); 7.4(s, 1H); 7.52(d, 1H); 7.65(s, 1H); 7.8(s, 1H); 8.15(d, 1H); 8.55(s, 1H)

MS(ESI): 459 [MH]$^+$

EXAMPLE 19

Using a procedure analogous to that described for Example 9, 4-chloro-6-methoxy-7-((1-methylpiperidin-4-yl)methoxy)quinazoline (0.13 g, 0.4 mol), (prepared as described for the starting material in Example 10), was reacted with 6-hydroxy-2H-4H-1,4-benzoxazin-3-one (83 mg, 0.5 mol), (J. Chem. Soc. C, 1971, 2696), to give 6-methoxy-7-((1-methylpiperidin-4-yl)methoxy)-4-(3-oxo-2H-4H-1,4-benzoxazin-6-yloxy)quinazoline (158 mg, 88%).

$^1$H NMR Spectrum: (DMSOd$_6$) 1.25-1.45(m, 2H); 1.8(d, 2H); 1.7-1.9(m, 1H); 1.9(t, 2H); 2.2(s, 3H); 2.8(d, 2H); 3.97 (s, 3H); 4.05(d, 2H); 4.65(s, 2H); 6.8(s, 1H); 6.85(d, 1H); 7.05(d, 1H); 7.35(s, 1H); 7.52(s, 1H); 8.55(s, 1H)

MS(ESI): 451 [MH]$^+$

EXAMPLE 20

Using a procedure analogous to that described for Example 9, 4-chloro-6-methoxy-7-(3-(pyrrolidin-1-yl)propoxy) quinazoline (0.13 g, 0.4 mol), (prepared as described for the starting material in Example 9), was reacted with 6-hydroxy-2H-4H-1,4-benzoxazin-3-one (83 mg, 0.5 mol), (J. Chem. Soc. C, 1971, 2696), to give 6-methoxy-7-(3-(pyrrolidin-1-yl)propoxy)-4-(3-oxo-2H-4H-1,4-benzoxazin-6-yloxy) quinazoline (170 mg, 94%).

$^1$H NMR Spectrum: (DMSOd$_6$, CF$_3$CO$_2$D) 1.8-2.0(m, 2H); 2.0-2.15(m, 2H); 2.2-2.35(m. 2H); 3.0-3.2(m, 2H); 3.4 (t, 2H); 3.6-3.75(m, 2H); 4.05(s, 3H); 4.35(t, 2H); 4.65(s, 2H); 6.85(s, 1H); 6.9(d, 1H); 7.1(d, 1H); 7.5(s, 1H); 7.7(s, 1H); 8.9(s, 1H)

MS(ESI): 451 [MH]$^+$

EXAMPLE 21

Using a procedure analogous to that described for Example 10, 4-chloro-6-methoxy-7-((1-methylpiperidin-4-yl)methoxy)quinazoline (74 mg, 0.23 mmol), (prepared as described for the starting material in Example 10), was reacted with 6-hydroxyquinoline (41 mg, 0.28 mol) to give 6-methoxy-7-((1-methylpiperidin-4-yl)methoxy)-4-(quinolin-6-yloxy) quinazoline (89 mg, 94%).

$^1$H NMR Spectrum: (DMSOd$_6$) 1.3-1.5(m, 2H); 1.8(d, 2H); 1.9(t, 2H); 1.8-1.9(m, 1H); 2.2(s, 3H); 2.82(d, 2H); 4.02(s,3H); 4.1(d, 2H); 7.4(s, 1H); 7.6(dd, 1H); 7.65(s, 1H); 7.75(d, 1H); 7.95(s, 1H); 8.15(d, 1H); 8.4(d, 1H); 8.55(s, 1H); 8.95(d, 1H)

MS(ESI): 431 [MH]$^+$

EXAMPLE 22

To 4-chloro-6-methoxy-7-(3-morpholinopropoxy) quinazoline (250 mg, 0.74 mmol), (prepared as described for the starting material in Example 1), in suspension in DMF (4 ml) were successively added 4-chloro-7-hydroxyquinoline (133 mg, 0.74 mmol) and potassium carbonate (153 mg, 1 mmol) and the reaction mixture heated to 100° C. More 4-chloro-7-hydroxyquinoline (27 mg, 0.15 mmol) was added after one hour and heating was continued for a further 30 minutes. The product precipitated upon cooling to ambient temperature. The reaction mixture was diluted with water, the product was collected by filtration and washed with more water. The dried solid was triturated with ether and filtered to give 4-(4-chloroquinolin-7-yloxy)-6-methoxy-7-(3-morpholinopropoxy)quinazoline (166 mg, 47%).

$^1$H NMR Spectrum: (DMSOd$_6$, CF$_3$CO$_2$D) 2.3(m, 2H); 3.2(m, 2H); 3.4(m, 2H); 3.5(m, $^2$H); 3.7(m, 2H); 4.0(m, 2H); 4.1(s, 3H); 4.4(m, 2H); 7.55(s, 1H); 7.75(s, 1H); 7.90(dd, 1H); 7.95(d, 1H); 8.15(d, 1H); 8.45 (d, 1H); 8.80(s, 1H); 9.05(d, 1H)

MS-ESI: 481 [MH]$^+$

| Elemental analysis: | Found | C 61.8 | H 5.1 | N 11.5 |
| --- | --- | --- | --- | --- |
| C$_{25}$H$_{25}$ClN$_4$O$_4$ | Requires | C 62.4 | H 5.2 | N 11.7% |

The starting material was prepared as follows:

A solution of 7-benzyloxy-4-chloroquinoline (17 g, 56 mmol), (Konishi et al. WO 96/11187), in TFA (170 ml) was heated at reflux for 2 hours. The solvent was removed under vacuum and the residue was triturated with ether, filtered and washed with ether. The solid was suspended in an aqueous solution of sodium hydrogen carbonate (5.5 g, 65 mmol in 200 ml of water) and stirred at ambient temperature for 30 minutes. The solid was collected by filtration, washed with water and dried overnight under vacuum and over phosphorus pentoxide to give 4-chloro-7-hydroxyquinoline (9.85 g, 98%).

$^1$H NMR Spectrum: (DMSOd$_6$) 7.37(s, 1H); 7.39(d, 1H); 7.62(d, 1H); 8.15(d, 1H); 8.8(d, 1H)

MS-EI: m/z 179 [M.]$^+$

EXAMPLE 23

A solution of 4-chloro-6-methoxy-7-((1-methylpiperidin-4-yl)methoxy)quinazoline (74 mg, 0.23 mmol), (prepared as described for the starting material in Example 10), and 2-hydroxynaphthalene (40 mg, 0.28 mmol) in DMF (1.5 ml) containing potassium carbonate (48 mg, 0.35 mmol) was stirred at 100° C. for 3.5 hours. After cooling, methylene chloride (4.5 ml) was added and the mixture was poured onto a column of silica (SiO2 Isolute®) and eluted with, successively, methylene chloride, methylene chloride/methanol (9/1), methylene chloride/methanol/3M ammonia in methanol (75/20/5). The fractions containing the product were evaporated under vacuum. The residues was triturated with ether, filtered and dried under vacuum to give 6-methoxy-7-((1-methylpiperidin-4-yl)methoxy)-4-(2-naphthyloxy)quinazoline (80 mg, 83%).

MS-ESI: 430 [MH]+

$^1$H NMR Spectrum: (DMSOd$_6$) 1.35-1.45 (m, 2H), 1.8 (d, 2H), 2.0 (t, 1H), 2.2 (s, 3H), 2.85 (d, 2H), 3.3-3.4 (m, 2H), 4.02 (s, 3H), 4.1 (d, 2H), 7.4 (s, 1H), 7.5 (dd, 1H), 7.55 (m, 2H), 7.65 (s, 1H), 7.88 (s, 1H), 7.98 (d, 1H), 8.0 (d, 1H), 8.1 (d, 1H), 8.55 (s, 1H)

EXAMPLE 24

A solution of 4-chloro-6-methoxy-7-(3-morpholinopropoxy)quinazoline (74 mg, 0.23 mmol), (prepared as described for the starting material in Example 1), and 3,4-(methylenedioxy)aniline (53 mg, 0.24 mmol) in a solution of isopropanol (3.5 ml) containing 5.5M hydrogen chloride in isopropanol (42 μl) was heated for 3 hours. After cooling to ambient temperature, the reaction mixture was cooled to 0° C. and maintained at this temperature overnight. The precipitate was collected by filtration, washed with ethyl acetate and dried under vacuum to give 4-(1,3-benzodioxol-5-ylamino)-6-methoxy-7-(3-morpholinopropoxy)quinazoline (82 mg, 76%).

MS-ESI: 439 [MH]+

$^1$H NMR Spectrum: (DMSOd$_6$) 2.3-2.4 (m, 2H), 3.05-3.2 (m, 2H), 3.25-3.35 (m, 2H), 3.5 (d, 2H), 3.82 (t, 2H), 4.0 (d, 2H), 4.05 (s, 3H), 4.32 (t, 2H), 6.1 (s, 2H), 7.02 (d, 1H), 7.1 (dd, 1H), 7.3 (s, 1H), 7.4 (s, 1H), 8.32 (s, 1H), 8.8 (s, 1H)

EXAMPLES 25-29

Using an analogous procedure to that described in Example 24, 4-chloro-6-methoxy-7-(3-morpholinopropoxy)quinazoline, (prepared as described for the starting material in Example 1), was used in the synthesis of the compounds described in Table I hereinafter as detailed in the notes a)-e) to Table I.

TABLE I

| Example No. | Weight (mg) | yield % | MS-ESI [MH]+ | note | R |
|---|---|---|---|---|---|
| 25 | 104 | 90 | 435.1 | a | 1-H-indazol-6-yl |
| 26 | 102 | 89 | 435.1 | b | 1-H-indazol-5-yl |
| 27 | 99 | 84 | 452 | c | 1,3-benzothiazol-6-yl |
| 28 | 108 | 91 | 466 | d | 2-methyl-1,3-benzothiazol-5-yl |
| 29 | 102 | 95 | 435.1 | e | 2,3-dihydro-1H-inden-5-yl |

Notes
a) 4-Chloro-6-methoxy-7-(3-morpholinopropoxy)quinazoline (74 mg) was reacted with 6-aminoindazole (32 mg) to give 4-(1-H-indazol-6-ylamino)-6-methoxy-7-(3-morpholinopropoxy)quinazoline.

$^1$H NMR Spectrum: (DMSOd$_6$) 2.3-2.4 (m, 2H), 3.05-3.2 (m, 2H), 3.2-3.3 (m, 2H), 3.52 (d, 2H), 3.85 (t, 2H), 4.0 (d, 2H), 4.05 (s, 3H), 4.32 (t, 2H), 7.42 (s, 1H), 7.45 (d, 1H), 7.85 (d, 1H), 7.98 (s, 1H), 8.1 (s, 1H), 8.42 (s, 1H), 8.85 (s, 1H)

b) 4-Chloro-6-methoxy-7-(3-morpholinopropoxy)quinazoline (74 mg) was reacted with 5-aminoindazole (32 mg) to give 4-(1-H-indazol-5-ylamino)-6-methoxy-7-(3-morpholinopropoxy)quinazoline.

$^1$H NMR Spectrum: (DMSOd$_6$) 2.3-2.4 (m, 2H), 3.05-3.2 (m, 2H), 3.25-3.3 (m, 2H), 3.45-3.55 (m, 2H), 3.8-3.9 (m, 2H), 3.9-4.02 (m, 2H), 4.05 (s, 3H), 4.32 (t, 2H), 7.42 (s, 1H), 7.65 (m, 2H), 8.05 (s, 1H), 8.15 (s, 1H), 8.4 (s, 1H), 8.75 (s, 1H)

c) 4-Chloro-6-methoxy-7-(3-morpholinopropoxy)quinazoline (74 mg) was reacted with 6-aminothiazole (36 mg) to give 4-(1,3-benzothiazol-6-ylamino)-6-methoxy-7-(3-morpholinopropoxy)quinazoline.

$^1$H NMR Spectrum: (DMSOd$_6$) 2.3-2.4 (m, 2H), 3.05-3.2 (m, 2H), 3.2-3.3 (m, 2H), 3.55 (d, 2H), 3.8 (t, 2H), 4.0 (d, 2H), 4.08 (s, 3H), 4.32 (t, 2H), 7.4 (s, 1H), 7.88 (dd, 1H), 8.2 (d, 1H), 8.4 (s, 1H), 8.55 (s, 1H), 8.85 (s, 1H), 9.42 (s, 1H)

d) 4-Chloro-6-methoxy-7-(3-morpholinopropoxy)quinazoline (74 mg) was reacted with 6-amino-2-methylthiazole (57 mg) to give 6-methoxy-4-(2-methyl-1,3-benzothiazol-5-ylamino)-7-(3-morpholinopropoxy)quinazoline.

$^1$H NMR Spectrum: (DMSOd$_6$) 2.3-2.4 (m, 2H), 2.85 (s, 3H), 3.05-3.2 (m, 2H), 3.3 (t, 2H), 3.4-3.5 (m, 2H), 3.85 (t, 2H), 4.0 (d, 2H), 4.05 (s, 3H), 4.35 (t, 2H), 7.42 (s, 1H), 7.75 (dd, 1H), 8.15 (d, 1H), 8.3 (s, 1H), 8.42 (s, 1H), 8.85 (s, 1H)

e) 4-Chloro-6-methoxy-7-(3-morpholinopropoxy)quinazoline (74 mg) was reacted with 5-aminoindan (32 mg) to give 4-(2,3-dihydro-1H-inden-5-ylamino)-6-methoxy-7-(3-morpholinopropoxy)quinazoline.

$^1$H NMR Spectrum: (DMSOd$_6$) 2.08 (m, 2H), 2.3-2.4 (m, 2H), 2.9 (m, 4H), 3.05-3.2 (m, 2H), 3.2-3.3 (m, 2H), 3.5 (d, 2H), 3.82 (t, 2H), 4.0 (d, 2H), 4.05 (s, 3H), 4.3 (t, 2H), 7.32 (d, 1H), 7.4 (m, 2H), 7.55 (s, 1H), 8.32 (s, 1H), 8.8 (s, 1H)

EXAMPLE 30

A suspension of 4-chloro-6-methoxy-7-(1-methylpiperidin-4-ylmethoxy)quinazoline (130 mg, 0.4 mmol), (prepared as described for the starting material in Example 10), 7-hydroxy-2-methylchromone (88 mg, 0.5 mmol), (Bull Soc. Chim. Fr. 1995, 132, 233), and potassium carbonate (83 mg, 0.6 mmol) was heated at 100° C. for 1.5 hours. After cooling, the mixture was partitioned between water and ethyl acetate. The organic layer was washed with water, brine, dried (MgSO$_4$), and the volatiles were removed by evaporation. The residue was triturated with ether, collected by filtration, washed with ether and dried under vacuum to give 6-methoxy-4-(2-methyl-4-oxo-4H-chromen-7-yloxy)-7-(1-methylpiperidin-4-ylmethoxy)quinazoline (170 mg, 92%).

MS-ESI: 462 [MH]+

$^1$H NMR Spectrum: (DMSOd$_6$) 1.3-1.5 (m, 2H); 1.75-1.95 (m, 5H); 2.2 (s, 3H), 2.42 (s, 3H); 4.0 (s, 3H); 4.1 (d, 2H); 6.3 (s, 2H); 7.4 (s, 1H); 7.45 (dd, 1H); 7.6 (s, 1H); 7.7 (s, 1H); 8.15 (d, 1H); 8.61 (s, 1H)

EXAMPLES 31-33

Using an analogous procedure to that described in Example 30, the compounds described in Table II hereinafter and detailed in the notes a)-c) to Table II, were made.

TABLE II

| Example No. | Weight (mg) | yield % | MS-ESI [MH]+ | note | Q | R |
|---|---|---|---|---|---|---|
| 31 | 180 | 85 | 451 | a | 1-methyl-piperidin-4-ylmethoxy | 4-methyl-3,4-dihydro-2H-1,4-benzoxazin-6-yloxy |
| 32 | 160 | 87 | 462 | b | 3-pyrrolidin-1-ylpropoxy | 2-methyl-4-oxo-4H-chromen-7-yloxy |
| 33 | 100 | 56 | 451 | c | 3-pyrrolidin-1-ylpropoxy | 4-methyl-3,4-dihydro-2H-1,4-benzoxazin-6-yloxy | a) 4-Chloro-6-methoxy-7-(1-methylpiperidin-4-yloxy)quinazoline (130 mg), (prepared as described for the starting material in Example 10), was reacted with 3,4-dihydro-4-methyl-2H-1,4-benzoxazin-6-ol (83 mg), (J. Org. Chem. 1971, 36 (1)), to give 6-methoxy-4-(4-methyl-3,4-dihydro-2H-1,4-benzoxazin-6-yloxy)-7-(1-methylpiperidin-4-ylmethoxy)quinazoline $^1$H NMR Spectrum: (DMSOd$_6$) 1.6-1.75 (m, 2H); 1.9-2.3 (m, 5H); 2.8 (s, 3H); 2.9 (s, 3H); 3.0-3.15 (m, 2H); 3.3 (br s, 2H); 3.5-3.6 (d, 2H); 4.1 (s, 3H); 4.2 (d, 2H); 4.3 (t, 2H); 6.55 (m, 1H); 6.75 (s, 1H); 6.8 (d, 1H); 7.6 (s, 1H); 7.75 (s, 1H); 9.15 (s, 1H)

b) 4-Chloro-6-methoxy-7-(3-pyrrolidin-1-ylpropoxy)quinazoline (130 mg), (prepared as described for the starting material in Example 9), was reacted with 7-hydroxy-2-methylchromone (88 mg), (Bull Soc. Chim Fr. 1995, 132, 233). After cooling, water was added (20 ml) and the precipitate was collected by filtration and dried under vacuum over phosphorus pentoxide at 60° C. to give 6-methoxy-4-(2-methyl-4-oxo-4H-chromen-7-yloxy)-7-(3-pyrrolidin-1-ylpropoxy)quinazoline.

$^1$H NMR Spectrum: (DMSOd$_6$, CF$_3$COOD) 1.8-2.0 (m, 2H); 2.0-2.15 (m, 2H); 2.2-2.3 (m, 2H); 2.4 (s, 3H); 3.05-3.15 (m, 2H); 3.3-3.4 (m, 2H); 3.6-3.7 (m, 2H); 4.05 (s, 3H); 4.35 (t, 2H); 6.3 (s, 1H); 7.45 (d, 1H); 7.5 (s, 1H); 7.65 (s, 1H); 7.72 (s, 1H); 8.15 (d, 1H); 8.75 (s, 1H)

c) 4-Chloro-6-methoxy-7-(3-pyrrolidin-1-ylpropoxy)quinazoline (130 mg), (prepared as described for the starting material in Example 9), was reacted with 3,4-dihydro-4-methyl-2H-1,4-benzoxazin-6-ol (83 mg), (J. Org. Chem. 1971, 36 (1)), to give 6-methoxy-4-(4-methyl-3,4-dihydro-2H-1,4-benzoxazin-6-yloxy)-7-(3-pyrrolidin-1-ylpropoxy)quinazoline.

$^1$H NMR Spectrum: (DMSOd$_6$) 1.85-2.0 (m, 2H); 2.0-2.15 (m, 2H); 2.25-2.35 (m, 2H); 2.83 (s, 3H); 3.05-3.15 (m, 2H); 3.3 (t, 2H); 3.4 (t, 2H); 3.7 (br m, 2H); 4.1 (s, 3H); 4.3 (t, 2H); 4.4 (t, 2H); 6.52 (d, 1H); 6.7 (s, 1H); 6.8 (d, 1H); 7.55 (s, 1H); 7.75 (s, 1H); 9.1 (s, 1H)

EXAMPLE 34

A solution of 4-chloro-6-methoxy-7-(1-methylpiperidin-4-ylmethoxy)quinazoline (110 mg, 0.34 mmol), (prepared as described for the starting material in Example 10), and 5-hydroxyindole (55 mg, 0.41 mmol) in DMF (1.5 ml) containing potassium carbonate (70 mg, 0.51 mmol) was heated at 100° C. for 2 hours. After cooling, water was added and the precipitate was collected by filtration, washed with water followed by ether, and dried under vacuum over phosphorus pentoxide to give 4-(indol-5-yloxy)-6-methoxy-7-(1-methylpiperidin-4-ylmethoxy)quinazoline (90 mg, 64%).

MS-ESI: 419 [MH]$^+$

NMR Spectrum: (DMSOd$_6$) 1.35-1.5 (m, 2H); 1.8 (d, 2H); 1.95 (t, 2H); 1.7-2.0 (m, 1H); 2.2 (s, 3H); 2.85 (d, 2H); 4.02 (s, 3H); 4.1 (d, 2H); 6.45 (s, 1H); 7.0 (d, 1H); 7.35 (s, 1H); 7.4-7.5 (m, 3H); 7.6 (s, 1H); 8.5 (1H)

| Elemental analysis: | Found | C 67.4 | H 6.5 | N 13.1 |
| C$_{24}$H$_{26}$N$_4$O$_3$ 0.5H$_2$O | Requires | C 67.4 | H 6.4 | N 13.1% |

EXAMPLE 35

Using an analogous procedure to that described in Example 34, 4-chloro-6-methoxy-7-(1-methylpiperidin-4-ylmethoxy)quinazoline (110 mg, 0.34 mmol), (prepared as described for the starting material in Example 10), was reacted with 2,3-dimethyl-5-hydroxyindole (66 mg, 0.41 mmol), (Arch. Pharm. 1972, 305, 159). The crude product was purified by column chromatography eluting with methanol/methylene chloride (1/9) followed by 3M ammonia in methanol/methanol/methylene chloride (5/15/80) to give 4-(2,3-dimethylindol-5-yloxy)-6-methoxy-7-(1-methylpiperidin-4-ylmethoxy)quinazoline (60 mg, 40%).

MS-ESI: 447 [MH]+

$^1$H NMR Spectrum: (DMSOd$_6$) 1.2-1.4 (m, 2H); 1.7 (d, 2H); 1.8 (t, 2H); 1.7-1.9 (m, 1H); 2.05 (s, 3H); 2.12 (s, 3H); 2.25 (s, 3H); 2.75 (d, 2H); 3.9 (s, 3H); 4.0 (d, 2H); 6.8 (d, 1H); 7.15 (s, 1H); 7.2 (d, 1H); 7.3 (s, 1H); 7.52 (s, 1H); 8.45 (s, 1H)

| Elemental analysis: | Found | C 68.6 | H 6.9 | N 12.5 |
| C$_{26}$H$_{30}$N$_4$O$_3$ 0.4H$_2$O | Requires | C 68.8 | H 6.8 | N 12.4% |

EXAMPLE 36

Using an analogous procedure to that described in Example 34, 4-chloro-6-methoxy-7-(3-pyrrolidin-1-ylpropoxy)quinazoline (110 mg, 0.34 mmol), (prepared as described for the starting material in Example 9), was reacted with 5-hydroxyindole (55 mg, 0.41 mmol). The crude product was purified by chromatography on alumina, eluting with methanol/ethyl acetate/methylene chloride (5/45/50) to give 4-(indol-5-yloxy)-6-methoxy-7-(3-pyrrolidin-1-ylpropoxy)quinazoline (70 mg, 50%).

MS-ESI 419 [MH]+

$^1$H NMR Spectrum: (DMSOd$_6$, CF$_3$COOD) 1.9-2.0 (m, 2H); 2.1 (m, 2H); 2.3 (t, 2H); 3.0-3.15 (m, 2H); 3.4 (t, 2H); 3.6-3.75 (m, 2H); 4.1 (s, 3H); 4.4 (t, 2H); 6.5 (s, 1H); 7.05 (d, 1H); 7.5 (s, 1H); 7.5-7.6 (m, 2H); 7.85 (s, 1H); 9.11 (s, 1H)

| Elemental analysis: | Found | C 63.7 | H 6.4 | N 12.1 |
| C$_{24}$H$_{26}$N$_4$O$_3$ 1.9H$_2$O | Requires | C 63.7 | H 6.6 | N 12.4% |

EXAMPLE 37

A suspension of 4-chloro-6-methoxy-7-(1-methylpiperidin-4-ylmethoxy)quinazoline (100 mg, 0.31 mmol), (prepared as described for the starting material in Example 10), and 5-amino-2,3-dimethylindole (55 mg, 0.34 mmol) in isopropanol (6 ml) containing 5.5M hydrogen chloride in isopropanol (60 µL) was heated for 30 minutes at 70° C. After cooling, the solid was collected by filtration, washed with isopropanol, followed by ether and dried under vacuum to give 4-(2,3-dimethylindol-5-ylamino)-6-methoxy-7-(1-methylpiperidin-4-ylmethoxy)quinazoline hydrochloride (118 mg, 74%).

MS-ESI: 446 [MH]+

$^1$H NMR Spectrum: (DMSOd$_6$): 1.8-1.9 (m, 2H); 2.0 (d, 2H); 2.1-2.2 (m, 1H); 2.16 (s, 3H); 2.33 (s, 3H); 2.75 (br s, 3H); 2.95-3.05 (m, 2H); 3.5 (d, 2H); 4.0 (s, 3H); 4.07 (d, 2H); 7.25 (d, 1H); 7.4 (d, 1H); 7.42 (s, 1H); 7.52 (s, 1H); 8.25 (s, 1H); 8.75 (s, 1H); 10.0 (br s, 1H); 10.9 (s, 1H); 11.25 (br s, 1H)

| Elemental analysis: | Found | C 58.5 | H 6.8 | N 12.9 |
| --- | --- | --- | --- | --- |
| $C_{26}H_{31}N_5O_2$ 1H$_2$O 1.9HCl | Requires | C 58.6 | H 6.6 | N 13.1% |

EXAMPLE 38

Using an analogous procedure to that described in Example 37, 4-chloro-6-methoxy-7-(3-pyrrolidin-1-ylpropoxy)quinazoline (100 mg, 0.31 mmol), (prepared as described for the starting material in Example 9), was reacted with 5-amino-2,3-dimethylindole (55 mg, 0.34 mmol) to give 4-(2,3-dimethylindol-5-ylamino)-6-methoxy-7-(3-pyrrolidin-1-ylpropoxy)quinazoline hydrochloride (114 mg, 72%).

MS-ESI: 446 [MH]+

$^1$H NMR Spectrum: (DMSOd$_6$, CF$_3$COOD) 1.85-2.0 (m, 2H); 2.05-2.15 (m, 2H); 2.1 (s, 3H); 2.2 (s, 3H); 2.25-2.35 (m, 2H); 2.35 (s, 3H); 3.0-3.15 (m, 2H); 3.32-3.42 (m, 2H); 3.6-3.7 (m, 2H); 4.05 (s, 3H); 4.3 (t, 2H); 7.2 (d, 1H); 7.3 (s, 1H); 7.35 (d, 1H); 7.57 (s, 1H); 8.2 (s, 1H); 8.8 (s, 1H)

| Elemental analysis: | Found | C 58.8 | H 7.0 | N 12.5 |
| --- | --- | --- | --- | --- |
| $C_{26}H_{31}N_5O$ 1.9H$_2$O 1.9HCl 0.1isopropanol | Requires | C 58.6 | H 7.1 | N 12.9% |

EXAMPLE 39

Using an analogous procedure to that described in Example 38, 4-chloro-6-methoxy-7-(3-pyrrolidin-1-ylpropoxy)quinazoline (100 mg, 0.31 mmol), (prepared as described for the starting material in Example 9), was reacted with 5-amino-2-methylindole (50 mg, 0.34 mmol) to give 6-methoxy-4-(2-methylindol-5-ylamino)-7-(3-pyrrolidin-1-ylpropoxy)quinazoline hydrochloride (138 mg, 89%).

MS-ESI: 432 [MH]+

$^1$H NMR Spectrum: (DMSOd$_6$) 1.8-1.9 (m, 2H); 2.0-2.1 (m, 2H); 2.15-2.35 (m, 2H); 2.4 (s, 3H); 3.0-3.1 (m, 2H); 3.2-3.3 (m, 2H); 3.5-3.6 (m, 2H); 4.0 (s, 3H); 4.32 (t, 2H); 6.2 (s, 1H); 7.2 (d, 1H); 7.3 (m, 2H); 7.65 (s, 1H); 8.25 (s, 1H); 8.75 (s, 1H); 10.75 (br s, 1H); 11.15 (s, 1H); 11.25 (br s, 1H)

| Elemental analysis: | Found | C 58.9 | H 6.6 | N 13.5 |
| --- | --- | --- | --- | --- |
| $C_{25}H_{29}N_5O_2$ 2.2HCl 0.1isopropanol | Requires | C 58.7 | H 6.2 | N 13.5% |

EXAMPLE 40

A mixture of 4-chloro-6-methoxy-7-(3-pyrrolidin-1-ylpropoxy)quinazoline (100 mg, 0.31 mmol), (prepared as described for the starting material in Example 9), and 7-hydroxy-2,4-dimethylquinoline (64 mg, 0.36 mmol), (Chem. Berichte, 1903, 36, 4016), in DMF (3 ml) containing potassium carbonate (86 mg, 0.62 mmol) was heated at 90° C. for 3 hours. After cooling, the mixture was poured onto a column of silica and eluted with 2.5M ammonia in methanol/methylene chloride (5/95) to give 4-(2,4-dimethylquinolin-7-yloxy)-6-methoxy-7-(3-pyrrolidin-1-ylpropoxy)quinazoline (50 mg, 35%).

MS-ESI: 459 [MH]+

$^1$H NMR Spectrum: (CDCl$_3$) 1.8 (br s, 4H); 2.2 (m, 4H); 2.55 (br s, 4H); 2.7 (2s, 6H); 2.68 (m, 2H); 4.05 (s, 3H); 4.3 (t, 2H); 7.15 (s, 1H); 7.35 (s, 1H); 7.45 (d, 1H); 7.6 (s, 1H); 7.9 (s, 1H); 8.05 (d, 1H); 8.6 (s, 1H)

| Elemental analysis: | Found | C 70.4 | H 7.1 | N 12.1 |
| --- | --- | --- | --- | --- |
| $C_{27}H_{30}N_4O_3$ 0.2ether | Requires | C 70.5 | H 6.8 | N 11.8% |

EXAMPLE 41

Using an analogous procedure to that described in Example 37, 4-chloro-6-methoxy-7-(1-methylpiperidin-4-ylmethoxy)quinazoline (50 mg, 0.155 mmol), (prepared as described for the starting material in Example 10), was reacted with 5-amino-2-methylindole (0.171 mmol) to give 6-methoxy-4-(2-methylindol-5-ylamino)-7-(1-methylpiperidin-4-ylmethoxy)quinazoline hydrochloride (72 mg, quant.).

MS-ESI: 432 [MH]+

$^1$H NMR Spectrum: (DMSOd$_6$, CF$_3$COOD) 1.5-1.7 (m, 2H); 2.05 (d, 2H); 2.1-2.2 (m, 1H); 2.45 (s, 3H); 2.8 (s, 3H); 3.05 (t, 2H); 3.5 (d, 2H); 4.0 (s, 3H); 4.1 (d, 2H); 6.2 (s, 1H); 7.2 (d, 1H); 7.32 (d, 1H); 7.4 (d, 1H); 7.6 (s, 1H); 8.2 (s, 1H); 8.85 (s, 1H)

| Elemental analysis: | Found | C 53.9 | H 6.8 | N 12.4 |
| --- | --- | --- | --- | --- |
| $C_{25}H_{29}N_5O_2$ 2.6H$_2$O 2.07HCl | Requires | C 54.2 | H 6.6 | N 12.6% |

EXAMPLE 42

A suspension of 4-chloro-6-methoxy-7-(3-pyrrolidin-1-ylpropoxy)quinazoline (100 mg, 0.31 mmol), (prepared as described for the starting material in Example 9), and 7-hydroxy-2-methylquinoline (54 mg, 0.34 mmol), (J. Med. Chem. 1998, 41, 4062), in DMF (3 ml) containing potassium carbonate (86 mg, 0.62 mmol) was heated at 90° C. for 2 hours. After cooling, the mixture was partitioned between ethyl acetate and water. The organic layer was separated, washed with water, brine, dried and the volatiles were removed by evaporation. The residue was triturated with minimal ether, collected by filtration and dried under vacuum to give 6-methoxy-4-(2-methylquinolin-7-yloxy)-7-(3-pyrrolidin-1-ylpropoxy)quinazoline (95 mg, 69%).

MS-ESI: 445 [MH]+

$^1$H NMR Spectrum: (CDCl$_3$) 1.8 (br s, 4H); 2.2 (m, 2H); 2.5 (br s, 4H); 2.7 (t, 2H); 2.8 (s, 3H); 4.1 (s, 3H); 4.3 (t, 2H); 7.3 (d, 1H); 7.35 (s, 1H); 7.45 (dd, 1H); 7.6 (s, 1H); 7.85 (d, 1H); 7.9 (s, 1H); 8.1 (d, 1H); 8.6 (s, 1H)

EXAMPLE 43

Using an analogous procedure to that described in Example 42, 4-chloro-6-methoxy-7-(1-(2-methylsulphonylethyl)piperidin-4-ylmethoxy)quinazoline (156 mg, 0.38 mmol), (prepared as described for the starting material in Example 12), was reacted with 7-hydroxy-2-methylquinoline (66 mg, 0.4 mmol), (J. Med. Chem. 1998, 41, 4062), to give 6-methoxy-7-(1-(2-methylsulphonylethyl)piperidin-4-ylmethoxy)-4-(2-methylquinolin-7-yloxy)quinazoline (166 mg, 82%).

MS-ESI: 537 [MH]+

$^1$H NMR Spectrum: (DMSOd$_6$) 1.3-1.5 (m, 2H); 1.75-1.95 (m, 3H); 1.95-2.15 (m, 2H); 2.7 (s, 3H); 2.7-2.8 (m, 2H);

2.9-3.0 (m, 2H); 3.05 (s, 3H); 3.2-3.35 (m, 2H); 4.02 (s, 3H); 4.1 (d, 2H); 7.4 (s, 1H); 7.45 (d, 1H); 7.55 (d, 1H); 7.65 (s, 1H); 7.8 (s, 1H); 8.05 (d, 1H); 8.35 (d, 1H); 8.55 (s, 1H)

| Elemental analysis: | Found | C 62.2 | H 6.3 | N 10.4 |
|---|---|---|---|---|
| $C_{28}H_{32}N_4O_5S$ 0.35ether 0.2DMF | Requires | C 62.4 | H 6.4 | N 10.2% |

EXAMPLE 44

A suspension of 4-chloro-6-methoxy-7-(1-methylpiperidin-4-ylmethoxy)quinazoline (50 mg, 0.155 mmol), (prepared as described for the starting material in Example 10), and 5-hydroxy-2-trifluoromethylindole (34 mg, 0.17 mmol) in DMF (1.5 ml) containing potassium carbonate (43 mg, 0.31 mmol) was heated at 90° C. for 2 hours. After cooling, the mixture was partitioned between ethyl acetate and water. The organic layer was separated, washed with brine, dried ($MgSO_4$) and the volatiles were removed by evaporation. The residue was purified by column chromatography eluting with methanol/ethyl acetate/methylene chloride (10/50/40) followed by 2.5M ammonia in methanol/ethyl acetate/methylene chloride (10/50/40) to give 6-methoxy-7-(1-methylpiperidin-4-ylmethoxy)-4-(2-trifluoromethylindol-5-yloxy)quinazoline (35 mg, 48%).

MS-ESI: 487 [MH]+

$^1$H NMR Spectrum: ($DMSOd_6$) 1.25-1.4 (m, 2H); 1.75 (d, 2H); 1.8 (t, 2H); 1.7-2.0 (m, 1H); 2.2 (s, 3H); 2.75 (d, 2H); 4.0 (s, 3H); 4.1 (d, 2H); 7.0 (s, 1H); 7.25 (d, 1H); 7.4 (s, 1H); 7.6 (d, 1H); 7.8 (s, 1H); 8.5 (s, 1H); 12.5 (s, 1H)

| Elemental analysis: | Found | C 60.2 | H 5.8 | N 10.9 |
|---|---|---|---|---|
| $C_{25}H_{25}F_3N_4O_3$ 0.7$H_2O$ 0.2ether | Requires | C 60.3 | H 5.6 | N 10.9% |

The starting material was prepared as follows:

A solution of (4-methoxy-2-methylphenyl)-carbamic acid-1,1-dimethylethyl ester (2 g, 8.43 mmol), (J. Med. Chem. 1996, 39, 5119), in dry THF (25 ml) was cooled to −40° C. and sec-butyllithium (15 ml, 19.5 mmol) was added. After stirring for 15 minutes at this temperature, N-methyl-N-methoxytrifluoroacetamide (1.32 g, 8.43 mmol) in THF (20 ml) was added in portions. Stirring was continued for 1 hour at −40° C. and then the mixture was allowed to warm to ambient temperature. The mixture was poured onto ether/1M hydrochloric acid. The organic layer was separated, washed with water, brine, dried ($MgSO_4$) and the volatiles were removed by evaporation.

The crude residue (1.4 g) was dissolved in methylene chloride (8 ml) and TFA was added (1.5 ml). After stirring for 3 hours at ambient temperature, the volatiles were removed under vacuum. The crude product was partitoned between methylene chloride and water. The organic layer was separated, washed with water, brine, dried ($MgSO_4$) and the volatiles were removed by evaporation. The residue was purified by column chromatography, eluting with ether/petroleum ether (1/9) to give 5-methoxy-2-trifluoromethylindole (845 mg, 47% over 2 steps).

$^1$H NMR Spectrum: ($CDCl_3$) 3.83 (s, 3H), 6.82 (s, 1H), 7.0 (dd, 1H), 7.1 (s, 1H), 7.3 (d, 1H), 8.15 (br s, 1H)

A solution of 5-methoxy-2-trifluoromethylindole (800 mg, 3.7 mmol) in methylene chloride (6 ml) was cooled to −15° C. and a solution of 1M boron tribromide in methylene chloride (7.44 ml, 7.4 mmol) was added in portions. The mixture was allowed to warm to ambient temperature and was stirred for 45 minutes. After cooling to 0° C., saturated aqueous sodium hydrogen carbonate (25 ml) was added. The mixture was extracted with ethyl acetate. The organic layer was dried ($MgSO_4$) and the volatiles were removed by evaporation. The residue was purified by column chromatography eluting with ethyl acetate/petroleum ether. After removal of the volatiles by evaporation, the solid was triturated with pentane, collected by filtration and dried under vacuum to give 5-hydroxy-2-trifluoromethylindole (290 mg, 39%).

MS-EI: 201 [M.]+

$^1$H NMR Spectrum: ($CDCl_3$) 4.64 (s, 1H), 6.8 (s, 1H), 6.92 (dd, 1H), 7.1 (s, 1H), 7.3 (d, 1H), 8.3 (br s, 1H)

| Elemental analysis: | Found | C 53.3 | H 2.9 | N 6.8 |
|---|---|---|---|---|
| $C_9H_6F_3NO$ 0.1 $H_2O$ | Requires | C 53.3 | H 3.1 | N 6.9% |

EXAMPLE 45

Using an analogous procedure to that described in Example 44, 4-chloro-6-methoxy-7-(3-pyrrolidin-1-ylpropoxy)quinazoline (100 mg, 0.3 mmol), (prepared as described for the starting material in Example 9), was reacted with 5-hydroxy-2-trifluoromethylindole (75 mg, 0.37 mmol), (prepared as described for the starting material in Example 44), to give 6-methoxy-7-(3-pyrrolidin-1-ylpropoxy)-4-(2-trifluoromethylindol-5-yloxy)quinazoline (105 mg, 70%).

MS-ESI: 487 [MH]+

$^1$H NMR Spectrum: ($CDCl_3$) 1.8 (m, 4H); 2.1-2.3 (m, 2H); 2.55 (br s, 4H); 2.7 (t, 2H); 4.1 (s, 3H); 4.3 (t, 2H); 6.95 (s, 1H); 7.2 (dd, 1H); 7.35 (s, 1H); 7.5 (d, 1H); 7.55 (s, 1H); 7.6 (s, 1H); 8.6 (s, 1H); 8.8 (s, 1H)

| Elemental analysis: | Found | C 61.7 | H 5.5 | N 11.5 |
|---|---|---|---|---|
| $C_{25}H_{25}F_3N_4O_3$ | Requires | C 61.7 | H 5.2 | N 11.5% |

EXAMPLE 46

Using an analogous procedure to that described in Example 42, 4-chloro-6-methoxy-7-(1-methylpiperidin-4-ylmethoxy)quinazoline (100 mg, 0.31 mmol), (prepared as described for the starting material in Example 10), was reacted with 7-hydroxy-2-methylquinoline (54 mg, 0.34 mmol), (J. Med. Chem. 1998, 41, 4062), to give 6-methoxy-7-(1-methylpiperidin-4-ylmethoxy)-4-(2-methylquinolin-7-yloxy)quinazoline (86 mg, 63%).

MS-ESI: 445 [MH]+

$^1$H NMR Spectrum: ($CDCl_3$) 1.4-1.6 (m, 2H); 1.95 (d, 2H); 2.05 (t, 2H); 1.9-2.1 (m, 1H); 2.35 (s, 3H); 2.8 (s, 3H); 2.95 (d, 2H); 4.1 (s, 3H); 4.15 (d, 2H); 7.3 (m, 2H); 7.45 (dd, 1H); 7.6 (s, 1H); 7.9 (d, 1H); 7.95 (s, 1H); 8.1 (d, 1H); 8.6 (s, 1H)

| Elemental analysis: | Found | C 69.7 | H 6.5 | N 12.8 |
|---|---|---|---|---|
| $C_{26}H_{28}N_4O_3$ 0.2$H_2O$ | Requires | C 69.7 | H 6.4 | N 12.5% |

EXAMPLE 47

A suspension of 4-chloro-6-methoxy-7-(3-pyrrolidin-1-ylpropoxy)quinazoline (110 mg, 0.34 mmol), (prepared as described for the starting material in Example 9), and 2,3-dimethyl-5-hydroxyindole (66 mg, 0.41 mmol), (Arch. Pharm. 1972, 305, 159), in DMF (1.5 ml) containing potassium carbonate (70 mg, 0.51 mmol) was heated at 100° C. for 2 hours. After cooling, the residue was purified by chromatography, eluting with methanol/methylene chloride (1/9) followed by 2.5M ammonia in methanol/methanol/methylene chloride (5/10/85) to give 4-(2,3-dimethylindol-5-yloxy)-6-methoxy-7-(3-pyrrolidin-1-ylpropoxy)quinazoline (50 mg, 33%).

MS-ESI: 447 [MH]+

$^1$H NMR Spectrum: (DMSOd$_6$, CF$_3$COOD) 1.9-2.0 (m, 2H); 2.05-2.15 (m, 2H); 2.15 (s, 3H); 2.3-2.4 (m, 2H); 2.4 (s, 3H), 3.05-3.15 (m, 2H); 3.35-3.45 (t, 2H); 3.7 (br s, 2H); 4.1 (s, 3H); 4.4 (t, 2H); 6.95 (d, 1H); 7.3 (s, 1H); 7.35 (d, 1H); 7.55 (s, 1H); 7.85 (s, 1H); 9.15 (s, 1H)

| Elemental analysis: | Found | C 67.7 | H 6.8 | N 12.2 |
|---|---|---|---|---|
| C$_{26}$H$_{30}$N$_4$O$_3$ 0.8H$_2$O | Requires | C 67.8 | H 6.9 | N 12.2% |

EXAMPLE 48

Using an analogous procedure to that described in Example 32, 7-benzyloxy-4-chloro-6-methoxyquinazoline (1 g, 3.33 mmol), (prepared as described for the starting material in Example 1), was reacted with 5-hydroxy-2-methylindole (0.59 g, 4 mmol) to give 7-benzyloxy-6-methoxy-4-(2-methylindol-5-yloxy)quinazoline (1.25 g, 91%).

MS-ESI: 412 [MH]+

$^1$H NMR Spectrum: (DMSOd$_6$) 2.4 (s, 3H); 4.0 (s, 3H); 5.35 (s, 2H); 6.15 (s, 1H); 6.85 (s, 1H); 7.2-7.6 (m, 9H); 8.5 (s, 1H)

| Elemental analysis: | Found | C 72.2 | H 5.1 | N 10.2 |
|---|---|---|---|---|
| C$_{25}$H$_{21}$N$_3$O$_3$ 0.2H$_2$O | Requires | C 72.3 | H 5.2 | N 10.1% |

The starting material may be prepared as follows:

A solution of boron tribromide (32.5 ml, 341 mmol) in methylene chloride (60 ml) was added in portions to a solution of 5-methoxy-2-methylindole (25 g, 155 mmol) in methylene chloride (250 ml) cooled at −45° C. After stirring for 15 minutes at −30° C., the mixture was warmed up to ambient temperature and stirred for 1 hour. Methylene chloride (300 ml) was added in portions and the mixture was cooled to 0° C. Water was added in portions and the mixture was adjusted to pH6 with 4N sodium hydroxide. The organic layer was separated. The aqueous layer was extracted with methylene chloride and the organic layers were combined, washed with water, brine, dried (MgSO$_4$) and the volatiles were removed by evaporation. The residue was purified by column chromatography eluting with ethyl acetate/methylene chloride (1/9 followed by 15/85) to give 5-hydroxy-2-methylindole (21.2 g, 93%).

$^1$H NMR Spectrum: (DMSOd$_6$) 2.35 (s, 3H); 5.95 (s, 1H); 6.5 (dd, 1H); 6.7 (s, 1H); 7.05 (d, 1H); 8.5 (s, 1H)

EXAMPLE 49

A solution of 7-benzyloxy-6-methoxy-4-(2-methylindol-5-yloxy)quinazoline (0.2 g, 0.5 mmol), (prepared as described in Example 48), in a mixture of methylene chloride (5 ml) and DMF (2 ml) containing 10% palladium-on-charcoal (50 mg) was treated with hydrogen at 1.8 atmospheres pressure for 2 hours. The suspension was filtered and the catalyst was washed with methanol followed by methylene chloride. The volatiles were removed from the filtrate by evaporation. The residue was triturated with water. The resulting solid was washed with water and dried under vacuum over phosphorus pentoxide at 60° C. to give 7-hydroxy-6-methoxy-4-(2-methylindol-5-yloxy)quinazoline (140 mg, 89%).

MS-ESI: 322 [MH]+

$^1$H NMR Spectrum: (DMSOd$_6$) 2.4 (s, 3H); 4.0 (s, 3H); 6.15 (s, 1H); 6.9 (d, 1H); 7.2 (s, 1H); 7.25 (s, 1H); 7.3 (d, 1H); 7.6 (s, 1H); 8.4 (s, 1H)

EXAMPLE 50

A suspension of 4-chloro-6-methoxy-7-(3-methylsulphonylpropoxy)quinazoline (150 mg, 0.45 mmol) and 5-hydroxy-2-trifluoromethylindole (109 mg, 0.54 mmol), (prepared as described for the starting material in Example 44), in DMF (1.5 ml) containing potassium carbonate (94 mg, 0.67 mmol) was heated at 100° C. for 1 hour. After cooling, the precipitate was collected by filtration, washed with ether, and dried under vacuum to give 6-methoxy-7-(3-methylsulphonylprop oxy)-4-(2-trifluoromethylindol-5-yloxy)quinazoline (195 mg, 87%).

MS-ESI: 496 [MH]$^+$ $^1$H NMR Spectrum: (DMSOd$_6$, CF$_3$COOD) 2.25-2.4 (m, 2H), 3.1 (s, 3H), 3.35 (t, 2H), 4.1 (s, 3H), 4.4 (t, 2H), 7.1 (s, 1H), 7.3 (d, 1H), 7.5 (s, 1H), 7.6 (d, 1H), 7.7 (s, 1H), 7.78 (s, 1H), 8.9 (s, 1H)

The starting material was prepared as follows:

A solution of 3-(methylthio)-1-propanol (5.3 g, 50 mmol) in methanol (500 ml) was added to a solution of OXONE, (trade mark of E.I. du Pont de Nemours & Co., Inc), (30 g) in water (150 ml) and the mixture stirred at ambient temperature for 24 hours. The precipitated solid was removed by filtration and the methanol removed from the filtrate by evaporation. The aqueous residue was saturated with sodium chloride and extracted with methylene chloride (4×25 ml). The aqueous residue was then saturated with ammonium chloride and extracted with ethyl acetate (4×25 ml). The extracts were combined, dried (MgSO$_4$) and the solvent removed by evaporation to give 3-(methylsulphonyl)-1-propanol (610 mg, 9%) as an oil.

$^1$H NMR Spectrum: (CDCl$_3$) 2.10(m, 2H); 2.96(s, 3H); 3.20(t, 2H); 3.80(t, 2H)

MS-ESI: 139 [MH]$^+$

Alternatively the 3-(methylsulphonyl)-1-propanol may be prepared as follows:

m-Chloroperoxybenzoic acid (67%, 25g, 97.2 mmol) was added in portions to 3-(methylthio)-1-propanol (5 ml, 48.6 mmol) in solution in dichloromethane. Some m-chlorobenzoic acid precipitated out and was removed by filtration. The filtrate was evaporated and the residue was purified over alumina using first dichloromethane (100%) then dichloromethane/methanol (95/5) to give 3-(methylsulphonyl)-1-propanol (4.18 g, 62%) as an oil.

Triphenylphosphine (8.9 g, 35.2 mmol) was added to a suspension of 7-hydroxy-6-methoxy-3-((pivaloyloxy)methyl)-3,4-dihydroquinazolin-4-one (6 g, 19.6 mmol), (prepared as described for the starting material in Example 12), in methylene chloride (150 ml). This was followed by the addition of 3-(methylsulphonyl)-1-propanol (3.5 g, 25.4 mmol) and diethyl azodicarboxylate (5.55 ml, 35.2 mmol) in portions. The reaction was complete once the reaction became homogeneous. Silica was added and the volatiles were removed by evaporation. The free flowing powder was placed on the top of a flash chromatography column pre-equilibrated with ethyl acetate (100%). Elution was done using ethyl acetate (100%) followed by methylene chloride/ethyl acetate/methanol (60/35/5). The volatiles were removed by evaporation to give 6-methoxy-7-(3-methylsulphonylpropoxy)-3-((pivaloyloxy)methyl)-3,4-dihydroquinazolin-4-one (7.58 g, 91%) as a white solid.

$^1$H NMR Spectrum: (CDCl$_3$) 1.2(s, 9H); 2.4-2.5(m, 2H); 3.0(s, 3H); 3.25-3.35(t, 2H); 5.95(s, 1H); 7.1(s, 1H); 7.65(s, 1H); 8.2(s, 1H)

6-Methoxy-7-(3-methylsulphonylpropoxy)-3-((pivaloyloxy)methyl)-3,4-dihydroquinazolin-4-one (7 g, 17 mmol) was suspended in methanol and 2M sodium hydroxide (3.3 ml, 6.6 mmol) was added with continuous stirring. The reaction mixture became homogeneous after 15 minutes. After a further 45 minutes water was added (7 ml) and the reaction mixture was adjusted to pH10 with 2M hydrochloric acid. The precipitate (a white solid) was collected by filtration, washed with water and dried over phosphorus pentoxide under vacuum to give 6-methoxy-7-(3-methylsulphonylpropoxy)-3,4-dihydroquinazolin-4-one (5g, 90%).

$^1$H NMR Spectrum: (DMSOd$_6$) 2.2-2.3(m, 2H); 3.05(s, 3H); 3.35(t, 2H); 3.9(s, 3H); 4.25(t, 2H); 7.15(s, 1H); 7.5(s, 1H); 8.0(s, 1H)

6-Methoxy-7-(3-methylsulphonylpropoxy)-3,4-dihydroquinazolin-4-one (3.6 g, 11.5 mmol) was suspended in thionyl chloride (40 ml). DMF (1.8 ml) was added under argon and the mixture was heated at reflux for 1.5 hours. The thionyl chloride was eliminated by several azeotropic distillations using toluene. The solid residue was suspended in ice/water and a saturated solution of sodium hydrogen carbonate was added to adjust the mixture to pH7. The solid was collected by filtration, washed with water and dried in a vacuum dessicator over phosphorus pentoxide to give 4-chloro-6-methoxy-7-(3-methylsulphonylpropoxy)quinazoline (3.35 g, 88%).

EXAMPLES 51-52

Using an analogous procedure to that described in Example 50, 4-chloro-6-methoxy-7-(3-methylsulphonylpropoxy)quinazoline, (prepared as described for the starting material in Example 50), was reacted with the appropriate phenol to give the compounds described in Table III:

TABLE III

| Example No. | Weight (mg) | Yield % | MS-ESI [MH]$^+$ | Ar | Note |
|---|---|---|---|---|---|
| 51 | 189 | 92 | 454 | 2-methylquinolin-7-yl | a |
| 52 | 175 | 90 | 428 | indol-5-yl | b | a) 4-Chloro-6-methoxy-7-(3-methylsulphonylpropoxy)quinazoline (150 mg, 0.45 mmol) was reacted with 7-hydroxy-2-methylquinoline (86.6 mg, 0.54 mmol), (J. Med. Chem. 1998, 41, 4062). After cooling, water was added and the precipitate was collected by filtration, washed with water, followed by ether and dried under vacuum to give 6-methoxy-7-(3-methylsulphonylpropoxy)-4-(2-methylquinolin-7-yloxy)quinazoline.

$^1$H NMR Spectrum: (DMSOd$_6$, CF$_3$COOD) 2.2-2.35 (m, 2H), 2.95 (s, 3H), 3.1 (s, 3H), 3.35 (m, 2H), 4.05 (s, 3H), 4.4 (t, 2H), 7.5 (s, 1H), 7.7 (s, 1H), 7.95 (dd, 1H), 8.02 (d,; 1H), 8.2 (s, 1H), 8.48 (d, 1H), 8.7 (s, 1H), 9.12 (d, 1H)

b) Using an analogous procedure to that described in note a), 4-chloro-6-methoxy-7-(3-(methylsulphonyl)propoxy)quinazoline (150 mg, 0.45 mmol) was reacted with 5-hydroxyindole (72.4 mg, 0.54 mmol) to give 4-(indol-5-yloxy)-6-methoxy-7-(3-methylsulphonylpropoxy)quinazoline.

$^1$H NMR Spectrum: (DMSOd$_6$) 2.2-2.35 (m, 2H), 3.1 (s, 3H), 3.3-3.4 (t, 2H), 4.0 (s, 3H), 4.4 (t, 2H), 6.5 (s, 1H), 7.0 (dd, 1H), 7.4 (s, 1H), 7.4-7.5 (m, 3H), 7.6 (s, 1H), 8.5 (s, 1H), 11.25 (s, 1H)

EXAMPLE 53

0.5M Triphenylphosphine in methylene chloride and diisopropyl azodicarboxylate (150 μl, 0.75 mmol) were added in portions to a suspension of 7-hydroxy-6-methoxy-4-(2-methylindol-5-yloxy)quinazoline (112 mg, 0.35 mmol), (prepared as described in Example 49), and N,N-dimethylethanolamine (62 mg, 0.7 mmol) in methylene chloride (2 ml). After stirring for 2 hours at ambient temperature, the reaction mixture was poured onto an Isolute® column (10 g of silica) and eluted with ethyl acetate/methylene chloride (1/1) followed by methanol/ethyl acetate/methylene chloride (10/40/50), methanol/methylene chloride (10/90), and 3M ammonia in methanol/methanol/methylene chloride (5/15/80). After removal of the volatiles by evaporation, the residue was dissolved in the minimum amount of methylene chloride (about 3 ml) and ether and petroleum ether (about 10 ml) was added. The resulting precipitate was collected by filtration and dried under vacuum to give 7-(2-(N,N-dimethylamino)ethoxy)-6-methoxy-4-(2-methylindol-5-yloxy)quinazoline (52 mg, 38%).

MS-ESI: 393 [MH]$^+$ $^1$H NMR Spectrum: (DMSOd$_6$) 2.25 (s, 6H), 2.4 (s, 3H), 2.75 (t, 2H), 4.0 (s, 3H), 4.3 (t, 2H), 6.15 (s, 1H), 6.87 (d, 1H), 7.25 (s, 1H), 7.3 (d, 1H), 7.4 (s, 1H), 7.6 (s, 1H), 7.5 (s, 1H)

EXAMPLES 54-56

Using an analogous procedure to that described in Example 53, the appropriate alcohols were reacted with 7-hydroxy-6-methoxy-4-(2-methylindol-5-yloxy)quinazoline, (prepared as described in Example 49), in analogous proportions to give the compounds described in Table IV:

TABLE IV

| Example No. | Weight (mg) | Yield % | MS-ESI [MH]+ | R | Note |
|---|---|---|---|---|---|
| 54 | 25 | 17 | 419 | 2-pyrrolidin-1-ylethoxy | a |
| 55 | 112 | 74 | 433 | 1-methylpiperidin-3-ylmethoxy | b |
| 56 | 115 | 72 | 456 | 2-(N-methyl-N-(4-pyridyl)amino)ethoxy | c | a) 7-Hydroxy-6-methoxy-4-(2-methylindol-5-yloxy)quinazoline was reacted with 1-(2-hydroxyethyppynolidine (81 mg) to give 6-methoxy-4-(2-methylindol-5-yloxy)-7-(2-pyrrolidin-1-ylethoxy)quinazoline.

¹H NMR Spectrum: (DMSOd₆) 1.65-1.8 (m, 4H), 2.4 (s, 3H), 2.6 (br s, 4H), 2.9 (t, 2H), 4.0 (s, 3H), 4.3 (t, 2H), 6.15 (s, 1H), 6.9 (d, 1H), 7.25 (s, 1H), 7.3 (d, 1H), 7.4 (s, 1H), 7.6 (s, 1H), 8.5 (s, 1H)

b) 7-Hydroxy-6-methoxy-4-(2-methylindol-5-yloxy) quinazoline was reacted with 1-methyl-3-piperidinemethanol (90 mg) to give 6-methoxy-4-(2-methylindol-5-yloxy)-7-(1-methylpiperidin-3-ylmethoxy)quinazoline.

¹H NMR Spectrum: (DMSOd₆) 1.45-2.2 (m, 7H), 2.18 (s, 3H), 2.4 (s, 3H), 2.6 (br d, 1H), 2.85 (br d, 1H), 4.0 (s, 3H), 4.1 (d, 2H), 6.15 (s, 1H), 6.9 (d, 1H), 7.25 (d, 1H), 7.3 (d, 1H), 7.35 (s, 1H), 7.6 (s, 1H), 8.5 (s, 1H)

c) 7-Hydroxy-6-methoxy-4-(2-methylindol-5-yloxy) quinazoline was reacted with 2-(N-methyl-N-(4-pyridyl)amino)ethanol (106 mg), (EP 0359389), to give 6-methoxy-4-(2-methylindol-5-yloxy)-7-(2-(N-methyl-N-(4-pyridypamino)ethoxy)quinazoline.

¹H NMR Spectrum: (DMSOd₆) 2.4 (s, 3H), 3.1 (s, 3H), 3.9 (t, 2H), 3.97 (s, 3H), 4.4 (t, 2H), 6.15 (s, 1H), 6.75 (d, 2H), 6.87 (dd, 1H), 7.25 (s, 1H), 7.3 (d, 1H), 7.35 (s, 1H), 7.6 (s, 1H), 8.15 (d, 2H), 8.5 (s, 1H)

EXAMPLES 57-66

Using an analogous procedure to that described in Example 53, except that ammonia in methanol was not necessary during the column chromatography, the appropriate alcohols were reacted with 7-hydroxy-6-methoxy-4-(2-methylindol-5-yloxy)quinazoline, (prepared as described in Example 49), in analogous proportions to give the compounds described in Table V:

TABLE V

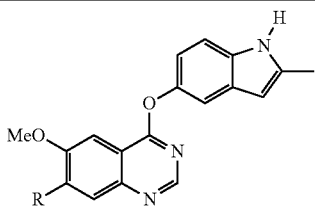

| Example No. | Weight (mg) | Yield % | MS-ESI [MH]⁺ | R | Note |
|---|---|---|---|---|---|
| 57 | 115 | 76 | 435 | 2-morpholinoethoxy | a |
| 58 | 64 | 42 | 433 | 2-piperidinoethoxy | b |
| 59 | 66 | 43 | 437 | 2-(N-(2-methoxyethyl)-N-methylamino)ethoxy | c |
| 60 | 118 | 75 | 449 | 3-morpholinopropoxy | d |
| 61 | 101 | 68 | 424 | 2-(2-methoxyethoxy)ethoxy | e |
| 62 | 81 | 57 | 407 | 3-(N,N-dimethylamino)propoxy | f |
| 63 | 160 | 92 | 497 | 3-(1,1-dioxothiomorpholino)propoxy | g |
| 64 | 121 | 83 | 417 | 2-(1H-1,2,4-triazol-1-yl)ethoxy | h |
| 65 | 38 | 22 | 492 | 2-(2-(4-methylpiperazin-1-yl)ethoxy)ethoxy | i |
| 66 | 80 | 48 | 479 | 2-(2-morpholinoethoxy)ethoxy | j | a) 7-Hydroxy-6-methoxy-4-(2-methylindol-5-yloxy) quinazoline was reacted with 4-(2-hydroxyethyl)morpholine (92 mg) to give 6-methoxy-4-(2-methylindol-5-yloxy)-7-(2-morpholinoethoxy)quinazoline.

¹H NMR Spectrum: (DMSOd₆) 2.4 (s, 3H), 2.5-2.7 (m, 4H), 2.8 (t, 2H), 3.6 (t, 4H), 4.0 (s, 3H), 4.35 (t, 2H), 6.15 (s, 1H), 6.87 (dd, 1H), 7.25 (s, 1H), 7.32 (d, 1H), 7.4 (s, 1H), 7.6 (s, 1H), 8.5 (s, 1H)

b) 7-Hydroxy-6-methoxy-4-(2-methylindol-5-yloxy) quinazoline was reacted with 1-(2-hydroxyethyl)piperidine (90 mg) to give 6-methoxy-4-(2-methylindol-5-yloxy)-7-(2-piperidinoethoxy)quinazoline.

¹H NMR Spectrum: (DMSOd₆) 1.3-1.45 (m, 2H), 1.4-1.6 (m, 4H), 2.4 (s, 3H), 2.4-2.5 (m, 4H), 2.75 (t, 2H), 3.97 (s, 3H), 4.3 (t, 2H), 6.15 (s, 1H), 6.9 (d, 1H), 7.25 (s, 1H), 7.3 (d, 1H), 7.4 (s, 1H), 7.6 (s, 1H), 8.5 (s, 1H)

c) 7-Hydroxy-6-methoxy-4-(2-methylindol-5-yloxy) quinazoline was reacted with 2-(N-(2-methoxyethyl)-N-methylamino)ethanol (93 mg) to give 6-methoxy-7-(2-(N-(2-methoxyethyl)-N-methylamino)ethoxy)-4-(2-methylindol-5-yloxy)quinazoline.

¹H NMR Spectrum: (DMSOd₆) 2.35 (s, 3H), 2.4 (s, 3H), 2.65 (t, 2H), 2.85 (t, 2H), 3.25 (s, 3H), 3.45 (t, 2H), 3.97 (s, 3H), 4.25 (t, 2H), 6.15 (s, 1H), 6.9 (dd, 1H), 7.25 (s, 1H), 7.32 (d, 1H), 7.4 (s, 1H), 7.6 (s, 1H), 8.5 (s, 1H)

The starting material was prepared as follows:

A mixture of 2-(methylamino)ethanol (5.4 g, 72 mmol), 2-bromoethyl methyl ether (10 g, 72 mmol) and triethylamine (10 ml, 72 mmol) in acetonitrile (70 ml) was refluxed overnight. After cooling, the solid was filtered and the filtrate was evaporated. The residue was triturated with ether. The ether layer was separated and evaporated to give 2-(N-(2-methoxyethyl)-N-methylamino)ethanol (3g, 31%).

MS-EI: 134 [MH]+

¹H NMR Spectrum: (CDCl₃) 2.35 (s, 3H); 2.6 (t, 2H); 2.65 (t, 2H); 3.35 (s, 3H); 3.5 (t, 2H); 3.6 (t, 2H)

d) 7-Hydroxy-6-methoxy-4-(2-methylindol-5-yloxy) quinazoline was reacted with 4-(3-hydroxypropyl)morpholine (102 mg) to give 6-methoxy-4-(2-methylindol-5-yloxy)-7-(3-morpholinopropoxy)quinazoline.

¹H NMR Spectrum: (DMSOd₆) 1.9-2.1 (m, 2H), 2.4 (s, 3H), 2.45 (t, 2H), 2.45-2.6 (s, 4H), 3.6 (t, 4H), 4.0 (s, 3H), 4.25 (t, 2H), 6.15 (s, 1H), 6.9 (d, 1H), 7.25 (s, 1H), 7.3 (d, 1H), 7.38 (s, 1H), 7.6 (s, 1H), 8.5 (s, 1H)

The starting material was prepared as follows:

Morpholine (94 g, 1.08 mol) was added dropwise to a solution of 3-bromo-1-propanol (75 g, 0.54 mol) in toluene (750 ml) and the reaction then heated at 80° C. for 4 hours. The mixture was allowed to cool to ambient temperature and the precipitated solid was removed by filtration. The volatiles were removed from the filtrate and the resulting yellow oil was purified by distillation at 0.4-0.7 mmHg to give 4-(3-hydroxypropyl)morpholine (40 g, 50%) as a colourless oil. b.p. 68-70° C. (~0.5 mmHg)

NMR Spectrum: (DMSOd₆) 1.65-1.78(m, 2H); 2.50(t, 4H); 2.60(t, 2H); 3.68(t, 4H); 3.78(t, 2H); 4.90(br d, 1H)

e) 7-Hydroxy-6-methoxy-4-(2-methylindol-5-yloxy) quinazoline was reacted with 2-(2-methoxyethoxy)ethanol (84 mg) to give 6-methoxy-7-(2-(2-methoxyethoxy)ethoxy)-4-(2-methylindol-5-yloxy)quinazoline.

¹H NMR Spectrum: (DMSOd₆) 2.42 (s, 3H), 3.27 (s, 3H), 3.5 (t, 2H), 3.65 (t, 2H), 3.85 (t, 2H), 4.0 (s, 3H), 4.32 (t, 2H), 6.15 (s, 1H), 6.9 (d, 1H), 7.3 (s, 1H), 7.35 (d, 1H), 7.4 (s, 1H), 7.6 (s, 1H), 8.5 (s, 1H)

f) 7-Hydroxy-6-methoxy-4-(2-methylindol-5-yloxy) quinazoline was reacted with 3-(N,N-dimethylamino)propanol (72 mg) to give 7-(3-N,N-dimethylaminopropoxy)-6-methoxy-4-(2-methylindol-5-yloxy)quinazoline.

¹H NMR Spectrum: (DMSOd₆) 1.9-2.0 (m, 2H), 2.17 (s, 6H), 2.4 (s, 3H), 3.98 (s, 3H), 4.22 (t, 2H), 6.14 (s, 1H), 6.88 (dd, 1H), 7.25 (s, 1H), 7.3 (d, 1H), 7.35 (s, 1H), 7.6 (s, 1H), 8.47 (s, 1H)

g) 7-Hydroxy-6-methoxy-4-(2-methylindol-5-yloxy) quinazoline was reacted with 3-(1,1-dioxothiomorpholino)-1-propanol (135 mg), (prepared as described for the starting material in Example 5), to give 7-(3-(1,1-dioxothiomorpholino)propoxy)-6-methoxy-4-(2-methylindol-5-yloxy)quinazoline.

$^1$H NMR Spectrum: (DMSOd$_6$) 1.9-2.0 (m, 2H), 2.38 (s, 3H), 2.65 (t, 2H), 2.9 (br s, 4H), 3.1 (br s, 4H), 3.96 (s, 3H), 4.25 (t, 2H), 6.12 (s, 1H), 6.85 (dd, 1H), 7.25 (s, 1H), 7.3 (d, 1H), 7.37 (s, 1H), 7.56 (s, 1H), 8.46 (s, 1H)

h)  7-Hydroxy-6-methoxy-4-(2-methylindol-5-yloxy)quinazoline was reacted with 2-(1H-1,2,4-triazol-1-yl)ethanol (79 mg), (Ann. Phar. Fr. 1977, 35, 503-508), to give 6-methoxy-4-(2-methylindol-5-yloxy)-7-(2-(1H-1,2,4-triazol-1-yl)ethoxy)quinazoline.

$^1$H NMR Spectrum: (DMSOd$_6$) 2.42 (s, 3H), 3.96 (s, 3H), 4.62 (m, 2H), 4.75 (m, 2H), 6.15 (s, 1H), 6.9 (dd, 1H), 7.27 (s, 1H), 7.32 (d, 1H), 7.47 (s, 1H), 7.63 (s, 1H), 8.03 (s, 1H), 8.51 (s, 1H), 8.60 (s, 1H)

i)  7-Hydroxy-6-methoxy-4-(2-methylindol-5-yloxy)quinazoline was reacted with 2-(2-(4-methylpiperazin-1-yl)ethoxy)ethanol (132 mg), (Arzneim. Forsch. 1966, 16, 1557-1560), to give 6-methoxy-4-(2-methylindol-5-yloxy)-7-(2-(2-(4-methylpiperazin-1-yl)ethoxy)ethoxy)quinazoline.

$^1$H NMR Spectrum: (DMSOd$_6$) 2.15 (s, 3H), 2.2-2.6 (m, 10H), 2.4 (s, 3H), 3.65 (t, 2H), 3.85 (t, 2H), 4.03 (s, 3H), 4.35 (m, 2H), 6.16 (s, 1H), 6.9 (dd, 1H), 7.3 (s, 1H), 7.35 (d, 1H), 7.4 (s, 1H), 7.61 (s, 1H), 8.5 (s, 1H)

j)  7-Hydroxy-6-methoxy-4-(2-methylindol-5-yloxy)quinazoline was reacted with 2-(2-morpholinoethoxy)ethanol (123 mg) to give 6-methoxy-4-(2-methylindol-5-yloxy)-7-(2-(2-morpholinoethoxy)ethoxy)quinazoline.

$^1$H NMR Spectrum: (DMSOd$_6$) 2.40 (s, 3H), 2.4-2.5 (m, 4H), 2.4-2.6 (m, 2H), 3.55 (t, 4H), 3.6 (t, 2H), 3.85 (t, 2H), 3.97 (br s, 3H), 4.15 (br s, 2H), 6.15 (s, 1H), 6.9 (d, 1H), 7.25 (s, 1H), 7.3 (d, 1H), 7.4 (s, 1H), 7.6 (s, 1H), 8.48 (s, 1H)

The starting material was prepared as follows:

2-(2-Chloroethoxy)ethanol (1.25 g, 10 mmol) was added to a mixture of morpholine (2.58 g, 30 mmol) and potassium carbonate (5.5 g, 40 mmol) in acetonitrile (50 ml). The mixture was heated at reflux for 6 hours and then stirred for 18 hours at ambient temperature. The insolubles were removed by filtration and the volatiles were removed from the filtrate by evaporation. The residue was purified by column chromatography eluting with methylene chloride/methanol (95/5 followed by 90/10 and then 80/20) to give 2-(2-morpholinoethoxy)ethanol (600 mg, 34%).

MS-(EI): 175 [M.]$^+$ $^1$H NMR Spectrum: (CDCl$_3$) 2.5(br s, 4H); 2.59(t, 2H); 3.6-3.85(m, 10H)

EXAMPLE 67

A solution of 4-chloro-6-methoxy-7-(3-piperidinopropoxy)quinazoline (100 mg, 0.29 mmol), 5-hydroxy-2-methylindole (53 mg, 0.36 mmol), (prepared as described for the starting material in Example 48), and potassium carbonate (62 mg, 0.44 mmol) in DMF (2 ml) was heated at 85° C. for 3 hours, followed by heating at 95° C. for 2 hours. After cooling, ice/water (15 ml) was added and the precipitate was collected by filtration and dried under vacuum. The solid was purified by column chromatography eluting with methylene chloride/methanol (95/5) followed by methylene chloride/methanol/3M ammonia in methanol (95/3/2) to give 6-methoxy-4-(2-methylindol-5-yloxy)-7-(3-piperidinopropoxy)quinazoline (71 mg, 54%).

MS-ESI: 447 [MH]$^+$ $^1$H NMR Spectrum: (DMSOd$_6$) 1.35-1.4 (m, 2H), 1.45-1.55 (m, 4H), 1.92-2.0 (m, 2H), 2.3-2.4 (m, 4H), 2.40 (s, 3H), 2.4-2.5 (m, 2H), 3.97 (s, 3H), 4.22 (t, 2H), 6.15 (s, 1H), 6.9 (d, 1H), 7.27 (s, 1H), 7.8 (d, 1H), 7.35 (s, 1H), 7.58 (s, 1H), 8.48 (s, 1H)

The starting material was prepared as follows:

Diethyl azodicarboxylate (3.9 ml, 24.5 mmol) was added in portions to a suspension of 7-hydroxy-6-methoxy-3-((pivaloyloxy)methyl)-3,4-dihydroquinazolin-4-one (5g, 16.3 mmol), (prepared as described for the starting material in Example 12), 3-bromo-1-propanol (2.21 ml, 24.5 mmol) and triphenylphosphine (6.42 g, 24.5 mmol) in methylene chloride (50 ml). After stirring for 2 hours at ambient temperature, the volatiles were removed under vacuum and the residue was purified by column chromatography eluting with methylene chloride followed by methylene chloride/methanol (95/5) to give 7-(3-bromopropoxy)-6-methoxy-3-((pivaloyloxy)methyl)-3,4-dihydroquinazolin-4-one (6 g, 86%).

MS-ESI: 427-429 [MH]$^+$ $^1$H NMR Spectrum: (DMSOd$_6$) 1.12 (s, 9H), 2.32 (t, 2H), 3.7 (t, 2H), 3.9 (s, 3H), 4.25 (t, 2H), 5.9 (s, 2H), 7.20 (s, 1H), 7.51 (s, 1H), 8.36 (s, 1H)

| Elemental analysis: | Found | C 50.1 | H 5.4 | N 6.4 |
| C$_{18}$H$_{23}$BrN$_2$O$_5$ 0.2H$_2$O | Requires | C 50.2 | H 5.5 | N 6.5% |

A solution of 7-(3-bromopropoxy)-6-methoxy-3-((pivaloyloxy)methyl)-3,4-dihydroquinazolin-4-one (2.89 g, 6.78 mmol) in piperidine (10 ml) was heated at 100° C. for 1 hour. After cooling, the volatiles were removed under vacuum. The residue was dissolved in methylene chloride, and washed with saturated ammonium chloride and brine. The organic layer was dried (MgSO$_4$) and the volatiles were removed by evaporation. The residue was dried under vacuum to give 6-methoxy-7-(3-piperidinopropoxy)-3-((pivaloyloxy)methyl)-3,4-dihydroquinazolin-4-one (2.4 g, 83%).

MS-ESI: 432 [MH]$^+$ $^1$H NMR Spectrum: (DMSOd$_6$) 1.15 (s, 9H), 1.35-1.5 (m, 1H), 1.6-1.8 (m, 3H), 1.8-1.9 (d, 2H), 2.2-2.3 (m, 2H), 2.95 (t, 2H), 3.25 (t, 2H), 3.55 (d, 2H), 3.95 (s, 3H), 4.25 (t, 2H), 5.94 (s, 2H), 7.24 (s, 1H), 7.56 (s, 1H), 8.46 (s, 1H)

A solution of 6-methoxy-7-(3-piperidinopropoxy)-3-((pivaloyloxy)methyl)-3,4-dihydroquinazolin-4-one (2.35 g, 5.45 mmol) in 7M ammonia in methanol (50 ml) was stirred overnight at ambient temperature. The volatiles were removed under vacuum and the residue was triturated with ether, filtered and washed with ether followed by ether/methylene chloride (1/1) and dried under vacuum to give 6-methoxy-7-(3-piperidinopropoxy)-3,4-dihydroquinazolin-4-one (1.65 g, 95%).

MS-ESI: 318 [MH]$^+$ $^1$H NMR Spectrum: (DMSOd$_6$) 1.3-1.4 (m, 2H), 1.4-1.55 (m, 4H), 1.85-1.95 (m, 2H), 2.35 (br s, 4H), 2.4 (t, 2H), 3.9 (s, 3H), 4.15 (t, 2H), 7.11 (s, 1H), 7.44 (s, 1H), 7.9 (s, 1H)

| Elemental analysis: | Found | C 63.5 | H 7.4 | N 13.1 |
| C$_{17}$H$_{23}$N$_3$O$_3$ 0.2H$_2$O | Requires | C 63.6 | H 7.4 | N 13.0% |

A solution of 6-methoxy-7-(3-piperidinopropoxy)-3,4-dihydroquinazolin-4-one (1.5 g, 4.7 mmol) in thionyl chloride (15 ml) containing DMF (1.5 ml) was heated at reflux for 3 hours. After cooling, the volatiles were removed under vacuum. The residue was azeotroped with toluene. The solid was partitioned between methylene chloride and sodium hydrogen carbonate. The aqueous layer was adjusted to pH10 with 6M aqueous sodium hydroxide. The organic layer was separated, washed with brine, dried (MgSO$_4$) and the volatiles were removed by evaporation. The residue was purified by column chromatography to give 4-chloro-6-methoxy-7-(3-piperidinopropoxy)quinazoline (1.21 g, 76%).

MS-ESI: 336 [MH]$^+$ $^1$H NMR Spectrum: (DMSOd$_6$) 1.35-1.45 (m, 2H), 1.5-1.6 (m, 4H), 1.9-2.05 (m, 2H), 2.4 (br s, 4H), 2.45 (t, 2H), 4.0 (s, 3H), 4.29 (t, 2H), 7.41 (s, 1H), 7.46 (s, 1H), 8.9 (s, 1H)

EXAMPLE 68

Using an analogous procedure to that described in Example 67, 4-chloro-6-methoxy-7-(3-piperidinopropoxy) quinazoline (100 mg), (prepared as described for the starting material in Example 67), was reacted with 5-hydroxyindole (48 mg, 0.36 mmol) to give 4-(indol-5-yloxy)-6-methoxy-7-(3-piperidinopropoxy)quinazoline (57 mg, 45%).

MS-ESI: 433 [MH]$^+$ $^1$H NMR Spectrum: (DMSOd$_6$) 1.4 (br s, 2H), 1.45-1.6 (br s, 4H), 1.9-2.1 (m, 2H), 2.4 (br s, 4H), 2.45 (t, 2H), 4.0 (s, 3H), 4.25 (t, 2H), 6.47 (s, 1H), 7.0 (d, 1H), 7.35 (s, 1H), 7.45 (s, 2H), 7.47 (d, 1H), 7.61 (s, 1H), 8.49 (s, 1H)

EXAMPLE 69

A solution of 7-hydroxy-6-methoxy-4-(2-methylindol-5-yloxy)quinazoline (161 mg, 0.5 mmol), (prepared as described in Example 49), 4-(4-methylphenylsulphonyloxymethyl)-1-tert-butoxycarbonylpiperidine (222 mg, 0.6 mmol), (prepared as described for the starting material in Example 10), and potassium carbonate (188 mg, 1 mol) in DMF (1.6 ml) was heated at 100° C. for 2 hours. After cooling, water was added. The precipitate was collected by filtration, washed with water, and dried under vacuum over phosphorus pentoxide at 60° C. The solid was triturated with petroleum ether, collected by filtration, washed with a mixture of ether/petroleum ether (1/1) and dried under vacuum to give 6-methoxy-4-(2-methylindol-5-yloxy)-7-(1-tert-butoxycarbonylpiperidin-4-ylmethoxy)quinazoline (200 mg, 77%).

MS-ESI: 541 [MNa]$^+$ $^1$H NMR Spectrum: (DMSOd$_6$) 1.1-1.3 (m, 2H), 1.4 (s, 9H), 1.8 (d, 2H), 1.95-2.1 (m, 1H), 2.4 (s, 1H), 2.7-2.85 (br s, 2H), 3.95 (s, 3H), 4.05 (d, 2H), 6.12 (s, 1H), 6.85 (d, 1H), 7.25 (s, 1H), 7.3 (d, 1H), 7.35 (s, 1H), 7.55 (s, 1H), 8.45 (s, 1H)

EXAMPLE 70

A solution of 6-methoxy-4-(2-methylindol-5-yloxy)-7-(1-tert-butoxycarbonylpiperidin-4-ylmethoxy)quinazoline (155 mg, 0.3 mmol), (prepared as described in Example 69), in methylene chloride (5 ml) containing TFA (1 ml) was stirred at ambient temperature for 30 minutes. The volatiles were removed under vacuum and the residue was treated with water and adjusted to pH12 with 2M sodium hydroxide. The mixture was extracted with methylene chloride. The organic layer was dried (MgSO$_4$), and the volatiles were removed by evaporation. The residue was purified by column chromatography eluting with methylene chloride/ethyl acetate/methanol (5/4/1) followed by methylene chloride/methanol (9/1) and by 3M ammonia in methanol/methanol/methylene chloride (5/15/80). After removal of the solvent by evaporation, the residue was dissolved in the minimum of methylene chloride, ether was added followed by petroleum ether. The precipitate was collected by filtration, washed with ether and dried under vacuum to give 6-methoxy-4-(2-methylindol-5-yloxy)-7-(piperidin-4-ylmethoxy)quinazoline (120 mg, 96%).

MS-ESI: 419 [MH]$^+$ $^1$H NMR Spectrum: (DMSOd$_6$, CF$_3$COOD) 1.5-1.7 (m, 2H), 2.05 (br d, 2H), 2.3-2.4 (m, 1H), 2.4 (s, 3H), 3.05 (t, 2H), 3.4 (d, 2H), 4.09 (s, 3H), 4.25 (d, 2H), 6.95 (dd, 1H), 7.35 (s, 1H), 7.4 (d, 1H), 7.6 (s, 1H), 7.85 (s, 1H), 9.15 (s, 1H)

EXAMPLE 71

Methoxyacetaldehyde (368 mg, 3.47 mol) (freshly distilled) followed by sodium triacetoxyborohydride (552 mg, 2.6 mol) were added to a solution of 6-methoxy-4-(2-methylindol-5-yloxy)-7-(piperidin-4-ylmethoxy)quinazoline (726 mg, 1.74 mmol), (prepared as described in Example 70), in a mixture of methylene chloride (15 ml) and methanol (15 ml). After stirring for 1.5 hours at ambient temperature, saturated sodium hydrogen carbonate was added. The volatiles were removed under vacuum and the residue was partitioned between methylene chloride and water. The organic layer, was separated, washed with water, brine, dried (MgSO$_4$) and the volatiles were removed by evaporation. The residue was purified by column chromatography eluting with methylene chloride/methanol (80/20). After removal of the solvent, the residue was triturated with ether, collected by filtration, washed with ether and dried under vacuum at 60° C. to give 6-methoxy-7-(1-(2-methoxyethyl)piperidin-4-ylmethoxy)-4-(2-methylindol-5-yloxy)quinazoline (392 mg, 47%).

MS-ESI 477 [MH]$^+$ $^1$H NMR Spectrum: (DMSOd$_6$, CF$_3$COOD) 1.6-1.8 (m, 2H), 2.05 (br d, 2H), 2.15-2.3 (m, 1H), 2.4 (s, 3H), 3.05 (t, 2H), 3.3 (br s, 2H), 3.32 (s, 3H), 3.58 (d, 2H), 3.65 (br s, 2H), 4.05 (s, 3H), 4.18 (d, 2H), 6.2 (s, 0.5 H (partly exchanged)), 6.92 (dd, 1H), 7.32 (s, 1H), 7.35 (d, 1H), 7.55 (s, 1H), 7.8 (s, 1H), 9.15 (s, 1H)

| Elemental analysis: | Found | C 68.0 | H 6.8 | N 11.8 |
| C$_{27}$H$_{32}$N$_4$O$_4$ | Requires | C 68.1 | H 6.8 | N 11.8% |

The starting material was prepared as follows:

A solution of 1,1,2-trimethoxyethane (90 g, 750 mmol) in water (570 ml) containing 12 N hydrochloric acid (3.75 ml) was stirred at 40° C. for 1.5 hours. After cooling, solid sodium chloride was added and the mixture was extracted with ether. The organic layer was dried (MgSO$_4$). The organic layer was distilled and the fraction from 70-90° C. was collected to give methoxyacetaldehyde (20.3 g) which was used directly in the next step.

EXAMPLE 72

Diphenylphosphoryl azide (83 mg, 0.3 mmol) was added in portions to a solution of 7-(2-carboxyvinyl)-6-methoxy-4-(2-methylindol-5-yloxy)quinazoline (75 mg, 0.2 mmol), triethylamine (40 mg, 0.4 mmol) and 1-(2-aminoethyl)pyrrolidine (46 mg, 0.4 mmol) in DMF (1.5 ml). After stirring for 5 hours at ambient temperature, the mixture was partitioned between ethyl acetate and water. The organic layer was separated, washed with water, brine, dried (MgSO$_4$) and the volatiles were removed by evaporation. The residue was purified by column chromatography eluting with methylene chloride/methanol (9/1) followed by methylene chloride/3M ammonia in methanol (9/1). After removal of the solvent, the solid was triturated with ether, collected by filtration, washed with ether and dried under vacuum to give 6-methoxy-4-(2-methylindol-5-yloxy)-7-((2-(2-pyrrolidin-1-ylethyl)carbamoyl)vinyl)quinazoline (25 mg, 26%).

MS-ESI: 472 [MH]+

$^1$H NMR Spectrum: (DMSOd$_6$, CF$_3$COOD) 1.8-1.95 (m, 2H), 1.95-2.1 (m, 2H), 2.48 (s, 3H), 3.0-3.2 (m, 2H), 3.35 (t, 2H), 3.6 (t, 2H), 3.65 (br s, 2H), 4.11 (s, 3H), 6.18 (s, 0.5H, partially exchanged), 6.95 (dd, 1H), 7.05 (d, 1H), 7.35 (s, 1H), 7.37 (d, 1H), 7.8 (s, 1H), 7.86 (d, 1H), 8.2 (s, 1H), 8.76 (s, 1H)

The starting material was prepared as follows:

Trifluoromethanesulphonic anhydride (338 mg, 1.2 mmol) was added to a suspension of 4-(4-chloro-2-fluorophenoxy)-7-hydroxy-6-methoxyquinazoline (320 mg, 1 mmol), (prepared as described for the starting material in Example 5), in methylene chloride (2 ml) containing pyridine (2 ml) cooled at 5° C. When the addition was complete, the mixture was left to warm to ambient temperature and stirred for 1 hour. After removal of the volatiles by evaporation, the residue was partitioned between ethyl acetate/ether and water. The organic layer was separated, washed with 0.5M hydrochloric acid, followed by water, brine, dried (MgSO$_4$) and evaporated to give 4-(4-chloro-2-fluorophenoxy)-6-methoxy-7-(trifluoromethylsulphonyloxy)quinazoline (400 mg, 88%).

MS-ESI: 453-455 [MH]+

$^1$H NMR Spectrum: (DMSOd$_6$) 4.15 (s, 3H), 7.5 (d, 1H), 7.62 (t, 1H), 7.78 (d, 1H), 8.02 (s, 1H), 8.27 (s, 1H), 8.77 (s, 1H)

Triethylamine (33 mg, 0.33 mmol) and tert-butyl acrylate (77 mg, 0.6 mmol) followed by diphenylpropylphosphine (3.4 mg, 0.008 mmol) and palladium(II) acetate (1.7 mg, 0.0075 mmol) were added to a solution of 4-(4-chloro-2-fluorophenoxy)-6-methoxy-7-(trifluoromethylsulphonyloxy)quinazoline (136 mg, 0.3 mmol) in DMF (1.5 ml) under argon. When the addition was complete the reaction flask was purged with argon. The mixture was stirred at 80-85° C. for 6 hours. After cooling, the mixture was partitioned between ethyl acetate and water. The aqueous layer was adjusted to pH6 with 2M hydrochloric acid. The organic layer was separated, washed with water, brine, dried (MgSO$_4$) and evaporated. The residue was purified by column chromatography eluting with methylene chloride followed by methylene chloride/ether (95/5). After removal of the solvent under vacuum, the solid was triturated with pentane/ether, collected by filtration and dried under vacuum to give 4-(4-chloro-2-fluorophenoxy)-6-methoxy-7-(2-(tert-butoxycarbonyl)vinyl)quinazoline (63 mg, 49%).

MS-ESI: 431 [MH]+

$^1$H NMR Spectrum: (DMSOd$_6$) 1.51 (s, 9H), 4.07 (s, 3H), 6.87 (d, 1H), 7.45 (d, 1H), 7.6 (t, 1H), 7.7 (s, 1H), 7.75 (d, 1H), 7.91 (d, 1H), 8.39 (s, 1H), 8.65 (s, 1H)

| Elemental analysis: | Found | C 61.1 | H 4.8 | N 6.6 |
|---|---|---|---|---|
| C$_{22}$H$_{20}$ClFN$_2$O$_3$ | Requires | C 61.3 | H 4.7 | N 6.5% |

A solution of 4-(4-chloro-2-fluorophenoxy)-6-methoxy-7-(2-(tert-butoxycarbonyl)vinyl)quinazoline (581 mg, 1.31 mmol) in a mixture of methylene chloride/TFA (2.5 ml/2.5 ml) was stirred at ambient temperature for 1.5 hours. After removal of the volatiles under vacuum, the residue was partitioned between ethyl acetate and water. The aqueous layer was adjusted to pH3 with 0.5M sodium hydroxide. The organic layer was separated and the aqueous layer was further extracted with ethyl acetate. The combined organic layers were washed with brine, dried (MgSO$_4$) and evaporated to give 7-(2-carboxyvinyl)-4-(4-chloro-2-fluorophenoxy)-6-methoxyquinazoline (430 mg, 85%).

$^1$H NMR Spectrum: (DMSOd$_6$) 4.08 (s, 3H), 6.9 (d, 1H), 7.45 (s, 1H), 7.6 (t, 1H), 7.70 (s, 1H), 7.73 (d, 1H), 7.95 (d, 1H), 8.39 (s, 1H), 8.66 (s, 1H)

$^1$M Sodium HMDS in THF (0.84 ml, 8.4 mmol) was added to a suspension of 7-(2-carboxyvinyl)-4-(4-chloro-2-fluorophenoxy)-6-methoxyquinazoline (105 mg, 0.28 mmol) and 5-hydroxy-2-methylindole (82 mg, 0.56 mmol), (prepared as described for the starting material in Example 48), in DMSO (1.5 ml). After stirring for 2 hours at ambient temperature, the mixture was partitioned between ethyl acetate and water. The aqueous layer was adjusted to pH3 with 2M hydrochloric acid. The organic layer was washed with water, brine, dried (MgSO$_4$) and evaporated. The residue was purified by column chromatography eluting with methylene chloride/methanol (95/5 followed by 90/10 and 70/30) to give 7-(2-carboxyvinyl)-6-methoxy-4-(2-methylindol-5-yloxy)quinazoline (75 mg, 71%).

$^1$H NMR Spectrum: (DMSOd$_6$) 2.4 (s, 3H), 4.06 (s, 3H), 6.15 (s, 1H), 6.82 (d, 1H), 6.9 (dd, 1H), 7.3 (s, 1H), 7.35 (d, 1H), 7.68 (s, 1H), 7.84 (d, 1H), 8.25 (s, 1H), 8.55 (s, 1H)

EXAMPLE 73

A suspension of 7-hydroxy-6-methoxy-4-(2-methylindol-5-yloxy)quinazoline (321 mg, 1mmol), (prepared as described in Example 49), 1-bromo-3-chloropropane (120 µl, 1.2 mmol) and potassium carbonate (359 mg, 2.6 mmol) in DMF (5 ml) was stirred at ambient temperature overnight. After addition of water, the precipitate was collected by filtration, washed with water and dried over phosphorus pentoxide at 60° C. to give 7-(3-chloropropoxy)-6-methoxy-4-(2-methylindol-5-yloxy)quinazoline (280 mg, 70%).

MS-ESI: 398 [MH]+

$^1$H NMR Spectrum: (DMSOd$_6$) 2.2-2.35 (m, 2H), 2.4 (s, 3H), 3.85 (t, 2H), 4.0 (s, 3H), 4.32 (t, 2H), 6.15 (s, 1H), 6.88 (d, 1H), 7.27 (s, 1H), 7.3 (d, 1H), 7.4 (s, 1H), 7.6 (s, 1H), 8.5 (s, 1H)

EXAMPLE 74

A solution of 7-(3-chloropropoxy)-6-methoxy-4-(2-methylindol-5-yloxy)quinazoline (150 mg, 0.38 mmol), (prepared as described in Example 73), in 1-methylpiperazine (2 ml) was heated at 100° C. for 2 hours. After cooling, the mixture was partitioned between ethyl acetate and aqueous 5% sodium hydrogen carbonate. The organic layer was separated, washed with water, brine, dried (MgSO$_4$) and evaporated. The residue was purified by column chromatography on an isolute column eluting with methanol/ethyl acetate/methylene chloride (1/4/5 followed by 1/9/0) and 3M ammonia in methanol/methanol/methylene chloride (5/10/80). After removal of the solvent under vacuum, the solid was dissolved in the minimum of methylene chloride and ether/petroleum ether was added. The precipitate was collected by filtration, and dried under vacuum to give 6-methoxy-4-(2-methylindol-5-yloxy)-7-(3-(4-methypiperazin-1-yl)propoxy)quinazoline (55 mg, 32%).

MS-ESI: 462 [MH]+

$^1$H NMR Spectrum: (DMSOd$_6$, CF$_3$COOD, 60° C.) 2.2-2.3 (m, 2H), 2.4 (s, 3H), 2.9 (s, 3H), 3.4-3.5 (m, 4H), 3.5-3.8 (m, 6H), 4.07 (s, 3H), 4.4 (t, 2H), 6.95 (d, 1H), 7.35 (s, 1H), 7.4 (d, 1H), 7.55 (s, 1H), 7.8 (s, 1H), 8.95 (s, 1H)

EXAMPLE 75

Triphenylphosphine (262 mg, 1 mmol) and N,N-diethylethanolamine (88 mg, 0.75 mmol) were added to a suspension of 7-hydroxy-6-methoxy-4-(2-methylindol-5-yloxy) quinazoline (160 mg, 0.5 mmol), (prepared as described in Example 49), in methylene chloride (5 ml), followed by the addition, in portions, of diethyl azodicarboxylate (165 μl, 1 mmol). After stirring for 1 hour at ambient temperature, the volatiles were removed under vacuum. The residue was purified by column chromatography eluting with methylene chloride/methanol (95/5) followed by methylene chloride/3M ammonia in methanol (90/10) to give 7-(2-(N,N-diethylamino)ethoxy)-6-methoxy-4-(2-methylindol-5-yloxy) quinazoline (147 mg, 70%).

MS-ESI 421 [MH]$^+$ $^1$H NMR Spectrum: (DMSOd$_6$) 1.0 (t, 6H), 2.41 (s, 3H), 2.6 (q, 4H), 2.88 (t, 2H), 3.97 (s, 3H), 4.24 (t, 2H), 6.14 (s, 1H), 6.89 (dd, 1H), 7.25 (s, 1H), 7.32 (d, 1H), 7.38 (s, 1H), 7.58 (s, 1H), 8.48 (s, 1H)

| Elemental analysis: | Found | C 66.2 | H 6.9 | N 13.1 |
|---|---|---|---|---|
| C$_{24}$H$_{28}$N$_4$O$_3$ 0.8H$_2$O | Requires | C 66.3 | H 6.9 | N 12.9% |

EXAMPLE 76

Using an analogous procedure to that described in Example 75, 7-hydroxy-6-methoxy-4-(2-methylindol-5-yloxy)quinazoline (321 mg, 1 mmol), (prepared as described in Example 49), was reacted with 2-((1-tertbutoxycarbonyl)piperidin-4-yloxy)ethanol (294 mg, 1.2 mmol) to give 6-methoxy-4-(2-methylindol-5-yloxy)-7-(2-((1-tertbutoxycarbonyl)piperidin-4-yloxy)ethoxy)quinazoline (420 mg, 76%).

MS-ESI: 549 [MH]$^+$ $^1$H NMR Spectrum: (DMSOd$_6$) 1.4 (s, 9H), 1.3-1.5 (m, 2H), 1.7-1.9 (m, 2H), 2.38 (s, 3H), 3.0 (br t, 2H), 3.5-3.7 (m, 3H), 3.85 (m, 2H), 3.98 (s, 3H), 4.3 (t, 2H), 6.12 (s, 1H), 6.85 (d, 1H), 7.22 (s, 1H), 7.3 (d, 1H), 7.4 (s, 1H), 7.55 (s, 1H), 8.48 (s, 1H)

The starting material was prepared as follows:

tert-Butoxycarbonyl anhydride (1.52 g, 7 mmol) in acetone (3.5 ml) was added to a solution of 4,4-(ethylenedioxy)piperidine (1 g, 7 mmol) in acetone/trichloromethane (3.5 ml/3.5 ml) cooled at 0° C. After stirring for 4 hours at ambient temperature, the volatiles were removed under vacuum. The residue was dissolved in ether and the ether solution was washed with water, brine, dried (MgSO$_4$) and evaporated to give 4,4-(ethylenedioxy)-1-tertbutoxycarbonylpiperidine (1.7 g, quant.).

$^1$H NMR Spectrum: (CDCl$_3$): 1.46 (s, 9H), 1.65 (t, 4H), 3.5 (t, 4H), 3.97 (s, 41-1)

Freshly distilled boron trifluoride etherate (54 μl, 0.41 mmol), followed by sodium cyanoborohydride (38 mg, 0.6 mmol) were added to a solution of 4,4-(ethylenedioxy)-1-tertbutoxycarbonylpiperidine (100 mg, 0.41 mmol) in THF (1.4 ml) cooled at 0° C. After stirring for 6 hours at ambient temperature, boron trifluoride etherate (520) and sodium cyanoborohydride (26 mg, 0.41 mmol) were added. After stirring overnight at ambient temperature, the mixture was partitioned between ethyl acetate and 2M sodium hydroxide. The organic layer was washed with water, brine, dried (MgSO$_4$) and evaporated. The residue was purified by column chromatography eluting with methylene chloride/methanol (95/5) followed by methylene chloride/methanol/3M ammonia in methanol (80/15/5) to give 24(1-tertbutoxycarbonyl)piperidin-4-yloxy)ethanol (42 mg, 42%).

MS-ESI: 268 [MNa]$^+$ $^1$H NMR Spectrum: (CDCl$_3$) 1.48 (s, 9H), 1.5-1.6 (m, 2H), 1.8-1.9 (m, 2H), 2.0 (t, 1H), 3.05-3.15 (m, 2H), 3.5 (m, 1H), 3.57 (t, 2H), 3.7-3.9 (m, 4H)

EXAMPLE 77

A solution of 6-methoxy-4-(2-methylindol-5-yloxy)-7-(2-((1-tertbutoxycarbonyl)piperidin-4-yloxy)ethoxy)quinazoline (379 mg, 0.69 mmol), (prepared as described in Example 76), in methylene chloride (7 ml) containing TFA (2.5 ml) was stirred for 1.5 hours at ambient temperature. After removal of the volatiles under vacuum, the residue was partitioned between ethyl acetate and water. Solid sodium hydrogen carbonate and 2N sodium hydroxide were added to adjust the aqueous layer to about pH10. The organic layer was washed with water, followed by brine, dried (MgSO$_4$) and evaporated. The residue was triturated with ether, filtered, washed with ether and dried under vacuum to give 6-methoxy-4-(2-methylindol-5-yloxy)-7-(2-(piperidin-4-yloxy)ethoxy)quinazoline (164 mg, 53%).

$^1$H NMR Spectrum: (DMSOd$_6$) 1.2-1.4 (m, 2H), 1.8-1.9 (m, 2H), 2.47 (s, 3H), 2.4-2.5 (m, 2H), 2.9-3.0 (d, 2H), 3.3-3.5 (m, 1H), 3.95 (s, 2H), 4.0 (s, 3H), 4.35 (s, 2H), 6.15 (s, 1H), 6.9 (dd, 1H), 7.28 (s, 1H), 7.32 (d, 1H), 7.41 (s, 1H), 7.60 (s, 1H), 8.49 (s, 1H)

MS-ESI: 448 [M.]$^+$

EXAMPLE 78

A solution of 7-hydroxy-6-methoxy-4-(2-methylindol-5-yloxy)quinazoline (193 mg, 0.6 mmol), (prepared as described in Example 49), 4-(2-hydroxyethoxy)pyridine (166 mg, 1.2 mmol), (J. Chem. Soc. Perkin II, 1987, 1867), in methylene chloride (5 ml) containing triphenylphosphine (330 mg, 1.26 mmol) and diisopropyl azodicarboxylate (255 mg, 1.26 mmol) was stirred at ambient temperature for 2 hours. The precipitate was filtered, triturated with ether followed by ethyl acetate, and dried under vacuum to give 6-methoxy-4-(2-methylindol-5-yloxy)-7-(2-(4-pyridyloxy)ethoxy)quinazoline (142 mg, 54%).

$^1$H NMR Spectrum: (DMSOd$_6$) 2.40 (s, 3H), 3.97 (s, 3H), 4.52 (t, 2H), 4.58 (t, 2H), 6.14 (s, 1H), 6.89 (dd, 1H), 7.07 (d, 2H), 7.26 (s, 1H), 7.31 (d, 1H), 7.46 (s, 1H), 7.61 (s, 1H), 8.41 (d, 2H), 8.5 (s, 1H)

MS-ESI: 443 [MH]$^+$

| Elemental analysis | Found | C 66.6 | H 5.0 | N 12.5 |
|---|---|---|---|---|
| C$_{25}$H$_{22}$N$_4$O$_4$ 0.12 CH$_2$Cl$_2$ | Requires | C 66.9 | H 5.0 | N 12.4% |

EXAMPLE 79

A suspension of 6-methoxy-4-(2-methylindol-5-yloxy)-7-(2-(N-methyl-N-tert-butoxycarbonylamino)ethoxy) quinazoline (148 mg, 0.31 mmol), (prepared as described in Example 149), in methylene chloride (4 ml) containing TFA (1 ml) was stirred for 1 hour. After removing the volatiles under vacuum, the residue was azeotroped with toluene. The residue was dissolved in methylene chloride (3 ml) and triethylamine (215 μl, 1.5 mmol) was added followed by methanesulphonyl chloride (48 μl, 0.62 mmol). After stirring for 1 hour at ambient temperature, the mixture was partitioned between methylene chloride and water. The organic layer was separated, washed with water, brine, dried (MgSO$_4$) and evaporated. The residue was purified by column chromatography eluting with ethylacetate/methanol (99/1 followed by 97/3). After evaporation of the solvent, the solid was triturated with ether, filtered, washed with ether and dried under vacuum to give 6-methoxy-4-(2-methylindol-5-yloxy)-7-(2-(N-methyl-N-methylsulphonylamino)ethoxy)quinazoline (54 mg, 38%).

$^1$H NMR Spectrum: (DMSOd$_6$) 2.4 (s, 3H), 2.93 (s, 3H), 3.0 (s, 3H), 3.62 (t, 2H), 4.0 (s, 3H), 4.38 (t, 2H), 6.14 (s, 1H), 6.88 (dd, 1H), 7.26 (s, 1H), 7.3 (d, 1H), 7.43 (s, 1H), 7.61 (s, 1H), 8.49 (s, 1H)

MS-ESI: 457 [MH]$^+$

EXAMPLE 80

A solution of 6-methoxy-4-(2-methylindol-5-yloxy)-7-(2-(piperidin-4-yloxy)ethoxy)quinazoline (76 mg, 0.17 mmol), (prepared as described in Example 77), in acrylonitrile (0.5 ml), methylene chloride (1 ml) and methanol (1 ml) was stirred overnight at ambient temperature. After removal of the volatiles under vacuum the residue was purified by column chromatography eluting with methylene chloride/methanol (98/2 followed by 95/5 and 90/10). The residue was triturated with ethyl acetate and ether. The resulting solid was filtered and dried under vacuum to give 7-(2-(1-(2-cyanoethyl)piperidin-4-yloxy)ethoxy)-6-methoxy-4-(2-methylindol-5-yloxy)quinazoline (73 mg, 86%).

$^1$H NMR Spectrum: (DMSOd$_6$) 1.4-1.55 (m, 2H), 1.8-1.9 (m, 2H), 2.15 (t, 2H), 2.4 (s, 3H), 2.55 (t, 2H), 2.65 (t, 2H), 2.7-2.8 (m, 2H), 3.4-3.5 (m, 1H), 3.85 (m, 2H), 4.0 (s, 3H), 4.3 (t, 2H), 6.15 (s, 1H), 6.9 (dd, 1H), 7.25 (s, 1H), 7.3 (d, 1H), 7.4 (s, 1H), 7.6 (s, 1H), 8.5 (s, 1H)

MS-ESI: 502 [MH]$^+$

| Elemental analysis | Found | C 67.0 | H 6.2 | N 14.0 |
|---|---|---|---|---|
| $C_{28}H_{31}N_5O_4$ | Requires | C 67.1 | H 6.2 | N 14.0% |

EXAMPLE 81

A solution of 4-chloro-6-methoxy-7-(3-pyrrolidin-1-yl-propoxy)quinazoline (100 mg, 0.31 mmol), (prepared as described for the starting material in Example 9), 6-hydroxyindole (50 mg, 0.37 mmol) and potassium carbonate (64 mg, 0.466 mmol) in DMF (1 ml) was heated at 95° C. for 4 hours. After cooling, the mixture was diluted with methylene chloride and poured onto a silica column. The product was eluted with methylene chloride, followed by methylene chloride/methanol (80/20 followed by 70/30 and 50/50). After removal of the solvent by evaporation, the precipitate was triturated with ether, filtered and dried under vacuum to give 6-methoxy-4-(indol-6-yloxy)-7-(3-(pyrrolidin-1-yl)propoxy)quinazoline (90 mg, 69%).

$^1$H NMR Spectrum: (DMSOd$_6$) 1.85 (br s, 4H), 2.15-2.25 (m, 2H), 2.85-3.15 (m, 6H), 4.01 (s, 3H), 4.32 (t, 2H), 6.5 (s, 1H), 6.95 (dd, 1H), 7.32 (s, 1H), 7.4 (s, 2H), 7.6 (d, 1H), 7.65 (s, 1H), 8.52 (s, 1H)

MS-ESI: 419 [MH]$^+$

EXAMPLE 82

Diisopropyl azodicarboxylate (146 mg, 0.72 mmol) was added to a solution of 7-hydroxy-4-(2-methylindol-5-yloxy)quinazoline (100 mg, 0.34 mmol), triphenyl phosphine (189 mg, 0.72 mol), and 3-pyrrolidinopropan-1-ol (89 mg, 0.686 mmol), (J. Org. Chem. 1988, 53, 3164), in methylene chloride (2.5 ml). After stirring overnight at ambient temperature, the solid was filtered. The filtrate was purified by column chromatography eluting with ethyl acetate/methylene chloride (1/1) followed by ethyl acetate/methylene chloride/methanol (4/5/1), methylene chloride/methanol (9/1) and 3N ammonia in methanol/methylene chloride (1/9). After removal of the solvent, the residue was triturated with ether, filtered, and dried under vacuum to give 4-(2-methylindol-5-yloxy)-7-(3-(pyrrolidin-yl)propoxy)quinazoline (49 mg, 35%).

$^1$H NMR Spectrum: (DMSOd$_6$) 1.8-2.0 (m, 2H), 2.0-2.15 (m, 2H), 2.2-2.32 (m, 2H), 2.41 (s, 3H), 3.0-3.2 (m, 2H), 3.4 (t, 2H), 3.6-3.7 (m, 2H), 4.35 (t, 2H), 6.2 (s, 1H), 6.95 (dd, 1H), 7.3 (s, 1H), 7.35 (d, 1H), 7.5 (s, 1H), 7.57 (dd, 1H), 8.5 (d, 1H), 9.15 (s, 1H)

MS-ESI: 403 [MH]$^+$

The starting material was prepared as follows:

Sodium (368 mg, 16 mmol) was added to benzyl alcohol (10 ml, 96 mmol) and the mixture was heated at 148° C. for 30 minutes. 7-Fluoro-3,4-dihydroquinazolin-4-one (656 mg, 4 mmol), (J. Chem. Soc. section B 1967, 449), was added and the mixture maintained at 148° C. for 24 hours. The reaction mixture was allowed to cool, the solution was poured on to water (170 ml) and the aqueous mixture adjusted to pH3 with concentrated hydrochloric acid. The precipitate was collected by filtration, washed with water, ether and dried under vacuum to give 7-benzyloxy-3,4-dihydroquinazolin-4-one (890 mg, 89%) as a white solid.

m.p. 267-269° C.

$^1$H NMR Spectrum: (DMSO-d$_6$; CF$_3$COOD) 5.32(s, 2H); 7.25(d, 1H); 7.32-7.52(m, 6H); 8.12(d, 1H); 8.99(s, 1H)

MS-ESI: 252 [MH]$^+$

| Elemental analysis: | Found | C 71.4 | H 4.9 | N 10.7 |
|---|---|---|---|---|
| $C_{15}H_{12}N_2O_2$ 0.04H$_2$O | Requires | C 71.2 | H 4.8 | N 11.1% |

A mixture of 7-benzyloxy-3,4-dihydroquinazolin-4-one (11 g, 43.6 mmol) and DMF (1 ml) in thionyl chloride (100 ml) was heated at reflux for 1.5 hours. Excess thionyl chloride was removed by evaporation and the residue azeotroped with toluene. The residue was partitioned between methylene chloride and water and saturated aqueous sodium hydrogen carbonate was added until the aqueous layer was at about pH9. The organic layer was separated, washed with water, brine, dried (MgSO$_4$) and evaporated to give 7-benzyloxy-4-chloroquinazoline (10.5 g, 89%).

$^1$H NMR Spectrum: (DMSO-d$_6$) 5.4 (s, 2H); 7.35-7.65 (m, 6H); 8.2 (d, 1H); 9.0 (s, 1H)

MS-ESI: 270 [MH]$^+$

A solution of 7-benzyloxy-4-chloroquinazoline (2 g, 7.4 mmol), 5-hydroxy-2-methylindole (1.3 g, 8.9 mmol), (prepared as described for the starting material in Example 48), in DMF (20 ml) containing potassium carbonate (1.53 g, 11.1 mmol) was stirred at 80° C. for 3 hours. After cooling, the mixture was poured in portions into ice/water. The precipitate was filtered and washed with water and dried under vacuum. The solid was dissolved in methylene chloride and was purified by column chromatography eluting with ethyl acetate and methylene chloride (1/1) to give 7-benzyloxy-4-(2-methylindol-5-yloxy)quinazoline (2.28 g, 81%).

MS-ESI: 382 [MH]$^+$.

$^1$H NMR Spectrum: (DMSOd$_6$) 2.41 (s, 3H), 5.4 (s, 2H), 6.15 (s, 1H), 6.9 (dd, 1H), 7.3 (s, 1H), 7.35 (d, 1H), 7.4 (d, 1H), 7.4-7.5 (m, 4H), 7.55 (d, 2H), 8.32 (d, 1H), 8.6 (s, 1H).

10% Palladium on charcoal (200 mg) followed by ammonium formate (4.34 g, 69 mmol) were added to a solution of 7-benzyloxy-4-(2-methylindol-5-yloxy)quinazoline (1.75 g, 4.58 mmol) in DMF (60 ml). After stirring for 1 hour at ambient temperature, the mixture was filtered. The filtrate was evaporated. The residue was triturated with water, filtered, washed with ethyl acetate, and dried under vacuum to give 7-hydroxy-4-(2-methylindol-5-yloxy)quinazoline (1.24 g, 93%).

$^1$H NMR Spectrum: (DMSOd$_6$) 2.4 (s, 3H), 6.14 (s, 1H), 6.88 (dd, 1H), 7.17 (s, 1H), 7.25-7.3 (m, 2H), 7.30 (d, 1H), 8.24 (d, 1H), 8.5 (s, 1H)

EXAMPLES 83-89

Using an analogous procedure to that described in Example 82, the appropriate alcohols were reacted with 7-hydroxy-4-(2-methylindol-5-yloxy)quinazoline, (prepared as described for the starting material in Example 82), to give the compounds described in Table VI below.

TABLE VI

| Example number | Weight (mg) | Yield % | MS-ESI [MH]+ | R | Note |
|---|---|---|---|---|---|
| 83 | 34 | 24 | 412 | methylsulphonylpropoxy | a |
| 84 | 45 | 32 | 405 | morpholinoethoxy | b |
| 85 | 5 | 3 | 417 | piperidinopropoxy | c |
| 86 | 56 | 35 | 467 | (1,1-dioxothiomorpholino)ethoxy | d |
| 87 | 63 | 44 | 419 | morpholinoethoxy | e |
| 88 | 24 | 17 | 403 | piperidinoethoxy | f |
| 89 | 84 | 63 | 387 | imidazolylethoxy | g | a) 7-Hydroxy-4-(2-methylindol-5-yloxy)quinazoline (100 mg) was reacted with 3-(methylsulphonyl)-1-propanol (95 mg), (prepared as described for the starting material in Example 50), to give 7-(3-(methylsulphonyl)propoxy)-4-(2-methylindol-5-yloxy)quinazoline.

$^1$H NMR Spectrum: (DMSOd$_6$, CF$_3$COOD) 2.2-2.3 (m, 2H), 2.4 (s, 3H), 3.05 (s, 3H), 3.3-3.45 (m, 2H), 4.4 (t, 2H), 6.2 (s, 1H), 6.95 (dd, 1H), 7.38 (s, 1H), 7.4 (d, 1H), 7.5 (s, 1H), 7.6 (dd, 1H), 8.5 (d, 1H), 9.2 (s, 1H)

| Elemental analysis | Found | C 60.2 | H 5.3 | N 10.6 |
|---|---|---|---|---|
| C$_{21}$H$_{21}$N$_3$O$_4$S 0.4 DMF | Requires | C 60.5 | H 5.4 | N 10.8% | b) 7-Hydroxy-4-(2-methylindol-5-yloxy)quinazoline (100 mg) was reacted with 4-(2-hydroxyethyl)morpholine (90 mg) to give 4-(2-methylindol-5-yloxy)-7-(2-morpholinoethoxy)quinazoline.

$^1$H NMR Spectrum: (DMSOd$_6$, CF$_3$COOD) 2.4 (s, 3H), 3.1-3.3 (m, 2H), 3.62 (d, 2H), 3.7-3.9 (m, 4H), 4.05 (d, 2H), 4.7 (t, 2H), 6.2 (s, 0.5 H, partially exchanged), 6.95 (dd, 1H), 7.35 (s, 1H), 7.39 (d, 1H), 7.6 (s, 1H), 7.65 (dd, 1H), 8.55 (d, 1H), 9.15 (s, 1H)

| Elemental analysis | Found | C 67.2 | H 6.0 | N 13.5 |
|---|---|---|---|---|
| C$_{23}$H$_{24}$N$_4$O$_3$ 0.3 H$_2$O | Requires | C 67.4 | H 6.1 | N 13.7% | c) 7-Hydroxy-4-(2-methylindol-5-yloxy)quinazoline (100 mg) was reacted with 1-(3-hydroxypropyl)piperidine (98 mg) to give 4-(2-methylindol-5-yloxy)-7-(3-(piperidin-1-yl)propoxy)quinazoline.

$^1$H NMR Spectrum: (DMSOd$_6$, CF$_3$COOD) 1.2-1.5 (m, 2H), 1.6-1.8 (m, 2H), 1.8-1.9 (m, 2H), 2.25-2.35 (m, 2H), 2.45 (s, 3H), 2.95 (t, 2H), 3.25-3.3 (m, 2H), 3.55 (d, 2H), 4.4 (t, 2H), 6.95 (dd, 1H), 7.4 (s, 1H), 7.45 (d, 1H), 7.5 (s, 1H), 7.6 (d, 1H), 8.55 (d, 1H), 9.15 (s, 1H)

d) 7-Hydroxy-4-(2-methylindol-5-yloxy)quinazoline (100 mg) was reacted with 3-(1,1-dioxothiomorpholino)-1-propanol (133 mg), (prepared as described for the starting material in Example 5), to give 4-(2-methylindol-5-yloxy)-7-(3-(1,1-dioxothiomorpholino)propoxy)quinazoline.

$^1$H NMR Spectrum: (DMSOd$_6$) 1.9-2.0 (m, 2H), 2.4 (s, 3H), 1.6-1.7 (m, 2H), 2.9 (br s, 4H), 3.1 (br s, 4H), 4.25 (t, 2H), 6.12 (s, 1H), 6.85 (d, 1H), 7.22 (s, 1H), 7.3 (d, 1H), 7.3-7.4 (m, 2H), 8.25 (d, 1H), 8.55 (s, 1H)

e) 7-Hydroxy-4-(2-methylindol-5-yloxy)quinazoline (100 mg) was reacted with 4-(3-hydroxypropyl)morpholine (100 mg), (prepared as described for the starting material in Example 60), to give 4-(2-methylindol-5-yloxy)-7-(3-morpholinopropoxy)quinazoline.

$^1$H NMR Spectrum: (DMSOd$_6$) 1.95-2.05 (m, 2H), 2.42 (s, 3H), 2.5 (t, 2H), 2.55 (t, 4H), 3.6 (t, 4H), 4.3 (t, 2H), 6.18 (s, 1H), 6.9 (dd, 1H), 7.3 (s, 1H), 7.35 (d, 1H), 7.3-7.4 (m, 2H), 8.3 (d, 1H), 8.6 (s, 1H)

| Elemental analysis | Found | C 66.5 | H 6.2 | N 12.7 |
|---|---|---|---|---|
| C$_{24}$H$_{26}$N$_4$O$_3$ 0.14 CH$_2$Cl$_2$ 0.7 H$_2$O | Requires | C 66.7 | H 6.4 | N 13.0% | f) 7-Hydroxy-4-(2-methylindol-5-yloxy)quinazoline (100 mg) was reacted with 1-(2-hydroxyethyl)piperidine (89 mg) to give 4-(2-methylindol-5-yloxy)-7-(2-(piperidin-1-yl)ethoxy)quinazoline.

$^1$H NMR Spectrum: (DMSOd$_6$) 1.4-1.5 (br s, 2H), 1.5-1.7 (br s, 4H), 2.42 (s, 3H), 2.5-2.7 (br s, 4H), 2.8-3.0 (br s, 2H), 4.35 (br s, 2H), 6.18 (s, 1H), 6.9 (dd, 1H), 7.3 (s, 1H), 7.35 (d, 1H), 7.4 (d, 1H), 7.42 (s, 1H), 8.3 (d, 1H), 8.6 (s, 1H)

| Elemental analysis | Found | C 69.0 | H 6.6 | N 13.4 |
|---|---|---|---|---|
| C$_{24}$H$_{26}$N$_4$O$_2$ 0.8 H$_2$O | Requires | C 69.1 | H 6.7 | N 13.4% | g) 7-Hydroxy-4-(2-methylindol-5-yloxy)quinazoline (100 mg) was reacted with 2-(1H-1,2,4-triazol-1-yl)ethanol (78 mg), (Ann. Phar. Fr. 1977, 35, 503-508), to give 4-(2-methylindol-5-yloxy)-7-(2-(1H-1,2,4-triazol-1-yl)ethoxy)quinazoline.

$^1$H NMR Spectrum: (DMSOd$_6$) 2.4 (s, 3H), 4.6 (m, 2H), 4.7 (m, 2H), 6.15 (s, 1H), 6.9 (dd, 1H), 7.28 (s, 1H), 7.3 (d, 2H), 7.4 (s, 1H), 8.02 (s, 1H), 8.3 (d, 1H), 8.6 (s, 1H), 8.65 (s, 1H)

| Elemental analysis | Found | C 63.7 | H 4.8 | N 21.5 |
|---|---|---|---|---|
| C$_{21}$H$_{18}$N$_6$O$_2$ 0.5 H$_2$O | Requires | C 63.8 | H 4.8 | N 21.3% |

EXAMPLE 90

A solution of 7-hydroxy-4-(2-methylindol-5-yloxy)quinazoline (423 mg, 1.45 mol), (prepared as described for the starting material in Example 82), triphenylphosphine (685 mg, 2.61 mmol), 4-hydroxymethyl-1-tert-butoxycarbonylpiperidine (500 mg, 2.32 mmol), (prepared as described for the starting material in Example 10), and diisopropyl azodicarboxylate (528 mg, 2.61 mmol) in methylene chloride (18 ml) was stirred overnight at ambient temperature. The mixture was then poured onto a column of silica and eluted with ethyl acetate. After evaporation of the solvent, the residue was triturated with ether, filtered, and dried under vacuum to give 7-(1-tert-butoxycarbonylpiperidin-4-ylmethoxy)-4-(2-methylindol-5-yloxy)quinazoline (478 mg, 68%).

$^1$H NMR Spectrum: (DMSOd$_6$) 1.3-1.4 (m, 2H), 1.42 (s, 9H), 1.85 (d, 2H), 2.0-2.1 (m, 1H), 2.42 (s, 3H), 2.7-2.9 (br s, 2H), 3.95-4.05 (m, 2H), 4.1 (d, 2H), 6.15 (s, 1H), 6.9 (dd, 1H), 7.3 (s, 1H), 7.33 (d, 1H), 7.38 (s, 1H), 7.35-7.4 (m, 1H), 8.3 (d, 1H), 8.6 (s, 1H)

MS-ESI: 489 [MH]$^+$

| Elemental analysis | Found | C 68.7 | H 6.7 | N 11.3 |
|---|---|---|---|---|
| C$_{28}$H$_{32}$N$_4$O$_4$ | Requires | C 68.8 | H 6.6 | N 11.5% |

EXAMPLE 91

To a suspension of 4-(2,3-dimethylindol-5-yloxy)-7-hydroxy-6-methoxyquinazoline (124 mg, 0.32 mmol) in methylene chloride (2.5 ml) was added triphenylphosphine (179 mg, 0.628 mmol), 1-(2-hydroxyethyl)pyrrolidine (75 mg, 0.65 mmol) followed by diisopropyl azodicarboxylate (134 µl, 0.68 mmol) in portions. After stirring overnight at ambient temperature the mixture was poured onto a column of silica and eluted with ethyl acetate/methylene chloride (1/1) followed by ethyl acetate/methylene chloride/methanol (4/5/1) followed by methylene chloride/methanol (9/1). After removal of the solvent, the solid was triturated with ether, filtered, washed with ether and dried under vacuum to give 4-(2,3-dimethylindol-5-yloxy)-6-methoxy-7-(2-(pyrrolidin-1-yl)ethoxy)quinazoline (51 mg, 37%).

$^1$H NMR Spectrum: (DMSOd$_6$) 1.6-1.75 (m, 4H), 2.12 (s, 3H), 2.28 (s, 3H), 2.52 (br s, 4H), 3.85 (t, 2H), 3.93 (s, 3H), 4.25 (t, 2H), 6.8 (d, 1H), 7.17 (s, 1H), 7.22 (d, 1H), 7.33 (s, 1H), 7.54 (s, 1H), 8.43 (s, 1H)

The starting material was prepared as follows:

To a solution of 2,3-dimethyl-5-methoxyindole (175 mg, 1 mmol), (J. Chem. Soc. 1957, 3175-3180) in methylene (5 ml) cooled at −60° C. was added boron tribromide (210 µl, 2.2 mmol) dropwise. After completion of addition, the mixture was left to warm up to ambient temperature and was stirred for 1 hour. Water was added and the pH was adjusted to 6 with 2N sodium hydroxide. The mixture was extracted with ethyl acetate and the organic layer was separated, washed with brine, dried (MgSO$_4$) and evaporated to give 2,3-dimethyl-5-hydroxyindole (124 mg, 77%).

$^1$H NMR Spectrum: (DMSOd$_6$) 2.1 (s, 3H); 2.3 (s, 3H); 6.5 (dd, 1H); 6.65 (d, 1H); 7.0 (d, 1H); 8.45 (s, 1H)

Under nitrogen, to a solution of 2,3-dimethyl-5-hydroxyindole (643 mg, 4 mmol), in DMF (10 ml) was added potassium carbonate (690 mg, 5 mmol). After stirring for 15 minutes at ambient temperature, 7-benzyloxy-4-chloro-6-methoxyquinazoline (1 g, 3.33 mmol), (prepared as described for the starting material in Example 1), was added. The mixture was heated at 90° C. for 2 hours followed by 30 minutes at 95° C. After cooling, the mixture was poured onto water (100 ml) cooled at 5° C. The precipitate was filtered, washed with water, followed by ether and dried under vacuum to give 7-benzyloxy-4-(2,3-dimethylindol-5-yloxy)-6-methoxyquinazoline (1.4 g, 95%).

$^1$H NMR Spectrum: (DMSOd$_6$) 2.15 (s, 3H); 2.35 (s, 3H); 4.02 (s, 3H); 5.4 (s, 2H); 6.9 (dd, 1H); 7.22 (d, 1H); 7.3 (d, 1H); 7.35-7.6 (m, 6H); 7.65 (s, 1H); 8.5 (s, 1H)

A solution of 7-benzyloxy-4-(2,3-dimethylindol-5-yloxy)-6-methoxyquinazoline (2 g, 4.7 mmol) in DMF (120 ml) containing ammonium formate (11 gr, 174 mmol) and 10% palladium on charcoal (200 mg) was stirred for 2.5 hours at ambient temperature. The mixture was filtered, and the filtrate was evaporated under vacuum. The residue was triturated with ether and the solid was filtered, washed with water followed by ether and dried under vacuum at 50° C. to give 4-(2,3-dimethylindol-5-yloxy)-7-hydroxy-6-methoxyquinazoline (1.1 g, 69%).

$^1$H NMR Spectrum: (DMSOd$_6$) 2.1 (s, 3H); 2.32 (s, 3H); 3.97 (s, 3H); 7.85 (dd, 1H); 7.2 (bs, 2H); 7.25 (d, 1H); 7.58 (s, 1H); 8.4 (s, 1H)

EXAMPLES 92-106

Using an analogous procedure to that described in Example 91, the appropriate alcohol was reacted with 4-(2,3-dimethylindol-5-yloxy)-7-hydroxy-6-methoxyquinazoline, (prepared as described for the starting material in Example 91), to give the compounds described in the Table VII below.

TABLE VII

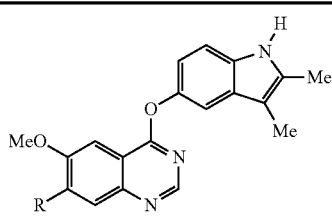

| Example number | Weight (mg) | Yield % | MS-ESI [MH]$^+$ | R | HPLC* RT (min) | Note |
|---|---|---|---|---|---|---|
| 92 | 91 | 65 | 431 | 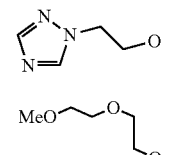 | — | a |
| 93 | 78 | 55 | 438 | MeO⌒O⌒⌒O | — | b |
| 94 | 34 | 27 | 435 | 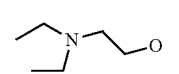 | — | c |

TABLE VII-continued

| Example number | Weight (mg) | Yield % | MS-ESI [MH]+ | R | HPLC* RT (min) | Note |
|---|---|---|---|---|---|---|
| 95 | 39 | 33 | 407 | | — | d |
| 96 | 58 | 44 | 449 | | — | e |
| 97 | 58 | 47 | 421 | | — | f |
| 98 | 85 | 66 | 447 | | — | g |
| 99 | 24 | 18 | 447 | | — | h |
| 100 | 110 | 82 | 461 | | — | i |
| 101 | 9 | 7 | 447 | | — | j |
| 102 | 81 | 62 | 463 | | 3.4 | k |
| 103 | 75 | 57 | 451 | | — | l |
| 104 | 96 | 65 | 511 | | — | m |
| 105 | 103 | 78 | 457 | | — | n |
| 106 | 64 | 49 | 456 | | — | o |

*HPLC conditions 2) as described hereinbefore.

a) 4-(2,3-Dimethylindol-5-yloxy)-7-hydroxy-6-methoxyquinazoline (124 mg) was reacted with 2-(1H-1,2,4-triazol-1-yl)ethanol (74 mg), (Ann. Phar. Fr. 1977, 35, 503-508), to give 4-(2,3-dimethylindol-5-yloxy)-6-methoxy-7-(2-(1H-1,2,4-triazol-1-yl)ethoxy)quinazoline.
$^1$H NMR Spectrum: (DMSOd$_6$) 2.10 (s, 3H), 2.30 (s, 3H), 3.93 (s, 3H), 4.52 (m, 2H), 4.55-4.65 (m, 2H), 6.85 (d, 1H), 7.2 (s, 1H), 7.25 (d, 1H), 7.4 (d, 1H), 7.58 (s, 1H), 8.0 (s, 1H), 8.48 (s, 1H), 8.58 (s, 1H)

b) 4-(2,3-Dimethylindol-5-yloxy)-7-hydroxy-6-methoxyquinazoline (124 mg) was reacted with 2-(2-methoxyethoxy)ethanol (78 mg) to give 4-(2,3-dimethylindol-5-yloxy)-6-methoxy-7-(2-(2-methoxyethoxy)ethoxy)quinazoline.
$^1$H NMR Spectrum: (DMSOd$_6$) 2.14 (s, 3H), 2.35 (s, 3H), 3.3 (s, 3H), 3.5 (t, 2H), 3.65 (t, 2H), 3.85 (t, 2H), 4.0 (s, 3H), 4.32 (t, 2H), 6.9 (d, 1H), 7.25 (d, 1H), 7.28 (d, 1H), 7.4 (s, 1H), 7.6 (s, 1H), 8.5 (s, 1H)

c) 4-(2,3-Dimethylindol-5-yloxy)-7-hydroxy-6-methoxyquinazoline (97 mg) was reacted with N,N-diethylethanolamine (68 mg) to give 7-(2-(N,N-diethylamino)ethoxy)-4-(2,3-dimethylindol-5-yloxy)-6-methoxyquinazoline.
$^1$H NMR Spectrum: (DMSOd$_6$) 1.05 (t, 6H), 2.15 (s, 3H), 2.35 (s, 3H), 2.6-2.7 (m, 4H), 2.92 (br s, 2H), 4.0 (s, 3H), 4.25 (t, 2H), 6.9 (dd, 1H), 7.25 (s, 1H), 7.3 (d, 1H), 7.4 (s, 1H), 7.6 (s, 1H), 8.5 (s, 1H)

d) 4-(2,3-Dimethylindol-5-yloxy)-7-hydroxy-6-methoxyquinazoline (97 mg) was reacted with N,N-dimethylethanolamine (52 mg) to give 7-(2-(N,N-dimethylamino)ethoxy)-4-(2,3-dimethylindol-5-yloxy)-6-methoxyquinazoline.
$^1$H NMR Spectrum: (DMSOd$_6$) 2.15 (s, 3H), 2.35 (s, 9H), 2.85 (br s, 2H), 4.0 (s, 3H), 4.35 (t, 2H), 6.87 (dd, 1H), 7.22 (s, 1H), 7.3 (d, 1H), 7.42 (s, 1H), 7.6 (s, 1H), 8.5 (s, 1H)

e) 4-(2,3-Dimethylindol-5-yloxy)-7-hydroxy-6-methoxyquinazoline (97 mg) was reacted with 4-(2-hydroxyethyl)morpholine (59 mg) to give 4-(2,3-dimethylindol-5-yloxy)-6-methoxy-7-(2-morpholinoethoxy)quinazoline.
$^1$H NMR Spectrum: (DMSOd$_6$) 2.15 (s, 3H), 2.35 (s, 3H), 3.25-3.4 (m, 2H), 3.65 (d, 2H), 3.7-3.8 (m, 4H), 4.0-4.1 (m, 2H), 4.1 (s, 3H), 4.7 (t, 2H), 6.95 (dd, 1H), 7.3 (s, 1H), 7.35 (d, 1H), 7.6 (s, 1H), 7.8 (s, 1H), 9.0 (s, 1H)

f) 4-(2,3-Dimethylindol-5-yloxy)-7-hydroxy-6-methoxyquinazoline (97 mg) was reacted with 3-(N,N-dimethylamino)propan-1-ol (60 mg) to give 7-(3-(N,N-dimethylamino)propoxy)-4-(2,3-dimethylindol-5-yloxy)-6-methoxyquinazoline.
$^1$H NMR Spectrum: (DMSOd$_6$) 1.95-2.05 (m, 2H), 2.15 (s, 3H), 2.2 (s, 6H), 2.35 (s, 3H), 2.45 (t, 2H), 4.0 (s, 3H), 4.25 (t, 2H), 6.9 (dd, 1H), 7.22 (d, 1H), 7.3 (d, 1H), 7.37 (s, 1H), 7.6 (s, 1H), 8.5 (s, 1H)

g) 4-(2,3-Dimethylindol-5-yloxy)-7-hydroxy-6-methoxyquinazoline (97 mg) was reacted with 1-(2-hydroxyethyl)-2-pyrrolidinone (75 mg) to give 4-(2,3-dimethylindol-5-yloxy)-6-methoxy-7-(2-(2-oxopyrrolidin-1-yl)ethoxy)quinazoline.
$^1$H NMR Spectrum: (DMSOd$_6$) 1.9-2.05 (m, 4H), 2.15 (s, 3H), 2.25 (t, 2H), 2.35 (s, 3H), 3.65 (t, 2H), 4.0 (s, 3H), 4.35 (t, 2H), 6.9 (d, 1H), 7.25 (s, 1H), 7.3 (d, 1H), 7.45 (s, 1H), 7.62 (s, 1H), 8.5 (s, 1H)

h) 4-(2,3-Dimethylindol-5-yloxy)-7-hydroxy-6-methoxyquinazoline (97 mg) was reacted with 2-(2-hydroxyethyl)piperidine (75 mg) to give 4-(2,3-dimethylindol-5-yloxy)-6-methoxy-7-(2-(piperidin-2-yl)ethoxy)quinazoline.
$^1$H NMR Spectrum: (DMSOd$_6$) 1.0-1.15 (m, 1H), 1.25-1.4 (m, 2H), 1.5 (br s, 1H), 1.65 (d, 1H), 1.7-1.8 (m, 1H), 1.8-1.9

(m, 2H), 2.15 (s, 3H), 2.35 (s, 3H), 2.5 (d, 1H), 2.6-2.7 (m, 1H), 2.9-3.0 (m, 1H), 4.0 (s, 3H), 4.2-4.35 (m, 2H), 6.88 (dd, 1H), 7.2 (s, 1H), 7.27 (d, 1H), 7.4 (s, 1H), 7.6 (s, 1H), 8.5 (s, 1H)

i) 4-(2,3-Dimethylindol-5-yloxy)-7-hydroxy-6-methoxyquinazoline (97 mg) was reacted with 1-(2-hydroxyethyl)pyrrolidin-2,5-dione (83 mg) to give 4-(2,3-dimethylindol-5-yloxy)-7-(2-(2,5-dioxopyrrolidin-1-yl)ethoxy)-6-methoxyquinazoline.

$^1$H NMR Spectrum: (DMSOd$_6$) 2.12 (s, 3H), 2.35 (s, 3H), 2.68 (s, 4H), 3.85 (t, 2H), 3.95 (s, 3H), 4.35 (t, 2H), 6.88 (dd, 1H), 7.22 (s, 1H), 7.25 (d, 1H), 7.4 (s, 1H), 7.6 (s, 1H), 8.5 (s, 1H)

j) 4-(2,3-Dimethylindol-5-yloxy)-7-hydroxy-6-methoxyquinazoline (97 mg) was reacted with 1-methyl-3-piperidinemethanol (75 mg) to give 4-(2,3-dimethylindol-5-yloxy)-6-methoxy-7-(1-methylpiperidin-3-ylmethoxy)quinazoline.

k) 4-(2,3-Dimethylindol-5-yloxy)-7-hydroxy-6-methoxyquinazoline (97 mg) was reacted with 4-(3-hydroxypropyl)morpholine (75 mg), (prepared as described for the starting material in Example 60), to give 4-(2,3-dimethylindol-5-yloxy)-6-methoxy-7-(3-morpholinopropoxy)quinazoline.

$^1$H NMR Spectrum: (DMSOd$_6$) 1.95-2.05 (m, 2H), 2.15 (s, 3H), 2.35 (s, 3H), 2.42 (hr s, 4H), 2.5 (t, 2H), 3.6 (m, 4H), 4.0 (s, 3H), 4.25 (t, 2H), 6.85 (dd, 1H), 7.25 (s, 1H), 7.3 (d, 1H), 7.4 (s, 1H), 7.6 (s, 1H), 8.5 (s, 1H).

l) 4-(2,3-Dimethylindol-5-yloxy)-7-hydroxy-6-methoxyquinazoline (97 mg) was reacted with 2-(N-(2-methoxyethyl)-N-methylamino)ethanol (77 mg), (prepared as described for the starting material in Example 59), to give 4-(2,3-dimethylindol-5-yloxy)-6-methoxy-7-(2-(N-(2-methoxyethyl)-N-methylamino)ethoxy)quinazoline.

$^1$H NMR Spectrum: (DMSOd$_6$) 2.15 (s, 3H), 2.35 (s, 6H), 2.65 (t, 2H), 2.9 (t, 2H), 3.25 (s, 3H), 3.45 (t, 2H), 4.0 (s, 3H), 4.3 (t, 2H), 6.9 (dd, 1H), 7.22 (s, 1H), 7.3 (d, 1H), 7.4 (s, 1H), 7.6 (s, 1H), 8.5 (s, 1H)

m) 4-(2,3-Dimethylindol-5-yloxy)-7-hydroxy-6-methoxyquinazoline (97 mg) was reacted with 3-(1,1-dioxothiomorpholino)-1-propanol (112 mg), (prepared as described for the starting material in Example 5), to give 4-(2,3-dimethylindol-5-yloxy)-7-(3-(1,1-dioxothiomorpholino)propoxy)-6-methoxyquin azoline.

$^1$H NMR Spectrum: (DMSOd$_6$) 1.95-2.05 (m, 2H), 2.15 (s, 3H), 2.35 (s, 3H), 2.7 (t, 2H), 2.95 (br s, 4H), 3.15 (br s, 4H), 4.0 (s, 3H), 4.29 (t, 2H), 6.9 (dd, 1H), 7.25 (s, 1H), 7.3 (d, 1H), 7.4 (s, 1H), 7.61 (s, 1H), 8.5 (s, 1H)

n) 4-(2,3-Dimethylindol-5-yloxy)-7-hydroxy-6-methoxyquinazoline (97 mg) was reacted with 2-(4-pyridyloxy)ethanol (81 mg), (J. Chem. Soc. Perkin Trans 2, 1987, 12, 1867), to give 4-(2,3-dimethylindol-5-yloxy)-6-methoxy-7-(2-(4-pyridyloxy)ethoxy)quinazoline.

$^1$H NMR Spectrum: (DMSOd$_6$) 2.15 (s, 3H), 2.35 (s, 3H), 4.0 (s, 3H), 4.55 (m, 2H), 4.6 (m, 2H), 6.88 (dd, 1H), 7.08 (d, 2H), 7.22 (s, 1H), 7.28 (d, 1H), 7.48 (s, 1H), 7.6 (s, 1H), 8.42 (d, 2H), 8.5 (s, 1H), 10.78 (s, 1H)

o) 4-(2,3-Dimethylindol-5-yloxy)-7-hydroxy-6-methoxyquinazoline (97 mg) was reacted with 3-(methylsulphonyl)-1-propanol (80 mg), (prepared as described for the starting material in Example 50), to give 4-(2,3-dimethylindol-5-yloxy)-6-methoxy-7-(3-methylsulphonylpropoxy)quinazoline.

$^1$H NMR Spectrum: (DMSOd$_6$) 1.8-1.9 (m, 2H), 2.15 (s, 3H), 2.25-2.35 (m, 2H), 2.35 (s, 3H), 3.0 (s, 3H), 4.02 (s, 3H), 4.35 (t, 2H), 6.9 (dd, 1H), 7.25 (s, 1H), 7.3 (d, 1H), 7.4 (s, 1H), 7.7 (s, 1H), 8.52 (s, 1H)

EXAMPLE 107

Using an analogous procedure to that described in Example 91, 7-hydroxy-4-(indol-5-yloxy)-6-methoxyquinazoline (89 mg) was reacted with 2-(2-methoxyethoxy)ethanol (70 mg) to give 4-(indol-5-yloxy)-6-methoxy-7-(2-(2-methoxyethoxy)ethoxy)quinazoline (50 mg, 42%).

$^1$H NMR Spectrum: (DMSOd$_6$) 3.3 (s, 3H), 3.5 (m, 2H), 3.65 (m, 2H), 3.85 (m, 2H), 4.02 (s, 3H), 4.35 (t, 2H), 6.58 (s, 1H), 7.0 (dd, 1H), 7.4 (s, 1H), 7.45 (br s, 2H), 7.47 (d, 1H), 7.61 (s, 1H), 8.5 (s, 1H)

MS-ESI: 410 [MH]$^+$

The starting material was prepared as follows:

A mixture of 7-benzyloxy-4-chloro-6-methoxyquinazoline (3 g, 10 mmol), (prepared as described for the starting material in Example 1), 5-hydroxyindole (1.46 g, 11 mmol) in DMF (30 ml) containing potassium carbonate (2.75 g, 20 mmol) was heated at 95° C. for 2 hours. After cooling the mixture was poured onto water (100 ml). The precipitate was filtered, washed with water and dried under vacuum at 50° C. over phosphorus pentoxide. The solid was triturated with ether, filtered, washed with ether and dried under vacuum to give 7-benzyloxy-4-(indol-5-yloxy)-6-methoxyquinazoline (3.5 g, 88%).

$^1$H NMR Spectrum: (DMSOd$_6$) 4.02 (s, 3H), 5.4 (s, 2H), 6.5 (s, 1H), 7.0 (dd, 1H), 7.4-7.6 (m, 9H), 7.65 (s, 1H), 8.5 (s, 1H), 11.23 (s, 1H)

MS-ESI: 398 [MH]$^+$

A solution of 7-benzyloxy-4-(indol-5-yloxy)-6-methoxyquinazoline (8 g, 20 mmol) in DMF (50 ml) and methylene chloride (100 ml) containing 10% palladium on charcoal (2g) was hydrogenated at 1.8 atmospheres pressure until uptake of hydrogen had ceased. The solution was filtered, the catalyst was washed with DMF and the filtrate was evaporated. The residue was purified by column chromatography eluting with methylene chloride, followed by methylene chloride/methanol (95/5 and 90/10). After evaporation of the solvent, the residue was triturated with ether, filtered and dried under vacuum to give 7-hydroxy-4-(indol-5-yloxy)-6-methoxyquinazoline (2.7 g; 44%).

$^1$H NMR Spectrum: (DMSOd$_6$) 4.0 (s, 3H), 6.46 (s, 1H), 7.01 (dd, 1H), 7.2 (s, 1H), 7.4-7.5 (m, 3H), 7.6 (s, 1H), 8.41 (s, 1H)

EXAMPLES 108-118

Using an analogous procedure to that described in Example 107, the appropriate alcohol was reacted with 7-hydroxy-4-(indol-5-yloxy)-6-methoxyquinazoline, (prepared as described for the starting material in Example 107), to give the compounds described in the Table VIII below.

TABLE VIII

| Example number | Weight (mg) | Yield % | MS-ESI [MH]+ | R | Note |
|---|---|---|---|---|---|
| 108 | 58 | 49 | 407 | (CH3CH2)2N-CH2CH2-O- | r |
| 109 | 14 | 13 | 379 | (CH3)2N-CH2CH2-O- | s |
| 110 | 55 | 48 | 393 | (CH3)2N-CH2CH2CH2-O- | t |
| 111 | 27 | 23 | 405 | (2S)-1-methylpyrrolidin-2-yl-CH2-O- | u |
| 112 | 58 | 47 | 421 | (CH3CH2)2N-CH2CH2CH2-O- | v |
| 113 | 63 | 52 | 419 | piperidin-2-yl-CH2CH2-O- | w |
| 114 | 64 | 53 | 419 | piperidin-1-yl-CH2CH2-O- | x |
| 115 | 106 | 84 | 435 | morpholino-CH2CH2CH2-O- | y |
| 116 | 76 | 62 | 423 | MeO-CH2CH2-N(CH3)-CH2CH2-O- | z |
| 117 | 113 | 81 | 483 | 1,1-dioxothiomorpholino-CH2CH2CH2-O- | aa |
| 118 | 24 | 19 | 429 | pyridin-4-yloxy-CH2CH2-O- | bb | r) 7-Hydroxy-4-(indol-5-yloxy)-6-methoxyquinazoline (89 mg) was reacted with N,N-diethylethanolamine (68 mg) to give 7-(2-(N,N-diethylamino)ethoxy)-4-(indol-5-yloxy)-6-methoxyquinazoline.

s) 7-Hydroxy-4-(indol-5-yloxy)-6-methoxyquinazoline (89 mg was reacted with N,N-dimethylethanolamine (52 mg) to give 7-(2-(N,N-dimethylamino)ethoxy)-4-(indol-5-yloxy)-6-methoxyquinazoline.

$^1$H NMR Spectrum: (DMSOd$_6$) 2.3 (s, 6H), 2.8 (t, 2H), 4.0 (s, 3H), 4.3 (t, 2H), 6.45 (s, 1H), 7.0 (dd, 1H), 7.4-7.5 (m, 4H), 7.6 (s, 1H), 8.5 (s, 1H)

t) 7-Hydroxy-4-(indol-5-yloxy)-6-methoxyquinazoline (89 mg) was reacted with 3-(N,N-dimethylamino)propan-1-ol (60 mg) to give 7-(3-(N,N-dimethylamino)propoxy)-4-(indol-5-yloxy)-6-methoxyquinazoline.

$^1$H NMR Spectrum: (DMSOd$_6$) 1.9-2.05 (m, 2H), 2.21 (s, 6H), 2.45 (t, 2H), 4.02 (s, 3H), 4.25 (t, 2H), 6.47 (s, 1H), 7.0 (dd, 1H), 7.38 (s, 1H), 7.35-7.4 (m, 2H), 7.45 (d, 1H), 7.6 (s, 1H), 8.5 (s, 1H)

u) 7-Hydroxy-4-(indol-5-yloxy)-6-methoxyquinazoline (89 mg) was reacted with (2S)-2-(hydroxymethyl)-1-methylpyrrolidine (67 mg) to give (2S)-4-(indol-5-yloxy)-6-methoxy-7-(1-methylpyrrolidin-2-yl)quinazoline.

v) 7-Hydroxy-4-(indol-5-yloxy)-6-methoxyquinazoline (89 mg) was reacted with 3-(N,N-diethylamino)-1-propanol (76 mg) to give 7-(3-(N,N-diethylamino)propoxy)-4-(indol-5-yloxy)-6-methoxyquinazoline.

$^1$H NMR Spectrum: (DMSOd$_6$) 0.95 (t, 6H), 1.9-2.0 (m, 2H), 2.5 (m, 4H), 2.6 (t, 2H), 4.0 (s, 3H), 4.25 (t, 2H), 6.48 (s, 1H), 7.0 (dd, 1H), 7.38 (s, 1H), 7.42-7.5 (m, 3H), 7.6 (s, 1H), 8.5 (s, 1H)

w) 7-Hydroxy-4-(indol-5-yloxy)-6-methoxyquinazoline (89 mg) was reacted with 2-(2-hydroxyethyl)piperidine (75 mg) to give 4-(indol-5-yloxy)-6-methoxy-7-(2-(piperidin-2-yl)ethoxy)quinazoline.

$^1$H NMR Spectrum: (DMSOd$_6$) 1.45-1.75 (m, 3H), 1.75-1.85 (m, 2H), 2.0-2.1 (m, 1H), 2.1-2.2 (m, 1H), 2.25-2.35 (m, 1H), 2.95 (t, 1H), 3.3-3.4 (m, 2H), 4.1 (s, 3H), 4.4-4.5 (m, 2H), 6.5 (s, 1H), 7.05 (dd, 1H), 7.45-7.6 (m, 4H), 7.75 (s, 1H), 9.0 (s, 1H)

x) 7-Hydroxy-4-(indol-5-yloxy)-6-methoxyquinazoline (89 mg) was reacted with 1-(2-hydroxyethyl)piperidine (75 mg) to give 4-(indol-5-yloxy)-6-methoxy-7-(2-(piperidin-1-yl)ethoxy)quinazoline.

$^1$H NMR Spectrum: (DMSOd$_6$) 1.1-1.3 (m, 1H), 1.35-1.5 (m, 1H), 1.65-1.8 (m, 2H), 1.8-1.9 (m, 2H), 3.1 (t, 2H), 3.6 (d, 2H), 3.65 (t, 2H), 4.1 (s, 3H), 4.7 (t, 2H), 6.5 (d, 1H), 7.05 (dd, 1H), 7.45 (s, 1H), 7.5-7.55 (m, 2H), 7.61 (s, 1H), 7.8 (s, 1H), 9.0 (m, 1H)

y) 7-Hydroxy-4-(indol-5-yloxy)-6-methoxyquinazoline (89 mg) was reacted with 4-(3-hydroxypropyl)morpholine (84 mg), (prepared as described for the starting material in Example 60), to give 4-(indol-5-yloxy)-6-methoxy-7-(3-morpholinopropoxy)quinazoline.

$^1$H NMR Spectrum: (DMSOd$_6$) 1.9-2.1 (m, 2H), 2.4 (br s, 4H), 2.5 (t, 2H), 3.6 (t, 4H), 4.0 (s, 3H), 4.25 (t, 2H), 6.45 (s, 1H), 7.0 (dd, 1H), 7.4 (s, 1H), 7.4-7.45 (m, 2H), 7.47 (d, 1H), 7.6 (s, 1H), 8.5 (s, 1H)

z) 7-Hydroxy-4-(indol-5-yloxy)-6-methoxyquinazoline (89 mg) was reacted with 2-(N-(2-methoxyethyl)-N-methylamino)ethanol (77 mg), (prepared as described for the starting material in Example 59), to give 4-(indol-5-yloxy)-6-methoxy-7-(2-(N-(2-methoxyethyl)-N-methylamino)ethoxy)quinazoline.

$^1$H NMR Spectrum: (DMSOd$_6$) 2.35 (s, 3H), 2.65 (t, 2H), 2.9 (t, 2H), 3.25 (s, 3H), 3.45 (t, 2H), 4.0 (s, 3H), 4.3 (t, 2H), 6.45 (s, 1H), 7.05 (dd, 1H), 7.4-7.5 (m, 4H), 7.6 (s, 1H), 8.5 (s, 1H)

aa) 7-Hydroxy-4-(indol-5-yloxy)-6-methoxyquinazoline (89 mg) was reacted with 3-(1,1-dioxothiomorpholino)-1-propanol (112 mg), (prepared as described for the starting material in Example 5), to give 7-(3-(1,1-dioxothiomorpholino)propoxy)-4-(indol-5-yloxy)-6-methoxyquinazoline.

¹H NMR Spectrum: (DMSOd₆) 2.0 (m, 2H), 2.65 (m, 2H), 2.9 (br s, 4H), 3.15 (br s, 4H), 4.0 (s, 3H), 4.25 (t, 2H), 6.5 (s, 1H), 7.0 (dd, 1H), 7.35-7.5 (m, 4H), 7.65 (s, 1H), 8.5 (s, 1H bb) 7-Hydroxy-4-(indol-5-yloxy)-6-methoxyquinazoline (89 mg) was reacted with 2-(4-pyridyloxy)ethanol (81 mg), (J. Chem. Soc. Perkin Trans 2, 1987, 12, 1867), to give 4-(indol-5-yloxy)-6-methoxy-7-(2-(4-pyridyloxy)ethoxy) quinazoline.

EXAMPLE 119

A solution of 4-chloro-6-methoxy-7-(3-piperidinopropoxy)quinazoline (200 mg, 0.59 mmol), (prepared as described for the starting material in Example 67), 6-hydroxyindole (96 mg, 0.715 mmol) in DMF (3 ml) containing cesium carbonate (291 mg, 0.894 mmol) was heated at 90° C. for 4 hours. After cooling, the mixture was diluted with water, the precipitate was filtered, washed with water and dried under vacuum. The solid was purified by column chromatography eluting with methylene chloride/methanol (90/10 increasing to 50/50) to give 4-(indol-6-yloxy)-6-methoxy-7-(3-piperidinopropoxy)quinazoline (240 mg, 93%).

¹H NMR Spectrum: (DMSOd₆) 1.35-1.45 (m, 2H), 1.45-1.55 (m, 4H), 1.9-2.05 (m, 2H), 2.3-2.4 (m, 4H), 2.45 (t, 2H), 4.0 (s, 3H), 4.22 (t, 2H), 6.5 (s, 1H), 6.9 (dd, 1H), 7.3 (s, 1H), 7.35-7.40 (m, 2H), 7.55-7.65 (m, 2H), 8.5 (s, 1H)

MS-ESI: 433 [MH]⁺

| Elemental analysis | Found | C 68.4 | H 6.4 | N 12.8 |
|---|---|---|---|---|
| $C_{25}H_{28}N_4O_3$ 0.4 $H_2O$ | Requires | C 68.3 | H 6.6 | N 12.7% |

EXAMPLE 120

A solution of 4-chloro-6-methoxy-7-(3-methylsulphonylpropoxy)quinazoline (200 mg, 0.6 mmol), (prepared as described for the starting material in Example 50), and 6-hydroxyindole (97 mg, 0.73 mmol) in DMF (3 ml) containing potassium carbonate (125 mg, 0.91 mmol) was heated at 90° C. for 2.5 hours. After cooling, water was added. The precipitate was filtered, washed with water and dried under vacuum. The residue was triturated with ether, filtered, washed with ether and dried under vacuum to give 4-(indol-6-yloxy)-6-methoxy-7-(3-methylsulphonylpropoxy)quinazoline (130 mg, 50%).

¹H NMR Spectrum: (DMSOd₆) 2.2-2.35 (m, 2H), 3.05 (s, 3H), 3.3 (m, 2H), 4.0 (s, 3H), 4.35 (t, 2H), 6.48 (s, 1H), 6.9 (dd, 1H), 7.3 (s, 1H), 7.4 (2s, 2H), 7.6 (d, 1H), 7.65 (s, 1H), 7.9 (s, 1H)

MS-ESI: 428 [MH]⁺

| Elemental analysis | Found | C 56.2 | H 4.9 | N 9.3 |
|---|---|---|---|---|
| $C_{21}H_{21}N_3O_5S$ 1.1 $H_2O$ | Requires | C 56.4 | H 5.2 | N 9.4% |

EXAMPLE 121

Using an analogous procedure to that described for Example 120, 4-chloro-6-methoxy-7-(3-morpholinopropoxy)quinazoline (200 mg, 0.59 mmol), (prepared as described for the starting material in Example 1), was reacted with 6-hydroxyindole (95 mg, 0.71 mmol) to give 4-(indol-6-yloxy)-6-methoxy-7-(3-morpholinopropoxy)quinazoline (155 mg, 60%).

¹H NMR Spectrum: (DMSOd₆) 1.95-2.05 (m, 2H), 2.4 (br s, 4H), 2.48 (t, 2H), 3.6 (t, 4H), 4.0 (s, 3H), 4.27 (t, 2H), 6.5 (s, 1H), 6.93 (dd, 1H), 7.3 (s, 1H), 7.4 (br s, 2H), 7.6 (d, 1H), 7.61 (s, 1H), 8.5 (s, 1H)

MS-ESI: 435 [MH]⁺

| Elemental analysis | Found | C 62.0 | H 6.2 | N 12.1 |
|---|---|---|---|---|
| $C_{24}H_{26}N_4O_4$ 1.6 $H_2O$ | Requires | C 62.2 | H 6.4 | N 12.1% |

EXAMPLE 122

A suspension of 7-(1-tert-butoxycarbonylpiperidin-4-ylmethoxy)-4-(2-methylindol-5-yloxy)quinazoline (150 mg, 0.31 mmol), (prepared as described in Example 90), in methylene chloride (2 ml) and TFA (1.5 ml) was stirred for 1 hour at ambient temperature. After removal of the volatiles under vacuum the residue was azeotroped with toluene. The residue was partitioned between methylene chloride and water and the aqueous layer was adjusted to pH11. The organic layer was separated, washed with brine, dried (MgSO₄), and evaporated. The residue was triturated with ether, filtered, washed with ether and dried under vacuum to give 4-(2-methylindol-5-yloxy)-7-(piperidin-4-ylmethoxy)quinazoline (80 mg, 67%).

¹H NMR Spectrum: (DMSOd₆, CF₃COOD) 1.5-1.65 (m, 2H), 2.0 (d, 2H), 2.15-2.3 (m, 1H), 2.4 (s, 3H), 2.95 (t, 2H), 3.38 (d, 2H), 4.2 (d, 2H), 6.2 (s, 0.5H, partially exchanged), 6.9 (dd, 1H), 7.35 (s, 1H), 7.4 (d, 1H), 7.5 (s, 1H), 7.58 (dd, 1H), 8.5 (d, 1H), 9.1 (s, 1H)

MS-ESI: 389 [MH]⁺

| Elemental analysis | Found | C 68.9 | H 6.2 | N 13.7 |
|---|---|---|---|---|
| $C_{23}H_{24}N_4O_2$ 0.2 $H_2O$ 0.12 $CH_2Cl_2$ | Requires | C 69.0 | H 6.2 | N 13.9% |

EXAMPLE 123

Using an analogous procedure to that described for Example 71, 4-(2-methylindol-5-yloxy)-7-(piperidin-4-ylmethoxy)quinazoline (150 mg, 0.386 mmol), (prepared as described in Example 122), was reacted with methoxyacetaldehyde (83 mg, 0.772 mmol), (prepared as described for the starting material in Example 71), to give 7-(1-(2-methoxyethyl)piperidin-4-ylmethoxy)-4-(2-methylindol-5-yloxy) quinazoline (80 mg, 46%).

¹H NMR Spectrum: (DMSOd₆) 1.3-1.42 (m, 2H), 1.7-1.9 (m, 3H), 2.0 (t, 2H), 2.4 (s, 3H), 2.48 (t, 2H), 2.92 (d, 2H), 3.22 (s, 3H), 3.42 (t, 2H), 4.05 (d, 2H), 6.15 (s, 1H), 6.88 (dd, 1H), 7.25 (s, 1H), 7.3 (d, 1H), 7.35 (s, 1H), 7.37 (d, 1H), 8.28 (d, 1H), 8.6 (s, 1H)

MS-ESI: 447 [MH]⁺

| Elemental analysis | Found | C 68.4 | H 6.7 | N 12.2 |
|---|---|---|---|---|
| $C_{26}H_{30}N_4O_3$ 0.5 $H_2O$ | Requires | C 68.6 | H 6.9 | N 12.3% |

EXAMPLE 124

Diethyl azodicarboxylate (117 mg, 0.67 mmol) was added in portions to a solution of 7-hydroxy-6-methoxy-4-(2-methylindol-5-yloxy)quinazoline (120 mg, 0.37 mmol), (prepared as described in Example 49), and 3-(ethylsulphonyl)-1-propanol (74 mg, 0.48 mmol) in methylene chloride (3.5 ml) and triphenylphosphine (176 mg, 0.67 mmol). After stirring for 2 hours at ambient temperature, the residue was poured onto a column of silica and eluted with ethyl acetate/methylene chloride (1/1) followed by methylene chloride/methanol (97/3 followed by 95/5). After removal of the solvent under vacuum, the residue was triturated with ether, filtered and dried under vacuum to give 7-(3-(ethylsulphonyl)propoxy)-6-methoxy-4-(2-methylindol-5-yloxy)quinazoline (93 mg, 55%).

$^1$H NMR Spectrum: (DMSOd$_6$) 1.25 (t, 3H), 2.2-2.3 (m, 2H), 2.4 (s, 3H), 3.2 (q, 2H), 3.3 (t, 2H), 4.0 (s, 3H), 4.35 (t, 2H), 6.15 (s, 1H), 6.9 (dd, 1H), 7.28 (s, 1H), 7.32 (d, 1H), 7.4 (s, 1H), 7.62 (s, 1H), 8.5 (s, 1H)

MS-ESI: 456 [MH]$^+$

| Elemental analysis | Found | C 60.3 | H 5.6 | N 9.2 |
|---|---|---|---|---|
| C$_{23}$H$_{25}$N$_3$O$_5$S | Requires | C 60.6 | H 5.5 | N 9.2% |

The starting material was prepared as follows:

A solution of ethylthiopropanol (1.2 g, 10 mmol) in methylene chloride (30 ml) containing 3-chloroperoxybenzoic acid (5 g, 20 mmol) was stirred at ambient temperature for 30 minutes. The precipitate was filtered, washed with methylene chloride and the filtrate was poured onto a column of aluminium oxide and eluted with methylene chloride, followed by methylene chloride/methanol (95/5 and 90/10). After removal of the solvent, the residue was dissolved in methylene chloride, dried (MgSO$_4$) and evaporated to give 3-(ethylsulphonyl)-1-propanol (1.05 g, 69%).

$^1$H NMR Spectrum: (DMSOd$_6$) 1.25 (t, 3H), 1.75-1.9 (m, 2H), 3.0-3.2 (m, 4H), 3.5 (q, 2H), 4.7 (t, 1H)

MS-ESI: 153 [MH]$^+$

EXAMPLE 125

Using an analogous procedure to that described for Example 124, 4-(2,3-dimethylindol-5-yloxy)-7-hydroxy-6-methoxyquinazoline (120 mg, 0.36 mol), (prepared as described for the starting material in Example 91), was reacted with 3-(ethylsulphonyl)-1-propanol (71 mg, 0.46 mol), (prepared as described for the starting material in Example 124), to give 4-(2,3-dimethylindol-5-yloxy)-7-(3-ethylsulphonylpropoxy)-6-methoxyquinazoline (96 mg, 57%).

$^1$H NMR Spectrum: (DMSOd$_6$) 1.25 (t, 3H), 2.15 (s, 3H), 2.2-2.3 (m, 2H), 2.35 (s, 3H), 3.2 (q, 2H), 3.3 (t, 2H), 4.02 (s, 3H), 4.35 (t, 2H), 6.9 (dd, 1H), 7.22 (s, 1H), 7.3 (d, 1H), 7.4 (s, 1H), 7.63 (s, 1H), 8.51 (s, 1H)

MS-ESI: 470 [MH]$^+$

| Elemental analysis | Found | C 60.6 | H 6.0 | N 8.8 |
|---|---|---|---|---|
| C$_{24}$H$_{27}$N$_3$O$_5$S 0.4 H$_2$O | Requires | C 60.5 | H 5.9 | N 8.8% |

EXAMPLE 126

Using an analogous procedure to that described for Example 124, 7-hydroxy-6-methoxy-4-(2-methylindol-5-yloxy)quinazoline (128 mg, 0.4 mmol), (prepared as described in Example 49), was reacted with 4-(2-hydroxyethyl)-(1-tert-butoxycarbonyl)piperidine (119 mg, 0.52 mmol) overnight to give 7-(2-(1-tert-butoxycarbonyl)piperidin-4-yl)ethoxy)-6-methoxy-4-(2-methylindol-5-yloxy)quinazoline (34 mg, 16%).

$^1$H NMR Spectrum: (DMSOd$_6$) 1.05-1.2 (m, 2H), 1.42 (s, 9H), 1.62-1.85 (m, 5H), 2.42 (s, 3H), 2.62-2.82 (m, 2H), 3.9-4.0 (m, 2H), 4.0 (s, 3H), 4.25 (t, 2H), 6.17 (s, 1H), 6.9 (dd, 1H), 7.3 (d, 1H), 7.32 (d, 1H), 7.4 (s, 1H), 7.6 (s, 1H), 8.5 (s, 1H)

MS-ESI: 533 [MH]$^+$

| Elemental analysis | Found | C 67.8 | H 6.9 | N 10.5 |
|---|---|---|---|---|
| C$_{30}$H$_{36}$N$_4$O$_5$ | Requires | C 67.7 | H 6.8 | N 10.5% |

The starting material was prepared as follows:

A solution of 4-(2-hydroxyethyl)pyridine (1.8 g, 14.6 mol) in acetic acid (15 ml) containing platinum oxide (200 mg) was hydrogenated for 20 hours at 3.3-4 atmospheres pressure. After filtration, the filtrate was evaporated and azeotroped twice with toluene. The residue was triturated with 2N sodium hydroxide and solid sodium hydroxide was added to adjust the pH to 13. The volatiles were removed under vacuum and the residue was triturated with ether, filtered, washed with methylene chloride, and dried under vacuum to give 2-(piperidin-4-yl)-1-ethanol (860 mg, 46%).

$^1$H NMR Spectrum: (DMSOd$_6$, CF$_3$COOD) 1.3-1.5 (m, 4H), 1.6-1.7 (m, 1H), 1.7-1.9 (d, 2H), 1.75 (t, 2H), 3.25 (d, 2H), 3.55 (t, 2H)

A solution of 2-(piperidin-4-yl)-1-ethanol (830 mg, 6.4 mmol) in DMF (5 ml) containing tertbutyl dicarbonate anhydride (1.4 g, 6.4 mol) was stirred at ambient temperature for 48 hours. After removal of the volatiles under vacuum, the residue was partitioned between ether and water. The organic layer was separated, washed with water, brine, dried (MgSO$_4$) and evaporated to give 4-(2-hydroxyethyl)-(1-tert-butoxycarbonyl)piperidine (1 g, 68%).

$^1$H NMR Spectrum: (DMSOd$_6$) 0.9-1.1 (m, 2H), 1.3-1.6 (m, 3H), 1.4 (s, 9H), 1.6 (d, 2H), 2.5-2.8 (br s, 2H), 3.45 (dd, 2H), 3.9 (d, 2H), 4.35 (t, 1H)

EXAMPLE 127

Using an analogous procedure to that described for Example 121, 4-chloro-6-methoxy-7-(3-morpholinopropoxy)quinazoline (160 mg, 0.47 mol), (prepared as described for the starting material in Example 1), was reacted with 6-hydroxy-2-methylindole (84 mg, 0.57 mol), (Eur. J. Med. Chem. 1975, 10, 187), to give 6-methoxy-4-(2-methylindol-6-yloxy)-7-(3-morpholinopropoxy)quinazoline (157 mg, 73%).

$^1$H NMR Spectrum: (DMSOd$_6$, CF$_3$COOD) 2.25-2.35 (m, 2H), 2.38 (s, 3H), 3.15 (t, 2H), 3.35 (t, 2H), 3.5 (d, 2H), 3.68 (t, 2H), 4.0 (d, 2H), 4.05 (s, 3H), 4.35 (t, 2H), 6.18 (s, 1H), 6.9 (d, 1H), 7.22 (s, 1H), 7.45 (d, 1H), 7.52 (s, 1H), 7.8 (s, 1H), 9.05 (s, 1H)

MS-ESI: 449 [MH]$^+$

| Elemental analysis | Found | C 66.4 | H 6.4 | N 12.4 |
|---|---|---|---|---|
| C$_{25}$H$_{28}$N$_4$O$_4$ 0.2 H$_2$O | Requires | C 66.4 | H 6.3 | N 12.4% |

EXAMPLE 128

Using an analogous procedure to that described for the synthesis of 4-(2-methylindol-5-yloxy)-7-(piperidin-4-ylmethoxy)quinazoline, (prepared as described in Example 122), 7-(2-(1-tert-butoxycarbonylpiperidin-4-yl)ethoxy)-6-methoxy-4-(2-methylindol-5-yloxy)quinazoline (400 mg, 0.75 mmol), (prepared as described in Example 126), was used to give 6-methoxy-4-(2-methylindol-5-yloxy)-7-(2-(piperidin-4-yl)ethoxy)quinazoline (284 mg, 87%).

$^1$H NMR Spectrum: (DMSOd$_6$, CF$_3$COOD) 1.3-1.5 (m, 2H), 1.8-2.0 (m, 5H), 2.4 (s, 3H), 2.9 (t, 2H), 3.3 (d, 2H), 4.05 (s, 3H), 4.35 (t, 2H), 6.2 (s, 1H), 6.95 (dd, 1H), 7.35 (s, 1H), 7.37 (d, 1H), 7.52 (s, 1H), 7.8 (s, 1H), 9.1 (s, 1H)

MS-ESI: 433 [MH]$^+$

EXAMPLE 129

Diethyl azodicarboxylate (65 µl, 0.4 mmol) was added in portions to a suspension of 4-(2,3-dimethylindol-5-ylamino)-7-hydroxy-6-methoxyquinazoline (68 mg, 0.2 mmol), triphenylphosphine (107 mg, 0.4 mmol), (E)-4-(pyrrolidin-1-yl)but-2-en-1-ol (40 mg, 0.28 mmol) in DMF (0.4 ml) and dichloromethane (1.5 ml) cooled at 0° C. The reaction mixture was left to warm up to ambient temperature and was stirred overnight. The mixture was poured onto a column of silica and was eluted with methylene chloride followed by methylene chloride/methanol (98/2), followed by methylene chloride/3N ammonia in methanol (95/5 and 90/10) to give 4-(2,3-dimethylindol-5-ylamino)-6-methoxy-7-((E)-4-(pyrrolidin-1-yl)but-2-en-1-yloxy)quinazoline (51 mg, 55%).

$^1$H NMR Spectrum: (DMSOd$_6$) 1.6-1.7 (m, 4H), 2.15 (s, 3H), 2.3 (s, 3H), 2.4 (br s, 4H), 3.1 (d, 2H), 3.97 (s, 3H), 4.7 (d, 2H), 5.8-6.0 (m, 2H), 7.15 (s, 1H), 7.22 (d, 1H), 7.3 (d, 1H), 7.55 (s, 1H), 7.87 (s, 1H), 8.3 (s, 1H), 9.4 (s, 1H), 10.62 (s, 1H)

MS-ESI: 458 [MH]$^+$

The starting material was prepared as follows:

Thionyl chloride (9.3 ml, 128 mmol) was added in portions to a stirred solution of 2-butyne-1,4-diol (10 g, 116 mmol) in toluene (15 ml) and pyridine (10.3 ml) cooled at 0° C. The mixture was stirred for 3.5 hours at ambient temperature and then poured onto ice water. The mixture was extracted with ether, the organic layer was washed with saturated aqueous sodium hydrogen carbonate solution and then brine, dried (MgSO$_4$) and the volatiles removed by evaporation. The residue was purified by column chromatography eluting with petroleum ether/ether (7/3) to give 4-chlorobut-2-yn-1-ol (4.74 g, 39%).

$^1$H NMR Spectrum: (CDCl$_3$) 1.68(t, 1H); 4.18(d, 2H); 4.33(d, 2H)

Pyrrolidine (7.8 ml, 94 mmol) was added dropwise to a solution of 4-chlorobut-2-yn-1-ol (4.74 g, 45 mmol) in toluene (40 ml) and the mixture stirred and heated at 60° C. for 1 hour. The volatiles were removed by evaporation and the residue was purified by chromatography eluting with methylene chloride/methanol (96/4) to give 4-(pyrrolidin-1-yl)but-2-yn-1-ol (4.3 g, 69%).

$^1$H NMR Spectrum: (CDCl$_3$) 1.82(t, 4H); 2.63(t, 4H); 3.44 (t, 2H), 4.29(t, 2H)

A solution of 4-(pyrrolidin-1-yl)but-2-yn-1-ol (4.3 g, 31 mmol) in THF (20 ml) was added dropwise to a suspension of lithium aluminium hydride (2.35 g, 62 mmol) in anhydrous THF (8 ml) and the mixture stirred and heated at 60° C. for 2 hours. The mixture was cooled to 5° C. and 2M aqueous sodium hydroxide solution (28 ml) was added dropwise. The resulting suspension was filtered and the volatiles removed from the filtrate by evaporation. The residue was dissolved in a mixture of methylene chloride/ethyl acetate, dried (MgSO$_4$) and the solvent removed by evaporation. The residue was purified by column chromatography on aluminum oxide eluting with methylene chloride/methanol (97/3) to give (E)-4-(pyrrolidin-1-yl)but-2-en-1-ol (3.09 g, 70%).

$^1$H NMR Spectrum: (CDCl$_3$) 1.82(m, 4H); 2.61(m, 4H); 3.17(m, 2H); 4.13(s, 2H); 5.84(m, 2H)

A solution of 4-chloro-6-methoxy-7-benzyloxyquinazoline (7 g, 23 mmol), (prepared as described for the starting material in Example 1), and 5-amino-2,3-dimethylindole (4.5 g, 28 mmol) in isopropanol (90 ml) containing 6.2 N hydrogen chloride in isopropanol (380 µl) was heated at reflux for 3 hours and stirred overnight at ambient temperature. The mixture was triturated with ether and the solid was filtered, washed with ether and dried under vacuum to give 7-benzyloxy-4-(2,3-dimethylindol-5-ylamino)-6-methoxyquinazoline (10.5 g, quant.).

$^1$H NMR Spectrum: (DMSOd$_6$) 2.16 (s, 3H), 2.33 (s, 3H), 4.0 (s, 3H), 5.34 (s, 2H), 7.2 (d, 1H), 7.32 (d, 1H), 7.35-7.55 (m, 7H), 8.2 (s, 1H), 8.7 (s, 1H), 10.9 (s, 1H), 11.15 (s, 1H)

MS-ESI: 425 [MH]$^+$

Ammonium formate (20 g, 326 mmol) and 10% palladium on carbon (1 g) were added to a solution of 7-benzyloxy-4-(2,3-dimethylindol-5-ylamino)-6-methoxyquinazoline (10 g, 22 mmol) in DMF (100 ml) and methanol (300 ml). After stirring for 3 hours at ambient temperature, aqueous ammonia (120 ml) was added. The precipitate was filtered, washed with water and dried under vacuum. The residue was triturated with ethyl acetate and ether and was filtered, dried under vacuum and purified by column chromatography eluting with methanol/methylene chloride (5/95 followed by 10/90) to give 4-(2,3-dimethylindol-5-ylamino)-7-hydroxy-6-methoxyquinazoline (5.5 g, 75%).

$^1$H NMR Spectrum: (DMSOd$_6$) 2.2 (s, 3H), 2.35 (s, 3H), 3.97 (s, 3H), 7.0 (s, 1H), 7.22 (d, 1H), 7.3 (d, 1H), 7.55 (s, 1H), 7.85 (s, 1H), 8.28 (s, 1H), 9.35 (s, 1H), 10.2 (br s, 1H), 10.62 (s, 1H)

MS-ESI: 335 [MH]$^+$

EXAMPLES 130-145

Using an analogous procedure to that described in Example 129, 4-(2,3-dimethylindol-5-ylamino)-7-hydroxy-6-methoxyquinazoline (68 mg, 0.2 mmol), (prepared as described for the starting material in Example 129), was reacted with the appropriate alcohol to give the compounds described in Table IX.

TABLE IX

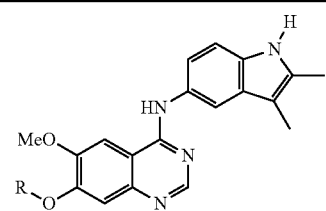

| Example number | Weight (mg) | Yield % | MS-ESI [MH]$^+$ | R | Note |
|---|---|---|---|---|---|
| 130 | 10 | 11 | 458 | 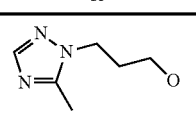 | a |
| 131 | 63 | 69 | 450 | | b |

TABLE IX-continued

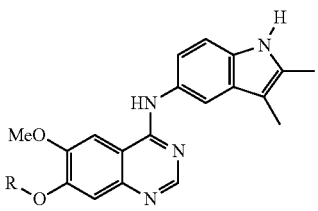

| Example number | Weight (mg) | Yield % | MS-ESI [MH]+ | R | Note |
|---|---|---|---|---|---|
| 132 | 5 | 6 | 443 | (imidazole-ethoxy) | c |
| 133 | 35 | 36 | 475 | (N-methylpiperazine-propoxy) | d |
| 134 | 53 | 51 | 510 | (sulfonylmorpholine-propoxy) | e |
| 135 | 56 | 58 | 469 | (N-methyl-N-(pyridin-4-yl)amino-ethoxy) | f |
| 136 | 4 | 4.6 | 415 | (furan-2-ylmethoxy) | g |
| 137 | 29 | 35 | 406 | (dimethylamino-ethoxy) | h |
| 138 | 49 | 56 | 432 | (pyrrolidin-1-yl-ethoxy) | i |
| 139 | 8 | 8.6 | 481 | (MeO-CH2CH2-O-CH2CH2-O-CH2CH2-O-) | j |
| 140 | 15 | 15 | 477 | (dimethyldioxane-ethoxy) | k |
| 141 | 38 | 42 | 446 | (piperidin-1-yl-ethoxy) | l |
| 142 | 69 | 72 | 470 | (N-methyl-N-(pyridazin-4-yl)amino-ethoxy) | m |
| 143 | 21 | 21 | 492 | (morpholino-ethoxy-ethoxy) | n |
| 144 | 36 | 40 | 440 | (pyridin-3-yl-ethoxy) | o |
| 145 | 31 | 33 | 460 | (2-oxopyrrolidin-1-yl-propoxy) | p | a) 4-(2,3-Dimethylindol-5-ylamino)-7-hydroxy-6-methoxyquinazoline (68 mg, 0.2 mmol) was reacted with 3-(5-methyl-[1,2,4]-triazol-1-yl)propan-1-ol (40 mg) to give 4-(2,3-dimethylindol-5-ylamino)-6-methoxy-7-(3-(5-methyl-1H-[1,2,4]-triazol-1-yl)propoxy)quinazoline.

The starting material was prepared as follows:

Under argon, 1,2,4-triazole (13.8 g, 200 mmol) was added to a solution of sodium ethoxide (freshly prepared from sodium (4.6 g) and ethanol (250 ml)). After complete dissolution, 3-bromopropan-1-ol (18 ml, 200 mmol) was added dropwise. The mixture was refluxed for 18 hours and the solid was filtered and washed with ethanol. The filtrate was evaporated and the residue was purified by column chromatography eluting with methylene chloride/methanol (9/1) to give 3-(1,2,4-triazol-1-yl)propan-1-ol (22.8 g, 90%).

$^1$H NMR Spectrum: (CDCl$_3$): 2.12 (m, 2H); 2.6 (br s, 1H); 3.65 (t, 2H); 4.35 (t, 2H); 7.95 (s, 1H); 8.1 (s, 1H)

To a solution of 3-(1,2,4-triazol-1-yl)propan-1-ol (7 g, 55 mmol) in DMF (70 ml) was added tertbutyldimethylsilyl chloride (9.1 g, 60 mmol) followed by DMAP (336 mg, 2.7 mmol) followed by imidazole (4.5gr, 66 mmol). After stirring overnight at ambient temperature, the volatiles were removed under vacuum and the residue was partitioned between water and ethyl acetate/ether. The organic layer was separated, washed with water, brine, dried (MgSO$_4$) and evaporated. The residue was purified by column chromatography eluting with methylene chloride/ether (6/4) to give 3-(tertbutyldimethylsilyloxy)-1-(1,2,4-triazol-1-yl)propane (11.1 gr, 84%).

MS-EI: 242 [MH]+

$^1$H NMR Spectrum: (CDCl$_3$) 0.25 (s, 6H); 0.9 (s, 9H); 2.05 (m, 2H); 3.52 (t, 2H); 4.25 (t, 2H); 7.9 (s, 1H); 8.02 (s, 1H)

To a solution of 3-(tertbutyldimethylsilyloxy)-1-(1,2,4-triazol-1-yl)propane (7 g, 29 mmol) in DMF (100 ml) cooled at −70° C. was added 2.5M n-butyllithium (17.4 ml) over 45 minutes. After stirring for 90 minutes at −70° C., methyl iodide (3.6 ml, 58 mmol) was added. After stirring for 2 hours at ambient temperature, the mixture was poured onto saturated ammonium chloride. The mixture was then diluted with ether and ethyl acetate. The organic layer was separated, washed with aqueous sodium thiosulphate followed by brine, dried (MgSO$_4$) and evaporated to give 3-(tertbutyldimethylsilyloxy)-1-(5-methyl-[1,2,4]-triazol-1-yl)propane (7.3 g, 98%).

MS-EI: 256 [MH]+

$^1$H NMR Spectrum: (CDCl$_3$) 0.25 (s, 6H); 0.85 (s, 9H); 2.0 (, 2H); 2.4 (s, 3H); 3.52 (t, 2H); 4.15 (t, 2H); 7.72 (s, 1H)

To a solution of ammonium fluoride (10.4 g, 280 mmol) in methanol (110 ml) was added a solution of 3-(tertbutyldimethylsilyloxy)-1-(5-methyl-[1,2,4]-triazol-1-yl)propane (7.2 g, 28 mmol) in methanol (30 ml). The mixture was refluxed for 4.5 hours. After cooling, silica (100 g) was added and the volatiles were removed under vacuum. The residue was added onto a column of silica and eluted with a mixture of methylene chloride/ethyl acetate (1/1) followed by methylene chloride/methanol (9/1) to give 3-(5-methyl-[1,2,4]-triazol-1-yl)propan-1-ol (3.65 g, 92%).

MS-ESI: 142 [MH]+

$^1$H NMR Spectrum: (CDCl$_3$) 2.05 (m, 2H); 2.5 (s, 3H); 3.62 (t, 2H); 4.25 (t, 2H); 7.8 (s, 1H)

b) 4-(2,3-Dimethylindol-5-ylamino)-7-hydroxy-6-methoxyquinazoline (68 mg, 0.2 mmol) was reacted with 2-(N-(2-methoxyethyl)-N-methylamino)ethanol (38 mg), (prepared as described for the starting material in Example 59), to give 4-(2,3-dimethylindol-5-ylamino)-6-methoxy-7-(2-(N-(2-methoxyethyl)-N-methylamino)ethoxy)quinazoline.

$^1$H NMR Spectrum: (DMSOd$_6$) 2.15 (s, 3H), 2.35 (s, 6H), 2.65 (t, 2H), 2.85 (t, 2H), 3.25 (s, 3H), 3.45 (t, 2H), 3.95 (s, 3H), 4.2 (t, 2H), 7.15 (s, 1H), 7.22 (s, 1H), 7.3 (dd, 1H), 7.55 (s, 1H), 7.85 (s, 1H), 8.3 (s, 1H), 9.4 (s, 1H), 10.62 (s, 1H)

c) 4-(2,3-Dimethylindol-5-ylamino)-7-hydroxy-6-methoxyquinazoline (68 mg, 0.2 mmol) was reacted with 2-(1-methylimidazol-2-ypethanol (36 mg), (EP 06751112 A1), to give 4-(2,3-dimethylindol-5-ylamino)-6-methoxy-7-(2-(1-methylimidazol-2-yl)ethoxy)quinazoline $^1$H NMR Spectrum: (DMSOd$_6$) 2.15 (s, 3H), 2.32 (s, 3H), 3.2 (t, 2H), 3.7 (s, 3H), 3.95 (s, 3H), 4.45 (t, 2H), 6.8 (s, 1H), 7.05 (s, 1H), 7.15 (s, 1H), 7.22 (d, 1H), 7.3 (dd, 1H), 7.55 (s, 1H), 7.88 (s, 1H), 8.32 (s, 1H), 9.4 (s, 1H), 10.62 (s, 1H)

d) 4-(2,3-Dimethylindol-5-ylamino)-7-hydroxy-6-methoxyquinazoline (68 mg, 0.2 mmol) was reacted with 1-(3-hydroxypropyl)-4-methylpiperazine (45 mg) to give 4-(2,3-dimethylindol-5-ylamino)-6-methoxy-7-(3-(4-methylpiperazin-1-yl)propoxy)quinazoline.

$^1$H NMR Spectrum: (DMSOd$_6$) 1.9-2.0 (m, 2H), 2.15 (2s, 6H), 2.0-2.9 (m, 8H), 2.32 (s, 3H), 2.45 (t, 2H), 3.95 (s, 3H), 4.2 (t, 2H), 7.1 (s, 1H), 7.22 (d, 1H), 7.3 (dd, 1H), 7.55 (s, 1H), 7.85 (s, 1H), 8.3 (s, 1H), 9.4 (s, 1H), 10.62 (s, 1H)

The starting material was prepared as follows:

3-Bromopropan-1-ol (20 ml, 20 mmol) was added dropwise to a solution of 1-methylpiperazine (29 ml, 26 mmol) in ethanol (200 ml). Potassium carbonate (83 gr, 60 mmol) was added and the mixture was refluxed for 20 hours. After cooling, the solid was filtered and the filtrate was evaporated. The residue was triturated with ether, filtrate and evaporated. The residue was distilled at about 60-70° C. under about 0.2 mm Hg to give 1-(3-hydroxypropyl)-4-methylpiperazine (17 g, 53%).

$^1$H NMR Spectrum: (CDCl$_3$) 1.72 (m, 2H); 2.3 (s, 3H); 2.2-2.8 (m, 8H); 2.6 (t, 2H); 3.8 (t, 2H); 5.3 (br s, 1H)

e) 4-(2,3-Dimethylindol-5-ylamino)-7-hydroxy-6-methoxyquinazoline (68 mg, 0.2 mmol) was reacted with 3-(1,1-dioxothiomorpholino)-1-propanol (55 mg), (prepared as described for the starting material in Example 5), to give 4-(2,3-dimethylindol-5-ylamino)-6-methoxy-7-(3-(1,1-dioxothiomorpholino)propoxy)quinazoline.

$^1$H NMR Spectrum: (DMSOd$_6$) 1.9-2.0 (m, 2H), 2.5 (s, 9H), 2.65 (t, 2H), 2.9 (br s, 4H), 3.15 (br s, 4H), 3.95 (s, 3H), 4.25 (t, 2H), 7.2 (s, 1H), 7.85 (s, 1H), 8.0 (dd, 1H), 8.15 (d, 1H), 8.2 (s, 1H), 8.45 (s, 1H), 9.6 (s, 1H), 10.95 (s, 1H)

f) 4-(2,3-Dimethylindol-5-ylamino)-7-hydroxy-6-methoxyquinazoline (68 mg, 0.2 mmol) was reacted with 2-(N-methyl-N-(4-pyridyl)amino)ethanol (43 mg), (EP 0359389), to give 4-(2,3-dimethylindol-5-ylamino)-6-methoxy-7-(2-(N-methyl-N-(4-pyridyl)amino)ethoxy) quinazoline.

$^1$H NMR Spectrum: (DMSOd$_6$) 2.15 (s, 3H), 2.35 (s, 3H), 3.07 (s, 3H), 3.85 (t, 2H), 3.95 (s, 3H), 4.3 (t, 2H), 6.7 (d, 2H), 7.15 (s, 1H), 7.22 (d, 1H), 7.3 (dd, 1H), 7.55 (s, 1H), 7.85 (s, 1H), 8.15 (d, 2H), 8.3 (s, 1H), 9.4 (s, 1H), 10.65 (s, 1H)

g) 4-(2,3-Dimethylindol-5-ylamino)-7-hydroxy-6-methoxyquinazoline (68 mg, 0.2 mmol) was reacted with 2-furanmethanol (28 mg) to give 4-(2,3-dimethylindol-5-ylamino)-6-methoxy-7-(2-furylmethoxy)quinazoline.

h) 4-(2,3-Dimethylindol-5-ylamino)-7-hydroxy-6-methoxyquinazoline (68 mg, 0.2 mmol) was reacted with 2-N,N-dimethylethanolamine (25 mg) to give 4-(2,3-dimethylindol-5-ylamino)-6-methoxy-7-(2-(N,N-dimethylamino)ethoxy)quinazoline.

$^1$H NMR Spectrum: (DMSOd$_6$) 2.15 (s, 3H), 2.25 (s, 6H), 2.32 (s, 3H), 2.72 (t, 2H), 3.95 (s, 3H), 4.2 (t, 2H), 7.15 (s, 1H), 7.22 (d, 1H), 7.3 (dd, 1H), 7.55 (s, 1H), 7.85 (s, 1H), 8.32 (s, 1H), 9.4 (s, 1H), 10.6 (s, 1H)

i) 4-(2,3-Dimethylindol-5-ylamino)-7-hydroxy-6-methoxyquinazoline (68 mg, 0.2 mmol) was reacted with 1-(2-hydroxyethyl)pyrrolidine (33 mg) to give 4-(2,3-dimethylindol-5-ylamino)-6-methoxy-7-(2-(pyrrolidin-1-yl)ethoxy)quinazoline.

$^1$H NMR Spectrum: (DMSOd$_6$) 1.65-1.75 (m, 4H), 2.15 (s, 3H), 2.35 (s, 3H), 2.55-2.65 (m, 4H), 2.9 (t, 2H), 3.95 (s, 3H), 4.25 (t, 2H), 7.15 (s, 1H), 7.22 (d, 1H), 7.3 (dd, 1H), 7.55 (s, 1H), 7.85 (s, 1H), 8.32 (s, 1H), 9.4 (s, 1H), 10.62 (s, 1H)

j) 4-(2,3-Dimethylindol-5-ylamino)-7-hydroxy-6-methoxyquinazoline (68 mg, 0.2 mmol) was reacted with triethylene glycol monomethyl ether (47 mg) to give 4-(2,3-dimethylindol-5-ylamino)-6-methoxy-7-(2-(2-(2-methoxyethoxy)ethoxy)ethoxy)quinazoline.

k) 4-(2,3-Dimethylindol-5-ylamino)-7-hydroxy-6-methoxyquinazoline (68 mg, 0.2 mmol) was reacted with 5,5-dimethyl-1,3-dioxane-2-ethanol (46 mg) to give 7-(2-(5,5-dimethyl-1,3-dioxan-2-yl)ethoxy)-4-(2,3-dimethylindol-5-ylamino)-6-methoxyquinazoline.

$^1$H NMR Spectrum: (DMSOd$_6$) 0.7 (s, 3H), 1.15 (s, 3H), 2.05-2.1 (m, 2H), 2.1 (s, 3H), 2.6 (s, 3H), 3.42 (d, 2H), 3.57 (d, 2H), 4.0 (s, 3H), 4.22 (t, 2H), 4.7 (t, 1H), 7.2 (s, 1H), 7.82 (s, 1H), 8.0 (dd, 1H), 8.17 (d, 1H), 8.3 (s, 1H), 8.45 (s, 1H), 9.6 (s, 1H), 10.95 (s, 1H)

l) 4-(2,3-Dimethylindol-5-ylamino)-7-hydroxy-6-methoxyquinazoline (68 mg, 0.2 mmol) was reacted with 1-(2-hydroxyethyl)piperidine (37 mg) to give 4-(2,3-dimethylindol-5-ylamino)-6-methoxy-7-(2-piperidinoethoxy) quin azoline.

$^1$H NMR Spectrum: (DMSOd$_6$) 1.3-1.45 (m, 2H), 1.45-1.6 (m, 4H), 2.15 (s, 3H), 2.35 (s, 3H), 2.45 (br s, 4H), 2.75 (t, 2H), 3.95 (s, 3H), 4.25 (t, 2H), 7.15 (s, 1H), 7.22 (d, 1H), 7.3 (dd, 1H), 7.55 (s, 1H), 7.85 (s, 1H), 8.3 (s, 1H), 9.4 (s, 1H), 10.62 (s, 1H)

m) 4-(2,3-Dimethylindol-5-ylamino)-7-hydroxy-6-methoxyquinazoline (68 mg, 0.2 mmol) was reacted with 2-(N-methyl-N-(pyridazin-4-yl)amino)ethanol (44 mg) to give 4-(2,3-dimethylindol-5-ylamino)-6-methoxy-7-(2-(N-methyl-N-(pyridazin-4-yl)amino)ethoxy)quinazoline.

$^1$H NMR Spectrum: (DMSOd$_6$) 2.15 (s, 3H), 2.32 (s, 3H), 3.1 (s, 3H), 3.9 (s, 3H), 3.95 (t, 2H), 4.35 (t, 2H), 6.85 (dd, 1H), 7.15 (s, 1H), 7.20 (d, 1H), 7.28 (dd, 1H), 7.55 (s, 1H), 7.85 (s, 1H), 8.3 (s, 1H), 8.58 (d, 1H), 8.9 (d, 1H), 9.4 (s, 1H), 10.62 (s, 1H)

The starting material was prepared as follows:

A solution of 4-bromo-3,6-dichloro-pyridazine (1.11 g, 5 mmol), (J. Chem. Soc., Perkin Trans I, 1974, 696), and 2-(methylamino)ethanol (0.75 g, 10 mmol) in isopropanol (10 ml) was heated at reflux for 30 minutes. The solvent was removed by evaporation, the residue was partitioned between methylene chloride and water and the aqueous layer was adjusted to pH9 with solid potassium carbonate. The organic layer was separated, washed with brine, dried (MgSO$_4$) and the solvent removed by evaporation. The residue was triturated with ether, collected by filtration and dried under vacuum to give 2-(N-(3,6-dichloropyridazin-4-yl)-N-methylamino)ethanol (1 g, 90%).

$^1$H NMR Spectrum: (CDCl$_3$) 2.1(br s, 1H); 3.09(s, 3H); 3.71(t, 2H); 3.93(t, 2H); 6.8(s, 1H)

MS-ESI: 221 [MH]$^+$

A mixture of 2-(N-(3,6-dichloropyridazin-4-yl)-N-methylamino)ethanol (444 mg, 2 mmol) and 10% palladium-on-charcoal catalyst (150 mg) in ethanol (15 ml), methanol (5 ml) and aqueous ammonia (15 ml) was stirred under hydrogen at 3 atmospheres pressure for 4 hours. The catalyst was removed by filtration and the solvent removed from the filtrate by evaporation. The residue was dissolved in methylene chloride, the insoluble material was removed by filtration and the solvent was removed from the filtrate by evaporation. The residue was purified by column chromatography on neutral aluminum oxide eluting with methylene chloride/methanol (95/5 followed by 90/10). The purified product was triturated with petroleum ether, the solid product was collected by filtration and dried under vacuum to give 2-(N-methyl-N-(pyridazin-4-yl)amino)ethanol (275 mg, 91%).

$^1$H NMR Spectrum: (CDCl$_3$) 3.06(s, 3H); 3.57(t, 2H); 3.89(t, 2H); 6.52(dd, 1H); 8.48(d, 1H); 8.54 (d, 1H)

MS-ESI: 153 [MH]$^+$ n)  4-(2,3-Dimethylindol-5-ylamino)-7-hydroxy-6-methoxyquinazoline (68 mg, 0.2 mmol) was reacted with 2-(2-morpholinoethoxy)ethanol (50 mg) to give 4-(2,3-dimethylindol-5-ylamino)-6-methoxy-7-(2-(2-morpholinoethoxy)ethoxy)quinazoline.

$^1$H NMR Spectrum: (DMSOd$_6$) 2.18 (s, 3H), 2.35 (s, 3H), 2.35-2.45 (m, 4H), 2.45-2.5 (m, 2H), 3.5-3.55 (m, 4H), 3.65 (t, 2H), 3.8-3.85 (m, 2H), 3.95 (s, 1H), 4.25 (m, 2H), 7.15 (s, 1H), 7.22 (d, 1H), 7.3 (dd, 1H), 7.55 (s, 1H), 7.85 (s, 1H), 8.3 (s, 1H), 9.4 (s, 1H), 10.62 (s, 1H)

The starting material was prepared as follows:

2-(2-Chloroethoxy)ethanol (1.25 g, 10 mmol) was added to a mixture of morpholine (2.58 g, 30 mmol) and potassium carbonate (5.5 g, 40 mmol) in acetonitrile (50 ml). The mixture was heated at reflux for 6 hours and then stirred for 18 hours at ambient temperature. The insolubles were removed by filtration and the volatiles were removed from the filtrate by evaporation. The residue was purified by column chromatography eluting with methylene chloride/methanol (95/5 followed by 90/10 and then 80/20) to give 2-(2-morpholinoethoxy)ethanol (600 mg, 34%).

$^1$H NMR Spectrum: (CDCl$_3$) 2.5(br s, 4H); 2.59(t, 2H); 3.6-3.85(m, 10H)

MS-(EI): 175 [M.]$^+$ o)  4-(2,3-Dimethylindol-5-ylamino)-7-hydroxy-6-methoxyquinazoline (68 mg, 0.2 mmol) was reacted with 3-(2-hydroxyethyl)pyridine (35 mg) to give 4-(2,3-dimethylindol-5-ylamino)-6-methoxy-7-(2-(3-pyridyl)ethoxy)quinazoline.

$^1$H NMR Spectrum: (DMSOd$_6$) 2.15 (s, 3H), 2.32 (s, 3H), 3.15 (t, 2H), 3.95 (s, 3H), 4.4 (t, 2H), 7.2 (s, 1H), 7.22 (d, 1H), 7.3 (dd, 1H), 7.35 (dd, 1H), 7.55 (s, 1H), 7.8 (d, 1H), 7.85 (s, 1H), 8.32 (s, 1H), 8.45 (dd, 1H), 8.6 (s, 1H), 9.4 (s, 1H), 10.68 (s, 1H)

p)  4-(2,3-Dimethylindol-5-ylamino)-7-hydroxy-6-methoxyquinazoline (68 mg, 0.2 mmol) was reacted with 1-(3-hydroxypropyl)pyrrolidin-2-one (41 mg) to give 4-(2,3-dimethylindol-5-ylamino)-6-methoxy-7-(3-(2-oxopyrrolidin-1-yl)propoxy)quinazoline.

$^1$H NMR Spectrum: (DMSOd$_6$) 1.9-2.05 (m, 4H), 2.12 (s, 3H), 2.15-2.3 (m, 2H), 2.6 (s, 3H), 3.3-3.45 (m, 4H), 4.0 (s, 3H), 4.15 (t, 2H), 7.15 (s, 1H), 7.82 (s, 1H), 8.0 (dd, 1H), 8.17 (d, 1H), 8.3 (s, 1H), 8.45 (s, 1H), 9.6 (s, 1H), 10.95 (s, 1H)

EXAMPLE 146

Using an analogous procedure to that described for Example 121, 4-chloro-6-methoxy-7-(3-pyrrolidinopropoxy)quinazoline (150 mg, 0.47 mmol), (prepared as described for the starting material in Example 9), was reacted with 6-hydroxy-2-methylindole (83 mg, 0.56 mol), (Eur. J. Med. Chem. 1975, 10, 187), to give 6-methoxy-4-(2-methylindol-6-yloxy)-7-(3-(pyrrolidin-1-yl)propoxy)quinazoline (170 mg, 85%).

$^1$H NMR Spectrum: (DMSOd$_6$) 1.65-1.8 (m, 4H), 1.95-2.05 (m, 2H), 2.42 (s, 3H), 2.5 (br s, 1H), 2.6 (t, 2H), 4.0 (s, 3H), 4.27 (t, 2H), 6.2 (s, 1H), 6.85 (dd, 1H), 7.2 (s, 1H), 7.4 (s, 1H), 7.45 (d, 1H), 7.6 (s, 1H), 8.5 (s, 1H)

MS-ESI: 433 [MH]$^+$

| Elemental analysis | Found | C 68.3 | H 6.4 | N 12.8 |
|---|---|---|---|---|
| C$_{25}$H$_{28}$N$_4$O$_3$ 0.4 H$_2$O | Requires | C 68.3 | H 6.6 | N 12.7% |

EXAMPLE 147

Using an analogous procedure to that described in Example 123, 6-methoxy-4-(2-methylindol-5-yloxy)-7-(2-(piperidin-4-yl)ethoxy)quinazoline (120 mg, 0.28 mmol) was used to give 7-(2-(1-(2-methoxyethyl)piperidin-4-yl)ethoxy)-6-methoxy-4-(2-methylindol-5-yloxy)quinazoline (55 mg, 40%).

$^1$H NMR Spectrum: (DMSOd$_6$) 1.15-1.3 (m, 2H), 1.4-1.55 (m, 1H), 1.65-1.8 (m, 4H), 1.95 (t, 2H), 2.4 (s, 3H), 2.42 (t, 2H), 2.85 (d, 2H), 3.25 (s, 3H), 3.42 (t, 2H), 4.0 (s, 3H), 4.22 (t, 2H), 6.15 (s, 1H), 6.85 (dd, 1H), 7.25 (s, 1H), 7.3 (d, 1H), 7.38 (s, 1H), 7.59 (s, 1H), 8.5 (s, 1H).

MS-ESI: 491 [MH]$^+$

| Elemental analysis | Found | C 65.3 | H 7.1 | N 10.9 |
|---|---|---|---|---|
| C$_{28}$H$_{34}$N$_4$O$_4$ 1.3 H$_2$O | Requires | C 65.4 | H 7.2 | N 10.9% |

EXAMPLE 148

Using an analogous procedure to that described in Example 120 OR 121 PER PP, 4-chloro-6-methoxy-7-(3-morpholinopropoxy)quinazoline (160 mg, 0.48 mmol), (prepared as described for the starting material in Example 1), was reacted with 1,2-dimethyl-5-hydroxyindole (92 mg, 0.57 mol), (Tetrahedron 1994, 50, 13433), to give 4-(1,2-dimethylindol-5-yloxy)-6-methoxy-7-(3-morpholinopropoxy) quinazoline (163 mg, 74%).

$^1$H NMR Spectrum: (DMSOd$_6$) 1.95-2.1 (m, 2H), 2.4 (br s, 4H), 2.45 (s, 3H), 2.5 (t, 2H), 3.65 (t, 4H), 3.75 (s, 3H), 4.0 (s, 3H), 4.25 (t, 2H), 6.25 (s, 1H), 6.95 (dd, 1H), 7.3 (s, 1H), 7.38 (s, 1H), 7.45 (d, 1H), 7.6 (s, 1H), 8.5 (s, 1H)

MS-ESI: 463 [MH]$^+$

| Elemental analysis | Found | C 67.2 | H 6.5 | N 12.1 |
|---|---|---|---|---|
| $C_{26}H_{30}N_4O_4$ | Requires | C 67.5 | H 6.5 | N 12.1% |

EXAMPLE 149

Using an analogous procedure to that described in Example 124, 7-hydroxy-6-methoxy-4-(2-methylindol-5-yloxy)quinazoline (2.3 g, 7.16 mmol), (prepared as described in Example 49), was reacted with (N-methyl-N-tert-butoxycarbonyl)ethanolamine (1.51 g, 8.6 mmol) to give 6-methoxy-4-(2-methylindol-5-yloxy)-7-(2-(N-methyl-N-tert-butoxycarbonylamino)ethoxy)quinazoline (1.93 g, 56%).

$^1$H NMR Spectrum: (DMSOd$_6$) 1.4 (s, 9H), 2.4 (s, 3H), 2.90 (s, 3H), 3.65 (t, 2H), 4.0 (s, 3H), 4.35 (t, 2H), 6.15 (s, 1H), 6.8 (dd, 1H), 7.28 (s, 1H), 7.35 (d, 1H), 7.42 (s, 1H), 7.6 (s, 1H), 8.5 (s, 1H);

MS-ESI: 479 [MH]$^+$

| Elemental analysis | Found | C 65.0 | H 6.4 | N 11.7 |
|---|---|---|---|---|
| $C_{26}H_{30}N_4O_5S$ | Requires | C 65.3 | H 6.3 | N 11.7% |

EXAMPLE 150

A solution of 6-methoxy-4-(2-methylindol-5-yloxy)-7-(2-(N-methyl-N-tert-butoxycarbonylamino)ethoxy)quinazoline (550 mg, 1.15 mmol), (prepared as described in Example 149), in methylene chloride (10 ml) containing TFA (12 ml) was stirred for 3 hours at ambient temperature. After removal of the volatiles under vacuum, the residue was partitioned between methylene chloride and sodium hydrogen carbonate. The pH of the aqueous layer was adjusted to 11 with 2N sodium hydroxide. The organic layer was separated, washed with water, brine, dried (MgSO$_4$) and evaporated. The residue was triturated with ether, filtered and dried under vacuum to give 6-methoxy-4-(2-methylindol-5-yloxy)-7-(2-(N-methylamino)ethoxy)quinazoline (356 mg, 82%).

$^1$H NMR Spectrum: (DMSOd$_6$) 2.4 (s, 3H), 2.5 (s, 3H), 2.9 (t, 2H), 4.0 (s, 3H), 4.25 (t, 2H), 6.25 (s, 1H), 6.9 (dd, 1H), 7.25 (s, 1H), 7.3 (d, 1H), 7.4 (s, 1H), 7.6 (s, 1H), 8.5 (s, 1H), 11.0 (s, 1H)

MS-ESI: 379 [MH]+

| Elemental analysis | Found | C 64.6 | H 5.8 | N 14.2 |
|---|---|---|---|---|
| $C_{21}H_{22}N_4O_3$ 0.7 $H_2O$ | Requires | C 64.5 | H 6.0 | N 14.3% |

EXAMPLE 151

A mixture of 6-methoxy-4-(2-methylindol-5-yloxy)-7-(piperidin-4-ylmethoxy)quinazoline (419 mg, 1 mmol), (prepared as described in Example 70), in DMF (6 ml) containing chloroacetonitrile (114 mg, 1.5 mmol), potassium carbonate (346 mg, 2.5 mmol) and potassium iodide (50 mg, 0.3 mmol) was stirred at ambient temperature overnight. The mixture was poured into water and the precipitate was filtered, washed with water and dried under vacuum. The residue was purified by column chromatography, eluting with methylene chloride, followed by methylene chloride/methanol (98/2 and 95/5). After removal of the solvent under vacuum, the residue was triturated with ether, filtered, washed with ether and dried under vacuum to give 7-((1-cyanomethyl)piperidin-4-ylmethoxy)-6-methoxy-4-(2-methylindol-5-yloxy)quinazoline (304 mg, 66%).

$^1$H NMR Spectrum: (DMSOd$_6$, CF$_3$COOD) 1.6-1.8 (m, 2H), 2.05-2.2 (d, 2H), 2.2-2.3 (m, 1H), 2.45 (s, 3H), 3.2 (t, 2H), 3.65 (d, 2H), 4.1 (s, 3H), 4.22 (d, 2H), 4.6 (s, 2H), 6.2 (s, 0.5H, partially exchanged), 6.9 (dd, 1H), 7.35 (s, 1H), 7.4 (d, 1H), 7.55 (s, 1H), 7.8 (s, 1H), 9.1 (s, 1H)

MS-ESI: 458 [MH]$^+$

| Elemental analysis | Found | C 67.6 | H 6.1 | N 15.2 |
|---|---|---|---|---|
| $C_{26}H_{27}N_5O_3$ 0.2 $H_2O$ | Requires | C 67.7 | H 6.0 | N 15.2% |

EXAMPLE 152

A mixture of 4-chloro-6-methoxy-7-(3-(N-methyl-N-methylsulphonylamino)propoxy)quinazoline (360 mg, 1.00 mmol), potassium carbonate (215 mg, 1.56 mmol) and 5-hydroxyindole (147 mg, 1.10 mmol) in DMF (8.0 ml) was stirred at 100° C. for 5 hours and allowed to cool to ambient temperature. The solvent was removed by evaporation and the residue purified by silica column chromatography eluting with methanol (2.5 to 5%) in dichloromethane. The resulting solid was recrystallised from ethyl acetate, filtered and washed with diethyl ether to give 4-(indol-5-yloxy)-6-methoxy-7-(3-(N-methyl-N-methylsulphonylamino)propoxy) quinazoline (77 mg, 17%).

$^1$H NMR Spectrum: (DMSOd$_6$) 2.07 (m, 2H), 2.78 (s, 3H), 2.87 (s, 3H), 3.25 (t, 2H), 3.97 (s, 3H), 4.23 (t, 2H), 6.43 (br s, 1H), 6.96 (dd, 1H), 7.32 (s, 1H), 7.41 (m, 3H), 7.59 (d, 1H), 8.48 (s, 1H) and 11.17 (s, 1H)

MS(ESI): 457 (MH)$^+$

| Elemental analysis | Found | C 57.5 | H 5.3 | N 12.0 |
|---|---|---|---|---|
| $C_{22}H_{24}N_4O_5S$ | Requires | C 57.9 | H 5.3 | N 12.3% |

The starting material was prepared as follows:

Using an analogous procedure to that described for the synthesis of the starting material in Example 5, 4-(4-bromo-2-fluorophenoxy)-7-hydroxy-6-methoxyquinazoline was made in a similar way to 4-(4-chloro-2-fluorophenoxy)-7-hydroxy-6-methoxyquinazoline using 4-bromo-2-fluorophenol instead of 4-chloro-2-fluorophenol.

A mixture of 4-(4-bromo-2-fluorophenoxy)-7-hydroxy-6-methoxyquinazoline (9.64 g, 26.4 mmol) and triphenylphosphine (20.9 g, 79.8 mmol) in dichloromethane (240 ml) was stirred under nitrogen, at ambient temperature for 30 minutes. 3-(N-tertButoxycarbonyl)-propanolamine (6.26 g, 35.8 mmol) was added followed by diethyl azodicarboxylate (12.4 ml, 13.7 g, 78.7 mmol). The reaction mixture was stirred for 2 hours. The solvent was then removed by evaporation and the residue taken up in acetonitrile (250 ml). The solution was concentrated to half the original volume and cooled. The resulting crystalline solid was filtered, washed with ether and dried to give 4-(4-bromo-2-fluorophenoxy)-7-(3-(N-tertbutoxycarbonylamino)propoxy)-6-methoxyquinazoline (10.0 g, 73%).

¹H NMR Spectrum: (DMSOd₆) 1.37 (s, 9H), 1.94 (t, 2H), 3.13 (q, 2H), 3.97 (s, 3H), 4.21 (t, 2H), 6.89 (br s, 1H), 7.38 (s, 1H), 7.43-7.53 (m, 2H), 7.57 (s, 1H), 7.78 (dd, 1H) and 8.55 (s, 1H)

MS(ESI): 522 (MH)⁺

| Elemental analysis | Found | C 52.1 | H 4.7 | N 7.9 |
| --- | --- | --- | --- | --- |
| $C_{23}H_{25}N_3BrFO_5$ | Requires | C 52.3 | H 4.9 | N 8.0% |

4-(4-Bromo-2-fluorophenoxy)-7-(3-(N-tertbutoxycarbonylamino)propoxy)-6-methoxyquinazoline (5.46 g, 10.5 mmol) was taken up in trifluoroacetic acid (75 ml) and heated at 85° C. for 1.5 hours. The solution was allowed to cool and the excess trifluoroacetic acid removed by evaporation. The residue was then treated with aqueous ammonia (0.88) solution, extracted with dichloromethane (3×150 ml) and filtered through phase separating paper. The solvent was removed by evaporation to give 7-(3-aminopropoxy)-4-(4-bromo-2-fluorophenoxy)-6-methoxyquinazoline (4.42 g, 100%).

¹H NMR Spectrum: (DMSOd₆) 1.87 (m, 2H), 2.73 (t, 2H), 3.98 (s, 3H), 4.26 (t, 2H), 7.40 (s, 1H), 7.50 (m, 2H), 7.55 (s, 1H), 7.78 (dd, 1H) and 8.55 (s, 1H)

MS(ESI): 422 (MH)⁺

A solution of 7-(3-aminopropoxy)-4-(4-bromo-2-fluorophenoxy)-6-methoxyquinazoline (2.71 g, 6.4 mmol) and triethylamine (1.1 ml, 0.80 g, 7.9 mmol) in dichloromethane (15 ml) was treated with a solution of methanesulphonyl chloride (0.53 ml, 0.79 g, 6.9 mmol) in dichloromethane (10 ml) and stirred at ambient temperature, under nitrogen for 18 hours. The dichloromethane was then removed by evaporation and THF (4 ml) added. The resulting solution was treated with saturated aqueous sodium hydrogen carbonate solution (to pH 8), stirred vigorously for 30 minutes and the precipitate filtered, washed with water and dried to give 4-(4-bromo-2-fluorophenoxy)-6-methoxy-7-(3-(N-methylsulphonylamino)propoxy)quinazoline (2.98 g, 93%).

¹H NMR Spectrum: (DMSOd₆) 2.01 (m, 2H), 2.90 (s, 3H), 3.15 (t, 2H), 3.96 (s, 3H), 4.25 (t, 2H), 7.06 (s, 1H), 7.40 (s, 1H), 7.49 (m, 2H), 7.56 (s, 1H), 7.78 (dd, 1H) and 8.54 (s, 1H)

MS(ESI): 500/502 (MH)⁺

4-(4-Bromo-2-fluorophenoxy)-6-methoxy-7-(3-(N-methylsulphonylamino)propoxy)quinazoline (1.0 g, 2 mmol) was taken up in DMF (10 ml), treated with sodium hydride (60% dispersion in mineral oil, 0.11 g, 2.7 mmol) and stirred, under nitrogen for 30 minutes. Methyl iodide (0.16 ml, 2.6 mmol) was added and the mixture stirred for 18 hours. The solvent was removed by evaporation and the residue taken up in water and extracted with dichloromethane (3×30 ml). The organic solution was then washed with water, brine, dried (MgSO₄) and evaporated to dryness. The crude product was purified by silica column chromatography eluting with methanol (2.5 to 5%) in dichloromethane to give 4-(4-bromo-2-fluorophenoxy)-6-methoxy-7-(3-(N-methyl N-methylsulphonylamino) propoxy)quinazoline (0.86 g, 83%).

¹H NMR Spectrum: (DMSOd₆) 2.06 (m, 2H), 2.78 (s, 3H), 2.87 (s, 3H), 3.24 (t, 2H), 3.97 (s, 3H), 4.23 (t, 2H), 7.39 (s, 1H), 7.48 (m, 2H), 7.55 (s, 1H), 7.78 (dd, 1H) and 8.54 (s, 1H)

MS(ESI): 514/516 (MH)⁺

4-(4-Bromo-2-fluorophenoxy)-6-methoxy-7-(3-(N-methyl N-methylsulphonylamino)propoxy)quinazoline (4.70 g, 9.1 mmol) was dissolved in 2N aqueous hydrochloric acid solution (85 ml) and heated at reflux for 1 hour. After cooling, the solution was carefully poured into saturated aqueous sodium hydrogen carbonate solution (to pH8) and stirred vigorously for 30 minutes. The resulting precipitate was filtered and dried. The filter cake was then taken up as a suspension in acetone, filtered, washed with diethyl ether and dried to give 6-methoxy-7-(3-(N-methyl-N-methylsulphonylamino)propoxy)quinazolin-4-one (3.23 g, 88%).

¹H NMR Spectrum: (DMSOd₆) 2.02 (m, 2H), 2.77 (s, 3H), 2.86 (s, 3H), 3.22 (t, 2H), 3.86 (s, 3H), 4.13 (t, 2H), 7.09 (s, 1H), 7.42 (s, 1H), 7.95 (s, 1H) and 12.02 (s, 1H)

MS(ESI): 342 (MH)⁺

6-Methoxy-7-(3-(N-methyl-N-methylsulphonylamino) propoxy)quinazolin-4-one (2.24 g, 6.6 mmol) was taken up in thionyl chloride (25 ml) and treated with DMF (5 drops). The resulting solution was then heated at reflux for 1 hour followed by cooling to ambient temperature. The excess thionyl chloride was removed by evaporation followed by azeotroping with toluene (3×). The residue was basified with saturated aqueous sodium hydrogen carbonate solution (to pH8) and extracted twice with ethyl acetate. The organic solution was washed with water, brine, dried (MgSO₄) and evaporated to dryness to give 4-chloro-6-methoxy-7-(3-(N-methyl-N-methylsulphonylamino)propoxy)quinazoline (1.90 g, 80%).

¹H NMR Spectrum: (DMSOd₆) 2.08 (m, 2H), 2.78 (s, 3H), 2.88 (s, 3H), 3.24 (t, 2H), 3.98 (s, 3H), 4.26 (t, 2H), 7.37 (s, 1H), 7.42 (s, 1H) and 8.86 (s, 1H)

MS(ESI): 360 (MH)⁺

EXAMPLE 153

A mixture of 4-chloro-6-methoxy-7-(3-(N-methyl-N-methylsulphonylamino)propoxy)quinazoline (360 mg, 1.00 mmol), (prepared as described for the starting material in Example 152), potassium carbonate (215 mg, 1.56 mmol) and 5-hydroxy-2-methylindole (162 mg, 1.10 mmol) in DMF (8.0 ml) was stirred at 100° C. for 5 hours and allowed to cool to ambient temperature. The solvent was removed by evaporation and the residue was purified by silica column chromatography eluting with methanol (2.5 to 5%) in dichloromethane. The resulting solid was recrystallised from ethyl acetate, filtered and washed with diethyl ether to give 6-methoxy-4-(2-methylindol-5-yloxy)-7-(3-(N-methyl-N-methylsulphonylamino)propoxy)quinazoline (166 mg, 35%).

¹H NMR Spectrum: (DMSOd₆) 2.06 (m, 2H), 2.38 (s, 3H), 2.79 (s, 3H), 2.89 (s, 3H), 3.24 (t, 2H), 3.96 (s, 3H), 4.21 (t, 2H), 6.11 (br s, 1H), 6.87 (dd, 1H), 7.23 (d, 1H), 7.30 (d, 1H), 7.35 (s, 1H), 7.57 (s, 1H), 8.46 (s, 1H) and 10.98 (s, 1H)

MS(ESI): 471 (MH)⁺

| Elemental analysis | Found | C 58.3 | H 5.6 | N 11.7 |
| --- | --- | --- | --- | --- |
| $C_{23}H_{26}N_4O_5S$ | Requires | C 58.7 | H 5.6 | N 11.9% |

EXAMPLE 154

A mixture of 4-chloro-6-methoxy-7-(3-(N-methyl-N-methylsulphonylamino)propoxy)quinazoline (150 mg, 0.42 mmol), (prepared as described for the starting material in Example 152), potassium carbonate (90 mg, 0.63 mmol) and 7-hydroxyquinoline (67 mg, 0.46 mmol) in DMF (5.0 ml) was stirred at 100° C. for 2 hours and allowed to cool to ambient temperature. The solvent was removed by evaporation and the residue taken up in 2N. aqueous sodium hydroxide solution. The precipitate was filtered off, dried, taken up in dichloromethane and the solution filtered through phase separating paper. The filtrate was then evaporated to dryness. The resulting solid was recrystallised from acetonitrile, filtered and washed with diethyl ether to give 6-methoxy-7-(3-(N- methyl-N-methylsulphonylamino)propoxy)-4-(quinolin-7-yloxy)quinazoline (122 mg, 63%).

$^1$H NMR Spectrum: (DMSOd$_6$) 2.09 (m, 2H), 2.79 (s, 3H), 2.90 (s, 3H), 3.26 (t, 2H), 3.99 (s, 3H), 4.26 (t, 2H), 7.39 (s, 1H), 7.54 (dd, 1H), 7.56 (dd, 1H), 7.60 (s, 1H), 7.91 (d, 1H), 8.09 (d, 1H), 8.44 (d, 1H), 8.55 (s, 1H) and 8.93 (dd, 1H)

MS(ESI): 469 (MH)$^+$

| Elemental analysis | Found | C 58.6 | H 5.1 | N 11.9 |
|---|---|---|---|---|
| C$_{23}$H$_{24}$N$_4$O$_5$S | Requires | C 59.0 | H 5.2 | N 12.0% |

EXAMPLE 155

A mixture of 4-chloro-6-methoxy-7-(3-(N-methyl-N-methylsulphonylamino)propoxy)quinazoline (150 mg, 0.42 mmol), (prepared as described for the starting material in Example 152), potassium carbonate (90 mg, 0.63 mmol) and 7-hydroxy-4-methylquinoline (71 mg, 0.46 mmol), (Chem. Berich. 1967, 100, 2077), in DMF (5.0 ml) was stirred at 100° C. for 2 hours and allowed to cool to ambient temperature. The DMF solvent was removed by evaporation and the residue was taken up in 2N aqueous sodium hydroxide solution. The precipitate was filtered off, dried, taken up in dichloromethane and then filtered through phase separating paper. The solution was then evaporated to dryness. The resulting solid was recrystallised from acetonitrile, filtered and washed with diethyl ether to give 6-methoxy-7-(3-(N-methyl-N-methylsulphonylamino)propoxy)-4-(4-methylquinolin-7-yloxy)quinazoline (84 mg, 42%).

$^1$H NMR Spectrum: (DMSOd$_6$) 2.09 (m, 2H), 2.71 (s, 3H), 2.79 (s, 3H), 2.89 (s, 3H), 3.25 (t, 2H), 3.98 (s, 3H), 4.25 (t, 2H), 7.37 (s, 1H), 7.38 (d, 1H), 7.61 (dd, 1H), 7.63 (s, 1H), 7.89 (d, 1H), 8.20 (d, 1H), 8.54 (s, 1H) and 8.76 (d, 1H)

MS(ESI): 483 (MH)$^+$

| Elemental analysis | Found | C 59.1 | H 5.3 | N 11.5 |
|---|---|---|---|---|
| C$_{24}$H$_{26}$N$_4$O$_5$S | Requires | C 59.1 | H 5.0 | N 12.0% |

EXAMPLE 156

A mixture of (R,S)-4-chloro-6-methoxy-74(1-methylpiperidin-3-yl)methoxy)quinazoline (90 mg, 0.28 mmol), (prepared as described for the starting material in Example 7), potassium carbonate (60 mg, 0.44 mmol) and 7-hydroxy-4-trifluoromethylquinoline (65 mg, 0.31 mmol), (prepared as in Ukr. Khim. Zh. (Russ. Ed) Vol. 59, No. 4, pp. 408-411, 1993), in DMF (2 ml) was stirred at 100° C. for 6 hours and then allowed to cool to ambient temperature. The DMF solvent was removed by evaporation, the residue was taken up in methanol/dichloromethane (1/1) and pre-absorbed onto silica. The crude mixture was purified by silica column chromatography eluting with dichloromethane/methanol/0.880 aqueous ammonia (95/5/1) and the product recrystallised from acetonitrile to give (R,S)-6-methoxy-7-((1-methylpiperidin-3-yl)methoxy)-4-(4-trifluoromethylquinolin-7-yloxy)quinazoline (58 mg, 42%).

$^1$H NMR Spectrum: (DMSOd$_6$ 100° C.) 1.24 (m, 1H), 1.59 (m, 1H), 1.70 (m, 1H), 1.83 (m, 1H), 2.05 (m, 2H), 2.17 (m, 1H), 2.24 (s, 3H), 2.64 (dt, 1H), 2.84 (dd, 1H), 4.05 (s, 3H), 4.18 (d, 2H), 7.43 (s, 1H), 7.69 (s, 1H), 7.87 (dd, 1H), 7.96 (d, 1H), 8.18 (s, 1H), 8.25 (dd, 1H), 8.59 (s, 1H) and 9.16 (d, 1H)

MS(ESI): 499 (MH)$^+$

| Elemental analysis | Found | C 62.2 | H 5.1 | N 11.0 |
|---|---|---|---|---|
| C$_{26}$H$_{25}$N$_4$F$_3$O$_3$ | Requires | C 62.6 | H 5.1 | N 11.2% |

EXAMPLE 157

A mixture of (R,S)-4-chloro-6-methoxy-74(1-methylpiperidin-3-yl)methoxy)quinazoline (150 mg, 0.46 mmol), (prepared as described for the starting material in Example 7), potassium carbonate (106 mg, 0.77 mmol) and 3-fluoro-7-hydroxyquinoline (119 mg, 0.73 mmol) in DMF (5 ml) was stirred at 100° C. for 2 hours and then allowed to cool to ambient temperature. The solvent was removed by evaporation and the residue treated with 1.0 N aqueous sodium hydroxide solution (30 ml) then allowed to stir for 30 minutes. The crude solid was collected by filtration and washed with water. The resultant solid was dissolved in dichloromethane and filtered through phase separating paper. The solvent was removed by evaporation and the solid residue was recrystallised from acetonitrile to give (R,S)-4-(3-fluoroquinolin-7-yloxy)-6-methoxy-7-((1-methylpiperidin-3-yl)methoxy)quinazoline (83 mg, 40%).

$^1$H NMR Spectrum: (DMSOd$_6$) 1.11 (m, 1H), 1.50 (m, 1H), 1.64 (m, 1H), 1.84 (m, 3H), 2.10 (m, 1H), 2.15 (s, 3H), 2.62 (d, 1H), 2.83 (d, 1H), 4.00 (s, 3H), 4.08 (d, 2H), 7.38 (s, 1H), 7.62 (s, 1H), 7.68 (dd, 1H), 7.97 (d, 1H), 8.10 (d, 1H), 8.34 (dd, 1H), 8.54 (s, 1H) and 8.97 (d, 1H)

MS(ESI): 449 (MH)$^+$

| Elemental analysis | Found | C 66.2 | H 5.6 | N 12.3 |
|---|---|---|---|---|
| C$_{25}$H$_{25}$N$_4$FO$_3$ 0.2 H$_2$O | Requires | C 66.4 | H 5.7 | N 12.4% |

The starting material, 3-fluoro-7-hydroxyquinoline was prepared as follows:

3-Fluoro-7-methoxyquinol-2(1H)-one (300 mg, 1.55 mmol), (prepared as in Tetrahedron, Vol. 52, No. 9, pp. 3223-3228, 1996), was dissolved in thionyl chloride (3 ml), treated with DMF (1 drop) and heated at reflux for 1 hour. The excess thionyl chloride was removed by evaporation and the residue azeotroped with toluene (3×). The residue was basified to pH8 with saturated aqueous sodium hydrogen carbonate solution and extracted with ethyl acetate (3×20 ml). The organic solution was washed with water and brine then dried (MgSO$_4$) and evaporated to dryness to give 2-chloro-3-fluoro-7-methoxyquinoline (320 mg, 97%).

$^1$H NMR Spectrum: (CDCl$_3$) 3.95 (s, 3H), 7.25 (dd, 1H), 7.37 (d, 1H), 7.67 (d, 1H) and 7.78 (d, 1H)

MS(ESI): 212 (MH)$^+$

A mixture of 2-chloro-3-fluoro-7-methoxyquinoline (310 mg, 1.47 mmol), triethylamine (310 mg, 0.4 ml, 3.07 mmol) and 10% palladium on activated charcoal (50 mg) in dry ethanol (5 ml) was stirred under hydrogen gas at ambient temperature for 24 hours. The mixture was then filtered through celite. The celite was washed with methanol and the solvent was removed by evaporation from the combined filtrates. The crude material was purified by chromatography on silica, eluting with 10% ethyl acetate in isohexane to give 3-fluoro-7-methoxyquinoline (130 mg, 54%).

¹H NMR Spectrum: (CDCl₃) 3.96 (s, 3H), 7.24 (dd, 1H), 7.44 (d, 1H), 7.66 (d, 1H) and 7.73 (dd, 1H) and 8.76 (d, 1H)
MS(ESI): 178 (MH)⁺

3-Fluoro-7-methoxyquinoline (130 mg, 0.74 mmol) was taken up in dichloromethane (2 ml) under nitrogen and treated with boron tribromide (4 ml of a 1.0M solution of in dichloromethane). The reaction mixture was stirred for 24 hours at ambient temperature followed by quenching the reaction by the slow addition of excess methanol. The solution was stirred for a further 2 hours and evaporated to dryness to give 3-fluoro-7-hydroxyquinoline which was used without further purification.
MS(ESI): 164 (MH)⁺

EXAMPLE 158

A mixture of (R,S)-4-chloro-6-methoxy-74(1-methylpiperidin-3-yl)methoxy)quinazoline (240 mg, 0.75 mmol), (prepared as described for the starting material in Example 7), potassium carbonate (160 mg, 1.16 mmol) and 3-fluoro-7-hydroxy-2-methylquinoline (150 mg, 0.85 mmol) in DMF (6 ml) was stirred at 100° C. for 5 hours and then allowed to cool to ambient temperature. The solvent was removed by evaporation, then the residue was treated with water and 1.0 N aqueous sodium hydroxide solution (30 ml) then allowed to stir for 30 minutes. The crude solid was collected by filtration and washed with water. The resulting solid was dissolved in dichloromethane and filtered through phase separating paper. The solvent was removed by evaporation to give a solid residue which was recrystallised from acetonitrile to give 4-(3-fluoro-2-methylquinolin-7-yloxy)-6-methoxy-7-((1-methylpiperidin-3-yl)methoxy)quinazoline (71 mg, 21%).
¹H NMR Spectrum: (DMSOd₆) 1.11 (m, 1H), 1.68 (m, 5H), 2.10 (m, 1H), 2.20 (s, 3H), 2.64 (m, 4H), 2.87 (d, 1H), 3.98 (s, 3H), 4.09 (d, 2H), 7.37 (s, 1H), 7.57 (dd, 1H), 7.60 (s, 1H), 7.86 (d, 1H), 8.02 (d, 1H), 8.20 (d, 1H) and 8.53 (s, 1H)
MS(ESI): 463 (MH)⁺

| Elemental analysis | Found | C 66.4 | H 6.1 | N 11.8 |
| $C_{26}H_{27}N_4FO_3$ 0.4 H₂O | Requires | C 66.5 | H 6.0 | N 11.9% |

The starting material was prepared as follows:
2-Chloro-3-fluoro-7-methoxyquinoline (210 g, 1 mmol), (prepared as described for the starting material in Example 157), in anhydrous THF (1 ml) was added to a mixture of copper(I)bromide (570 mg, 4.0 mmol) and methylmagnesium bromide (3.0M solution in diethyl ether, 2.7 ml, 8 mmol) in anhydrous THF (20 ml) at −78° C. The mixture was stirred for 1 hour at −78° C., allowed to warm to ambient temperature and then stirred for a further 18 hours. Saturated aqueous ammonium chloride solution and 5N aqueous sodium hydroxide solution (pH 12) were added and the product extracted with ethyl acetate (3×). The organic solution was washed with water, brine, dried (MgSO₄) and evaporated to dryness to yield 3-fluoro-7-methoxy-2-methylquinoline (0.17 g, 91%).
¹H NMR Spectrum: (CDCl₃) 2.70 (d, 3H), 3.94 (s, 3H), 7.17 (dd, 1H), 7.37 (d, 1H) and 7.61 (m, 2H)
MS(ESI): 192 (MI)⁺

3-Fluoro-7-methoxy-2-methylquinoline (0.16 g, 0.85 mmol) was taken up in dichloromethane (4 ml) under nitrogen and treated with boron tribromide solution (4 ml of a 1.0M solution in dichloromethane, 4.0 mmol). The reaction was stirred for 24 hours at ambient temperature followed by the slow addition of excess methanol. The solution was stirred for a further 2 hours and then evaporated to dryness to give 3-fluoro-7-hydroxy-2-methylquinoline which was used without further purification.
MS(ESI): 178 (MH)⁺

EXAMPLE 159

A mixture of 4-chloro-6-methoxy-7-(3-piperidinopropoxy)quinazoline (400 mg, 1.19 mmol), (prepared as described for the starting material in Example 67), potassium carbonate (255 mg, 1.84 mmol) and 7-hydroxyquinoline (180 mg, 1.32 mmol) in DMF (10 ml) was stirred at 100° C. for 4 hours and then allowed to cool to ambient temperature. The resulting mixture was treated with 1.0 N aqueous sodium hydroxide solution (30 ml) and allowed to stir for 1 hour. The crude solid was collected by filtration and washed with water. The resulting solid was dissolved in dichloromethane and filtered through phase separating paper. The solvent was removed by evaporation to give a solid residue which was recrystallised from acetonitrile to give 6-methoxy-7-(3-piperidinopropoxy)-4-(quinolin-7-yloxy)quinazoline (0.27 g, 52%).
¹H NMR Spectrum: (DMSOd₆) 1.37 (m, 2H), 1.51 (m, 4H), 1.95 (m, 2H), 2.32 (m, 4H), 2.42 (t, 2H), 3.98 (s, 3H), 4.23 (t, 2H), 7.38 (s, 1H), 7.56 (m, 2H), 7.62 (s, 1H), 7.91 (d, 1H), 8.09 (d, 1H), 8.44 (d, 1H), 8.54 (s, 1H) and 8.91 (dd, 1H)
MS(ESI): 445 (MH)⁺

| Elemental analysis | Found | C 70.9 | H 6.3 | N 12.7 |
| $C_{26}H_{28}N_4O_3$ | Requires | C 70.3 | H 6.3 | N 12.6% |

EXAMPLE 160

A mixture of 4-chloro-6-methoxy-7-(3-(N-methyl-N-methylsulphonylamino)propoxy)quinazoline (360 mg, 1.00 mmol), (prepared as described for the starting material in Example 152), potassium carbonate (215 mg, 1.56 mmol) and 2,3-dimethyl-5-hydroxyindole (177 mg, 1.10 mmol), (Arch. Pharm. 1972, 305, 159), in DMF (8.0 ml) was stirred at 100° C. for 5 hours and allowed to cool to ambient temperature. The solvent was removed by evaporation and the residue purified by silica column chromatography eluting with methanol (2.5%) in dichloromethane. The resulting solid was recrystallised from tertbutyl methyl ether/acetonitrile, filtered and washed with diethyl ether to give 4-(2,3-dimethylindol-5-yloxy)-6-methoxy-7-(3-(N-methyl-N-methylsulphonylamino)propoxy)quinazoline (201 mg, 42%).
¹H NMR Spectrum: (DMSOd₆) 2.07 (m, 2H), 2.12 (s, 3H), 2.31 (s, 3H), 2.79 (s, 3H), 2.89 (s, 3H), 3.25 (t, 2H), 3.97 (s, 3H), 4.23 (t, 2H), 6.86 (dd, 1H), 7.20 (d, 1H), 7.25 (d, 1H), 7.35 (s, 1H), 7.58 (s, 1H), 8.46 (s, 1H) and 11.17 (s, 1H)
MS(ESI): 485 (MH)⁺

| Elemental analysis | Found | C 59.5 | H 5.8 | N 11.4 |
| $C_{24}H_{28}N_4O_5S$ | Requires | C 59.5 | H 5.8 | N 11.6% |

EXAMPLE 161

A mixture of 7-hydroxy-6-methoxy-4-(2-methylindol-5-yloxy)quinazoline (322 mg, 1.00 mmol), (prepared as described in Example 49), potassium carbonate (414 mg, 3.00 mmol) and epibromohydrin (274 mg, 2.00 mmol) in DMF (7.0 ml) was stirred at 60° C. for 2 hours and allowed to cool to ambient temperature. The solvent was removed by evaporation and the residue taken up in dichloromethane (10 ml). An aliquot (5 ml) of this solution was treated with morpholine (48 µl, 0.6 mmol) and stirred for 24 hours at ambient temperature. The solvent was removed by evaporation, treated with water and stirred vigorously for 30 minutes. The precipitate was filtered, washed with water and dried. The resultant solid was stirred as a suspension in acetone, filtered, washed with diethyl ether and dried to give 7-(2-hydroxy-3-morpholinopropoxy)-6-methoxy-4-(2-methylindol-5-yloxy)quinazoline (127 mg, 27%).

$^1$H NMR Spectrum: (DMSOd$_6$) 2.38 (s, 3H), 2.45 (m, 6H), 3.57 (t, 4H), 3.95 (s, 3H), 4.03-4.14 (m, 2H), 4.23 (m, 1H), 4.95 (s, 1H), 6.12 (s, 1H), 6.86 (dd, 1H), 7.23 (d, 1H), 7.29 (d, 1H), 7.37 (s, 1H), 7.57 (s, 1H), 8.47 (s, 1H) and 10.98 (s, 1H)

MS(ESI): 465 (MH)$^+$

| Elemental analysis | Found | C 62.7 | H 5.9 | N 11.5 |
|---|---|---|---|---|
| C$_{25}$H$_{28}$N$_4$O$_5$0.7H$_2$O | Requires | C 62.9 | H 6.2 | N 11.7% |

EXAMPLE 162

A mixture of 7-(2,3-epoxypropoxy)-6-methoxy-4-(2-methylindol-5-yloxy)quinazoline (100 mg, 0.27 mmol) and piperidine (79 µl, 0.8 mmol) in DMF (4 ml) was heated at 70° C. for 24 hours. The solvent was removed by evaporation and the residue was recrystallised from acetonitrile. The solid was filtered, washed with diethyl ether and dried to give 7-(2-hydroxy-3-piperidinopropoxy)-6-methoxy-4-(2-methylindol-5-yloxy)quinazoline (80 mg, 65%).

$^1$H NMR Spectrum: (DMSOd$_6$) 1.35 (m, 2H), 1.51 (m, 4H), 2.39 (m, 9H), 3.96 (s, 3H), 4.08 (m, 2H), 4.21 (dd, 1H), 4.86 (br s, 1H), 6.11 (s, 1H), 6.87 (dd, 1H), 7.23 (d, 1H), 7.29 (d, 1H), 7.37 (s, 1H), 7.56 (s, 1H), 8.45 (s, 1H) and 10.98 (s, 1H)

MS(ESI): 464 (MH)$^+$

| Elemental analysis | Found | C 66.2 | H 6.4 | N 11.9 |
|---|---|---|---|---|
| C$_{26}$H$_{30}$N$_4$O$_4$0.4H$_2$O | Requires | C 66.5 | H 6.6 | N 11.9% |

The starting material was prepared as follows:

A mixture of 7-hydroxy-6-methoxy-4-(2-methylindol-5-yloxy)quinazoline (1.89 g, 5.90 mmol), (prepared as described in Example 49), potassium carbonate (2.43 g, 17.6 mmol) and epibromohydrin (1.61 g, 11.7 mmol) in DMF (40 ml) was stirred at 60° C. for 2 hours and allowed to cool to ambient temperature. The insoluble inorganic material was removed by filtration and the solvent was removed by evaporation. The residue was triturated with diethyl ether, filtered, washed with further diethyl ether and dried to give 7-(2,3-epoxypropoxy)-6-methoxy-4-(2-methylindol-5-yloxy)quinazoline (1.97 g, 89%).

$^1$H NMR Spectrum: (DMSOd$_6$) 2.38 (s, 3H), 2.76 (m, 1H), 2.90 (t, 1H), 3.43 (m, 1H), 3.97 (s, 3H), 4.04 (m, 1H), 4.57 (dd, 1H), 6.11 (s, 1H), 6.86 (dd, 1H), 7.27 (m, 2H), 7.38 (s, 1H), 7.59 (s, 1H), 8.46 (s, 1H) and 10.92 (s, 1H)

MS(ESI): 378 (MH)$^+$

EXAMPLE 163

A mixture of 7-(2,3-epoxypropoxy)-6-methoxy-4-(2-methylindol-5-yloxy)quinazoline (100 mg, 0.27 mmol), (prepared as described for the starting material in Example 162), and pyrrolidine (67 µl, 0.8 mmol) in DMF (4 ml) was heated at 70° C. for 24 hours. The solvent was removed by evaporation and the residue purified by silica column chromatography eluting with dichloromethane/methanol/0.880 aqueous ammonia (100/8/1). The relevant fractions were evaporated to dryness then the residue treated with a little dichloromethane and dried under high vacuum to give 7-(2-hydroxy-3-pyrrolidin-1-ylpropoxy)-6-methoxy-4-(2-methylindol-5-yloxy)quinazoline (44 mg, 37%) as a white foam.

$^1$H NMR Spectrum: (DMSOd$_6$) 1.69 (br s, 4H), 2.38 (s, 3H), 2.50 (m, 6H), 3.97 (s, 3H), 4.07 (m, 2H), 4.21 (dd, 1H), 4.96 (br s, 1H), 6.11 (s, 1H), 6.86 (dd, 1H), 7.23 (d, 1H), 7.29 (d, 1H), 7.35 (s, 1H), 7.56 (s, 1H), 8.46 (s, 1H) and 10.98 (s, 1H)

MS(ESI): 450 (MH)$^+$

| Elemental analysis | Found | C 65.5 | H 6.3 | N 11.8 |
|---|---|---|---|---|
| C$_{25}$H$_{28}$N$_4$O$_4$0.4H$_2$O | Requires | C 65.9 | H 6.4 | N 12.3% |

EXAMPLE 164

A mixture of 7-(2,3-epoxypropoxy)-6-methoxy-4-(2-methylindol-5-yloxy)quinazoline (100 mg, 0.27 mmol), (prepared as described for the starting material in Example 162), and diethylamine (100 µl, 0.8 mmol) in DMF (4 ml) was heated at 70° C. for 24 hours. The solvent was removed by evaporation and the residue was purified by silica column chromatography eluting with dichloromethane/methanol/0.880 aqueous ammonia (100/8/1). The relevant fractions were evaporated to dryness then the residue treated with a little dichloromethane and dried under high vacuum to give 7-(3-(N,N-diethylamino)-2-hydroxypropoxy)-6-methoxy-4-(2-methylindol-5-yloxy)quinazoline (55 mg, 46%) as a white foam.

$^1$H NMR Spectrum: (DMSOd$_6$) 0.96 (t, 6H), 2.38 (s, 3H), 2.52 (m, 6H), 3.96 (s, 3H), 3.97 (m, 1H), 4.09 (m, 1H), 4.23 (dd, 1H), 4.84 (br s, 1H), 6.12 (s, 1H), 6.88 (dd, 1H), 7.24 (d, 1H), 7.29 (d, 1H), 7.36 (s, 1H), 7.56 (s, 1H), 8.45 (s, 1H) and 10.98 (s, 1H)

MS(ESI): 452 (MH)$^+$

| Elemental analysis | Found | C 66.2 | H 6.7 | N 12.4 |
|---|---|---|---|---|
| C$_{25}$H$_{30}$N$_4$O$_4$ | Requires | C 66.6 | H 6.7 | N 12.4% |

EXAMPLE 165

A mixture of 7-(2,3-epoxypropoxy)-6-methoxy-4-(2-methylindol-5-yloxy)quinazoline (100 mg, 0.27 mmol), (prepared as described for the starting material in Example 162), and N-methylpiperazine (200 µl, 1.8 mmol) in DMF (4 ml) was heated at 70° C. for 24 hours. The solvent was removed by evaporation and the residue was recrystallised from acetonitrile. The solid was filtered, washed with diethyl ether and dried to give 7-(2-hydroxy-3-(4-methylpiperazin-1-yl)propoxy)-6-methoxy-4-(2-methylindol-5-yloxy)quinazoline (41 mg, 32%).

$^1$H NMR Spectrum: (DMSOd$_6$): 2.11 (s, 3H), 2.29 (m, 4H), 2.40 (s, 3H), 2.47 (m, 6H), 3.96 (s, 3H), 4.07 (m, 2H), 4.20 (dd, 1H), 4.89 (d, 1H), 6.11 (s, 1H), 6.87 (dd, 1H), 7.23 (d, 1H), 7.29 (d, 1H), 7.35 (s, 1H), 7.58 (s, 1H), 8.46 (s, 1H) and 10.98 (s, 1H)

MS(ESI): 479 (MH)$^+$

| Elemental analysis | Found | C 64.4 | H 6.5 | N 14.4 |
|---|---|---|---|---|
| $C_{26}H_{31}N_5O_4 \cdot 3H_2O$ | Requires | C 64.7 | H 6.6 | N 14.5% |

EXAMPLE 166

A mixture of 7-(2,3-epoxypropoxy)-6-methoxy-4-(2-methylindol-5-yloxy)quinazoline (100 mg, 0.27 mmol), (prepared as described for the starting material in Example 162), and isopropylamine (100 μl, 0.8 mmol) in DMF (4 ml) was heated at 70° C. for 24 hours. The solvent was removed by evaporation and the residue was purified by silica column chromatography eluting with dichloromethane/methanol/0.880 aqueous ammonia (100/8/1) to give 7-(2-hydroxy-3-(isopropylamino)propoxy)-6-methoxy-4-(2-methylindol-5-yloxy)quinazoline (18 mg, 16%).

$^1$H NMR Spectrum: (DMSOd$_6$) 1.00 (d, 6H), 2.40 (s, 3H), 2.56-2.78 (m, 3H), 3.97 (m, 4H), 4.07-4.28 (m, 2H), 5.04 (m, 1H), 6.12 (s, 1H), 6.88 (dd, 1H), 7.22-7.33 (m, 2H), 7.38 (s, 1H), 7.58 (s, 1H), 8.48 (s, 1H) and 10.98 (s, 1H)

MS(ESI): 437 (MH)$^+$

EXAMPLE 167

A mixture of 4-chloro-6-methoxy-7-(3-piperidinopropoxy)quinazoline (168 mg, 0.5 mmol), (prepared as described for the starting material in Example 67), potassium carbonate (276 mg, 2.0 mmol) and 5-hydroxy-6-trifluoromethylindole (110 mg, 0.55 mmol) and DMA (4.0 ml) were stirred at 95° C. for 1.5 hours and allowed to cool to ambient temperature. The reaction mixture was filtered and the filtrate evaporated under vacuum. The residue was purified by silica column chromatography eluting with dichloromethane/methanol/0.880 aqueous ammonia (89/10/1) to give a partially purified oil. This oil was further purified by high performance column chromatography on octadecylsilane reverse phase silica eluting with acetonitrile/water/trifluoroacetic acid (60/39.8/0.2) to give an oil which was dissolved in dichloromethane and washed with saturated aqueous sodium hydrogen carbonate solution. The dichloromethane layer was evaporated to give 6-methoxy-7-(3-piperidinopropoxy)-4-(6-trifluoromethylindol-5-yloxy)quinazoline (62 mg, 25%).

$^1$H NMR Spectrum: (DMSOd$_6$) 1.45 (m, 2H), 1.60 (m, 4H), 2.13 (m, 2H), 2.44 (m, 4H), 2.56 (m, 2H), 4.04 (s, 3H), 4.27 (t, 2H), 6.63 (br s, 1H), 7.33 (s, 1H), 7.40 (t, 1H), 7.61 (s, 1H), 7.67 (s, 1H), 7.75 (s, 1H) and 8.60 (m, 2H)

MS(ESI): 501 (MH)$^+$

| Elemental analysis | Found | C 62.0 | H 5.6 | N 10.6 |
|---|---|---|---|---|
| $C_{26}H_{27}F_3N_4O_3 \cdot 0.35\ H_2O$, | Requires | C 61.6 | H 5.5 | N 11.0% |

The starting material was prepared as follows:

Sodium hydride (1.8 g, of a 60% dispersion in oil, 45 mmol) was added in portions to a stirred solution of benzyl alcohol (10.8 g, 100 mmol) in DMA (100 ml) with vigorous stirring under an atmosphere of nitrogen at ambient temperature. After warming to 45° C. for 30 minutes the mixture was cooled to ambient temperature and added dropwise to a stirred solution of 2-chloro-5-nitro-trifluoromethylbenzene (11.3 g, 50 mmol) in DMA (30 ml), keeping the temperature below 10° C. The mixture was stirred at 25° C. for 1 hour, then acidified with acetic acid and evaporated to give a yellow solid. The residue was dissolved in dichloromethane, washed with water then dried (MgSO$_4$), and evaporated. The residue was suspended in a mixture of hexane (70 ml) and diethyl ether (10 ml) and the resulting solid filtered off to give 2-benzyloxy-5-nitro-trifluoromethylbenzene (6.6 g, 49%).

$^1$H NMR Spectrum: (CDCl$_3$) 5.33 (s, 2H), 7.13 (d, 1H), 7.31-7.43 (m, 5H), 8.35 (dd, 1H), 8.52 (d, 1H)

Potassium tert-butoxide (3.94 g, 35.4 mmol) was dissolved in anhydrous DMF (15 ml) and a mixture of 2-benzyloxy-5-nitro-trifluoromethylbenzene (3.5 g, 16.1 mmol) and 4-chlorophenylacetonitrile (2.96 g, 17.7 mmol) in DMF (20 ml) was added over 30 minutes keeping the temperature at −15° C. The mixture was stirred at −10° C. for 1 hour, then poured into 1M hydrochloric acid (150 ml) and the product extracted with dichloromethane (2×100 ml). The organic extracts were dried (MgSO$_4$) and purified by silica column chromatography eluting with dichloromethane/hexane (1/1) to give 5-benzyloxy-2-nitro-4-(trifluoromethyl)phenylacetonitrile (5.2 g, 77%).

$^1$H NMR Spectrum: (CDCl$_3$) 4.30 (s, 2H), 5.38 (s, 2H), 7.25 (s, 1H), 7.33-7.50 (m, 5H) and 8.51 (s, 1H)

MS(ESI): 335 (M−H)$^-$

5-Benzyloxy-2-nitro-4-(trifluoromethyl)phenylacetonitrile (2.22 g, 6.6 mmol) was dissolved in ethanol (45 ml), water (5 ml) and acetic acid (0.32 ml) then hydrogenated with 10% palladium on carbon at 1 atmosphere pressure for 2 hours. The catalyst was filtered off and filtrate evaporated to give 5-hydroxy-6-trifluoromethylindole (1.12 g, 84%).

$^1$H NMR Spectrum: (CDCl$_3$) 4.48 (s, 1H), 6.48 (m, 1H), 7.14 (s, 1H), 7.32 (t, 1H), 7.57 (s, 1H) and 8.20 (br s, 1H)

MS(ESI): 200 (M−H)$^-$

EXAMPLE 168

A mixture of 4-chloro-6-methoxy-7-(3-piperidinopropoxy)quinazoline (200 mg, 0.6 mmol), (prepared as described for the starting material in Example 67), potassium carbonate (248 mg, 1.8 mmol) and 5-hydroxy-6-methoxyindole (127 mg, 0.78 mmol) in DMA (4.0 ml) was stirred at 95° C. for 2.5 hours. The reaction mixture was allowed to cool to ambient temperature, filtered and the filtrate evaporated under vacuum. The residue was purified by silica column chromatography eluting with dichloromethane/methanol/0.880 aqueous ammonia (89/10/1) and the resulting oil triturated with diethyl ether to give 4-(6-methoxyindol-5-yloxy)-6-methoxy-7-(3-piperidinopropoxy)quinazoline (106 mg, 38%).

$^1$H NMR Spectrum: (DMSOd$_6$) 1.38 (m, 2H), 1.47 (m, 4H), 1.95 (m, 2H), 2.32 (m, 4H), 2.40 (m, 2H), 3.66 (3H, s), 3.97 (s, 3H), 4.28 (t, 2H), 6.35 (br s, 1H), 7.06 (s, 1H), 7.24 (t, 1H), 7.34 (s, 1H), 7.36 (s, 1H), 7.55 (s, 1H) and 8.41 (s, 1H)

MS(ESI): 463 (MH)$^+$

| Elemental analysis | | Found | C 65.2 | H 6.8 | N 11.2 |
|---|---|---|---|---|---|
| $C_{26}H_{30}N_4O_4 \cdot 1.0\ H_2O$, 0.3 diethyl ether | Requires | C 64.9 | H 7.0 | N 11.1% |

The 5-hydroxy-6-methoxyindole starting material was made as follows:

5-Benzyloxy-6-methoxyindole (253 mg, 1.0 mmol) was hydrogenated at 1 atmosphere pressure in methanol (10 ml) with 10% palladium on carbon (50 mg) for 2 hours at 25° C.

The catalyst was filtered off and the filtrate evaporated to give 5-hydroxy-6-methoxyindole (141 mg, 87%).

$^1$H NMR Spectrum: (CDCl$_3$) 3.92 (s, 3H), 5.40 (s, 1H), 6.42 (br s, 1H), 6.87 (s, 1H), 7.07 (m, 1H), 7.13 (s, 1H), 7.93 (br s, 1H)

MS(ESI): 162 (M−H)$^−$

EXAMPLE 169

A mixture of 4-chloro-6-methoxy-7-(3-piperidinopropoxy)quinazoline (200 mg, 0.595 mmol), (prepared as described for the starting material in Example 67), potassium carbonate (411 mg, 2.98 mmol) and 4-hydroxyindole (103 mg, 0.774 mmol) in DMA (2.0 ml) was stirred at 85° C. for 3 hours and allowed to cool to ambient temperature. The reaction mixture was filtered and the filtrate evaporated to give a solid residue. The residue was purified by silica column chromatography, with gradient elution using dichloromethane with 0%, 2%, 4%, 10% methanolic ammonia to give 4-(indol-4-yloxy)-6-methoxy-7-(3-piperidinopropoxy)quinazoline (131 mg, 51%).

$^1$H NMR Spectrum: (DMSOd$_6$) 1.39 (m, 2H), 1.50 (m, 4H), 1.98 (t, 2H), 2.35 (m, 4H), 2.40 (t, 2H), 3.98 (s, 3H), 4.25 (t, 2H), 6.10 (t, 1H), 6.90 (d, 1H), 7.15 (t, 1H), 7.30 (t, 1H), 7.35 (d, 1H), 7.38 (s, 1H), 7.62 (s, 1H), 8.45 (s, 1H) and 11.29 (s, 1H)

MS(ESI): 433 (MH)$^+$ m.p. 80-82° C.

EXAMPLE 170

A mixture of 4-chloro-6-methoxy-7-(3-piperidinopropoxy)quinazoline (200 mg, 0.595 mmol), (prepared as described for the starting material in Example 67), potassium carbonate (411 mg, 2.98 mmol) and 3-hydroxycarbazole (142 mg, 0.774 mmol) in DMA (2.0 ml) was stirred at 85° C. for 3 hours then allowed to cool to ambient temperature. The reaction mixture was filtered and the filtrate evaporated to give a solid residue. The residue was purified by silica column chromatography with gradient elution using dichloromethane with 0%, 2%, 4%, 10% methanolic ammonia to give 4-(9H-carbazol-3-yloxy)-6-methoxy-7-(3-piperidinopropoxy) quinazoline (212 mg, 74%).

$^1$H NMR Spectrum: (DMSOd$_6$) 1.39 (m, 2H), 1.50 (m, 4H), 2.35 (m, 4H), 2.40 (t, 2H), 3.98 (s, 3H), 4.25 (t, 2H), 7.05 (dd, 1H), 7.15 (t, 1H), 7.35 (t, 1H), 7.38 (s, 1H), 7.40 (s, 1H), 7.50 (d, 1H), 7.60 (s, 1H), 8.10 (d, 1H), 8.15 (d, 1H), 8.55 (s, 1H) and 11.33 (s, 1H)

MS(ESI): 483 (MH)$^+$

EXAMPLE 171

A mixture of 4-chloro-6-methoxy-7-(3-piperidinopropoxy)quinazoline (84 mg, 0.24 mmol), (prepared as described for the starting material in Example 67), potassium carbonate (162 mg, 1.18 mmol) and ethyl 7-chloro-5-hydroxyindole-2-carboxylate (62 mg, 0.26 mmol) in DMA (2.0 ml) was stirred at 100° C. for 2 hours and allowed to cool to ambient temperature. The reaction mixture was filtered and the filtrate evaporated. The residue was purified by silica column chromatography using gradient elution dichloromethane with 2.5%, 5%, 10% methanol, then dichloromethane with 2% ammonia) to give 4-(7-chloro-2-(ethoxycarbonyl)indol-5-yloxy)-6-methoxy-7-(3-piperidinopropoxy)quinazoline (78 mg, 63%).

$^1$H NMR Spectrum: (DMSOd$_6$) 1.30 (t, 3H), 1.40 (m, 2H), 1.50 (m, 4H), 1.98 (t, 2H), 2.35 (m, 4H), 2.40 (t, 2H), 3.98 (s, 3H), 4.25 (t, 2H), 4.30 (q, 2H), 7.15 (m, 1H), 7.18 (s, 1H), 7.60 (s, 1H), 8.40 (s, 1H) and 12.60 (s, 1H)

MS(ESI): 539 (MH)$^+$

| Elemental analysis | Found | C 61.2 | H 5.9 | N 10.3 |
|---|---|---|---|---|
| C$_{28}$H$_{31}$ClN$_4$O$_5$ 0.5 H$_2$O | Requires | C 61.4 | H 5.9 | N 10.2% |

The starting material was prepared as follows:

2-Chloro-4-methoxyaniline (2.719 g, 14 mmol) was added to 8.0M aqueous hydrochloric acid (15 ml) and the suspension cooled to −5° C. Sodium nitrite (1.063 g, 15.4 mmol) was added as a solution in water (3 ml). After addition the pH was brought to pH 4-5 by addition of sodium acetate. In a separate flask, ethyl-α-ethyl acetoacetate (2.18 ml, 15.4 mmol) in ethanol (15 ml) at −5° C. was treated with potassium hydroxide (864 mg, 15.4 mmol) in water (3 ml) followed by ice (4 g). The diazonium salt prepared initially was then added rapidly to the second solution and stirred at −5° C. for 4 hours then allowed to warm to ambient temperature overnight. The mixture was extracted with ethyl acetate (3×100 ml) and the organic solutions dried (MgSO$_4$), filtered and solvent removed in vacuo to give an orange oil. This oil was dissolved in ethanol (35 ml) and the flask fitted with a reflux condenser. Concentrated sulphuric acid (35 ml) was then added dropwise, this caused the reaction to reflux with no external heating. The solution was stirred for 1 hour then the solvent removed by evaporation. The residue was taken up in water then extracted with ethyl acetate (3×100 ml). The organic solution was washed with brine, dried (MgSO$_4$), filtered and evaporated to give a brown oil. The crude oil was purified by silica column chromatography, eluting with dichloromethane to give ethyl 7-chloro-5-methoxyindole-2-carboxylate (125 mg, 4%).

$^1$H NMR Spectrum: (CDCl$_3$) 1.40 (t, 3H), 3.98 (s, 3H), 4.40 (q, 2H), 6.60 (d, 1H), 7.05 (d, 1H), 7.15 (s, 1H) and 9.10 (s, 1H)

MS(ESI): 254 (MH)$^+$

To a solution of ethyl 7-chloro-5-methoxyindole-2-carboxylate (82 mg, 0.323 mmol) in dichloromethane (5 ml) at −78° C. was added boron tribromide (1.07 ml of a 1.0M solution in DCM, 1.07 mmol) and the reaction stirred at −78° C. for 30 minutes then allowed to warm to ambient temperature overnight. Water was carefully added and the pH adjusted to pH 6-7 by addition of 2M sodium hydroxide. The mixture was extracted with ethyl acetate (2×50 ml), and the organic solution washed with brine, dried (MgSO$_4$), filtered and evaporated to give ethyl 7-chloro-5-hydroxyindole-2-carboxylate (55 mg, 71%) as an orange solid.

$^1$H NMR Spectrum: (DMSOd$_6$) 1.38 (t, 3H), 4.35 (q, 2H), 6.60 (d, 1H), 6.95 (d, 1H), 7.10 (d, 1H), 9.80 (s, 1H) and 11.80 (s, 1H)

MS(ESI): 238 (MH)$^−$

EXAMPLE 172

A mixture of 7-benzyloxy-4-chloro-6-methoxyquinazoline (1.5 g, 4.99 mmol), (prepared as described for the starting material in Example 1), potassium carbonate (2.07 g, 15 mmol) and 2,3-dimethyl-5-hydroxyindole (1.21 g, 7.5 mmol), (Arch. Pharm. 1972, 305, 159), in DMF (75 ml) was stirred at 100° C. for 2 hours and allowed to cool to ambient temperature. The reaction mixture was filtered and the filtrate evaporated. The solid residue was purified by silica column chromatography, eluting with 2.5% methanol in dichoromethane to give 7-benzyloxy-4-(2,3-dimethylindol-5-yloxy)-6-methoxyquinazoline (976 mg, 46%).

$^1$H NMR Spectrum: (CDCl$_3$) 2.10 (s, 3H), 2.30 (s, 3H), 3.98 (s, 3H), 5.30 (s, 2H), 6.85 (dd, 1H), 7.20 (d, 1H), 7.25 (d, 1H), 7.40 (m, 6H), 7.60 (s, 1H), 8.40 (s, 1H) and 10.74 (s, 1H)

MS(ESI): 426 (MH)$^+$

EXAMPLE 173

A mixture of 7-benzyloxy-4-(2,3-dimethylindol-5-yloxy)-6-methoxyquinazoline (912 mg, 2.14 mmol), (prepared as described in Example 172), di-tert-butyl dicarbonate (1.871 g, 8.56 mmol) and 4-dimethylaminopyridine (70 mg, 5 mol %) in acetonitrile (40 ml) was stirred at ambient temperature overnight. The solvent was then evaporated and the residue dissolved in ethyl acetate. The organic solution was washed with 2N hydrochloric acid twice and then with brine. The organic layer was then dried (MgSO$_4$), filtered and evaporated to give 7-benzyloxy-4-(1-tert-butoxycarbonyl-2,3-dimethylindol-5-yloxy)-6-methoxyquinazoline (1.108 g, 99%) as a yellow solid.

$^1$H NMR Spectrum: (CDCl$_3$) 1.70 (s, 9H), 2.08 (s, 3H), 2.50 (s, 3H), 4.10 (s, 3H), 5.35 (s, 2H), 7.15 (dd, 1H), 7.38 (m, 6H), 7.60 (s, 1H), 8.20 (d, 1H) and 8.60 (s, 1H)

MS(ESI): 526 (MH)$^+$

EXAMPLE 174

A mixture of 4-chloro-6-methoxy-7-(3-morpholinopropoxy)quinazoline (225 mg, 0.67 mmol), (prepared as described for the starting material in Example 1), potassium carbonate (106 mg, 0.77 mmol) and 2-hydroxyquinoline (111 mg, 0.76 mmol) in DMF (7.5 ml) was stirred at 100° C. for 5 hours and allowed to cool to ambient temperature. The reaction mixture was treated with 1.0 N aqueous sodium hydroxide solution (40 ml) and allowed to stir at ambient temperature for a few minutes. The reaction mixture was extracted 3 times with ethyl acetate and the extracts washed with water and brine. The organic extracts were dried over magnesium sulphate, filtered and the solvent removed by evaporation. The residue was purified by silica column chromatography eluting with dichloromethane/methanol (95/5) to give a solid which was triturated with ether, filtered and dried to give 6-methoxy-7-(3-morpholinopropoxy)-4-(quinolin-2-yloxy)-quinazoline (33 mg, 11%).

$^1$H NMR Spectrum: (DMSOd$_6$) 1.98 (m, 2H), 2.38 (m, 4H), 2.48 (t, 2H), 3.58 (m, 4H), 3.98 (s, 3H), 4.26 (t, 2H), 7.41 (s, 1H), 7.52 (d, 1H), 7.58 (s, 1H), 7.64 (t, 1H), 7.78 (m, 1H), 7.88 (d, 1H), 8.06 (d, 1H), 8.56 (d, 1H) and 8.57 (s, 1H)

MS(ESI): 447 (MH)$^+$

| Elemental analysis | Found | C 66.8 | H 5.9 | N 12.4 |
| --- | --- | --- | --- | --- |
| $C_{25}H_{26}N_4O_4$ 0.2 H$_2$O | Requires | C 66.7 | H 5.9 | N 12.4% |

EXAMPLE 175

A mixture of 4-chloro-6-methoxy-7-(3-morpholinopropoxy)quinazoline (225 mg, 0.67 mmol), (prepared as described for the starting material in Example 1), potassium carbonate (106 mg, 0.77 mmol) and 5-hydroxyquinoline (111 mg, 0.77 mmol) in DMF (7.5 ml) was stirred at 100° C. for 5 hours and allowed to cool to ambient temperature. The reaction mixture was treated with 1.0 N aqueous sodium hydroxide solution (40 ml) and allowed to stir at ambient temperature for a few minutes. The resulting precipitate was filtered off, washed with water and air dried for a short while. The damp solid was dissolved in dichloromethane, filtered through phase separating paper and the filtrate evaporated under vacuum. The residue was triturated with ether, filtered and dried to give 6-methoxy-7-(3-morpholinopropoxy)-4-(quinolin-5-yloxy)-quinazoline (178 mg, 59%).

$^1$H NMR Spectrum: (DMSO-d$_6$) 1.98 (m, 2H), 2.39 (m, 4H), 2.48 (t, 2H), 3.59 (t, 4H), 4.01 (s, 3H), 4.28 (t, 2H), 7.42 (s, 1H), 7.50 (m, 1H), 7.59 (d, 1H), 7.74 (s, 1H), 7.87 (t, 1H), 8.02 (d, 1H), 8.20 (m, 1H), 8.44 (s, 1H) and 8.96 (m, 1H)

MS(ESI): 447 (MH)$^+$

| Elemental analysis | Found | C 66.2 | H 5.7 | N 12.4 |
| --- | --- | --- | --- | --- |
| $C_{25}H_{26}N_4O_4$ 0.4 H$_2$O | Requires | C 66.2 | H 6.0 | N 12.4% |

EXAMPLE 176

A mixture of 4-chloro-6-methoxy-7-(3-(4-methylpiperazin-1-yl)propoxy)quinazoline (200 mg, 0.57 mmol), potassium carbonate (106 mg, 0.77 mmol) and 7-hydroxyquinoline (111 mg, 0.76 mmol) in DMF (7 ml) was stirred at 100° C. for 5 hours and allowed to cool to ambient temperature. The reaction mixture was treated with 1.0 N aqueous sodium hydroxide solution (40 ml) and allowed to stir at ambient temperature for a few minutes. The reaction mixture was extracted 4 times with ethyl acetate and the organic extracts washed with water and brine. The organic extracts were dried over magnesium sulphate, filtered and the solvent removed by evaporation. The residue was triturated with ether/isohexane, filtered and dried to give 6-methoxy-7-(3-(4-methylpiperazin-1-yl)propoxy)-4-(quinolin-7-yloxy)quinazoline (102 mg, 39%).

$^1$H NMR Spectrum: (DMSOd$_6$) 1.96 (m, 2H), 2.15 (s, 3H), 2.35 (m, 8H), 2.46 (t, 2H), 3.99 (s, 3H), 4.24 (t, 2H), 7.39 (s, 1H), 7.56 (m, 1H), 7.61 (m, 1H), 7.62 (s, 1H), 7.92 (d, 1H), 8.10 (d, 1H), 8.44 (d, 1H), 8.54 (s, 1H) and 8.92 (m, 1H)

MS(ESI): 460 (MH)$^+$

| Elemental analysis | Found | C 67.2 | H 6.2 | N 15.0 |
| --- | --- | --- | --- | --- |
| $C_{26}H_{29}N_5O_3$ 0.3 H$_2$O | Requires | C 67.2 | H 6.4 | N 15.1% |

The starting material was prepared as follows:

A solution of 1-(3-hydroxypropyl)-4-methylpiperazine (2.4 g, 15 mmol), (prepared as described for the starting material in Example 133), in dichloromethane (60 ml) was treated with triethylamine (4.6 ml, 33 mmol) and p-toluenesulphonyl chloride (3.2 g, 17 mmol) and stirred at ambient temperature for 2 hours. The solution was washed with saturated aqueous sodium hydrogen carbonate solution followed by water and filtered through phase separating paper. The filtrate was evaporated under vacuum to give 3-(4-methylpiperazin-1-yl)propyl-4-toluene sulphonate as an oil which crystallised on standing (3.7 g, 78%).

MS(ESI): 313 (MH)$^+$

A mixture of 2-amino-4-benzyloxy-5-methoxybenzamide (J. Med. Chem. 1977, vol 20, 146-149, 10 g, 0.04 mol) and Gold's reagent (7.4 g, 0.05 mol) in dioxane (100 ml) was stirred and heated at reflux for 24 hours. Sodium acetate (3.02 g, 0.037 mol) and acetic acid (1.65 ml, 0.029 mol) were added to the reaction mixture and it was heated for a further 3 hours. The mixture was evaporated, water was added to the residue, the solid was filtered off, washed with water and dried. Recrystallisation from acetic acid gave 7-benzyloxy-6-methoxy-3,4-dihydroquinazolin-4-one (8.7 g, 84%).

A mixture of 7-benzyloxy-6-methoxy-3,4-dihydroquinazolin-4-one (2.82 g, 0.01 mol), thionyl chloride (40 ml) and DMF (0.28 ml) was stirred and heated at reflux for 1 hour. The mixture was evaporated and azeotroped with toluene to give 7-benzyloxy-4-chloro-6-methoxyquinazoline hydrochloride (3.45 g).

4-Chloro-2-fluoro-phenol (264 mg, 1.8 mmol) was added to a solution of 7-benzyloxy-4-chloro-6-methoxyquinazoline hydrochloride (506 mg, 1.5 mmol) in pyridine (8 ml) and the mixture heated at reflux for 45 minutes. The solvent was removed by evaporation and the residue partitioned between ethyl acetate and water. The organic layer was washed with 0.1M HCl, water and brine, dried (MgSO$_4$) and the solvent removed by evaporation. The solid residue was triturated with petroleum ether and the crude product collected by filtration and purified by flash chromatography eluting with methylene chloride/ether (9/1) to give 7-benzyloxy-4-(4-chloro-2-fluorophenoxy)-6-methoxyquinazoline (474 mg, 77%) as a cream solid.

m.p. 179-180° C.

$^1$H NMR Spectrum: (DMSOd$_6$) 3.99(s, 3H); 5.36(s, 2H); 7.35-7.5(m, 4H); 7.55-7.65(m, 5H); 7.72(d, 1H); 8.6(s, 1H)

MS-ESI: 411 [MH]$^+$

| Elemental analysis: | Found | C 63.38 | H 4.07 | N 6.78 |
|---|---|---|---|---|
| C$_{22}$H$_{16}$ClFN$_2$O$_3$ 0.06 H$_2$O 0.05 CH$_2$Cl$_2$ | Requires | C 63.64 | H 3.93 | N 6.73% |

A solution of 7-benzyloxy-4-(4-chloro-2-fluorophenoxy)-6-methoxyquinazoline (451 mg, 1.1 mmol) in TFA (4.5 ml) was heated at reflux for 3 hours. The mixture was diluted with toluene and the volatiles removed by evaporation. The residue was triturated with methylene chloride, collected by filtration, washed with ether and dried under vacuum to give 4-(4-chloro-2-fluorophenoxy)-7-hydroxy-6-methoxyquinazoline (320 mg, 90%).

$^1$H NMR Spectrum: (DMSOd$_6$) 4.0(s, 3H); 7.27(s, 1H); 7.43(dd, 1H); 7.56(t, 1H); 7.57(s, 1H); 7.72(dd, 1H); 8.5(s, 1H)

MS-ESI: 321 [MH]$^+$

A mixture of the trifluoroacetic acid salt of 4-(4-chloro-2-fluorophenoxy)-7-hydroxy-6-methoxyquinazoline (3.2 g, 7.4 mmol), potassium carbonate (6.1 g, 44.2 mmol) and 3-(4-methyl-1-piperazinyl)propyl-4-toluene sulphonate (3.0 g, 9.6 mmol) in DMF (60 ml) was stirred at 90° C. for 5 hours and allowed to cool to ambient temperature. The reaction mixture was poured into water (700 ml) and extracted 5 times with ethyl acetate. The combined extracts were washed with water, saturated aqueous sodium hydrogen carbonate, water and saturated brine. The ethyl acetate solution was dried over magnesium sulphate, filtered and the solvent removed under vacuum to give a residue which was purified by silica column chromatography, eluting with dichloromethane/methanol/0.880 aqueous ammonia (100/8/1). The relevant fractions were combined and evaporated under vacuum to give a residue which was triturated with ether, filtered and dried to give 4-(4-chloro-2-fluorophenoxy)-6-methoxy-7-(3-(4-methylpiperazin-1-yl)propoxy)quinazoline (1.64 g, 48%).

$^1$H NMR Spectrum: (DMSOd$_6$) 1.95 (m, 2H), 2.14 (s, 3H), 2.35 (m, 8H), 2.44 (t, 2H), 3.96 (s, 3H), 4.22 (t, 2H), 7.38 (s, 1H), 7.40 (m, 1H), 7.54 (m, 2H), 7.68 (m, 1H) and 8.55 (s, 1H)

MS(ESI): 461 (MH)$^+$

| Elemental analysis | Found | C 59.6 | H 5.7 | N 12.2 |
|---|---|---|---|---|
| C$_{23}$H$_{26}$ClFN$_4$O$_3$ | Requires | C 59.9 | H 5.7 | N 12.2% |

4-(4-Chloro-2-fluorophenoxy)-6-methoxy-7-(3-(4-methylpiperazin-1-yl)propoxy)quinazoline (2.6 g, 5.6 mmol) was treated with 2.0 N aqueous hydrochloric acid (45 ml) and the mixture stirred at 95° C. for 2 hours. The mixture was cooled, basified by the addition of solid sodium hydrogen carbonate and the water removed by azeotroping with toluene. The residue was purified by silica column chromatography eluting with dichloromethane/methanol/0.880 aqueous ammonia (50/8/1) to give 6-methoxy-7-(3-(4-methylpiperazin-1-yl)propoxy)-3,4-dihydroquinazolin-4-one (1.8 g, 96%).

MS(ESI): 333 (MH)$^+$

6-Methoxy-7-(3-(4-methylpiperazin-1-yl)propoxy)-3,4-dihydroquinazolin-4-one (2.15 g, 6.48 mmol) was suspended in thionyl chloride (25 ml) and DMF (0.18 ml) and stirred under reflux for 2 hours. The thionyl chloride was evaporated under vacuum and the residue azeotroped twice with toluene. The residue was taken up in water, basified with saturated with aqueous sodium hydrogen carbonate solution and the aqueous solution extracted 4 times with dichloromethane. The combined extracts were washed with water and brine then filtered through phase separating paper. The filtrate was evaporated under vacuum and the residue purified by silica column chromatography eluting with dichloromethane/methanol/0.880 aqueous ammonia (100/8/1) to give a solid which was triturated with a little acetone, filtered and dried to give 4-chloro-6-methoxy-7-(3-(4-methylpiperazin-1-yl)propoxy)quinazoline (1.2 g, 53%). This was used without further purification.

MS(ESI): 351 (MH)$^+$

EXAMPLE 177

A mixture of 4-chloro-6-methoxy-7-(2-(2-methoxyethoxy)ethoxy)quinazoline (200 mg, 0.64 mmol), potassium carbonate (102 mg, 0.74 mmol) and 7-hydroxyquinoline (107 mg, 0.74 mmol) in DMSO (5 ml) was stirred at 100° C. for 5 hours and allowed to cool to ambient temperature. The mixture was poured into water, washed with dichloromethane and extracted twice with a 10/1 mixture of dichloromethane/methanol. The extracts were washed with water and brine, dried over magnesium sulphate, filtered and the filtrate evaporated under vacuum. The residue was purified by silica column chromatography, eluting with dichloromethane/methanol/0.880 aqueous ammonia (100/8/1) to give an oil which crystallised on trituration with ether to give 6-methoxy-7-(2-(2-methoxyethoxy)ethoxy)-4-(quinolin-7-yloxy)quinazoline (148 mg, 55%).

$^1$H NMR Spectrum: (DMSOd$_6$) 3.25 (s, 3H), 3.50 (t, 2H), 3.60 (t, 2H), 3.80 (t, 2H), 4.00 (s, 3H), 4.30 (t, 2H), 7.40 (s, 1H), 7.55 (m, 1H), 7.60 (m, 1H), 7.65 (s, 1H), 7.90 (d, 1H), 8.10 (d, 1H), 8.40 (m, 1H), 8.50 (s, 1H) and 8.90 (m, 1H)

MS(ESI): 422 (MH)$^+$

| Elemental analysis | Found | C 65.8 | H 5.2 | N 10.0 |
|---|---|---|---|---|
| C$_{23}$H$_{23}$N$_3$O$_5$ | Requires | C 65.6 | H 5.5 | N 10.0% |

The starting material was prepared as follows:

Diethyl azodicarboxylate (864 μl, 5.5 mmol) was added dropwise to a mixture of 7-hydroxy-6-methoxy-3-((pivaloyloxy)methyl)-3,4-dihydroquinazolin-4-one (1.2 g, 3.9 mmol) (prepared as described for the starting material in Example 12), triphenylphosphine (1.44 g, 5.5 mmol) and 2-(2-methoxyethoxy)ethanol (653 μl, 5.5 mmol) in methylene chloride (70 ml) cooled at 0° C. The mixture was stirred for 1.5 hours at ambient temperature and the solvent was removed by evaporation. The residue was purified by column chromatography eluting with a mixture of ethyl acetate/methylene chloride (50/50 followed by 80/20). The purified solid was suspended in ether, collected by filtration and dried under vacuum to give 6-methoxy-7-(2-(2-methoxyethoxy)ethoxy)-3-((pivaloyloxy)methyl)-3,4-dihydroquinazolin-4-one (1.70 g, 100%).

$^1$H NMR Spectrum: (DMSOd$_6$) 1.13(s, 9H); 3.26(s, 3H); 3.5(m, 2H); 3.65(m, 2H); 3.85(m, 2H); 3.91(s, 3H); 4.3(m, 2H); 5.9(s, 2H); 7.2(s, 1H); 7.5(s, 1H); 8.4(s, 1H)

Saturated methanolic ammonia (20 ml) was added to a solution of 6-methoxy-7-(2-(2-methoxyethoxy)ethoxy)-3-((pivaloyloxy)methyl)-3,4-dihydroquinazolin-4-one (2.26 g, 5.5 mmol) in a mixture of ethanol (40 ml) and methylene chloride (15 ml). The mixture was stirred for 24 hours at ambient temperature, and further methanolic ammonia (20 ml) was added. The mixture was stirred for a further 24 hours at ambient temperature and the volatiles were removed by evaporation. The residue was triturated with ether, collected by filtration, dried under vacuum to give 6-methoxy-7-(2-(2-methoxyethoxy)cthoxy)-3,4-dihydroquinazolin-4-one (975 mg, 78%).

$^1$H NMR Spectrum: (DMSOd$_6$) 3.25(s, 3H); 3.45(t, 2H); 3.6(t, 2H); 3.8(t, 2H); 3.9(s, 3H); 4.2(t, 2H); 7.15(s, 1H); 7.45(s, 1H); 8.0(s, 1H)

MS-EI: 294 [M]$^+$

A solution of 6-methoxy-7-(2-(2-methoxyethoxy)ethoxy)-3,4-dihydroquinazolin-4-one (930 mg, 3.16 mmol) in thionyl chloride (15 ml) and DMF (150 μl) was heated at 60° C. for 1.5 hours. The mixture was allowed to cool and the volatiles were removed by evaporation and by azeotroping with toluene. The residue was dissolved in methylene chloride and 5% aqueous sodium hydrogen carbonate solution was added until the aqueous layer was at pH8. The organic layer was separated, washed with brine, dried (MgSO$_4$) and the solvent removed by evaporation. The residue was purified by flash chromatography eluting with ethyl acetate to give 4-chloro-6-methoxy-7-(2-(2-methoxyethoxy)ethoxy)quinazoline (863 mg, 87%).

$^1$H NMR Spectrum: (DMSOd$_6$) 3.24(s, 3H); 3.47(m, 2H); 3.62(m, 2H); 3.84(t, 2H); 4.01(s, 3H); 4.25(t, 2H); 7.41(s, 1H); 7.49(s, 1H); 8.88(s, 1H)

EXAMPLE 178

A mixture of 4-chloro-6-methoxy-7-(3-piperidinopropoxy)quinazoline (168 mg, 0.5 mmol), (prepared as described for the starting material in Example 67), potassium carbonate (207 mg, 1.5 mmol), 3-methyl-5-hydroxyindole (88 mg, 0.6 mmol), (Can. J. Chem. 1964, 42, 514), and DMA (2.0 ml) was purged with nitrogen for 5 minutes at 25° C. This mixture was then stirred at 100° C. for 3 hours then allowed to cool to ambient temperature, was filtered and the filtrate evaporated under vacuum. The residue was purified by silica column chromatography eluting with dichloromethane/methanolic ammonia (7M) (90/10) to give 6-methoxy-4-(3-methylindol-5-yloxy)-7-(3-piperidinopropoxy)quinazoline (155 mg, 69%).

$^1$H NMR Spectrum: (DMSOd$_6$) 1.37 (m, 2H), 1.50 (m, 4H), 1.95 (m, 2H), 2.21 (s, 3H), 2.34 (m, 4H), 2.42 (t, 2H), 3.96 (s, 3H), 4.22 (t, 2H), 6.95 (dd, 1H), 7.16 (s, 1H), 7.35 (m, 3H), 7.58 (s, 1H), 8.48 (s, 1H) and 10.82 (s, 1H)

MS(ESI): 447 (MH)$^+$

| Elemental analysis | Found | C 68.2 | H 6.8 | N 12.6 |
|---|---|---|---|---|
| C$_{26}$H$_{30}$N$_4$O$_3$ 0.5 H$_2$O, | Requires | C 68.5 | H 6.8 | N 12.3% |

EXAMPLE 179

Using an analogous procedure to that described in Example 178, 4-chloro-6-methoxy-7-(3-(pyrrolidin-1-yl)propoxy)quinazoline, (prepared as described for the starting material in Example 9), was used to give 6-methoxy-4-(3-methylindol-5-yloxy)-7-(3-(pyrrolidin-1-yl)propoxy) quinazoline (154 mg, 79%).

$^1$H NMR Spectrum: (DMSOd$_6$) 1.68 (m, 4H), 1.97 (m, 2H), 2.22 (s, 3H), 2.43 (m, 4H), 2.55 (t, 2H), 3.96 (s, 3H), 4.22 (t, 2H), 6.93 (dd, 1H), 7.16 (s, 1H), 7.35 (m, 3H), 7.58 (s, 1H), 8.48 (s, 1H) and 10.82 (br s, 1H)

MS(ESI): 433 (MH)$^+$ m.p. 75-77° C.

EXAMPLE 180

Using an analogous procedure to that described in Example 178, 4-chloro-6-methoxy-7-(2-piperidinoethoxy) quinazoline was used to give 6-methoxy-4-(3-methylindol-5-yloxy)-7-(2-piperidinoethoxy)quinazoline (156 mg, 80%).

$^1$H NMR Spectrum: (DMSOd$_6$) 1.38 (m, 2H), 1.50 (m, 4H), 2.24 (s, 3H), 2.73 (t, 2H), 3.96 (s, 3H), 4.28 (t, 2H), 6.93 (dd, 1H), 7.16 (s, 1H), 7.32 (d, 1H), 7.37 (m, 2H), 7.58 (s, 1H), 8.47 (s, 1H) and 10.82 (br s, 1H)

MS(ESI): 433 (MH)$^+$

| Elemental analysis | Found | C 67.0 | H 6.5 | N 13.0 |
|---|---|---|---|---|
| C$_{25}$H$_{28}$N$_4$O$_3$ 0.75 H$_2$O | Requires | C 67.3 | H 6.6 | N 12.6% |

The starting material was prepared as follows:

1-(2-Chloroethyl)piperidine hydrochloride (0.83 g, 4.5 mmol) was added to 7-hydroxy-6-methoxy-4-phenoxyquinazoline (1.0 g, 3.73 mmol), (prepared as described for the starting material in Example 1), and potassium carbonate (2.6 g, 18.8 mmol) in DMF (30 ml), and the mixture heated at 110° C. for 2.5 hours and allowed to cool. The insolubles were removed by filtration, and the volatiles were removed from the filtrate by evaporation. The residue was purified by column chromatography eluting with methylene chloride/methanol (9/1) to give 6-methoxy-4-phenoxy-7-(2-piperidinoethoxy)quinazoline (1.2 g, 85%).

$^1$H NMR Spectrum: (DMSOd$_6$) 1.38(m, 2H); 1.50(m, 4H); 2.4-2.5(m, 4H); 2.75(t, 2H); 3.95(s, 3H); 4.27(t, 2H); 7.30(m, 3H); 7.40(s, 1H); 7.46(m, 2H); 7.54(s, 1H); 8.52(s, 1H)

MS-ESI: 380 [MH]$^+$

A mixture of 6-methoxy-4-phenoxy-7-(2-piperidinoethoxy)quinazoline (1.15 g, 3.0 mmol) and 2M hydrochloric acid (20 ml) was heated at 90° C. for 2 hours and allowed to cool. The mixture was neutralised with solid sodium hydrogen carbonate and extracted with methylene chloride. The organic phase was separated, passed through phase separating paper and the volatiles removed by evaporation to give a solid product (230 mg). The aqueous phase was adjusted to pH10, the resulting precipitate was collected by filtration, washed with water and dried to give a second crop of product (220 mg). The products were combined to give 6-methoxy-7-(2-piperidinoethoxy)-3,4-dihydroquinazolin-4-one (450 mg, 50%).

MS-ESI: 304 [MH]+

A mixture of 6-methoxy-7-(2-piperidinoethoxy)-3,4-dihydroquinazolin-4-one (440 mg, 1.45 mmol), thionyl chloride (15 ml) and DMF (3 drops) was heated at reflux for 3 hours then allowed to cool. The excess thionyl chloride was removed by evaporation and the residue was azeotroped with toluene to give a crude 4-chloro-6-methoxy-7-(2-piperidinoethoxy)quinazoline hydrochloride (640 mg).

4-Chloro-6-methoxy-7-(2-piperidinoethoxy)quinazoline hydrochloride was suspended in methylene chloride (10 ml) and saturated aqueous sodium hydrogen carbonate solution (5 ml) then stirred vigorously for 10 minutes at ambient temperature. The layers were separated and the organic layer dried ($MgSO_4$) then evaporated to give a white solid. This solid was triturated with methanol (2.5 ml), the resulting solid filtered off, washed with cold methanol and dried to give 4-chloro-6-methoxy-7-(2-piperidinoethoxy)quinazoline (0.36 g).

EXAMPLE 181

Using an analogous procedure to that described in Example 178, 4-chloro-6-methoxy-7-(3-(N-methyl-N-methylsulphonylamino)propoxy)quinazoline, (prepared as described for the starting material in Example 152), was used to give 6-methoxy-4-(3-methylindol-5-yloxy)-7-(3-(N-methyl-N-methylsulphonylamino)propoxy)quinazoline (104 mg, 49%).

$^1$H NMR Spectrum: ($DMSOd_6$) 2.08 (m, 2H), 2.22 (s, 3H), 2.80 (s, 3H), 2.88 (s, 3H), 3.27 (t, 2H), 3.97 (s, 3H), 4.22 (t, 2H), 6.95 (dd, 1H), 7.17 (s, 1H), 7.35 (m, 3H), 7.59 (s, 1H), 8.48 (s, 1H) and 10.82 (br s, 1H)

MS(ESI): 471 (MH)+

| Elemental analysis | Found | C 57.0 | H 5.6 | N 11.4 |
|---|---|---|---|---|
| $C_{23}H_{26}F_4N_4O_5S$ 0.5 $H_2O$, | Requires | C 57.5 | H 5.7 | N 11.7% |

EXAMPLE 182

A mixture of 4-chloro-6-methoxy-7-(3-(pyrrolidin-1-yl)propoxy)quinazoline (218 mg, 0.68 mmol), (prepared as described for the starting material in Example 9), 5-hydroxy-1H-pyrrolo[2,3-b]pyridine (100 mg, 0.75 mmol) and potassium carbonate (280 mg, 2.0 mmol) in DMF (4 ml) was stirred at 95° C. for 6 hours and allowed to cool to ambient temperature. The reaction mixture was treated with 1.0 N aqueous sodium hydroxide solution and allowed to stir at ambient temperature for a few minutes. The resulting precipitate was filtered off, washed with water and air dried to give a crude product which was purified by column chromatography, eluting with dichloromethane/methanol/880 ammonia (100/8/1). The relevant fractions were combined and evaporated 'in vacuo' to give a white solid. This was recolumned using dichloromethane/methanol (4/1) solvent to give a white solid which was triturated with acetone, filtered and dried to give 6-methoxy-7-(3-(pyrrolidin-1-yl)propoxy)-4-(1H-pyrrolo[2,3-b]pyridin-5-yloxy)quinazoline (50 mg, 18%).

m.p. 184.0-185.5° C.

$^1$H NMR Spectrum: ($DMSOd_6$) 1.70 (m, 4H), 1.99 (m, 2H), 2.46 (m, 4H), 2.58 (t, 2H), 4.00 (s, 3H), 4.26 (t, 2H), 6.48 (t, 1H), 7.36 (s, 1H), 7.55 (t, 1H), 7.60 (s, 1H), 7.92 (d, 1H), 8.19 (d, 1H), 8.50 (s, 1H) and 11.78 (br s, 1H)

MS(ESI): 420 (MH)+

| Elemental analysis | Found | C 63.9 | H 5.9 | N 16.1 |
|---|---|---|---|---|
| $C_{23}H_{25}N_5O_3$ 0.7 $H_2O$ | Requires | C 63.9 | H 6.2 | N 16.2% |

The starting material was prepared as follows:—

A suspension of 5-methoxy-1H-pyrrolo[2,3-b]pyridine (210 mg, 1.42 mmol), (Heterocycles 50, (2), 1065-1080, (1999)), in dichloromethane (10 ml) was stirred in an inert atmosphere, a 1.0M solution of boron tribromide in dichloromethane (4.3 ml, 4.3 mmol) added dropwise and the mixture stirred at ambient temperature overnight. The reaction mixture was taken to pH6 by the dropwise addition of 5N aqueous sodium hydroxide and further diluted with water. The aqueous solution was extracted several times with ethyl acetate, the extracts combined, washed with water followed by brine and dried over magnesium sulphate. The ethyl acetate solvent was removed 'in vacuo' and the residue purified by column chromatography, eluting with dichloromethane/methanol (95/5), to give a white solid. The solid was triturated with ether, filtered and dried to give 5-hydroxy-1H-pyrrolo[2,3-b]pyridine (108 mg, 57%).

m.p. 206-209° C.

$^1$H NMR Spectrum: ($DMSOd_6$) 6.25 (s, 1H), 7.27 (s, 1H), 7.33 (s, 1H), 7.82 (s, 1H), 9.00 (s, 1H) and 11.20 (s, 1H)

MS(ESI): 135 (MH)+

EXAMPLE 183

A mixture of 4-chloro-6-methoxy-7-(3-piperidinopropoxy)quinazoline (168 mg, 0.5 mmol), (prepared as described for the starting material in Example 67), potassium carbonate (345 mg, 5.0 mmol), 5-hydroxy-2-indolecarboxylic acid (106 mg, 0.6 mmol) and DMA (2.0 ml) was purged with nitrogen for 5 minutes at 25° C. This mixture was then stirred at 100° C. for 3 hours, allowed to cool to ambient temperature, filtered and the filtrate evaporated under vacuum. The residue was purified on octadecylsilane reverse phase silica eluting with acetonitrile/water/trifluoroacetic acid (as a gradient from 30/69.8/0.2 to 50/49.8/0.2) and the product further purified by silica column chromatography eluting with dichloromethane/methanolic ammonia (7M) (90/10) to give 4-(2-carboxyindol-5-yloxy)-6-methoxy-7-(3-piperidinopropoxy)quinazoline (85 mg 36%).

$^1$H NMR Spectrum: ($DMSOd_6$) 1.43 (m, 2H), 1.56 (m, 4H), 2.04 (m, 2H), 2.59 (m, 6H), 3.97 (s, 3H), 4.24 (t, 2H), 7.01 (s, 1H), 7.11 (dd, 1H), 7.36 (s, 1H), 7.48 (m, 2H), 7.58 (s, 1H), 8.48 (s, 1H) and 11.53 (br s, 1H)

MS(ESI): 477 (MH)+

EXAMPLE 184

4-Chloro-6-methoxy-7-(3-methylsulphonylpropoxy) quinazoline (0.15 g, 0.45 mmol), (prepared as described for the starting material in Example 50), potassium carbonate (94 mg, 0.68 mmol) and 7-hydroxyquinoline (79 mg, 0.54 mmol) were suspended in anhydrous DMF (1.5 ml) and heated to 90° C. overnight. The compound was precipitated upon addition of water. The precipitate was collected by filtration, washed with water and dried under vacuum over phosphorus pentoxide to give 6-methoxy-7-(3-methylsulphonylpropoxy)-4-(quinolin-7-yloxy)quinazoline (161 mg, 81%).

¹H NMR Spectrum: (DMSOd₆) 2.26 (m, 2H); 3.08 (s, 3H); 3.35 (m, 2H); 4.03 (s, 3H); 4.38 (m, 2H); 7.45 (s, 1H); 7.60 (m, 1H); 7.65 (m, 1H); 7.70 (s, 1H); 7.95 (d, 1H); 8.15 (d, 1H); 8.46 (d, 1H); 8.60 (s, 1H); 8.95 (d, 1H)

MS(ESI): 440 [MH]⁺

EXAMPLES 185-188

Using an analogous procedure to that described in Example 184, 4-chloro-6-methoxy-7-(3-methylsulphonylpropoxy)quinazoline (0.15 g, 0.45 mmol), (prepared as described for the starting material in Example 50), was reacted with the appropriate phenols to give the compounds in Table X.

TABLE X

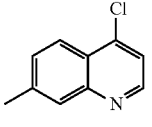

| Example number | weight (mg) | yield % | MS-ESI [MH]+ | AR | note |
|---|---|---|---|---|---|
| 185 | 199 | 93 | 474 | 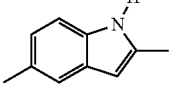 | a |
| 186 | 171 | 85 | 422 | 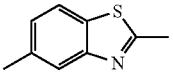 | b |
| 187 | 183 | 88 | 460 | 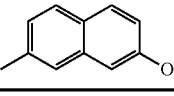 | c |
| 188 | 83 | 40 | 455 |  | d | a) Using 4-chloro-7-hydroxyquinoline (96 mg) gave 4-(4-chloroquinolin-7-yloxy)-6-methoxy-7-(3-methylsulphonylpropoxy)quinazoline.

¹H NMR Spectrum: (DMSOd₆) 2.24 (m, 2H); 3.04 (s, 3H); 3.35 (m, 2H); 3.99 (s, 3H); 4.32 (m, 2H); 7.42 (s, 1H); 7.64 (s, 1H); 7.80 (d, 2H); 8.04 (d, 1H); 8.29 (d, 1H); 8.55 (s, 1H); 8.87 (d, 1H)

b) Using 5-hydroxy-2-methylindole (80 mg) gave 6-methoxy-4-(2-methylindol-5-yloxy)-7-(3-methylsulphonylpropoxy)quinazoline.

¹H NMR Spectrum: (DMSOd₆) 2.24 (m, 2H); 2.40 (s, 3H); 3.05 (s, 3H); 3.35 (m, 2H); 4.0 (s, 3H); 4.32 (m, 2H); 6.13 (s, 1H); 6.88 (d, 1H); 7.25 (d, 1H); 7.32 (d, 1H); 7.39 (s, 1H); 7.60 (s, 1H); 8.50 (s, 1H)

c) Using 5-hydroxy-2-methylbenzothiazole (90 mg) gave 6-methoxy-4-(2-methyl-1,3-benzothiazol-5-yloxy)-7-(3-methylsulphonylpropoxy)quinazoline.

¹H NMR Spectrum: (DMSOd₆) 2.24 (m, 2H); 2.28 (s, 3H); 3.05 (s, 3H); 3.35 (m, 2H); 4.0 (s, 3H); 4.32 (m, 2H); 7.36 (d, 1H); 7.41 (s, 1H); 7.65 (s, 1H); 7.87 (d, 1H); 8.11 (d, 1H); 8.53 (s, 1H)

d) Using 2,7-dihydroxynaphtalene (87 mg) gave 4-(7-hydroxy-2-naphtyloxy)-6-methoxy-7-(3-methylsulphonylpropoxy)quinazoline.

¹H NMR Spectrum: (DMSOd₆) 2.24 (m, 2H); 3.05 (s, 3H); 3.35 (m, 2H); 3.98 (s, 3H); 4.32 (m, 2H); 7.06 (d, 1H); 7.12 (s, 1H); 7.18 (d, 1H); 7.40 (d, 1H); 7.59 (m, 2H); 7.85 (m, 2H); 8.55 (d, 1H); 9.8 (br s, 1H)

EXAMPLE 189

To a portion of 2-chloro-5-hydroxybenzimidazole (191 mg, 0.75 mmol) in DMF (3 ml) was added sodium hydride (60 mg, 1.5 mmol) under argon at ambient temperature. Ten minutes later 4-chloro-6-methoxy-7-(1-methylpiperidin-4-yl)methoxyquinazoline (200 mg, 0.62 mmol), (prepared as described for the starting material in Example 10), was added and the mixture heated at 100° C. for 2 hours. More 2-chloro-5-hydroxybenzimidazole (30 mg, 0.12 mmol) and sodium hydride (11 mg, 0.28 mmol) were then added as the reaction was found to be incomplete. The heating was continued for an additional 1 hour. Work-up using ethyl acetate and a saturated aqueous solution of ammonium chloride followed by drying of the organic phase (MgSO₄) and evaporation of the solvent gave a crude product which was adsorbed on alumina using dichloromethane/methanol and purified by flash chromatography using neutral alumina and dichloromethane/methanol (98:2) as the eluent. Evaporation of the solvent and trituration in ether gave 4-(2-chloro-1H-benzimidazol-6-yloxy)-6-methoxy-7-((1-methylpiperidin-4-yl)methoxy)quinazoline (46 mg, 16%).

¹H NMR Spectrum: (DMSOd₆+TFA) 1.60 (m, 2H); 2.05 (d, 2H); 2.15 (m, 1H); 2.80 (s, 3H); 3.05 (m, 2H); 3.55 (m, 2H); 4.05 (s, 3H); 4.15 (d, 2H); 7.20 (dd, 1H); 7.50 (dd, 2H); 7.65 (d, 1H); 7.70 (s, 1H); 8.80 (s, 1H)

MS(ESI): 454 [MH]⁺

The starting material was synthesised as follows:

2-Chloro-5-methoxybenzimidazole (0.3 g, 1.64 mmol) was suspended in dichloromethane (20 ml) under argon followed by the addition of boron tribromide (233 ul, 2.46 mmol). The reaction mixture was stirred for 2 hours at ambient temperature. The solvent was evaporated and the resulting powder was added in portions to methanol (30 ml). Silica was added and the solvent was evaporated. The resulting powder was placed on the top of a silica column and the product was eluted off using dichloromethane/methanol (95/5). Evaporation of the solvent and trituration in ether gave 2-chloro-5-hydroxybenzimidazole (440 mg, 99%).

EXAMPLE 190

Using an analogous procedure to that described in Example 189, 4-chloro-6-methoxy-7-(1-methylpiperidin-4-yl)methoxyquinazoline, (prepared as described for the starting material in Example 10), was reacted with 5-hydroxy-2-methylbenzimidazole (200 mg, 0.62 mmol) and after work-up and purification on a 10 g silica ISOLUTE column using successively dichloromethane, dichloromethane/methanol (95/5) and dichloromethane/methanol saturated with ammonia (95/5), gave 6-methoxy-4-(2-methyl-1H-benzimidazol-6-yloxy)-7-((1-methylpiperidin-4-yl)methoxy)quinazoline (68 mg, 25%).

¹H NMR Spectrum: (DMSOd₆+TFA) 1.60 (m, 2H); 2.10 (m, 2H); 2.20 (m, 1H); 2.80 (s, 3H); 2.85 (s, 3H); 3.05 (m, 2H); 3.50 (m, 2H); 4.05 (s, 3H); 4.15 (d, 2H); 7.50 (s, 1H); 7.55 (d, 1H); 7.70 (s, 1H); 7.85 (d, 1H); 7.90 (d, 1H); 8.65 (s, 1H)

MS(ESI): 434 [MH]⁺

The starting material was prepared as follows:

The free base of 4-methoxy-1,2-phenylenediamine dihydrochloride (10 g) was obtained by shaking it with a mixture of ethyl acetate and a saturated aqueous solution of sodium hydrogen carbonate. The organic phase was then washed with brine, dried (MgSO$_4$) and the solvent evaporated. The obtained dark oil (6.08 g, 50 mmol) was solubilised in toluene (60 ml) and p-toluene sulfonic acid (60 mg) and triethyl orthoacetate (9.15 ml, 50 mmol) were added in turn. The mixture was heated to 110° C. until no more ethanol distilled off. The remaining toluene was removed by rotary evaporation and the residue purified by flash chromatography using dichloromethane/methanol (95/5) as the eluent. The obtained dark oil was triturated in ether and the solid collected by filtration to give 5-methoxy-2-methylbenzimidazole (4.15 g, 51%).

$^1$H NMR Spectrum: (DMSOd$_6$+TFA) 2.75 (s, 3H); 3.85 (s, 3H); 7.15 (dd, 1H); 7.25 (s, 1H); 7.70 (d, 1H)

Using an analogous procedure to that described for the synthesis of 2-chloro-5-hydroxybenzimidazole in Example 189, 5-methoxy-2-methylbenzimidazole (4.0 g, 25 mmol) was reacted with boron tribromide (7 ml, 74 mmol) in dichloromethane (150 ml) to give, after work-up and purification by flash chromatography using dichloromethane/methanol (90/10), 5-hydroxy-2-methylbenzimidazole (4.4 g, 76%).

$^1$H NMR Spectrum: (DMSOd$_6$) 2.70 (s, 3H); 6.95 (dd, 1H); 7.00 (d, 1H); 7.55 (d, 1H)

EXAMPLE 191

4-Chloro-6-methoxy-7-((1-methylpiperidin-4-yl)methoxy)quinazoline (200 mg, 0.62 mmol), (prepared as described for the starting material in Example 10), was suspended in DMF (3 ml) under argon. 3-Cyano-7-hydroxyquinoline (116 mg, 0.68 mmol) and potassium carbonate (129 mg, 0.93 mmol) were added and the reaction mixture was heated at 95° C. for 90 minutes. Upon cooling to ambient temperature the mixture was diluted with dichloromethane and poured on the top of an ISOLUTE silica column. Elution was done using successively dichloromethane, dichloromethane/methanol (95/5) and dichloromethane/methanol saturated with ammonia (95/5). Evaporation of the solvent and trituration of the solid in ether gave 4-(3-cyanoquinolin-7-yloxy)-6-methoxy-7-((1-methylpiperidin-4-yl)methoxy)quinazoline (244 mg, 86%).

$^1$H NMR Spectrum: (DMSOd$_6$+TFA) 1.60 (m, 2H); 2.10 (m, 3H); 2.85 (s, 3H); 3.05 (m, 2H); 3.55 (m, 2H); 4.05 (s, 3H); 4.20 (d, 2H); 7.55 (s, 1H); 7.80 (s, 1H); 7.85 (dd, 1H); 8.15 (s, 1H); 8.3 (d, 1H); 8.85 (s, 1H); 9.20 (s, 1H); 9.25 (s, 1H)

MS(ESI): 456 [MH]$^+$456

The starting material was prepared as follows:

m-Anisidine (50 g, 407 mmol) and diethyl ethoxymethylenemalonate (102 g, 407 mmol) were heated at 60° C. for 20 minutes. Diphenyl ether (270 ml) was then added and the temperature was raised to 240° C. over 30 minutes. The ethanol formed distilled off. Heating was maintained at this temperature for 1 hour then the reaction mixture was allowed to cool to 120° C. at which point the reaction mixture was diluted with heptane and allowed to stand overnight at ambient temperature. The brown solid was collected by filtration and washed with methanol and ether to give ethyl 7-methoxy-4-oxo-1,4-dihydroquinoline-3-carboxylate (45 g, 45%). This reaction was repeated twice.

$^1$H NMR Spectrum: (DMSOd$_6$) 1.25 (t, 3H); 3.85 (s, 3H); 4.20 (q, 2H); 6.95 (d, 1H); 7.00 (s, 1H); 8.05 (d, 1H); 8.50 (s, 1H)

Phosphorus oxychloride (88 ml) was added to ethyl 7-methoxy-4-oxo-1,4-dihydroquinoline-3-carboxylate (58 g, 235 mmol) and the mixture was heated at reflux for 45 minutes under anhydrous conditions. Upon cooling to ambient temperature, phosphorus oxychloride was evaporated and the solid residue was added in portions to a mixture of ammonia (150 ml) and ice (200 g). External cooling as well as further addition of ammonia to maintain the pH around 8 was needed during this hydrolysis step. The aqueous phase was extracted with dichloromethane and the organic phase was washed with water and brine, dried (MgSO$_4$) and concentrated to about 300 ml. Pentane (400 ml) was added and the precipitate formed collected by filtration. Drying under vacuum gave 4-chloro-3-ethoxycarbonyl-7-methoxyquinoline (45.5 g, 73%).

$^1$H NMR Spectrum: (DMSOd$_6$) 1.40 (t, 3H); 4.00 (s, 3H); 4.45 (q, 2H); 7.45 (dd, 1H); 7.55 (d, 1H); 8.30 (d, 1H); 9.10 (s, 1H)

4-Chloro-3-ethoxycarbonyl-7-methoxyquinoline (43 g, 162 mmol) was dissolved in acetic acid (250 ml), with 10% palladium on charcoal (1.5 g) and hydrogenated at atmospheric pressure during 8 hours. The catalyst was removed by filtration over a pad of celite and the solvent evaporated. The residue was diluted with water and the pH adjusted to 7-8 with a saturated solution of sodium hydrogen carbonate. The solid was collected by filtration, washed with water and dried under vacuum over phosphorus pentoxide to give 3-ethoxycarbonyl-7-methoxyquinoline (33g, 88%) as a beige powder.

$^1$H NMR Spectrum: (DMSOd$_6$) 1.40 (t, 3H); 3.95 (s, 3H); 4.40 (q, 2H); 7.35 (dd, 1H); 7.50 (d, 1H); 8.15 (d, 1H); 8.90 (d, 1H); 9.25 (d, 1H)

3-Ethoxycarbonyl-7-methoxyquinoline (28 g, 120 mmol) was added to a methanol solution saturated with ammonia. The suspension was stirred at ambient temperature in a glass pressure vessel for 2 weeks. The white solid was collected by filtration, washed with methanol and dried under vacuum to give 3-carbamoyl-7-methoxyquinoline (21 g, 86%).

$^1$H NMR Spectrum (DMSOd$_6$) 3.95 (s, 3H); 7.35 (dd, 1H); 7.45 (d, 1H); 7.60 (br s, 1H); 8.00 (d, 1H); 8.20 (br s, 1H); 8.75 (s, 1H); 9.25 (s, 1H)

3-Carbamoyl-7-methoxyquinoline (4 g, 20 mmol) was suspended in anhydrous dichloromethane (60 ml) under argon. Anhydrous dimethyl sulphoxide (2.25 ml, 32 mmol) was added, the mixture was cooled to −78° C. and a solution of oxalyl chloride (2.08 ml, 24 mmol) in dichloromethane (20 ml) was added dropwise over the course of 1 hour. 15 Minutes after the end of the addition, triethylamine (8.3 ml, 60 mmol) was added dropwise and the heterogeneous reaction mixture stirred for an additional 1 hour at −78° C. then left to rise to ambient temperature. The unreacted starting material was removed by filtration and the filtrate was diluted with water and extracted with ethyl acetate. The organic phases were combined, washed with brine, dried (MgSO$_4$) and the solvent evaporated. The residue was purified by flash chromatography using dichloromethane/methanol (97/3). The obtained solid was triturated with ether and gave, after drying under vacuum, 3-cyano-7-methoxyquinoline (1.47 g, 40%).

$^1$H NMR Spectrum (DMSOd$_6$) 4.00 (t, 3H); 7.40 (dd, 1H); 7.50 (d, 1H); 8.00 (d, 1H); 8.95 (s, 1H); 9.10 (d, 1H)

3-Cyano-7-methoxyquinoline (380 mg, 2.1 mmol) was suspended in benzene (10 ml), aluminium trichloride (826 mg, 6.2 mmol) was added and the mixture heated at reflux for 30 minutes. More aluminium trichloride (275 mg, 2.1 mmol) was added and the mixture refluxed for a further 2 hours. The solvent was evaporated, the dark green solid was added to ice and extracted with ethyl acetate. The organic phase was washed with brine, dried (MgSO$_4$) and evaporated. The solid was found to contain some aluminium salts which were removed as follows. The solid was dissolved in dichloromethane (200 ml) was stirred vigorously with a saturated sodium hydrogen carbonate solution for 1 hour. The product was collected by filtration of the aqueous phase and dried over phosphorus pentoxide under vacuum to give 3-cyano-7-hydroxyquinoline (238 mg, 68%).

$^1$H NMR Spectrum (DMSOd$_6$) 7.25 (d, 1H); 7.30 (d, 1H); 7.95 (d, 1H); 8.85 (d, 1H); 9.00 (d, 1H)

EXAMPLE 192

To 6-methoxy-7-(3-morpholinopropoxy)-4-((1-tertbutoxycarbonyl-1,2,3,4-tetrahydroquinolin-6-yl)oxy)quinazoline (110 mg, 0.2 mmol) in solution in dichloromethane (3 ml) was added TFA (0.3 ml) and the mixture stirred for 1 hour at ambient temperature. The solvents were evaporated and the remaining oil was diluted with dichloromethane and the pH adjusted to 9 with a saturated solution of sodium hydrogen carbonate. The organic phase was washed with, brine, dried (MgSO$_4$), filtered and the solvent evaporated to give 6-methoxy-7-(3-morpholinopropoxy)-4-(1,2,3,4-tetrahydroquinolin-6-yloxy)quinazoline (84 mg, 93%).

$^1$H NMR Spectrum: (CDCl$_3$) 1.95 (m, 2H); 2.15 (m, 2H); 2.45 (m, 4H); 2.60 (t, 2H); 2.80 (t, 2H); 3.35 (t, 2H); 3.75 (m, 4H); 3.90 (br s, 1H); 4.05 (s, 3H); 4.30 (t, 2H); 6.55 (d, 1H); 6.85 (m, 2H); 7.30 (s, 1H); 7.55 (s, 1H); 8.65 (s, 1H)

MS(ESI): 451 [MH]$^+$

| Elemental analysis: | Found | C 66.4 | H 6.9 | N 12.4 |
|---|---|---|---|---|
| C$_2$H$_1$N$_1$O$_1$; 1 HCl, 2 H$_2$O | Requires | C 66.7 | H 6.7 | N 12.4% |

The starting material was prepared as follows:

6-Hydroxyquinoline (1 g, 6.9 mmol) was dissolved in methanol and hydrogenated at 3 atmospheres pressure with platinum(IV) oxide (276 mg) over 24 hours. The catalyst was removed by filtration over a pad of celite and the solvent was evaporated. The solid was washed with ether to give 6-hydroxy-(1,2,3,4)-tetrahydroquinoline (698 mg, 68%).

$^1$H NMR Spectrum (DMSOd$_6$) 1.75 (m, 2H); 2.60 (m, 2H); 3.05 (m, 2H); 4.90 (br s, 1H); 6.30 (m, 3H); 8.25 (br s, 1H)

6-Hydroxy-(1,2,3,4)-tetrahydroquinoline (250 mg, 1.7 mmol) was suspended in acetone (1 ml) and trichloromethane (1 ml) under argon. Tert-Butoxycarbonylanhydride (365 mg, 1.7 mmol) in solution in acetone was added dropwise followed by THF (2 ml) to help the solubilisation. The reaction mixture was stirred overnight at ambient temperature, the solvent was evaporated, the residue was partitioned between ethyl acetate and water, the organic phase was washed with water, brine, dried (MgSO$_4$), filtered and the solvent evaporated. The resulting gum was purified by flash chromatography using dichloromethane/methanol (97/3) as solvent. Evaporation of the solvent gave 6-hydroxy-4-(1-tertbutoxycarbonyl-1,2,3,4-tetrahydroquinoline (344 mg, 82%) as a brown foam.

$^1$H NMR Spectrum (DMSOd$_6$) 1.50 (m, 9H); 1.90 (m, 2H); 2.70 (t, 2H); 3.65 (t, 2H); 4.75 (br s, 1H); 6.55 (d, 1H); 6.65 (dd, 1H); 7.45 (d, 1H)

6-Hydroxy-4-(1-tertbutoxycarbonyl-1,2,3,4-tetrahydroquinoline (82 mg, 0.32 mmol) was dissolved in anhydrous dimethylformamide under argon, with potassium carbonate (61 mg, 0.44 mmol) and 4-chloro-6-methoxy-7-(3-morpholinopropoxy)quinazoline (100 mg, 0.3 mmol), (prepared as described for the starting material in Example 1). No reaction occurred after 2 hours at 60° C. Sodium hydride (12 mg, 0.3 mmol) was added and the reaction mixture was heated at 120° C. for 90 minutes. The cooled mixture was poured into water and ethyl acetate. The organic phase was washed with water, brine, dried (MgSO$_4$), filtered and the solvent evaporated. The residue was purified by flash chromatography using first dichloromethane/methanol (97/3) as solvent. Evaporation of the solvent gave 6-methoxy-7-(3-morpholinopropoxy)-4-((1-tertbutoxycarbonyl-1,2,3,4-tetrahydroquinolin-6-yl)oxy)quinazoline (115 mg, 71%) as a white solid.

$^1$H NMR Spectrum: (DMSOd$_6$) 1.55 (s, 9H); 1.95 (m, 2H); 2.15 (m, 2H); 2.50 (m, 4H); 2.60 (t, 2H); 2.85 (t, 2H); 3.75 (m, 6H); 4.05 (s, 3H); 4.30 (t, 2H); 7.00 (m, 2H); 7.35 (s, 1H); 7.55 (s, 1H); 7.80 (d, 1H); 8.65 (s, 1H)

EXAMPLE 193

Using an analogous procedure to that described in Example 192, 4-(1-tertbutoxycarbonyl-2,3-dihydro-indol-5-yloxy)-6-methoxy-7-(3-(pyrrolidin-1-yl)propoxy)quinazoline (169 mg, 0.32 mmol) was reacted with TFA (1 ml) to give, after work-up and purification, 4-(2,3-dihydro-1H-indol-5-yl)oxy-6-methoxy-7-(3-(pyrrolidin-1-yl)propoxy) quinazoline (124 mg, 91%).

$^1$H NMR Spectrum: (CDCl$_3$) 1.90 (br, 4H); 2.30 (br, 2H); 2.70 (br d, 6H); 3.10 (t, 2H); 3.65 (t, 2H); 4.05 (s, 3H); 4.30 (t, 2H); 6.70 (d, 1H); 6.80 (dd, 1H); 7.00 (s, 1H); 7.30 (s, 1H); 7.55 (s, 1H); 8.65 (s, 1H)

MS(ESI): 421 [MH]$^+$

The starting material was prepared as follows:

5-Hydroxyindole (2 g, 15 mmol) was dissolved in methanol (60 ml) under argon. Sodium cyanoborohydride (1.89 g, 30 mmol) and trifluoroboron etherate (4.2 ml, 33 mmol) were added and the mixture was heated at reflux for 3 hours then left to cool to ambient temperature. The solvent was evaporated and the residue was partitioned between ethyl acetate and water. Ammonia was added to adjust the pH to 10 and the aqueous phase was extracted with more ethyl acetate. The combined organic phases were washed with water, brine, dried (MgSO$_4$), filtered and the solvent evaporated. The residue was purified by flash chromatography using dichloromethane/methanol (95/5) as solvent. Evaporation of the solvent gave 5-hydroxy-2,3-dihydro-1H-indole (1.45 g, 73%) as an off white solid.

$^1$H NMR Spectrum: (DMSOd$_{6+}$TFA) 3.15 (t, 2H); 3.70 (t, 2H); 6.75 (dd, 1H); 6.85 (d, 1H); 7.30 (d, 1H)

5-Hydroxy-2,3-dihydro-1H-indole (1.5 g, 11.1 mmol) was suspended in a mixture of acetone (7 ml) trichloromethane (7 ml) and THF (6 ml). tert-Butoxycarbonylanhydride (2.42 g, 11 mmol) in solution in THF (7 ml) was added dropwise. The reaction mixture was stirred overnight at ambient temperature, the solvent was evaporated, the residue was partitioned between ethyl acetate and water, the organic phase was washed with water, brine, dried (MgSO$_4$), filtered and the solvent evaporated. The solid was purified by flash chromatography using dichloromethane/methanol (95/5) as solvent. Evaporation of the solvent gave 5-hydroxy-(1-tertbutoxycarbonyl)-2,3-dihydroindole (2.28 g, 87%) as an off white solid.

$^1$H NMR Spectrum: (CDCl$_3$) 3.05 (t, 2H); 3.95 (br s, 2H); 4.70 (br s, 1H); 6.60 (d, 1H); 6.65 (s, 1H); 7.70 (br s, 1H)

Sodium hydride (22 mg, 0.56 mmol) was suspended in anhydrous dimethylformamide under argon. 5-Hydroxy-(1-tertbutoxycarbonyl)-2,3-dihydroindole (131 mg, 0.56 mmol) was added followed 10 minutes later by 4-chloro-6-methoxy-7-(3-(pyrrolidin-1-yl)propoxy)quinazoline (150 mg, 0.47 mmol), (prepared as described for the starting material in Example 9). The reaction mixture was heated at 110° C. for 3 hours, cooled to ambient temperature and partitioned between ethyl acetate and water. The organic phase was washed with water, brine, dried (MgSO$_4$), filtered and the solvent evaporated. The residue was purified by flash chromatography using increasingly polar solvent mixtures starting with dichloromethane/methanol (90/10) and ending with dichloromethane/methanol/methanol saturated with ammonia (80/15/5). Evaporation of the solvent gave 4-(1-tertbutoxycarbonyl-2,3-dihydro-indol-5-yloxy)-6-methoxy-7-(3-(pyrrolidin-1-yl)propoxy)quinazoline (178 mg, 73%) as a white solid.

$^1$H NMR Spectrum: (DMSOd$_6$) 1.60 (s, 9H); 1.80 (m, 4H); 2.20 (m, 2H); 2.55 (m, 4H); 2.70 (t, 2H); 3.15 (t, 2H); 4.05 (br s, 5H); 4.30 (t, 2H); 7.00 (d, 1H); 7.05 (s, 1H); 7.30 (s, 1H); 7.55 (s, 1H); 7.90 (br s, 1H); 8.60 (s, 1H)

EXAMPLE 194

Using an analogous procedure to that described in Example 192, 4-(1-tertbutoxycarbonyl-2,3-dihydro-indol-5-yloxy)-6-methoxy-7-(1-methylpiperidin-4-ylmethoxy)quinazoline (191 mg, 0.37 mmol) was reacted with TFA (1 ml) to give, after work-up and purification, 4-(2,3-dihydro-indol-5-yloxy)-6-methoxy-7-(1-methylpiperidin-4-ylmethoxy)quinazoline (103 mg, 67%).

$^1$H NMR Spectrum: (CDCl$_3$) 1.65 (m, 2H); 2.00 (m, 3H); 2.25 (m, 2H); 2.45 (s, 3H); 3.10 (m, 4H); 3.65 (t, 2H); 4.05 (s, 3H); 4.10 (d, 2H); 6.70 (d, 1H); 6.85 (dd, 1H); 7.0 (s, 1H); 7.25 (s, 1H); 7.55 (s, 1H); 8.60 (s, 1H)

MS(ESI): 421 [MH]$^+$

The starting material was prepared as follows:

Using an analogous procedure to that described in Example 193, 4-chloro-6-methoxy-7-(1-methylpiperidin-4-ylmethoxy)quinazoline (150 mg, 0.47 mmol), (prepared as described for the starting material in Example 10), was reacted with 5-hydroxy-(1-tertbutoxycarbonyl)-2,3-dihydroindole (132 mg, 0.56 mmol), (prepared as described for the starting material in Example 193), to give, after work-up and purification, 4-(1-tertbutoxycarbonyl-2,3-dihydro-indol-5-yloxy)-6-methoxy-7-(1-methylpiperidin-4-ylmethoxy)quinazoline (197 mg, 81%) as a white solid.

$^1$H NMR Spectrum: (CDCl$_3$) 1.50 (br s, 1H); 2.00 (m, 5H); 2.30 (s, 3H); 2.90 (d, 2H); 3.15 (t, 2H); 4.05 (br s, 7H); 7.05 (br s, 2H); 7.30 (s, 1H); 7.55 (s, 1H); 7.95 (br s, 1H); 8.60 (s, 1H)

EXAMPLE 195

To a suspension of 4-chloro-6-methoxy-7-(2-piperidinoethoxy)quinazoline (250 mg, 0.78 mmol), (prepared as described for the starting material in Example 180), in DMF (10 ml) was added anhydrous potassium carbonate (320 mg, 2.30 mmol) and 7-hydroxyquinoline (135 mg, 0.94 mmol), and the reaction heated under reflux at 90° C for 1 hour. The reaction was cooled to ambient temperature and 1N aqueous sodium hydroxide added. The resulting precipitate was filtered, washed with water and acetone, and dried under suction to give 6-methoxy-7-(2-piperidinoethoxy)-4-(quinolin-7-yloxy)quinazoline (248 mg, 0.58 mmol, 75%) as a white solid.

$^1$H NMR Spectrum: d$_H$ (300 MHz, CDCl$_3$): 1.5 (2H, m; NCH$_2$CH$_2$CH$_2$), 1.6 (4H, m; 2×NCH$_2$CH$_2$), 2.6 (4H, t; 2×NCH$_2$); 2.9 (2H, t; NCH$_2$), 4.1 (3H, s; OCH$_3$), 4.3 (2H, t; OCH$_2$), 7.3 (1H, s; ArH), 7.4 (1H, dd; ArH), 7.5 (1H, dd; ArH), 7.6 (1H, s; ArH), 7.9 (1H, d; ArH), 8.0 (1H, d; ArH), 8.2 (1H, d; ArH), 8.6 (1H, s; ArH) and 8.9 (1H, dd; ArH)

m/z (ESP+) 431 (MH$^+$, 100%)

EXAMPLE 196

To a suspension of 7-benzyloxy-4-chloro-6-methoxyquinazoline (1.82 g, 6.1 mmol), (prepared as described for the starting material in Example 1), in DMF (50 ml) was added potassium carbonate (2.50 g, 18.1 mmol) and 7-hydroxyquinoline (1.06 g, 7.3 mmol), and the reaction heated under reflux at 90C for 4 hours. The reaction was poured into 1N aqueous sodium hydroxide and the resulting precipitate filtered, washed with water, and dried under suction. Further drying in a vacuum oven gave 7-benzyloxy-6-methoxy-4-(quinolin-7-yloxy)quinazoline (1.50 g, 3.7 mmol, 60%) as a cream solid.

$^1$H NMR Spectrum: d$_H$ (300 MHz, DMSO-d$_6$): 4.0 (3H, s; OCH$_3$), 5.4 (2H, s; OCH$_2$), 7.3-7.7 (9H, m; 9×ArH), 7.9 (1H, br s; ArH), 8.1 (1H, d; ArH), 8.4 (1H, d; ArH), 8.5 (1H, s; ArH) and 8.9 (1H, d; ArH)

EXAMPLE 197

A solution of 7-benzyloxy-6-methoxy-4-(quinolin-7-yloxy)quinazoline (1.50 g, 3.70 mmol), (prepared as described in Example 196), in trifluoroacetic acid (50 ml) was heated at reflux for 150 minutes. The reaction was concentrated in vacuo and the reaction neutralised with saturated aqueous ammonium hydroxide. The resulting precipitate was filtered, washed with acetone and dried under suction to give 7-hydroxy-6-methoxy-4-(quinolin-7-yloxy)quinazoline (0.90 g, 2.82 mmol, 76%) as a white solid.

$^1$H NMR Spectrum: d$_H$ (300 MHz, DMSO-d$_6$): 4.0 (3H, s; OCH$_3$), 7.1 (1H, s; ArH), 7.3-7.4 (3H, m; 3×ArH), 7.9 (1H, br s; ArH), 8.1 (1H, d; ArH), 8.4-8.5 (2H, d; 2×ArH) and 8.9 (1H, d; ArH)

m/z (ESP+) 320 (MH$^+$, 100%)

EXAMPLE 198

To a suspension of 7-hydroxy-6-methoxy-4-(quinolin-7-yloxy)quinazoline (450 mg, 1.40 mmol), (prepared as described in Example 197), in DMF (50 ml) was added anhydrous potassium carbonate (773 mg, 5.60 mmol) and 4-(2-hydroxyethyl)morpholine (335 mg, 1.80 mmol), and the reaction heated under reflux for 2 hours. The DMF was evaporated in vacuo, and the residue partitioned between dichloromethane and 1N aqueous sodium hydroxide. The mixture was extracted with dichloromethane (3×200 ml), dried (MgSO$_4$) and concentrated in vacuo. The crude product was triturated with hexane/ether to afford a solid which was filtered and dried under suction to give 6-methoxy-7-(2-morpholinoethoxy)-4-(quinolin-7-yloxy)quinazoline (430 mg, 1.00 mmol, 71%) as a light brown solid.

$^1$H NMR Spectrum: d$_H$ (300 MHz, CDCl$_3$): 2.7 (4H, t; 2×NCH$_2$); 3.0 (2H, t; NCH$_2$), 3.7 (4H, t; 2×OCH$_2$), 4.1 (3H, s; OCH$_3$), 4.4 (2H, t; OCH$_2$), 7.2 (1H, s; ArH), 7.4 (1H, dd; ArH), 7.5 (1H, dd; ArH), 7.6 (1H, s; ArH), 7.9 (1H, d; ArH), 8.0 (1H, br s; ArH), 8.2 (1H, d; ArH), 8.6 (1H, s; ArH) and 8.9 (1H, dd; ArH)

m/z (ESP+) 433 (MH$^+$, 100%)

| Elemental analysis | Found | C 65.0 | H 5.6 | N 12.6 |
|---|---|---|---|---|
| C$_{24}$H$_{24}$N$_4$O$_4$ 0.5H$_2$O | Requires | C 65.3 | H 5.7 | N 12.7% |

EXAMPLE 199

To a solution of 7-hydroxy-6-methoxy-4-(quinolin-7-yloxy)quinazoline (100 mg, 0.31 mmol), (prepared as described in Example 197), and (S)-(+)-5-(hydroxymethyl)-2-pyrrolidinone (101 mg, 0.47 mmol) in dichloromethane (10 ml) was added triphenylphosphine (244 mg, 0.93 mmol) and DEAD (0.15 ml, 162 mg, 0.93 mmol), and the reaction stirred at ambient temperature overnight. The reaction mixture was placed directly onto a 2g SCX ion-exchange column, and eluted with dichloromethane, then dichloromethane/methanol (4/1), then dichloromethane/methanol/ammonium hydroxide (20/5/1). The appropriate fractions were concentrated in vacuo, and the residue triturated with ether to give a solid which was filtered and dried under suction to give (5S)-6-methoxy-7-(5-oxo-pyrrolidin-2-ylmethoxy)-4-(quinolin-7-yloxy)quinazoline (55 mg, 0.13 mmol, 43%) as a yellow solid.

$^1$H NMR Spectrum: $d_H$ (300 MHz, CDCl$_3$): 2.3-2.5 (4H, m; 2×pyrrolidinone-CH$_2$), 4.0-4.1 (4H, m; pyrrolidinone-CH; OCH$_3$), 4.2-4.3 (2H, m; OCH$_2$), 6.1 (1H, br s; NH), 7.3 (1H, s; ArH), 7.4 (1H, dd; ArH), 7.5 (1H, dd; ArH), 7.9 (1H, d; ArH), 8.0 (1H, br s; ArH), 8.2 (1H, d; ArH), 8.6 (1H, s; ArH) and 8.9 (1H, dd; ArH)

m/z (ESP+) 417 (MH$^+$, 100%)

EXAMPLE 200

To a solution of 4-chloro-6-methoxy-7-(3-(pyrrolidin-1-yl)propoxy)quinazoline (100 mg, 0.31 mmol), (prepared as described for the starting material in Example 9), in DMF (10 ml) was added potassium carbonate (124 mg, 0.9 mmol, 3 eq.) followed by 2-hydroxycarbazole (66 mg, 0.36 mmol, 1.2 eq.) and the reaction heated at 100° C. for 4 hours. The DMF was removed in vacuo, the residue dissolved in dichloromethane and placed onto a 2g SCX ion-exchange column. Elution with dichloromethane, followed by 20% methanol/dichloromethane then 20% methanol/dichloromethane+3% ammonium hydroxide, gave the crude product as a brown solid. Further purification by silica bond elut chromatography eluting with dichloromethane to 15% methanol/dichloromethane+1% ammonium hydroxide, followed by trituration with ether gave 4-(9H-carbazol-2-yloxy)-6-methoxy-7-(3-(pyrrolidin-1-yl)propoxy)quinazoline (31 mg, 22%) as a white solid.

$^1$H NMR Spectrum: $d_H$ (300 MHz, DMSO-d$_6$) 1.7 (4H, m; 2×pyrrolidine-CH$_2$), 2.0 (2H, t; OCH$_2$CH$_2$), 2.5 (4H, m; 2×pyrrolidine-NCH$_2$), 2.6 (2H, t; NCH$_2$), 4.0 (3H, s; OCH$_3$), 4.2 (2H, t; OCH$_2$), 7.1 (1H, br d; ArH), 7.2 (1H, t; ArH), 7.3-7.4 (3H, m; 3×ArH), 7.5 (1H, br d; ArH), 7.6 (1H, s; ArH), 8.1-8.2 (2H, m; 2×ArH), 8.5 (1H, s; ArH), 11.3 (1H, s; carbazole NH)

m/z (ESP+) 469 (MH$^+$, 100%)

EXAMPLE 201

To a solution of 7-hydroxy-4-(indol-5-ylamino)-6-methoxyquinazoline (98 mg, 0.32 mmol), 2-((N-(3,6-dichloropyridazin-4-yl)-N-methyl)amino)ethanol (107 mg, 0.48 mmol), (prepared as described for the starting material in Example 142), triphenylphosphine (168 mg, 0.64 mmol) in methylene chloride (1 ml) and DMF (0.5 ml) cooled at 4° C. was added a solution of diethyl azodicarboxylate (101 μl, 0.64 mmol) in methylene chloride (0.4 ml). The mixture was stirred for 12 hours at 4° C. and overnight at ambient temperature. The precipitate was filtered, washed with ether and dried under vacuum to give 7-(2-((N-(3,6-dichloropyridazin-4-yl)-N-methyl)amino)ethoxy)-4-(indol-5-ylamino)-6-methoxyquinazoline (72 mg, 44%).

MS-ESI: 510-512 [MH]$^+$ $^1$H NMR Spectrum: (DMSOd$_6$) 3.12 (s, 3H); 3.85 (s, 3H); 4.1 (t, 2H); 4.45 (t, 2H); 6.45 (s, 1H); 7.2 (s, 1H); 7.3 (s, 1H); 7.35 (m, 2H); 7.42 (d, 1H); 7.8 (s, 1H); 7.85 (s, 1H); 8.35 (s, 1H); 9.45 (s, 1H)

The starting material was prepared as follows:

A solution of 7-benzyloxy-4-chloro-6-methoxyquinazoline (5 g, 16.6 mmol), (prepared as described for the starting material in Example 1), 5-aminoindole (2.4 g, 18.2 mmol) in isopropanol (60 ml) containing 5N hydrogen chloride in isopropanol (260 μl, 1.6 mmol) was refluxed for 90 minutes. After cooling the volatiles were removed under vacuum. The solid was triturated with isopropanol, filtered, washed with isopropanol followed by ether and dried under vacuum to give 7-benzyloxy-4-(indol-5-ylamino)-6-methoxyquinazoline hydrochloride (6.9 g, 96%).

$^1$H NMR Spectrum: (DMSOd$_6$) 4.05 (s, 3H); 5.35 (s, 2H); 6.5 (s, 1H); 7.3 (d, 1H); 7.4-7.65 (m, 9H); 7.8 (s, 1H); 8.3 (s, 1H); 8.7 (s, 1H)

A solution of give 7-benzyloxy-4-(indol-5-ylamino)-6-methoxyquinazoline hydrochloride (10 g, 23.1 mmol) in methanol (300 ml) and DMF (100 ml) containing ammonium formate (22 gr, 347 mmol) and 10% palladium on charcoal (1 g) was stirred overnight at ambient temperature. The solution was filtered over celite and washed with DMF followed by methanol. The filtrate was evaporated. The residue was dissolved in aqueous ammonia 2 mM (300 ml) and stirred for 15 minutes. The solid was filtered, washed with water followed by ethyl acetate and ether and dried under vacuum at 50° C. for 2 days. The solid was purified by column chromatography eluting with methanol/methylene chloride (1/9). The volatiles were removed under vacuum and the solid was left under vacuum at 70° C. for 2 days to give 7-hydroxy-4-(indol-5-ylamino)-6-methoxyquinazoline (6.8 g, 97%)

MS-ESI: 307 [MH]+

$^1$H NMR Spectrum: (DMSOd$_6$) 3.98 (s, 3H); 6.42 (s, 1H); 7.0 (s, 1H); 7.3-7.45 (m, 3H); 7.85 (s, 2H); 8.28 (s, 1H); 9.35 (s, 1H); 10.25 (br s, 1H); 11.05 (s, 1H)

EXAMPLES 202-204

Using an analogous procedure to that described in Example 201, 7-hydroxy-4-(indol-5-ylamino)-6-methoxyquinazoline, (prepared as described for the starting material in Example 201), was used in the synthesis of the compounds described in Table XI.

TABLE XI

| Example number | Weight (mg) | Yield % | MS-ESI [MH]+ | Note | R |
|---|---|---|---|---|---|
| 202 | 83 | 59 | 441 | a | 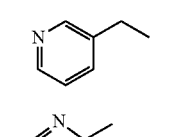 |
| 203 | 91 | 72 | 398 | b | 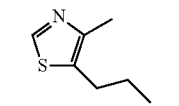 |
| 204 | 76 | 55 | 432 | c | 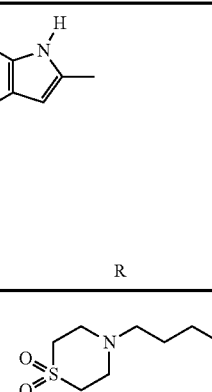 | a) 7-Hydroxy-4-(indol-5-ylamino)-6-methoxyquinazoline was reacted with 2-(N-methyl-N-(4-pyridyl)amino)ethanol (73 mg), (EP 0359389), to give 4-(indol-5-ylamino)-6-methoxy-7-(2-(N-methyl-N-(4-pyridyl)amino)ethoxy) quinazoline.

$^1$H NMR Spectrum: (DMSOd$_6$) 3.08 (s, 3H); 3.9 (t, 2H); 3.95 (s, 3H); 4.35 (t, 2H); 6.45 (s, 1H); 6.75 (d, 2H); 7.15 (s, 1H); 7.35 (m, 2H); 7.4 (d, 1H); 7.85 (s, 1H); 7.9 (s, 1H); 8.15 (d, 2H); 8.38 (s, 1H); 9.45 (s, 1H)

b) 7-Hydroxy-4-(indol-5-ylamino)-6-methoxyquinazoline was reacted with 3-hydroxymethyl pyridine (53 mg) to give 4-(indol-5-ylamino)-6-methoxy-7-((3-pyridyl)methoxy)quinazoline.

$^1$H NMR Spectrum: (DMSOd$_6$) 4.0 (s, 3H); 5.35 (s, 2H); 6.42 (s, 1H); 7.3-7.55 (m, 5H); 7.8-8.0 (m, 3H); 8.4 (s, 1H); 8.6 (d, 1H); 8.75 (s, 1H); 9.5 (s, 1H)

c) 7-Hydroxy-4-(indol-5-ylamino)-6-methoxyquinazoline was reacted with 5-(2-hydroxyethyl)-4-methylthiazole (69 mg) to give 4-(indol-5-ylamino)-6-methoxy-7-(2-(4-methyl-1,3-thiazol-5-yl)ethoxy)quinazoline.

$^1$H NMR Spectrum: (DMSOd$_6$) 2.45 (s, 3H); 3.32 (t, 2H); 3.95 (s, 3H); 4.32 (t, 2H); 6.45 (s, 1H); 7.15 (s, 1H); 7.3-7.45 (m, 3H); 7.85 (s, 1H); 7.9 (s, 1H); 8.35 (s, 1H); 8.85 (s, 1H); 9.45 (s, 1H)

EXAMPLE 205

To a solution of 7-hydroxy-6-methoxy-4-(2-methylindol-5-ylamino)quinazoline (102 mg, 0.32 mmol), 4-(3-hydroxypropyl)morpholine (70 mg, 0.48 mmol), (prepared as described for the starting material in Example 60), triphenylphosphine (168 mg, 0.64 mmol) in methylene chloride (1 ml) and DMF (0.5 ml) cooled at 4° C. was added a solution of diethyl azodicarboxylate (101 μl, 0.64 mmol) in methylene chloride (0.4 ml). The mixture was stirred for 12 hours at 4° C. and overnight at ambient temperature. The mixture was poured onto a column of silica (IST Isolute®10 g of silica) and was eluted with methylene chloride (15 ml) followed by 5% methanol in methylene chloride (45 ml) followed by 5% methanol (saturated with ammonia) in methylene chloride (30 ml) followed by 10% methanol (saturated with ammonia) in methylene chloride (45 ml) followed by 15% methanol (saturated with ammonia) in methylene chloride (30 ml). The fractions containing the expected product were evaporated to give 6-methoxy-4-(2-methylindol-5-ylamino)-7-(3-morpholinopropoxy)quinazoline (63 mg, 44%).

MS-ESI: 448 [MH]+

$^1$H NMR Spectrum: (DMSOd$_6$) 2.0 (m, 2H); 2.4 (s, 3H); 2.3-2.6 (m, 6H); 3.6 (t, 4H); 3.95 (s, 3H); 4.2 (t, 2H); 6.12 (s, 1H); 7.12 (s, 1H); 7.3 (br s, 2H); 7.7 (s, 1H); 7.85 (s, 1H); 8.35 (s, 1H); 9.4 (s, 1H)

The starting material was prepared as follows:

A solution of 2-methyl-5-nitroindole (1 g, 5.7 mmol) in ethanol (25 ml) and THF (25 ml) containg 10% palladium on charcoal (128 mg) was hydrogenated until uptake of hydrogen ceased. The mixture was filtered and the filtrate was evaporated to give 5-amino-2-methylindole (830 mg, quant.).

$^1$H NMR Spectrum: (DMSOd$_6$) 2.3 (s, 3H): 4.3 (br s, 2H); 5.8 (s, 1H); 6.35 (d, 1H); 6.55 (s, 1H); 6.95 (d, 1H); 10.35 (br s, 1H)

Using an analogous procedure to that described for the synthesis of the starting material in Example 201, 7-benzyloxy-4-chloro-6-methoxyquinazoline (2 g, 6.6 mmol), (prepared as described for the starting material in Example 1), was reacted with 5-amino-2-methylindole (1.07 g, 7.3 mmol) to give 7-benzyloxy-6-methoxy-4-(2-methylindol-5-ylamino)quinazoline hydrochloride (2.9 g, quanti).

MS-ESI: 411 [NM]+

$^1$H NMR Spectrum: (DMSOd$_6$) 2.41 (s, 3H); 4.01 (s, 3H); 5.33 (s, 2H); 6.18 (s, 1H); 7.25 (d, 1H); 7.3-7.7 (m, 8H); 8.3 (s, 1H); 8.7 (s, 1H); 11.1 (s, 1H); 11.4 (s, 1H)

Using an analogous procedure to that described for the synthesis of the starting material in Example 201, 7-benzyloxy-6-methoxy-4-(2-methylindol-5-ylamino)quinazoline hydrochloride (2.87 g, 6.4 mmol) was reacted with ammonium formate (6 g, 9.6 mmol) to give 7-hydroxy-6-methoxy-4-(2-methylindol-5-ylamino)quinazoline (1.91 g, 93%).

MS-ESI: 321 [MH]+

$^1$H NMR Spectrum: (DMSOd$_6$) 2.4 (s, 3H); 3.95 (s, 3H); 6.12 (s, 1H); 7.0 (s, 1H); 7.25 (s, 1H); 7.7 (s, 1H); 7.85 (s, 1H); 8.3 (s, 1H); 9.35 (s, 1H); 10.2 (br s, 1H); 10.9 (s, 1H)

EXAMPLES 206-207

Using an analogous procedure to that described for Example 205, 7-hydroxy-6-methoxy-4-(2-methylindol-5-ylamino)quinazoline, (prepared as described for the starting material in Example 205), was used in the synthesis of the compounds described in Table XII.

TABLE XII

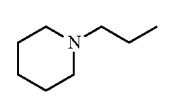

| Example Number | Weight (mg) | Yield % | MS-ESI [MH]+ | Note | R |
|---|---|---|---|---|---|
| 206 | 65 | 41 | 496 | a | |
| 207 | 62 | 45 | | b | | a) 7-Hydroxy-6-methoxy-4-(2-methylindol-5-ylamino)quinazoline (98 mg) was reacted with 3-(1,1-dioxothiomorpholino)-1-propanol (93 mg), (prepared as described for the starting material in Example 5), to give 7-(3-(1,1-dioxothiomorpholino)propoxy)-6-methoxy-4-(2-methylindol-5-ylamino)quinazoline.

$^1$H NMR Spectrum: (DMSOd$_6$) 2.0 (m, 2H); 2.4 (s, 3H); 2.7 (t, 2H); 2.95 (m, 4H); 3.15 (m, 4H); 3.95 (s, 3H); 4.2 (t, 2H); 6.15 (s, 1H); 7.18 (s, 1H); 7.28 (m, 2H); 7.7 (s, 1H); 7.85 (s, 1H); 8.35 (s, 1H); 9.4 (s, 1H)

b) 7-Hydroxy-6-methoxy-4-(2-methylindol-5-ylamino)quinazoline (98 mg) was reacted with 1-(2-hydroxyethyl)piperidine (62 mg) to give 6-methoxy-4-(2-methylindol-5-ylamino)-7-(2-piperidinoethoxy)quinazoline.

$^1$H NMR Spectrum: (DMSOd$_6$) 1.4 (m, 2H); 1.45-1.6 (m, 4H); 2.42 (s, 3H); 2.45 (br s, 4H); 2.75 (t, 2H); 3.95 (s, 3H); 4.25 (t, 2H); 6.15 (s, 1H); 7.15 (s, 1H); 7.25 (br s, 2H); 7.7 (s, 1H); 7.88 (s, 1H); 8.35 (s, 1H); 9.4 (s, 1H)

EXAMPLE 208

Using an analogous procedure to that described in Example 205, 7-hydroxy-4-(indol-5-ylamino)-6-methoxyquinazoline (98 mg, 0.32 mmol), (prepared as described for the starting material in Example 201), was reacted with 3-(1,2,3-triazol-1-yl)propan-1-ol (61 mg, 0.48 mmol) to give 4-(indol-5-ylamino)-6-methoxy-7-(3-(1,2,3-triazol-1-yl)propoxy)quinazoline (56 mg, 42%).

MS-ESI: 416 [MH]$^+$ $^1$H NMR Spectrum: (DMSOd$_6$) 2.4 (m, 2H); 4.0 (s, 3H); 4.2 (t, 2H); 4.65 (t, 2H); 6.45 (s, 1H); 7.15 (s, 1H); 7.35 (m, 2H); 7.42 (d, 1H); 7.75 (s, 1H); 7.88 (s, 1H); 7.9 (s, 1H); 8.2 (s, 1H); 8.38 (s, 1H); 9.42 (s, 1H)

The starting material was prepared as follows:

A mixture of 1,2,3-triazole (5 g, 72.4 mmol) and ethyl acrylate (7.8 ml, 72.4 mmol) containing pyridine (50 drops) was heated at 90° C. for 4 hours. After cooling, the volatiles were removed under vacuum and the residue was purified by column chromatography eluting with methylene chloride/ether to give ethyl (1H-1,2,3-triazol-1-yl)propanoate (8.96 g, 73%).

$^1$H NMR Spectrum: (CDCl$_3$) 1.25 (t, 3H); 2.95 (t, 2H); 4.15 (q, 2H); 4.7 (t, 2H); 7.65 (s, 1H); 7.7 (s, 1H)

A solution of ethyl (1H-1,2,3-triazol-1-yl)propanoate (8.96 g, 53 mmol) in THF (50 ml) was added dropwise to a suspension of lithium aluminium hydride (3 g, 79 mmol) in THF (250 ml) cooled at 0° C. After stirring for 1 hour at 5° C., the mixture was stirred for 1 hour at ambient temperature. The mixture was cooled at 0° C. and 4N sodium hydroxide (30 ml) was added dropwise. The mixture was filtered and the solid was washed with THF followed by ethyl acetate. The filtrate was dried (MgSO$_4$) and evaporated. The residue was purified by column chromatography, eluting with methylene chloride/methanol (94/6) to give 3-(1,2,3-triazol-1-yl)propan-1-ol (6.2 g, 92%).

$^1$H NMR Spectrum: (CDCl$_3$): 2.1-2.2 (m, 3H); 3.65 (m, 2H); 4.6 (t, 2H); 7.6 (s, 1H); 7.72 (s, 1H)

EXAMPLES 209-216

Using an analogous procedure to that described in Example 208, 7-hydroxy-4-(indol-5-ylamino)-6-methoxyquinazoline, (prepared as described for the starting material in Example 201), was used in the synthesis of the compounds described in Table XIII.

TABLE XIII

| Example Number | Weight (mg) | Yield % | MS-ESI [MH]$^+$ | Note | R |
|---|---|---|---|---|---|
| 209 | 77 | 57 | 422 | a | MeO-CH$_2$CH$_2$-N(Me)-CH$_2$CH$_2$CH$_3$ |
| 210 | 64 | 45 | 446 | b | succinimido-butyl |
| 211 | 76 | 49 | 482 | c | 1,1-dioxothiomorpholino-butyl |
| 212 | 70 | 48 | 462 | d | 1-methyl-1H-1,2,4-triazol-3-ylthio-butyl |
| 213 | 85 | 59 | 447 | e | 4-methylpiperazin-1-yl-butyl |
| 214 | 62 | 54 | 365 | f | MeO-propyl |
| 215 | 71 | 54 | 409 | g | MeO-CH$_2$CH$_2$-O-CH$_2$CH$_2$- |
| 216 | 73 | 55 | 418 | h | piperidin-1-yl-ethyl | a) 7-Hydroxy-4-(indol-5-ylamino)-6-methoxyquinazoline (98 mg) was reacted with 2-(N-(2-methoxyethyl)-N-methylamino)ethanol (64 mg), (prepared as described for the starting material in Example 59), to give 4-(indol-5-ylamino)-6-methoxy-7 -(2-(N-(2-methoxyethyl)-N-methylamino)ethoxy)quinazoline.

$^1$H NMR Spectrum: (DMSOd$_6$) 2.35 (s, 3H); 2.68 (t, 2H); 2.82 (t, 2H); 3.25 (s, 3H); 3.5 (t, 2H); 3.97 (s, 3H); 4.22 (t, 2H), 6.45 (s, 1H); 7.18 (s, 1H); 7.3-7.45 (m, 3H); 7.88 (m, 2H); 8.35 (s, 1H); 9.42 (s, 1H)

b) 7-Hydroxy-4-(indol-5-ylamino)-6-methoxyquinazoline (98 mg) was reacted with 1-(3-hydroxypropyl)pyrrolidin-2,5-dione (76 mg) to give 7-(3-(2,5 -dioxopyrrolidin-1-yl)propoxy)-4-(indol-5-ylamino)-6-methoxyquinazoline.

$^1$H NMR Spectrum: (DMSOd$_6$) 2.05 (m, 2H); 2.65 (s, 3H); 3.6 (t, 2H); 3.98 (s, 2H); 4.15 (t, 2H); 6.45 (s, 1H); 7.1 (s, 1H); 7.3-7.45 (m, 3H); 8.7 (s, 1H); 8.8 (s, 1H); 8.35 (s, 1H); 9.45 (s, 1H)

The starting material was prepared as follows:

A solution of pyrrolidine-2,5-dione (5 g, 50.5 mmol) and 3-bromopropan-1-ol (6.85 ml, 76 mmol) in acetonitrile (80 ml) containing potassium carbonate (14 g, 100 mmol) was refluxed overnight. After cooling, the mixture was filtered and the filtrate was evaporated. The residue was dissolved in methylene chloride and purified by column chromatography, eluting with ethylacetate/petroleum ether (4/1). After evaporation of the volatiles, the residue was distilled at 100-125° C. under about 0.1 mm Hg to give 1-(3-hydroxypropyl)pyrrolidin-2,5-dione (2.6 g, 34%).

¹H NMR Spectrum: (CDCl₃) 1.8 (m, 2H); 2.52 (t, 1H); 2.78 (s, 4H); 3.58 (q, 2H); 3.7 (t, 2H)

c) 7-Hydroxy-4-(indol-5-ylamino)-6-methoxyquinazoline (98 mg) was reacted with 3-(1,1-dioxothiomorpholino)-1-propanol (93 mg), (prepared as described for the starting material in Example 5), to give 7-(3-(1,1-dioxothiomorphohno)propoxy)-4-(indol-5-ylamino)-6-methoxyquinazoline.

¹H NMR Spectrum: (DMSOd₆) 2.0 (m, 2H); 2.7 (t, 2H); 2.95 (br s, 4H); 3.15 (br s, 4H); 3.97 (s, 3H); 4.2 (t, 2H); 6.45 (s, 1H); 7.2 (s, 1H); 7.3-7.5 (m, 3H); 7.9 (2s, 2H); 8.35 (s, 1H); 9.42 (s, 1H)

d) 7-Hydroxy-4-(indol-5-ylamino)-6-methoxyquinazoline (98 mg) was reacted with 3-((4-methyl-4H-1,2,4-triazol-3-yl)sulphanyl)propan-1-ol (83 mg) to give 4-(indol-5-ylamino)-6-methoxy-7-(3-((4-methyl-4H-1,2,4-triazol-3-yDsulphanyl)propoxy)quinazoline.

¹H NMR Spectrum: (DMSOd₆) 2.22 (m, 2H); 3.3 (m, 2H); 3.65 (s, 3H); 3.95 (s, 3H); 4.25 (t, 2H); 6.45 (s, 1H); 7.15 (s, 1H); 7.3-7.45 (m, 3H); 7.88 (s, 1H); 8.0 (s, 1H); 8.35 (s, 1H); 8.58 (s, 1H); 9.45 (s, 1H)

The starting material was prepared as follows:

A solution of 4-methyl-4-H-1,2,4-triazole-3-thiol (1.72 g, 15 mmol) and 3-bromopropan-1-ol (1.39 g, 10 mmol) in DMF (10 ml) containing potassium carbonate (1.57 g, 14 mmol) was heated at 40° C. for 30 minutes. The mixture was then partitioned between saturated ammonium chloride and ethyl acetate. The aqueous layer was evaporated to dryness and the residue was triturated with ethyl acetate and methylene chloride. The suspension was filtered and the filtrate was dried (MgSO₄) and evaporated. The residue was purified by column chromatography eluting with methylene chloride/methanol (9/1) to give 3-((4-methyl-4H-1,2,4-triazol-3-yl)sulphanyl)propan-1-ol (510 mg, 30%).

¹H NMR Spectrum: (CDCl₃) 2.02 (m, 2H); 3.45 (t, 2H); 3.55 (s, 3H); 3.75 (t, 2H); 8.15 (s, 1H)

e) 7-Hydroxy-4-(indol-5-ylamino)-6-methoxyquinazoline (98 mg) was reacted with 1-(3-hydroxypropyl)-4-methylpiperazine (76 mg), (prepared as described for the starting material in Example 133), to give 4-(indol-5-ylamino)-6-methoxy-7-(3-(4-methylpiperazin-1-yl)propoxy)quinazoline.

¹H NMR Spectrum: (DMSOd₆) 2.0 (m, 2H); 2.2 (s, 3H); 2.25-2.55 (m, 10H); 4.0 (s, 3H); 4.2 (t, 2H); 6.45 (s, 1H); 7.15 (s, 1H); 7.35 (m, 2H); 7.42 (d, 1H); 7.88 (br s, 2H); 8.38 (s, 1H); 9.42 (s, 1H)

f) 7-Hydroxy-4-(indol-5-ylamino)-6-methoxyquinazoline (98 mg) was reacted with 2-methoxyethanol (37 mg) to give 4-(indol-5-ylamino)-6-methoxy-7-(2-methoxyethoxy)quinazoline.

¹H NMR Spectrum: (DMSOd₆) 3.4 (s, 3H); 3.75 (t, 2H); 3.98 (s, 3H); 4.38 (t, 2H); 6.45 (s, 1H); 7.18 (s, 1H); 7.35 (m, 2H); 7.42 (d, 1H); 7.85 (s, 1H); 7.9 (s, 1H); 8.38 (s, 1H); 9.5 (s, 1H)

g) 7-Hydroxy-4-(indol-5-ylamino)-6-methoxyquinazoline (98 mg) was reacted with 2-(2-methoxyethoxy)ethanol (58 mg) to give 4-(indol-5-ylamino)-6-methoxy-7-(2-(2-methoxyethoxy)ethoxy)quinazoline.

¹H NMR Spectrum: (DMSOd₆) 3.3 (s, 3H); 3.5 (t, 2H); 3.65 (t, 2H); 3.85 (t, 2H); 4.0 (s, 3H); 4.28 (t, 2H); 6.45 (s, 1H); 7.18 (s, 1H); 7.35 (m, 2H); 7.45 (d, 1H); 7.88 (s, 1H); 7.9 (s, 1H); 8.35 (s, 1H); 9.45 (s, 1H)

h) 7-Hydroxy-4-(indol-5-ylamino)-6-methoxyquinazoline (98 mg) was reacted with 1-(2-hydroxyethyl)piperidine (62 mg) to give 4-(indol-5-ylamino)-6-methoxy-7-(2-piperidinoethoxy)quinazoline.

¹H NMR Spectrum: (DMSOd₆) 1.3-1.6 (m, 6H); 2.5 (br s, 4H); 2.7 (t, 2H); 3.98 (s, 3H); 4.25 (t, 2H); 6.45 (s, 1H); 7.18 (s, 1H); 7.35 (m, 2H); 7.42 (d, 1H); 7.9 (br s, 2H); 8.38 (s, 1H); 9.42 (s, 1H)

EXAMPLE 217-223

Using an analogous procedure to that described in Example 205, 7-hydroxy-4-(indol-6-ylamino)-6-methoxyquinazoline was used in the synthesis of the compounds described in Table XIV.

The starting material was prepared as follows:

Using an analogous procedure to that described for the preparation of the starting material in Example 201, 6-nitroindole (500 mg, 3 mmol) was hydrogenated to give 6-aminoindole (395 mg, quant.).

¹H NMR Spectrum: (DMSOd₆) 6.41 (s, 1H); 6.6 (dd, 1H); 6.63 (s, 1H); 7.0 (t, 1H); 7.4 (d, 1H); 7.87 (br s, 1H)

Using an analogous procedure to that described for the preparation of the starting material in Example 201, 7-benzyloxy-4-chloro-6-methoxyquinazoline (2.5 g, 8.3 mmol), (prepared as described for the starting material in Example 1), was reacted with 6-aminoindole (1.5 g, 11.4 mmol) to give 7-benzyloxy-4-(indol-6-ylamino)-6-methoxyquinazoline hydrochloride (3.18 g, 89%).

MS-ESI: 397 [MH]+

¹H NMR Spectrum: (DMSOd₆) 4.02 (s, 3H); 5.35 (s, 2H); 6.5 (s, 1H); 7.25 (dd, 1H); 7.35-7.6 (m, 5H); 7.63 (d, 1H); 7.72 (s, 1H); 8.3 (s, 1H); 8.75 (s, 1H); 11.3 (br s, 1H)

Using an analogous procedure to that described for the preparation of the starting material in Example 201, 7-benzyloxy-4-(indol-6-ylamino)-6-methoxyquinazoline hydrochloride was treated with ammonium formate (655 mg, 10.4 mmol) to give 7-hydroxy-4-(indol-6-ylamino)-6-methoxyquinazoline (162 mg, 76%).

MS-ESI: 307 [MH]+

¹H NMR Spectrum: (DMSOd₆) 4.0 (s, 3H); 6.4 (s, 1H); 7.0 (s, 1H); 7.3 (m, 2H); 7.5 (d, 1H); 7.85 (s, 1H); 8.0 (s, 1H); 8.35 (s, 1H); 9.35 (s, 1H); 11.05 (s, 1H)

TABLE XIV

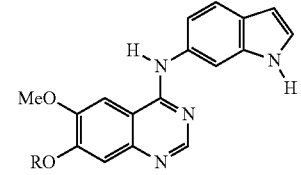

| Example number | Weight (mg) | Yield % | MS-ESI [MH]⁺ | Note | R |
|---|---|---|---|---|---|
| 217 | 46 | 35 | 416 | a | |
| 218 | 57 | 37 | 482 | b | |

TABLE XIV-continued

[Structure: quinazoline with MeO at 6-position, RO at 7-position, and NH-indol-6-yl at 4-position]

| Example number | Weight (mg) | Yield % | MS-ESI [MH]+ | Note | R |
|---|---|---|---|---|---|
| 219 | 37 | 25 | 462 | c | [triazolyl-S-butyl group] |
| 220 | 38 | 29 | 418 | d | [piperidinyl-propyl group] |
| 221 | 10 | 7 | 418 | e | [pyrrolidinyl-propyl group] |
| 222 | 94 | 61 | 483 | f | [2,6-dimethylpyridyl-N(Me)-propyl-OH group] |
| 223 | 56 | 44 | 398 | g | [pyridyl-methyl group] | a) 7-Hydroxy-4-(indol-6-ylamino)-6-methoxyquinazoline (98 mg) was reacted with 3-(1,2,3-triazol-1-yl)propan-1-ol (61 mg), (prepared as described for the starting material in Example 208), to give 4-(indol-6-ylamino)-6-methoxy-7-(3-(1,2,3-triazol-1-yl)propoxy)quinazoline.
$^1$H NMR Spectrum: (DMSOd$_6$) 2.42 (t, 2H); 4.02 (s, 3H); 4.2 (t, 2H); 4.62 (t, 2H); 6.42 (s, 1H); 7.15 (s, 1H); 7.3 (m, 2H); 7.55 (d, 1H); 7.75 (s, 1H); 7.92 (s, 1H); 8.02 (s, 1H); 8.2 (s, 1H); 8.42 (s, 1H); 9.45 (s, 1H)

b) 7-Hydroxy-4-(indol-6-ylamino)-6-methoxyquinazoline (98 mg) was reacted with 3-(1,1-dioxothiomorpholino)-1-propanol (93 mg), (prepared as described for the starting material in Example 5), to give 7-(3-(1,1-dioxothiomorpholino)propoxy)-4-(indol-6-ylamino)-6-methoxyquinazoline.
$^1$H NMR Spectrum: (DMSOd$_6$) 2.0 (m, 2H); 2.7 (t, 2H); 2.95 (br s, 4H); 3.12 (br s, 4H); 4.0 (s, 3H); 4.2 (t, 2H); 6.42 (s, 1H); 7.2 (s, 1H); 7.3 (m, 2H); 7.55 (d, 1H); 7.9 (s, 1H); 8.02 (s, 1H); 8.42 (s, 1H); 9.48 (s, 1H)

c) 7-Hydroxy-4-(indol-6-ylamino)-6-methoxyquinazoline (98 mg) was reacted with 34(4-methyl-4H-1,2,4-triazol-3-yl)sulphanyl)propan-1-ol (83 mg), (prepared as described for the starting material in Example 212), to give 4-(indol-6-ylamino)-6-methoxy-7-(3-((4-methyl-4H-1,2,4-triazol-3-yl)sulphanyl)propoxy)quinazoline.
$^1$H NMR Spectrum: (DMSOd$_6$) 2.22 (t, 2H); 3.3 (t, 2H); 3.6 (s, 3H); 4.0 (s, 3H); 4.28 (t, 2H); 6.4 (s, 1H); 7.18 (s, 1H); 7.3 (m, 2H); 7.53 (d, 1H); 7.9 (s, 1H); 8.02 (s, 1H); 8.42 (s, 1H); 8.58 (s, 1H); 9.45 (s, 1H)

d) 7-Hydroxy-4-(indol-6-ylamino)-6-methoxyquinazoline (98 mg) was reacted with 1-(2-hydroxyethyl)piperidine (62 mg) to give 4-(indol-6-ylamino)-6-methoxy-7-(2-piperidinoethoxy)quinazoline.
$^1$H NMR Spectrum: (DMSOd$_6$) 1.3-1.6 (m, 6H); 2.5 (br s, 4H); 2.75 (t, 2H); 4.0 (s, 3H); 4.25 (t, 2H); 6.42 (s, 1H); 7.2 (s, 1H); 7.3 (m, 2H); 7.55 (d, 1H); 7.9 (s, 1H); 8.02 (s, 1H); 8.42 (s, 1H); 9.45 (s, 1H)

e) 7-Hydroxy-4-(indol-6-ylamino)-6-methoxyquinazoline (98 mg) was reacted with 1-(3-hydroxypropyl)pyrrolidine (62 mg) to give 4-(indol-6-ylamino)-6-methoxy-7-(3-pyrrolidin-1-ylpropoxy)quinazoline.
The starting material was prepared as follows:
A solution of pyrrolidine (50 g, 0.7 mol) and 3-chloropropan-1-ol (66.15 g, 0.7 mol) in acetonitrile (1l) containing potassium carbonate (145 g, 1.05 mol) was refluxed for 20 hours. After cooling, the mixture was filtered, the solid was washed with acetonitrile and the filtrate was evaporated. The residue was distilled at about 130° C. under about 70 mmHg to give 1-(3-hydroxypropyl)pyrrolidine (62.1 g, 69%).
MS-ESI: 130 [MH]+
$^1$H NMR Spectrum: (CDCl$_3$) 1.6-1.8 (m, 6H); 2.55 (br s, 4H); 2.75 (t, 2H); 3.85 (t, 2H); 5.2-5.8 (br s, 1H)

f) 7-Hydroxy-4-(indol-6-ylamino)-6-methoxyquinazoline (98 mg) was reacted with 3-((N-(2,6-dimethyl-4-pyridyl)-N-methyl)amino)propan-1-ol (93 mg) to give 7-(3-((N-(2,6-dimethyl-4-pyridyl)-N-methyl)amino)propoxy)-4-(indol-6-ylamino)-6-methoxyquinazoline.
$^1$H NMR Spectrum: (DMSOd$_6$) 2.08 (m, 2H); 2.22 (s, 6H); 2.95 (s, 3H); 3.6 (t, 2H); 4.05 (s, 3H); 4.15 (t, 2H); 6.35 (s, 2H); 6.42 (s, 1H); 7.15 (s, 1H); 7.3 (m, 2H); 7.55 (d, 1H); 7.92 (s, 1H); 8.02 (s, 1H); 8.4 (s, 1H); 9.45 (s, 1H)
The starting material was prepared as follows:
A solution of 4-chloro-2,6-dimethylpyridine (2.12 g, 15 mmol) and 3-(N-methylamino)-propan-1-ol (4 g, 45 mmol) containing 2N hydrogen chloride in ether (10 drops) was heated at 140° C. for 1 hour. The mixture was diluted with water (10 ml) and poured onto a suspension of MgSO$_4$ (125 g) in ethyl acetate (200 ml). The mixture ws filtered. The filtrate was evaporated and the residue was triturated with ether. The solid was filtered and dried under vacuum to give 3-((N-(2,6-dimethyl-4-pyridyl)-N-methyl)amino)propan-1-ol (1.76 g, 61%).
MS-EI: 194 [M.]+
$^1$H NMR Spectrum: (CDCl$_3$) 1.75-1.95 (m, 2H); 2.4 (s, 6H); 3.0 (s, 3H); 3.48 (t, 2H); 3.7 (t, 2H); 6.25 (s, 2H)

g) 7-Hydroxy-4-(indol-6-ylamino)-6-methoxyquinazoline (98 mg) was reacted with 3-hydroxymethylpyridine (53 mg) to give 4-(indol-6-ylamino)-6-methoxy-7-((3-pyridyl)methoxy)quinazoline.
$^1$H NMR Spectrum: (DMSOd$_6$) 4.02 (s, 3H); 5.35 (s, 2H); 6.42 (s, 1H); 7.22-7.4 (m, 3H); 7.5 (m, 1H); 7.55 (d, 1H); 7.95 (s, 1H); 7.97 (d, 1H); 8.0 (s, 1H); 8.42 (s, 1H); 8.6 (d, 1H); 8.78 (s, 1H); 9.5 (s, 1H)

EXAMPLE 224

Using an analogous procedure to that described in Example 208, 7-hydroxy-4-(indol-5-ylamino)-6-methoxyquinazoline (98 mg, 0.32 mmol), (prepared as described for the starting material in Example 201), was reacted with (E)-4-(pyrrolidin-1-yl)but-2-en-1-ol (68 mg, 0.48 mmol), (prepared as described for the starting material in Example 129). After evaporation of the fractions containing the expected product, the residue was triturated with isopropanol (1 ml) containing 6.2 N hydrogen chloride in isopropanol (100 µl). After stirring at ambient temperature for 10 minutes, ether (500 µl) was added. The precipitate was filtered and washed several times with ether to give 4-(indol-5-ylamino)-6-methoxy-7-((E)4-(pyrrolidin-1-yl)but-2-en-1-yloxy)quinazoline hydrochloride (14 mg, 10%).

MS-ESI: 430 [MH]+

¹H NMR Spectrum: (DMSOd₆) 1.85-2.7 (br s, 4H); 2.95-3.1 (br s, 2H); 3.0 (m, 2H); 3.4-3.5 (m, 2H); 3.8 (d, 2H); 4.0 (s, 3H); 4.8 (d, 2H); 6.0-6.3 (m, 2H); 6.5 (s, 1H); 7.2-7.53 (m, 4H); 7.75 (s, 1H); 8.25 (s, 1H); 8.8 (br s, 1H)

EXAMPLE 225

7-Hydroxy-4-(indol-5-ylamino)-6-methoxyquinazoline, (prepared as described for the starting material in Example 201), was treated as follows. After purification by chromatography and evaporation of the solvent, the residue was triturated in a solution of isopropanol (1 ml) containing 6.2 N hydrogen chloride in isopropanol (100 μl). After stirring for 10 minutes at ambient temperature, ether (500 μl) was added. The solid was filtered and dried under vacuum to give 7-hydroxy-4-(indol-5-ylamino)-6-methoxyquinazoline hydrochloride.

Using an analogous procedure to that described in Example 224, 7-hydroxy-4-(indol-5-ylamino)-6-methoxyquinazoline hydrochloride was used in the synthesis of the compounds described in Table XV.

TABLE XV

| Example Number | Weight (mg) | Yield % | MS-ESI [MH]+ | Note | R |
|---|---|---|---|---|---|
| 225 | 77 | 50 | 483 | a | | a) 7-Hydroxy-4-(indol-5-ylamino)-6-methoxyquinazoline hydrochloride (98 mg) was reacted with 3-((N-(2,6-dimethyl-4-pyridyl)-N-methyl)amino)propan-1-ol (93 mg), (prepared as described for the starting material in Example 222), to give 7-(3-((N-(2,6-dimethyl-4-pyridyl)-N-methyl)amino)propoxy)-4-(indol-5-ylamino)-6-methoxyquinazoline.

¹H NMR Spectrum: (DMSOd₆) 2.2 (m, 2H); 2.5 (2br s, 6H); 3.2 (s, 3H); 3.8 (t, 2H); 4.1 (s, 3H); 4.25 (t, 2H); 6.52 (s, 1H); 6.75 (br s, 1H); 6.9 (br s, 1H); 7.35 (dd, 1H); 7.45 (br s, 2H); 7.5 (d, 1H); 7.8 (s, 1H); 8.4 (s, 1H); 8.75 (s, 1H)

EXAMPLE 226

Using an analogous procedure to that described in Example 224, 7-hydroxy-4-(indol-6-ylamino)-6-methoxyquinazoline, (prepared as described for the starting material in Example 217), (98 mg, 0.32 mmol) was reacted with 4-(3-hydroxypropyl)morpholine (70 mg, 0.48 mmol), (prepared as described for the starting material in Example 60), to give 4-(indol-6-ylamino)-6-methoxy-7-(3-morpholinopropoxy) quinazoline hydrochloride (26 mg, 19%).

MS-ESI: 434 [MH]+

¹H NMR Spectrum: (DMSOd₆, CF₃COOD) 2.35 (m, 2H); 3.15 (m, 2H); 3.3 (t, 2H); 3.52 (d, 2H); 3.8 (t, 2H); 4.0 (d, 2H); 4.1 (s, 3H); 4.3 (t, 2H); 6.5 (s, 0.5H, partly exchanged); 7.3 (d, 1H); 7.4 (s, 1H); 7.45 (s, 1H); 7.65 (d, 1H); 7.75 (s, 1H); 8.3 (s, 1H); 8.75 (s, 1H)

EXAMPLES 227-229

Using an analogous procedure to that described in Example 226, 7-hydroxy-4-(indol-6-ylamino)-6-methoxyquinazoline, (prepared as described for the starting material in Example 217), was used in the synthesis of the compounds described in Table XVI.

TABLE XVI

| Example number | Weight (mg) | Yield % | MS-ESI [MH]+ | Note | R |
|---|---|---|---|---|---|
| 227 | 24 | 17 | 441 | a | |
| 228 | 14 | 10 | 430 | b | |
| 229 | 15 | 10 | 447 | c | | a) 7-Hydroxy-4-(indol-6-ylamino)-6-methoxyquinazoline (98 mg) was reacted with 2-((N-methyl-N-(4-pyridyl))amino)ethanol (73 mg), (EP 0359389A1), to give 4-(indol-6-ylamino)-6-methoxy-7-(2-((N-methyl-N-(4-pyridyl))amino)ethoxy)quinazoline hydrochloride.

¹H NMR Spectrum: (DMSOd₆) 3.3 (s, 3H); 4.0 (s, 3H); 4.18 (t, 2H); 4.45 (t, 2H); 6.5 (s, 1H); 7.35 (d, 1H); 7.35-7.5 (m, 4H); 7.62 (d, 1H); 7.75 (s, 1H); 8.3 (d, 2H); 8.4 (s, 1H); 8.75 (s, 1H)

b) 7-Hydroxy-4-(indol-6-ylamino)-6-methoxyquinazoline (98 mg) was reacted with (E)-4-(pyrrolidin-1-yl)but-2-en-1-ol (68 mg, 0.48 mmol), (prepared as described for the starting material in Example 129) to give 4-(indol-6-ylamino)-6-methoxy-7-((E)-4-(pyrrolidin-1-yl)but-2-en-1-yloxy)quinazoline hydrochloride.

¹H NMR Spectrum: (DMSOd₆) 1.8-2.1 (m, 4H); 2.9-3.1 (m, 2H); 3.4-3.5 (br s, 2H); 3.87 (d, 2H); 4.05 (s, 3H); 4.9 (d, 2H); 6.1 (m, 1H); 6.3 (m, 1H); 6.5 (s, 1H); 7.25 (d, 1H); 7.45 (m, 2H); 7.65 (d, 1H); 7.75 (s, 1H); 8.3 (s, 1H); 8.8 (s, 1H)

c) 7-Hydroxy-4-(indol-6-ylamino)-6-methoxyquinazoline (98 mg) was reacted with 1-(3-hydroxypropyl)-4-methylpiperazine (76 mg), (prepared as described for the starting material in Example 133), to give 4-(indol-6-ylamino)-6-methoxy-7-(3-(4-methylpiperazin-1-yl)propoxy) quinazoline hydrochloride.

EXAMPLE 230

Using an analogous procedure to that described in Example 224, 7-hydroxy-6-methoxy-4-(2-methylindol-5-ylamino)quinazoline (102 mg, 0.32 mmol), (prepared as described for the starting material in Example 205), was reacted with 1-(3-hydroxypropyl)-2-methylimidazole (67 mg, 0.48 mmol), (EP 0060696 A1), to give 6-methoxy-7-(3-(2-methylimidazol-1-yl)propoxy)-4-(2-methylindol-5-ylamino)quinazoline (53 mg, 37%).

MS-ESI: 443 [MH]$^+$ $^1$H NMR Spectrum: (DMSOd$_6$) 2.42 (s, 3H); 2.62 (s, 3H); 4.03 (s,3H); 4.3 (t, 2H); 4.35 (t, 2H); 6.2 (s, 1H); 7.22 (d, 1H); 7.35 (d, 1H); 7.45 (s, 1H); 7.6 (dd, 1H); 7.65 (dd, 1H); 7.7 (s, 1H); 8.35 (s, 1H); 8.75 (s, 1H)

EXAMPLES 231-235

Using an analogous procedure to that described in Example 224, 7-hydroxy-6-methoxy-4-(2-methylindol-5-ylamino)quinazoline (102 mg, 0.32 mmol), (prepared as described for the starting material in Example 205), was used in the synthesis of the compounds described in Table XVII.

TABLE XVII

| Example number | Weight (mg) | Yield % | MS-ESI [MH]$^+$ | Note | R |
|---|---|---|---|---|---|
| 231 | 49 | 31 | 497 | a | |
| 232 | 25 | 18 | 444 | b | |
| 233 | 23 | 15 | 476 | c | |
| 234 | 33 | 22 | 461 | d | |
| 235 | 26 | 19 | 423 | e | | a) 7-Hydroxy-6-methoxy-4-(2-methylindol-5-ylamino)quinazoline (102 mg) was reacted with 3-((N-(2,6-dimethyl-4-pyridyl)-N-methyl)amino)propan-1-ol (93 mg), (prepared as described for the starting material in Example 222), to give 7-(3-((N-(2,6-dimethyl-4-pyridyl)-N-methyl)amino)propoxy)-6-methoxy-4-(2-methylindol-5-ylamino)quinazoline.

$^1$H NMR Spectrum: (DMSOd$_6$) 2.2 (m, 2H); 2.4 (s, 6H); 2.45 (s, 3H); 3.15 (s, 3H); 3.75 (t, 2H); 4.02 (s, 3H); 4.25 (t, 2H); 6.2 (s, 1H); 6.72 (br s, 1H); 6.85 (br s, 1H); 7.2 (dd, 1H); 7.3-7.4 (m, 2H); 7.62 (s, 1H); 8.3 (s, 1H); 8.7 (s, 1H)

b) 7-Hydroxy-6-methoxy-4-(2-methylindol-5-ylamino)quinazoline (102 mg) was reacted with (E)-4-(pyrrolidin-1-yl)but-2-en-1-ol (68 mg, 0.48 mmol), (prepared as described for the starting material in Example 129) to give 6-methoxy-4-(2-methylindol-5-ylamino)-74(E)-4-(pyrrolidin-1-yl)but-2-en-1-yloxy)quinazoline.

$^1$H NMR Spectrum: (DMSOd$_6$) 1.8-2.1 (m, 4H); 2.4 (s, 3H); 2.9-3.1 (m, 2H); 3.4-3.6 (m, 2H); 3.9 (d, 2H); 4.05 (s, 3H); 4.9 (d, 2H); 6.1 (m, 1H); 6.2 (s, 1H); 6.3 (d, t, 1H); 7.2 (m, 1H); 7.37 (d, 1H); 7.4 (s, 1H); 7.32 (s, 1H); 8.3 (s, 1H); 8.75 (s, 1H)

c) 7-Hydroxy-6-methoxy-4-(2-methylindol-5-ylamino)quinazoline (102 mg) was reacted with 3-((4-methyl-4H-1,2,4-triazol-3-yl)sulphanyl)propan-1-ol (83 mg), (prepared as described for the starting material in Example 212), to give 6-methoxy-4-(2-methylindol-5-ylamino)-7-(3-((4-methyl-4H-1,2,4-triazol-3-yl)sulphanyl)propoxy)quinazoline.

$^1$H NMR Spectrum: (DMSOd$_6$) 2.25 (m, 2H); 2.45 (s, 3H); 3.35 (t, 2H); 3.65 (s, 3H); 4.05 (s, 3H); 4.35 (t, 2H); 6.2 (s, 1H); 7.2 (d, 1H); 7.35 (s, 1H); 7.37 (d, 1H); 7.62 (s, 1H); 8.25 (s, 1H); 8.75 (s, 1H); 8.9 (s, 1H)

d) 7-Hydroxy-6-methoxy-4-(2-methylindol-5-ylamino)quinazoline (102 mg) was reacted with 1-(3-hydroxypropyl)-4-methylpiperazine (76 mg), (prepared as described for the starting material in Example 133), to give 6-methoxy-4-(2-methylindol-5-ylamino)-7-(3-(4-methylpiperazin-1-yl)propoxy)quinazoline.

e) 7-Hydroxy-6-methoxy-4-(2-methylindol-5-ylamino)quinazoline (102 mg) was reacted with 2-(2-methoxyethoxy)ethanol to give 6-methoxy-7-(2-(2-methoxyethoxy)ethoxy)-4-(2-methylindol-5-ylamino)quinazoline.

$^1$H NMR Spectrum: (DMSOd$_6$) 2.45 (s, 3H); 3.28 (s, 3H); 3.5 (t, 2H), 3.65 (t, 2H); 3.9 (t, 2H); 4.02 (s, 3H); 4.33 (t, 2H); 6.2 (s, 1H); 7.2 (d, 1H); 7.4 (m. 2H); 7.63 (s, 1H); 8.28 (s, 1H); 8.73 (s, 1H)

EXAMPLE 236

A solution of 4-chloro-6-methoxy-7-((1-cyanomethylpiperidin-4-yl)methoxy)quinazoline (200 mg, 0.58 mmol) and 5-hydroxyindole (85 mg, 0.63 mmol) in DMF (3 ml) containing cesium carbonate (282 mg, 0.86 mmol) was stirred at 90° C. for 90 minutes. After cooling, the mixture was poured onto water (25 ml). The precipitate was filtered, dried under vacuum and purified by reverse phase column chromatography on silica (Kromasil® C18) eluting with methanol/water (1% acetic acid) (1/1). The fractions containing the expected product were combined and evaporated to give 7-((1-cyanomethyl)piperidin-4-ylmethoxy)-4-(indol-5-yloxy)-6-methoxyquinazoline (44 mg, 17%).

MS-ESI: 444 [MH]$^+$

1H NMR Spectrum: (DMSOd$_6$, CF$_3$COOD) 1.7 (m, 2H); 2.15 (d, 2H); 2.2-2.35 (m, 1H); 3.20 (t, 2H); 3.65 (d, 2H); 4.1 (s, 3H); 4.25 (d, 2H); 4.62 (s, 2H); 6.5 (s, 0.5H, partly exchanged); 7.1 (dd, 1H); 7.5 (s, 1H); 7.5-7.6 (m, 3H); 7.85 (s, 1H); 9.1 (s, 1H)

The starting material was prepared as follows:

To a suspension of 6-methoxy-7-(piperidin-4-ylmethoxy)-3-((pivaloyloxy)methyl)-3,4-dihydroquinazolin-4-one hydrochloride (34 g, 84 mmol), (prepared as described for the starting material in Example 12), in water cooled at 0° C. was added 1N sodium hydroxide until the mixture was at pH8. The solution was extracted with trichloromethane and the organic layer was dried (MgSO$_4$), filtered and evaporated to give 6-methoxy-7-(piperidin-4-ylmethoxy)-3-((pivaloyloxy)methyl)-3,4-dihydroquinazolin-4-one (29 g).

To a solution of 6-methoxy-7-(piperidin-4-ylmethoxy)-3-((pivaloyloxy)methyl)-3,4-dihydroquinazolin-4-one (28.9 g, 72 mmol) and aqueous formaldehyde 12 M (11.95 ml, 141 mmol) in methanol/THF (1/1) (580 ml) was added sodium cyanoborohydride (5.7 g, 86 mmol) in portions. After stirring for 90 minutes at ambient temperature, the volatiles were removed under vacuum and the residue was partitioned between methylene chloride and water. The organic layer was separated, dried (MgSO$_4$) and evaporated. The residue was dissolved in methanol saturated with ammonia (500 ml). The mixture was stirred for 36 hours at ambient temperature. The volatiles were removed under vacuum. The residue was triturated with a mixture ether/methylene chloride, filtered, washed with ether and dried under vacuum. The solid was dissolved in thionyl chloride (180 ml) and DMF (1.8 ml) was added. After stiffing at 80° C. for 75 minutes the volatiles were removed under vacuum. The residue was azeotroped with toluene twice and the solid was partitioned between methylene chloride and water and the pH of the aqueous layer was adjusted to 9 with 2N sodium hydroxide. The organic layer was dried (MgSO$_4$) and evaporated. The residue was purified by column chromatography on aluminium oxide eluting with methylene chloride, followed by methylene chloride/ethyl acetate (70/30 followed by 50/50) followed by ethyl acetate and ethyl acetate/methanol (80/20) to give 4-chloro-6-methoxy-7((1-methylpiperidin-4-yl)methoxy)quinazoline (11.2 g) (identical to the starting material prepared in Example 10) and 4-chloro-6-methoxy-7-((1-(cyanomethyl)piperidin-4-yl)methoxy)quinazoline (2.55 g).

MS-ESI: 347 [MH]$^+$

1H NMR Spectrum: (DMSOd$_6$) 1.42 (m, 2H); 1.85 (d, 2H); 1.8-1.9 (m, 1H); 2.2 (t, 2H); 2.85 (d, 2H); 3.75 (s, 2H); 4.05 (s, 3H); 4.15 (d, 2H); 7.42 (s, 1H); 7.5 (s, 1H); 8.9 (s, 1H)

EXAMPLE 237

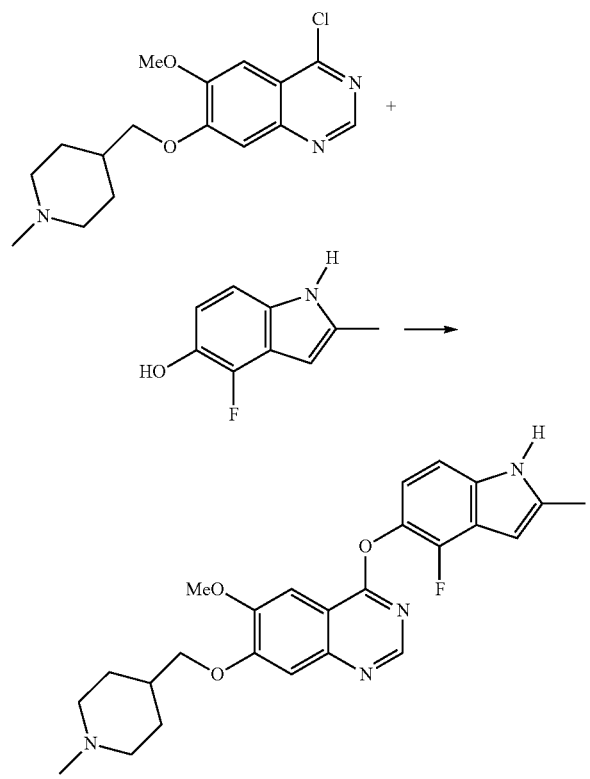

A solution of 4-chloro-6-methoxy-7-((1-methylpiperidin-4-yl)methoxy)quinazoline (2 gr, 6.22 mmol), (prepared as described for the starting material in Example 10), and 4-fluoro-5-hydroxy-2-methylindole (1.23 g, 7.46 mmol) in DMF (30 ml) containing potassium carbonate (1.28 g, 9.33 mmol) was stirred at 95° C. for 2 hours. After cooling, the volatiles were removed under vacuum and the residue was triturated with ether, filtered and dried under vacuum. The residue was purified by column chromatography eluting with methanol/methylene chloride (1/9) followed by methanol/methanol saturated with ammonia/methylene chloride (20/1/79 followed by 20/5/75). The fractions containing the expected product were combined and evaporated. The solid was triturated with methanol, filtered and dried under vacuum to give 4-(4-fluoro-2-methylindol-5-yloxy)-6-methoxy-7-((1-methylpiperidin-4-yl)methoxy)quinazoline (1.95 g, 69%).

MS-ESI: 451 [MH]$^+$ $^1$H NMR Spectrum (DMSOd$_6$) 1.4 (m, 2H); 1.8 (d, 2H); 1.7-1.9 (m, 1H); 1.9 (t, 2H); 2.2 (s, 3H); 2.45 (s, 3H); 2.8 (d, 2H); 4.02 (s, 3H); 4.1 (d, 2H); 6.25 (s, 1H); 7.0 (dd, 1H); 7.2 (d, 1H); 7.4 (s, 1H); 7.62 (s, 1H); 8.5 (s, 1H)

| Elemental analysis: | Found | C 64.2 | H 6.5 | N 11.7 |
|---|---|---|---|---|
| C$_{25}$H$_{27}$FN$_4$O$_3$ 0.91 methanol 0.08CH$_2$Cl$_2$ 0.1H$_2$O | Requires | C 63.9 | H 6.4 | N 11.5% |

The starting material was prepared as follows:

To a solution of 2-fluoro-4-nitroanisole (9.9 g, 58 mmol) and 4-chlorophenoxyacetonitrile (10.7 g, 64 mmol) in DMF (50 ml) cooled at −15° C. was added potassium tert-butoxide (14.3 g, 127 mmol) in DMF (124 ml). After stirring for 30 minutes at −15° C., the mixture was poured onto cooled 1N hydrochloric acid. The mixture was extracted with ethyl acetate. The organic layer was washed with 1N sodium hydroxide, brine, dried (MgSO$_4$) and evaporated. The residue was purified by column chromatography eluting with methylene chloride. The fractions containing the expected product were combined and evaporated. The residue was dissolved in ethanol (180 ml) and acetic acid (24 ml) containing 10% palladium on charcoal (600 mg) and the mixture was hydrogenated under 3 atmospheres pressure for 2 hours. The mixture was filtered, and the volatiles were removed under vacuum. The residue was partitioned between ethyl acetate and water. The organic layer was separated, and washed with saturated sodium hydrogen carbonate followed by brine, dried (MgSO$_4$) and evaporated. The residue was purified by column chromatography eluting with methylene chloride to give a mixture of 4-fluoro-5-methoxyindole and 6-fluoro-5-methoxyindole (5.64 g, 59%) in a ratio 1/2.

$^1$H NMR Spectrum: (DMSOd$_6$) 3.85 (s, 3H); 6.38 (s, 11-1, 6-Fluoro); 6.45 (s, 1H; 4-Fluoro); 6.9-7.4 (m, 3H)

A solution of 4-fluoro-5-methoxyindole and 6-fluoro-5-methoxyindole in a ratio 1/2 (496 mg, 3 mmol), di-tertbutyl dicarbonate (720 mg, 3.3 mmol) in acetonitrile (12 ml) containing DMAP (18 mg, 0.15 mmol) was stirred at ambient temperature for 24 hours. The volatiles were removed under vacuum. The residue was dissolved in ethyl acetate, washed with 1N hydrochloric acid, followed by water, brine, dried (MgSO$_4$) and evaporated to give a mixture of 4-fluoro-5-methoxy-1-tert-butoxycarbonylindole and 6-fluoro-5-methoxy-1-tert-butoxycarbonylindole in a ratio 1/2 (702 mg, 88%).

$^1$H NMR Spectrum: (DMSOd$_6$) 1.65 (s, 9H); 3.9 (s, 3H); 6.6 (d, 1H, 6-fluoro); 6.72 (d, 1H, 4-fluoro); 7.2 (t, 1H, 6-fluoro); 7.4 (d, 1H, 4-fluoro); 7.62 (d, 1H, 6-fluoro); 7.68 (d, 11-1,4-fluoro); 7.78 (s, 1H, 4-fluoro); 7.85 (s, 1H 6-fluoro)

To a solution of 4-fluoro-5-methoxy-1-tert-butoxycarbonylindole and 6-fluoro-5-methoxy-1-tert-butoxycarbonylindole in a ratio 1/2 (8.1 g, 30.5 mmol) in THF (100 ml) cooled at −65° C. was added tert-butyllithium (1.7 M) (23 ml, 35.7 mmol). After stirring for 4 hours at −70° C., methyl iodide (8.66 g, 61 mmol) was added and the mixture was left to warm-up to ambient temperature. Water was added and the mixture was extracted with ether. The organic layer was washed with water, brine, dried (MgSO$_4$) and evaporated and was used directly in the next step.

The crude product was dissolved in methylene chloride (100 ml) and TFA (25 ml) was added. After stirring for 1 hour at ambient temperature, the volatiles were removed under vacuum. The residue was dissolved in ethyl acetate and the organic layer was washed with 1N sodium hydroxide, followed by water, brine, dried (MgSO$_4$) and evaporated. The residue was purified by column chromatography, eluting with ethyl acetate/petroleum ether (3/7) to give 6-fluoro-5-methoxy-2-methylindole (1.6 g) and 4-fluoro-5-methoxy-2-methylindole (0.8 g, 48%).

6-fluoro-5-methoxy-2-methylindole:
MS-ESI: 180 [MH]$^+$
$^1$H NMR Spectrum: (DMSOd$_6$) 2.35 (s, 3H); 3.8 (s, 3H); 6.05 (s, 1H); 7.1 (s, 1H); 7.12 (s, 1H); 10.8 (s, 1H)

4-fluoro-5-methoxy-2-methylindole:
MS-ESI: 180 [MH]$^+$
$^1$H NMR Spectrum: (DMSOd$_6$) 2.35 (s, 3H); 3.8 (s, 3H); 6.15 (s, 1H); 6.9 (t, 1H); 7.05 (d, 1H); 11.0 (s, 1H)

To a solution of 4-fluoro-5-methoxy-2-methylindole (709 mg, 3.95 mmol) in methylene chloride (9 ml) cooled at −30° C. was added a solution of boron tribromide (2.18 g, 8.7 mmol) in methylene chloride (1 ml). After stirring for 1 hour at ambient temperature, the mixture was poured onto water and was diluted with methylene chloride. The pH of the aqueous layer was adjusted to 6. The organic layer was separated, washed with water, brine, dried (MgSO$_4$) and evaporated. The residue was purified by column chromatography, eluting with ethyl acetate/petroleum ether (3/7) to give 4-fluoro-5-hydroxy-2-methylindole (461 mg, 70%).

MS-ESI: 166 [MH]$^+$
1H NMR Spectrum: (DMSOd$_6$) 2.35 (s, 3H); 6.05 (s, 1H); 6.65 (dd, 1H); 6.9 (d, 1H); 8.75 (s, 1H); 10.9 (s, 1H)
$^{13}$C NMR Spectrum: (DMSOd$_6$) 13.5; 94.0; 106.0; 112; 118.5 (d); 132 (d); 136 (d); 136.5; 142.5 (d)

Alternatively the 4-fluoro-5-hydroxy-2-methylindole may be prepared as follows:

To a suspension of sodium hydride (5.42 g, 226 mmol) (prewashed with pentane) in THF (100 ml) cooled at 10° C. was added ethyl acetoacetate (29.4 g, 226 mmol) while keeping the temperature below 15° C. After completion of addition, the mixture was further stirred for 15 minutes and cooled to 5° C. A solution of 1,2,3-trifluoro-4-nitrobenzene (20 g, 113 mmol) in THF (150 ml) was added while keeping the temperature below 5° C. The mixture was then left to warm up to ambient temperature and stirred for 24 hours. The volatiles were removed under vacuum and the residue was partitioned between ethyl acetate and 2N aqueous hydrochloric acid. The organic layer was washed with water, brine, dried (MgSO$_4$) and evaporated. The residue was dissolved in concentrated hydrochloric acid (650 ml) and acetic acid (600 ml) and the mixture was refluxed for 15 hours. After cooling, the volatiles were removed under vacuum and the residue was partitioned between aqueous sodium hydrogen carbonate (5%) and ethyl acetate. The organic layer was washed with sodium hydrogen carbonate, water, brine, dried (MgSO$_4$) and evaporated. The residue was purified by column chromatography eluting with ethylacetate/petroleum ether (75/25) to give 3-acetylmethyl-1,2-difluoro-4-nitrobenzene (17.5 g, 72%).

$^1$H NMR Spectrum: (CDCl$_3$) 2.4 (s, 3H); 4.25 (s, 2H); 7.25 (dd, 1H); 8.0 (dd, 1H)

A solution of 3-acetylmethyl-1,2-difluoro-4-nitrobenzene (500 mg, 2.3 mmol) in methylene chloride (5 ml) containing montmorillonite K10 (1 g) and trimethyl orthoformate (5 ml) was stirred for 24 hours at ambient temperature. The solid was filtered, washed with methylene chloride and the filtrate was evaporated to give 1,2-difluoro-3-(2,2-dimethoxypropyl)-4-nitrobenzene (534 mg, 88%).

$^1$H NMR Spectrum: (CDCl$_3$) 1.2 (s, 3H); 3.2 (s, 6H); 3.52 (s, 2H); 7.18 (dd, 1H); 7.6 (m, 1H)

To a solution of benzyl alcohol (221 mg, 2.05 mmol) in DMA (1.5 ml) was added 60% sodium hydride (82 mg, 2.05 mmol). The mixture was stirred for 1 hour at ambient temperature. A solution of 1,2-difluoro-3-(2,2-dimethoxypropyl)-4-nitrobenzene (534 mg, 2.05 mmol) in DMA (1.5 ml) was added and the mixture was stirred for 3 hours at ambient temperature. The mixture was diluted with 1N hydrochloric acid (10 ml) and extracted with ethyl acetate. The organic layer was evaporated and the residue was dissolved in THF (2 ml) and 6N hydrochloric acid (0.3 ml) was added. The mixture was stirred for 1 hour at ambient temperature and the solvents were removed under vacuum. The residue was partitioned between ethyl acetate and water. The organic layer was separated, washed with brine, dried (MgSO$_4$) and evaporated. The solid was triturated with ether, filtered, washed with ether and dried under vacuum to give 3-acetylmethyl-1-benzyloxy-2-fluoro-4-nitrobenzene (350 mg, 56%).

$^1$H NMR Spectrum: (CDCl$_3$) 2.35 (s, 3H); 4.25 (s, 2H); 5.25 (s, 2H); 7.0 (dd, 1H); 7.32-7.5 (m, 5H); 8.0 (dd, 1H)

A solution of 3-acetylmethyl-1-benzyloxy-2-fluoro-4-nitrobenzene (300 mg, 0.99 mmol) in ethanol (10 ml) and acetic acid (1 ml) containing 10% palladium on charcoal (30 mg) was hydrogenated at 2 atmospheres pressure for 2 hours. The mixture was filtered and the filtrate was evaporated. The residue was dissolved in ethyl acetate and the organic layer was washed with aqueous sodium hydrogen carbonate, brine and evaporated to give 4-fluoro-5-hydroxy-2-methylindole. The residue was purified by column chromatography eluting with ethyl acetate/petroleum ether (3/7) to give 4-fluoro-5-hydroxy-2 -methylindole (63 mg, 30%). Analytical data as above.

Alternatively the 4-fluoro-5-methoxy-2-methylindole can be prepared as follows:

A solution of sodium methoxide (freshly prepared from sodium (1.71 g) and methanol (35 ml)) was added to a solution of 1,2-difluoro-3-(2,2-dimethoxypropyl)-4-nitrobenzene (16.2 g, 62 mmol), (prepared as described above), in methanol (200 ml) cooled at 5° C. The mixture was left to warm to ambient temperature and was stirred for 3 days. The volatiles were removed under vacuum and the residue was partitioned between ethyl acetate and 2N hydrochloric acid (1 ml). The organic layer was concentrated to a total volume of 100 ml and THF (100 ml) and 6N hydrochloric acid (25 ml) were added. The mixture was stirred for 1 hour at ambient temperature. The volatiles were removed under vacuum and the residue was partitioned between ethyl acetate and water. The organic layer was separated, washed with water, brine, dried (MgSO$_4$) and evaporated. The residue was purified by column chromatography eluting with ethyl acetate/petroleum ether (3/7) to give 3-acetylmethyl-2-fluoro-1-methoxy-4-nitrobenzene (12.7 g, 90%).

MS-ESI: 250 [MNa]+
$^1$H NMR Spectrum: (CDCl$_3$) 2.38 (s, 3H); 4.0 (s, 3H); 4.25 (s, 2H); 7.0 (dd, 1H); 8.05 (d, 1H)

To a solution of 3-acetylmethyl-2-fluoro-1-methoxy-4-nitrobenzene (11.36 g, 50 mmol) in acetone (200 ml) was added 4M aqueous ammonium acetate (700 ml) followed by a solution of titanium trichloride (15% in water, 340 ml) dropwise. The mixture was stirred for 10 minutes at ambient temperature and the mixture was extracted with ether. The organic layer was washed with 0.5N aqueous sodium hydroxide followed by water, brine, dried (MgSO$_4$) and the volatiles were removed under vacuum. The residue was purified by column chromatography eluting with methylene chloride to give 4-fluoro-5-methoxy-2-methylindole (8.15 g, 90%).

$^1$H NMR Spectrum: (DMSO) 2.35 (s, 3H); 3.8 (s, 3H); 6.1 (s, 1H); 6.85 (dd, 1H); 7.02 (d, 1H)

Cleavage of 4-fluoro-5-methoxy-2-methylindole with boron tribromide to give 4-fluoro-5-hydroxy-2-methylindole is described above.

EXAMPLE 238

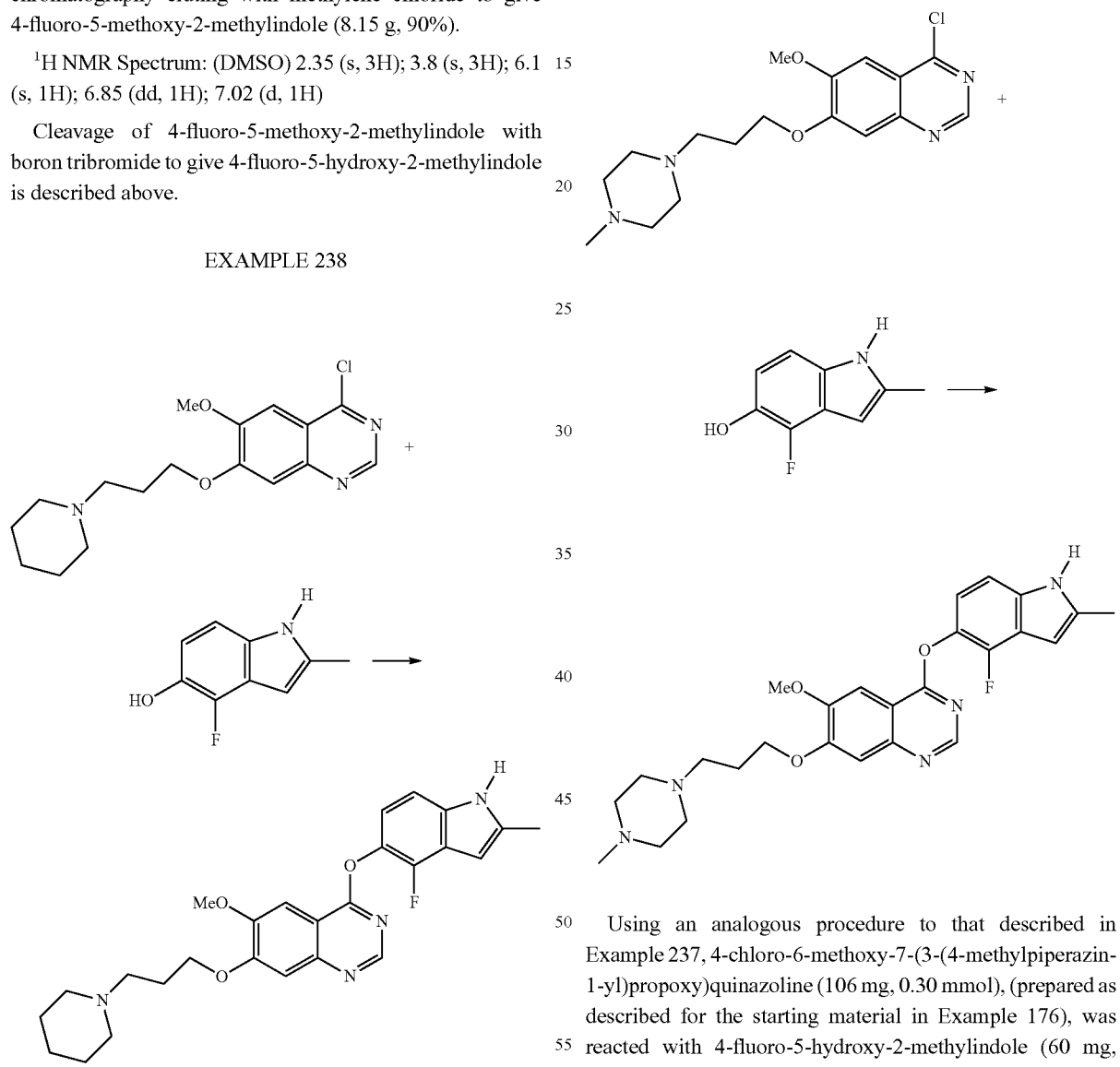

Using an analogous procedure to that described in Example 237, 4-chloro-6-methoxy-7-(3-piperidinopropoxy)quinazoline (1.65 g, 4.89 mmol), (prepared as described for the starting material in Example 67), was reacted with 4-fluoro-5-hydroxy-2-methylindole (970 mg, 5.88 mmol), (prepared as described for the starting material in Example 237), to give 4-(4-fluoro-2-methylindol-5-yloxy)-6-methoxy-7-(3-piperidinopropoxy)quinazoline (1.9 g, 83%).

MS-ESI: 465 [MH]$^+$ $^1$H NMR Spectrum: (DMSOd$_6$) 1.4 (br s, 2H); 1.5 (m, 4H); 1.95 (m, 2H); 2.25-2.5 (m, 6H); 2.45 (s, 3H); 4.0 (s, 3H); 4.25 (t, 2H); 6.25 (s, 1H); 7.0 (dd, 1H); 7.15 (d, 1H); 7.4 (s, 1H); 7.6 (s, 1H); 8.5 (s, 1H)

EXAMPLE 239

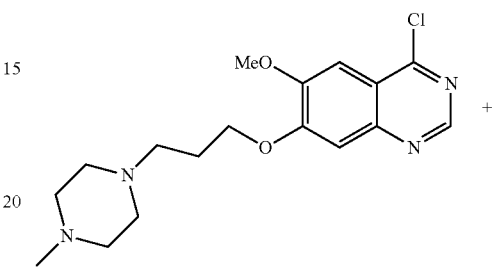

Using an analogous procedure to that described in Example 237, 4-chloro-6-methoxy-7-(3-(4-methylpiperazin-1-yl)propoxy)quinazoline (106 mg, 0.30 mmol), (prepared as described for the starting material in Example 176), was reacted with 4-fluoro-5-hydroxy-2-methylindole (60 mg, 0.36 mmol), (prepared as described for the starting material in Example 237), to give 4-(4-fluoro-2-methylindol-5-yloxy)-6-methoxy-7-(3-(4-methylpiperazin-1-yl)propoxy)quinazoline (100 mg, 70%).

MS-ESI: 480 [MH]$^+$ $^1$H NMR Spectrum: (DMSOd$_6$) 2.0 (t, 2H); 2.15 (s, 3H); 2.45 (s, 3H); 2.2-2.6 (m, 10H); 4.02 (s, 3H); 4.25 (t, 2H); 6.25 (s, 1H); 7.0 (dd, 1H); 7.18 (d, 1H); 7.4 (s, 1H); 7.62 (s, 1H); 8.5 (s, 1H)

EXAMPLE 240

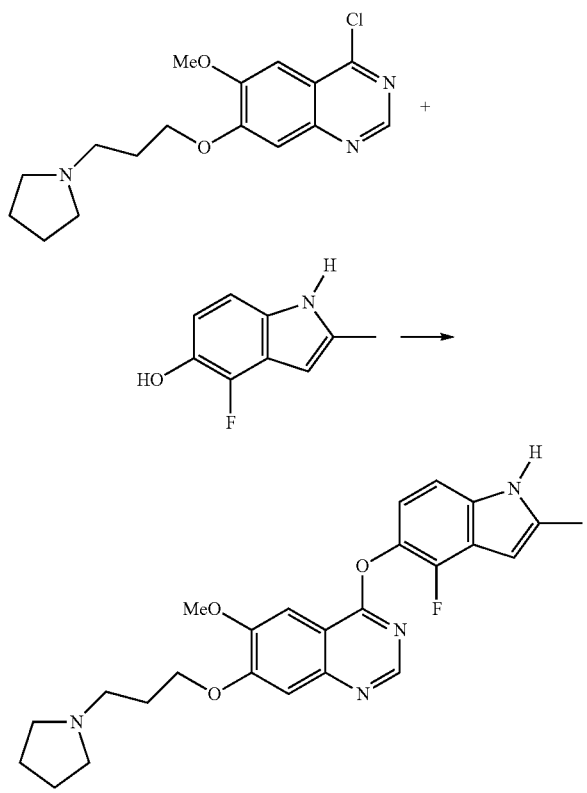

Using a procedure identical to that described in Example 237, 4-chloro-6-methoxy-7-(3-(pyrrolidin-1-yl)propoxy) quinazoline (2 g, 6.22 mmol), (prepared as described for the starting material in Example 9), was reacted with 4-fluoro-5-hydroxy-2-methylindole (1.23 g, 7.46 mmol), (prepared as described for the starting material in Example 237), to give 4-(4-fluoro-2-methylindol-5-yloxy)-6-methoxy-7-(3-(pyrrolidin-1-yl)propoxy)quinazoline (1.41 g, 50%).

MS-ESI: 451 [MH]+

$^1$H NMR Spectrum: (DMSOd$_6$) 1.7 (br s, 4H); 2.0 (m, 2H); 2.41 (s, 3H); 2.5 (br s, 4H); 2.6 (t, 2H); 4.0 (s, 3H); 4.25 (t, 2H); 6.25 (s, 1H); 7.0 (dd, 1H); 7.2 (d, 1H); 7.4 (s, 1H); 7.6 (s, 1H); 8.5 (s, 1H)

| Elemental analysis: | Found | C 63.3 | H 6.4 | N 11.9 |
|---|---|---|---|---|
| C$_{25}$H$_{27}$FN$_4$O$_3$ 1.08 H$_2$O; 0.16 methanol | Requires | C 63.6 | H 6.3 | N 11.8% |

EXAMPLE 241

A solution of 4-chloro-6-methoxy-7-(2-(1-methylpiperidin-4-yl)ethoxy)quinazoline (300 mg, 0.9 mmol) and 4-fluoro-5-hydroxyindole (162 mg, 1 mmol), (prepared as described for the starting material in Example 242), in DMF (4.5 ml) containing potassium carbonate (185 mg, 1.3 mmol) was stirred at 90° C. for 1 hour. After cooling, the mixture was filtered and the solid was washed with DMF. The filtrate was evaporated and the residue was purified by column chromatography, eluting with methylene chloride followed by methanol/methylene chloride (1/99) followed by methanol saturated with ammonia/methylene chloride (2/98). The fractions containing the expected product were combined and evaporated. The solid was triturated with ether, filtered, washed with ether and dried under vacuum to give 4-(4-fluoroindol-5-yloxy)-6-methoxy-7-(2-(1-methylpiperidin-4-yl)ethoxy)quinazoline (282 mg, 69%).

MS-ESI: 451 [MH]+

$^1$H NMR Spectrum: (DMSOd$_6$) 1.2-1.3 (m, 2H); 1.4-1.55 (m, 1H); 1.7-1.9 (m, 6H); 2.15 (s, 3H); 2.75 (d, 2H); 4.0 (s, 3H); 4.3 (t, 2H); 6.55 (s, 1H); 7.1 (dd, 1H); 7.3 (d, 1H); 7.4 (s, 1H); 7.5 (s, 1H); 7.6 (s, 1H); 8.5 (s, 1H); 11.5 (s, 1H)

The starting material was prepared as follows:

To a solution of 4-(2-hydroxyethyl)-(1-tert-butoxycarbonyl)piperidine (12.9 g, 56 mmol), (prepared as described for the starting material in Example 126), in tert-butyl methyl ether (120 ml) containing 1,4-diazabicyclo[2.2.2]octane (9.8 g, 87 mmol) cooled at −5° C. was added a solution of tosyl chloride (14.5 gr, 76 mmol) in tert-butyl methyl ether (120 ml) dropwise whilst keeping the temperature below 0° C. After completion of addition, the mixture was left to warm up to ambient temperature and stirred for 1 hour. The mixture was poured onto petroleum ether (240 ml). The precipitae was filtered and washed with petroleum ether. The filtrate was evaporated and the residue was dissolved in ether. The ether layer was washed with 0.5 N hydrochloric acid, followed by saturated sodium hydrogen carbonate, dried (MgSO$_4$) and evaporated to give 4-(2-(4-methylphenylsulphonyloxy) ethyl)-1-tert-butoxycarbonyl)piperidine (20.9 g, 97%).

$^1$H NMR Spectrum: (CDCl$_3$) 0.95-1.05 (m, 4H); 1.45 (s, 9H); 1.4-1.6 (m, 3H) 2.45 (s, 3H); 2.62 (t, 2H); 3.9-4.1 (m, 2H); 4.1 (t, 2H); 7.35 (d, 2H); 7.8 (d, 2H)

A suspension of 7-hydroxy-6-methoxy-3-((pivaloyloxy) methyl)-3,4-dihydroquinazolin-4-one (7 g, 23 mmol), (prepared as described for the starting material in Example 12), 4-(2-(4-methylphenylsulphonyloxy)ethyl)-1-tert-butoxycarbonylpiperidine (11.4 g, 30 mmol) in DMF (70 ml) containing potassium carbonate (6.32 g, 46 mmol) was stirred at 100° C. for 3 hours. After cooling, the volatiles were removed under vacuum and the residue was partitioned between ether and water. The organic layer was separated, washed with water, brine, dried (MgSO$_4$) and evaporated. The solid was triturated with pentane, filtered and dried under vacuum to give 7-(2-(1-tertbutoxycarbonylpiperidin-4-yl)ethoxy)-6-methoxy-3-((pivaloyloxy)methyl)-3,4-dihydroquinazolin-4-one (10.5 g, 88%).

MS-ESI: 540 [MNa]$^+$ $^1$H NMR Spectrum: (CDCl$_3$) 1.2 (s, 9H); 1.15-1.25 (m, 2H); 1.48 (s, 9H); 1.65-1.75 (m, 1H); 1.7 (d, 2H); 1.9 (dd, 2H); 2.72 (t, 2H); 4.0 (s, 3H); 4.0-4.2 (m, 2H); 4.2 (t, 2H); 5.95 (s, 2H); 7.1 (s, 1H); 7.65 (s, 1H); 8.2 (s, 1H)

A solution of 7-(2-(1-tertbutoxycarbonylpiperidin-4-yl) ethoxy)-6-methoxy-3-((pivaloyloxy)methyl)-3,4-dihydroquinazolin-4-one (10.5 g, 20 mmol) in methylene chloride (100 ml) containing TPA (25 ml) was stirred for 1 hour at ambient temperature. Water (50 ml) and methylene chloride (100 ml) were added and the pH of the aqueous layer was adjusted to 8 with solid sodium hydrogen carbonate. The organic layer was separated, washed with water, brine, dried (MgSO$_4$) and evaporated. The residue was triturated with ether and the solid was filtered and dried under vacuum to give 7-(2-(piperidin-4-yl)ethoxy)-6-methoxy-3-((pivaloyloxy)methyl)-3,4-dihydroquinazolin-4-one (8.3 g, 100%).

¹H NMR Spectrum: (CDCl₃) 1.2 (s, 9H); 1.65 (m, 2H); 1.9 (br s, 2H); 1.8-1.9 (m, 1H); 2.0 (d, 2H); 2.9 (t, 2H); 3.45 (d, 2H); 4.0 (s, 3H); 4.2 (t, 2H); 5.95 (s, 2H); 7.1 (s, 1H); 7.65 (s, 1H); 8.2 (s, 1H)

To a solution of 7-(2-(piperidin-4-yl)ethoxy)-6-methoxy-3-((pivaloyloxy)methyl)-3,4-dihydroquinazolin-4-one (6 g, 14.4 mmol) in methanol (30 ml) and methylene chloride (60 ml) was added 37% aqueous formaldehyde (2.2 ml; 28.9 mmol) followed by acetic acid (990 μl; 17.3 mmol). Sodium borohydride triacetate (4.6 g, 21.6 mmol) was added in portions. After stirring for 1 hour at ambient temperature, the volatiles were removed under vacuum and the residue was partitioned between water (50 ml) and methylene chloride (50 ml). The pH of the aqueous layer was adjusted to 7, washed with water, brine, dried (MgSO₄) and evaporated. The solid was triturated with ether, filtered, washed with ether and dried under vacuum to give 7-(2-(1-methylpiperidin-4-yl)ethoxy)-6-methoxy-3-((pivaloyloxy)methyl)-3,4-dihydroquinazolin-4-one (4.2 g, 68%).

MS-ESI: 432 [MH]⁺

1H NMR Spectrum: (CDCl₃) 1.22 (s, 9H); 1.68 (br s, 3H); 1.9 (m, 4H); 2.32 (br s, 2H); 2.52 (s, 3H); 3.18 (d, 2H); 4.0 (s, 3H); 4.2 (t, 2H); 5.95 (s, 2H); 7.1 (s, 1H); 7.65 (s, 1H); 8.2 (s, 2H)

A solution of 7-(2-(1-methylpiperidin-4-yl)ethoxy)-6-methoxy-3-((pivaloyloxy)methyl)-3,4-dihydroquinazolin-4-one (4.2 g, 9.7 mmol) in methanol saturated with ammonia (150 ml) was stirred overnight at ambient temperature. The volatiles were removed under vacuum and the residue was triturated with ether. The solid was filtered, washed with ether and dried under vacuum to give 7-(2-(1-methylpiperidin-4-yl)ethoxy)-6-methoxy-3,4-dihydroquinazolin-4-one (3.12 g, 100%).

MS-ESI: 318 [MH]⁺

¹H NMR Spectrum: (DMSOd₆) 1.3 (m, 2H); 1.58 (br s, 1H); 1.72 (dd, 2H); 1.8 (d, 2H); 2.4 (s, 3H); 2.2-2.45 (m, 2H); 3.0 (br s, 2H); 3.85 (s, 3H); 4.15 (t, 2H); 7.15 (s, 1H); 7.45 (s, 1H); 8.0 (s, 1H)

A solution of 7-(2-(1-methylpiperidin-4-yl)ethoxy)-6-methoxy-3,4-dihydroquinazolin-4-one (3.1 g, 9.8 mmol) in thionyl chloride (40 ml) containing DMF (400 μl) was refluxed for 4 hours. After cooling, the volatiles were removed under vacuum. The residue was partitioned between methylene chloride and water and the pH of the aqueous layer was adjusted to 11 with solid sodium hydrogen carbonate and aqueous ammonia. The organic layer was separated, dried (MgSO₄) and evaporated. The residue was triturated with ether, filtered, washed with ether and dried under vacuum to give 4-chloro-6-methoxy-7-(2-(1-methylpiperidin-4-yl)ethoxy)quinazoline (1.83 g, 54%).

MS-ESI: 336 [MH]⁺

¹H NMR Spectrum: (CDCl₃) 1.4-1.7 (m, 3H); 1.8 (d, 2H); 1.9 (dd, 2H); 2.05 (t, 2H); 2.35 (s, 3H); 2.95 (d, 2H); 4.05 (s, 3H); 4.25 (t, 2H); 7.3 (s, 1H); 7.4 (s, 1H); 8.88 (s, 1H)

EXAMPLE 242

A solution of 4-chloro-6-methoxy-7-((1-methylpiperidin-4-yl)methoxy)quinazoline (213 mg, 0.662 mmol), (prepared as described for the starting material in Example 10), and 6-fluoro-5-hydroxyindole (120 mg, 0.794 mmol) in DMF (3 ml) containing potassium carbonate (137 mg, 0.994 mmol) was stirred at 95° C. for 3.5 hours. After cooling, the mixture was poured onto water. The mixture was filtered and the solid was washed with water. The solid was dissolved in methylene chloride. The organic layer was dried (MgSO₄), and evaporated. The residue was triturated with ether/ethyl acetate and the solid was filtered and dried under vacuum to give 4-(6-fluoroindol-5-yloxy)-6-methoxy-7-(1-methylpiperidin-4-ylmethoxy)quinazoline (135 mg, 46%).

MS-ESI: 437 [MH]⁺

¹H NMR Spectrum: (DMSOd₆) 1.3-1.45 (m, 2H); 1.8 (d, 2H); 1.9 (t, 2H); 1.7-1.9 (m, 1H); 2.17 (s, 3H); 2.8 (d, 2H); 4.0 (s, 3H); 4.1 (d, 2H); 6.48 (br s, 1H); 7.38 (d, 1H); 7.4 (s, 1H); 7.42 (t, 1H); 7.58 (d, 1H); 7.6 (s, 1H); 8.5 (s, 1H)

| Elemental analysis | Found | C 65.0 H 5.8 N 12.7 |
|---|---|---|
| $C_{24}H_{25}FN_4O_3$ 0.4 $H_2O$ | Requires | C 65.0 H 5.9 N 12.6% |

The starting material was prepared as follows:

A mixture of 2-fluoro-4-nitrophenol (15gr, 95.5 mmol) and benzyl bromide (18 g, 105 mmol) in acetone (125 ml) containing potassium carbonate (26.5 gr, 190 mmol) was refluxed for 2 hours. The volatiles were removed and the residue was partitioned between 2N hydrochloric acid and ethyl acetate. The organic layer was separated, washed with water, brine, dried (MgSO₄) and the volatiles were removed under vacuum. The solid was triturated with petroleum ether to give 2-fluoro-4-nitro-benzyloxybenzene (23g, 97%).

¹H NMR Spectrum: (CDCl₃) 5.3 (s, 2H); 7.1 (t, 1H); 7.35-7.55 (m, 5H); 8.0 (m, 2H)

To a solution of potassium tert-butoxide (1.72 g, 15.4 mmol) in DMF (15 ml) cooled at −30° C., was added dropwise a solution of 2-fluoro-4-nitro-benzyloxybenzene (1.73 g, 7 mmol) and 4-chlorophenoxyacetonitrile (1.29 g, 7.7 mmol) while maintaining the temperature below −25° C. After completion of addition, the mixture was stirred for 30 minutes at −20° C. and then poured onto a mixture of cold 1N hydrochloric acid and ether. The organic layer was separated, washed with 1N sodium hydroxide, followed by water, brine, dried (MgSO₄). The volatiles were removed under vacuum and the residue was purified by column chromatography eluting with methylene chloride/petroleum ether (3/1) to give a mixture of 3-cyanomethyl-2-fluoro-4-nitrobenzyloxybenzene and 5-cyanomethyl-2-fluoro-4-nitrobenzyloxybenzene (1.2 g, 60%).

¹H NMR Spectrum: (DMSOd₆) 4.22 (s, 2H, 3-cyanomethyl isomer); 4.3 (s, 2H, 5-cyanomethyl isomer); 5.32 (s, 2H, 5-cyanomethyl isomer); 5.36 (s, 2H, 3-cyanomethyl isomer); 7.3-7.7 (m, 6H); 8.1 (d, 1H, 3-cyanomethyl isomer); 8.2 (d, 1H, 5-cyanomethyl isomer)

A solution of a mixture of 3-cyanomethyl-2-fluoro-4-nitrobenzyloxybenzene and 5-cyanomethyl-2-fluoro-4-nitrobenzyloxybenzene (23 g, 80.4 mmol) in ethanol (220 ml) and acetic acid (30 ml) containing 10% palladium on charcoal (600 mg) was hydrogenated under 3 atmospheres pressure until hydrogen uptake ceased. The mixture was filtered and the filtrate was evaporated under vacuum. The residue was purified on column chromatography using a Prochrom® equipment eluting with methylene chloride/petroleum ether (20/80) to give 4-fluoro-5-hydroxyindole (2.48 g) and 6-fluoro-5-hydroxyindole (3.5 g).

4-fluoro-5-hydroxyindole:

¹H NMR Spectrum: (DMSOd₆) 6.32 (s, 1H); 6.75 (dd, 1H); 7.0 (d, 1H); 7.28 (dd, 1H); 8.8 (br s, 1H); 11.05 (br s, 1H)

6-fluoro-5-hydroxyindole:

¹H NMR Spectrum: (DMSOd₆) 6.25 (s, 1H); 7.0 (d, 1H); 7.12 (d, 1H); 7.2 (dd, 1H); 9.0 (br s, 1H)

EXAMPLE 243

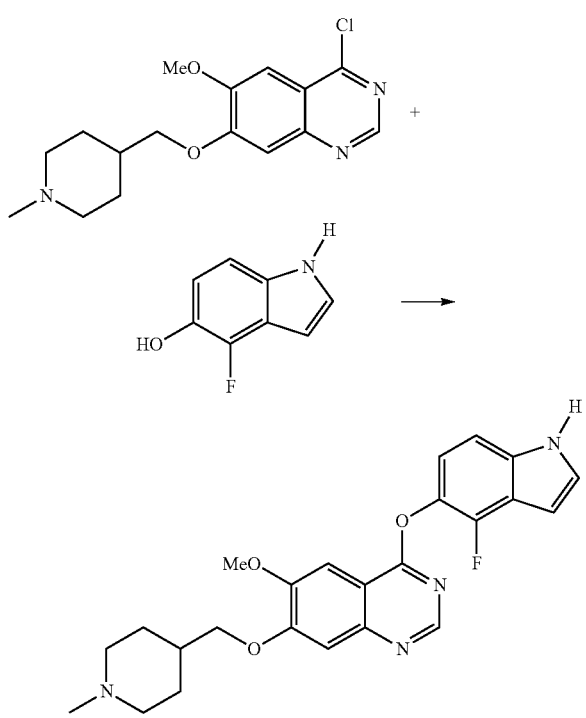

A solution of 4-chloro-6-methoxy-7-((1-methylpiperidin-4-yl)methoxy)quinazoline (213 mg, 0.662 mmol), (prepared as described for the starting material in Example 10), and 4-fluoro-5-hydroxyindole (120 mg, 0.794 mmol), (prepared as described for the starting material in Example 242), in DMF (3 ml) containing potassium carbonate (137 mg, 0.994 mmol) was stirred at 95° C. for 3 hours. After cooling, the mixture was partitioned between ethyl acetate and water. The organic layer was washed with water, brine, dried (MgSO₄) and evaporated. The residue was triturated in cold ether. The solid was filtered and dried under vacuum to give 4-(4-fluoroindol-5-yloxy)-6-methoxy-7-(1-methylpiperidin-4-yl-methoxy)quinazoline (77 mg, 26%).

MS-ESI: 437 [MH]⁺

¹H NMR Spectrum: (DMSOd₆) 1.3-1.5 (m, 2H); 1.8 (d, 2H); 1.9 (t, 2H); 1.7-1.95 (m, 1H); 2.2 (s, 3H); 2.8 (d, 2H); 4.02 (s, 3H); 4.1 (d, 2H); 6.55 (s, 1H); 7.1 (t, 1H); 7.3 (d, 1H); 7.4 (s, 1H); 7.48 (t, 1H); 7.62 (s, 1H); 8.5 (s, 1H)

| Elemental analysis | Found | C 64.8 H 5.8 N 12.6 |
| C₂₄H₂₅FN₄O₃ 0.4 H₂O | Requires | C 65.0 H 5.9 N 12.6% |

EXAMPLE 244

A mixture of 4-chloro-6-methoxy-7-(3-(4-methylpiperazin-1-yl)propoxy)quinazoline (282 mg, 0.662 mmol), 6-fluoro-5-hydroxyindole (120 mg, 0.794 mmol), (prepared as described for the starting material in Example 242), in DMF (3 ml) containing potassium carbonate (137 mg, 0.994 mmol) was heated at 95° C. for 3 hours. After cooling, the residue was poured in water (12 ml) and the pH was adjusted to 8. The mixture was extracted with ethyl acetate. The organic layer was separated, washed with water, brine, dried (MgSO₄) and evaporated. The residue was purified by preparative column chromatography on C¹⁸ silica eluting with 60% methanol in aqueous ammonium carbonate (2g ammonium carbonate/liter saturated with CO₂). The fractions containing the expected product were combined and evaporated. The residue was triturated with ether and the solid was filtered, dried under vacuum to give 4-(6-fluoroindol-5-yloxy)-6-methoxy-7-(3-(4-methylpiperazin-1-yl)propoxy)quinazoline (147 mg, 48%).

MS-ESI: 466 [MH]⁺

¹H NMR Spectrum: (DMSOd₆, CF₃COOD) 2.3-2.4 (m, 2H); 3.0 (s, 3H); 3.2-3.9 (m, 8H); 3.5 (t, 2H); 4.1 (s, 3H); 4.4 (t, 2H); 6.52 (d, 1H); 7.45 (d, 1H); 7.48 (s, 1H); 7.6 (s, 1H); 7.65 (d, 1H); 7.82 (s, 1H); 9.0 (s, 1H)

| Elemental analysis | Found | C 62.1 H 6.4 N 14.2 |
| C₂₅H₂₈FN₅O₃ 0.9 H₂O | Requires | C 62.3 H 6.2 N 14.5% |

The starting material was prepared as follows:

To a suspension of 7-hydroxy-6-methoxy-3-((pivaloyloxy)methyl)-3,4-dihydroquinazolin-4-one (29 g, 94.7 mmol), (prepared as described for the starting material in Example 12), in methylene chloride (280 ml) coiled at 5° C. was added triphenylphosphine (37.1 g, 141.6 mmol) followed by 3-bromo-1-propanol (12.8 ml, 141.6 mmol) and diethyl azodicarboxylate (2.4 ml, 141.6 mmol) dropwise. After stirring for 2 hours at ambient temperature, the volatiles were removed under vacuum and the residue was purified by column chromatography eluting with methylene chloride/methanol (98/2). The fractions containing the expected product were combined and evaporated and the solid was triturated with ether, filtered, washed with ether and dried under vacuum to give 7-(3-bromopropoxy)-6-methoxy-3-((pivaloyloxy)methyl)-3,4-dihydroquinazolin-4-one (37.22 g, 92%).

MS-ESI: 427-429 [MH]+

¹H NMR Spectrum: (DMSOd₆) 1.18 (s, 9H); 2.32 (m, 2H); 3.7 (t, 2H); 3.92 (s, 3H); 4.28 (t, 2H); 5.95 (s, 2H); 7.2 (s, 1H); 7.5 (s, 1H); 8.4 (s, 1H)

A suspension of 7-(3-bromopropoxy)-6-methoxy-3-((pivaloyloxy)methyl)-3,4-dihydroquinazolin-4-one (36.7 g, 86 mmol) in 1-methylpiperazine (370 ml) was stirred at 100° C. for 90 minutes. After removal of the volatiles under vacuum, the residue was partitioned between methylene chloride and aqueous ammonium chloride. The organic layer was separated, washed with water, brine, dried (MgSO₄) and evaporated. The solid was triturated with ether, filtered, washed with ether and dried under vacuum to give 7-(3-(4-methylpiperazin-1-yl)propoxy)-6-methoxy-3-((pivaloyloxy)methyl)-3,4-dihydroquinazolin-4-one (31.9 gr, 83%).

MS-ESI: 447 [MH]+

¹H NMR Spectrum: (DMSOd₆, CF₃COOD) 1.15 (s, 9H); 2.25 (t, 2H); 2.5 (s, 3H); 3.45 (t, 2H); 3.2-4.0 (m, 8H); 3.9 (s, 3H); 4.25 (t, 2H); 5.95 (s, 2H); 7.22 (s, 1H); 7.55 (s, 1H); 8.6 (s, 1H)

A suspension of 7-(3-(4-methylpiperazin-1-yl)propoxy)-6-methoxy-3-((pivaloyloxy)methyl)-3,4-dihydroquinazolin-4-one (31.8 g, 71.3 mmol) in methanol saturated with ammonia was stirred at ambient temperature overnight. The volatiles were removed under vacuum. The solid was triturated with ether containing about 10% of methylene chloride, filtered, washed with ether containing about 10% methylene chloride and dried under vacuum to give 7-(3-(4-methylpiperazin-1-yl)propoxy)-6-methoxy-3,4-dihydroquinazolin-4-one (22.63 g, 95%).

MS-ESI: 333 [MH]+

$^1$H NMR Spectrum: (DMSOd$_6$) 1.92 (m, 2H); 2.15 (s, 3H); 2.2-2.5 (m, 10H); 3.88 (s, 3H); 4.15 (t, 2H); 7.1 (s, 1H); 7.45 (s, 1H); 7.98 (s, 1H)

A solution of 7-(3-(4-methylpiperazin-1-yl)propoxy)-6-methoxy-3,4-dihydroquinazolin-4-one (22.6 g, 68 mmol) in thionyl chloride (300 ml) cotaining DMF (5 ml) was refluxed for 2 hours. After cooling, the volatiles were removed under vacuum and the residue was azeotroped with toluene twice. The solid was dissolved in methulene chloride and water was added. The mixture was cooled to 0° C. and the pH of the aqueous layer was adjusted to 7 with solid hydrogen carbonate and then raised to 10 with 6N Sodium hydroxide. The organic layer was separated and the aqueous layer was extracted with methylene chloride. The organic layer was washed with brine, dried (MgSO$_4$), filtered and the volatiles were removed under vacuum. The residue was triturated with ether, filtered, washed with ether and dried under vacuum to give 4-chloro-6-methoxy-7-(3-(4-methylpiperazin-1-yl)propoxy)quinazoline (16.3 gr, 68%).

MS-ESI: 351-353 [MH]+

$^1$H NMR Spectrum: (DMSOd$_6$) 1.98 (t, 2H); 2.18 (s, 3H); 2.45 (t, 2H); 2.22-2.5 (m, 8H); 4.05 (s, 3H); 4.28 (t, 2H); 7.4 (s, 3H); 7.45 (s, 1H); 8.9 (s, 1H)

EXAMPLE 245

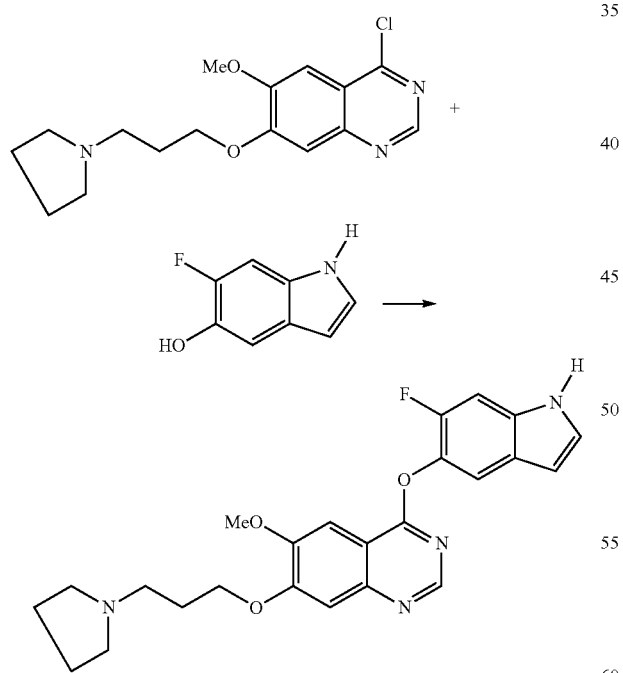

Using an analogous procedure to that described in Example 243, 4-chloro-6-methoxy-7-(3-(pyrrolidin-1-yl)propoxy)quinazoline (213 mg, 0.662 mmol), (prepared as described for the starting material in Example 9), was reacted with 6-fluoro-5-hydroxyindole (120 mg, 0.794 mmol), (prepared as described for the starting material in Example 242), in DMF (3 ml) containing potassium carbonate (137 mg, 0.993 mmol) to give 4-(6-fluoroindol-5-yloxy)-6-methoxy-7-(3-(pyrrolidin-1-yl)propoxy)quinazoline (154 mg, 53%).

MS-ESI: 437 [MH]+

$^1$H NMR Spectrum: (DMSOd$_6$) 1.7-1.8 (m, 4H); 2.0-2.1 (m, 2H); 2.48 (br s, 4H); 2.6 (t, 2H); 4.02 (s, 3H); 4.3 (t, 2H); 6.5 (s, 1H); 7.4 (d, 1H); 7.4 (s, 1H); 7.45 (t, 1H); 7.6 (d, 1H); 7.62 (s, 1H); 8.52 (s, 1H)

| Elemental analysis | Found | C 65.4 H 6.0 N 12.9 |
|---|---|---|
| C$_{24}$H$_{25}$HN$_4$O$_3$ 0.2 H$_2$O | Requires | C 65.5 H 5.8 N 12.7% |

EXAMPLE 246

To a solution of 6-methoxy-4-(2-methylindol-5-yloxy)-7-(piperidin-4-ylmethoxy)quinazoline (500 mg, 1.2 mmol), (prepared as described in Example 70), in methanol (11.5 ml) containing potassium iodide (99 mg, 0.6 mmol) was added 4-(2-chloroethyl)morpholine hydrochloride (134 mg, 0.72 mmol) followed by sodium hydrogen carbonate (151 mg, 1.8 mmol). After stirring for 1 hour at reflux, 4-(2-chloroethyl)morpholine hydrochloride (134 mg, 0.72 mmol) and sodium hydrogen carbonate (151 mg, 1.8 mmol) were added. After stirring 1 hour at reflux, the mixture was cooled and the precipitate was filtered, washed with methanol followed by water and dried over phosphorus pentoxide to give 6-methoxy-4-(2-methylindol-5-yloxy)-7-(1-(2-morpholinoethyl)piperidin-4-ylmethoxy)quinazoline (470 mg, 73%).

MS-ESI: 532 [MH]+

$^1$H NMR Spectrum: (DMSOd$_6$) 1.3-1.45 (m, 2H); 1.8 (d, 2H); 1.7-1.9 (m, 1H); 2.0 (t, 2H); 2.3-2.45 (m, 8H); 2.4 (s, 3H); 2.95 (d, 2H); 3.6 (t, 4H); 4.0 (s, 3H); 4.08 (d, 2H); 6.18 (s, 1H); 6.9 (dd, 1H); 7.3 (s, 1H); 7.35 (d, 1H); 7.4 (s, 1H); 7.6 (s, 1H); 8.5 (s, 1H); 11.05 (s, 1H)

| Elemental analysis | Found | C 65.3 H 7.1 N 12.6 |
|---|---|---|
| C$_{30}$H$_{37}$N$_5$O$_4$ 0.6 H$_2$O 0.6 Methanol | Requires | C 65.4 H 7.3 N 12.5% |

EXAMPLE 247

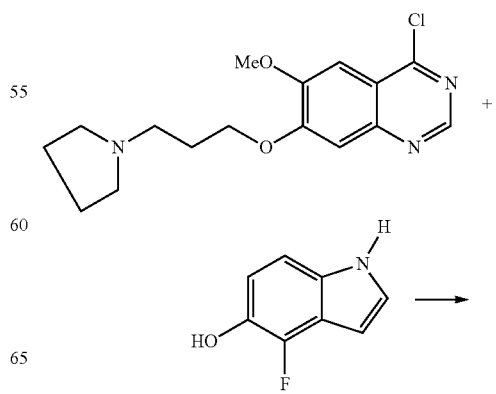

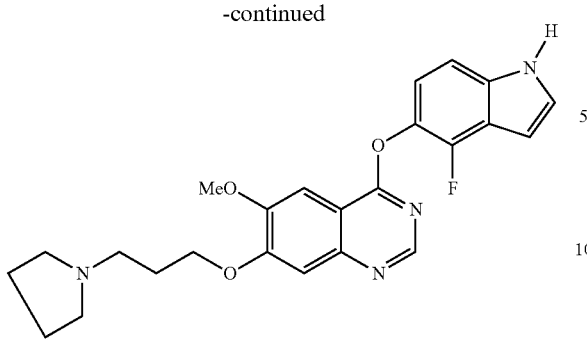

A solution of 4-chloro-6-methoxy-7-(3-(pyrrolidin-1-yl)propoxy)quinazoline (1.76 g, 5.47 mmol), (prepared as described for the starting material in Example 9), 4-fluoro-5-hydroxyindole (0.992 g, 6.57 mmol), (prepared as described for the starting material in Example 242), in DMF (25 ml) containing potassium carbonate (1.14 g; 8.21 mmol) was heated at 95° C. for 1 hour. After cooling, the mixture was filtered and washed with DMF. The filtrate was evaporated and the residue was purified by column chromatography eluting with methanol/methylene chloride (1/9) followed by methanol/methanol chloride/methanol (containing ammonia) (16/80/4). The fractions containing the expected product were combined and evaporated. The residue was repurified by column chromatography eluting with a gradient of methylene chloride/methanol (80/20 to 40/60). The fractions containing the expected product were combined and evaporated. The residue was triturated in cold methanol and the solid was filtered, washed with ether and dried under vacuum to give 4-(4-fluoroindol-5-yloxy)-6-methoxy-7-(3-(pyrrolidin-1-yl)propoxy)quinazoline (1.24 g, 52%).

MS-ESI: 437 [MH]$^+$ $^1$H NMR Spectrum: (DMSOd$_6$) 1.7 (br s, 4H); 2.0 (m, 2H); 2.45 (br s, 4H); 2.6 (t, 2H); 4.05 (s, 3H); 4.28 (t, 2H); 6.58 (s, 1H); 7.1 (t, 2H); 7.35 (d, 1H); 7.4 (s, 1H); 7.5 (t, 1H); 7.65 (s, 1H); 8.52 (s, 1H)

| Elemental analysis | Found | C 65.3 H 5.9 N 12.6 |
|---|---|---|
| C$_{24}$H$_{25}$FN$_4$O$_3$ 0.19 Methanol, 0.17 H$_2$O | Requires | C 65.2 H 5.9 N 12.6% |

EXAMPLE 248

A mixture of 4-chloro-6-methoxy-7-(3-piperidinopropoxy)quinazoline (222 mg, 0.662 mmol), (prepared as described for the starting material in Example 67), and 6-fluoro-5-hydroxyindole (120 mg, 0.794 mmol), (prepared as described for the starting material in Example 242), in DMF (3 ml) containing potassium carbonate (137 mg, 0.993 mmol) was heated at 95° C. for 3.5 hours. After cooling the mixture was poured onto water and extracted with ethyl acetate. The organic layers were washed with water, brine, dried (MgSO$_4$) and evaporated. The residue was triturated with ether, filtered and dried under vacuum to give 4-(6-fluoroindol-5-yloxy)-6-methoxy-7-(3-piperidinopropoxy)quinazoline (139 mg, 46%).

MS-ESI: 451 [MH]$^+$ $^1$H NMR Spectrum: (DMSOd$_6$) 1.35-1.45 (m, 2H); 1.45-1.6 (m, 4H); 2.0 (m, 2H); 2.35 (br s, 4H); 2.42 (t, 2H); 4.05 (s, 3H); 4.25 (t, 2H); 6.5 (s, 1H); 7.4 (d, 1H); 7.42 (s, 1H); 7.44 (t, 1H); 7.6 (d, 1H); 7.65 (s, 1H); 8.5 (s, 1H)

| Elemental analysis | Found | C 65.9 H 6.2 N 12.3 |
|---|---|---|
| C$_{25}$H$_{27}$FN$_4$O$_3$ 0.3 H$_2$O | Requires | C 65.9 H 6.1 N 12.3% |

EXAMPLE 249

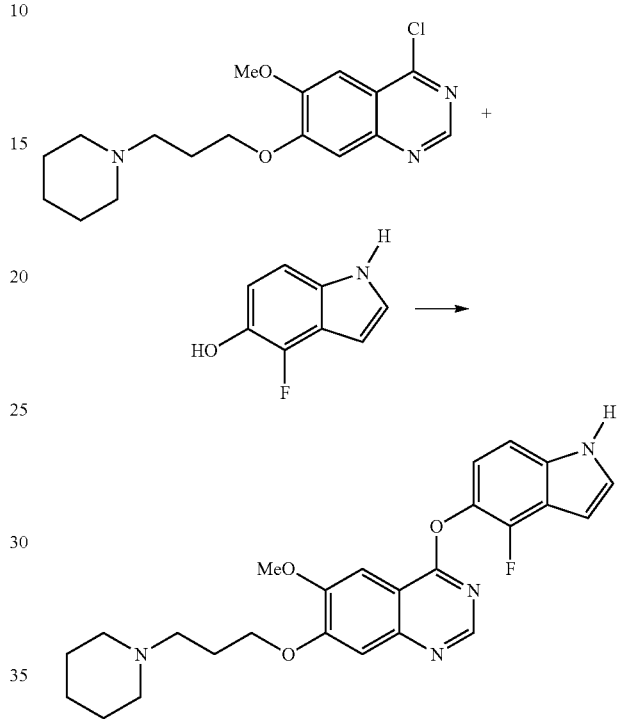

Using an analogous procedure to that described in Example 244, 4-chloro-6-methoxy-7-(3-piperidinopropoxy)quinazoline (407 mg, 1.21 mmol), (prepared as described for the starting material in Example 67), 4-fluoro-5-hydroxyindole (220 mg, 1.45 mmol) (prepared as described for the starting material in Example 242), and potassium carbonate (251 mg, 1.82 mmol) in DMF (6 ml) were heated at 95° C. for 90 minutes and purified to give 4-(4-fluoroindol-5-yloxy)-6-methoxy-7-(3-piperidinopropoxy)quinazoline (367 mg, 67%).

MS-ESI: 451 [MH]$^+$ $^1$H NMR Spectrum: (DMSOd$_6$) 1.35-1.45 (m, 2H); 1.55 (m, 4H); 2.0 (m, 2H); 2.38 (br s, 4H); 2.45 (t, 2H); 4.02 (s, 3H); 4.25 (t, 2H); 6.55 (s, 1H); 7.12 (dd, 1H); 7.32 (d, 1H); 7.4 (s, 1H); 7.5 (s, 1H); 7.65 (s, 1H); 8.52 (s, 1H)

| Elemental analysis | Found | C 66.0 H 6.2 N 12.4 |
|---|---|---|
| C$_{25}$H$_{27}$FN$_4$O$_3$ 0.2 H$_2$O | Requires | C 66.1 H 6.1 N 12.3% |

EXAMPLE 250

Using an analogous procedure to that described in Example 248, 4-chloro-6-methoxy-7-(3-(pyrrolidin-1-yl)propoxy)quinazoline (268 mg, 0.833 mmol), (prepared as described for the starting material in Example 9), was reacted with 6-fluoro-5-hydroxy-2-methylindole (165 mg, 1 mmol)

in DMF (3.5 ml) containing potassium carbonate (173 mg, 1.25 mmol) to give 4-(6-fluoro-2-methylindol-5-yloxy)-6-methoxy-7-(3-(pyrrolidin-1-yl)propoxy)quinazoline (215 mg, 57%).

MS-ESI: 451 [MH]+

$^1$H NMR Spectrum: (DMSOd$_6$) 1.65-1.8 (br s, 4H); 2.02 (m, 2H); 2.4 (s, 3H); 2.48 (br s, 4H); 2.6 (t, 2H); 4.02 (s, 3H); 4.3 (t, 2H); 6.18 (s, 1H); 7.25 (d, 1H); 7.4 (s, 1H); 7.45 (d, 1H); 7.6 (s, 1H); 8.5 (s, 1H)

| Elemental analysis | Found | C 65.6 H 6.1 N 12.2 |
| $C_{25}H_{27}FN_4O_3$ 0.4 $H_2O$ | Requires | C 65.6 H 6.1 N 12.2% |

The starting material was prepared as follows:

To a solution of 6-fluoro-5-methoxy-2-methylindole (1.23 g, 6.86 mmol), (prepared as described for the starting material in Example 237), in methylene chloride (15 ml) cooled at −30° C. was added a solution of boron tribromide (3.78 g, 15.1 mmol) in methylene chloride (2 ml). After stirring for 90 minutes at ambient temperature, the mixture was poured onto ice and diluted with methylene chloride. The pH of the aqueous layer was adjusted to 6. The organic layer was separated, washed with water, brine, dried (MgSO$_4$) and evaporated. The residue was purified by column chromatography eluting with ethylacetate/petroleum ether (8/2) to give 6-fluoro-5-hydroxy-2-methylindole (905 mg, 80%).

MS-ESI: 166 [MH]+

$^1$H NMR Spectrum: (DMSOd$_6$) 2.3 (s, 3H); 5.95 (s, 1H); 6.9 (d, 1H); 7.0 (d, 1H); 8.85 (s, 1H); 10.6 (s, 1H)

$^{13}$C NMR Spectrum: (DMSOd$_6$) 13.3; 97.4 (d); 98.3; 105.5; 124.5; 128.8 (d); 135.6; 138.5 (d); 148.3 (d).

EXAMPLE 251

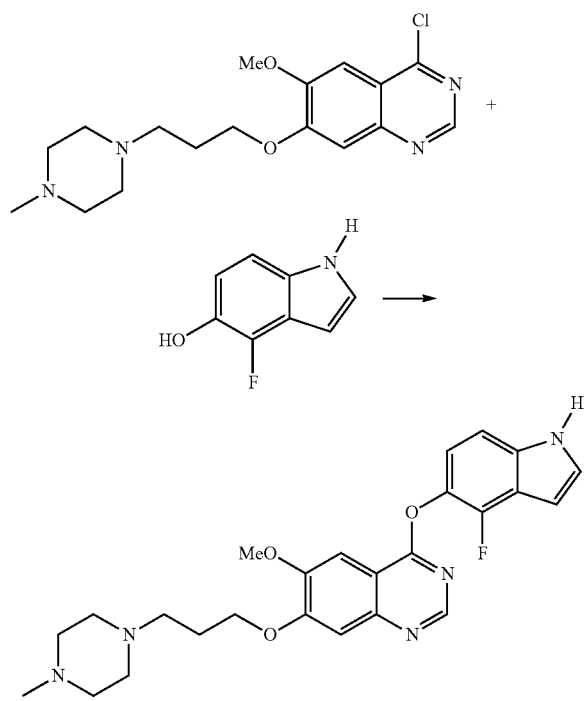

EXAMPLE 252

A mixture of 4-chloro-6-methoxy-7-(3-(4-methylpiperazin-1-yl)propoxy)quinazoline (232 mg, 0.662 mmol), (prepared as described for the starting material in Examples 176 or 244), and 4-fluoro-5-hydroxyindole (120 mg, 0.794 mmol), (prepared as described for the starting material in Example 242), in DMF (3 ml) containing potassium carbonate (137 mg, 1 mmol) was stirred at 95° C. for 3 hours. After cooling, the residue was poured onto water (12 ml) and extracted with ethyl acetate. The organic layer was washed with water, brine, dried (MgSO$_4$) and evaporated. The residue was purified by reversed phase C$_{18}$ column chromatography eluting with methanol/ammonium carbonate (2g of ammonium carbonate/liter saturated with CO$_2$) (60/40 followed by 70/30). The fractions containing the expected product were combined and evaporated. The residue was dissolved in ethyl acetate, dried (MgSO$_4$) and the volatiles were removed under vacuum. The residue was triturated with ether, filtered and dried under vacuum to give 4-(4-fluoroindol-5-yloxy)-6-methoxy-7-(3-(4-methylpiperazin-1-yl)propoxy)quinazoline (130 mg, 42%).

MS-ESI: 466 [MH]+

$^1$H NMR Spectrum: (DMSOd$_6$, CF$_3$COOD) 2.3-2.4 (m, 2H); 2.97 (s, 3H); 3.2-4.1 (m, 8H); 3.5 (t, 2H); 4.07 (s, 3H); 4.4 (t, 2H); 6.6 (d, 1H); 7.15 (t, 1H); 7.38 (d, 1H); 7.5 (d, 1H); 7.6 (s, 1H); 7.82 (s, 1H); 8.95 (s, 1H)

| Elemental analysis | Found | C 64.4 H 6.1 N 15.0 |
| $C_{25}H_{28}FN_5O_3$ | Requires | C 64.5 H 6.1 N 15.0% |

EXAMPLE 252

A mixture of 6-methoxy-4-(2-methylindol-5-yloxy)-7-(piperidin-4-ylmethoxy)quinazoline (600 mg, 1.43 mmol), (prepared as described in Example 70), 1-(2-chloroethyl)-pyrrolidine (292 mg, 1.72 mmol) in methanol (14 ml) containing sodium carbonate (262 mg, 4.3 mmol) and potassium iodide (48 mg, 0.29 mmol) was heated at 50° C. for 20 hours. After cooling, the volatiles were removed under vacuum. The residue was purified by preparation HPLC on reverse C$_{18}$ silica eluting with methanol/aqueous ammonium carbonate (2g ammonium carbonate per liter saturated with CO$_2$) (60/40 followed by 70/30). The fractions containing the expected product were combined and the volatiles were removed under vacuum. The residue was triturated with ether and the solid was filtered, washed with ether and dried under vacuum to give 6-methoxy-4-(2-methylindol-5-yloxy)-7-(1-(2-(pyrrolidin-1-yl)ethyl)-piperidin-4-ylmethoxy)quinazoline (102 mg, 20%).

MS-ESI: 516 [MH]+

$^1$H NMR Spectrum: (DMSOd$_6$) 1.3-1.5 (m, 2H); 1.6-1.75 (m, 4H); 1.8 (d, 2H); 1.7-1.9 (m, 1H); 1.95 (t, 2H); 2.45 (s, 3H); 2.4-2.5 (m, 5H); 2.95 (d, 2H); 3.35 (d, 2H); 4.0 (s, 3H); 4.1 (d, 2H); 6.18 (s, 1H); 6.9 (d, 1H); 7.25 (s, 1H); 7.35 (d, 1H); 7.38 (s, 1H); 7.6 (s, 1H); 8.5 (s, 1H); 11.05 (s, 1H)

| Elemental analysis | Found | C 68.6 H 7.2 N 13.3 |
| $C_{30}H_{37}N_5O_3$ 0.5 $H_2O$ | Requires | C 68.7 H 7.3 N 13.4% |

EXAMPLE 253

A mixture of 4-chloro-6-methoxy-7-(3-morpholinopropoxy)quinazoline (110 mg, 0.325 mmol), (prepared as described for the starting material in Example 1), and 6-fluoro-5-hydroxyindole (59 mg, 0.39 mmol), (prepared as described for the starting material in Example 242), in DMF (1.8 ml) containing potassium carbonate (67 mg, 0.487 mmol) was heated at 90° C. for 2 hours. After cooling, water was added. The solid was separated and triturated with methanol. Water was added and the solid was filtered, washed with water and dried under vacuum to give 4-(6-fluoroindol-5-yloxy)-6-methoxy-7-(3-morpholinopropoxy)quinazoline (55 mg, 41%).

MS-ESI: 453 [MH]$^+$ $^1$H NMR Spectrum: (DMSOd$_6$) 1.95-2.05 (m, 2H); 2.45 (br s, 4H); 2.5 (t, 2H); 3.62 (t, 4H); 4.02 (s, 3H); 4.3 (t, 2H); 6.5 (s, 1H); 7.4 (d, 1H); 7.45 (s, 1H); 7.47 (t, 1H); 7.58 (d, 1H); 7.62 (s, 1H); 8.5 (s, 1H)

| Elemental analysis | Found | C 61.6 H 5.5 N 11.9 |
|---|---|---|
| C$_{24}$H$_{25}$FN$_4$O$_4$ 0.8 H$_2$O | Requires | C 61.7 H 5.7 N 12.0% |

EXAMPLE 254

To a solution of 7-hydroxy-4-(indol-5-yloxy)-6-methoxyquinazoline (183 mg, 0.6 mmol), (prepared as described for the starting material in Example 107), triphenylphosphine (235 mg, 0.89 mmol) and 4-(2-hydroxyethyl)morpholine (93 mg, 0.72 mmol) in methylene chloride (4 ml) cooled at 10° C. was added diethyl azodicarboxylate (140 μl, 0.89 mmol). After stirring at ambient temperature for 3 hours, the mixture was left overnight at 5° C. The mixture was poured onto a column of silica and eluted with methylene chloride followed by methanol/methylene chloride (2/98) followed by 3N ammonia methanol/methylene chloride (2/98). The fractions containing the expected products were combined and evaporated to give 4-(indol-5-yloxy)-6-methoxy-7-(2-morpholinoethoxy)quinazoline (137 mg, 55%).

MS-ESI: 421 [MH]$^+$ $^1$H NMR Spectrum: (DMSOd$_6$, CF$_3$COOD) 3.30 (t, 2H); 3.65 (d, 2H); 3.7-3.8 (m, 4H); 4.05 (d, 2H); 4.1 (s, 3H); 4.7 (t, 2H); 6.5 (s, 1H); 7.05 (dd, 1H); 7.4-7.6 (m, 3H); 7.65 (s, 1H); 7.82 (s, 1H); 9.0 (s, 1H)

EXAMPLES 255-257

Using an analogous procedure to that described in Example 254, 7-hydroxy-4-(indol-5-yloxy)-6-methoxyquinazoline (183 mg, 0.6 mmol), (prepared as described for the starting material in Example 107), was used to prepare the compounds in Table XVIII.

TABLE XVIII

| Example number | Weight (mg) | Yield % | MS-ESI [MH]$^+$ | R | Note |
|---|---|---|---|---|---|
| 255 | 123 | 51 | 405 | | a |
| 256 | 124 | 48 | 434 | | b |
| 257 | 165 | 62 | 448 | | c | a) 7-Hydroxy-4-(indol-5-yloxy)-6-methoxyquinazoline (183 mg, 0.6 mmol) was reacted with 1-(2-hydroxyethyl)pyrrolidine (82 mg) to give 4-(indol-5-yloxy)-6-methoxy-7-(2-(pyrrolidin-1-yl)ethoxy)quinazoline.

$^1$H NMR Spectrum: (DMSOd$_6$) 1.72 (br s, 4H); 2.6 (br s, 4H); 2.9 (t, 2H); 4.0 (s, 3H); 4.3 (t, 2H); 6.48 (s, 1H); 7.0 (dd, 1H); 7.4-7.5 (m, 3H); 7.6 (s, 1H); 8.5 (s, 1H); 11.3 (br s, 1H)

b) 7-Hydroxy-4-(indol-5-yloxy)-6-methoxyquinazoline (183 mg, 0.6 mmol) was reacted with 4-(2-hydroxyethyl)-1-methylpiperazine (103 mg) to give 4-(indol-5-yloxy)-6-methoxy-7-(2-(4-methylpiperazin-1-yl)ethoxy)quinazoline.

$^1$H NMR Spectrum: (DMSOd$_6$, CF$_3$COOD) 2.5 (s, 3H); 3.35 (t, 2H); 3.65 (d, 2H); 3.7-3.8 (m, 4H); 4.05 (d, 2H); 4.1 (s, 3H); 4.7 (t, 2H); 7.05 (dd, 1H); 7.45 (s, 1H); 7.5-7.6 (m, 2H); 7.65 (s, 1H); 7.82 (s, 1H); 9.0 (s, 1H)

The starting material was prepared as follows:—

2-Bromoethanol (2.36 g, 19 mmol) was added dropwise to a mixture of 1-methylpiperazine (1.26 g, 13 mmol) and potassium carbonate (5.0 g, 36 mmol) in absolute ethanol (150 ml) and the mixture heated at reflux for 18 hours. The mixture was allowed to cool and the precipitates were removed by filtration and the solvent volatiles were removed by evaporation. The residue was treated with acetone/methylene chloride, the insolubles were removed by filtration and the solvent was removed from the filtrate by evaporation to give 4-(2-hydroxyethyl)-1-methylpiperazine (870 mg, 48%) as a light brown oil.

$^1$H NMR Spectrum: (CDCl$_3$) 2.18(s, 3H); 2.3-2.7(br m, 8H); 2.56(t, 2H); 3.61(t, 2H)

MS-ESI: 145 [MH]$^+$ c) 7-Hydroxy-4-(indol-5-yloxy)-6-methoxyquinazoline (183 mg, 0.6 mmol) was reacted with 1-(3-hydroxypropyl)-4-methylpiperazine (113 mg), (prepared as described for the starting material in Example 133), to give 4-(indol-5-yloxy)-6-methoxy-7-(3-(4-methylpiperazin-1-yl)propoxy)quinazoline.

¹H NMR Spectrum: (DMSOd$_6$) 2.15 (s, 3H); 2.3-2.4 (br s, 4H); 2.5-2.6 (m, 4H); 2.8 (t, 2H); 4.0 (s, 3H); 4.35 (t, 2H); 6.45 (s, 1H); 7.0 (dd, 1H); 7.4-7.5 (m, 4H); 7.62 (s, 1H); 8.5 (s, 1H)

EXAMPLE 258

A solution of (2R)-7-(2-acetoxy-3-(pyrrolidin-1-yl)propoxy)-4-(4-fluoro-2-methylindol-5-yloxy)-6-methoxyquinazoline (570 mg, 1.12 mmol) in methanol saturated with ammonia (7 ml) was stirred overnight at ambient temperature. The volatiles were removed under vacuum and the residue was purified by column chromatography eluting with methylene chloride/methanol containing ammonia (approximately 3N) to give (2R)-7-(2-hydroxy-3-(pyrrolidin-1-yl)propoxy)-4-(4-fluoro-2-methylindol-5-yloxy)-6-methoxyquinazoline (390 mg; 75%).

MS-ESI: 467 [MH]+

¹H NMR Spectrum: (DMSOd$_6$, CF$_3$COOD) 1.85-2.0 (m, 2H); 2.0-2.15 (m, 2H); 2.42 (s, 3H); 3.15 (m, 2H); 3.4 (d, 2H); 3.65 (m, 2H); 4.1 (s, 3H); 4.32 (d, 2H); 4.4 (m, 1H); 7.05 (dd, 1H); 7.22 (d, 1H); 7.6 (s, 1H); 7.85 (s, 1H); 9.02 (s, 1H)

The starting material was prepared as follows:

A suspension of 7-hydroxy-6-methoxy-3-((pivaloyloxy)methyl)-3,4-dihydroquinazolin-4-one (1.2 g, 3.91 mmol), (prepared as described for the starting material in Example 12), and 2-(R)-(-)-Glycidyl tosylate (1.25 g, 5.47 mmol) in DMF (10 ml) containing potassium carbonate (1.61 g, 11.7 mmol) was stirred at 60° C. for 4 hours. After cooling, the mixture was filtered and the solid was washed with DMA. The filtrate was evaporated and the residue was partitioned between ethyl acetate and aqueous ammonia. The organic layer was separated, washed with water, brine, dried (MgSO$_4$) and evaporated. The residue was purified by column chromatography eluting with ethyl acetate. The fractions containing the expected product were combined and evaporated to give (2R)-7-(oxiran-2-ylmethoxy)-6-methoxy-3-((pivaloyloxy)methyl)-3,4-dihydroquinazolin-4-one (1.21 g, 85%).

MS-ESI: 363 [MH]$^+$

¹H NMR Spectrum: (DMSOd$_6$) 1.12 (s, 9H); 2.75 (m, 1H); 2.9 (t, 1H); 3.4 (m, 1H); 3.93 (s, 3H); 4.0 (dd, 1H); 4.52 (dd, 1H); 5.9 (s, 2H); 7.2 (s, 1H); 7.52 (s, 1H); 8.35 (s, 1H)

A solution of (2R)-7-(oxiran-2-ylmethoxy)-6-methoxy-3-((pivaloyloxy)methyl)-3,4-dihydroquinazolin-4-one (1.1 g, 3 mmol) and pyrrolidine (216 mg, 3 mmol) in trichloromethane (15 ml) was refluxed for 11 hours. The volatiles were removed under vacuum and the residue was purified by column chromatography eluting with methylene chloride/methanol (85/15 followed by 70/30) to give (2R)-7-(2-hydroxy-3-(pyrrolidin-1-yl)propoxy)-6-methoxy-3-((pivaloyloxymethyl)-3,4-dihydroquinazolin-4-one (1.18 g, 90%).

¹H NMR Spectrum: (DMSOd$_6$) 1.15 (s, 9H); 1.7 (br s, 4H); 2.48 (m, 1H); 2.5 (br s, 4H); 2.65 (dd, 1H); 3.9 (s, 3H); 4.0 (br s, 1H); 4.05 (dd, 1H); 4.18 (dd, 1H); 4.95 (br s, 1H); 5.9 (s, 2H); 7.2 (s, 1H); 7.5 (s, 1H); 8.35 (s, 1H)

A solution of (2R)-7-(2-hydroxy-3-(pyrrolidin-1-yl)propoxy)-6-methoxy-3-((pivaloyloxymethyl)-3,4-dihydroquinazolin-4-one (778 mg, 1.8 mmol) in methanol saturated with ammonia (20 ml) was stirred for 24 hours at ambient temperature. The volatiles were removed under vacuum. The residue was triturated with ether and the residue was filtered, washed with ether and dried under vacuum to give (2R)-7-(2-hydroxy-3-(pyrrolidin-1-yl)propoxy)-6-methoxy-3,4-dihydroquinazolin-4-one (800 mg, quant.).

¹H NMR Spectrum: (DMSOd$_6$, CF$_3$COOD) 1.92 (m, 2H); 2.05 (m, 2H); 3.15 (m, 2H); 3.35 (d, 2H); 3.62 (m, 2H); 3.98 (s, 3H); 4.18 (d, 2H); 4.32 (m, 1H); 7.35 (s, 1H); 7.6 (s, 1H); 9.2 (s, 1H)

A mixture of (2R)-7-(2-hydroxy-3-(pyrrolidin-1-yl)propoxy)-6-methoxy-3,4-dihydroquinazolin-4-one (803 mg, 2.51 mmol) in acetic anhydride (1.2 ml, 12.5 mmol) was stirred at ambient temperature for 1 hour. Water (360 µl, 20 mmol) was added and stirring was continued for 90 minutes. The mixture was partitioned between aqueous sodium hydrogen carbonate and methylene chloride. The organic layer was separated, washed with brine, dried (MgSO$_4$) and evaporated. The residue was triturated with ether, filtered and dried under vacuum to give (2R)-7-(2-acetoxy-3-(pyrrolidin-1-yl)propoxy)-6-methoxy-3,4-dihydroquinazolin-4-one (595 mg, 65%).

MS-ESI: 362 [MH]+

¹H NMR Spectrum: (DMSOd$_6$) 1.7 (br s, 4H); 2.05 (s, 3H); 2.5 (br s, 4H); 2.72 (m, 2H); 3.9 (s, 3H); 4.3 (m, 2H); 5.25 (m, 1H); 7.2 (s, 1H); 7.45 (s, 1H); 8.0 (s, 1H)

A solution of (2R)-7-(2-acetoxy-3-(pyrrolidin-1-yl)propoxy)-6-methoxy-3,4-dihydroquinazolin-4-one (556 mg, 1.54 mmol) in thionyl chloride (6 ml) containing DMF (3 drops) was heated at 80° C. for 4 hours. The volatiles were removed under vacuum. The residue was dissolved in methylene chloride and the organic layer was washed with aqueous sodium hydrogen carbonate, brine, dried (MgSO$_4$) and evaporated to give (2R)-7-(2-acetoxy-3-(pyrrolidin-1-yl)propoxy)-4-chloro-6-methoxyquinazoline (530 mg, 90%).

¹H NMR Spectrum: (DMSOd$_6$) 1.7 (br s, 4H); 2.05 (s, 3H); 2.55 (br s, 4H); 2.75 (br s, 2H); 4.02 (s, 3H); 4.35-4.5 (m, 2H); 5.3 (m, 1H); 7.4 (s, 1H); 7.5 (s, 1H); 7.9 (s, 1H)

A suspension of (2R)-7-(2-acetoxy-3-(pyrrolidin-1-yl)propoxy)-4-chloro-6-methoxyquinazoline (530 mg, 1.4 mmol) and 4-fluoro-5-hydroxy-2-methylindole (277 mg, 1.68 mmol), (prepared as described for the starting material in Example 237), in DMF (8 ml) containing potassium carbonate (290 mg, 2.1 mmol) was stirred at 90° C. for 2 hours. After cooling, the volatiles were removed under vacuum and the residue was purified by column chromatography eluting with methylene chloride/methanol (95/5) to give (2R)-7-(2-acetoxy-3-(pyrrolidin-1-yl)propoxy)-4-(4-fluoro-2-methylindol-5-yloxy)-6-methoxyquinazoline (580 mg, 81%).

¹H NMR Spectrum: (DMSOd$_6$) 1.7 (br s, 4H); 2.05 (s, 3H); 2.4 (s, 3H); 2.52 (br s, 4H); 2.65-2.82 (m, 2H); 4.0 (s, 3H); 4.4 (m, 2H); 5.3 (m, 1H); 6.25 (s, 1H); 7.0 (dd, 1H); 7.18 (d, 1H); 7.48 (s, 1H); 7.62 (s, 1H); 8.5 (s, 1H)

EXAMPLE 259

A solution of 4-chloro-6-methoxy-7-(3-(pyrrolidin-1-yl)propoxy)quinazoline (61 mg, 0.19 mmol), (prepared as described for the starting material in Example 9), and 5-aminoindole (30 mg, 0.23 mmol) in isopropanol (2 ml) containing 6.2 N hydrogen chloride in isopropanol (33 µl) was heated at 80° C. for 6 hours. After cooling, the precipitate was filtered, washed with ether and dried under vacuum to give 4-(indol-5-ylamino)-6-methoxy-7-(3-(pyrrolidin-1-yl)propoxy)quinazoline hydrochloride (80 mg, 72%).

MS-ESI: 418 [MH]$^+$

¹H NMR Spectrum: (DMSOd$_6$, CF$_3$COOD) 1.9 (m, 2H); 2.05 (m, 2H); 2.3 (m, 2H); 3.1 (m, 2H); 3.4 (t, 2H); 3.65 (m, 2H); 4.05 (s, 3H); 4.35 (t, 2H); 6.5 (s, 0.5H, partly exchanged); 7.3 (d, 1H); 7.4 (s, 1H); 7.45 (s, 1H); 7.55 (d, 1H); 7.8 (s, 1H); 8.25 (s, 1H); 8.8 (s, 1H)

EXAMPLES 260-265

Using an analogous procedure to that described in Example 259, 5-aminoindole (30 mg, 0.23 mmol) was used in the synthesis of the compounds described in Table XIX.

TABLE XIX

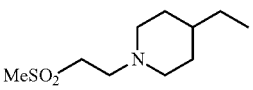

| Example number | Weight (mg) | Yield (%) | MS-ESI [MH]+ | Note | R |
|---|---|---|---|---|---|
| 260 | 101 | 76 | 510 | a | 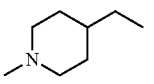 |
| 261 | 92 | 83 | 418 | b | 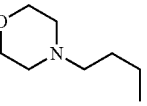 |
| 262 | 92 | 80 | 434 | c | 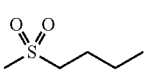 |
| 263 | 84 | 80 | 427 | d | 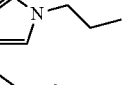 |
| 264 | 78 | 79 | 401 | e | 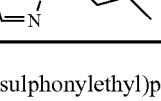 |
| 265 | 72 | 70 | 416 | f | | a) 4-Chloro-6-methoxy-7-((1-(2-methylsulphonylethyl)piperidin-4-yl)methoxy)quinazoline (78 mg), (prepared as described for the starting material in Example 12), was reacted with 5-aminoindole to give 4-(indol-5-ylamino)-6-methoxy-7-((1-(2-methylsulphonylethyl)piperidin-4-yl)methoxy)quinazoline hydrochloride.

$^1$H NMR Spectrum: (DMSO-d6) 1.65-1.8 (m, 2H); 2.05 (d, 2H); 2.2 (br s, 1H); 3.1 (br s, 2H); 3.2 (s, 3H); 3.5 (br s, 2H); 3.6 (d, 2H); 3.8 (m, 2H); 4.05 (s, 3H); 4.1 (d, 2H); 6.5 (s, 1H); 7.3 (d, 1H); 7.42 (m, 2H); 7.5 (d, 1H); 7.8 (s, 1H); 8.4 (s, 1H); 8.7 (s, 1H); 11.15 (br s, 1H); 11.32 (s, 1H). 11.5 (s, 1H).

b) 4-Chloro-6-methoxy-7-((1-methylpiperidin-4-yl)methoxy)quinazoline (61 mg), (prepared as described for the starting material in Example 10), was reacted with 5-aminoindole to give 4-(indol-5-ylamino)-6-methoxy-7-((1-methylpiperidin-4-yl)methoxy)quinazoline hydrochloride.

$^1$H NMR Spectrum: (DMSOd$_6$) 1.6-1.8 (m, 2H); 2.02 (d, 2H); 2.15 (br s, 1H); 2.75 (s, 3H); 3.0 (br s, 2H); 3.45 (d, 2H); 4.02 (s, 3H); 4.1 (d, 2H); 6.5 (s, 1H); 7.3 (d, 1H); 7.4 (m, 2H); 7.5 (d, 1H); 7.8 (s, 1H); 8.3 (s, 1H); 8.7 (s, 1H); 10.4 (br s, 1H); 11.3 (s, 1H)

The presence of a second form of the piperidine ring (due to protonation effects) is detectable in the NMR Spectrum as a doublet at 4.3 ppm (approximately 20% of parent compound).

c) 4-Chloro-6-methoxy-7-(3-morpholinopropoxy)quinazoline (64 mg), (prepared as described for the starting material in Example 1), was reacted with 5-aminoindole to give 4-(indol-5-ylamino)-6-methoxy-7-(3-morpholinopropoxy)quinazoline hydrochloride.

$^1$H NMR Spectrum (DMSOd$_6$; CF$_3$COOD): 2.35 (m, 2H); 3.15 (t, 2H); 3.3 (t, 2H); 3.57 (d, 2H); 3.8 (m, 2H); 4.02 (d, 2H); 4.03 (s, 3H); 4.3 (t, 2H); 6.5 (d, 1H); 7.3 (dd, 1H); 7.4 (s, 1H); 7.45 (s, 1H); 7.52 (d, 1H); 7.8 (s, 1H); 8.25 (s, 1H); 8.78 (s, 1H)

d) 4-Chloro-6-methoxy-7-(3-methylsulphonylpropoxy)quinazoline (62 mg), (prepared as described for the starting material in Example 50), was reacted with 5-aminoindole in the presence of 6.2N hydrogen chloride in isopropanol (4 µl) to give 4-(indol-5-ylamino)-6-methoxy-7-(3-methylsulphonylpropoxy)quinazoline hydrochloride.

$^1$H NMR Spectrum: (DMSOd$_6$, CF$_3$COOD) 2.2-2.4 (m, 2H); 3.07 (s, 3H); 3.35 (t, 2H); 4.05 (s, 3H); 4.35 (t, 2H); 6.5 (d, 0.5H, partly exchanged); 7.2-7.35 (m, 2H); 7.45 (s, 1H); 7.5 (d, 1H); 7.8 (s, 1H); 8.2 (s, 1H); 8.75 (s, 1H)

e) 4-Chloro-7-(2-(imidazol-1-yl)ethoxy)-6-methoxyquinazoline (58 mg) was reacted with 5-aminoindole in the presence of 6.2N hydrogen chloride in isopropanol (4 µl) to give 4-(indol-5-ylamino)-7-(2-(imidazol-1-yl)ethoxy)-6-methoxyquinazoline hydrochloride.

$^1$H NMR Spectrum: (DMSOd$_6$, CF$_3$COOD) 4.03 (s, 3H); 4.65 (t, 2H); 4.8 (t, 2H); 6.5 (d, 1H, partly exchanged); 7.30 (d, 1H); 7.4 (s, 1H); 7.45 (s, 1H); 7.52 (d, 1H); 7.75 (s, 1H); 7.8 (s, 1H); 7.9 (s, 1H); 8.25 (s, 1H); 8.75 (s, 1H); 9.25 (s, 1H)

The starting material was prepared as follows:

Diethyl azodicarboxylate (435 mg, 2.5 mmol) was added dropwise to a suspension of 7-hydroxy-6-methoxy-3-((pivaloyloxy)methyl)-3,4-dihydroquinazolin-4-one (612 mg, 2 mmol), (prepared as described for the starting material in Example 12), 2-(imidazol-1-yl)ethanol (280 mg, 2.5 mmol), (J. Med. Chem. 1993, 25 4052-4060), and triphenylphosphine (655 mg, 2.5 mmol) in methylene chloride (10 ml) at 5° C. The mixture was stirred for 10 minutes at 5° C. and then 1 hour at ambient temperature. The mixture was poured directly on to a silica column and eluted with methylene chloride/methanol (95/5) to give 7-(2-(imidazol-1-yl)ethoxy)-6-methoxy-3-((pivaloyloxy)methyl)-3,4-dihydroquinazolin-4-one (640 mg, 80%).

$^1$H NMR Spectrum: (CDCl$_3$) 1.19(s, 9H); 3.98(s, 3H); 4.34(m, 2H); 4.45(m, 2H); 5.94(s, 2H); 7.02(s, 1H); 7.07(s, 1H); 7.11(s, 1H); 7.64(s, 1H); 7.67(s, 1H); 8.17(s, 1H)

MS-ESI: 423 [MNa]+

| Elemental Analysis: | Found | C 58.3 H 6.4 N 13.9 |
|---|---|---|
| C$_{20}$H$_{24}$N$_4$O$_5$ 0.7H$_2$O | Requires | C 58.2 H 6.2 N 13.6% |

A solution of 7-(2-(imidazol-1-yl)ethoxy)-6-methoxy-3-((pivaloyloxy)methyl)-3,4-dihydroquinazolin-4-one (640 mg, 1.6 mmol) in saturated methanolic ammonia (10 ml) was stirred for 15 hours at ambient temperature. The volatiles were removed by evaporation, the solid was triturated with ether, collected by filtration and dried under vacuum to give 7-(2-(imidazol-1-yl)ethoxy)-6-methoxy-3,4-dihydroquinazolin-4-one (412 mg, 90%).

¹H NMR Spectrum: (DMSO-d₆) 3.89(s, 3H); 4.4-4.5(m, 4H); 6.9(s, 1H); 7.16(s, 1H); 7.28(s, 1H); 7.47(s, 1H); 7.7(s, 1H); 7.99(s, 1H)

MS-ESI: 287 [MH]⁺

| Elemental Analysis: | Found | C 57.8 H 5.2 N 19.3 |
|---|---|---|
| C₁₄H₁₄N₄O₃ 0.3H₂O | Requires | C 57.7 H 5.1 N 19.2% |

A mixture of 7-(2-(imidazol-1-yl)ethoxy)-6-methoxy-3,4-dihydroquinazolin-4-one (412 mg, 1.44 mmol), thionyl chloride (5 ml) and DMF (0.2 ml) was heated at reflux for 1 hour. The mixture was diluted with toluene and the volatiles were removed by evaporation. The residue was suspended in methylene chloride, cooled to 0° C. and aqueous sodium hydrogen carbonate solution was added. The resulting precipitate was collected by filtration and dried under vacuum to give 4-chloro-7-(2-(imidazol-1-yl)ethoxy)-6-methoxyquinazoline (258 mg, 59%).

¹H NMR Spectrum: (DMSOd₆) 4.01(s, 3H); 4.47(m, 2H); 4.53(m, 2H); 6.89(s, 1H); 7.27(s, 1H); 7.41(s, 1H); 7.49(s, 1H); 7.70(s, 1H); 8.88(s, 1H)

MS-ESI: 327 [MNa]⁺ f) 4-Chloro-6-methoxy-7-(3-(1H-1,2,4-triazol-1-yl)propoxy)quinazoline (61 mg) was reacted with 5-aminoindole in the presence of 6.2N hydrogen chloride in isopropanol (4 μl) to give 4-(indol-5-ylamino)-6-methoxy-7-(3-(1H-1,2,4-triazol-1-yl)propoxy)quinazoline hydrochloride.

¹H NMR Spectrum: (DMSOd₆, CF₃COOD) 2.5 (m, 2H); 4.0 (s, 3H); 4.3 (t, 2H); 4.6 (t, 2H); 6.52 (d, 0.5H partly exchanged); 7.3 (s, 1H); 7.35 (d, 1H); 7.45 (s, 1H); 7.55 (d, 1H); 7.8 (s, 1H); 8.16 (s, 1H); 8.66 (s, 1H); 8.77 (s, 1H); 9.43 (s, 1H).

EXAMPLE 266

A mixture of 4-chloro-6-methoxy-7-(3-piperidinopropoxy)quinazoline (144 mg, 0.43 mmol), (prepared as described for the starting material in Example 67), potassium carbonate (91 mg, 0.66 mmol) and 3-fluoro-7-hydroxyquinoline (77 mg, 0.47 mmol), (prepared as described for the starting material in Example 157), in DMF (3 ml) was stirred at 100° C. for 2 hours and then allowed to cool to ambient temperature. The reaction mixture was evaporated to dryness and the residue chromatographed on silica eluting with methanol/dichloromethane/aqueous ammonia (0.880) (5/100/1). The relevant fractions were combined and evaporated to dryness to give 4-(3-fluoro-quinolin-7-yloxy)-6-methoxy-7-(3-piperidinopropoxy)quinazoline (87 mg, 44%).

¹H NMR Spectrum: (DMSOd₆) 1.37(m, 2H); 1.49(m, 4H); 1.96(m, 2H); 2.34(m, 4H); 2.43(t, 2H); 4.00(s, 3H); 4.23(t, 2H); 7.38(s, 1H); 7.62(s, 1H); 7.69(dd, 1H); 8.00(d, 1H); 8.12(d, 1H); 8.34(dd, 1H); 8.54(s, 1H); 8.98(d, 1H)

MS(ESI): 463 (MH)⁺

EXAMPLE 267

A mixture of 4-chloro-6-methoxy-7-(3-(pyrrolidin-1-yl)propoxy)quinazoline (218 mg, 0.68 mmol), (prepared as described for the starting material in Example 9), potassium carbonate (138 mg, 1.13 mmol) and 3-fluoro-7-hydroxyquinoline (117 mg, 0.72 mmol), (prepared as described for the starting material in Example 157), in DMF (4.5 ml) was stirred at 100° C. for 4 hours and then allowed to cool to ambient temperature. The reaction mixture was evaporated to dryness and the residue taken up in dichloromethane, washed with water, brine and dried (MgSO₄). The organic fractions were evaporated to dryness and the residue recrystallised from acetonitrile to give 4-(3-fluoro-quinolin-7-yloxy)-6-methoxy-7-(3-(pyrrolidin-1-yl)propoxy)quinazoline (86 mg, 28%).

¹H NMR Spectrum: (DMSOd₆) 1.90(m, 2H); 2.00(m, 2H); 2.27(m, 2H); 3.02(m, 2H); 3.32(m, 2H); 3.59(m, 2H); 4.00(s, 3H); 4.33(t, 2H); 7.43(s, 1H); 7.62(s, 1H); 7.70(dd, 1H); 7.99(d, 1H); 8.11(d, 1H); 8.35(dd, 1H); 8.54(s, 1H); 8.97(d, 1H)

MS(ESI): 449 (MH)⁺

EXAMPLE 268

A mixture of 7-hydroxy-6-methoxy-4-(2-methylindol-5-yloxy)quinazoline (280 mg, 0.87 mmol), (prepared as described in Example 49), potassium carbonate (370 mg, 2.68 mmol) and 4-(1-methyl-2-oxopiperidin-4-yl)methyl-4-toluene sulphonate (260 mg, 0.87 mmol) in DMF (8 ml) was stirred at 95° C. for 4 hours and allowed to cool to ambient temperature. The reaction mixture was diluted with acetone, filtered and the filtrate evaporated 'in vacuo' to give a residue which was purified by column chromatography, eluting with dichloromethane/methanol/0.88 ammonia (100/8/1). The relevant fractions were combined and evaporated 'in vacuo' to give an oil which crystallised on trituration with diethyl ether to give 6-methoxy-4-(2-methylindol-5-yloxy)-7-(1-methyl-2-oxopiperidin-4-ylmethoxy)quinazoline (66 mg, 17%).

m. p. 250-251° C.

¹H NMR Spectrum: (DMSO-d₆) 1.66 (m, 1H), 2.10 (m, 2H), 2.40 (s, 3H), 2.50 (m, 2H), 2.84 (s, 3H), 3.34 (m, 2H), 3.99 (s, 3H), 4.12 (d, 2H), 6.12 (s, 1H), 6.86 (m, 1H), 7.25 (d, 1H), 7.30 (d, 1H), 7.38 (s, 1H), 7.59 (s, 1H), 8.48 (s, 1H) and 10.98 (br s, 1H).

MS(ESI): 447 (MH)⁺

| Elemental analysis | Found | C 66.8 H 5.9 N 12.4 |
|---|---|---|
| C₂₅H₂₆N₄O₄ 0.2 H₂O | Requires | C 66.7 H 5.9 N 12.5% |

The starting material was prepared as follows:—

A solution of 4-hydroxymethyl-1-methyl-2-piperidone (120 mg, 0.84 mmol), (Yakugaku Zasshi 88, (5), 573-582, (1968)), in dichloromethane was treated with triethylamine (187 mg, 1.85 mmol) followed by p-toluenesulphonyl chloride (176 mg, 0.92 mmol) and the mixture stirred at ambient temperature overnight. The reaction mixture was diluted with dichloromethane and washed successively with aqueous sodium hydrogen carbonate, water and brine. The dichloromethane solution was dried over magnesium sulphate, filtered and the filtrate evaporated 'in vacuo' to give a dark oily residue. This was washed several times with diethyl ether to remove the product from insoluble impurities, the washings combined and evaporated 'in vacuo' to give 4-(1-methyl-2-oxopiperidin-4-yl)methyl-4-toluene sulphonate as a light brown oil (130 mg, 52%). This was used without further purification.

MS(ESI): 298 (MH)⁺ and impurities

EXAMPLE 269

A mixture of (2R)-6-methoxy-4-(2-methylindol-5-yloxy)-7-(oxiran-2-ylmethoxy)quinazoline (300 mg, 0.79 mmol), and 1-methylpiperazine (0.26 ml, 2.38 mmol) in DMF (10 ml) was stirred at 70° C. for 24 hours and allowed to cool to ambient temperature.

The solvents were removed in vacuo and the residue purified by silica column chromatography, gradient elution (dichloromethane, 5% methanol/95% dichloromethane, dichloromethane/methanol/0.88 ammonia (100/8/1) and evaporated in vacuo to give (2R)-7-(2-hydroxy-3-(4-methylpiperazin-1-yl)propoxy)-6-methoxy-4-(2-methylindol-5-yloxy)quinazoline (344 mg, 91%).

$^1$H NMR Spectrum: (DMSO-$d_6$) 2.10 (s, 3H), 2.4 (m, 3H), 3.98 (s, 3H), 4.06 (m, 3H), 4.90 (br s, 1H), 6.12 (s, 1H), 6.85 (dd, 1H), 7.3 (m, 2H), 7.58 (s, 1H), 8.42 (s, 1H) and 10.98 (br s, 1H)

MS(ESI): 478 (MH)$^+$

| Elemental analysis: | Found | C 61.3 H 6.3 N 13.8 |
|---|---|---|
| $C_{26}H_{30}N_4O_4$ 0.2$H_2O$•0.5dichloromethane | Requires | C 61.9 H 6.2 N 13.4% |

The starting material was prepared as follows:

A mixture of 7-hydroxy-6-methoxy-4-(2-methylindol-5-yloxy)quinazoline (300 mg, 0.93 mmol), (prepared as described in Example 49), potassium carbonate (385 mg, 2.79 mmol) and (2R)-(−)-glycidyl tosylate (426 mg, 2.79 mmol) in DMF (15 ml) was stirred at 60° C. for 2 hours and allowed to cool to ambient temperature. The reaction mixture was filtered and the filtrate exaporated in vacuo. The residue was dissolved in dichloromethane and washed with saturated sodium hydrogen carbonate solution. The organic layer was then dried (MgSO$_4$), filtered and the solvent removed in vacuo to give a yellow solid. This was triturated with ether, filtered off and dried to give (2R)-6-methoxy-4-(2-methylindol-5-yloxy)-7-(oxiran-2-ylmethoxy)quinazoline as a yellow solid (185 mg, 53%).

$^1$H NMR Spectrum: (DMSOd$_6$) 2.40 (s, 3H), 2.75 (m, 1H), 2.90 (m, 1H), 3.40 (m, 1H), 3.98 (s, 3H), 4.05 (m, 1H), 4.60 (m, 1H), 6.15 (s, 1H), 6.85 (dd, 1H), 7.30 (m, 2H) 7.40 (s, 1H), 7.60 (s, 1H), 8.45 (s, 1H) and 10.98 (s, 1H)

MS(ESI): 378 (MH)$^+$

EXAMPLE 270

A mixture of (2R)-6-methoxy-4-(2-methylindol-5-yloxy)-7-(oxiran-2-ylmethoxy)quinazoline (300 mg, 0.79 mmol), (prepared as described for the starting material in Example 269), and diethylamine (0.25 ml, 2.38 mmol) in DMF (10 ml) was stirred at 70° C. for 24 hours and allowed to cool to ambient temperature. The solvents were removed in vacuo and the residue purified by silica column chromatography, gradient elution (dichloromethane, 5% methanol/95% dichloromethane, dichloromethane/methanol/0.88 ammonia (100/8/1)) to give (2R)-7-(3-(N,N-diethylamino)-2-hydroxypropoxy)-6-methoxy-4-(2-methylindol-5-yloxy)quinazoline (288 mg, 81%).

$^1$H NMR Spectrum: (DMSO-$d_6$) 0.95 (t, 6H), 2.10 (s, 3H), 2.4 (m, 6H), 3.98 (s, 3H), 4.14 (m, 3H), 4.84 (br s, 1H), 6.12 (s, 1H), 6.85 (dd, 1H), 7.3 (m, 3H), 7.58 (s, 1H), 8.42 (s, 1H) and 10.98 (br s, 1H)

MS(ESI): 448 (MH)$^+$

| Elemental analysis: | Found | C 64.3 H 6.6 N 12.0 |
|---|---|---|
| $C_{25}H_{30}N_4O_4$ 0.4dichloromethane | Requires | C 64.0 H 6.4 N 11.6% |

EXAMPLE 271

A mixture of 7-benzyloxy-6-methoxy-4-(3-methylindol-5-yloxy)quinazoline (7.76 g, 18.9 mmol), ammonium formate (17.82 g, 282 mmol) and 10% palladium on charcoal (800 mg) in DMF (350 ml) was stirred at ambient temperature for 1 hour. The catalyst was filtered off through celite and the cake washed with DMF. The solvent was removed in vacuo and the residue stirred with a saturated solution of sodium hydrogen carbonate for 2 hours. The suspension was then filtered, washed with water and dried to give 7-hydroxy-6-methoxy-4-(3-methylindol-5-yloxy)quinazoline (5.49 g, 91%).

$^1$H NMR Spectrum: (DMSO-$d_6$) 2.20 (s, 3H), 3.98 (s, 3H), 6.98 (dd, 1H), 7.18 (s, 1H), 7.20 (s, 1H), 7.35 (m, 3H), 7.58 (s, 1H), 8.40 (s, 1H) and 10.82 (br s, 1H)

MS(ESI): 322 (MH)$^+$

The starting material was prepared as follows:

A mixture of 7-benzyloxy-4-chloro-6-methoxyquinazoline (7.859 g, 26.1 mmol), (prepared as described for the starting material in Example 1), potassium carbonate (18.03 g, 130 mmol) and 5-hydroxy-3-methylindole (5.00 g, 34.0 mmol), (Journal of Organic Chemistry 1993, 58, 3757), in DMA (600 ml) was stirred at 75° C. for 2 hours and allowed to cool to ambient temperature. The reaction mixture was filtered and the filtrate evaporated in vacuo. The crude solid was purified by silica column chromatography, eluting with 2.5% methanol/97.5% dichloromethane to give 7-benzyloxy-6-methoxy-4-(3-methylindol-5-yloxy)quinazoline (7.791 g, 73%).

$^1$H NMR Spectrum: (CDCl$_3$) 2.30 (s, 3H), 4.10 (s, 3H), 5.36 (s, 2H), 7.04 (m, 2H), 7.43 (m, 8H), 7.62 (s, 1H), 8.02 (s, 1H), and 8.60 (s, 1H)

MS(ESI): 412 (MH)$^+$

EXAMPLE 272

A mixture of 7-hydroxy-6-methoxy-4-(3-methylindol-5-yloxy)quinazoline (800 mg, 2.49 mmol), (prepared as described in Example 271), potassium carbonate (687 mg, 4.98 mmol) and 1-chloro-3-morpholinopropane (448 mg, 2.74 mmol), (prepared as described for the starting material in Example 1), in DMF (20 ml) was stirred at 80° C. for 2 hours and allowed to cool to ambient temperature. The reaction mixture was filtered and the filtrate evaporated in vacuo. The residue was purified by silica column chromatography, gradient elution (dichloromethane, 5% methanol/95% dichloromethane, methanol/dichloromethane/0.880 saturated aqueous ammonia (100/8/1)) and the product was recrystallised from ethanol to give 6-methoxy-4-(3-methylindol-5-yloxy)-7-(3-morpholinopropoxy)quinazoline (570 mg, 51%).

$^1$H NMR Spectrum: (DMSO-$d_6$) 1.98 (m, 2H), 2.20 (s, 3H), 2.40 (t, 4H), 2.50 (m, 2H), 3.60 (t, 4H), 3.98 (s, 3H), 4.20 (t, 2H), 6.98 (dd, 1H), 7.18 (s, 1H), 7.35 (m, 3H), 7.60 (s, 1H), 8.45 (s, 1H), and 10.82 (br s, 1H)

MS(ESI): 449 (MH)$^+$

| Elemental analysis: | Found | C 64.2 H 6.0 N 11.8 |
|---|---|---|
| $C_{25}H_{28}N_4O_4$ 0.7$H_2O$ 0.7ethanol | Requires | C 64.2 H 6.9 N 11.4% |

EXAMPLE 273

A mixture of 7-hydroxy-6-methoxy-4-(3-methylindol-5-yloxy)quinazoline (800 mg, 2.49 mmol), (prepared as described for the starting material in Example 271), potassium carbonate (1.031 g, 7.47 mmol) and 4-(2-chloroethyl)morpholine hydrochloride (510 mg, 2.74 mmol) in DMF (25 ml) was stirred at 80° C. for 2 hours and allowed to cool to ambient temperature. The reaction mixture was filtered and the filtrate removed in vacuo. The residue was purified by silica column chromatography, gradient elution (dichloromethane, 5% methanol/95% dichloromethane, methanol/dichloromethane/0.880 saturated aqueous ammonia (100/8/1)) and the product recrystallised from ethanol to give 6-methoxy-4-(3-methylindol-5-yloxy)-7-(2-morpholinoethoxy)quinazoline (510 mg, 47%).

$^1$H NMR Spectrum: (DMSO-$d_6$) 2.20 (s, 3H), 2.55 (t, 4H), 2.80 (t, 2H), 3.60 (t, 4H), 3.98 (s, 3H), 4.30 (t, 2H), 6.98 (dd, 1H), 7.18 (s, 1H), 7.35 (m, 2H), 7.40 (s, 1H), 7.60 (s, 1H), 8.45 (s, 1H), and 10.82 (br s, 1H)

MS(ESI): 449 (MH)$^+$

| Elemental analysis: | Found | C 64.1 H 6.3 N 12.2 |
|---|---|---|
| $C_{24}H_{26}N_4O_4$ 0.4$H_2O$ 0.8ethanol | Requires | C 64.3 H 6.1 N 11.7% |

EXAMPLE 274

A mixture of 7-hydroxy-6-methoxy-4-(3-methylindol-5-yloxy)quinazoline (1.00 g, 3.11 mmol), (prepared as described for the starting material in Example 271), potassium carbonate (1.288 g, 9.33 mmol) and 4-(4-methylphenylsulphonyloxymethyl)-1-tert-butoxycarbonylpiperidine (1.264 g, 3.42 mmol), (prepared as described for the starting material in Example 10), in DMF (35 ml) was stirred at 80° C. for 2 hours and allowed to cool to ambient temperature. The reaction mixture was filtered and the solvent removed in vacuo. The residue was purified by silica column chromatography, 5% methanol/95% dichloromethane and the product was recrystallised from ethanol to give 6-methoxy-4-(3-methylindol-5-yloxy)-7-(1-tert-butoxycarbonylpiperidin-4-ylmethoxy)quinazoline (1.011 g, 63%).

$^1$H NMR Spectrum: (DMSO-$d_6$) 1.3 (m, 4H), 1.42 (s, 9H), 1.90 (d, 2H), 2.10 (m, 1H), 2.28 (s, 3H), 2.80 (m, 2H), 3.98 (s, 3H), 4.08 (d, 2H), 6.98 (dd, 1H), 7.18 (s, 1H), 7.35 (m, 3H), 7.60 (s, 1H), 8.45 (s, 1H), and 10.82 (br s, 1H)

MS(ESI): 519 (MH)$^+$

EXAMPLE 275

A mixture of 7-hydroxy-6-methoxy-4-(3-methylindol-5-yloxy)quinazoline (600 mg, 1.87 mmol), (prepared as described for the starting material in Example 271), potassium carbonate (773 mg, 5.60 mmol) and 3-(1,1-dioxothiomorphlino)propoxy tosylate (1.296 g, 3.74 mmol) in DMF (30 ml) was stirred at 75° C. overnight and allowed to cool to ambient temperature. The reaction mixture was filtered and the solvent removed in vacuo. The residue was purified by silica column chromatography, gradient elution (dichloromethane, 5% methanol/95% dichloromethane, methanol/dichloromethane/0.880 saturated aqueous ammonia (100/8/1)) and the product recrystallised from ethanol to give 7-(3-(1,1-dioxothiomorpholino)propoxy)-6-methoxy-4-(3-methylindol-5-yloxy)quinazoline (525 mg, 56%).

$^1$H NMR Spectrum: (DMSO-$d_6$) 1.98 (m, 2H), 2.17 (s, 3H), 2.65 (t, 2H), 2.90 (t, 4H), 3.10 (t, 4H), 3.98 (s, 3H), 4.25 (t, 2H), 6.95 (dd, 1H), 7.15 (s, 1H), 7.30 (d, 1H), 7.35 (m, 2H), 7.60 (s, 1H), 8.45 (s, 1H), and 10.82 (br s, 1H)

MS(ESI): 497 (MH)$^+$

| Elemental analysis: | Found | C 58.4 H 5.5 N 11.1 |
|---|---|---|
| $C_{25}H_{28}N_4O_5S$ 0.8$H_2O$ | Requires | C 58.8 H 5.8 N 11.0% |

EXAMPLE 276

A mixture of 6-methoxy-4-(3-methylindol-5-yloxy)-7-(1-tert-butoxycarbonylpiperidin-4-ylmethoxy)quinazoline (1.290 g, 2.49 mmol), (prepared as described in Example 274), in 25% trifluoroacetic acid/75% dichloromethane solution (75 ml) was stirred at ambient temperature for 2 hours. The solvents were then removed in vacuo and the dark yellow gum triturated with concentrated ammonia. The resulting solid was filtered off and dried to give 6-methoxy-4-(3-methylindol-5-yloxy)-7-(piperidin-4-ylmethoxy)quinazoline (648 mg, 62%).

$^1$H NMR Spectrum: (DMSO-$d_6$) 1.35 (m, 2H), 1.80 (m, 2H), 2.05 (m, 1H), 2.10 (s, 3H), 2.70 (m, 2H), 3.10 (m, 2H), 3.98 (s, 3H), 4.05 (d, 2H), 6.98 (dd, 1H), 7.18 (s, 1H), 7.34 (m, 3H), 7.60 (s, 1H), 8.45 (s, 1H), and 10.82 (br s, 1H)

MS(ESI): 419 (MH)$^+$

EXAMPLE 277

A mixture of 6-methoxy-4-(3-methylindol-5-yloxy)-7-(piperidin-4-ylmethoxy)quinazoline (460 mg, 1.10 mmol), (prepared as described in Example 276), triethylamine (5 ml) and chloroacetonitrile (0.38 ml, 6.05 mmol) in methanol (5 ml) was stirred at ambient temperature for 24 hours. The solvents were removed in vacuo and the residue purified by silica column chromatography using gradient elution (dichloromethane, 5% methanol/95% dichloromethane, methanol/dichloromethane/0.880 saturated aqueous ammonia (100/8/1)) and the product recrystallised from acetonitrile to give 7-(1-cyanomethylpiperidin-4-ylmethoxy)-6-methoxy-4-(3-methylindol-5-yloxy)quinazoline (178 mg, 35%).

$^1$H NMR Spectrum: (DMSO-$d_6$) 1.40 (m, 2H), 1.80 (m, 4H), 2.20 (m, 4H), 2.81 (m, 2H), 3.65 (s, 2H), 3.98 (s, 3H), 4.05 (d, 2H), 6.98 (dd, 1H), 7.15 (s, 1H), 7.35 (m, 3H), 7.60 (s, 1H), 8.45 (s, 1H), and 10.83 (br s, 1H)

MS(ESI): 458 (MH)$^+$

| Elemental analysis: | Found | C 66.3 H 6.1 N 14.8 |
|---|---|---|
| $C_{26}H_{27}N_5O_3$ 0.7$H_2O$ | Requires | C 66.4 H 6.1 N 14.9% |

EXAMPLE 278

A mixture of 7-hydroxy-6-methoxy-4-(3-methylindol-5-yloxy)quinazoline (1.35 g, 4.2 mmol), (prepared as described for the starting material in Example 271), potassium carbonate (1.74 g, 12.6 mmol) and (2R)-(−)-glycidyl tosylate (1.92 g, 8.4 mmol) in DMF (25 ml) was stirred at 60° C. for 2 hours and allowed to cool to ambient temperature. The reaction mixture was filtered and the solvent removed in vacuo. The residue was dissolved in dichloromethane and washed with saturated sodium hydrogen carbonate solution. The organic layer was then dried (MgSO$_4$), filtered and solvent removed in vacuo to give a solid. This was triturated with ether and the solid filtered off and dried to give (2R)-6-methoxy-4-(3-methylindol-5-yloxy)-7-(oxiran-2-ylmethoxy)quinazoline (842 mg, 53%).

¹H NMR Spectrum: (DMSO-d₆) 2.20 (s, 3H), 2.80 (m, 1H), 2.90 (m, 1H), 3.42 (m, 1H), 3.98 (s, 3H), 4.02 (m, 1H), 4.60 (m, 1H), 6.98 (dd, 1H), 7.18 (s, 1H) 7.35 (m, 3H), 7.60 (s, 1H), 8.45 (s, 1H) and 10.82 (s, 1H)

MS(ESI): 378 (MH)⁺

EXAMPLE 279

A mixture of (2R)-6-methoxy-4-(3-methylindol-5-yloxy)-7-(oxiran-2-ylmethoxy)quinazoline (300 mg, 0.65 mmol), (prepared as described in Example 278), and piperidine (0.2 ml, 2.04 mmol) in DMF (5 ml) was stirred at 60° C. for 24 hours and allowed to cool to ambient temperature. The solvents were removed in vacuo and the residue purified by silica column chromatography, gradient elution (dichloromethane, 5% methanol/95% dichloromethane, 1% 0.880 saturated aqueous ammonia/10% methanol/89% dichloromethane) (2R)-7-(2-hydroxy-3-piperidinopropoxy)-6-methoxy-4-(3-methylindol-5-yloxy)quinazoline (237 mg, 78%).

¹H NMR Spectrum: (DMSO-d₆) 1.38 (m, 2H), 1.50 (m, 4H), 2.34 (m, 9H), 3.98 (s, 3H), 4.16 (m, 3H), 4.85 (br s, 1H), 6.98 (dd, 1H), 7.18 (s, 1H), 7.35 (m, 3H), 7.60 (s, 1H), 8.42 (s, 1H) and 10.82 (br s, 1H)

MS(ESI): 464 (MH)⁺

| Elemental analysis: | Found | C 66.3 H 6.6 N 12.1 |
|---|---|---|
| $C_{26}H_{30}N_4O_4$ 0.5methanol | Requires | C 66.5 H 6.7 N 11.7% |

EXAMPLE 280

A mixture of (2R)-6-methoxy-4-(3-methylindol-5-yloxy)-7-(oxiran-2-ylmethoxy)quinazoline (300 mg, 0.65 mmol), (prepared as described in Example 278), and pyrrolidine (0.17 ml, 2.04 mmol) in DMF (5 ml) was stirred at 60° C. for 24 hours and allowed to cool to ambient temperature. The solvents were removed in vacuo and the residue purified by silica column chromatography using gradient elution (dichloromethane, 5% methanol/95% dichloromethane, methanol/dichloromethane/0.880 saturated aqueous ammonia (100/8/1)) to give (2R)-7-(2-hydroxy-3-(pyrrolidin-1-yl)propoxy)-6-methoxy-4-(3-methylindol-5-yloxy)quinazoline (257 mg, 88%).

¹H NMR Spectrum: (DMSO-d₆) 1.65 (m, 4H), 1.98 (m, 2H), 2.20 (s, 3H), 2.50 (m, 2H), 2.62 (m, 2H), 3.98 (s, 3H), 4.17 (m, 3H), 6.98 (dd, 1H), 7.18 (s, 1H), 7.35 (m, 3H), 7.60 (s, 1H), 8.42 (s, 1H) and 10.82 (br s, 1H)

MS(ESI): 449 (MH)⁺

| Elemental analysis: | Found | C 64.1 H 6.4 N 12.6 |
|---|---|---|
| $C_{25}H_{28}N_4O_4$ 1.0H₂O | Requires | C 64.4 H 6.5 N 12.0% |

EXAMPLE 281

A mixture of (2R)-6-methoxy-4-(3-methylindol-5-yloxy)-7-(oxiran-2-ylmethoxy)quinazoline (350 mg, 0.93 mmol), (prepared as described in Example 278), and 1-methylpiperazine (0.31 ml, 2.78 mmol) in DMF (5 ml) was stirred at 60° C. for 24 hours and allowed to cool to ambient temperature. The solvents were removed in vacuo and the residue purified by silica column chromatography using gradient elution (dichloromethane, 5% methanol/95% dichloromethane, methanol/dichloromethane/0.880 saturated aqueous ammonia (100/8/1)) to give (2R)-7-(2-hydroxy-3-(4-methylpiperazin-1-yl)propoxy)-6-methoxy-4-(3-methylindol-5-yloxy)quinazoline (352 mg, 80%).

¹H NMR Spectrum: (DMSO-d₆) 2.10 (s, 3H), 2.20 (s, 3H), 2.40 (m, 10H), 3.98 (s, 3H), 4.13 (m, 3H), 6.98 (dd, 1H), 7.18 (s, 1H), 7.35 (m, 3H), 7.60 (s, 1H), 8.42 (s, 1H) and 10.82 (br s, 1H)

MS(ESI): 478 (MH)⁺

| Elemental analysis: | Found | C 61.6 H 6.4 N 14.4 |
|---|---|---|
| $C_{26}H_{31}N_5O_4$ 1.0H₂O•0.25Methanol | Requires | C 61.6 H 6.8 N 13.9% |

EXAMPLE 282

A mixture of (2R)-6-methoxy-4-(3-methylindol-5-yloxy)-7-(oxiran-2-ylmethoxy)quinazoline (350 mg, 0.93 mmol), (prepared as described in Example 278), and morpholine (0.24 ml, 2.78 mmol) in DMF (5 ml) was stirred at 60° C. for 24 hours and allowed to cool to ambient temperature. The solvents were removed in vacuo and the residue purified by silica column chromatography using gradient elution (dichloromethane, 5% methanol/95% dichloromethane, methanol/dichloromethane/0.880 saturated aqueous ammonia (100/8/1)) to give (2R)-7-(2-hydroxy-3-morpholinopropoxy)-6-methoxy-4-(3-methylindol-5-yloxy)quinazoline (398 mg, 93%).

¹H NMR Spectrum: (DMSO-d₆) 2.20 (s, 3H), 2.44 (m, 6H), 3.48 (t, 4H), 3.98 (s, 3H), 4.13 (m, 3H), 4.98 (br s, 1H), 6.98 (dd, 1H), 7.18 (s, 1H), 7.35 (m, 3H), 7.60 (s, 1H), 8.42 (s, 1H) and 10.82 (br s, 1H)

MS(ESI): 465 (MH)⁺

| Elemental analysis: | Found | C 58.5 H 6.0 N 11.2 |
|---|---|---|
| $C_{25}H_{28}N_4O_5$ 2.5H₂O. | Requires | C 58.9 H 6.5 N 11.0% |

EXAMPLE 283

A mixture of (2R)-6-methoxy-4-(3-methylindol-5-yloxy)-7-(oxiran-2-ylmethoxy)quinazoline (350 mg, 0.93 mmol), (prepared as described in Example 278), and 2.0 M dimethylamine in ethanol (4.60 ml, 9.30 mmol) in DMF (5 ml) was stirred at 60° C. for 24 hours and allowed to cool to ambient temperature. The solvents were removed in vacuo and the residue purified by silica column chromatography, gradient elution (dichloromethane, 5% methanol/95% dichloromethane, methanol/dichloromethane/0.880 saturated aqueous ammonia (100/8/1)) to give (2R)-7-(2-hydroxy-3-dimethylaminopropoxy)-6-methoxy-4-(3-methylindol-5-yloxy)quinazoline (308 mg, 78%).

¹H NMR Spectrum: (DMSO-d₆) 2.10 (m, 9H), 2.20 (m, 2H), 3.98 (s, 3H), 4.13 (m, 3H), 4.98 (br s, 1H), 6.98 (dd, 1H), 7.18 (s, 1H), 7.35 (m, 3H), 7.60 (s, 1H), 8.42 (s, 1H) and 10.82 (br s, 1H)

MS(ESI): 423 (MH)⁺

| Elemental analysis: | Found | C 65.5 H 6.2 N 13.2 |
|---|---|---|
| $C_{23}H_{20}N_4O_4$ | Requires | C 65.4 H 6.2 N 13.3% |

EXAMPLE 284

A mixture of (2R)-6-methoxy-4-(3-methylindol-5-yloxy)-7-(oxiran-2-ylmethoxy)quinazoline (350 mg, 0.93 mmol), (prepared as described in Example 278), and diethylamine (0.29 ml, 2.78 mmol) in DMF (5 ml) was stirred at 60° C. for 24 hours and allowed to cool to ambient temperature. The solvents were removed in vacuo and the residue purified by silica column chromatography using gradient elution (dichloromethane, 5% methanol/95% dichloromethane, methanol/dichloromethane/0.880 saturated aqueous ammonia (100/8/1)) to give (2R)-7-(2-hydroxy-3-((N,N-diethylamino)propoxy))-6-methoxy-4-(3-methylindol-5-yloxy)quinazoline (338 mg, 81%).

$^1$H NMR Spectrum: (DMSO-$d_6$) 0.95 (t, 6H), 2.11 (s, 3H), 2.40 (m, 6H), 3.98 (s, 3H), 4.13 (m, 3H), 4.84 (br s, 1H), 6.98 (dd, 1H), 7.18 (s, 1H), 7.35 (m, 3H), 7.60 (s, 1H), 8.42 (s, 1H) and 10.82 (br s, 1H)

MS(ESI): 451 (MH)$^+$

| Elemental analysis: | Found | C 64.4 H 6.6 N 12.0 |
|---|---|---|
| $C_{25}H_{30}N_4O_4$ 1.0H$_2$O. | Requires | C 64.1 H 6.9 N 12.0% |

EXAMPLE 285

A mixture of (2R)-6-methoxy-4-(3-methylindol-5-yloxy)-7-(oxiran-2-ylmethoxy)quinazoline (350 mg, 0.93 mmol), (prepared as described in Example 278), and isopropylamine (0.29 ml, 4.65 mmol) in DMF (5 ml) was stirred at 100° C. for 24 hours and allowed to cool to ambient temperature. The solvents were removed in vacuo and the residue purified by silica column chromatography using gradient elution (dichloromethane, 5% methanol/95% dichloromethane, methanol/dichloromethane/0.880 saturated aqueous ammonia (100/8/1)) to give (2R)-7-(2-hydroxy-3-(isopropylamino)propoxy)-6-methoxy-4-(3-methylindol-5-yloxy)quinazoline (307 mg, 75%).

$^1$H NMR Spectrum: (DMSO-$d_6$) 0.98 (d, 6H), 2.20 (s, 3H), 2.55-2.80 (m, 3H), 3.98 (s, 3H), 4.02-4.20 (m, 3H), 4.98 (br s, 1H), 6.98 (dd, 1H), 7.18 (s, 1H), 7.30-7.40 (m, 3H), 7.60 (s, 1H), 8.42 (s, 1H) and 10.82 (br s, 1H)

MS(ESI): 437 (MH)$^+$

| Elemental analysis: | Found | C 63.3 H 6.3 N 12.4 |
|---|---|---|
| $C_{24}H_{28}N_4O_4$ 1.0H$_2$O. | Requires | C 63.4 H 6.7 N 12.3% |

EXAMPLE 286

A mixture of (2R)-6-methoxy-4-(3-methylindol-5-yloxy)-7-(oxiran-2-ylmethoxy)quinazoline (350 mg, 0.93 mmol), (prepared as described in Example 278), and diisopropylamine (0.78 ml, 5.58 mmol) in DMF (10 ml) was stirred at 130° C. for 24 hours and allowed to cool to ambient temperature. The solvents were removed in vacuo and the residue purified by silica column chromatography using gradient elution (dichloromethane, 5% methanol/95% dichloromethane, methanol/dichloromethane/0.880 saturated aqueous ammonia (100/8/1)) to give (2R)-7-(2-hydroxy-3-((N,N-diisopropyl)amino)propoxy)-6-methoxy-4-(3-methylindol-5-yloxy)quinazoline (398 mg, 93%).

$^1$H NMR Spectrum: (DMSO-$d_6$) 0.98 (d, 12H), 2.20 (s, 3H), 2.72 (m, 2H), 3.00 (m, 2H), 3.98 (s, 3H), 4.11 (m, 3H), 6.98 (dd, 1H), 7.18 (s, 1H), 7.35 (m, 3H), 7.60 (s, 1H), 8.42 (s, 1H) and 10.82 (br s, 1H)

MS(ESI): 479 (MH)$^+$

| Elemental analysis: | Found | C 65.4 H 6.8 N 11.3 |
|---|---|---|
| $C_{27}H_{34}N_4O_4$ 0.8H$_2$O. | Requires | C 55.8 H 7.2 N 11.4% |

EXAMPLE 287

A mixture of (2R)-6-methoxy-4-(3-methylindol-5-yloxy)-7-(oxiran-2-ylmethoxy)quinazoline (100 mg, 0.28 mmol), (prepared as described in Example 278), and 4-(3-aminopropyl)morpholine (0.12 ml, 0.84 mmol) in DMF (5 ml) was heated to 70° C. for 3 hours. The solvents were removed in vacuo and the residue taken up in dichloromethane. This was washed with water, dried (MgSO$_3$), filtered and evaporated. The residue was purified by silica column chromatography using gradient elution (dichloromethane, 5% methanol/95% dichloromethane, 20% methanolic ammonia (7M)/80% dichloromethane) to give (2R)-7-(2-hydroxy-3-(3-morpholinopropylamino)propoxy)-6-methoxy-4-(3-methylindol-5-yloxy)quinazoline (67 mg, 46%).

$^1$H NMR Spectrum: (DMSO-$d_6$) 1.28 (m, 2H), 2.30 (t, 4H), 2.56 (t, 2H), 2.650 (m, 4H), 3.55 (t, 4H), 3.98 (s, 3H), 4.15 (m, 3H), 6.42 (s, 1H), 6.98 (dd, 1H), 7.42 (m, 4H), 7.60 (s, 1H), 8.45 (s, 1H), and 11.19 (br s, 1H)

MS(ESI): 508 (MH)$^+$

| Elemental analysis: | Found | C 59.7 H 6.6 N 13.4 |
|---|---|---|
| $C_{27}H_{33}N_5O_5$ 1.8H$_2$O | Requires | C 60.1 H 6.8 N 13.0% |

EXAMPLE 288

A mixture of (2R)-6-methoxy-4-(3-methylindol-5-yloxy)-7-(oxiran-2-ylmethoxy)quinazoline (100 mg, 0.28 mmol), (prepared as described in Example 278), and 1-(3-aminopropyl)-4-methylpiperazine (132 mg, 0.84 mmol) in DMF (5 ml) was heated to 70° C. for 3 hours. The solvents were removed in vacuo and the residue taken up in dichloromethane. This was washed with water, dried (MgSO$_4$), filtered and evaporated. The residue was purified by silica column chromatography using gradient elution (dichloromethane, 5% methanol/95% dichloromethane, 20% methanolic ammonia (7M)/80% dichloromethane) to give (2R)-7-(2-hydroxy-3-(3-(4-methylpiperazin-1-yl)propylamino)propoxy)-6-methoxy-4-(3-methylindol-5-yloxy)quinazoline (44 mg, 31%).

$^1$H NMR Spectrum: (DMSO-$d_6$) 1.55 (m, 2H), 2.10 (s, 3H), 2.30 (t, 8H), 2.62 (m, 6H), 3.98 (s, 3H), 4.12 (m, 3H), 6.42 (s, 1H), 6.98 (dd, 1H), 7.42 (m, 4H), 7.60 (s, 1H), 8.45 (s, 1H), and 11.19 (br s, 1H)

MS(ESI): 521 (MH)$^+$

| Elemental analysis: | Found | C 61.3 H 7.3 N 16.1 |
|---|---|---|
| $C_{28}H_{36}N_6O_4$ 1.6H$_2$O | Requires | C 61.2 H 7.2 N 16.3% |

EXAMPLE 289

A mixture of (2R)-6-methoxy-4-(3-methylindol-5-yloxy)-7-(oxiran-2-ylmethoxy)quinazoline (70 mg, 0.19 mmol), (prepared as described in Example 278), and 1-(3-aminopropyl)pyrrolidine (74 mg, 0.58 mmol) in DMF (5 ml) was heated to 60° C. overnight. The solvents were removed in vacuo and the residue purified by column chromatography using gradient elution (dichloromethane, 5% methanol/95% dichloromethane, 20% methanolic ammonia (7M)/80% dichloromethane) to give (2R)-7-(2-hydroxy-3-(3-(pyrrolidin-1-yl)propylamino)propoxy)-6-methoxy-4-(3-methylindol-5-yloxy)quinazoline (64 mg, 68%).

$^1$H NMR Spectrum: (DMSO-$d_6$) 1.60 (m, 6H), 2.25 (m, 4H), 2.60 (m, 4H), 3.08 (m, 2H), 3.98 (s, 3H), 4.12 (m, 3H), 6.42 (s, 1H), 6.98 (dd, 1H), 7.34 (m, 4H), 7.58 (s, 1H), 8.42 (s, 1H), and 11.80 (br s, 1H)

MS(ESI): 492 (MH)$^+$

EXAMPLE 290

A mixture of 4-chloro-6-methoxy-7-(3-piperidinopropoxy)quinazoline (380 mg, 1.13 mmol), (prepared as described for the starting material in Example 67), potassium carbonate (469 mg, 3.4 mmol), 4-bromo-5-hydroxyindole (240 mg, 1.13 mmol) and DMA (4.0 ml) were stirred at 90° C. for 3 hours and allowed to cool to ambient temperature. The reaction mixture was filtered and the filtrate evaporated under vacuum. The residue was purified by column chromatography eluting with dichloromethane/methanolic ammonia (7M) (95/5) to give an oil. This oil was further purified by column chromatography eluting with dichloromethane/methanol (60/40) to give 4-(4-bromoindol-5-yloxy)-6-methoxy-7-(3-piperidinopropoxy)quinazoline (256 mg, 44%).

$^1$H NMR Spectrum: (CDCl$_1$) 1.47 (m, 2H), 1.60 (m, 4H), 2.14 (m, 2H), 2.44 (m, 4H), 2.54 (t, 2H), 4.08 (s, 3H), 4.27 (t, 2H), 6.67 (m, 1H), 7.15 (d, 1H), 7.32 (t, 1H), 7.36 (s, 1H), 7.42 (d, 1H), 7.69 (s, 1H) 8.55 (br s, 1H) and 8.62 (s, 1H)

MS(ESI): 511, 513 (MH)$^+$

| Elemental analysis | Found | C 58.2 H 5.3 N 10.8 |
|---|---|---|
| $C_{25}H_{27}BrN_4O_3$ 0.25 $H_2O$, | Requires | C 58.2 H 5.4 N 10.9% |

The starting material was prepared as follows:

Ethyl 4-bromo-5-hydroxyindole-2-carboxylate (1.49 g, 5 mmol), (Jnl. Org. Chem. 1984, 49, 4761), was dissolved in ethanol (10 ml) and water (3.5 ml). Potassium hydroxide (840 mg) was added and the mixture stirred at 50° C. under an atmosphere of nitrogen for 1 hour then cooled to ambient temperature. The solvent was evaporated and the residue re-dissolved in water (25 ml). 2M Aqueous hydrochloric acid was added until the reaction mixture was at pH4, giving a precipitate which was filtered off, washed with water and dried under vacuum to give 4-bromo-5-methoxyindole-2-carboxylic acid (1.30, 96%).

$^1$H NMR Spectrum: (DMSO-$d_6$) 3.83 (s, 3H), 6.90 (d, 1H), 7.16 (d, 1H), 7.40 (d, 1H). 11.88 (br s, 1H) and 13.19 (br s, 1H)

MS(ESI): 268, 270 (M–H)

4-Bromo-5-methoxyindole-2-carboxylic acid (1.25 g, 4.19 mmol), quinoline (15 ml) and copper chromite (313 mg) were mixed together. Nitrogen was gently bubbled through the mixture for 5 minutes, then the mixture heated quickly to 245° C. under an atmosphere of nitrogen. After 90 minutes the mixture was cooled to ambient temperature diluted with ethyl acetate (100 ml) and washed with 2M aqueous hydrochloric acid (60 ml). The ethyl acetate layer was filtered, the filtrate dried (MgSO$_4$) and the solvent evaporated. The residue was purified by silica column chromatography eluting with dichloromethane/hexane (1/1) to give 4-bromo-5-methoxyindole (635 mg, 60%).

$^1$H NMR Spectrum (CDCl$_3$) 3.94 (s, 3H), 6.55 (m, 1H), 6.93 (d, 1H), 7.27 (m, 2H). 8.18 (br s, 1H)

MS(ESI): 224, 226 (M–H)$^-$

A solution of 4-bromo-5-methoxyindole (540 mg, 2.4 mmol) in dichloromethane (12 ml) was cooled to −40° C. under an atmosphere of nitrogen. Boron tribromide (4.8 ml of a 1M solution in dichloromethane, 4.8 mmol) was added dropwise then the mixture warmed to ambient temperature and stirred for 1 hour. The mixture was diluted with dichloromethane (5 ml) and washed with 2M aqueous hydrochloric acid (3 ml). The organic layer was separated, dried (MgSO$_4$) and evaporated to give a dark oil. This was purified by silica column chromatography eluting with dichloromethane/ethyl acetate (8/2) to give 4-bromo-5-hydroxyindole (295 mg, 55%).

$^1$H NMR Spectrum: (CDCl$_3$) 6.46 (m, 1H), 7.92 (d, 1H), 7.22 (m, 2H), 8.80 (br s, 1H)

MS(ESI): 210, 212 (M–H)$^-$

EXAMPLE 291

Nitrogen was bubbled through a mixture of 4-chloro-6-methoxy-7-(3-piperidinopropoxy)quinazoline (335 mg, 0.68 mmol), (prepared as described for the starting material in Example 67), potassium carbonate (281.5 mg, 2.04 mmol), 5-hydroxy-1-methylindole (100 mg, 0.68 mmol) and DMA (4.0 ml) for 5 minutes. The mixture was then stirred at 90° C. for 4 hours under an atmosphere of nitrogen and allowed to cool to ambient temperature. The reaction mixture was filtered and the filtrate evaporated under vacuum. The residue was purified by trituration with methanol then water to give 6-methoxy-4-(1-methylindol-5-yloxy)-7-(3-piperidinopropoxy)quinazoline (148 mg, 49%).

$^1$H NMR Spectrum: (DMSO-$d_6$) 1.38 (m, 2H), 1.51 (m, 4H), 1.93 (m, 2H), 2.35 (m, 4H), 2.41 (t, 2H), 3.83 (s, 3H), 3.97 (s, 3H), 4.24 (t, 2H), 6.42 (d, 1H), 7.06 (dd, 1H), 7.33 (s, 1H), 7.42 (m, 2H), 7.50 (d, 1H), 7.59 (s, 1H) and 8.47 (s, 1H)

MS(ESI): 447 (MH)$^+$

| Elemental analysis | Found | C 69.5 H 6.8 N 12.5 |
|---|---|---|
| $C_{26}H_{30}N_4O_3$ | Requires | C 69.9 H 6.8 N 12.6% |

The starting material was prepared as follows:

A solution of 5-benzyloxy-1-methylindole (3.5 g, 15.7 mmol), in ethanol (100 ml) was hydrogenated at ambient temperature and 1 atmosphere pressure hydrogen for 4 hours using 10% palladium on carbon (0.5 g) as catalyst. The catalyst was filtered off and the filtrate evaporated in vacuo. The residue was purified by silica column chromatography eluting with ethyl acetate/dichloromethane (10/90) to give 5-hydroxy-1-methylindole (2.1 g, 97%).

MS(ESI): 146 (M–H)$^-$ $^1$H NMR Spectrum: (CDCl$_3$) 3.74 (s, 3H), 4.50 (S, 1H), 6.33 (d, 1H), 6.79 (dd, 1H), 7.00 (m, 2H), 7.17 (d, 1H)

EXAMPLE 292

A mixture of (2R)-4-(indol-5-yloxy)-6-methoxy-7-(oxiran-2-ylmethoxy)quinazoline (300 mg, 0.83 mmol), and pyrrolidine (176 mg, 2.48 mmol) in DMF (5 ml) was stirred at 75° C. for 3 hours under an atmosphere of nitrogen and allowed to cool to ambient temperature. The solvents were removed in vacuo and the residue purified on silica gel, gradient elution with dichloromethane, dichloromethane/methanol (95/5), dichloromethane/methanolic ammonia (7M) (98/2 to 90/10), to give (2R)-7-(2-hydroxy-3-(pyrrolidin-1-yl)propoxy)-4-(indol-5-yloxy)-6-methoxyquinazoline (326 mg, 87%).

$^1$H NMR Spectrum: (CDCl$_3$) 1.80 (m, 4H), 2.56 (m, 3H), 2.71 (m, 2H), 2.87 (m, 1H), 4.04 (s, 3H), 4.23 (m, 3H), 6.59 (m, 1H), 7.07 (dd, 1H), 7.25 (m, 1H), 7.32 (s, 1H), 7.45 (d, 1H), 7.50 (d, 1H), 7.61 (s, 1H), 8.30 (br s, 1H) and 8.60 (s, 1H)

MS(ESI): 435 (MH)$^+$

| Elemental analysis | Found | C 63.4 H 5.9 N 12.3 |
|---|---|---|
| C$_{24}$H$_{26}$N$_4$O$_4$•1H$_2$O | Requires | C 63.7 H 6.2 N 12.4% |

The starting material was prepared as follows:

Nitrogen was bubbled through a mixture of 7-hydroxy-4-(indol-5-yloxy)-6-methoxyquinazoline (3.07 g, 10 mmol), (prepared as described for the starting material in Example 107), potassium carbonate (4.14 g, 30 mmol) and (2R)-(–)-glycidyl tosylate (4.57 g, 20 mmol) in DMA (35 ml) for 5 minutes. The mixture was then stirred at 60° C. for 2 hours under an atmosphere of nitrogen and allowed to cool to ambient temperature. The reaction mixture was filtered and the filtrate evaporated in vacuo. The residue was purified by column chromatography on silica by gradient elution with dichloromethane/methanol (100/0 to 95/5), to give (2R)-4-(indol-5-yloxy)-6-methoxy-7-(oxiran-2-ylmethoxy)quinazoline as a yellow solid (1.92 g, 53%).

$^1$H NMR Spectrum: (DMSOd$_6$) 2.75 (m, 1H), 2.89 (m, 1H), 3.44 (m, 1H), 3.97 (s, 3H), 4.06 (m, 1H), 4.58 (dd, 1H), 6.44 (m, 1H), 6.95 (dd, 1H), 7.40 (m, 4H) 7.62 (s, 1H), 8.47 (s, 1H), 11.19 (br s 1H)

MS(ESI): 364 (MH)$^+$

EXAMPLE 293

Using an analogous procedure to that described in Example 292, (2R)-4-(indol-5-yloxy)-6-methoxy-7-(oxiran-2-ylmethoxy)quinazoline (300 mg, 0.83 mmol), (prepared as described for the starting material in Example 292), was reacted with morpholine (211 mg, 2.49 mmol) to give (2R)-7-(2-hydroxy-3-morpholinopropoxy)-4-(indol-5-yloxy)-6-methoxyquinazoline (338 mg, 85%).

$^1$H NMR Spectrum: (CDCl$_3$) 2.48 (m, 2H), 2.624 (m, 2H), 2.68 (m, 2H), 3.78 (m, 4H), 4.04 (s, 3H), 4.24 (m, 3H), 6.58 (m, 1H), 7.08 (dd, 1H), 7.29 (m, 1H), 7.34 (s, 1H), 7.46 (d, 1H), 7.50 (d, 1H), 7.62 (s, 1H), 8.31 (br s, 1H) and 8.62 (s, 1H)

MS(ESI): 451 (MH)$^+$

| Elemental analysis | Found | C 60.3 H 5.9 N 12.3 |
|---|---|---|
| C$_{24}$H$_{26}$N$_4$O$_5$•1.5H$_2$O | Requires | C 60.4 H 6.1 N 11.7% |

EXAMPLE 294

Using an analogous procedure to that described in Example 292, (2R)-4-(indol-5-yloxy)-6-methoxy-7-(oxiran-2-ylmethoxy)quinazoline (300 mg, 0.83 mmol), (prepared as described for the starting material in Example 292), was reacted with piperidine (211 mg, 2.49 mmol) to give (2R)-7-(2-hydroxy-3-piperidinopropoxy)-4-(indol-5-yloxy)-6-methoxyquinazoline (325 mg, 86%).

$^1$H NMR Spectrum: (CDCl$_3$) 1.47 (m, 2H), 1.61 (m, 4H), 2.39 (m, 2H), 2.54 (d, 2H), 2.64 (m, 2H), 4.04 (s, 3H), 4.24 (m, 3H), 6.58 (m, 1H), 7.08 (dd, 1H), 7.29 (m, 1H), 7.32 (s, 1H), 7.45 (d, 1H), 7.48 (d, 1H), 7.62 (s, 1H), 8.28 (br s, 1H) and 8.60 (s, 1H)

MS(ESI): 449 (MH)$^+$

| Elemental analysis | Found | C 65.9 H 6.3 N 12.3 |
|---|---|---|
| C$_{25}$H$_{28}$N$_4$O$_4$•0.5H$_2$O | Requires | C 65.6 H 6.4 N 12.3% |

EXAMPLE 295

A mixture of (2R)-4-(indol-5-yloxy)-6-methoxy-7-(oxiran-2-ylmethoxy)quinazoline (300 mg, 0.83 mmol), (prepared as described for the starting material in Example 292), and dimethylamine (1.24 ml of a 2M solution in THF, 2.48 mmol) in DMF (5 ml) was stirred at 75° C. for 3 hours under an atmosphere of nitrogen then allowed to cool to ambient temperature. The solvents were removed in vacuo and the residue purified by trituration with methanol to give (2R)-7-(2-hydroxy-3-dimethylaminopropoxy)-4-(indol-5-yloxy)-6-methoxyquinazoline (265 mg, 63%).

$^1$H NMR Spectrum: (DMSOd$_6$) 2.21 (s, 6H), 2.38 (m, 2H), 3.97 (s, 3H), 4.073 (m, 2H), 4.21 (m, 1H), 4.96 (d, 1H), 6.43 (m, 1H), 6.97 (dd, 1H), 7.37 (s, 1H), 7.43 (m, 3H), 7.62 (s, 1H), 8.48 (s, 1H) and 11.20 (br s, 1H)

MS(ESI): 409 (MH)$^+$

| Elemental analysis | Found | C 62.8 H 5.8 N 13.2 |
|---|---|---|
| C$_{22}$H$_{24}$N$_4$O$_4$•0.7H$_2$O | Requires | C 62.8 H 6.1 N 13.3% |

EXAMPLE 296

A mixture of (2R)-4-(indol-5-yloxy)-6-methoxy-7-(oxiran-2-ylmethoxy)quinazoline (300 mg, 0.83 mmol), (prepared as described for the starting material in Example 292), and diisopropylamine (1.35 ml, 9.7 mmol) in DMF (5 ml) was stirred at 70° C. for 19 hours under an atmosphere of nitrogen then allowed to cool to ambient temperature. The solvents were removed in vacuo and the residue purified on silica gel using gradient elution with dichloromethane, dichloromethane/methanol (95/5), dichloromethane/methanolic ammonia (7M) (98/2 to 90/10) to give (2R)-7-(2-hydroxy-3-((N,N-diisopropyl)amino)propoxy)-4-(indol-5-yloxy)-6-methoxyquinazoline (343 mg, 86%).

$^1$H NMR Spectrum: (CDCl$_3$) 1.08 (m, 12H), 1.57 (m, 1H), 1.75 (m, 1H), 3.10 (m, 2H), 4.04 (s, 3H), 4.16 (m, 3H), 6.58 (m, 1H), 7.08 (dd, 1H), 7.26 (m, 1H), 7.32 (s, 1H), 7.45 (d, 1H), 7.50 (d, 1H), 7.61 (s, 1H), 8.32 (br s, 1H) and 8.61 (s, 1H)

MS(ESI): 465 (MH)$^+$

| Elemental analysis | Found | C 64.8 H 6.8 N 11.9 |
|---|---|---|
| C$_{26}$H$_{32}$N$_4$O$_4$•1.0H$_2$O | Requires | C 64.6 H 7.0 N 11.6% |

EXAMPLE 297

A mixture of (2S)-4-(indol-5-yloxy)-6-methoxy-7-(oxiran-2-ylmethoxy)quinazoline (100 mg, 0.28 mmol), and pyrrolidine (60 mg, 0.84 mmol) in DMF (5 ml) was stirred at 75° C. for 3 hours under an atmosphere of nitrogen and then allowed to cool to ambient temperature. The solvents were removed in vacuo and the residue purified on silica gel, gradient elution with dichloromethane, dichloromethane/methanol (95/5), dichloromethane/methanolic ammonia (7M) (98/2 to 90/10), to give (2S)-7-(2-hydroxy-3-(pyrrolidin-1-yl)propoxy)-4-(indol-5-yloxy)-6-methoxyquinazoline (114 mg, 92%).

$^1$H NMR Spectrum: (CDCl$_3$) 1.80 (m, 4H), 2.56 (m, 3H), 2.71 (m, 2H), 2.86 (m, 1H), 4.04 (s, 3H), 4.23 (m, 3H), 6.59 (m, 1H), 7.07 (dd, 1H), 7.25 (m, 1H), 7.32 (s, 1H), 7.45 (d, 1H), 7.50 (d, 1H), 7.61 (s, 1H), 8.30 (br s, 1H) and 8.60 (s, 1H)

MS(ESI): 435 (MH)$^+$

| Elemental analysis | Found | C 64.7 H 6.0 N 12.6 |
|---|---|---|
| C$_{24}$H$_{26}$N$_4$O$_4$•0.5H$_2$O | Requires | C 64.9 H 6.1 N 12.7% |

The starting material was prepared as follows:

Nitrogen was bubbled through a mixture of 7-hydroxy-4-(indol-5-yloxy)-6-methoxyquinazoline (3.07 g, 10 mmol), (prepared as described for the starting material in Example 107), potassium carbonate (4.14 g, 30 mmol) and (2S)-(+)-glycidyl tosylate (4.57 g, 20 mmol) in DMA (35 ml) for 5 minutes. This mixture was then stirred at 60° C. for 2 hours under an atmosphere of nitrogen and allowed to cool to ambient temperature. The reaction mixture was filtered and the filtrate evaporated in vacuo. The residue was purified by column chromatography on silica by gradient elution with dichloromethane/methanol (100/0 to 95/5), to give after removal of the solvents in vacuo and trituration of the residue with ether, (2S)-4-(indol-5-yloxy)-6-methoxy-7-(oxiran-2-ylmethoxy)quinazoline (1.88 g, 52%) as a yellow solid.

$^1$H NMR Spectrum: (DMSOd$_6$) 2.75 (m, 1H), 2.89 (m, 1H), 3.44 (m, 1H), 3.97 (s, 3H), 4.06 (m, 1H), 4.58 (dd, 1H), 6.44 (m, 1H), 6.95 (dd, 1H), 7.46 (m, 4H) 7.62 (s, 1H), 8.47 (s, 1H) and 11.19 (br s 1H)

MS(ESI): 364 (MH)$^+$

EXAMPLE 298

Using an analogous procedure to that described in Example 297, (2S)-4-(indol-5-yloxy)-6-methoxy-7-(oxiran-2-ylmethoxy)quinazoline (100 mg, 0.28 mmol), (prepared as described for the starting material in Example 297), was reacted with morpholine (73.2 mg, 0.84 mmol) to give (2S)-7-(2-hydroxy-3-morpholinopropoxy)-4-(indol-5-yloxy)-6-methoxyquinazoline (82 mg, 63%).

$^1$H NMR Spectrum: (CDCl$_3$) 2.48 (m, 2H), 2.62 (m, 2H), 2.68 (m, 2H), 3.78 (m, 4H), 4.04 (s, 3H), 4.29 (m, 3H), 6.58 (m, 1H), 7.08 (dd, 1H), 7.29 (m, 1H), 7.34 (s, 1H), 7.46 (d, 1H), 7.50 (d, 1H), 7.62 (s, 1H), 8.31 (br s, 1H) and 8.62 (s, 1H)

MS(ESI): 451 (MH)$^+$

| Elemental analysis | Found | C 61.7 H 5.7 N 11.8 |
|---|---|---|
| C$_{24}$H$_{26}$N$_4$O$_5$•1.0H$_2$O | Requires | C 61.5 H 6.0 N 12.0% |

EXAMPLE 299

Using an analogous procedure to that described in Example 297, (2S)-4-(indol-5-yloxy)-6-methoxy-7-(oxiran-2-ylmethoxy)quinazoline (100 mg, 0.28 mmol), (prepared as described for the starting material in Example 297), was reacted with piperidine (70 mg, 0.83 mmol), to give (2S)-7-(2-hydroxy-3-piperidinopropoxy)-4-(indol-5-yloxy)-6-methoxyquinazoline (93 mg, 73%).

$^1$H NMR Spectrum: (CDCl$_3$) 1.47 (m, 2H), 1.61 (m, 4H), 2.39 (m, 2H), 2.54 (d, 2H), 2.64 (m, 2H), 4.04 (s, 3H), 4.29 (m, 3H), 6.58 (m, 1H), 7.08 (dd, 1H), 7.29 (m, 1H), 7.32 (s, 1H), 7.45 (d, 1H), 7.48 (d, 1H), 7.62 (s, 1H), 8.28 (br s, 1H) and 8.60 (s, 1H)

MS(ESI): 449 (MH)$^+$

| Elemental analysis | Found | C 65.8 H 6.2 N 12.2 |
|---|---|---|
| C$_{25}$H$_{28}$N$_4$O$_4$•0.5H$_2$O | Requires | C 65.6 H 6.4 N 12.3% |

EXAMPLE 300

A mixture of (2S)-4-(indol-5-yloxy)-6-methoxy-7-(oxiran-2-ylmethoxy)quinazoline (100 mg, 0.28 mmol), (prepared as described for the starting material in Example 297), and dimethylamine (0.42 ml of a 2M solution in THF, 0.84 mmol) in DMF (5 ml) was stirred at 75° C. for 3 hours under an atmosphere of nitrogen and then allowed to cool to ambient temperature. The solvents were removed in vacuo and the residue purified by trituration with methanol to give (2S)-7-(2-hydroxy-3-dimethylaminopropoxy)-4-(indol-5-yloxy)-6-methoxyquinazoline (100 mg, 85%).

$^1$H NMR Spectrum: (DMSOd$_6$) 2.21 (s, 6H), 2.38 (m, 2H), 3.97 (s, 3H), 4.083 (m, 2H), 4.21 (m, 1H), 4.96 (d, 1H), 6.43 (m, 1H), 6.97 (dd, 1H), 7.37 (s, 1H), 7.43 (m, 3H), 7.62 (s, 1H), 8.48 (s, 1H) and 11.20 (br s, 1H)

MS(ESI): 409 (MH)$^+$

| Elemental analysis | Found | C 63.6 H 6.0 N 13.3 |
|---|---|---|
| C$_{22}$H$_{24}$N$_4$O$_4$•0.5H$_2$O | Requires | C 63.3 H 6.0 N 13.4% |

EXAMPLE 301

A mixture of (2S)-4-(indol-5-yloxy)-6-methoxy-7-(oxiran-2-ylmethoxy)quinazoline (100 mg, 0.28 mmol), (prepared as described for the starting material in Example 297), and diisopropylamine (0.45 ml, 3.2 mmol) in DMF (5 ml) was stirred at 70° C. for 19 hours under an atmosphere of nitrogen and then allowed to cool to ambient temperature. The solvents were removed in vacuo and the residue purified on silica gel, using gradient elution with dichloromethane/methanol (100/0 to 95/5), dichloromethane/methanolic ammonia (7M) (98/2 to 90/10) to give (2S)-7-(2-hydroxy-3-((N,N-diisopropyl)amino)propoxy)-4-(indol-5-yloxy)-6-methoxyquinazoline (43 mg, 33%).

$^1$H NMR Spectrum: (CDCl$_3$) 1.08 (m, 12H), 1.57 (m, 1H), 1.759 (m, 1H), 3.10 (m, 2H), 4.04 (s, 3H), 4.16 (m, 3H), 6.58 (m, 1H), 7.08 (dd, 1H), 7.26 (m, 1H), 7.32 (s, 1H), 7.45 (d, 1H), 7.50 (d, 1H), 7.61 (s, 1H), 8.32 (br s, 1H) and 8.61 (s, 1H)

MS(ESI): 465 (MH)$^+$

| Elemental analysis | Found | C 67.2 H 7.0 N 11.9 |
|---|---|---|
| C$_{26}$H$_{32}$N$_4$O$_4$. | Requires | C 67.2 H 6.9 N 12.1% |

EXAMPLE 302

A mixture of (2R)-4-(indol-5-yloxy)-6-methoxy-7-(oxiran-2-ylmethoxy)quinazoline (100 mg, 0.28 mmol), (prepared as described for the starting material in Example 292), and isopropylamine (1.0 ml) in THF (10 ml) was stirred at 75° C. for 18 hours under an atmosphere of nitrogen and then allowed to cool to ambient temperature. The mixture was filtered and the filtrate evaporated in vacuo. The residue was purified by silica gel chromatography, gradient elution with dichloromethane/methanolic ammonia (7M) (100/0 to 90/10) to give (2R)-7-(2-hydroxy-3-(isopropylamino)propoxy)-4-(indol-5-yloxy)-6-methoxyquinazoline (82 mg, 68%).

$^1$H NMR Spectrum: (DMSOd$_6$) 0.98 (m, 6H), 2.68 (m, 3H), 3.96 (m, 4H), 4.13 (m, 2H), 5.06 (br s, 1H), 6.44 (s, 1H), 6.98 (dd, 1H), 7.439 (m, 4H), 7.60 (s, 1H), 8.46 (s, 1H) and 11.22 (s, 1H)

MS(ESI): 423 (MH)$^+$

| Elemental analysis | Found | C 63.6 H 6.4 N 12.9 |
|---|---|---|
| C$_{23}$H$_{26}$N$_4$O$_4$•0.6H$_2$O | Requires | C 63.8 H 6.3 N 12.9% |

EXAMPLE 303

A mixture of (2S)-4-(indol-5-yloxy)-6-methoxy-7-(oxiran-2-ylmethoxy)quinazoline (100 mg, 0.28 mmol), (prepared as described for the starting material in Example 297), and isopropylamine (1.0 ml) in THF (10 ml) was stirred at 75° C. for 18 hours under an atmosphere of nitrogen and then allowed to cool to ambient temperature. The mixture was filtered and the filtrate evaporated in vacuo. The residue was purified by silica gel chromatography using gradient elution with dichloromethane/methanolic ammonia (7M) (100/0 to 90/10) to give (2S)-7-(2-hydroxy-3-(isopropylamino)propoxy)-4-(indol-5-yloxy)-6-methoxyquinazoline (66 mg, 56%).

$^1$H NMR Spectrum: (DMSOd$_6$) 0.985 (m, 6H), 2.68 (m, 3H), 3.96 (m, 4H), 4.13 (m, 2H), 5.06 (br s, 1H), 6.44 (s, 1H), 6.98 (dd, 1H), 7.43 (m, 4H), 7.60 (s, 1H), 8.46 (s, 1H) and 11.22 (s, 1H)

MS(ESI): 423 (MH)$^+$

| Elemental analysis | Found | C 63.1 H 6.3 N 12.7 |
|---|---|---|
| C$_{23}$H$_{26}$N$_4$O$_4$•0.9 H$_2$O | Requires | C 63.0 H 6.4 N 12.8% |

EXAMPLE 304

A mixture of (2S)-6-methoxy-4-(2-methylindol-5-yloxy)-7-(oxiran-2-ylmethoxy)quinazoline (250 mg, 0.66 mmol), and pyrrolidine (1.5 ml) in THF (10 ml) was stirred at 75° C. for 3 hours under an atmosphere of nitrogen and then allowed to cool to ambient temperature. The mixture was filtered and the filtrate evaporated in vacuo. The residue was purified by silica gel chromatographyusing gradient elution with dichloromethane/methanolic ammonia (7M) (100/0 to 90/10) to give (2S)-7-(2-hydroxy-3-(pyrrolidin-1-yl)propoxy)-6-methoxy-4-(2-methylindol-5-yloxy)quinazoline (106 mg, 36%).

$^1$H NMR Spectrum: (DMSOd$_6$) 1.60 (s, 4H), 2.38 (s, 3H), 2.57 (m, 6H), 4.11 (m, 6H), 4.95 (d, 1H), 6.14 (s, 1H), 6.88 (dd, 1H), 7.29 (m, 2H), 7.37 (s, 1H), 7.59 (s, 1H), 8.48 (s, 1H) and 11.00 (s, 1H)

MS(ESI): 450 (MH)$^+$

| Elemental analysis | Found | C 67.0 H 6.5 N 12.0 |
|---|---|---|
| C$_{25}$H$_{28}$N$_4$O$_4$•0.1 H$_2$O | Requires | C 66.7 H 6.3 N 12.4% |

The starting material was prepared as follows:

A mixture of 7-hydroxy-6-methoxy-4-(2-methylindol-5-yloxy)quinazoline (300 mg, 0.93 mmol), (prepared as described in Example 49), potassium carbonate (385 mg, 2.79 mmol) and (2S)-(−)-glycidyl tosylate (426 mg, 2.79 mmol) in DMF (15 ml) was stirred at 60° C. for 2 hours and allowed to cool to ambient temperature. The reaction mixture was filtered and the filtrate evaporated in vacuo. The residue was dissolved in dichloromethane and washed with saturated sodium hydrogen carbonate solution. The organic layer was then dried (MgSO$_4$), filtered and the solvent removed in vacuo to give a yellow solid. This was triturated with ether, filtered off and dried to give (2S)-6-methoxy-4-(2-methylindol-5-yloxy)-7-(oxiran-2-ylmethoxy)quinazoline as a yellow solid (277 mg, 78%).

$^1$H NMR Spectrum: (DMSO) 2.40 (s, 3H), 2.75 (m, 1H), 2.90 (m, 1H), 3.40 (m, 1H), 3.98 (s, 3H), 4.05 (m, 1H), 4.60 (m, 1H), 6.15 (s, 1H), 6.85 (dd, 1H), 7.30 (m, 2H) 7.40 (s, 1H), 7.60 (s, 1H), 8.45 (s, 1H) and 10.98 (s, 1H)

MS(ESI): 378 (MH)$^+$

EXAMPLE 305

A mixture of the (2R)-6-methoxy-4-(2-methylindol-5-yloxy)-7-(oxiran-2-ylmethoxy)quinazoline (250 mg, 0.66 mmol), (prepared as described for the starting material in Example 269), and pyrrolidine (1.5 ml) in THF (10 ml) was stirred at 75° C. for 3 hours under an atmosphere of nitrogen and then allowed to cool to ambient temperature. The mixture was filtered and the filtrate evaporated in vacuo. The residue was purified by silica gel chromatography using gradient elution with dichloromethane/methanolic ammonia (7M) (100/0 to 90/10) to give (2R)-7-(2-hydroxy-3-(pyrrolidin-1-yl)propoxy)-6-methoxy-4-(2-methylindol-5-yloxy)quinazoline (165 mg, 55%).

$^1$H HNR Spectrum: (DMSOd$_6$) 1.60 (s, 4H), 2.38 (s, 3H), 2.57 (m, 6H), 4.11 (m, 6H), 4.95 (d, 1H), 6.14 (s, 1H), 6.88 (dd, 1H), 7.29 (m, 2H), 7.37 (s, 1H), 7.59 (s, 1H), 8.48 (s, 1H) and 11.00 (s, 1H)

MS(ESI): 450 (MH)$^+$

| Elemental analysis | Found | C 66.8 H 6.3 N 12.4 |
|---|---|---|
| C$_{25}$H$_{28}$N$_4$O$_4$•0.1 H$_2$O | Requires | C 66.7 H 6.3 N 12.4% |

EXAMPLE 306

A mixture of (2S)-6-methoxy-4-(2-methylindol-5-yloxy)-7-(oxiran-2-ylmethoxy)quinazoline (250 mg, 0.66 m.mol), (prepared as described for the starting material in Example 304), and isopropylamine (1.5 ml) in THF (10 ml) was stirred at 75° C. for 18 hours under an atmosphere of nitrogen and then allowed to cool to ambient temperature. The mixture was filtered and the filtrate evaporated in vacuo. The residue was purified by silica gel chromatography using gradient elution with dichloromethane/methanolic ammonia (7M) (100/0 to 90/10) to give (2S)-7-(2-hydroxy-3-(isopropylamino)propoxy)-6-methoxy-4-(2-methylindol-5-yloxy)quinazoline (210 mg, 73%).

¹H HNR Spectrum: (DMSOd₆) 0.99 (d, 6H), 2.39 (s, 3H), 2.66 (m, 3H), 4.07 (m, 6H), 5.08 (d, 1H), 6.14 (s, 1H), 6.88 (dd, 1H), 7.29 (m, 2H), 7.37 (s, 1H), 7.58 (s, 1H), 8.49 (s, 1H) and 11.03 (s, 1H)

MS(ESI): 437 (MH)⁺

| Elemental analysis | Found | C 64.3 H 6.4 N 12.3 |
|---|---|---|
| $C_{24}H_{28}N_4O_4 \cdot 0.5\ H_2O$ | Requires | C 64.7 H 6.6 N 12.6% |

EXAMPLE 307

A mixture of (2R)-6-methoxy-4-(2-methylindol-5-yloxy)-7-(oxiran-2-ylmethoxy)quinazoline (250 mg, 0.66 mmol), (prepared as described for the starting material in Example 269), and isopropylamine (1.5 ml) in THF (10 ml) was stirred at 75° C. for 18 hours under an atmosphere of nitrogen and then allowed to cool to ambient temperature. The mixture was filtered and the filtrate evaporated in vacuo. The residue was purified by silica gel chromatography using gradient elution with dichloromethane/methanolic ammonia (7M) (100/0 to 90/10) to give (2R)-7-(2-hydroxy-3-(isopropylamino)propoxy)-6-methoxy-4-(2-methylindol-5-yloxy)quinazoline (243 mg, 84%).

¹H HNR Spectrum: (DMSOd₆): 0.99 (d, 6H), 2.39 (s, 3H), 2.66 (m, 3H), 4.07 (m, 6H), 5.08 (d, 1H), 6.14 (s, 1H), 6.88 (dd, 1H), 7.29 (m, 2H), 7.37 (s, 1H), 7.58 (s, 1H), 8.49 (s, 1H) and 11.03 (s, 1H)

MS(ESI): 437 (MH)⁺

| Elemental analysis | Found | C 64.3 H 6.5 N 12.3 |
|---|---|---|
| $C_{24}H_{28}N_4O_4 \cdot 0.5\ H_2O$ | Requires | C 64.7 H 6.6 N 12.6% |

EXAMPLE 308

Nitrogen was bubbled through a mixture of 4-chloro-6-methoxy-7-(3-morpholinopropoxy)quinazoline (400 mg, 1.19 mmol), (prepared as described for the starting material in Example 1), potassium carbonate (476 mg, 3.45 mmol), 5-hdyroxy-1-methylindole (220 mg, 1.5 mmol), (prepared as described for the starting material in Example 291), and DMA (5.0 ml) for 5 minutes. The mixture was then stirred at 90° C. for 3 hours under an atmosphere of nitrogen and allowed to cool to ambient temperature. The reaction mixture was filtered and the filtrate evaporated in vacuo. The residue was purified by trituration with methanol to give 6-methoxy-4-(1-methylindol-5-yloxy)-7-(3-morpholinopropoxy)quinazoline (312 mg, 59%).

¹H HNR Spectrum: (CDCl₃) 2.13 (m, 2H), 1.48 (t, 4H), 1.57 (t, 2H), 3.72 (t, 4H), 3.84 (s, 3H), 4.05 (s, 3H), 4.3 (t, 2H), 6.50 (d, 1H), 7.08-7.13 (m, 2H), 7.32 (s, 1H), 7.37 (s, 1H), 7.47 (d, 1H), 7.62 (s, 1H) 8.59 (s, 1H)

MS(ESI): 449 (MH)⁺

| Elemental analysis | Found | C 66.5 H 6.4 N 12.3 |
|---|---|---|
| $C_{25}H_{28}N_4O_4 \cdot 0.1\ H_2O$ | Requires | C 66.7 H 6.3 N 12.4% |

EXAMPLE 309

Nitrogen was bubbled through a mixture of 4-chloro-6-methoxy-7-(2-piperidinoethoxy)quinazoline (400 mg, 1.24 mmol), (prepared as described for the starting material in Example 180), potassium carbonate (500 mg, 3.62 mmol), 5-hydroxy-1-methylindole (231 mg, 1.57 mmol), (prepared as described for the starting material in Example 291), and DMA (5.0 ml) for 5 minutes. The mixture was then stirred at 90° C. for 3 hours under an atmosphere of nitrogen and then allowed to cool to ambient temperature. The reaction mixture was filtered and the filtrate evaporated in vacuo. The residue was purified by trituration with methanol to give 6-methoxy-4-(1-methylindol-5-yloxy)-7-(2-piperidinopropoxy)quinazoline (447 mg, 83%).

¹H HNR Spectrum: (CDCl₃) 1.47 (m, 2H), 1.64 (m, 4H), 2.57 (t, 4H) 2.94 (t, 2H), 3.83 (s, 3H), 4.05 (s, 3H), 4.34 (t, 2H), 6.49 (d, 1H), 7.10 (m, 2H), 7.32 (s, 1H), 7.38 (d, 1H), 7.45 (d, 1H), 7.62 (s, 1H) 8.60 (s, 1H)

MS(ESI): 433 (MH)⁺

| Elemental analysis | Found | C 69.2 H 6.7 N 12.7 |
|---|---|---|
| $C_{25}H_{28}N_4O_3$ | Requires | C 69.4 H 6.5 N 13.0% |

EXAMPLE 310

Nitrogen was bubbled through a mixture of 4-chloro-6-methoxy-7-(3-(pyrrolidin-1-yl)propoxy)quinazoline (400 mg, 1.24 mmol), (prepared as described for the starting material in Example 9), potassium carbonate (500 mg, 3.62 mmol), 5-hydroxy-1-methylindole (231 mg, 1.57 mmol), (prepared as described for the starting material in Example 291), and DMA (5.0 ml) for 5 minutes. The mixture was then stirred at 90° C. for 3 hours under an atmosphere of nitrogen and allowed to cool to ambient temperature. The reaction mixture was filtered and the filtrate evaporated in vacuo. The residue was purified by column chromatography, gradient elution, with dichloromethane/methanolic ammonia (7M), (100/0 to 90/10) to give 6-methoxy-4-(1-methylindol-5-yloxy)-7-(3-(pyrrolidin-1-yl)prop oxy)quinazoline (247 mg, 44%).

¹H HNR Spectrum: (CDCl₃) 1.81 (m, 4H), 2.18 (m, 2H), 2.56 (m, 4H), 2.69 (t. 2H), 3.82 (s, 3H), 4.05 (s, 3H), 4.30 (t, 2H), 6.45 (d, 1H), 7.09 (dd, 2H), 7.31 (s, 1H), 7.38 (d, 1H), 7.47 (d, 1H), 7.62 (s, 1H) and 8.59 (s, 1H)

MS(ESI): 433 (MH)⁺

| Elemental analysis | Found | C 66.5 H 6.3 N 12.4 |
|---|---|---|
| $C_{25}H_{28}N_4O_3$ 0.1dichloromethane + 0.7 $H_2O$ | Requires | C 66.7 H 6.6 N 12.4% |

EXAMPLE 311

Nitrogen was bubbled through a mixture of 4-chloro-6-methoxy-7-(3-piperidinopropoxy)quinazoline (114 mg, 0.34 mmol), (prepared as described for the starting material in Example 67), potassium carbonate (141 mg, 1.02 mmol), 5-hydroxy-4-nitroindole (60.5 mg, 0.34 mmol) and DMA (8.5 ml) for 5 minutes at ambient temperature. This mixture was then stirred at 90° C. for 4 hours under an atmosphere of nitrogen and allowed to cool to ambient temperature. The reaction mixture was filtered and the filtrate evaporated in vacuo. The residue was purified by silica column chromatography using gradient elution with dichloromethane/methanol (100/0 to 95/5) followed by dichloromethane/methanolic ammonia (7M) (95/5) to give a partially purified oil. This oil was further purified by silica column chromatography, gradient elution with ethyl acetate/methanolic ammonia (95/5 to 80/20) to give 6-methoxy-(4-nitroindol-5-yloxy)-7-(3-piperidinopropoxy)quinazoline (63 mg, 39%).

$^1$H HNR Spectrum: (CDCl$_3$) 1.46 (m, 2H), 1.60 (m, 4H), 2.16 (m, 2H), 2.43 (m, 4H), 2.54 (t, 2H), 3.85 (s, 3H), 4.33 (t, 2H), 7.04 (d, 1H), 7.10 (s, 1H), 7.47 (s, 1H), 7.57 (d, 1H), 7.83 (d, 1H), 7.95 (d, 1H) and 9.09 (s, 1H)

MS(ESI): 478 (MH)$^+$

| Elemental analysis | Found | C 62.5 H 5.8 N 14.7 |
|---|---|---|
| C$_{25}$H$_{27}$N$_5$O$_5$ | Requires | C 62.9 H 5.7 N 14.7% |

The starting material was prepared as follows:

A mixture of ethyl 5-methoxyindole-2-carboxylate (8.15 g, 37.2 mmol), (prepared by the method described in Heterocycles Vol. 43, No. 2, p. 263-266), nitric acid adsorbed on silica gel (24 g) and dichloromethane (150 ml) was stirred at ambient temperature for 18 hours. The dichloromethane was removed in vacuo and the product washed off the silica with acetone. The acetone was evaporated in vacuo. The residue was treated again with nitric acid on silica (1 g) as above and the work up procedure repeated to give ethyl 5-hydroxy-4-nitroindole-2-carboxylate (5.8 g, 59%).

$^1$H HNR Spectrum: (DMSOd$_6$) 1.33 (t, 3H), 3.95 (s, 3H), 4.35 (q, 2H), 7.19 (d, 1H), 7.35 (d, 1H), 7.75 (d, 1H) and 12.45 (br s, 1H)

Ethyl 5-hydroxy-4-nitroindole-2-carboxylate (1.0 g, 3.8 mmol) was suspended in a mixture of ethanol (20 ml) and water (5 ml). Potassium hydroxide (840 mg) was added and the mixture stirred at 50° C. under an atmosphere of nitrogen for 1 hour then cooled to ambient temperature. The solvent was evaporated in vacuo and the residue re-dissolved in water (25 ml). The pH was adjusted to pH2 using aqueous hydrochloric acid (2M). The resulting precipitate was filtered off, washed with water and dried in vacuo to give 5-methoxy-4-nitroindole-2-carboxylic acid (790 mg). This was used without further purification.

The crude 5-methoxy-4-nitroindole-2-carboxylic acid (720 mg, 3.05 mmol), quinoline (9 ml) and copper chromite (180 mg) were stirred together. Nitrogen was gently bubbled through the mixture for 5 minutes, then the mixture was heated quickly to 225° C., and stirred at this temperature for 40 minutes under an atmosphere of nitrogen. The mixture was cooled to ambient temperature diluted with ethyl acetate (80 ml) and the insoluble material filtered off. The filtrate was extracted twice with aqueous hydrochloric acid (2M) and then with saturated aqueous sodium hydrogen carbonate solution. The ethyl acetate layer was dried (MgSO$_4$), evaporated and the residue purified by silica column chromatography eluting with dichloromethane to give 5-methoxy-4-nitroindole (129 mg, 22%).

$^1$H HNR Spectrum: (CDCl$_3$) 3.99 (s, 3H), 6.88 (t, 1H), 6.97 (d, 1H), 7.37 (t, 1H). 7.55 (d, 1H) and 8.38 (br s, 1H)

MS(ESI): 193 (MH)$^+$

A solution of 5-methoxy-4-nitroindole (110 mg, 0.57 mmol) in dichloromethane (12 ml) was cooled to −30° C. under an atmosphere of nitrogen. Boron tribromide (0.74 ml of a 1M solution in dichloromethane, 0.74 mmol) was added dropwise then the mixture warmed to ambient temperature and stirred for 1 hour. The mixture was cooled to 5° C., diluted with dichloromethane (5 ml), and water (10 ml). After stirring for 5 minutes the insoluble material was filtered off and the dichloromethane layer separated, dried (MgSO$_4$), and evaporated to give a dark oil which was and purified by silica column chromatography eluting with dichloromethane to give 5-hydroxy-4-nitroindole (68 mg, 67%).

$^1$H HNR Spectrum: (CDCl$_3$) 6.95 (d, 1H), 7.29 (m, 1H), 7.43 (t, 1H), 7.63 (d, 1H) and 11.60 (br s, 1H)

MS(ESI): 177 (M−H)$^−$

EXAMPLE 312

6-Methoxy-(4-nitroindol-5-yloxy)-7-(3-piperidinopropoxy)quinazoline (45 mg 0.094 mmol), (prepared as described in Example 311), ethanol (20 ml) and 10% palladium on charcoal were hydrogenated at 45° C. and 1 atmosphere pressure of hydrogen for 3.5 hours. The mixture was cooled to ambient temperature, the catalyst filtered off and the filtrate evaporated in vacuo. The residue was purified by silica column chromatography using gradient elution with dichloromethane/methanolic ammonia (7M) (100/0 to 95/5), to give 4-(4-amino-indol-5-yloxy)-6-methoxy-7-(3-piperidinopropoxy)quinazoline (39 mg, 87%).

$^1$H HNR Spectrum: (CDCl) 1.39(m, 2H), 1.50 (m, 4H), 1.96 (m, 2H), 2.35 (m, 4H), 2.43 (t, 2H), 3.80 (s, 3H), 4.28 (t, 2H), 4.84 (br s, 2H), 6.68 (d, 1H), 6.78 (d, 1H), 6.94 (s, 1H), 7.28 (s, 1H), 7.45 (s, 1H), 7.69 (s, 1H), 8.45 (br s, 1H) and 8.98 (s, 1H)

MS(ESI): 448 (MH)$^+$

| Elemental analysis | Found | C 64.0 H 6.4 N 14.4 |
|---|---|---|
| C$_{25}$H$_{29}$N$_5$O$_3$•0.3 H$_2$O + 0.4 dichloromethane | Requires | C 63.6 H 6.3 N 14.4% |

EXAMPLE 313

A mixture of 4-chloro-6-methoxy-7-(3-piperidinopropoxy)quinazoline (227 mg, 0.68 mmol), (prepared as described for the starting material in Example 67), 5-hydroxy-1H-pyrrolo[2,3-b]pyridine (100 mg, 0.75 mmol), (prepared as described for the starting material in Example 182), and potassium carbonate (350 mg, 2.5 mmol) in DMF (4 ml) was stirred at 95° C. for 6 hours and allowed to cool to ambient temperature. The reaction mixture was treated with 1.0 N aqueous sodium hydroxide solution and allowed to stir at ambient temperature for a few minutes. The resulting precipitate was filtered off, washed with water and air dried to give a crude product. This was purified by column chromatography, eluting initially with dichloromethane/methanol (85/15) to isolate a less polar impurity and then with dichloromethane/methanol/0.88 ammonia (100/8/1) to isolate the target compound. The relevant fractions were combined and evaporated in vacuo to give a white solid which was triturated with acetone, filtered and dried to give 6-methoxy-7-(3-piperidinopropoxy)-4-(1H-pyrrolo[2,3-b]pyridin-5-yloxy)quinazoline (58 mg, 20%).

$^1$H HNR Spectrum: (DMSO-d$_6$) 1.38 (m, 2H), 1.50 (m, 4H), 1.95 (m, 2H), 2.15 (m, 4H), 2.42 (t, 2H), 3.99 (s, 3H), 4.22 (t, 2H), 6.47 (m, 1H), 7.36 (s, 1H), 7.55 (m, 1H), 7.60 (s, 1H), 7.90 (d, 1H), 8.18 (d, 1H), 8.49 (s, 1H) and 11.76 (br s, 1H)

MS(ESI): 434 (MH)$^+$

| Elemental analysis | Found | C 63.9 H 6.4 N 15.4 |
|---|---|---|
| C$_{24}$H$_{27}$N$_5$O$_3$ 1.0 H$_2$O | Requires | C 63.8 H 6.5 N 15.5% |

EXAMPLE 314

To a solution of 7-(3-bromopropoxy)-4-(1H-indol-5-yloxy)-6-methoxyquinazoline (200 mg, 0.47 mmol) in methylene chloride was added 4-piperidinopiperidine (237 mg, 1.41 mmol) and the reaction heated at 40° C. for 1 hour. A further portion of 4-piperidinopiperidine (100 mg, 0.59 mmol) was added and reaction heated for a further 2 hours. The reaction was purified by flash chromatography eluting from methylene chloride to 15% methanol/methylene chloride (+1% ammonium hydroxide). The product was evaporated, triturated with ether and filtered to give 4-(indol-5-yloxy)-6-methoxy-7-(3-(4-piperidino)piperidinopropoxy)quinazoline (200 mg, 83%) as a yellow solid.

$^1$H HNR Spectrum: (CDCl$_3$) 1.48-2.18 (m, 19H), 2.58 (t, 2H), 3.06 (d, 2H), 4.05 (s, 3H), 4.26 (t, 2H), 6.59 (s, 1H), 7.08 (dd, 1H), 7.28 (d, 1H), 7.36 (s, 1H), 7.50 (d, 1H), 7.63 (s, 1H), 8.30 (s, 1H), 8.59 (s, 1H)

MS: 516 [MH]$^+$

The starting material was prepared as follows:

To a solution of 7-hydroxy-4-(1H-indol-5-yloxy)-6-methoxyquinazoline (1 g, 3.2 mmol), (prepared as described for the starting material in Example 107), in DMF (50 ml) was added powdered potassium carbonate (1.32 g, 9.6 mmol) and 1,3-dibromopropane (6.43 g, 32 mmol). The reaction was heated at 50° C. for 2 hours. The inorganic material was filtered off and then the DMF removed. The residue was partitioned between methylene chloride/water. The organics were separated, dried over MgSO$_4$, filtered, evaporated in vacuo and purified by flash chromatography eluting from methylene chloride to 5% methanol/95% methylene chloride. The product was concentrated in vacuo, triturated with ether and the resulting solid filtered to give 7-(3-bromopropoxy)-4-(1H-indol-5-yloxy)-6-methoxyquinazoline (900 mg, 66%) as a white solid.

$^1$H HNR Spectrum: (CDCl$_3$) 2.46-2.57 (m, 2H), 3.68 (t, 2H), 4.08 (s, 3H), 4.38 (t, 2H), 6.58 (s, 1H), 7.09 (d, 1H), 7.27 (s, 1H), 7.35 (s, 1H), 7.46 (d, 1H), 7.50 (s, 1H), 7.63 (s, 1H), 8.30 (s, 1H), 8.62 (s, 1H)

MS: 428 [MH]$^+$

EXAMPLE 315

To a solution of 7-hydroxy-6-methoxy-4-(2-methyl-1H-indol-5-yloxy)quinazoline (225 mg, 0.7 mmol), (prepared as described in Example 49), in DMF was added powdered potassium carbonate (290 mg, 2.1 mmol) and (5S)-5-(p-toluenesulphonylmethyl)-1-methyl-2-pyrrolidinone (340 mg, 1.2 mmol). The reaction was then heated at 95° C. for 5 hours. The inorganic material was filtered off and the DMF removed by evaporation. The residue was then purified by chromatography eluting from methylene chloride to 12% methanol/88% methylene chloride (+1% ammonium hydroxide). The product was evaporated, triturated with ether and filtered to give (5S)-6-methoxy-4-(2-methyl-1H-indol-5-yloxy)-7-(1-methyl-2-oxopyrrolidin-5-ylmethoxy)quinazoline (100 mg, 33%) as a white solid.

$^1$H HNR Spectrum: (DMSO-d$_6$) 1.84-1.96 (m, 1H), 2.10-2.30 (m, 2H), 2.39 (s, 3H), 2.43-2.53 (m, 1H), 2.80 (s, 3H), 3.98 (s, 4H), 4.22 (dd, 1H), 4.40 (dd, 1H), 6.10 (s, 1H), 6.84 (dd, 1H), 7.23 (d, 1H), 7.30 (d, 1H), 7.40 (s, 1H), 7.59 (s, 1H), 8.49 (s, 1H), 10.98 (br s, 1H)

MS: 429 [MH]+

| Elemental Analysis: | Found | C 64.4 H 5.4 N 12.6 |
|---|---|---|
| C$_{24}$H$_{24}$N$_4$O$_4$ 0.8H$_2$O | Requires | C 64.5 H 5.8 N 12.5% |

The starting material was prepared as follows:

(5S)-5-(p-Toluenesulphonylmethyl)-2-pyrrolidinone (0.8 g, 3 mmol) was dissolved in dry THF and cooled to −70° C. Lithium diisopropylamide was slowly added and the reaction stirred for 20 minutes before addition of methyl iodide (2 ml, excess). The reaction was allowed to warm to ambient temperature for over 2 hours. The reaction was partitioned between ethyl acetate and water, the organic layer separated, dried over MgSO$_4$, filtered, and evaporated in vacuo. The residue was purified by flash chromatography eluting from methylene chloride to 5% methanol/95% methylene chloride and the product evaporated to give (5S)-5-(p-toluenesulphonyl-methyl)-1-methyl-2-pyrrolidinone (340 mg, 40%) as a brown oil.

$^1$H HNR Spectrum: (CDCl$_3$) 2.10-2.44 (m, 4H), 2.48 (s, 3H), 2.76 (s, 3H), 3.30-3.54 (m, 1H), 4.04 (dd, 1H), 4.15 (dd, 1H), 7.38 (d, 2H), 7.78 (d, 2H)

MS: 284 [MH]+

EXAMPLE 316

To a solution of 7-hydroxy-4-(1H-indol-5-yloxy)-6-methoxyquinazoline (600 mg, 1.95 mmol), (prepared as described for the starting material in Example 107), in DMF (20 ml) was added powdered potassuim carbonate (540 mg, 3.9 mmol) and (5S)-5-(p-toluene-sulphonylmethyl)-2-pyrrolidinone (580 mg, 2.16 mmol). The reaction was then heated at 100° C. for 4 hours. The inorganic material was filtered off and the DMF removed by evaporation. The residue was then purified by chromatography eluting from methylene chloride to 12% methanol/88% methylene chloride (+1% ammonium hydroxide). The product was evaporated, triturated with ether, and filtered to give (5S)-4-(1H-indol-5-yloxy)-6-methoxy-7-(2-oxopyrrolidin-5-ylmethoxy)quinazoline (240 mg, 31%) as a white solid.

$^1$H HNR Spectrum: (DMSO-d$_5$) 1.87-2.48 (m, 4H), 3.97 (s, 3H), 4.17 (m, 2H), 6.45 (s, 1H), 6.96 (dd, 1H), 7.38-7.49 (m, 4H), 7.60 (s, 1H), 7.81 (s, 1H), 8.50 (s, 1H)

MS: 405 [MH]+

EXAMPLE 317

To a solution of 7-hydroxy-4-(1H-indol-5-yloxy)-6-methoxyquinazoline (800 mg, 2.6 mmol), (prepared as described for the starting material in Example 107), in DMF (20 ml) was added powdered potassuim carbonate (1.08 g, 7.8 mmol) and (5R)-5-(p-toluenesulphonylmethyl)-2-pyrrolidinone (1.13 g, 4.2 mmol). The reaction was then heated at 90° C. for 4 hours. The inorganic material was filtered off and the DMF removed by evaporation. The residue was then purified by chromatography eluting from methylene chloride to 12% methanol/88% methylene chloride (+1% ammonium hydroxide). A small portion was recolumned using the same gradient. The product was evaporated, triturated with ether and filtered to give (5R)-4-(1H-indol-5-yloxy)-6-methoxy-7-(2-oxopyrrolidin-5-yl-methoxy)quinazoline (70 mg, 6.5%) as a white solid.

$^1$H HNR Spectrum: (DMSO-d$_6$) 1.64-2.45 (m, 4H), 3.78 (m, 1H), 3.99 (s, 3H), 4.18 (t, 2H), 6.42 (s, 1H), 6.97 (dd, 1H), 7.38-7.48 (m, 3H), 7.60 (s, 1H), 7.73 (s, 2H), 8.48 (s, 1H), 11.18 (br s, 1H)

MS: 405 [MH]+

The starting material was prepared as follows:

To a solution of (5R)-5-hydroxymethyl-2-pyrrolidinone (5.0 g, 43 mmol) in methylene chloride (100 ml) was added 4-dimethylaminopyridine (15.7 g, 129 mmol) and p-toluenesulphonyl chloride (9.0 g, 47 mmol). The reaction was stirred at ambient temperature for 16 hours. The reaction was then washed with 1M hydrochloric acid and the organic layer separated. This was then dried over MgSO$_4$, filtered and evaporated to give (5R)-5-(p-toluenesulphonylmethyl)-2-pyrrolidinone (10.3 g, 89%) as a white solid.

$^1$H HNR Spectrum: (CDCl$_3$) 1.68-1.86 (m, 1H), 2.16-2.38 (m, 3H), 2.48 (s, 3H), 3.86-3.96 (m, 2H), 4.08 (dd, 1H), 6.20 (br s, 1H), 7.38 (d, 2H), 7.80 (d, 2H)

MS: 270 [MH]+

EXAMPLE 318

To a suspension of 7-hydroxy-6-methoxy-4-(2-methyl-1H-indol-5-yloxy)quinazoline (1.36 g, 4.24 mmol), (prepared as described in Example 49), in DMF (70 ml), was added potassium carbonate (2.34 g, 17.0 mmol, 4 eq.) followed by (5R)-5-(p-toluenesulphonylmethyl)-2-pyrrolidinone (1.25 g, 4.66 mmol, 1.1 eq.), (prepared as described for the starting material in Example 317), and the resulting yellow suspension heated at reflux. After 4 hours, some starting material remained, and a further addition of (5R)-5-(p-toluenesulphonylmethyl)-2-pyrrolidinone (0.57 g, 2.12 mmol, 0.5 eq.) was made. The reaction was heated at reflux for a further 2 hours resulting in consumption of starting material. The reaction was cooled to ambient temperature, the inorganic residue filtered off and the filtrate evaporated in vacuo to leave a brown oil which was purified by column chromatography (methylene chloride/methanol, (100/0 to 90/10)) to give a light brown oil. Trituration with ether afforded a thick oil, which upon chromatography eluting as above gave a yellow oil. Trituration of this oil with ether gave an initial crop of (5R)-6-methoxy-4-(2-methyl-1H-indol-5-yloxy)-7-(2-oxopyrrolidin-5-ylmethoxy)quinazoline (5 mg) as an off-white solid (ca. 90% pure by nmr). Chromatography of the residues (eluting as above) followed by ether trituration gave further crops of (5R)-6-methoxy-4-(2-methyl-1H-indol-5-yloxy)-7-(2-oxopyrrolidin-5-ylmethoxy)quinazoline as a white solid (180 mg, >95% pure by nmr), as an off-white solid (800 mg, ca. 95% pure by nmr).

$^1$H HNR Spectrum: (DMSOd$_6$) 1.8-2.2 (m, 5H), 2.4 (s, 3H), 4.0 (br s, 3H), 4.1-4.2 (m, 2H), 6.1 (br s, 1H), 6.9 (dd, 1H), 7.2 (d, 1H), 7.3 (d, 1H), 7.4 (s, 1H), 7.6 (s, 1H), 7.8 (s, 1H), 8.5 (s, 1H), 11.0 (br s, 1H)

MS: 419 [MH]+

| Elemental analysis: | Found | C 60.8 H 5.3 N 12.1 |
| --- | --- | --- |
| C$_{23}$H$_{22}$N$_4$O$_4$ 2H$_2$O | Requires | C 60.8 H 5.7 N 12.3% |

EXAMPLE 319

To a solution of 7-hydroxy-6-methoxy-4-(2-methyl-1H-indol-5-yloxy)quinazoline (4.8 g, 15.7 mmol), (prepared as described in Example 49), in DMF (100 ml), was added potassuim carbonate (6.5 g, 47 mmol) and 3-chloropropyl piperidine (3.3 g, 20.4 mmol). The reaction was then heated to 100° C. for 4 hours. The inorganic material was filtered off and the DMF removed by evaporation. The residue was then purified by chromatography eluting from methylene chloride to 10% methanol/90% methylene chloride (+1% ammonium hydroxide). The relevant fractions were concentrated and the residue dissolved in ethyl acetate. Hexane was added and the precipitae was filtered off. The filtrate was evaporated and the residue was triturated with ether and filtered to give 6-methoxy-4-(1-(3-piperidinopropyl)-1H-indol-5-yloxy)-7-(3-piperidinopropoxy)quinazoline (170 mg, 1.9%) as a white solid.

$^1$H HNR Spectrum: (DMSO-d$_6$) 1.38 (br s, 4H), 1.50 (br s, 8H), 1.92 (m, 4H), 2.14-2.48 (m, 12H), 3.98 (s, 3H), 4.24 (t, 4H), 6.43 (s, 1H), 7.02 (d, 1H), 7.38 (s, 1H), 7.42 (s, 2H), 7.53 (d, 1H), 7.58 (s, 1H), 8.44 (s, 1H)

MS: 558 [MH]+

EXAMPLE 320

A mixture of (2R)-6-methoxy-4-(2-methylindol-5-yloxy)-7-(oxiran-2-ylmethoxy)quinazoline (6.201 g, 16.4 mmol), (prepared as described for the starting material in Example 269), and piperidine (4.8 ml, 49.3 mmol) in DMF (100 ml) was stirred at 60° C. for 24 hours and allowed to cool to ambient temperature. The solvents were removed in vacuo and the residue purified on silica gel, eluting with dichloromethane, dichloromethane/methanol (95/5) then dichloromethane/methanol/0.880 aqueous ammonia (89:10:1). The product was then recrystallised from acetonitrile to give (2R)-6-methoxy-(2-methyl-1H-indol-5-yloxy)-7-(2-hydroxy-3-piperidinopropoxy)quinazoline (3.33 g, 44%) as an off-white solid.

$^1$H HNR Spectrum: (DMSO$_6$) 1.35 (m, 2H), 1.51 (m, 4H), 2.30-2.40 (m, 9H), 3.98 (s, 3H), 4.08 (m, 2H), 4.21 (m, 1H), 4.86 (m, 1H), 6.10 (s, 1H), 6.87 (dd, 1H), 7.25 (d, 1H) 7.30 (d, 1H), 7.40 (s, 1H), 7.60 (s, 1H), 8.45 (s, 1H) and 10.98 (br s, 1H)

MS(ESI): 463 (MH)$^+$

| Elemental analysis: | Found | C 66.5 H 6.6 N 12.0 |
| --- | --- | --- |
| C$_{26}$H$_{30}$N$_4$O$_4$ 0.4H$_2$O | Requires | C 66.5 H 6.6 N 11.9% |

EXAMPLE 321

A mixture of (2S)-6-methoxy-4-(2-methylindol-5-yloxy)-7-(oxiran-2-ylmethoxy)quinazoline (175 mg 0.46 mmol), (prepared as described for the starting material in Example 304), and piperidine (0.14 ml, 1.39 mmol) in DMF (5 ml) was stirred at 60° C. for 24 hours and allowed to cool to ambient temperature. The solvents were removed in vacuo and the residue purified on silica gel, gradient elution eluting with dichloromethane, dichloromethane/methanol (95/5) then dichloromethane/methanol/0.880 aqueous ammonia (89:10:1). The product was then recrystallised from acetonitrile to give (2S)-6-methoxy-(2-methyl-1H-indol-5-yloxy)-7-(2-hydroxy-3-piperidinopropoxy)quinazoline (88 mg, 41%) as an off-white solid.

$^1$H HNR Spectrum: (DMSO) 1.35 (m, 2H), 1.51 (m, 4H), 2.30-2.40 (m, 9H), 3.98 (s, 3H), 4.08 (m, 2H), 4.21 (m, 1H), 4.86 (m, 1H), 6.10 (s, 1H), 6.87 (dd, 1H), 7.25 (d, 1H) 7.30 (d, 1H), 7.40 (s, 1H), 7.60 (s, 1H), 8.45 (s, 1H) and 10.98 (br s, 1H)

MS(ESI): 463 (MH)$^+$

| Elemental analysis: | Found | C 66.2 H 6.8 N 11.9 |
| --- | --- | --- |
| C$_{26}$H$_{30}$N$_4$O$_4$ 0.5H$_2$O | Requires | C 66.2 H 6.6 N 11.9% |

EXAMPLE 322

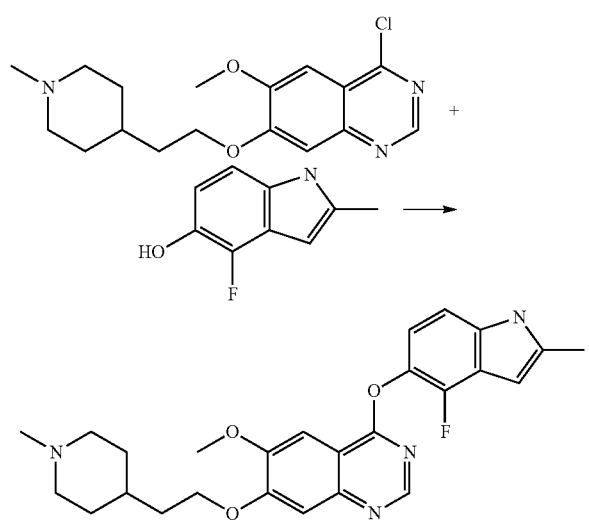

A solution of 4-chloro-6-methoxy-7-(2-(1-methylpiperidin-4-yl)ethoxy)quinazoline (1.22 g, 3.65 mmol), (prepared as described for the starting material in Example 241), 4-fluoro-5-hydroxy-2-methylindole (723 mg, 4.38 mmol), (prepared as described for the starting material in Example 237), in DMF (20 ml) containing potassium carbonate (756 mg, 5.48 mmol) was stirred at 95° C. for 3 hours. After cooling, the mixture was filtered and the filtrate was evaporated. The residue was purified by column chromatography eluting with methylene chloride/methanol (9/1) followed by methylene chloride/methanol/methanol saturated with ammonia (90/5/5). The fractions containing the expected product were combined and evaporated. The residue was triturated with ether, filtered, washed with ether and dried under vacuum. The solid was dissolved in methylene chloride/ethyl acetate and the minimum of methanol, filtered and the volatiles were removed under vacuum. The solid was triturated with ether, filtered, washed with ether and dried under vacuum at 50° C. to give 4-(4-fluoro-2-methylindol-5-yloxy)-6-methoxy-7-(2-(1-methylpiperidin-4-yl)ethoxy)quinazoline (1.06 g, 62%).

MS-ESI: 465 [MH]+

$^1$H HNR Spectrum: (DMSOd$_6$) 1.1-1.3 (m, 2H); 1.35-1.5 (m, 1H); 1.6-1.9 (m, 6H); 2.12 (s, 3H); 2.4 (s, 3H); 2.75 (d, 2H); 3.95 (s, 3H); 4.22 (t, 2H); 6.2 (s, 1H); 6.95 (dd, 1H); 7.15 (d, 1H); 7.4 (s, 1H); 7.6 (s, 1H); 8.5 (s, 1H)

EXAMPLE 323

Sodium hydride (71 mg, 1.8 mmol) was added to 5-hydroxy-2-methylbenzimidazole (204 mg, 0.89 mmol) in anhydrous DMF (2.5 ml) under an argon atmosphere. The mixture was stirred at ambient temperature for 10 minutes. 4-Chloro-6,7-dimethoxyquinazoline (200 mg, 0.89 mmol) was added and the reaction mixture stirred at 95° C. for 2 hours. Upon cooling to ambient temperature the mixture was poured in water and extracted with ethyl acetate. The organic phase was washed with brine, dried (MgSO$_4$), silica was added and the solvent evaporated off. The obtained powder was placed on the top of a disposable silica column (ISOLUTE) and the product eluted off using a gradient of methanol/dichloromethane (3/97, 5/95, 8/92). Evaporation of the solvent gave 6,7-dimethoxy-4-(2-methyl-1H-benzimidazol-6-yloxy)quinazoline (145 mg, 48%).

$^1$H HNR Spectrum: (DMSOd$_6$) 2.50 (s, 3H); 3.95 (s, 3H); 4.0 (s, 3H); 7.05 (d, 1H); 7.38 (s, 1H); 7.39 (d, 1H); 7.51 (d, 1H); 7.60 (s, 1H); 8.50 (s, 1H)

MS(ESI): 337 [MH]+

EXAMPLE 324

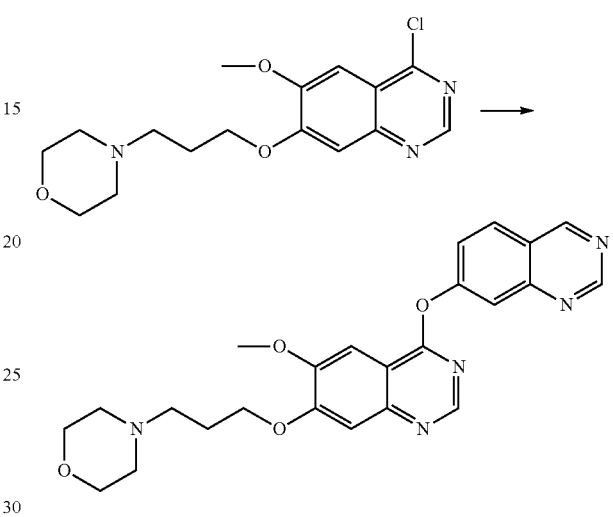

7-Hydroxyquinazoline (87 mg, 0.6 mmol) and potassium carbonate (110 mg, 0.8 mmol) were added to 4-chloro-6-methoxy-7-(3-morpholinopropoxy)quinazoline (180 mg, 0.53 mmol), (prepared as described for the starting material in Example 1), in suspension in DMF (3 ml) under an argon atmosphere. The reaction mixture was heated to 100° C. for 90 minutes. Upon cooling to ambient temperature the reaction was diluted with ethyl acetate and a saturated ammonium chloride solution. The aqueous phase was re-extracted with ethyl acetate, the organic phases combined, dried (MgSO$_4$) and the solvent evaporated. The residue was purified by flash chromatography using a gradient of methanol/dichloromethane (3/97, 4/96, 5/95). Evaporation of the solvent and trituration of the solid with ether gave 6-methoxy-7-(3-morpholinopropoxy)-4-(quinazolin-7-yloxy)quinazoline (197 mg, 83%).

$^1$H HNR Spectrum (DMSOd$_6$) 2.01 (t, 2H); 2.47 (m, 4H); 2.49 (m, 2H); 3.60 (m, 4H); 4.01 (s, 3H); 4.29 (t, 2H); 7.45 (s, 1H); 7.65 (s, 1H); 7.80 (d, 1H); 8.01 (d, 1H); 8.32 (d, 1H); 8.60 (s, 1H); 9.34 (s, 1H); 9.69 (s, 1H)

MS(ESI): 448 [MH]+

| Elemental analysis: | Found | C 63.4 H 5.7 N 15.6 |
|---|---|---|
| C$_{24}$H$_{25}$N$_5$O$_4$; 0.4 H$_2$O | Requires | C 63.4 H 5.7 N 15.4% |

The starting material was prepared as follows:

Raney Nickel (about 200 mg), (prewashed several times with ethanol), was added to a solution of 7-hydroxy-4-thiomethylquinazoline (400 mg, 2.08 mmol), (Tet. Lett. 1999, 40, 3881), and the solution was refluxed for 1 hour. Raney Nickel (100 mg) was added and the mixture was refluxed for a further 1 hour. The mixture was filtered, washed with ethanol and the volatiles were removed under vacuum. The residue was purified by column chromatography eluting with methylene chloride/methanol (97/3 followed by 96/4) to give 7-hydroxyquinazoline (62 mg, 20%).

EXAMPLE 325

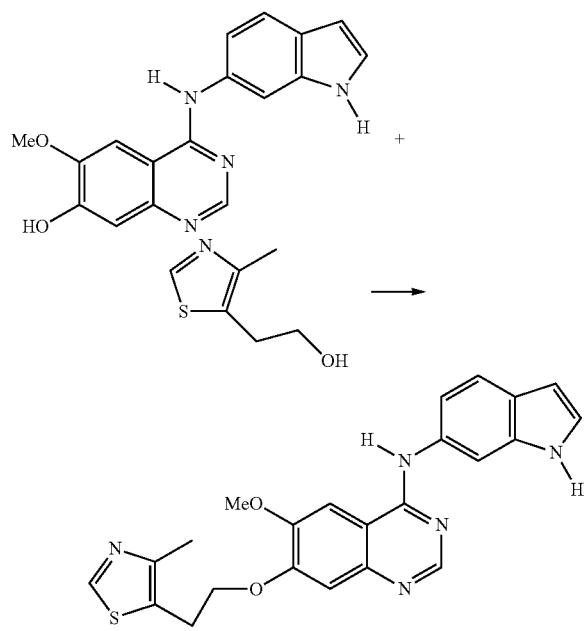

Using an analogous procedure to that described in Example 201, 7-hydroxy-4-(indol-6-ylamino)-6-methoxyquinazoline (98 mg, 0.32 mmol), (prepared as described for the starting material in Example 217), was reacted with 5-(2-hydroxyethyl)-4-methylthiazole (69 mg, 0.48 mmol) to give 6-methoxy-4-(indol-6-ylamino)-7-(2-(4-methylthiazol-5-yl)ethoxy)quinazoline (47 mg, 34%).

MS-ESI: 432 [MH]$^{30}$ $^1$H HNR Spectrum: (DMSOd$_6$) 2.4 (s, 3H); 3.3 (t, 2H); 4.0 (s, 3H); 4.35 (t, 2H); 6.45 (s, 1H); 7.2 (s, 1H); 7.25-7.4 (m, 2H); 7.55 (d, 1H); 7.9 (s, 1H); 8.05 (s, 1H); 8.45 (s, 1H); 8.87 (s, 1H); 9.45 (s, 1H)

EXAMPLE 326

The following illustrate representative pharmaceutical dosage forms containing the compound of formula I, or a pharmaceutically acceptable salt thereof (hereafter compound X), for therapeutic or prophylactic use in humans:

| (a) | Tablet I | mg/tablet |
|---|---|---|
| | Compound X | 100 |
| | Lactose Ph. Eur | 182.75 |
| | Croscarmellose sodium | 12.0 |
| | Maize starch paste (5% w/v paste) | 2.25 |
| | Magnesium stearate | 3.0 |
| (b) | Tablet II | mg/tablet |
| | Compound X | 50 |
| | Lactose Ph. Eur | 223.75 |
| | Croscarmellose sodium | 6.0 |
| | Maize starch | 15.0 |
| | Polyvinylpyrrolidone (5% w/v paste) | 2.25 |
| | Magnesium stearate | 3.0 |
| (c) | Tablet III | mg/tablet |
| | Compound X | 1.0 |
| | Lactose Ph. Eur | 93.25 |
| | Croscarmellose sodium | 4.0 |
| | Maize starch paste (5% w/v paste) | 0.75 |
| | Magnesium stearate | 1.0 |
| (d) | Capsule | mg/capsule |
| | Compound X | 10 |
| | Lactose Ph. Eur | 488.5 |
| | Magnesium stearate | 1.5 |
| (e) | Injection I | (50 mg/ml) |
| | Compound X | 5.0% w/v |
| | 1N Sodium hydroxide solution | 15.0% v/v |
| | 0.1N Hydrochloric acid (to adjust pH to 7.6) | |
| | Polyethylene glycol 400 | 4.5% w/v |
| | Water for injection to 100% | |
| (f) | Injection II | 10 mg/ml) |
| | Compound X | 1.0% w/v |
| | Sodium phosphate BP | 3.6% w/v |
| | 0.1N Sodium hydroxide solution | 15.0% v/v |
| | Water for injection to 100% | |
| (g) | Injection III | (1 mg/ml, buffered to pH 6) |
| | Compound X | 0.1% w/v |
| | Sodium phosphate BP | 2.26% w/v |
| | Citric acid | 0.38% w/v |
| | Polyethylene glycol 400 | 3.5% w/v |
| | Water for injection to 100% | |

Note

The above formulations may be obtained by conventional procedures well known in the pharmaceutical art. The tablets (a)-(c) may be enteric coated by conventional means, for example to provide a coating of cellulose acetate phthalate.

The invention claimed is:
1. A compound 4-fluoro-5-hydroxy-2-methylindole or a salt thereof.
2. A compound 4-fluoro-5-hydroxyindole or a salt thereof.
3. A compound 6-fluoro-5-hydroxy-2-methylindole or a salt thereof.
4. A compound 6-fluoro-5-hydroxyindole or a salt thereof.

* * * * *